US012799215B2

United States Patent

Sanjuan et al.

(10) Patent No.: US 12,799,215 B2
(45) Date of Patent: Nov. 17, 2026

(54) IL-4R AND TSLP INHIBITORS AND METHODS OF USE THEREOF

(71) Applicant: PRANA THERAPIES, INC., Encinitas, CA (US)

(72) Inventors: Miguel A. Sanjuan, La Jolla, CA (US); Sheila Gujrathi, Encinitas, CA (US); Ryan P. Sullivan, Ballwin, MO (US)

(73) Assignee: PRANA THERAPIES, INC., Encinitas, CA (US)

(*) Notice: Subject to any disclaimer, the term of this patent is extended or adjusted under 35 U.S.C. 154(b) by 0 days.

(21) Appl. No.: 19/384,849

(22) Filed: Nov. 10, 2025

(65) Prior Publication Data

US 2026/0098100 A1 Apr. 9, 2026

Related U.S. Application Data

(63) Continuation of application No. PCT/US2025/049461, filed on Oct. 3, 2025.

(60) Provisional application No. 63/874,419, filed on Sep. 2, 2025, provisional application No. 63/757,263, filed on Feb. 11, 2025, provisional application No. 63/703,494, filed on Oct. 4, 2024.

(51) Int. Cl.
*C07K 16/28* (2006.01)
*C07K 16/24* (2006.01)
*A61K 39/00* (2006.01)

(52) U.S. Cl.
CPC ........ *C07K 16/2866* (2013.01); *C07K 16/244* (2013.01); *A61K 2039/505* (2013.01); *C07K 2317/24* (2013.01); *C07K 2317/31* (2013.01); *C07K 2317/55* (2013.01); *C07K 2317/71* (2013.01); *C07K 2317/92* (2013.01); *C07K 2317/94* (2013.01)

(58) Field of Classification Search
CPC .................................................. C07K 16/2866
USPC ....................................................... 424/136.1
See application file for complete search history.

(56) References Cited

U.S. PATENT DOCUMENTS

| | | | |
|---|---|---|---|
| 7,083,784 B2 | 8/2006 | Dall'Acqua et al. |
| 7,608,693 B2 | 10/2009 | Martin et al. |
| 7,612,181 B2 | 11/2009 | Wu et al. |
| 7,982,016 B2 | 7/2011 | Comeau et al. |
| 8,075,887 B2 | 12/2011 | Martin et al. |
| 8,163,284 B2 | 4/2012 | Comeau et al. |
| 8,227,577 B2 | 7/2012 | Klein et al. |
| 8,242,247 B2 | 8/2012 | Klein et al. |
| 8,337,839 B2 | 12/2012 | Martin et al. |
| 8,735,095 B2 | 5/2014 | Martin et al. |
| 8,796,424 B2 | 8/2014 | Croasdale et al. |
| 8,945,559 B2 | 2/2015 | Dix et al. |
| 9,197,889 B2 | 11/2015 | Berbecel et al. |
| 9,238,692 B2 | 1/2016 | Dix et al. |
| 9,266,967 B2 | 2/2016 | Klein et al. |
| 9,284,372 B2 | 3/2016 | Comeau et al. |
| 9,382,323 B2 | 7/2016 | Brinkmann et al. |
| 9,574,004 B2 | 2/2017 | Ardeleanu et al. |
| 9,676,845 B2 | 6/2017 | Imhof-Jung et al. |
| 10,059,771 B2 | 8/2018 | Mannent et al. |
| 10,137,193 B2 | 11/2018 | Pirozzi et al. |
| 10,138,293 B2 | 11/2018 | Klein et al. |
| 10,287,348 B2 | 5/2019 | Comeau et al. |
| 10,435,473 B2 | 10/2019 | Dix et al. |
| 10,485,844 B2 | 11/2019 | Radin et al. |
| 10,640,555 B2 | 5/2020 | Imhof-Jung et al. |
| 10,669,341 B2 | 6/2020 | Stahl et al. |
| 10,676,530 B2 | 6/2020 | Stahl et al. |
| 10,828,365 B2 | 11/2020 | Parnes et al. |
| 10,927,163 B2 | 2/2021 | Klein et al. |
| 11,034,768 B2 | 6/2021 | Amin et al. |
| 11,059,896 B2 | 7/2021 | Dix et al. |
| 11,167,004 B2 | 11/2021 | Radin et al. |
| 11,214,621 B2 | 1/2022 | Mannent et al. |
| 11,485,788 B2 | 11/2022 | Stahl et al. |
| 11,504,426 B2 | 11/2022 | Hamilton et al. |
| 11,673,945 B2 | 6/2023 | Imhof-Jung et al. |

(Continued)

FOREIGN PATENT DOCUMENTS

| | | | |
|---|---|---|---|
| CN | 101896504 A | 11/2010 |
| CN | 101903404 A | 12/2010 |

(Continued)

OTHER PUBLICATIONS

Robbie et al (Antimicrobial Agents and Chemotherapy, 2013, 57(12): 6147-6153).*
Chothia, Cyrus et al. Conformations of Immunoglobulin Hypervariable Regions. Nature 342(6252):877-883 (1989).
Kabat, Elvin et al. Sequences of Proteins of Immunological Interest, 5th Edition . Public Health Service, National Institutes of Health, Bethesda, MD (1991).
Miller, Kathy et al. Design, Construction, and In Vitro Analyses of Multivalent Antibodies. The Journal of Immunology 170(9):4854-4861 (2003).

(Continued)

*Primary Examiner* — Sean E Aeder
(74) *Attorney, Agent, or Firm* — WILSON SONSINI GOODRICH & ROSATI

(57) ABSTRACT

Described herein is an antigen binding moiety comprising an anti-IL-4R moiety or an antigen binding portion thereof, an anti-TSLP moiety or an antigen binding portion thereof, and/or an anti-TSLPR moiety and methods of use. The antigen binding moiety described herein can block activity of IL4-IL-4R binding/interaction and/or TSLP-TSLPR/IL7Rα binding/interaction. In some embodiments, the antigen binding moiety described herein can block activity of TSLP and/or IL4 induced or mediated signaling, that is comparable or higher than that of a monospecific anti-IL-4R or anti-TSLP antibodies (e.g., Dupilumab and Tezepelumab, respectively) or a combination treatment (e.g., sequential or co-administration) of the monospecific anti-IL-4R and anti TSLP antibodies.

28 Claims, 70 Drawing Sheets

Specification includes a Sequence Listing.

(56) References Cited

U.S. PATENT DOCUMENTS

| | | | |
|---|---|---|---|
| 11,723,974 B2 | 8/2023 | Bryce et al. | |
| 11,771,743 B2 | 10/2023 | Hamilton et al. | |
| 11,845,800 B2 | 12/2023 | Ardeleanu et al. | |
| 11,904,053 B2 | 2/2024 | Huntington et al. | |
| 11,926,670 B2 | 3/2024 | Dix et al. | |
| 2010/0256338 A1 | 10/2010 | Brinkmann et al. | |
| 2013/0267686 A1* | 10/2013 | Brinkmann | C07K 16/32 435/69.6 |
| 2016/0009824 A1 | 1/2016 | Lo et al. | |
| 2018/0296669 A1* | 10/2018 | Parnes | A61P 11/06 |
| 2019/0040146 A1 | 2/2019 | Mannent et al. | |
| 2019/0169299 A1 | 6/2019 | Amin et al. | |
| 2021/0032354 A1* | 2/2021 | Staudinger | A61K 39/395 |
| 2021/0322546 A1 | 10/2021 | Pirozzi et al. | |
| 2021/0363237 A1 | 11/2021 | Radin et al. | |
| 2021/0363264 A1 | 11/2021 | Hamilton et al. | |
| 2021/0380705 A1 | 12/2021 | Amin et al. | |
| 2022/0110999 A1 | 4/2022 | Radin et al. | |
| 2022/0169739 A1 | 6/2022 | Xu et al. | |
| 2022/0204631 A1 | 6/2022 | Mannent et al. | |
| 2022/0220211 A1 | 7/2022 | Orengo et al. | |
| 2022/0298250 A1 | 9/2022 | Bansal | |
| 2022/0401365 A1 | 12/2022 | Manikwar et al. | |
| 2023/0078678 A1 | 3/2023 | Lueras et al. | |
| 2023/0081261 A1 | 3/2023 | Roschen et al. | |
| 2023/0146317 A1 | 5/2023 | Amin et al. | |
| 2023/0159647 A1 | 5/2023 | Stahl et al. | |
| 2023/0167171 A1 | 6/2023 | Bansal et al. | |
| 2023/0183362 A1 | 6/2023 | Laws et al. | |
| 2023/0220089 A1 | 7/2023 | Geba et al. | |
| 2023/0227584 A1 | 7/2023 | Amann et al. | |
| 2023/0272085 A1 | 8/2023 | Kostic et al. | |
| 2023/0348532 A1 | 11/2023 | Mattila et al. | |
| 2023/0357416 A1 | 11/2023 | Graham et al. | |
| 2023/0364231 A1 | 11/2023 | Bryce et al. | |
| 2024/0000931 A1 | 1/2024 | Bryce et al. | |
| 2024/0024472 A1 | 1/2024 | Tang | |
| 2024/0141051 A1 | 5/2024 | Bansal et al. | |
| 2024/0190951 A1 | 6/2024 | Zhang et al. | |
| 2024/0199751 A1 | 6/2024 | Ardeleanu et al. | |
| 2024/0350626 A1 | 10/2024 | Asrat et al. | |
| 2025/0032608 A1 | 1/2025 | Parnes et al. | |
| 2026/0109758 A1 | 4/2026 | Chen et al. | |

FOREIGN PATENT DOCUMENTS

| | | | |
|---|---|---|---|
| CN | 101903405 A | 12/2010 |
| CN | 101903406 A | 12/2010 |
| CN | 102459345 A | 5/2012 |
| CN | 103764681 A | 4/2014 |
| CN | 108290958 A | 7/2018 |
| EP | 1125584 A1 | 8/2001 |
| EP | 2225279 A1 | 9/2010 |
| EP | 2225280 A1 | 9/2010 |
| EP | 2231709 A1 | 9/2010 |
| EP | 2238173 A1 | 10/2010 |
| EP | 2356151 B1 | 4/2013 |
| EP | 2435473 B1 | 10/2013 |
| EP | 2443154 B1 | 12/2013 |
| EP | 2069403 B1 | 5/2014 |
| EP | 2205635 B1 | 5/2016 |
| EP | 3064511 B1 | 4/2018 |
| EP | 2748202 B1 | 7/2018 |
| EP | 2624865 B1 | 8/2018 |
| EP | 3356420 A1 | 8/2018 |
| EP | 2888281 B1 | 9/2018 |
| EP | 2414391 B1 | 11/2018 |
| EP | 3010539 B1 | 7/2019 |
| EP | 3524622 A1 | 8/2019 |
| EP | 3351560 B1 | 4/2020 |
| EP | 4011915 B1 | 10/2023 |
| EP | 3703818 B1 | 11/2023 |
| EP | 4289861 A1 | 12/2023 |
| EP | 3715372 B1 | 1/2024 |
| EP | 3110848 B1 | 2/2024 |
| EP | 4344706 A2 | 4/2024 |
| EP | 4345111 A2 | 4/2024 |
| EP | 4353254 A2 | 4/2024 |
| EP | 4345111 A3 | 5/2024 |
| EP | 4374919 A2 | 5/2024 |
| EP | 3416685 B1 | 6/2024 |
| EP | 4420733 A2 | 8/2024 |
| WO | WO-2009080251 A1 | 7/2009 |
| WO | WO-2009080252 A1 | 7/2009 |
| WO | WO-2009080253 A1 | 7/2009 |
| WO | WO-2009080254 A1 | 7/2009 |
| WO | WO-2010136172 A1 | 12/2010 |
| WO | WO-2010145792 A8 | 10/2011 |
| WO | WO-2013026831 A1 | 2/2013 |
| WO | WO-2016077675 A1 | 5/2016 |
| WO | WO-2017055537 A1 | 4/2017 |
| WO | WO-2017055539 A1 | 4/2017 |
| WO | WO-2018191479 A1 | 10/2018 |
| WO | WO-2021043221 A1 | 3/2021 |
| WO | WO-2021119028 A1 | 6/2021 |
| WO | WO-2021163504 A1 | 8/2021 |
| WO | WO-2021170020 A1 | 9/2021 |
| WO | WO-2022079036 A1 | 4/2022 |
| WO | WO-2022150605 A1 | 7/2022 |
| WO | WO-2023116925 A1 | 6/2023 |
| WO | WO-2023130010 A1 | 7/2023 |
| WO | WO-2024047021 A1 | 3/2024 |
| WO | WO-2024061279 A1 | 3/2024 |
| WO | WO-2024092064 A1 | 5/2024 |
| WO | WO-2024112935 A1 | 5/2024 |
| WO | WO-2024163978 A2 | 8/2024 |
| WO | WO-2024230704 A1 | 11/2024 |
| WO | WO-2024238877 A1 | 11/2024 |
| WO | WO-2025108394 A1 | 5/2025 |
| WO | WO-2026036112 A9 | 4/2026 |
| WO | WO-2026076381 A1 | 4/2026 |
| WO | WO-2026085202 A1 | 4/2026 |
| WO | WO-2026085414 A1 | 4/2026 |
| WO | WO-2026085415 A1 | 4/2026 |

OTHER PUBLICATIONS

Olafsen, Tove et al. Characterization Of Engineered Anti-p185HER-2 (scFv-CH3)2 Antibody Fragments (Minibodies) For Tumor Targeting. Protein Engineering, Design and Selection 17(4):315-323 (2004).

PCT/US2025/049461 International Search Report and Written Opinion dated Nov. 28, 2025.

Alekseychyk, Larysa et al. High-throughput screening and stability optimization of anti-streptavidin IgG1 and IgG2 formulations. Journal of Biomolecular Screening 19(9):1290-1301 (2014).

Correia, Ivan R. Stability of IgG isotypes in serum. mAbs 2(3):221-232 (2010).

Franey, Heather et al. Increased aggregation propensity of IgG2 subclass over IgG1: role of conformational changes and covalent character in isolated aggregates. Protein Science 19(9):1601-1615 (2010).

Heads, James T. et al. Relative stabilities of IgG1 and IgG4 Fab domains: Influence of the light-heavy interchain disulfide bond architecture. Protein Science 21(9):1315-1322 (2012).

Thakkar, Santosh V. et al. Understanding the relevance of local conformational stability and dynamics to the aggregation propensity of an IgG1 and IgG2 monoclonal antibodies. Protein Science 22(10):1295-1305 (2013).

* cited by examiner

B-04a

B-04b

B-05a

B-05b

WBP71460_37

WBP71460_38

WBP71460_39

WBP71460_40

IL-4R AND TSLP INHIBITORS AND METHODS OF USE THEREOF

CROSS-REFERENCE

This application is a bypass continuation of International Application No. PCT/US25/49461, filed Oct. 3, 2025, which application claims the benefit of U.S. Provisional Application No. 63/703,494, filed Oct. 4, 2024, U.S. Provisional Application No. 63/757,263, filed Feb. 11, 2025, and U.S. Provisional Application No. 63/874,419, filed Sep. 2, 2025, each of which is hereby incorporated by reference in its entirety.

INCORPORATION BY REFERENCE OF SEQUENCE LISTING

The present application is being filed along with a Sequence Listing in electronic format. The Sequence Listing is provided as a file entitled 62413-704_301_SL.xml, created Nov. 10, 2025, which is 255,260 bytes in size. The information in the electronic format of the Sequence Listing is incorporated by reference in its entirety.

BACKGROUND

TSLP, or thymic stromal lymphopoietin, is a cytokine that plays a crucial role in the initiation and modulation of immune responses. TSLP functions by binding to its receptor TSLPR, which is expressed on various immune cells, including T cells, dendritic cells and B cells. Once bound, TSLP-TSLPR signaling triggers a cascade of downstream events that ultimately result in the activation of immune cells and the release of proinflammatory cytokines.

Interleukin-4 (IL-4) and IL-13 are two factors central to type 2 immunity, and required to drive most of the key hallmarks associated with type 2 inflammation, such as immunoglobulin E production, and innate cell recruitment to inflammation sites. In some cases, IL-4 first binds to IL-4R chain with picomolar affinity, and recruits IL-2Rγc (γc) chain to form a type I IL-4 receptor complex, or alternatively recruits IL-13Rα1 to form a type II IL-4 receptor complex. Once the IL-4 receptor complexes are assembled, intracellular signaling molecules can be activated, STAT6 (signal transducer and activator of transcription 6) and IRS (insulin receptor substrate) signaling for example are responsive to the type I IL-4 receptor activation. The STAT6 signaling is important in TH2 cell differentiation and IL-4 production and the IRS molecules activate signaling pathways including PI3K and mTOR.

However, monospecific antibody or protein treatments against either TSLP or IL-4R have shown to have limited therapeutic efficacy in various diseases. There is a need for novel approaches to enhance efficacy.

SUMMARY

In some aspects, provided herein is an antigen binding moiety comprising: a binding complex comprising: (a) an anti-IL-4R moiety or an antigen binding portion thereof, wherein the anti-IL-4R moiety or the antigen binding portion thereof comprises a light chain ($L_{IL\text{-}4R}$) and a heavy chain ($H_{IL\text{-}4R}$); and (b) an anti-thymic stromal lymphopoietin (TSLP) moiety or an antigen binding portion thereof comprising a Fab, wherein the Fab comprises a first peptide chain comprising a heavy chain variable domain ($VH_{TSLP}$) and a heavy chain constant domain 1 ($CH1_{TSLP}$), and a second peptide chain comprising a light chain variable domain ($VL_{TSLP}$), and a light chain constant domain ($CL_{TSLP}$), wherein the $VH_{TSLP}$ or the $CH1_{TSLP}$ of the first peptide chain is exchanged for the $VL_{TSLP}$ or the $CL_{TSLP}$ of the second peptide chain, wherein the first peptide chain or the second peptide chain is associated with at least a portion of the anti-IL-4R moiety or the antigen binding portion thereof. In some embodiments, the $VL_{TSLP}$ or the $VH_{TSLP}$ of the anti-TSLP moiety or the antigen binding portion thereof is positioned at the N-terminus or the C-terminus of the $L_{IL\text{-}4R}$ or the $H_{IL\text{-}4R}$. In some embodiments, the $VL_{TSLP}$ or the $VH_{TSLP}$ of the anti-TSLP moiety or the antigen binding portion thereof is positioned at the C-terminus of the $H_{IL\text{-}4R}$. In some embodiments, the anti-TSLP moiety or the antigen binding portion thereof comprises, from N-terminus to C-terminus: the first peptide chain comprising [$VL_{TSLP}$]-[$CL_{TSLP}$] and the second peptide chain comprising [$VH_{TSLP}$]-[$CH1_{TSLP}$]; the first peptide chain comprising [$VL_{TSLP}$]-[$CH1_{TSLP}$] and the second peptide chain comprising [$VH_{TSLP}$]-[$CL_{TSLP}$]; or the first peptide chain comprising [$VH_{TSLP}$]-[$CL_{TSLP}$] and the second peptide chain comprising [$VL_{TSLP}$]-[$CH1_{TSLP}$]. In some embodiments, the first peptide chain and the second peptide chain are associated with each other. In some embodiments, the $VL_{TSLP}$ or the $VH_{TSLP}$ of the anti-TSLP moiety or the antigen binding portion thereof is associated with the $H_{IL\text{-}4R}$ at the C-terminus via a first linker, wherein the first linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20), wherein n is an integer between 1 and 100. In some embodiments, the first linker comprises SEQ ID NO: 23. In some embodiments, the $L_{IL\text{-}4R}$ comprises (a) a light-chain complementarity-determining region (LCDR) 1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the $L_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising to the amino acid sequence of SEQ ID NO: 16. In some embodiments, the $L_{IL\text{-}4R}$ comprises a light chain variable domain, wherein the light chain variable domain comprises an amino acid sequence having at least 80% sequence identity to the amino acid sequence of SEQ ID NO: 30. In some embodiments, the $L_{IL\text{-}4R}$ comprises a light chain variable domain comprising the amino acid sequence of SEQ ID NO: 30. In some embodiments, the $H_{IL\text{-}4R}$ comprises (a) a heavy-chain complementarity-determining region (HCDR) 1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the $H_{IL}$-4R comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the $H_{IL\text{-}4R}$ comprises a heavy chain variable domain, wherein the heavy chain variable domain comprises an amino acid sequence having at least 80% sequence identity to the amino acid sequence of SEQ ID NO: 32. In some embodiments, the $H_{IL\text{-}4R}$ comprises a heavy chain variable domain comprising the amino acid sequence of SEQ ID NO: 32. In some embodiments, the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4. In some embodiments, the $VH_{TSLP}$ comprises (a) a $HCDR1_{TSLP}$ comprising the amino acid sequence of SEQ ID NO: 2, (b) a $HCDR2_{TSLP}$ comprising the amino acid sequence of SEQ ID NO: 3, and/or (c) a $HCDR3_{TSLP}$ comprising the amino acid sequence of SEQ ID NO: 4. In some embodiments, the $VH_{TSLP}$ comprises an amino acid sequence having at least 90% sequence identity to the amino acid sequence of SEQ ID NO: 25. In some embodiments, the $VH_{TSLP}$ comprises the amino acid sequence of SEQ ID NO: 25. In some embodiments, the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8. In some embodiments, the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8. In some embodiments, the $VL_{TSLP}$ comprises an amino acid sequence having at least 90% sequence identity to the amino acid sequence of SEQ ID NO: 28. In some embodiments, the $VL_{TSLP}$ comprises the amino acid sequence of SEQ ID NO: 28. In some embodiments, the anti-TSLP moiety or the anti-IL-4R moiety comprises a Fc region. In some embodiments, the Fc region comprises one or more mutations, wherein the one or more mutations comprise a half-life extension modification, effector silencing, and/or prevention of Fab arm exchange of IgG. In some embodiments, the one or more mutations comprise M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the antigen binding moiety comprises, from N-terminus to C-terminus: a first polypeptide comprising [the $L_{IL\text{-}4R}$]; a second polypeptide comprising [the $H_{IL\text{-}4R}$]-[the first linker]-[the $VL_{TSLP}$]-[the $CL_{TSLP}$]; and a third polypeptide comprising [the $VH_{TSLP}$]-[the $CH1_{TSLP}$]. In some embodiments, the first polypeptide comprises an amino acid sequence having at least about 90% sequence identity to the amino acid sequence of SEQ ID NO: 103 or 127. In some embodiments, the second polypeptide comprises an amino acid sequence having at least about 90% sequence identity to the amino acid sequence of SEQ ID NO: 104 or 128. In some embodiments, the third polypeptide comprises an amino acid sequence having at least about 90% sequence identity to the amino acid sequence of SEQ ID NO: 105 or 129. In some embodiments, a first polynucleotide sequence encoding the first polypeptide, a second polynucleotide sequence encoding the second polypeptide, and/or a third polynucleotide sequence encoding third polypeptide comprises a nucleotide sequence encoding a signal peptide. In some embodiments, the signal peptide comprises an amino acid sequence having at least 80% sequence identity to the amino acid sequence of any one of SEQ ID NOs: 130-184. In some embodiments, the signal peptide comprises an amino acid sequence having at least 80% sequence identity to the amino acid sequence of SEQ ID NOs: 156. In some embodiments, the signal peptide comprises an amino acid sequence having the amino acid sequence of SEQ ID NOs: 156. In some embodiments, an $EC_{50}$ value of the antigen binding moiety is at least about 0.25 nM in a cell-based assay measuring IL-4R binding. In some embodiments, an $IC_{50}$ value of the antigen binding moiety is at least about 2.4 nM in a cell-based assay measuring IL-4 induced CD23 upregulation. In some embodiments, an $IC_{50}$ value of the antigen binding moiety is at least about 30 pM in a cell-based assay measuring TSLP-induced TARC/CCL17 secretion. In some embodiments, the antigen binding moiety reduces CD23 expression in vivo or in vitro, wherein the CD23 expression level is reduced by at least about 5%, at least about 10%, at least about 15%, at least about 20%, or more compared to a CD23 expression level after the treatment with a monospecific antibody or an antigen binding moiety comprising one or more scFv fragments. In some embodiments, serum half-life of the antigen binding moiety is at least about 10 days, at least about 20 days, at least about 30 days or more. In some embodiments, provided herein is a polynucleotide sequence encoding the antigen binding moiety disclosed herein. In some embodiments, provided herein is an expression vector comprising the polynucleotide sequence disclosed herein. In some embodiments, provided herein is a host cell comprising the polynucleotide sequence disclosed herein or the expression vector disclosed herein. In some embodiments, provided herein is a method of producing the antigen binding moiety disclosed herein. Provided herein are a pharmaceutical composition comprising the antigen binding moiety disclosed herein, the polynucleotide sequence disclosed herein, the expression vector disclosed herein, or the host cell disclosed herein, and a pharmaceutically acceptable excipient or carrier. Provided herein is a method of treating asthma, dermatitis, eosinophilic esophagitis, chronic obstructive pulmonary disease, eczema, and/or nasal polyps comprising administering a therapeutically effective amount of the antigen binding moiety disclosed herein, the polynucleotide sequence disclosed herein, the expression vector disclosed herein, the host cell disclosed herein, or the pharmaceutical composition disclosed herein to a subject in need thereof. Provided herein is a method of treating a disease or condition comprising administering a therapeutically effective amount of the antigen binding moiety disclosed herein, the polynucleotide sequence disclosed herein, the expression vector disclosed herein, the host cell disclosed herein, or the pharmaceutical composition disclosed herein to a subject in need thereof. Provided herein is use of a therapeutically effective amount of the antigen binding moiety disclosed herein, the polynucleotide sequence disclosed herein, the expression vector disclosed herein, the host cell disclosed herein, or the pharmaceutical composition disclosed herein in the manufacture of a medicament for the treatment of a disease or condition. Provided herein is a kit comprising the antigen binding moiety disclosed herein, the polynucleotide sequence disclosed herein, the expression vector disclosed herein, the host cell disclosed herein, or the pharmaceutical composition disclosed herein, and instructions for using the antigen binding complex. The antigen binding moiety disclosed herein, the polynucleotide sequence disclosed herein, the expression vector disclosed herein, the host cell disclosed herein, or the pharmaceutical composition disclosed herein for use as a medicament.

Provided herein is an antigen binding moiety comprising: a binding complex comprising: (a) an anti-IL-4R moiety or an antigen binding portion thereof, wherein the anti-IL-4R moiety or the antigen binding portion thereof comprises a light chain ($L_{IL\text{-}4R}$) and a heavy chain ($H_{IL\text{-}4R}$); and (b) an anti-thymic stromal lymphopoietin (TSLP) moiety or an antigen binding portion thereof, wherein the anti-TSLP moiety or the antigen binding portion thereof is associated with at least a portion of the $L_{IL\text{-}4R}$. In some embodiments, the anti-TSLP moiety or the antigen binding portion thereof is coupled to the $L_{IL\text{-}4R}$ via a first linker. In some embodiments, the anti-TSLP moiety or the antigen binding portion thereof comprises a light chain variable domain ($VL_{TSLP}$) and a heavy chain variable domain ($VH_{TSLP}$). In some embodiments, the $VL_{TSLP}$ and the $VH_{TSLP}$ are coupled to each other via a second linker. In some embodiments, the antigen binding moiety comprises, from N-terminus to C-terminus or from C-terminus to N-terminus: [the $L_{IL\text{-}4R}$]-[the first linker]-[the $VH_{TSLP}$]-[the second linker]-[$VL_{TSLP}$]; [the $L_{IL\text{-}4R}$]-[the first linker]-[the $VL_{TSLP}$]-[the second linker]-[the $VH_{TSLP}$]; [the $VL_{TSLP}$]-[the second linker]-[the $VH_{TSLP}$]-[the first linker]-[$L_{IL\text{-}4R}$]; or [the $VH_{TSLP}$]-[the second linker]-[the $VL_{TSLP}$]-[the first linker]-[the $L_{IL\text{-}4R}$]. In some embodiments, the first linker or the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20), wherein n is an integer between 1 and 100. In some embodiments, the first linker comprises the amino acid sequence of SEQ ID NO: 23. In some embodiments, the second linker comprises the amino acid sequence of SEQ ID NO: 23. In some embodiments, the $L_{IL\text{-}4R}$ comprises (a) a light-chain complementarity-determining region 1 (LCDR1) having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the $L_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the $L_{IL\text{-}4R}$ comprises a light chain variable domain, wherein the light chain variable domain comprises an amino acid sequence having at least 80% sequence identity to the amino acid sequence of SEQ ID NO: 30. In some embodiments, the $L_{IL\text{-}4R}$ comprises a light chain variable domain comprising the amino acid sequence of SEQ ID NO: 30. In some embodiments, the $L_{IL\text{-}4R}$ comprises an amino acid sequence having at least 90% sequence identity to the amino acid sequence of SEQ ID NO: 22. In some embodiments, the $L_{IL\text{-}4R}$ comprises the amino acid sequence of SEQ ID NO: 22. In some embodiments, the $H_{IL\text{-}4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the $H_{IL\text{-}4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the HIL-4R comprises a heavy chain variable domain, wherein the heavy chain variable domain comprises an amino acid sequence having at least 80% sequence identity to the amino acid sequence of SEQ ID NO: 32. In some embodiments, the $H_{IL\text{-}4R}$ comprises a heavy chain variable domain comprising the amino acid sequence of SEQ ID NO: 32. In some embodiments, the $H_{IL\text{-}4R}$ comprises an amino acid sequence having at least 90% sequence identity to the amino acid sequence of SEQ ID NO: 21. In some embodiments, the $H_{IL\text{-}4R}$ comprises the amino acid sequence of SEQ ID NO: 21. In some embodiments, the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4. In some embodiments, the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4. In some embodiments, the $VH_{TSLP}$ comprises an amino acid sequence having at least 90% sequence identity to the amino acid sequence of SEQ ID NO: 25. In some embodiments, the $VH_{TSLP}$ comprises the amino acid sequence of SEQ ID NO: 25. In some embodiments, the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8. In some embodiments, the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8. In some embodiments, the $VL_{TSLP}$ comprises an amino acid sequence having at least 90% sequence identity to the amino acid sequence of SEQ ID NO: 28. In some embodiments, the $VL_{TSLP}$ comprises the amino acid sequence of SEQ ID NO: 28. In some embodiments, the antigen binding moiety further comprises a Fc region. In some embodiments, the Fc region comprises one or more mutations, wherein the one or more mutations comprise a half-life extension modification. In some embodiments, the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc polypeptide and a second modified Fc polypeptide, wherein the first modified Fc polypeptide comprises a knob modification and the second modified Fc polypeptide comprises a hole modification. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, a light chain or a heavy chain of the anti-TSLP moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising a binding complex comprising: (a) an anti-IL-4R moiety or an antigen binding portion thereof, wherein the anti-IL-4R moiety or the antigen binding portion thereof comprises a light chain ($L_{IL-4R}$) and a heavy chain ($H_{IL-4R}$); (b) an anti-thymic stromal lymphopoietin (TSLP) moiety or an antigen binding portion thereof, and (c) a Fc region comprising a first Fc polypeptide and a second Fc polypeptide, wherein the anti-TSLP moiety or the antigen binding portion thereof is associated with at least a portion of the Fc region. In some embodiments, the anti-TSLP moiety or the antigen binding portion thereof is coupled to the second Fc polypeptide via a first linker or a second linker. In some embodiments, the anti-TSLP moiety or the antigen binding portion thereof comprises a light chain variable domain ($VL_{TSLP}$) and a heavy chain variable domain ($VH_{TSLP}$). In some embodiments, the $VL_{TSLP}$ and $VH_{TSLP}$ are coupled to each other via the second linker. In some embodiments, the $VL_{TSLP}$ or $VH_{TSLP}$ is coupled to a N-terminus of the Fc region or a C-terminus of the Fc region. In some embodiments, the antigen binding moiety comprises a hybrid chain wherein the hybrid chain comprises, from N-terminus to C-terminus or from C-terminus to N-terminus, [the $VL_{TSLP}$]-[the second linker]-[the $VH_{TSLP}$]-[the first linker]-[the first Fc polypeptide]; [the $VH_{TSLP}$]-[the second linker]-[the $VL_{TSLP}$]-[the first Fc polypeptide]; [the $VL_{TSLP}$]-[the second linker]-[the $VH_{TSLP}$]-[the first linker]-[the second Fc polypeptide]; or [the $VH_{TSLP}$]-[the second linker]-[the $VL_{TSLP}$]-[the second Fc polypeptide]. In some embodiments, the first linker or the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20), wherein n is an integer between 1 and 100. In some embodiments, the first linker comprises the amino acid sequence of SEQ ID NO: 23. In some embodiments, the second linker comprises the amino acid sequence of SEQ ID NO: 23. In some embodiments, the $L_{IL-4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the $L_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the $L_{IL-4R}$ comprises a light chain variable domain, wherein the light chain variable domain comprises an amino acid sequence having at least 80% sequence identity to the amino acid sequence of SEQ ID NO: 30. In some embodiments, the $L_{IL-4R}$ comprises a light chain variable domain comprising the amino acid sequence of SEQ ID NO: 30. In some embodiments, the $L_{IL-4R}$ comprises an amino acid sequence having at least 90% sequence identity to the amino acid sequence of SEQ ID NO: 22. In some embodiments, the $L_{IL-4R}$ comprises the amino acid sequence of SEQ ID NO: 22. In some embodiments, the $H_{IL-4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the $H_{IL}$-4R comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the $H_{IL-4R}$ comprises a heavy chain variable domain, wherein the heavy chain variable domain comprises an amino acid sequence having at least 80% sequence identity to the amino acid sequence of SEQ ID NO: 32. In some embodiments, the $H_{IL-4R}$ comprises the heavy chain variable domain comprising the amino acid sequence of SEQ ID NO: 32. In some embodiments, the $H_{IL-4R}$ comprises an amino acid sequence having at least 90% sequence identity to the amino acid sequence of SEQ ID NO: 21. In some embodiments, the $H_{IL-4R}$ comprises the amino acid sequence of SEQ ID NO: 21. In some embodiments, the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4. In some embodiments, the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4. In some embodiments, the $VH_{TSLP}$ comprises an amino acid sequence having at least 90% sequence identity to the amino acid sequence of SEQ ID NO: 25. In some embodiments, the $VH_{TSLP}$ comprises the amino acid sequence of SEQ ID NO: 25. In some embodiments, the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8. In some embodiments, the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8. In some embodiments, the $VL_{TSLP}$ comprises an amino acid sequence having at least 90% sequence identity to the amino acid sequence of SEQ ID NO: 28. In some embodiments, the $VL_{TSLP}$ comprises the amino acid sequence of SEQ ID NO: 28. In some embodiments, the Fc region comprises one or more mutations, wherein the one or more mutations comprise a half-life extension modification. In some embodiments, the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the first Fc polypeptide comprises a first modified Fc polypeptide, and the second Fc polypeptide comprises a second modified Fc polypeptide, wherein the first modified Fc polypeptide comprises a knob modification and the second modified Fc polypeptide comprises a hole modification. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, a light chain or a heavy chain of the anti-TSLP moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: (a) a binding complex comprising: an anti-IL-4R moiety or an antigen binding portion thereof, and an anti-thymic stromal lymphopoietin (TSLP) moiety or an antigen binding portion thereof; and (b) a Fc region, wherein the antigen binding moiety comprises: a first peptide chain comprising a light chain variable domain of the anti-IL-4R moiety or the antigen binding portion thereof ($VL_{IL-4R}$) associated with at least a portion of a second light chain variable domain of the anti-TSLP moiety or the antigen binding portion thereof ($VL_{TSLP}$), wherein the antigen binding moiety further comprises one or more mutations in the Fc region. In some embodiments, the first peptide chain further comprises a light chain constant domain of the anti-IL-4R moiety or the antigen binding portion thereof ($CL_{IL-4R}$) or a second light chain constant domain of the anti-TSLP moiety or the antigen binding portion thereof ($CL_{TSLP}$). In some embodiments, the first peptide chain comprises the $VL_{IL-4R}$ flanked by the $VL_{TSLP}$ and the $CL_{TSLP}$; or the $VL_{TSLP}$ flanked by the $VL_{IL-4R}$ and the $CL_{IL-4R}$. In some embodiments, the antigen binding moiety comprises, from N-terminus to C-terminus or from the C-terminus to the N-terminus: [the $VL_{TSLP}$]-[the $VL_{IL-4R}$]-[the $CL_{IL-4R}$]; [the $VL_{IL-4R}$]-[the $VL_{TSLP}$]-[the $CL_{TSLP}$]; [the $VL_{TSLP}$]-[the $VL_{IL-4R}$]-[the $CL_{TSLP}$]; [the $VL_{IL-4R}$]-[the $VL_{TSLP}$]-[the $CL_{IL-4R}$]; [the $VL_{TSLP}$]-[the $VL_{IL-4R}$]-[the $CL_{IL-4R}$]; [the $VL_{TSLP}$]-[the $VL_{IL-4R}$]-[the $CL_{IL-4R}$]; [the $VL_{IL-4R}$]-[the $VL_{TSLP}$]-[the $CL_{TSLP}$]; [the $VL_{TSLP}$]-[the $CL_{TSLP}$]-[the $VL_{IL-4R}$]-[the $CL_{IL-4R}$]; or [the $VL_{IL-4R}$]-[the $CL_{IL-4R}$]-[the $VL_{TSLP}$]-[the $CL_{TSLP}$]. In some embodiments, the antigen binding moiety further comprises a second peptide chain, wherein the second peptide chain comprises a heavy chain variable domain of the anti-IL-4R moiety or an antigen binding portion thereof ($VH_{IL-4R}$), a heavy chain variable domain of the anti-TSLP moiety or an antigen binding portion thereof ($VH_{TSLP}$), a heavy chain constant domain of the anti-IL-4R moiety or an antigen binding portion thereof ($CH_{IL-4R}$), or a heavy chain constant domain of the anti-TSLP moiety or an antigen binding portion thereof ($CH_{TSLP}$). In some embodiments, the antigen binding moiety comprises, from N-terminus to C-terminus or from C-terminus to N-terminus: [the $VH_{TSLP}$]-[the $VH_{IL-4R}$]-[the $CH_{IL-4R}$]; [the $VH_{IL-4R}$]-[the $VH_{TSLP}$]-[the $CH_{TSLP}$]; [the $VH_{TSLP}$]-[the $VH_{IL-4R}$]-[the $CH_{TSLP}$]; [the $VH_{IL-4R}$]-[the $VH_{TSLP}$]-[the $CH_{IL-4R}$]; [the $VH_{TSLP}$]-[the $VH_{IL-4R}$]-[the $CH_{IL-4R}$]; [the $VH_{TSLP}$]-[the $VH_{IL-4R}$]-[the $CH_{IL-4R}$]; [the $VH_{IL-4R}$]-[the $VH_{TSLP}$]-[the $CH_{TSLP}$]; [the $VH_{TSLP}$]-[the $CH_{TSLP}$]-[the $VH_{IL-4R}$]-[the $CH_{IL-4R}$]; or [the $VH_{IL-4R}$]-[the $CH_{IL-4R}$]-[the $VH_{TSLP}$]-[the $CH_{TSLP}$]. In some embodiments, the binding complex comprises: the first peptide chain comprising [the $VL_{TSLP}$]-[the $VL_{IL-4R}$]-[the $CL_{IL-4R}$], and the second peptide chain comprising [the $VH_{TSLP}$]-[the $VH_{IL-4R}$]-[the $CH_{IL-4R}$]. In some embodiments, the binding complex comprises: the first peptide chain comprising [the $VL_{IL-4R}$]-[the $VL_{TSLP}$]-[the $CL_{TSLP}$], and the second peptide chain comprising [the $VH_{IL-4R}$]-[the $VH_{TSLP}$]-[the $CH_{TSLP}$]. In some embodiments, the binding complex comprises: the first peptide chain comprising [the $VL_{TSLP}$]-[the $VL_{IL-4R}$]-[the $CL_{TSLP}$], and the second peptide chain comprising [the $VH_{TSLP}$]-[the $VH_{IL-4R}$]-[the $CH_{TSLP}$]. In some embodiments, the binding complex comprises: the first peptide chain comprising [the $VL_{IL-4R}$]-[the $VL_{TSLP}$]-[the $CL_{IL-4R}$], and the second peptide chain comprising [the $VH_{IL-4R}$]-[the $VH_{TSLP}$]-[the $CH_{IL-4R}$]. In some embodiments, the binding complex comprises: the first peptide chain comprising [the $VL_{IL-4R}$]-[the $VL_{TSLP}$]-[the $CL_{IL-4R}$], and the second peptide chain comprising [the $VH_{IL-4R}$]-[the $VH_{TSLP}$]-[the $CH_{IL-4R}$]. In some embodiments, the binding complex comprises: the first peptide chain comprising [the $VL_{TSLP}$]-[the $VL_{IL-4R}$]-[the $CL_{IL-4R}$], and the second peptide chain comprising [the $VH_{TSLP}$]-[the $VH_{IL-4R}$]-[the $CH_{IL-4R}$]. In some embodiments, binding complex comprises: the first peptide chain comprising [the $VL_{IL-4R}$]-[the $VL_{TSLP}$]-[the $CL_{TSLP}$], and the second peptide chain comprising [the $VH_{IL-4R}$]-[the $VH_{TSLP}$]-[the $CH_{TSLP}$]. In some embodiments, the $VL_{IL-4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the $VL_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the $VL_{IL-4R}$ comprises a light chain variable domain, wherein the light chain variable domain comprises an amino acid sequence having at least 80% sequence identity to the amino acid sequence of SEQ ID NO: 30. In some embodiments, the $VL_{IL-4R}$ comprises a light chain variable domain comprising the amino acid sequence of SEQ ID NO: 30. In some embodiments, the $VH_{IL-4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the $VH_{IL-4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the $VH_{IL}$-4R comprises a heavy chain variable domain, wherein the heavy chain variable domain comprises an amino acid sequence having at least 80% sequence identity to the amino acid sequence of SEQ ID NO: 32. In some embodiments, the $VH_{IL-4R}$ comprises the heavy chain variable domain comprising the amino acid sequence of SEQ ID NO: 32. In some embodiments, the $VH_{TSLP}$ comprises (a) a $HCDR1_{TSLP}$ having at least 80% sequence identity to the amino acid sequence of SEQ ID NO: 2, (b) a HCDR2$_{TSLP}$ having at least 80% sequence identity to the amino acid sequence of SEQ ID NO: 3, and/or (c) a HCDR3$_{TSLP}$ having at least 80% sequence identity to the amino acid sequence of SEQ ID NO: 4. In some embodiments, the VH$_{TSLP}$ comprises (a) a HCDR1$_{TSLP}$ having the amino acid sequence of SEQ ID NO: 2, (b) a HCDR2$_{TSLP}$ having the amino acid sequence of SEQ ID NO: 3, and/or (c) a HCDR3$_{TSLP}$ having the amino acid sequence of SEQ ID NO: 4. In some embodiments, the VH$_{TSLP}$ comprises an amino acid sequence having at least 90% sequence identity to the amino acid sequence of SEQ ID NO: 25. In some embodiments, the VH$_{TSLP}$ comprises the amino acid sequence of SEQ ID NO: 25. In some embodiments, the VL$_{TSLP}$ comprises (a) a LCDR1$_{TSLP}$ having at least 80% sequence identity to the amino acid sequence of SEQ ID NO: 6, (b) a LCDR2$_{TSLP}$ having at least 80% sequence identity to the amino acid sequence of SEQ ID NO: 7, and/or (c) a LCDR3$_{TSLP}$ having at least 80% sequence identity to the amino acid sequence of SEQ ID NO: 8. In some embodiments, the VL$_{TSLP}$ comprises (a) a LCDR1$_{TSLP}$ having the amino acid sequence of SEQ ID NO: 6, (b) a LCDR2$_{TSLP}$ having the amino acid sequence of SEQ ID NO: 7, and/or (c) a LCDR3$_{TSLP}$ having the amino acid sequence of SEQ ID NO: 8. In some embodiments, the VL$_{TSLP}$ comprises an amino acid sequence having at least 90% sequence identity to the amino acid sequence of SEQ ID NO: 28. In some embodiments, the VL$_{TSLP}$ comprises the amino acid sequence of SEQ ID NO: 28. In some embodiments, the one or more mutations comprise a half-life extension modification. In some embodiments, the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc polypeptide and a second modified Fc polypeptide, wherein the first modified Fc polypeptide comprises a knob modification, and the second modified Fc polypeptide comprises a hole modification. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, a light chain or a heavy chain of the anti-TSLP moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: (a) a binding complex comprising an anti-IL-4R moiety or an antigen binding portion thereof and an anti-thymic stromal lymphopoietin (TSLP) moiety or an antigen binding portion thereof, and (b) a Fc region, wherein the binding complex comprises: a first heavy chain variable domain associated with at least a portion of a second heavy chain variable domain, a first light chain variable domain associated with at least a portion of a second light chain variable domain, or a combination thereof, wherein the Fc region comprises one or more mutations. In some embodiments, the first heavy chain variable domain and the second heavy chain variable domain are coupled to each other via a first linker. In some embodiments, the first light chain variable domain and the second light chain variable domain are coupled to each other via a second linker. In some embodiments, the binding complex comprises, from N-terminus to C-terminus or from C-terminus to N-terminus: [the first heavy chain variable domain]-[the second heavy chain variable domain]; [the second heavy chain variable domain]-[the first heavy chain variable domain]; [the first light chain variable domain]-[the second light chain variable domain]; [the second light chain variable domain]-[the first light chain variable domain], or a combination thereof. In some embodiments, the binding complex is coupled to the N-terminus of the Fc region. In some embodiments, the first heavy chain variable domain comprises a heavy chain variable domain of the anti-TSLP moiety or the antigen binding portion thereof (VH$_{TSLP}$), the second heavy chain variable domain comprises a heavy chain variable domain of the anti-IL-4R moiety or the antigen binding portion thereof (VH$_{IL-4R}$), the first light chain variable domain comprises a light chain variable domain of the anti-TSLP moiety or the antigen binding portion thereof (VL$_{TSLP}$), the second light chain variable domain comprises a light chain variable domain of the anti-IL-4R moiety or the antigen binding portion thereof (VL$_{IL-4R}$). In some embodiments, the VL$_{IL-4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the VL$_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the VL$_{IL-4R}$ comprises a light chain variable domain, wherein the light chain variable domain comprises an amino acid sequence having at least 80% sequence identity to the amino acid sequence of SEQ ID NO: 30. In some embodiments, the VL$_{IL-4R}$ comprises a light chain variable domain comprising the amino acid sequence of SEQ ID NO: 30. In some embodiments, the VH$_{IL-4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the VH$_{IL-4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the VH$_{IL-4R}$ comprises a heavy chain variable domain, wherein the heavy chain variable domain comprises an amino acid sequence having at least 80% sequence identity to the amino acid sequence of SEQ ID NO: 32. In some embodiments, the VH$_{IL-4R}$ comprises the heavy chain variable domain comprising the amino acid sequence of SEQ ID NO: 32. In some embodiments, the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4. In some embodiments, the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4. In some embodiments, the $VH_{TSLP}$ comprises an amino acid sequence having at least 90% sequence identity to the amino acid sequence of SEQ ID NO: 25. In some embodiments, the $VH_{TSLP}$ comprises the amino acid sequence of SEQ ID NO: 25. In some embodiments, the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8. In some embodiments, the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8. In some embodiments, the $VL_{TSLP}$ comprises an amino acid sequence having at least 90% sequence identity to the amino acid sequence of SEQ ID NO: 28. In some embodiments, the $VL_{TSLP}$ comprises the amino acid sequence of SEQ ID NO: 28. In some embodiments, the first linker and the second linker are a polypeptide linker between 3 amino acids and 500 amino acids in length. In some embodiments, the first linker and the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20), wherein n is an integer between 1 and 100. In some embodiments, the first linker and the second linker are same. In some embodiments, the first linker and the second linker are different. In some embodiments, the antigen binding moiety comprises a plurality of the binding complexes. In some embodiments, the plurality of the binding complexes comprises at least one, at least two, at least three, or at least four binding complexes. In some embodiments, the Fc region is an IgG1, IgG2, IgG3, or IgG4 heavy chain Fc region. In some embodiments, the one or more mutations comprise a half-life extension modification. In some embodiments, half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc polypeptide and a second modified Fc polypeptide, wherein the first modified Fc polypeptide comprises a knob modification and the second modified Fc polypeptide comprises a hole modification. In some embodiments, the antigen binding moiety comprises: a first binding complex comprising, from N-terminus to C-terminus, the $VH_{TSLP}$-a $VH_{IL\text{-}4R}$, a second binding complex comprising, from N-terminus to C-terminus, the $VL_{TSLP}$-a $VL_{IL\text{-}4R}$, and the Fc region. In some embodiments, the antigen binding moiety is a dual variable domain immunoglobulin molecule. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, alight chain or a heavy chain of the anti-TSLP moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: (a) a first antigen binding region comprising a first heavy chain, wherein the first heavy chain comprises a first heavy chain variable region and a first heavy chain constant region, and (b) a second antigen binding region comprising a second heavy chain, wherein the second heavy chain comprises a second heavy chain variable region and a second heavy chain constant region, wherein the first heavy chain variable region comprises (a) a HCDR1 having at least 80% sequence identity to the amino acid sequence of SEQ ID NO: 2, (b) a HCDR2 having at least 80% sequence identity to the amino acid sequence of SEQ ID NO: 3, and/or (c) a HCDR3 having at least 80% sequence identity to the amino acid sequence of SEQ ID NO: 4, wherein the second heavy chain variable region comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12, wherein the first antigen binding region and the second antigen binding region are associated to a Fc region, and wherein the Fc region comprises one or more mutations. In some embodiments, the first heavy chain variable region comprises (a) a HCDR1 having the amino acid sequence of SEQ ID NO: 2, (b) a HCDR2 having the amino acid sequence of SEQ ID NO: 3, and/or (c) a HCDR3 having the amino acid sequence of SEQ ID NO: 4. In some embodiments, the first heavy chain variable region comprises an amino acid sequence having at least 90% sequence identity to the amino acid sequence of SEQ ID NO: 25. In some embodiments, the first heavy chain variable region comprises the amino acid sequence of SEQ ID NO: 25. In some embodiments, the second heavy chain variable region comprises (a) a HCDR1 comprises the amino acid sequence of SEQ ID NO: 10, (b) a HCDR2 comprises the amino acid sequence of SEQ ID NO: 11, and/or (c) a HCDR3 comprises the amino acid sequence of SEQ ID NO: 12. In some embodiments, the second heavy chain variable region comprises a heavy chain variable domain, wherein the heavy chain variable domain comprises an amino acid sequence having at least 80% sequence identity to the amino acid sequence of SEQ ID NO: 32. In some embodiments, the second heavy chain variable region comprises the heavy chain variable domain comprising the amino acid sequence of SEQ ID NO: 32. In some embodiments, the first antigen binding region further comprises a first light chain, wherein the first light chain comprises a first light chain variable region and a first light chain constant region, wherein the first light chain is coupled to the first heavy chain. In some embodiments, the first antigen binding region comprises: a first peptide chain comprising the first light chain variable region and the first light chain constant region, and a second peptide chain comprising the first heavy chain variable region and the first heavy chain constant region; a first peptide chain comprising the first heavy chain variable region and the first heavy chain constant region, and a second peptide chain comprising the first light chain variable region and the first light chain constant region; a first peptide chain comprising the first light chain variable region and the first heavy chain constant region, and a second peptide chain comprising the first heavy chain variable region and the first light chain constant region; a first peptide chain comprising the first heavy chain variable region and the first light chain constant region, and a second peptide chain comprising the first light chain variable region and the first heavy chain constant region; or a first peptide chain comprising the first light chain variable region and the first heavy chain constant region, and a second peptide chain comprising the first heavy chain variable region and the first light chain constant region. In some embodiments, the first light chain variable region comprises (a) a LCDR1 having at least 80% sequence identity to the amino acid sequence of SEQ ID NO: 6, (b) a LCDR2 having at least 80% sequence identity to the amino acid sequence of SEQ ID NO: 7, and/or (c) a LCDR3 having at least 80% sequence identity to the amino acid sequence of SEQ ID NO: 8. In some embodiments, the first light chain variable region comprises (a) a LCDR1 having the amino acid sequence of SEQ ID NO: 6, (b) a LCDR2 having the amino acid sequence of SEQ ID NO: 7, and/or (c) a LCDR3 having the amino acid sequence of SEQ ID NO: 8. In some embodiments, the first light chain variable region comprises an amino acid sequence having at least 90% sequence identity to the amino acid sequence of SEQ ID NO: 28. In some embodiments, the first light chain variable region comprises the amino acid sequence of SEQ ID NO: 28. In some embodiments, the antigen binding moiety further comprises a second light chain variable region and a second light chain constant region comprising: a first peptide chain comprising the second light chain variable region and the second light chain constant region, and a second peptide chain comprising the second heavy chain variable region and the second heavy chain constant region; a first peptide chain comprising the second heavy chain variable region and the second heavy chain constant region, and a second peptide chain comprising the second light chain variable region and the second light chain constant region; a first peptide chain comprising the second light chain variable region and the second heavy chain constant region, and a second peptide chain comprising the second heavy chain variable region and the second light chain constant region; a first peptide chain comprising the second heavy chain variable region and the second light chain constant region, and a second peptide chain comprising the second light chain variable region and the second heavy chain constant region; or a first peptide chain comprising the second light chain variable region and the second heavy chain constant region, and a second peptide chain comprising the second heavy chain variable region and the second light chain constant region. In some embodiments, the second light chain variable region comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the second light chain variable region comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the second light chain variable region comprises an amino acid sequence having at least 80% sequence identity to the amino acid sequence of SEQ ID NO: 30. In some embodiments, the second light chain variable region comprises the amino acid sequence of SEQ ID NO: 30. In some embodiments, the Fc region is an IgG1, IgG2, IgG3, or IgG4 heavy chain Fc region. In some embodiments, the one or more mutations comprise a half-life extension modification. In some embodiments, the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc polypeptide and a second modified Fc polypeptide, wherein the first modified Fc polypeptide comprises a knob modification and the second modified Fc polypeptide comprises a hole modification. In some embodiments, a moiety or an antigen binding portion thereof comprises a signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: a binding complex comprising an anti-IL-4R moiety or an antigen binding portion thereof and anti-thymic stromal lymphopoietin (TSLP) moiety or an antigen binding portion thereof, wherein the binding complex comprises: (a) a heavy chain variable domain of the anti-TSLP moiety or the antigen binding portion thereof ($VH_{TSLP}$), wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4; (b) a kappa light chain, and (c) a lambda light chain, wherein the binding complex is associated with a Fc region, wherein the Fc region comprises one or more mutations. In some embodiments, the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4. In some embodiments, the $VH_{TSLP}$ comprises an amino acid sequence having at least 90% sequence identity to the amino acid sequence of SEQ ID NO: 25. In some embodiments, the $VH_{TSLP}$ comprises the amino acid sequence of SEQ ID NO: 25. In some embodiments, the kappa light chain or the lambda light chain comprises a light chain variable domain of the anti-TSLP moiety or the antigen binding portion thereof ($VL_{TSLP}$), wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8. In some embodiments, the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8. In some embodiments, the $VL_{TSLP}$ comprises an amino acid sequence having at least 90% sequence identity to the amino acid sequence of SEQ ID NO: 28. In some embodiments, the $VL_{TSLP}$ comprises the amino acid sequence of SEQ ID NO: 28. In some embodiments, the anti-IL-4R moiety or the antigen binding portion thereof comprises a heavy chain variable region ($VH_{IL\text{-}4R}$) and a light chain variable region ($VL_{IL\text{-}4R}$). In some embodiments, the $VL_{IL\text{-}4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16. In some embodiments, the $VL_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the $VL_{IL\text{-}4R}$ comprises an amino acid sequence having at least 80% sequence identity to the amino acid sequence of SEQ ID NO: 30. In some embodiments, the $VL_{IL\text{-}4R}$ comprises the amino acid sequence of SEQ ID NO: 30. In some embodiments, the $VH_{IL\text{-}4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12. In some embodiments, the $VH_{IL\text{-}4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the $VH_{IL\text{-}4R}$ comprises an amino acid sequence having at least 80% sequence identity to the amino acid sequence of SEQ ID NO: 32. In some embodiments, the $VH_{IL\text{-}4R}$ comprises the amino acid sequence of SEQ ID NO: 32. In some embodiments, the one or more mutations comprise a half-life extension modification. In some embodiments, the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc and a second modified Fc, wherein the first modified Fc is a knob modified Fc and the second modified Fc is a hole modified Fc; or the second modified Fc is a knob modified Fc and the first modified Fc is a hole modified Fc. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, a light chain or a heavy chain of the anti-TSLP moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: a first single chain Fv (scFv) comprising: (a) a first heavy chain variable region comprising (a) a HCDR1 having at least 80% sequence identity to the amino acid sequence of SEQ ID NO: 2, (b) a HCDR2 having at least 80% sequence identity to the amino acid sequence of SEQ ID NO: 3, and/or (c) a HCDR3 having at least 80% sequence identity to the amino acid sequence of SEQ ID NO: 4, and (b) a first light chain variable region comprising (a) a LCDR1 having at least 80% sequence identity to the amino acid sequence of SEQ ID NO: 6, (b) a LCDR2 having at least 80% sequence identity to the amino acid sequence of SEQ ID NO: 7, and/or (c) a LCDR3 having at least 80% sequence identity to the amino acid sequence of SEQ ID NO: 8; a second scFv comprising (a) a second heavy chain variable region comprising (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12, and (b) a second light chain variable region comprising (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16; and a Fc region, wherein the Fc region comprises one or more mutations. In some embodiments, the second light chain variable region (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16. In some embodiments, the second light chain variable region comprises an amino acid sequence having at least 80% sequence identity to the amino acid sequence of SEQ ID NO: 30. In some embodiments, the second light chain variable region comprises the amino acid sequence of SEQ ID NO: 30. In some embodiments, the second heavy chain variable region comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12. In some embodiments, the second heavy chain variable region comprises an amino acid sequence having at least 80% sequence identity to the amino acid sequence of SEQ ID NO: 32. In some embodiments, the second heavy chain variable region comprises the heavy chain variable domain comprising the amino acid sequence of SEQ ID NO: 32. In some embodiments, the first heavy chain variable region comprises (a) a HCDR1 having the amino acid sequence of SEQ ID NO: 2, (b) a HCDR2 having the amino acid sequence of SEQ ID NO: 3, and/or (c) a HCDR3 having the amino acid sequence of SEQ ID NO: 4. In some embodiments, the first heavy chain variable region comprises an amino acid sequence having at least 90% sequence identity to the amino acid sequence of SEQ ID NO: 25. In some embodiments, the first heavy chain variable region comprises the amino acid sequence of SEQ ID NO: 25. In some embodiments, the first light chain variable region comprises (a) a LCDR1 having the amino acid sequence of SEQ ID NO: 6, (b) a LCDR2 having the amino acid sequence of SEQ ID NO: 7, and/or (c) a LCDR3 having the amino acid sequence of SEQ ID NO: 8. In some embodiments, the first light chain variable region comprises an amino acid sequence having at least 90% sequence identity to the amino acid sequence of SEQ ID NO: 28. In some embodiments, the first scFv comprises, from N-terminus to C-terminus or from the N-terminus to C-terminus, [the first heavy chain variable region]-[the first light chain variable region] or [the first light chain variable region]-[the first heavy chain variable region], wherein the first light chain variable region and the first heavy chain variable region are coupled to each other via a first linker. In some embodiments, the second scFv comprises, from N-terminus to C-terminus or from the C-terminus to N-terminus, [the second heavy chain variable region]-[the second light chain variable region] or [the second light chain variable region]-[the second heavy chain variable region], wherein the second light chain variable region and the second heavy chain variable region are coupled to each other via a second linker. In some embodiments, the first linker and the second linker comprises (GGS)n (SEQ ID NO: 17) or (GGGGS)n (SEQ ID NO: 18), wherein n is an integer between 1 and 100. In some embodiments, the first linker and the second linker are same. In some embodiments, the first linker and the second linker are different. In some embodiments, the antigen binding moiety comprises, from N-terminus to C-terminus or C-terminus to N-terminus, [the first scFv]-[the second scFv] or [the second scFv]-[the first scFv], wherein the first scFv and the second scFv are coupled to each other via a third linker. In some embodiments, the third linker comprises (GGS)n (SEQ ID NO: 17) or (GGGGS)n (SEQ ID NO: 18), wherein n is an integer between 1 and 100. In some embodiments, the one or more mutations comprise a half-life extension modification. In some embodiments, the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a first modified Fc and a second modified Fc, wherein the first modified Fc is a knob modified Fc and the second modified Fc is a hole modified Fc; or the second modified Fc is a knob modified Fc and the first modified Fc is a hole modified Fc. In some embodiments, an antigen binding moiety or an antigen binding portion thereof further comprises a signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is an antigen binding moiety comprising: two or more of: an anti-IL-4R moiety or an antigen binding portion thereof, an anti-thymic stromal lymphopoietin receptor (TSLPR) moiety or an antigen binding portion thereof, or an anti-IL-7 moiety or an antigen binding portion thereof, wherein the antigen binding moiety comprises a Fc region, wherein the Fc region comprises a first modified Fc polypeptide and a second modified Fc polypeptide wherein: the first modified Fc polypeptide comprises a knob modification and the second modified Fc polypeptide comprises a hole modification. In some embodiments, the anti-IL-4R moiety or the antigen binding portion thereof is an antibody comprising a first heavy chain and/or a second heavy chain. In some embodiments, the anti-IL-7 moiety or the antigen binding portion thereof is coupled to a C-terminus of the first heavy chain of the anti-IL-4R moiety or the antigen binding portion thereof. In some embodiments, the anti-IL7 moiety or the antigen binding portion thereof is coupled to the C-terminus of the first heavy chain of the anti-IL-4R moiety or the antigen binding portion thereof via a first linker. In some embodiments, the anti-TSLPR moiety or the antigen binding portion thereof is coupled to the C-terminus of the second heavy chain of the anti-IL-4R moiety. In some embodiments, the anti-TSLPR moiety or the antigen binding portion thereof is coupled to the C-terminus of the second heavy chain of the anti-IL-4R moiety via a second linker. In some embodiments, the anti-IL-4R moiety or the antigen binding portion thereof comprises (a) a HCDR1 comprising an amino acid sequence having at least 80% sequence identity to the amino acid sequence of SEQ ID NO: 10, (b) a HCDR2 comprising an amino acid sequence having at least 80% sequence identity to the amino acid sequence of SEQ ID NO: 11, and/or (c) a HCDR3 comprising an amino acid sequence having at least 80% sequence identity to the amino acid sequence of SEQ ID NO: 12, and a light chain variable region comprising (d) a LCDR1 comprising an amino acid sequence having at least 80% sequence identity to the amino acid sequence of SEQ ID NO: 14, (e) a LCDR2 comprising an amino acid sequence having at least 80% sequence identity to the amino acid sequence of SEQ ID NO: 15, and/or (f) a LCDR3 comprising an amino acid sequence having at least 80% sequence identity to the amino acid sequence of SEQ ID NO: 16. In some embodiments, the anti-IL-4R moiety or the antigen binding portion thereof comprises (a) a HCDR1 having the amino acid sequence of SEQ ID NO: 10, (b) a HCDR2 having the amino acid sequence of SEQ ID NO: 11, and/or (c) a HCDR3 having the amino acid sequence of SEQ ID NO: 12, and a light chain variable region comprising (d) a LCDR1 having the amino acid sequence of SEQ ID NO: 14, (e) a LCDR2 having the amino acid sequence of SEQ ID NO: 15, and/or (f) a LCDR3 having the amino acid sequence of SEQ ID NO: 16. In some embodiments, the anti-TSLPR moiety or the antigen binding portion thereof comprise an amino acid sequence having at least 80% sequence identity to the amino acid sequence of SEQ ID NO: 34. In some embodiments, the anti-TSLPR moiety or the antigen binding portion thereof comprise the amino acid sequence of SEQ ID NO: 34. In some embodiments, the anti-IL-7 moiety or the antigen binding portion thereof comprise an amino acid sequence having at least 80% sequence identity to the amino acid sequence of SEQ ID NO: 35. In some embodiments, the anti-IL-7 moiety or the antigen binding portion thereof comprise the amino acid sequence of SEQ ID NO: 35. In some embodiments, the life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the anti-IL-4R moiety or an antigen binding portion thereof further comprises a signal peptide. In some embodiments, a light chain or a heavy chain of the anti-IL-4R moiety or an antigen binding portion thereof comprises the signal peptide. In some embodiments, the anti-TSLP moiety or an antigen binding portion thereof further comprises a signal peptide. In some embodiments, alight chain or a heavy chain of the anti-TSLP moiety or an antigen binding portion thereof further comprises the signal peptide. In some embodiments, the anti-IL7 moiety or an antigen binding portion thereof further comprises a signal peptide. In some embodiments, a light chain or a heavy chain of the anti-IL7 moiety or an antigen binding portion thereof further comprises the signal peptide. In some embodiments, the signal peptide comprises an amino acid sequence having at least 80% sequence identity to the amino acid sequence of any one of SEQ ID NOs: 130-184. In some embodiments, the signal peptides comprise the amino acid sequence of any one of SEQ ID NOs: 130-184. In some embodiments, the signal peptide comprises an amino acid sequence having the amino acid sequence of any one of SEQ ID NOs: 130-184. In some embodiments, the signal peptide comprises an amino acid sequence having at least 80% sequence identity to the amino acid sequence of SEQ ID NOs: 156 or 130.

Provided herein is a polynucleotide sequence encoding the antigen binding moiety described herein. Also provided herein is an expression vector comprising the polynucleotide sequence described herein. Provided herein is a host cell comprising the polynucleotide sequence described herein or the expression vector described herein. Provided herein is a method of producing the antigen binding moiety described herein. Provided herein is are pharmaceutical composition comprising the antigen binding moiety described herein, the polynucleotide sequence described herein, the expression vector described herein or the host cell described herein and a pharmaceutically acceptable excipient or carrier. Provided herein is a method of treating asthma, chronic obstructive pulmonary disease, eczema, and/or nasal polyps comprising administering a therapeutically effective amount of the antigen binding moiety of described herein, the polynucleotide sequence described herein, the expression vector described herein or the host cell described herein or the pharmaceutical composition described herein to a subject in need thereof. Further provided herein is a method of treating a disease or condition comprising administering a therapeutically effective amount of the antigen binding moiety described herein, the polynucleotide sequence described herein, the expression vector described herein or the host cell described herein or the pharmaceutical composition described herein to a subject in need thereof. Provided herein is a use of a therapeutically effective amount of the antigen binding moiety described herein, the polynucleotide sequence described herein, the expression vector described herein or the host cell described herein or the pharmaceutical composition described herein in the manufacture of a medicament for the treatment of a disease or condition. Further provided herein is a kit comprising the antigen binding moiety of described herein, the polynucleotide sequence described herein, the expression vector described herein or the host cell described herein or the pharmaceutical composition described herein and instructions for using the antigen binding complex. Provided herein is an antigen binding moiety described herein, the polynucleotide sequence described herein, the expression vector described herein or the host cell described herein or the pharmaceutical composition described herein for use as a medicament, for use in the treatment of a disease, or for use in the treatment of an inflammation related disease.

In some aspects, provided herein is an antigen binding moiety comprising a binding complex comprising (a) a first antibody or an antigen binding portion thereof comprising a Fab fragment that specifically binds to a first antigen, wherein the Fab fragment comprises a first peptide chain comprising a heavy chain variable domain and a heavy chain constant domain 1, and a second peptide chain comprising a light chain variable domain and a light chain constant domain; and (b) a second antibody or an antigen binding portion thereof that specifically binds to a second antigen, wherein the second antibody comprises a third peptide chain comprising a light chain and a fourth peptide chain comprising a heavy chain, wherein the second peptide chain is associated with the fourth peptide chain. In some embodiments, the first peptide chain comprises, from N-terminus to C-terminus: [the heavy chain variable domain]-[the heavy chain constant domain 1] or [the heavy chain constant domain 1]-[the heavy chain variable domain], wherein "-" indicates an optional linker. In some embodiments, the second peptide chain comprises, from N-terminus to C-terminus: [the light chain variable domain]-[the light chain constant domain] or [the light chain constant domain]-[the light chain variable domain], wherein "-" indicates an optional linker. In some embodiments, the first peptide chain and the second peptide chain are associated with each other to form the Fab fragment. In some embodiments, the second peptide chain is associated with the fourth peptide chain at the N-terminus of the fourth peptide chain via an optional linker. In some embodiments, the second peptide chain is associated with the fourth peptide chain at the C-terminus of the fourth peptide chain via an optional linker. In some embodiments, the optional linker comprises an amino acid sequence having at least 80% sequence identity to the amino acid sequence of any one of SEQ ID NOs: 40-47, 185-188, or 223-226. In some embodiments, the heavy chain constant domain 1 of the first antibody or the antigen binding portion thereof is of the human IgG subtype comprising IgG1, IgG2, IgG3, or IgG4. In some embodiments, the light chain constant domain of the first antibody or the antigen binding portion thereof is of a lambda light chain or a kappa light chain. In some embodiments, the heavy chain of the second antibody or the antigen binding portion thereof is of the human IgG subtype comprising IgG1, IgG2, IgG3, or IgG4. In some embodiments, the light chain of the second antibody or the antigen binding portion thereof is of a lambda light chain or a kappa light chain. In some embodiments, the first antibody or the antigen binding portion thereof comprises the heavy chain constant domain 1 derived from the human IgG2 subtype and the light chain constant domain derived from the lambda light chain. In some embodiments, the second antibody or the antigen binding portion thereof comprises the heavy chain derived from the human IgG4 subtype and the light chain derived from the kappa light chain. In some embodiments, the second antibody or the antigen binding portion thereof comprises a Fc region. In some embodiments, the Fc region comprises one or more mutations, wherein the one or more mutations comprise a half-life extension modification, effector silencing, and/or prevention of Fab arm exchange of IgG. In some embodiments, the one or more mutations comprise M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the Fc region comprises a heterodimerization-promoting mutation. In some embodiments, the heterodimerization-promoting mutation comprises a knob-in-hole modification. In some embodiments, the first antibody or the antigen binding portion thereof is an anti-TSLP or an antigen binding portion thereof or anti-IL-4R or an antigen binding portion thereof. In some embodiments, the second antibody or the antigen binding portion thereof is an anti-TSLP or an antigen binding portion thereof or anti-IL-4R or an antigen binding portion thereof. In some embodiments, the first antibody or the antigen binding portion thereof is the anti-TSLP or the antigen binding portion thereof, and the second antibody or the antigen binding portion thereof is the anti-IL-4R or the antigen binding portion thereof. Provided herein is a polynucleotide sequence encoding the antigen binding moiety disclosed herein. Provided herein is an expression vector comprising the polynucleotide sequence disclosed herein. Provided herein is a host cell comprising the polynucleotide sequence disclosed herein or the expression vector disclosed herein. Provided herein is a method of producing the antigen binding moiety disclosed herein. Provided herein are a pharmaceutical composition comprising the antigen binding moiety disclosed herein, the polynucleotide sequence disclosed herein, the expression vector disclosed herein, or the host cell disclosed herein and a pharmaceutically acceptable excipient or carrier. Provided herein is a method of treating asthma, dermatitis, eosinophilic esophagitis, chronic obstructive pulmonary disease, eczema, and/or nasal polyps comprising administering a therapeutically effective amount of the antigen binding moiety disclosed herein, the polynucleotide sequence disclosed herein, the expression vector disclosed herein, the host cell disclosed herein, or the pharmaceutical composition disclosed herein to a subject in need thereof. Provided herein is a method of treating a disease or condition comprising administering a therapeutically effective amount of the antigen binding moiety disclosed herein, the polynucleotide sequence disclosed herein, the expression vector disclosed herein, the host cell disclosed herein, or the pharmaceutical composition disclosed herein to a subject in need thereof. In some embodiments, the disease or condition comprises cancer, autoimmune disorders, inflammatory disorders, infectious diseases, and/or degenerative diseases. In some embodiments, the cancer comprises breast cancer, lung cancer, colorectal cancer, gastric cancer, pancreatic cancer, liver cancer, ovarian cancer, prostate cancer, renal cancer, melanoma, head and neck cancer, leukemia, lymphoma, or multiple myeloma. In some embodiments, the autoimmune disorders or inflammatory disorders comprise inflammatory arthritis, rheumatoid arthritis, psoriatic arthritis, psoriasis, inflammatory bowel disease, ulcerative colitis, Crohn's disease, systemic lupus erythematosus, multiple sclerosis, type 1 diabetes, autoimmune thyroiditis, ankylosing spondylitis, asthma, dermatitis, eosinophilic esophagitis, chronic obstructive pulmonary disease, eczema, nasal polyps, sinusitis, pruritus, atopic dermatitis, allergic rhinitis, airway hyperresponsiveness, airway inflammation, a food allergy, chronic urticaria, occupational allergy, allergic conjunctivitis, hay fever, airborne allergic sensitivities, stinging insect allergy, hypersensitivity pneumonitis, eosinophilic lung diseases, or drug allergies. In some embodiments, the infectious diseases comprise viral infections, bacterial infections, fungal infections, or parasitic infections. Provided herein is a use of a therapeutically effective amount of the antigen binding moiety disclosed herein, the polynucleotide sequence disclosed herein, the expression vector disclosed herein, the host cell disclosed herein, or the pharmaceutical composition disclosed herein in the manufacture of a medicament for the treatment of a disease or condition. Provided herein is a kit comprising the antigen binding moiety disclosed herein, the polynucleotide sequence disclosed herein, the expression vector disclosed herein, the host cell disclosed herein, or the pharmaceutical composition disclosed herein, and instructions for using the antigen binding complex. Provided herein is the antigen binding moiety disclosed herein, the polynucleotide sequence disclosed herein, the expression vector disclosed herein, the host cell disclosed herein, or the pharmaceutical composition disclosed herein for use as a medicament.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows an anti-TSLP scFv heavy chain variable region associated with an anti-IL-4R Fc region. FIG. 1B shows an anti-TSLP scFv light chain variable region associated with an anti-IL-4R Fc region. FIG. 1C shows an anti-TSLP scFv heavy chain variable region associated with an anti-IL-4R light chain. FIG. 1D shows an anti-TSLP scFv light chain variable region associated with an anti-IL-4R light chain.

FIG. 2A shows an anti-TSLP scFv heavy chain variable region associated with an anti-IL-4R Fc region at N-terminus. FIG. 2B shows an anti-TSLP scFv light chain variable region associated with an anti-IL-4R Fc region at N-terminus. The Fc region can have a first modified Fc polypeptide and a second modified Fc polypeptide, where the first modified Fc polypeptide comprises a knob modification and the second modified Fc polypeptide comprises a hole modification.

FIG. 3A shows an anti-TSLP scFv light chain variable region associated with an anti-IL-4R heavy chain. FIG. 3B shows an anti-TSLP scFv heavy chain variable region associated with an anti-IL-4R heavy chain. FIG. 3C shows an anti-TSLP scFv light chain variable region associated with an anti-IL-4R light chain. FIG. 3D shows an anti-TSLP scFv heavy chain variable region associated with an anti-IL-4R light chain.

FIG. 4A shows a construct comprising anti-TSLP Fab and anti-IL-4R, wherein the anti-TSLP Fab is associated with an anti-IL-4R antigen binding domain at N-terminus. FIG. 4B shows a construct comprising anti-TSLP and anti-IL-4R Fab, wherein the anti-IL-4R Fab is associated with an anti-TSLP antigen binding domain at N-terminus. FIG. 4C shows a construct comprising anti-TSLP Fab and anti-IL-4R, wherein the anti-TSLP Fab is associated with an anti-IL-4R antigen binding domain at the C-terminus, wherein the constant domain of the anti-TSLP Fab replaces the constant domain of the anti-IL-4R. FIG. 4D shows a construct comprising anti-TSLP and anti-IL-4R Fab, wherein an anti-IL-4R Fab associated with an anti-TSLP antigen binding domain at the C-terminus, wherein the constant domain of the anti-IL-4R Fab replaces the constant domain of the anti-TSLP. FIG. 4E shows a construct comprising an anti-TSLP heavy chain variable region and light chain variable region, and an anti-IL-4R, wherein the anti-TSLP heavy chain is flanked by the heavy chain variable region and the heavy chain constant region of the anti-IL-4R antigen binding domain, and anti-TSLP light chain variable region is flanked by the light chain variable region and the light chain constant region of the anti-IL-4R antigen binding domain. FIG. 4F shows a construct comprising an anti-TSLP and an anti-IL-4R heavy chain variable region and light chain variable region, wherein the anti-IL-4R heavy chain variable region is flanked by the heavy chain variable region and the heavy chain constant region of the anti-TSLP antigen binding domain, and the anti-IL-4R light chain variable region is flanked by the light chain variable region and the light chain constant region of the anti-TSLP antigen binding domain.

FIG. 5A shows a single anti-TSLP Fab associated with an anti-IL-4R Fc region in a knob-in-hole format. FIG. 5B shows a single anti-IL-4R Fab associated with an anti-TSLP Fc region in a knob-in-hole format. FIG. 5C shows multiple anti-TSLP Fabs associated with an anti-IL-4R moiety in a CrossMab-Fab format comprising Fab heavy/light crossovers (VH-CH1↔VL-CL). FIG. 5D shows multiple anti-IL-4R Fabs associated with an anti-TSLP moiety in a CrossMab-Fab format comprising Fab heavy/light crossovers (VH-CH1H↔VL-CL). FIG. 5E shows multiple anti-TSLP Fabs associated with an anti-IL-4R moiety in a CrossMab VH-VL format comprising constant-domain crossovers (CH1↔CL). FIG. 5F shows multiple anti-IL-4R Fabs associated with an anti-TSLP moiety in a CrossMab VH-VL format comprising constant-domain crossovers (CH1↔CL). The Fc region can have a first modified Fc polypeptide and a second modified Fc polypeptide, where the first modified Fc polypeptide comprises a knob modification and the second modified Fc polypeptide comprises a hole modification. FIG. 5G shows a single anti-TSLP Fab (comprising heavy/light crossovers (VH-CH1↔VL-CL)) associated with an anti-IL-4R Fc region in a knob-in-hole format.

FIG. 6A shows a TSLP-TRAP complex (e.g, IL-7Rα-TSLPR) associated with an anti-IL-4R Fc region. FIG. 6B shows a TSLP-TRAP complex (e.g TSLPR-IL-7Rα) associated with an anti-IL-4R Fc region. FIG. 6C shows a TSLP-TRAP complex (e.g., a complex comprising IL-7Rα-20 amino acid linker-TSLPR) associated with an anti-IL-4R Fc region. FIG. 6D shows a TSLP-TRAP complex (e.g., a complex comprising IL-7Rα-20 amino acid linker-TSLPR) associated with an anti-IL-4R Fc region.

FIG. 7A shows a single TRAP construct format (e.g., IL-7Rα and TSLPR) associated with an anti-IL-4R Fc region. FIG. 7B shows a single TRAP construct format (e.g., TSLPR and IL-7Rα) associated with an anti-IL-4R Fc region. FIG. 7C shows a single TRAP construct format (e.g., IL-7Rα and TSLPR) associated with an anti-IL-4R Fc region, wherein IL-7Rα and TSLPR are further associated with each other (e.g., by introduction of a disulfide bond, or mutations to further enforce interactions). FIG. 7D shows a single TRAP construct format (e.g., TSLPR and IL-7Rα) associated with an anti-IL-4R Fc region, wherein TSLPR and IL-7Rα are further associated with each other. The Fc region can have a first modified Fc polypeptide and a second modified Fc polypeptide, where the first modified Fc polypeptide comprises a knob modification and the second modified Fc polypeptide comprises a hole modification.

FIG. 8A shows an anti-IL-4R scFv heavy chain variable region associated with an anti-TSLP Fc region. FIG. 8B shows an anti-IL-4R scFv light chain variable region associated with an anti-TSLP Fc region. FIG. 8C shows an anti-IL-4R scFv heavy chain variable region associated with an anti-TSLP light chain constant region. FIG. 8D shows an anti-IL-4R scFv light chain variable region associated with an anti-TSLP light chain constant region.

FIG. 9A shows an anti-IL-4R scFv heavy chain variable region associated with an anti-TSLP Fc region at N-terminus. FIG. 9B shows an anti-IL-4R scFv light chain variable region associated with an anti-TSLP Fc region at N-terminus. The Fc region can have a first modified Fc polypeptide and a second modified Fc polypeptide, where the first modified Fc polypeptide comprises a knob modification and the second modified Fc polypeptide comprises a hole modification.

FIG. 10A shows an anti-IL-4R scFv light chain variable region associated with an anti-TSLP heavy chain. FIG. 10B shows an anti-IL-4R scFv heavy chain variable region associated with an anti-TSLP heavy chain. FIG. 10C shows an anti-IL-4R scFv light chain variable region associated with an anti-TSLP light chain. FIG. 10D shows an anti-IL-4R scFv heavy chain variable region associated with an anti-TSLP light chain.

FIG. 14A shows the inhibition of TARC/CCL-17 secretion by PBMCs after incubation with each candidate antigen binding moiety in Donor 1. FIG. 14B shows the inhibition of TARC/CCL-17 secretion by PBMCs after incubation with each candidate antigen binding moiety in Donor 2. Data are expressed in pg/mL.

FIG. 16A shows the binding of each candidate antigen binding moiety when the His-tagged TSLP is administered at a concentration of 0.2 μg/mL. FIG. 16B shows the binding of each candidate antigen binding moiety when the His-tagged TSLP is administered at a concentration of 0 μg/ml (e.g., a control).

FIG. 17A shows the inhibition of TARC/CCL-17 secretion by PBMCs after incubation with each candidate antigen binding moiety in Donor 1. FIG. 17B shows the percentage inhibition of TARC/CCL-17 secretion by PBMCs was inhibited after incubation with each candidate antigen binding moiety in Donor 1.

FIG. 18A shows the inhibition of TARC/CCL-17 secretion by PBMCs after incubation with each candidate antigen binding moiety in Donor 2. FIG. 18B shows the % inhibition of TARC/CCL-17 secretion by PBMCs was inhibited after incubation with each candidate antigen binding moiety in Donor 2.

FIG. 19A shows the inhibition of IL-4-induced CD23 expression in CD19+ cells in Donor 1 by each candidate antigen binding moiety. Data are shown as median fluorescent intensity of CD23. FIG. 19B shows the percentage of CD19+ cells expressing CD23 in Donor 1. FIG. 19C shows the percentage by which IL-4 induced CD23 expression was inhibited in CD19+ cells in Donor 1. FIG. 19D shows the inhibition of IL-4-induced CD23 expression in CD19+ cells in Donor 2 by each candidate antigen binding moiety. Data are shown as median fluorescent intensity of CD23. FIG. 19E shows the amount of CD23 detected in CD19+ cells in Donor 2. FIG. 19F shows the percentage of CD19+ cells expressing CD23 in CD19+ cells in Donor 2.

FIG. 20A shows the binding by WBP71460_16 (Candidate 19.1). FIG. 20B shows the binding by WBP71460_17. FIG. 20C shows the binding by WBP71460_19.

FIG. 21A shows the binding of WBP71460_9 to IL-4R following 0-, 7-, or 14-day incubation in human serum. FIG. 21B shows the binding of WBP71460_10 to IL-4R following 0-, 7-, or 14-day incubation in human serum. FIG. 21C shows the binding of WBP71460_11 to IL-4R following 0-, 7-, or 14-day incubation in human serum. FIG. 21D shows the binding of WBP71460_15 to IL-4R following 0-, 7-, or 14-day incubation in human serum. FIG. 21E shows the binding of WBP71460_16 to IL-4R following 0-, 7-, or 14-day incubation in human serum. FIG. 21F shows the binding of WBP71460_17 to IL-4R following 0-, 7-, or 14-day incubation in human serum. FIG. 21G shows the binding of WBP71460_19 to IL-4R following 0-, 7-, or 14-day incubation in human serum.

FIG. 22A illustrates IgE reduction in humanized TSLP/TSLPR mice. FIG. 22B illustrates IgE reduction in humanized IL4/IL-4R mice.

FIG. 31A shows how administration of a 1:200 dilution of cynomolgus monkey serum from monkeys dosed with each candidate antigen binding moiety inhibits a TSLP-mediated reporter gene. FIG. 31B shows how administration of a 1:800 dilution of cynomolgus monkey serum with each candidate antigen binding moiety inhibits a TSLP-mediated reporter gene. FIG. 31C shows how administration of a 1:3200 dilution of cynomolgus monkey serum with each candidate antigen binding moiety inhibits a TSLP-mediated reporter gene.

FIG. 32A shows how administration of a 1:200 dilution of cynomolgus monkey serum from monkeys dosed with each candidate antigen binding moiety inhibits an IL-4-mediated reporter gene. FIG. 32B shows how administration of a 1:800 dilution of cynomolgus monkey serum with each candidate antigen binding moiety inhibits an IL-4-mediated reporter gene. FIG. 32C shows how administration of a 1:3200 dilution of cynomolgus monkey serum with each candidate antigen binding moiety inhibits an IL-4-mediated reporter gene.

FIG. 33A shows the percentage by which administration of candidate 19.1 (group 7), Dupilumab (group 8), other candidate antigen binding moieties (groups 1-6) inhibits a TSLP-mediated reporter gene using cynomolgus monkey serum from monkeys dosed with candidate antigen binding moieties. FIG. 33B shows the percentage by which administration of candidate 19.1 (group 7), Dupilumab (group 8), or other candidate antigen binding moieties (groups 1-6) inhibits an IL-4-mediated reporter gene in cynomolgus monkey serum.

FIG. 36A shows an exemplary construct format for candidate antigen binding moiety WBP71460_16. FIG. 36B shows an exemplary construct format for candidate antigen binding moiety WBP71460_33 and WBP71460_34. FIG. 36C shows an exemplary construct format for candidate antigen binding moiety WBP71460_35. FIG. 36D shows an exemplary construct format for candidate antigen binding moiety WBP71460_36. FIG. 36E shows an exemplary construct format for candidate antigen binding moiety WBP71460_37. FIG. 36F shows an exemplary construct format for candidate antigen binding moiety WBP71460_38. FIG. 36G shows an exemplary construct format for candidate antigen binding moiety WBP71460_39. FIG. 36H shows an exemplary construct format for candidate antigen binding moiety WBP71460_40.

DETAILED DESCRIPTION

Overview

Figure 1A:
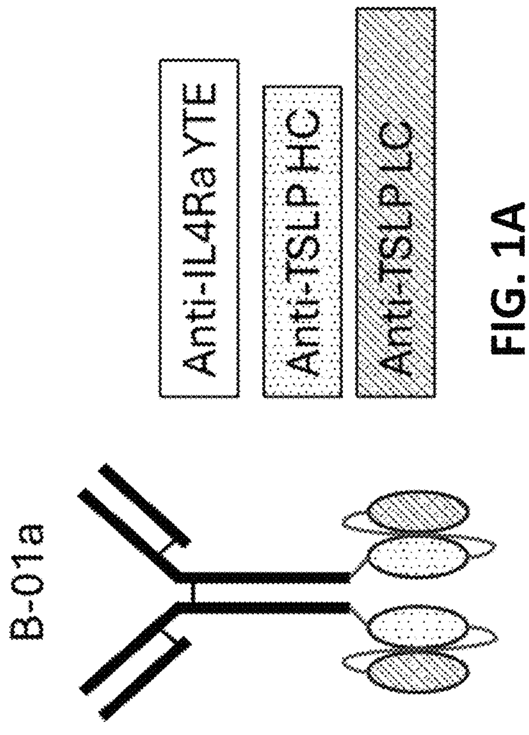
FIG. 1A-FIG. 1D show anti-TSLP single-chain variable fragment (scFv) and anti-IL-4R construct formats.

Described herein, in some aspects, is an antigen binding moiety. In some embodiments, an antigen binding moiety can comprise a binding complex. In some embodiments, the binding complex disclosed herein can comprise a first antibody or an antigen binding portion thereof that specifically binds to a first antigen. In some embodiments, the binding complex disclosed herein can comprise a second antibody or an antigen binding portion thereof that specifically binds to a second antigen. In some embodiments, the binding complex disclosed herein can comprise a third antibody or an antigen binding portion thereof that specifically binds to a third antigen. In some embodiments, the binding complex disclosed herein can comprise a fourth antibody or an antigen binding portion thereof that specifically binds to a fourth antigen. In some embodiments, the binding complex disclosed herein can comprise a fifth antibody or an antigen binding portion thereof that specifically binds to a fifth antigen. In some embodiments, the binding complex disclosed herein can comprise a first antibody or an antigen binding portion thereof that specifically binds to a first epitope of a first antigen, and a second antibody or an antibody binding portion thereof that specifically binds a second epitope of the first antigen. In some embodiments, the first antibody or the antigen binding portion thereof and the second antibody or the antigen binding portion thereof can be associated with each other (e.g., via an optional linker e.g., any one of SEQ ID NOs: 40-47,185-188, or 223-226.) to form an antigen binding moiety.

In some embodiments, the antigen binding portion can include, but are not limited to, a Fab fragment, Fab', F(ab')2 fragment, a domain-crossover Fab (e.g., CrossMab), a single-chain variable fragment (scFv), a single-domain antibody (VHH or nanobody), a single-variable domain (sdAb), a minibody, a diabody, a tribody, or a combination thereof.

In some embodiments, an antigen binding moiety disclosed herein can comprise an antigen binding portion (e.g., of a first antibody) associated with a second antibody. In some embodiments, the antigen binding portion of the first antibody can be a Fab fragment. For example, in some cases, the antigen binding portion of the first antibody (e.g., a Fab fragment) can comprise a first peptide chain and a second peptide chain. In some embodiments, the first peptide chain of the Fab fragment can comprise a heavy chain variable domain (VH) and a heavy chain constant domain 1 (CH1). In some embodiments, the second peptide chain of the Fab fragment can comprise a light chain variable domain (VL) and a light chain constant domain (CL). In some embodiments, the first peptide chain can comprise, from N-terminus to C-terminus: [VH]-[CH1] or [CH1]-[VH]. In some embodiments, the second peptide chain can comprise, from N-terminus to C-terminus: [VL]-[CL] or [CL]-[VL]. In some embodiments, the first peptide chain and the second peptide chain can be associated with each other (e.g., via non-covalent VH-VL pairing and/or CH1-CL disulfide bond) to form a Fab fragment. In some embodiments, the first peptide chain (e.g., comprising VH and CH1) can be associated with the second antibody (e.g., comprising a heavy chain and a light chain). In some embodiments, the first peptide chain can be associated with the second antibody at the N-terminus or C-terminus of the light chain of the second antibody. In some embodiments, the first peptide chain can be associated with the second antibody at the N-terminus or C-terminus of the heavy chain of the second antibody. For example, in some cases, the antigen binding portion thereof can comprise, from N-terminus to C-terminus: [VH]-[CH1]-[heavy chain of the second antibody]; [CH1]-[VH]-[heavy chain of the second antibody]; [heavy chain of the second antibody]-[VH]-[CH1]; or [heavy chain of the second antibody]-[CH1]-[VH].

In some embodiments, the antigen binding moiety disclosed herein can comprise: a first polypeptide sequence comprising a light chain variable domain (VL) and a light chain constant domain (CL) of a Fab fragment of a first antibody; a second polypeptide sequence comprising a heavy chain (e.g., comprising VH, CH1, CH2, and CH3) of a second antibody associated with a heavy chain variable domain and a heavy chain constant domain 1 (CH1) of the Fab fragment of the first antibody, wherein the heavy chain of the second antibody and the heavy chain variable domain of the first antibody can be associated via an optional linker; and a third polypeptide sequence comprising a VL and a CL of the second antibody. In some embodiments, the first polypeptide sequence can be associated with the second polypeptide sequence (e.g., with the VH and CH1 of the Fab fragment of the first antibody) to form a first Fab region, and the third polypeptide sequence can be associated with the second polypeptide sequence (e.g., with the VH and CH1 of the second antibody) to form a second Fab region. In some embodiments, the antigen binding moiety can comprise a fourth polypeptide sequence (e.g., VL and CL of the Fab fragment of the first antibody) and a fifth polypeptide sequence (e.g., comprising VL and CL of the second antibody), each comprising light chains that associate respectively with a sixth polypeptide sequence comprising a heavy chain of the second antibody associated with the VH and CH1 of the Fab fragment of the first antibody to form a third and a fourth Fab regions. In some embodiments, the CH2 and CH3 domains of the second polypeptide sequence and the CH2 and CH3 domains of the sixth polypeptide sequence can form an Fc region. In some embodiments, the optional linker can comprise an amino acid sequence having at least 80% sequence identity to the amino acid sequence of any one of SEQ ID NOs: 40-47,185-188, or 223-226.

In some embodiments, the antigen binding portion of the first antibody or the second antibody can be a domain-crossover Fab. For example, in some cases, the antigen binding portion of the first antibody (e.g., a Fab fragment) can comprise a first peptide chain and a second peptide chain. In some embodiments, at least one domain of the first peptide chain and at least one domain of the second peptide chain may be exchanged. For example, in some embodiments, at least one domain of the Fab fragment of a first antibody or an antigen binding portion thereof or a Fab fragment of a second antibody or an antigen binding portion thereof can comprise a Fab-heavy/light crossover (VH-CH1↔VL-CL), e.g., a domain-crossover Fab in which the VH-CH1 segment and the VL-CL segment are exchanged between the chains such that, for the affected binding site, the heavy-chain polypeptide (e.g., the chain that includes CH2 and CH3) comprises VL-CL and the light-chain polypeptide comprises VH-CH1. In some embodiments, an antigen binding portion of an antibody can be modified such that the full heavy chain variable and constant CH1 domains (Heavy) and the full light chain variable and constant domains (Light) are crossed. In some cases, a Fab fragment of a first antibody or an antigen binding portion thereof or a Fab fragment of a second antibody or an antigen binding region thereof can comprise a variable-domain crossover (VH↔VL), e.g., a domain-crossover Fab in which the VH and VL domains are exchanged between chains, while CH1 and CL remain on their native chains. In some embodiments, an antigen binding portion of an antibody can be modified such that a heavy chain variable region (VH) and a light chain variable region (VL) is crossed. In some cases, a Fab fragment of a first antibody or an antigen binding portion thereof or a Fab fragment of a second antibody or an antigen binding portion thereof can comprise a constant-domain crossover (CH1 ↔CL), e.g., a domain-crossover Fab in which the CH1 and CL domains are exchanged between chains, while VH and VL remain on their native chains.

For example, in some cases, the antigen binding portion of the first antibody (e.g., a cross-over Fab fragment) can comprise a first peptide chain and a second peptide chain. In some embodiments, the first peptide chain of the Fab fragment can comprise a light chain variable domain (VL) and a light chain constant domain (CL). In some embodiments, the second peptide chain of the Fab fragment (e.g., a cross-over Fab fragment) can comprise a heavy chain variable domain (VH) and a heavy chain constant domain 1 (CH1). In some embodiments, the first peptide chain can comprise, from N-terminus to C-terminus: [VL]-[CL] or [CL]-[VL]. In some embodiments, the second peptide chain can comprise, from N-terminus to C-terminus: [VH]-[CH1] or [CH1]-[VH]. In some embodiments, the first peptide chain and the second peptide chain can be associated with each other (e.g., via non-covalent VH-VL pairing and/or CH1-CL disulfide bond) to form a Fab fragment (e.g., a cross-over Fab fragment). In some embodiments, the first peptide chain (e.g., comprising VL and CL) can be associated with the second antibody (e.g., comprising a heavy chain and a light chain). In some embodiments, the first peptide chain can be associated with the second antibody at the N-terminus or C-terminus of the light chain of the second antibody. In some embodiments, the first peptide chain can be associated with the second antibody at the N-terminus or C-terminus of the heavy chain of the second antibody. For example, in some cases, the antigen binding portion thereof can comprise, from N-terminus to C-terminus: [VL]-[CL]-[heavy chain of the second antibody]; [CL]-[VL]-[heavy chain of the second antibody]; [heavy chain of the second antibody]-[VL]-[CL]; or [heavy chain of the second antibody]-[CL]-[VL]. In some embodiments, the antigen binding moiety disclosed herein can comprise: a first polypeptide sequence comprising a heavy chain variable domain (VH) and a heavy chain constant domain (CH1) of a Fab fragment of a first antibody; a second polypeptide sequence comprising a heavy chain (e.g., comprising VH, CH1, CH2, and CH3) of a second antibody linked to a light chain variable domain (VL) and a light chain constant domain (CL) of the Fab fragment (e.g., a cross-over Fab fragment) of the first antibody, wherein the heavy chain of the second antibody and the light chain variable domain of the first antibody can be linked via an optional linker; and a third polypeptide sequence comprising a VL and a CL of the second antibody. In some embodiments, the first polypeptide sequence can associate with the second polypeptide sequence (e.g., with the VL and CL of the Fab fragment of the first antibody) to form a first Fab region, and the third polypeptide sequence can associate with the second polypeptide sequence (e.g., with VH, CH1 of the second antibody) to form a second Fab region. In some embodiments, the antigen binding moiety can comprise a fourth polypeptide sequence (e.g., VH and CH1 of the Fab fragment of the first antibody) and a fifth polypeptide sequence (e.g., comprising VL and CL of the second antibody) that associate respectively with a sixth polypeptide sequence comprising a light chain of the Fab fragment of the first antibody (e.g., VL and CL of the Fab fragment of the first antibody) or VH and CH1 of the second antibody to form a third Fab region and a fourth Fab region. In some embodiments, the CH2 and CH3 domains of the second polypeptide sequence and the CH2 and CH3 domains of the sixth polypeptide sequence can form an Fc region. In some embodiments, the optional linker can comprise an amino acid sequence having at least 80% sequence identity to the amino acid sequence of any one of SEQ ID NOs: 40-47,185-188, or 223-226.

In some embodiments, the Fc region can comprise one or more mutations, wherein the one or more mutations comprise a half-life extension modification, effector silencing, and/or prevention of Fab arm exchange of IgG. In some embodiments, the one or more mutations can comprise M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more mutations can comprise any one of the mutations set forth in Table 33. In some embodiments, the Fc region can comprise a heterodimerization-promoting mutation. In some embodiments, the heterodimerization-promoting mutation comprises a knob-in-hole modification.

In some cases, the first antibody or the antigen binding portion thereof or the second antibody or the antigen binding portion thereof can be derived from the human IgG subtype comprising IgG1, IgG2, IgG3, or IgG4. In some cases, a light chain constant domain of the first antibody or the antigen binding portion thereof or a light chain constant domain of the second antibody or the antigen binding portion thereof can be of a lambda light chain or a kappa light chain. For example, in some cases, the first antibody or the antigen binding portion thereof can comprise a heavy chain constant domain derived from hIgG2, while the second antibody or the antigen binding portion thereof can comprise a heavy chain constant domain derived from hIgG4. In some cases, the first antibody or the antigen binding portion thereof can comprise a light chain constant domain derived from the lambda light chain, while the second antibody or the antigen binding portion thereof can comprise a light chain constant domain derived from the lambda light chain.

In some embodiments, a therapeutically effective amount of the antigen binding moiety disclosed herein can be administered to a subject to treat a disease or condition. In some embodiments, the disease or condition can comprise cancer, autoimmune disorders, inflammatory disorders, infectious diseases, and/or degenerative diseases. For example, in some embodiments, a therapeutically effective amount of the antigen binding moiety disclosed herein can be administered to a patient having or suspected having cancer. In some embodiments, the patient may have breast cancer, lung cancer, colorectal cancer, gastric cancer, pancreatic cancer, liver cancer, ovarian cancer, prostate cancer, renal cancer, melanoma, head and neck cancer, leukemia, lymphoma, or multiple myeloma. In some embodiments, a therapeutically effective amount of the antigen binding moiety disclosed herein can be administered to a patient having or suspected having an autoimmune disorder or an inflammatory disorder. In some embodiments, the patient may have (or suspected to have) inflammatory arthritis, rheumatoid arthritis, psoriatic arthritis, psoriasis, inflammatory bowel disease, ulcerative colitis, Crohn's disease, systemic lupus erythematosus, multiple sclerosis, type 1 diabetes, autoimmune thyroiditis, ankylosing spondylitis, asthma, dermatitis, eosinophilic esophagitis, chronic obstructive pulmonary disease, eczema, nasal polyps, sinusitis, pruritus, atopic dermatitis, allergic rhinitis, airway hyperresponsiveness, airway inflammation, a food allergy, chronic urticaria, occupational allergy, allergic conjunctivitis, hay fever, airborne allergic sensitivities, stinging insect allergy, hypersensitivity pneumonitis, eosinophilic lung diseases, or drug allergies. In some embodiments, a therapeutically effective amount of the antigen binding moiety disclosed herein can be administered to a patient having or suspected having viral infections, bacterial infections, fungal infections, or parasitic infections.

In some embodiments, a first antibody (or an antigen binding portion thereof) or a second antibody (or an antigen binding portion thereof) can be any antibody or an antigen-binding portion thereof, including a fragment, variant, derivative, or moiety, disclosed herein. In some embodiments, the first antibody or the antigen binding portion thereof can be an anti-IL-4R or an antigen binding portion thereof. In some embodiments, the first antibody or the antigen binding portion thereof can be an anti-TSLP or an antigen binding portion thereof. In some embodiments, the second antibody or the antigen binding portion thereof can be an anti-IL4R or an antigen binding portion thereof. In some embodiments, the second antibody or the antigen binding portion thereof can be an anti-TSLP or an antigen binding portion thereof. For example, in some cases, the first antibody or the antigen binding portion thereof can be an anti-TSLP or an antigen binding portion thereof, and the second antibody or the antigen binding portion thereof can be anti-IL-4R or an antigen binding portion thereof. In some embodiments, the first antibody or the antigen binding portion thereof can be an anti-IL-4R or an antigen binding portion thereof, and the second antibody or the antigen binding portion thereof can be anti-TSLP or an antigen binding portion thereof. In some embodiments, the antigen binding moiety can comprise a binding complex comprising an anti-IL-4R moiety (e.g., anti-IL-4R) or an antigen binding portion thereof and an anti-thymic stromal lymphopoietin (TSLP) moiety or an antigen binding portion thereof. In some embodiments, an antigen binding moiety comprises an antigen binding portion (e.g., a scFv or a Fab) of the anti-IL-4R moiety associated with an anti-TSLP moiety. In some embodiments, an antigen binding moiety comprises an antigen binding portion of the anti-TSLP moiety (e.g., a scFv or a Fab) associated with an anti-IL-4R moiety.

In some embodiments, an antigen binding region can comprise a single-chain variable fragment (scFv). In some embodiments, an antigen binding portion of an anti-IL-4R moiety is an anti-IL-4R scFv. In some embodiments, an antigen binding portion of an anti-TSLP moiety is an anti-TSLP scFv. In some embodiments, an antigen binding region can comprise a fragment antigen-binding region (Fab). In some embodiments, an antigen binding region can comprise a domain-crossover Fab (also referred as CrossMab). As used herein, a "domain-crossover Fab" or "CrossMab" is Fab region (e.g., at least one Fab region of the antigen binding moiety disclosed herein) in which one or more domains (of the light chain—comprising VL-CL—and the heavy chain—comprising VH-CH1-) that are normally located on the heavy-chain polypeptide and/or the light-chain polypeptide of a wild-type immunoglobulin are positioned on the opposite polypeptide chain or swapped, thereby promoting cognate heavy/light pairing in multi-specific antibodies.

Also provided herein is an antigen binding moiety comprising a TSLP-TRAP associated with a moiety via a first linker. In some aspects, the TSLP-TRAP comprises an extracellular domain of thymic stromal lymphopoietin protein receptor (TSLPR) and an extracellular domain of interleukin-7 receptor subunit alpha (IL-7Rα) joined via a second linker. In some embodiments, the TSLPR is joined to a first portion of the moiety and the IL-7Rα is joined to a second portion of the moiety. In some embodiments, TSLP-TRAPs can be associated with a variety of moieties that alter its properties including extending half-life and binding additional target molecules. In some aspects, the moiety comprises: 1) a probe; 2) an antibody domain; 3) an antibody or an antigen binding portion thereof, 4) a receptor; and/or 5) a half-life extender. In some aspects, the moiety is the probe, wherein the probe is a His tag, a GST tag, a flag tag, or a fluorescent molecule.

In some aspects, an antigen binding moiety described herein can comprise an Fc region having one or more amino acid mutations. In some embodiments, the one or more amino acid mutations can comprise additions, deletions, and/or substitutions. In some embodiments, the one or more mutations can (i) extend half-life of the antigen binding moiety (e.g., a half-life extender that enhance FcRn binding), (ii) silence or reduce effector function (e.g., by reducing Fcγ receptor or complement binding), and/or (iii) reduce or prevent Fab-arm exchange of IgG molecules. In some aspects, the half-life extender can be albumin, PEG, or a suitable polymer to extend half-life in blood or body. In some embodiments, an antigen binding moiety described herein is symmetric and comprises a dimeric assembly of two identical heavy chains. In some embodiments, an antigen binding moiety described herein is asymmetric. In some embodiments, an asymmetric moiety is generated using knobs-into-holes (KiH). In some embodiments, an asymmetric moiety is generated using knobs-into-holes (KiH). In some embodiments, an antibody comprising a Fc region with KiH mutation described herein may have an improved heterodimerization, enhanced stability, and an increase in therapeutic efficacy compared to that of a control antibody lacking the KiH mutation.

In some embodiments, an antigen binding moiety described herein can be a monospecific or a polyspecific (e.g., bi-specific, tri-specific, etc.) binder. In some aspects, an antigen binding moiety can be a monospecific binder that only binds to TSLP or to IL-4R or antigenic portions thereof. In some aspects, an antigen binding moiety can be a bispecific binder. For example, in some embodiments, an antigen binding moiety described herein can bind to TSLP or an antigenic portion thereof and the associated antibody or an antigen binding portion thereof that specifically binds to a second antigen. In some embodiments, for example, the first antigen can be TSLP, and the second antigen can be human interleukin-4 receptor (hIL-4R), human interleukin-4 (hIL-4), human interleukin-13 receptor (hIL-13R), human interleukin-13 (hIL-13), human interleukin-5 (hIL-5), human interleukin-5 receptor (hIL-5R), human interleukin-33 (hIL-33) or human interleukin-31 (hIL-31). In some embodiments, the second antigen is IL-4R. IN some embodiments, the first antigen can be human interleukin-4 receptor (hIL-4R), human interleukin-4 (hIL-4), human interleukin-13 receptor (hIL-13R), human interleukin-13 (hIL-13), human interleukin-5 (hIL-5), human interleukin-5 receptor (hIL-5R), human interleukin-33 (hIL-33) or human interleukin-31 (hIL-31). In some embodiments, the second antigen is IL-4R, and the second antigen can be TSLP. In some aspects, the antibody or antigen-binding portion thereof associated with (e.g., directly or indirectly coupled to) the TSLP or TSLP-TRAP is dupilumab. In some embodiments, an antigen binding moiety described herein can bind to IL-4R (e.g., IL-4Rα) and the associated antibody or the antigen binding portion thereof specifically binds to a second antigen. In some embodiments, the second antigen can be, for example, TSLP. In some aspects, the antibody or antigen-binding portion thereof associated with the TSLP is Tezepelumab. In some aspects, the antibody or the antigen binding portion thereof further comprises a Fc region. In some embodiments, the Fc region can comprise one or more mutations to extend half-life (e.g. YTE mutation) or to enhance stability. In some embodiments, the Fc region described herein can have a first modified Fc polypeptide and a second modified Fc polypeptide, where the first modified Fc polypeptide comprises a knob modification and the second modified Fc polypeptide comprises a hole modification.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "a" and "an" refers to one or more (e.g., at least one) of the grammatical object of the article. By way of example, "a polypeptide" encompasses one or more polypeptides.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

Unless otherwise specified, a "nucleotide sequence encoding a protein" includes all nucleotide sequences that are degenerate versions of each other and thus encode the same amino acid sequence.

The term "transduced", "transfected", or "transformed" refers to a process by which exogenous nucleic acid is introduced or transferred into a cell. A "transduced," "transfected," or "transformed" cell (e.g., a mammalian cell, a hepatocyte) is one that has been transduced, transfected or transformed with exogenous nucleic acid (e.g., an expression vector) that includes an exogenous nucleic acid encoding a polypeptide).

The term "subject" is intended to include any mammal. In some embodiments, the subject is a cat, a dog, a goat, a human, a non-human primate, a rodent (e.g., a mouse or a rat), a pig, or a sheep.

The term "nucleic acid" refers to a deoxyribonucleic acid (DNA) or ribonucleic acid (RNA), or a combination thereof, in either a single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

Modifications can be introduced into a nucleotide sequence by standard techniques known in the art, such as site-directed mutagenesis and polymerase chain reaction (PCR)-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., arginine, lysine and histidine), acidic side chains (e.g., aspartic acid and glutamic acid), uncharged polar side chains (e.g., asparagine, cysteine, glutamine, glycine, serine, threonine, tyrosine, and tryptophan), nonpolar side chains (e.g., alanine, isoleucine, leucine, methionine, phenylalanine, proline, and valine), beta-branched side chains (e.g., isoleucine, threonine, and valine), and aromatic side chains (e.g., histidine, phenylalanine, tryptophan, and tyrosine), and aromatic side chains (e.g., histidine, phenylalanine, tryptophan, and tyrosine).

The term "antigen-binding domain," "antigen binding region," or "antigen binding portion" is used to refer to one or more antibody variable domain(s) (e.g., formed from amino acids from a single polypeptide or formed from amino acids from two or more polypeptides (e.g., the same or different polypeptides) that is capable of specifically binding to one or more different antigen(s). The antigen binding domain comprises one or more variable regions of the heavy and/or light chains of the antibody or a fragment thereof, wherein the variable regions define the unique antigen specificity. In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art. In some cases, the terms—"antigen-binding domain," "antigen binding region," or "antigen binding portion"—can be used interchangeably.

The term "heavy chain" as used herein refers to the polypeptide chain that comprises both a variable region (VH) and a constant region (CH). As used herein, the constant region of the heavy chain can include the constant domain 1 of the heavy chain (CH1) and the Fc region. The Fc region can comprise the constant domain 2 and constant domain 3 of the heavy chain (CH2 and CH3 domains, respectively). The term "light chain" is used to refer to a polypeptide chain that comprises a variable region (VL) and a constant region (CL). The term "LCDR" refers to a complementary-determining region (CDR) within alight chain variable region. The term "HCDR" refers to a complementary-determining region (CDR) within a heavy chain variable region.

The term "N-terminally positioned" when referring to a position of a first domain or sequence relative to a second domain or sequence in a polypeptide primary amino acid sequence means that the first domain is located closer to the N-terminus of the polypeptide primary amino acid sequence. In some embodiments, there may be additional sequences and/or domains between the first domain or sequence and the second domain or sequence.

The term "C-terminally positioned" when referring to a position of a first domain or sequence relative to a second domain or sequence in a polypeptide primary amino acid sequence means that the first domain is located closer to the C-terminus of the polypeptide primary amino acid sequence. In some embodiments, there may be additional sequences and/or domains between the first domain or sequence and the second domain or sequence.

The term "exogenous" refers to any material introduced from or originating from outside a cell, a tissue, or an organism that is not produced by or does not originate from the same cell, tissue, or organism in which it is being introduced.

The term "endogenous" refers to any material originating from inside a cell, a tissue, or an organism that is not introduced by or does not originate from outside the same cell, tissue, or organism in which it is being introduced.

The term "antibody" refers to a protein with an immunoglobulin fold that specifically binds to an antigen via its variable region or regions. The term "antibody" is used herein in the broadest sense and encompasses monoclonal antibodies, polyclonal antibodies, dimers, multimers, multispecific antibodies (e.g., bispecific antibodies), and antibody fragments, so long as they exhibit the desired biological activity (Miller et al., J. Immunol. 170:4854-4861, 2003). Antibodies may be murine, human, humanized, chimeric, or derived from other species. (Janeway, C., Travers, P., Walport, M., Shlomchik (2001) Immunol. Biology, 5$^{th}$ Ed., Garland Publishing, New York). A target antigen generally has numerous binding sites, also called epitopes, recognized by CDRs (complementarity determining regions) on multiple antibodies. Each antibody that specifically binds to a different epitope may have a different structure. Thus, one antigen may have more than one corresponding antibody. An antibody can, e.g., include a full-length immunoglobulin molecule or an immunologically active portion of a full-length immunoglobulin molecule, e.g., a molecule that contains an antigen-binding site that immunospecifically binds an antigen of a target of interest or part thereof. The immunoglobulin described herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

Antibodies bound to various types of molecules, such as polyethylene glycols (PEGs), and albumin may be used as modified antibodies. Methods for modifying antibodies are already established in the art.

The term "antibody fragments" refers to a portion of a full-length antibody or a polypeptide that includes a portion of a full-length antibody that retains antigen-binding activity via its variable region or regions. Examples of antibody fragments include Fab, Fab', F(ab')2, and Fv fragments; diabodies; linear antibodies; minibodies (Olafsen et al., Protein Eng. Design & Sel. 17(4):315-323, 2004), fragments produced by a Fab expression library, single-chain antibody molecules; and multispecific antibodies formed from antibody fragments.

The term "complementarity determining region" or "CDR" refers to one of the three hypervariable regions (or HVRs) that are known to confer (at least in part) antigen-binding specificity in each antibody light chain and each antibody heavy. The three CDRs in the antibody heavy chain and the antibody light chain interrupt four framework regions in the heavy chain variable domain and the light chain variable domain. The CDRs of each chain are typically referred to as CDR1, CDR2, and CDR3, numbered sequentially starting from the N-terminus, and are also typically identified by the chain in which the particular CDR is located.

The "framework regions" or "FRs" of different light immunoglobulin chains and different heavy immunoglobulin chains are relatively conserved within different antibodies produced by a mammal. The framework regions of light and heavy immunoglobulin chains serve to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

"Monospecific" antigen-binding complex refers to the ability of the antigen-binding complex, such as a TSLP-TRAP, to bind specifically to one epitope. "Bispecific" antigen-binding complex refers to the ability of the antigen-binding complex to bind two different epitopes. "Polyspecific" antigen-binding complex refers to the ability of the antigen-binding complex to bind more than one epitope. In some embodiments, a polyspecific antigen-binding complex, such as a polyspecific TSLP-TRAP complex, encompasses a bispecific antigen-binding polypeptide. For bispecific and polyspecific antigen-binding complexes provided herein, the epitopes can be on the same antigen, or each epitope can be on a different antigen. Therefore, in some embodiments, a polyspecific antigen-binding complex provided herein, such as a bispecific TSLP-TRAP complex, binds to two different antigens. In some embodiments, the polyspecific antigen-binding complex, such as a bispecific TSLP-TRAP complex, binds to different epitopes on one antigen. In some embodiments, a polyspecific antigen-binding complex provided herein binds to each epitope with a dissociation constant (Kd) of about <1 M, about <100 nM, about <10 nM, about <1 nM, about <0.1 nM, about <0.01 nM, or about <0.001 nM (e.g., about $10^{-8}$ M or less, e.g., from about $10^{-8}$ M to about $10^{-13}$M, e.g., from about $10^{-9}$ M to about $10^{-10}$ M).

An "amino acid substitution" refers to the replacement of at least one existing amino acid residue in a predetermined amino acid sequence with another different "replacement" amino acid residue. The replacement residue or residues may be "naturally occurring amino acid residues" (e.g., encoded by the genetic code) and selected from the group consisting of alanine (Ala); arginine (Arg); asparagine (Asn); aspartic acid (Asp); cysteine (Cys); glutamine (Gin); glutamic acid (Giu); glycine (Giy); histidine (His); isoleucine (He): leucine (Leu); lysine (Lys); methionine (Met); phenylalanine (Phe); proline (Pro); serine (Ser); threonine (Thr); tryptophan (Trp); tyrosine (Tyr); and valine (Val). In some embodiments, the replacement residue or residues may be unnatural residues.

The term "administer" refers to a method of getting polypeptides or compositions to the desired site of biological action. These methods include, but are not limited to, topical delivery, parenteral delivery, intravenous delivery, intradermal delivery, intramuscular delivery, colonic delivery, rectal delivery, or intraperitoneal delivery. In one embodiment, the compositions described herein are administered intravenously.

The term "promoter" means a DNA sequence recognized by enzymes/proteins in a cell (e.g., a mammalian cell, a hepatocyte) required to initiate the transcription of an operably linked coding sequence (e.g., a nucleic acid encoding a polypeptide (e.g., any of the exemplary polypeptides described herein). A promoter typically refers to, e.g., a nucleotide sequence to which an RNA polymerase and/or any associated factor binds and at which transcription is initiated. The promoter can be constitutive, inducible, or tissue-specific (e.g., a liver-specific promoter).

The term "enhancer" refers to a nucleotide sequence that can increase the transcription of an operably linked nucleic acid (e.g., a nucleic acid encoding a polypeptide (e.g., any of the exemplary polypeptides described herein). An enhancer can increase the level of transcription by providing additional binding sites for transcription-associated proteins (e.g., transcription factors). Unlike promoters, enhancers can act at distances further away from the transcription start site (e.g., as compared to a promoter). The terms "identical" or percent "identity," in the context of two or more polypeptide sequences, refer to two or more sequences or subsequences that are the same or have a specified percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window or designated region, as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 or Megalign. The parameters employed for an alignment to achieve maximal alignment can be determined by one of skill in the art. For sequence comparison of polypeptide sequences for purposes of this application, the BLASTP algorithm standard protein BLAST for aligning two protein sequences with the default parameters is used.

The term "affinity" refers to the strength of the sum of all non-covalent interactions between an antigen-binding site and its antigen. Unless otherwise indicated, "affinity" refers to intrinsic binding affinity, which reflects a 1:1 interaction between an antigen-binding domain and an antigen. Affinity can be measured, e.g., using surface plasmon resonance (SPR) technology (e.g., BIACORE®) or biolayer interferometry (e.g., FORTEBIO®). Additional methods for determining the affinity of an antigen-binding domain and its antigen are known in the art.

The term "antigen binding complex" means a complex of two or more (e.g., 2, 3, 4, 5, 6, 7, or 8) polypeptide chains (e.g., the same or different polypeptide chains) that covalently and/or non-covalently associate with each other where at least one of the polypeptide chains binds an antigen. For example, two or more polypeptide chains of a multi-chain polypeptide can associate through the use of two domains that associate with each other.

"Linker" can mean a molecule capable of associating two or more moieties. A linker can mean a molecule capable of forming covalent bonds to both TSLP-TRAP and to a moiety. Suitable linkers are well known to those of skill in the art and include, but are not limited to, straight or branched-chain carbon linkers, heterocyclic carbon linkers, or peptide linkers. Where the TSLP-TRAP and the moiety are polypeptides, the linkers may be joined to the constituent amino acids through their side groups (e.g., through a disulfide linkage to cysteine). In some embodiments, the linkers will be joined to the alpha carbon amino and carboxyl groups of the terminal amino acids. Linkers are generally classified into three categories according to their structures: flexible linkers (e.g., (G)n (SEQ ID NO: 227) or (GGGGS)n) (SEQ ID NO:40), rigid linkers (e.g., (EAAAK)n (SEQ ID NO:41)), wherein n is an integer between 1 and 100, and in vivo cleavable linkers (e.g., disulfide or protease sensitive sequences). In some embodiments, a linker comprises ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20). In some embodiments, a "first" linker refers to a polypeptide between 4 amino acids and 500 amino acids in length that associates a first moiety and a second moiety, for example the TSLP-TRAP to the moiety. In some embodiments, a "second" linker can refer to a different polypeptide between 4 amino acids and 500 amino acids in length that associates a first moiety and a second moiety, for example the extracellular domain of TSLPR to the extracellular domain of IL-7Rα.

The term "TSLP-TRAP" means a complex of the extracellular domain of thymic stromal lymphopoietin protein receptor (TSLPR) and the extracellular domain of interleukin-7 receptor subunit alpha (IL-7Rα).

The term "TSLP-TRAP complex" refers to a TSLP-TRAP associated with a moiety via a linker.

The section headings used herein are for organizational purposes only and are not to be construed as limiting the subject matter described.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, $5^{th}$ Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. The Kabat numbering of residues may be determined for a given antibody by alignment at regions of homology of the sequence of the antibody with a "standard" Kabat numbered sequence. It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342:877-883.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the 'minimum binding unit'. The minimum binding unit may be a sub-portion of a CDR. Table 1 below represents one definition using each numbering convention for each CDR or binding unit. The Kabat numbering scheme is used in Table 1 to number variable domain amino acid sequence. In should be noted that some of the CDR definitions may vary depending on the individual publication used.

TABLE 1

| | The numbering scheme | | | | |
|---|---|---|---|---|---|
| | Kabat CDR | Chothia CDR | AbM CDR | Contact CDR | Minimum Binding Unit |
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

IL-4R-TSLP Binding Complex

In some embodiments, described herein is an antigen binding moiety comprising an anti-IL-4R moiety or an antigen binding portion thereof, or an anti-TSLP or an antigen binding portion thereof that has binding affinity/activity to TSLP and/or IL-4R. In some embodiments, the antigen binding moiety described herein can block activity of IL4-IL-4R binding/interaction and/or TSLP-TSLPR/IL7Rα binding/interaction. In some embodiments, the antigen binding moiety described herein can block activity of TSLP and/or IL4 induced or mediated signaling, that is comparable or higher than that of a monospecific anti-IL-4R or anti-TSLP antibodies (e.g., Dupilumab and Tezepelumab, respectively) or a combination treatment (e.g., sequential or co-administration) of the monospecific anti-IL-4R and anti-TSLP antibodies.

In some embodiments, the antigen binding moiety described herein comprises (1) an anti-IL-4R moiety comprising a heavy chain (e.g., comprising a heavy chain variable region and a heavy chain constant region 1) and a light chain (e.g., comprising a light chain variable region and a light chain constant region), and (2) an anti-TSLP antigen binding portion of an anti-TSLP moiety. In some embodiments, the antigen binding moiety described herein can comprise (1) an anti-TSLP moiety comprising a heavy chain (e.g., comprising a heavy chain variable region and a heavy chain constant region 1) and a light chain (comprising a light chain variable region and a light chain constant region), and (2) an anti-IL-4R antigen binding region of an anti-IL-4R moiety.

Non-limiting examples of an antigen binding portion of an antibody can be a Fab fragment, Fab', F(ab')2 fragment, a domain-crossover Fab (e.g., CrossMab), a single-chain variable fragment (scFv), a single-domain antibody (VHH or nanobody), a single-variable domain (sdAb), a minibody, a diabody, a tribody, or a combination thereof. Fab and Fab' can be antigen-binding fragments that comprise a variable heavy chain (VH) and a constant region of the heavy chain domain 1 (CH1 domain) linked to a variable light chain (VL) and a constant region of the light chain domain (CL) via a disulfide bond. A F(ab')2 can comprise two Fab or Fab' that are joined by disulfide bonds. An Fv can comprise the VH and VL domains, e.g., held together by non-covalent interactions. An scFv (single-chain variable fragment) is a fusion protein that can comprise VH and VL domains connected by a linker (e.g., a peptide linker). Manipulation of the orientation of the VH and VL domains and the linker length can be used to create different forms of molecules that can be monomeric, dimeric (diabody), trimeric (triabody), or tetrameric (tetrabody). Minibodies are scFv-CH3 fusion proteins that assemble into bivalent dimers.

In some embodiments, an antigen binding moiety described herein can comprise a domain-crossover Fab. For example, in some embodiments, a Fab region of an anti-IL-4R moiety or an antigen binding region thereof or a Fab region of an anti-TSLP or an antigen binding region thereof can comprise a Fab-heavy/light crossover (VH-CH1↔VL- CL), e.g., a domain-crossover Fab in which the VH-CH1 segment and the VL-CL segment are exchanged between chains such that, for the affected binding site, the heavy-chain polypeptide (e.g., the chain that includes CH2 and CH3) comprises VL-CL and the light-chain polypeptide comprises VH-CH1. In some embodiments, an antigen binding portion of an antibody can be modified such that the full heavy chain variable and constant CH1 domains (Heavy) and the full light chain variable and constant domains (Light) are crossed (e.g., CrossMab$^{Fab}$). In some cases, a Fab region of an anti-IL-4R moiety or an antigen binding region thereof or a Fab region of an anti-TSLP or an antigen binding region thereof can comprise a variable-domain crossover (VH↔VL), e.g., a domain-crossover Fab in which the VH and VL domains are exchanged between chains, while CH1 and CL remain on their native chains. In some embodiments, an antigen binding portion of an antibody can be modified such that a heavy chain variable region (VH) and a light chain variable region (VL) is crossed (e.g., CrossMab$^{VH\text{-}VL}$). In some cases, a Fab region of an anti-IL-4R moiety or an antigen binding region thereof or a Fab region of an anti-TSLP or an antigen binding region thereof can comprise a constant-domain crossover (CH1↔CL), e.g., a domain-crossover Fab in which the CH1 and CL domains are exchanged between chains, while VH and VL remain on their native chains. In some embodiments, an antigen binding portion of an antibody can be modified such that at least a portion of a heavy chain constant region (e.g., CH1) and a light chain constant region (CL) is crossed (e.g., CrossMab$^{CH1\text{-}CL}$).

The variable (V) domain(s) of an antibody can mediate antigen binding and define the specificity of a particular antibody for an antigen. The variable domain can comprise relatively invariant sequences called framework regions, and hypervariable regions, which differ considerably in sequence among antibodies of different binding specificities. Within hypervariable regions can be amino acid residues that primarily determine the binding specificity of the antibody in most cases. Sequences comprising these residues can be known as complementarity determining regions (CDRs). One antigen binding site of an antibody with heavy and light chains or variable domains therefrom can comprise six CDRs, three in the hypervariable regions of the light chain variable domain, and three in the hypervariable regions of the heavy chain variable domain. The CDRs in the light chain can be designated L1, L2, and L3, while the CDRs in the heavy chain can be designated H1, H2, and H3. CDRs can also be designated LCDR1, LCDR2, LCDR3, HCDR1, HCDR2, and HCDR3 (or LC-CDR-1, LC-CDR-2, LC-CDR-3, HC-CDR-1, HC-CDR-2, and HC-CDR-3, respectively). The contribution of each CDR to antigen binding can vary among antibodies, but in some embodiments, heavy chain CDRs, in particular HCDR3, can contribute most to antigen-specific binding. CDRs can vary in length.

An antigen binding moiety can comprise an immunoglobulin constant domain, such as an Fc region. An immunoglobulin constant domain can be described with reference to the basic four chain antibody unit, which comprises two heavy chain (H) polypeptide sequences and two light chain (L) polypeptide sequences. Each of the heavy chains of the basic four chain antibody unit can comprise one N-terminal heavy chain variable domain (VH) and three or four C-terminal constant domains (CH1, CH2, and CH3, and in some cases CH4). Each of the light chains of the basic four chain antibody unit can comprise one N-terminal light chain variable domain (VL) and one C-terminal constant (CL) domain. The light chain variable domain in the basic four chain antibody unit can be aligned with the heavy chain variable domain and the light chain constant domain can be aligned with heavy chain constant domain CH1. Each light chain can be linked to a heavy chain by one covalent disulfide bond. The two heavy chains can be linked to each other by one or more disulfide bonds depending on the heavy chain isotype. Each heavy and light chain also can comprise regularly-spaced intrachain disulfide bridges. The C-terminal constant domains of the heavy chains (e.g., CH2 and CH3, or CH2, CH3, and CH4) can comprise the Fc region, Fc domain, or Fc fragment of the antibody, which can mediate effector functions, for example, through interactions with Fc receptors or complement proteins. The terms "VH" and "HV" can be used interchangeably herein to refer to a heavy chain variable domain. The terms "VL" and "LV" can be used interchangeably herein to refer to a light chain variable domain. The term "portion," "region," or "domain" can be used interchangeably.

The light chain can be designated kappa or lambda based on the amino acid sequence of the constant region. The heavy chain can be designated alpha, delta, epsilon, gamma, or mu based on the amino acid sequence of the constant region. Antibodies can be categorized into five immunoglobulin classes, or isotypes, based on the heavy chain. IgA can comprise alpha heavy chains, IgD can comprise delta heavy chains, IgE can comprise epsilon heavy chains, IgG can comprise gamma heavy chains, and IgM can comprise mu heavy chains. Antibodies of the IgG, IgD, and IgE classes can comprise monomers of the four chain unit described above (two heavy and two light chains), while the IgM and IgA classes can comprise multimers of the four chain unit.

Antigen binding moiety disclosed herein can comprise an immunoglobulin constant domain from a heavy chain and/or light chain of an antibody isotype, class, or subclass disclosed herein. As used herein, "immunoglobulin constant domain" can describe at least one domain from the full immunoglobulin constant region. In some embodiments, an immunoglobulin constant domain can be a CH2 and CH3, for example of an IgG, IgG1, IgG2, IgG3, IgG4, IgA, IgA1, IgA2, IgM, IgD, or IgE. In some embodiments, an immunoglobulin constant domain can be a CH2, CH3, and a hinge or fragment thereof, for example of an IgG, IgG1, IgG2, IgG3, IgG4, IgA, IgA1, IgA2, IgM, IgD, or IgE. In some embodiments, an immunoglobulin constant domain can be a CH1, hinge, CH2, and CH3, for example of an IgG, IgG1, IgG2, IgG3, IgG4, IgA, IgA1, IgA2, IgM, IgD, or IgE. In some embodiments, an immunoglobulin constant domain can be a CL.

In some embodiments, modifications to the constant domains can affect characteristics of an antibody or antigen binding moiety such as enhancement or reduction of half-life. Modifications can include, for example, amino acid mutations, altering post-translational modifications (e.g., glycosylation), combining domains from different isotypes or subclasses, or a combination thereof. An antigen binding moiety disclosed herein can comprise an immunoglobulin constant domain or Fc region that is modified to achieve desirable characteristics, for example, reduced binding to one or more particular Fc receptors, reduced induction of immune effector functions, and/or enhanced half-life in vivo.

An antigen binding moiety disclosed herein can comprise an immunoglobulin constant domain or Fc region that is selected or modified to provide suitable characteristics, for example, suitable characteristics for treating a disease or condition as disclosed herein. Non-limiting examples of immunoglobulin constant domain modifications and their effects are provided in Table 33. The numbering used can be EU numbering.

TABLE 33

Non-limiting examples of immunoglobulin constant domain modifications

| Effect | Isotype | Mutation(s)/Modification(s) |
|---|---|---|
| Increased half-life | IgG4 | M252Y/T256D |
| Increased half-life | IgG4 | T256D/T307Q |
| Increased half-life | IgG4 | T256D/T307W |
| Increased half-life | IgG4 | M252Y/T256D(or E)/ T307Q(or W)/N434F(or Y) |
| Increased half-life | IgG4 | M252Y/S254T/T256E |
| Increased half-life | IgG4 | M428L/N434S |
| Increased half-life | IgG4 | R435H |
| Increased half-life | IgG4 | M428L/N434S |
| Increased half-life | IgG4 | T307A/E380A/N434A |
| Increased half-life | IgG4 | T250Q/M428L |
| Increased half-life | IgG4 | H310D/N434E |
| Increased half-life | IgG4 | M252Y/T256D/Y407E |
| Increased half-life | IgG4 | M428L/N434S/G236A/I253E |
| Increased half-life | IgG4 | M252Y/S254T/S255M/ T256D/Y407E |
| Increased half-life | IgG4 | V308P |
| Effector silencing | IgG1 | L234A/L235A |
| Effector silencing | IgG1 | L234A/L235A/P329G |
| Reduced Fab arm exchange | IgG4 | S228P |

Antigen binding moiety disclosed herein can utilize heterodimeric heavy chains, Fc regions, or immunoglobulin constant regions as a dimerization or multimerization domain. For example, an antigen binding moiety can comprise two peptide chains (which can be referred to, e.g., as a first peptide or polypeptide chain and second peptide or polypeptide chain). Each of the first peptide chain or polypeptide chain and second peptide chain or polypeptide chain can comprise a portion of a dimerization or multimerization module, facilitating dimerization or multimerization. The portions of the dimerization module can be or comprise, for example, heavy chains or Fc regions thereof (e.g., with CH2 and CH3 domains, or CH2, CH3, and CH4 domains).

In some embodiments, knob-in-hole modifications of immunoglobulin constant domains or Fc regions of heavy chains can be used to promote formation of heterodimers between the first peptide chain (e.g., heavy/Fc chain) and the second peptide chain (e.g., heavy/Fc chain). The "knobs in holes" approach allows the generation of complementary interacting interfaces by manipulating key amino acid residues that participate in the Fc dimeric interaction. Amino acids with small side chains can be replaced by ones with larger side chains, thereby creating a knob or protrusion in one chain, and vice versa to create a hole or socket in the partner chain.

The "knob" heavy chain can contain a mutation of threonine at a position equivalent to 366 in CH3 of IgG, such as a T366 W or T366Y mutation. The "knob" heavy chain can also contain, for example, an F405A mutation.

The "hole" heavy chain can contain multiple mutations, e.g., T366S, L368A, T394 W, F405A, and/or Y407V/T). In some embodiments, the "hole" heavy chain can comprise T366S, L368A, and Y407V substitutions. In some embodiments, the "hole" heavy chain comprises T366S, L368A, and Y407V substitutions.

In some embodiments, "LALA modification" (e.g., L234A/L235A) or "LALAPG modification" (e.g., L234A/L235A/P329G) of immunoglobulin constant domains or Fc regions of heavy chains (in the CH2 domain) can be used to reduce binding to Fcγ receptors and complement proteins, thereby decreasing antibody-dependent cellular cytotoxicity (ADCC) and complement-dependent cytotoxicity (CDC).

In some cases, anti-TSLP Fab or parts thereof may be lambda isotypes, while anti-IL-4R antibody or parts thereof may be of the kappa isotypes. In some other cases, anti-TSLP Fab may be kappa isotypes, while anti-IL-4R antibody may be of the lambda isotypes. In some cases, at least one domain of the anti-IL-4R moiety may comprise an IgG4 backbone, while at least one domain of the anti-TSLP Fab may comprise an IgG2 backbone. In some other cases, at least one domain of the anti-IL-4R moiety may comprise an IgG2 backbone, while at least one domain of the anti-TSLP Fab may comprise an IgG4 backbone. In some cases, the antigen binding moiety described herein may not require the C-terminal portion of the CH1 domain of the heavy chain, as in IgG1 domain-crossover Fab (e.g., CrossMab), for proper structural or functional activity. In some cases, the deletion, substitution, or omission of the C' segment of the CH1 domain or parts thereof, including but not limited to the EPKSC motif (SEQ ID NO: 228), does not adversely affect heavy and light chain paring, antigen-binding capacity, or overall structural stability.

In some embodiments, the antigen binding moiety described herein may comprise an anti-IL-4R moiety comprising an IgG4 backbone. In some cases, the anti-IL-4R moiety may comprise a kappa light chain. In some cases, the antigen binding moiety described herein may comprise an anti-TSLP antigen binding portion (e.g., anti-TSLP Fab) comprising an IgG2-(CH1) Fab. In some cases, the anti-TSLP IgG2-(CH1) Fab may comprise a lambda light chain. In some cases, a heavy chain and a light chain of the anti-TSLP IgG2-(CH1) Fab may be crossed or exchanged (e.g., swapped).

Anti-TSLP Constructs

In some cases, an anti-TSLP antigen binding portion can be a scFv (comprising a light chain variable region and a heavy chain variable region). In some embodiments, the anti-TSLP scFv can comprise, from N-terminus to C-terminus, an anti-TSLP heavy chain variable region associated with an anti-TSLP light chain variable region. In some embodiments, the anti-TSLP scFv can comprise, from N-terminus to C-terminus, an anti-TSLP light chain variable region associated with an anti-TSLP heavy chain variable region. In some embodiments, the heavy chain variable region and the light chain variable regions can be associated with each other via a linker.

In some embodiments, an anti-TSLP scFv can be associated with at least a portion of the heavy chain (e.g., an anti-IL-4R heavy chain variable region) or the light chain (e.g., an anti-IL-4R light chain variable region) of an anti-IL-4R moiety. In some embodiments, the anti-TSLP scFv can be associated with the N-terminus of the anti-IL-4R heavy chain variable region. In some embodiments, the anti-TSLP scFv can be associated with the N-terminus of the anti-IL-4R heavy chain constant region. In some embodiments, the anti-TSLP scFv can be associated with the C-terminus of the anti-IL-4R heavy chain variable region. In some embodiments, the anti-TSLP scFv can be associated with the C-terminus of the anti-IL-4R heavy chain constant region. In some embodiments, the anti-TSLP scFv can be associated with the N-terminus of the anti-IL-4R light chain variable region. In some embodiments, the anti-TSLP scFv can be associated with the N-terminus of the anti-IL-4R light chain constant region. In some embodiments, the anti-TSLP scFv can be associated with the C-terminus of the anti-IL-4R light chain variable region. In some embodiments, the anti-TSLP scFv can be associated with the C-terminus of the anti-IL-4R light chain constant region. In some embodiments, the anti-TSLP scFv can replace an IgG Fab of the anti-IL-4R.

In some cases, an anti-TSLP antigen binding portion can be a Fab. In some embodiments, the anti-TSLP Fab can comprise, from N-terminus to C-terminus: a first polypeptide comprising a heavy chain variable domain and a heavy chain constant domain (CH1), and a second polypeptide comprising a light chain variable domain and a light chain constant domain; a first polypeptide comprising a heavy chain constant domain (CH1) and a heavy chain variable domain, and a second polypeptide comprising a light chain constant domain and a light chain variable domain; a first polypeptide comprising a heavy chain variable domain and a light chain constant domain, and a second polypeptide comprising a light chain variable domain and a heavy chain constant domain; a first polypeptide comprising a heavy chain constant domain and a light chain variable domain, and a second polypeptide comprising a light chain constant domain and a heavy chain variable domain; or a first polypeptide comprising a heavy chain variable domain, and a second polypeptide comprising a light chain variable domain. In some embodiments, the first polypeptide and the second polypeptide associate to form an anti-TSLP binding region. In some embodiments, the anti-TSLP Fab described herein can comprise, from N-terminus to C-terminus: a first polypeptide comprising a heavy chain variable domain and a second polypeptide comprising a light chain variable domain or a first polypeptide comprising a light chain variable domain and a second polypeptide comprising a heavy chain variable domain.

In some embodiments, an anti-TSLP Fab can be associated with at least a portion of a heavy chain (e.g., a heavy chain variable domain or a heavy chain constant domain) or a light chain (e.g., a light chain variable domain or a light chain constant domain) of the anti-IL-4R moiety. In some embodiments, the anti-TSLP Fab can be associated with the N-terminus of the anti-IL-4R heavy chain variable region. In some embodiments, the anti-TSLP Fab can be associated with the N-terminus of the anti-IL-4R heavy chain constant region. In some embodiments, the anti-TSLP Fab can be associated with the C-terminus of the anti-IL-4R heavy chain variable region. In some embodiments, the anti-TSLP Fab can be associated with the C-terminus of the anti-IL-4R heavy chain constant region. In some embodiments, the anti-TSLP Fab can be associated with the N-terminus of the anti-IL-4R light chain variable region. In some embodiments, the anti-TSLP Fab can be associated with the N-terminus of the anti-IL-4R light chain constant region. In some embodiments, the anti-TSLP Fab can be associated with the C-terminus of the anti-IL-4R light chain variable region. In some embodiments, the anti-TSLP Fab can be associated with the C-terminus of the anti-IL-4R light chain constant region. In some embodiments, an anti-TSLP Fab can be disposed in between or flanked by a heavy chain and a light chain of the anti-IL-4R. For example, in some embodiments, an anti-Fab polypeptide (e.g., comprising a polypeptide comprising a light chain variable domain) can be flanked by an anti-IL-4R light chain variable domain and an anti-IL-4R light chain constant domain. In some embodiments, an anti-Fab polypeptide (e.g., comprising a polypeptide comprising a heavy chain variable domain) can be flanked by an anti-IL-4R heavy chain variable domain and an anti-IL-4R heavy chain constant domain.

In some embodiments, an anti-TSLP antigen binding region can be a domain-crossover Fab (e.g., CrossMab). For example, in some cases, an anti-TSLP antigen binding region (domain-crossover Fab) can comprise (i) Fab heavy/light crossovers (VH-CH1↔VL-CL), (ii) constant-domain crossovers (CH1↔CL), or (iii) variable-domain crossovers (VH↔VL). In some embodiments, the anti-TSLP antigen binding region with a domain-crossover Fab can comprise, from N-terminus to C-terminus: a first peptide chain comprising a light chain variable domain and a light chain constant domain and a second peptide chain comprising a heavy chain variable domain and heavy chain constant domain (CH1); or a first peptide chain comprising a light chain variable domain and a heavy chain constant domain (CH1) and a second polypeptide comprising a heavy chain variable domain and a slight chain constant domain, wherein the first peptide chain and the second peptide chain are associated with each other.

In some embodiments, the anti-TSLP antigen binding region with a domain-crossover Fab can be associated with at least a portion of a heavy chain (e.g., C-terminus or N-terminus of the heavy chain) or a light chain (e.g., C-terminus or N-terminus of the light chain) of the anti-IL-4R moiety. In some embodiments, the anti-TSLP antigen binding region with the domain-crossover Fab can be associated with the N-terminus of the anti-IL-4R heavy chain variable region. In some embodiments, the anti-TSLP antigen binding region with the domain-crossover Fab can be associated with the N-terminus of the anti-IL-4R heavy chain constant region. In some embodiments, the anti-TSLP antigen binding region with the domain-crossover Fab can be associated with the C-terminus of the anti-IL-4R heavy chain variable region. In some embodiments, the anti-TSLP antigen binding region with the domain-crossover Fab can be associated with the C-terminus of the anti-IL-4R heavy chain constant region. In some embodiments, the anti-TSLP antigen binding region with the domain-crossover Fab can be associated with the N-terminus of the anti-IL-4R light chain variable region. In some embodiments, the anti-TSLP antigen binding region with the domain-crossover Fab can be associated with the N-terminus of the anti-IL-4R light chain constant region. In some embodiments, the anti-TSLP antigen binding region with the domain-crossover Fab can be associated with the C-terminus of the anti-IL-4R light chain variable region. In some embodiments, the anti-TSLP antigen binding region with the domain-crossover Fab can be associated with the C-terminus of the anti-IL-4R light chain constant region.

In some embodiments, the anti-TSLP antigen binding region with the domain-crossover Fab can be disposed in between or flanked by a heavy chain and a light chain of the anti-IL-4R. For example, in some embodiments, the first peptide chain (e.g., comprising a light chain variable domain and a light chain constant domain or a light chain variable domain and a heavy chain constant domain (CH1)) of the anti-TSLP antigen binding region with the domain-crossover Fab can be flanked by an anti-IL-4R light chain variable domain and an anti-IL-4R light chain constant domain. In some embodiments, the second peptide chain (e.g., comprising a heavy chain variable domain and heavy chain constant domain (CH1) or a heavy chain variable domain and a slight chain constant domain) of the anti-TSLP antigen binding region with the domain-crossover Fab can be flanked by an anti-IL-4R heavy chain variable domain and an anti-IL-4R heavy chain constant domain.

In some embodiments, a polynucleotide sequence encoding the light chain or the heavy chain of the antibody (e.g., anti-IL-4R or anti-TSLP) or the antigen binding portion thereof (e.g., comprising a heavy chain variable region and a light chain variable region) can further comprise a polynucleotide sequence encoding a signal peptide. For example, in some embodiments, the polynucleotide sequence encoding the signal peptide (e.g., any one of SEQ ID NOs: 130-184) can be associated with 5'- or 3'- of the polynucleotide sequence encoding the light chain (e.g., a light chain variable region or a light chain constant region). In some embodiments, the polynucleotide sequence encoding the signal peptide can be associated with 5'- or 3'- of the polynucleotide sequence encoding the heavy chain (e.g., a heavy chain variable region, a heavy chain constant domain (CH1), or a heavy chain constant region (CH1, CH2, or CH3). In some embodiments, the polynucleotide sequence encoding the signal peptide (e.g., any one of SEQ ID NOs: 130-184) can be associated with 5'- or 3'- of the polynucleotide sequence encoding the anti-TSLP scFv (e.g., comprising a heavy chain variable region or a light chain variable region), anti-TSLP Fab (e.g., comprising a heavy chain variable region, a heavy chain CH1, a light chain variable region, or a light chain constant region), or anti-TSLP domain-crossed Fab. In some embodiments, the polynucleotide sequence encoding the signal peptide (e.g., any one of SEQ ID NOs: 130-184) can be associated with 5'- or 3'- of the polynucleotide sequence encoding the anti-IL-4R moiety light chain or heavy chain.

Anti-IL-4R Constructs

In some cases, an anti-IL-4R antigen binding portion can be a scFv (comprising a light chain variable region and a heavy chain variable region). In some embodiments, the anti-IL-4R scFv can comprise, from N-terminus to C-terminus, an anti-IL-4R heavy chain variable region associated with an anti-IL-4R light chain variable region. In some embodiments, the anti-IL-4R scFv can comprise, from N-terminus to C-terminus, an anti-IL-4R light chain variable region associated with an anti-IL-4R heavy chain variable region. In some embodiments, the heavy chain variable region and the light chain variable regions can be associated via a linker.

In some embodiments, an anti-IL-4R scFv can be associated with at least a portion of the heavy chain or the light chain of an anti-TSLP moiety. In some embodiments, the anti-IL-4R scFv can be associated with the N-terminus of the anti-TSLP moiety heavy chain variable region. In some embodiments, the anti-IL-4R scFv can be associated with the N-terminus of the anti-TSLP moiety heavy chain variable region. In some embodiments, the anti-IL-4R scFv can be associated with the N-terminus of the anti-TSLP moiety heavy chain constant region. In some embodiments, the anti-IL-4R scFv can be associated with the C-terminus of the anti-TSLP moiety heavy chain variable region. In some embodiments, the anti-IL-4R scFv can be associated with the C-terminus of the anti-TSLP moiety heavy chain constant region. In some embodiments, the anti-IL-4R scFv can be associated with the N-terminus of the anti-TSLP moiety light chain variable region. In some embodiments, the anti-IL-4R scFv can be associated with the N-terminus of the anti-TSLP moiety light chain constant region. In some embodiments, the anti-IL-4R scFv can be associated with the C-terminus of the anti-TSLP moiety light chain variable region. In some embodiments, the anti-IL-4R scFv can be associated with the C-terminus of the anti-TSLP moiety light chain constant region.

In some cases, an anti-IL-4R antigen binding portion can be a Fab. In some embodiments, the anti-IL-4R Fab can comprise, from N-terminus to C-terminus, a first polypeptide comprising a heavy chain variable domain and a heavy chain constant domain, and a second polypeptide comprising a light chain variable domain and a light chain constant domain; a first polypeptide comprising a heavy chain constant domain and a heavy chain variable domain, and a second polypeptide comprising a light chain constant domain and a light chain variable domain; a first polypeptide comprising a heavy chain variable domain and a light chain constant domain, and a second polypeptide comprising a light chain variable domain and a heavy chain constant domain; a first polypeptide comprising a heavy chain constant domain and a light chain variable domain, and a second polypeptide comprising a light chain constant domain and a heavy chain variable domain; or a first polypeptide comprising a heavy chain variable domain, and a second polypeptide comprising a light chain variable domain. In some embodiments, the first polypeptide and the second polypeptide associate to form an anti-IL-4R binding region. In some embodiments, the anti-IL-4R Fab described herein can comprise, from N-terminus to C-terminus: a first polypeptide comprising a heavy chain variable domain and a second polypeptide comprising a light chain variable domain or a first polypeptide comprising a light chain variable domain and a second polypeptide comprising a heavy chain variable domain.

In some embodiments, an anti-IL-4R Fab can be associated with at least a portion of a heavy chain (e.g. a heavy chain variable domain) or a light chain (e.g. a light chain variable domain) of the anti-TSLP moiety. In some embodiments, the anti-IL-4R Fab can be associated with the N-terminus of the anti-TSLP moiety heavy chain variable region. In some embodiments, the anti-IL-4R Fab can be associated with the N-terminus of the anti-TSLP moiety heavy chain constant region. In some embodiments, the anti-IL-4R Fab can be associated with the C-terminus of the anti-TSLP moiety heavy chain variable region. In some embodiments, the anti-IL-4R Fab can be associated with the C-terminus of the anti-TSLP moiety heavy chain constant region. In some embodiments, the anti-IL-4R Fab can be associated with the N-terminus of the anti-TSLP moiety light chain variable region. In some embodiments, the anti-IL-4R Fab can be associated with the N-terminus of the anti-TSLP moiety light chain constant region. In some embodiments, the anti-IL-4R Fab can be associated with the C-terminus of the anti-TSLP moiety light chain variable region. In some embodiments, the anti-IL-4R Fab can be associated with the C-terminus of the anti-TSLP moiety light chain constant region. In some embodiments, an anti-IL-4R Fab can be disposed in between or flanked by a heavy chain and a light chain of the anti-TSLP moiety. For example, in some embodiments, an anti-IL-4R Fab polypeptide (e.g., comprising a polypeptide comprising a light chain variable domain) can be flanked by an anti-TSLP light chain variable domain and an anti-TSLP moiety light chain constant domain. In some embodiments, an anti-IL-4R Fab polypeptide (e.g., comprising a polypeptide comprising a heavy chain variable domain) can be flanked by an anti-TSLP moiety heavy chain variable domain and an anti-TSLP moiety heavy chain constant domain.

In some embodiments, an anti-IL-4R antigen binding region can be in a domain-crossover Fab. For example, in some cases, an anti-IL-4R antigen binding region (domain-crossover Fab) can comprise (i) Fab heavy/light crossovers (VH-CH1↔VL-CL), (ii) constant-domain crossovers (CH1↔CL), or (iii) variable-domain crossovers (VH↔VL). In some embodiments, the anti-IL-4R antigen binding region with a domain-crossover Fab can comprise, from N-terminus to C-terminus: a first peptide chain comprising a light chain variable domain and a light chain constant domain and a second peptide chain comprising a heavy chain variable domain and heavy chain constant domain (CH1); or a first peptide chain comprising a light chain variable domain and a heavy chain constant domain (CH1) and a second polypeptide comprising a heavy chain variable domain and a slight chain constant domain, wherein the first peptide chain and the second peptide chain are associated with each other.

In some embodiments, the anti-IL-4R antigen binding region with the domain-crossover Fab can be associated with at least a portion of a heavy chain (e.g., C-terminal or N-terminal of the heavy chain) or a light chain (e.g., C-terminal or N-terminal of the light chain) of the anti-TSLP moiety. In some embodiments, the anti-IL-4R antigen binding region with the domain-crossover Fab can be associated with the N-terminus of the anti-TSLP heavy chain variable region. In some embodiments, the anti-IL-4R antigen binding region with the domain-crossover Fab can be associated with the N-terminus of the anti-TSLP heavy chain constant region. In some embodiments, the anti-IL-4R antigen binding region with the domain-crossover Fab can be associated with the C-terminus of the anti-TSLP heavy chain variable region. In some embodiments, the anti-IL-4R antigen binding region with the domain-crossover Fab can be associated with the C-terminus of the anti-TSLP heavy chain constant region. In some embodiments, the anti-IL-4R antigen binding region with the domain-crossover Fab can be associated with the N-terminus of the anti-TSLP light chain variable region. In some embodiments, the anti-IL-4R antigen binding region with the domain-crossover Fab can be associated with the N-terminus of the anti-TSLP light chain constant region. In some embodiments, the anti-IL-4R antigen binding region with the domain-crossover Fab can be associated with the C-terminus of the anti-TSLP light chain variable region. In some embodiments, the anti-IL-4R antigen binding region with the domain-crossover Fab can be associated with the C-terminus of the anti-TSLP light chain constant region. In some embodiments, the anti-IL-4R antigen binding region with the domain-crossover Fab can be disposed in between or flanked by a heavy chain and a light chain of the anti-TSLP. For example, in some embodiments, the first peptide chain (e.g., comprising a light chain variable domain and a light chain constant domain or a light chain variable domain and a heavy chain constant domain (CH1)) of the anti-IL-4R antigen binding region with the domain-crossover Fab can be flanked by an anti-TSLP light chain variable domain and an anti-TSLP light chain constant domain. In some embodiments, the second peptide chain (e.g., comprising a heavy chain variable domain and heavy chain constant domain (CH1) or a heavy chain variable domain and a slight chain constant domain) of the anti-IL-4R antigen binding region with the domain-crossover Fab can be flanked by an anti-TSLP heavy chain variable domain and an anti-TSLP heavy chain constant domain.

In some embodiments, a polynucleotide sequence encoding a light chain or a heavy chain of the anti-IL-4R antigen binding portion (e.g., Fab or scFv) or a polynucleotide sequence encoding the anti-TSLP moiety can further comprise a polynucleotide sequence encoding a signal peptide. For example, in some embodiments, the polynucleotide sequence encoding the signal peptide (e.g., any one of SEQ ID NOs: 130-184) can be associated with 5'- or 3'- of the polynucleotide sequence encoding an anti-IL-4R scFv (e.g., comprising a heavy chain variable region or a light chain variable region), anti-IL-4R Fab (e.g., comprising a heavy chain variable region, a heavy chain CH1, a light chain variable region, or a light chain constant region), or anti-IL-4R domain-crossed Fab. In some embodiments, the polynucleotide sequence encoding the signal peptide (e.g., any one of SEQ ID NOs: 130-184) can be associated with 5'- or 3'- the polynucleotide sequence encoding the anti-TSLP moiety light chain or heavy chain.

In some embodiments, a polynucleotide sequence encoding a light chain or a heavy chain of the anti-TSLP antigen binding portion (e.g., Fab, domain-crossed Fab, or scFv) or a polynucleotide sequence encoding the anti-IL-4R moiety can further comprise a polynucleotide sequence encoding a signal peptide. For example, in some embodiments, the polynucleotide sequence encoding the signal peptide (e.g., any one of SEQ ID NOs: 130-184) can be associated with 5'- or 3'- of the polynucleotide sequence encoding an anti-TSLP scFv (e.g., comprising a heavy chain variable region or a light chain variable region), anti-TSLP Fab (e.g., comprising a heavy chain variable region, a heavy chain CH1, a light chain variable region, or a light chain constant region), or anti-TSLP domain-crossover Fab. In some embodiments, the polynucleotide sequence encoding the signal peptide (e.g., any one of SEQ ID NOs: 130-184) can be associated with 5'- or 3'- of the polynucleotide sequence encoding a light chain or heavy chain of the anti-IL-4R moiety.

Exemplary Constructs

In some embodiments, the antigen binding moiety described herein can comprise:

B-01a (FIG. 1A)

Figure 1B:
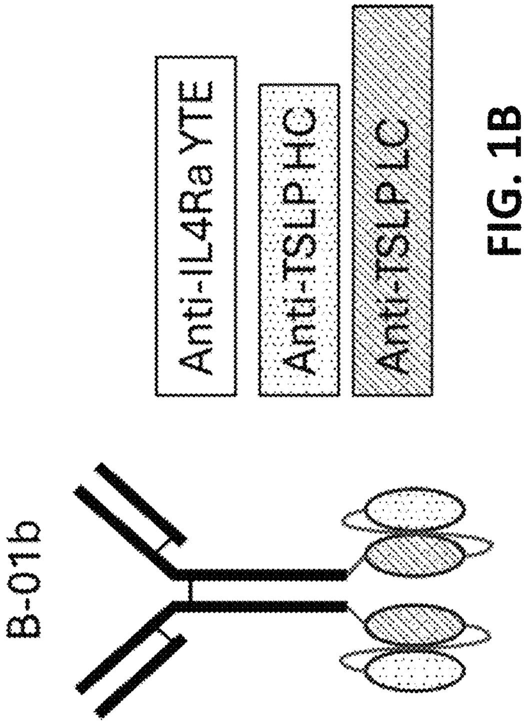

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a heavy chain variable region, an optional linker, and a light chain variable region, wherein the Fc region of the anti-IL-4R moiety is associated with the heavy chain variable region of the anti-TSLP scFv via a linker;

B-01b (FIG. 1B)

Figure 1C:
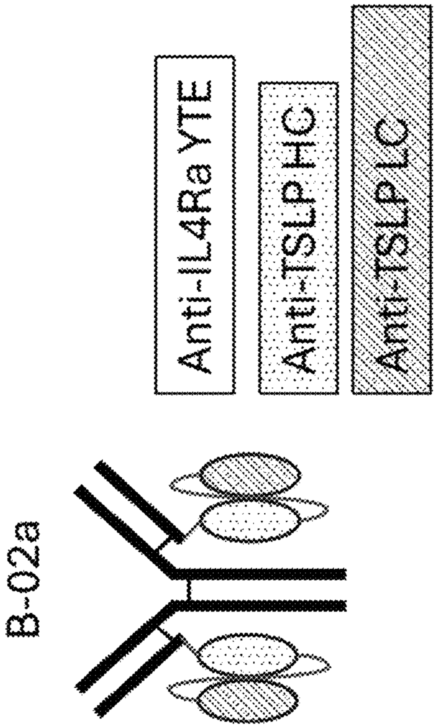

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the Fc region of the anti-IL-4R moiety is associated with the light chain variable region of the anti-TSLP scFv via a linker;

B-02a (FIG. 1C)

Figure 1D:
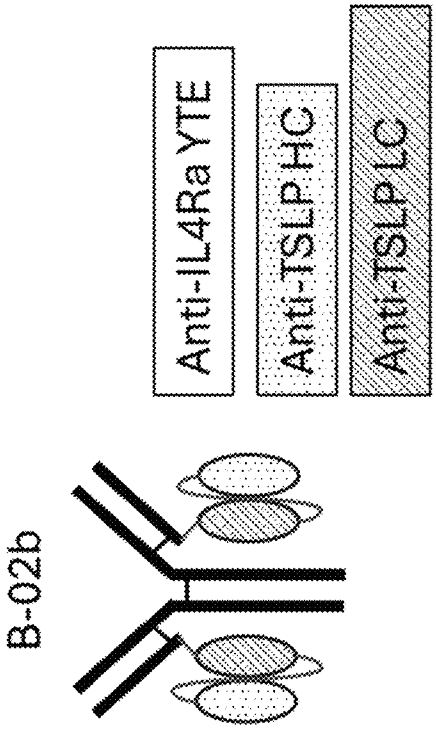

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the light chain of the anti-IL-4R moiety is associated with the heavy chain variable region of the anti-TSLP scFv via a linker;

B-02b (FIG. 1D)

Figure 3A:
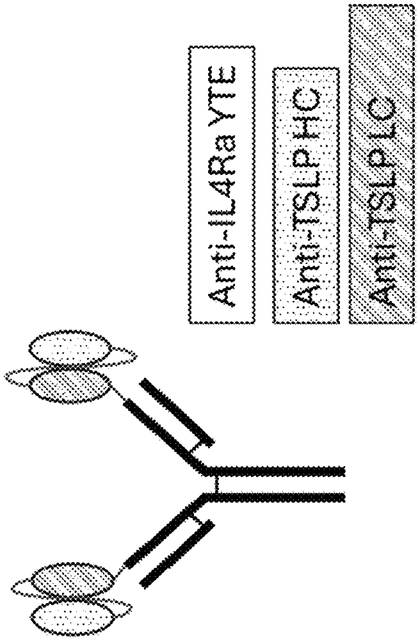
FIG. 3A-FIG. 3D show anti-TSLP scFv and anti-IL-4R construct formats.

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the light chain of the anti-IL-4R moiety is associated with the light chain variable region of the anti-TSLP scFv via a linker;

B-04a (FIG. 3A)

Figure 3B:
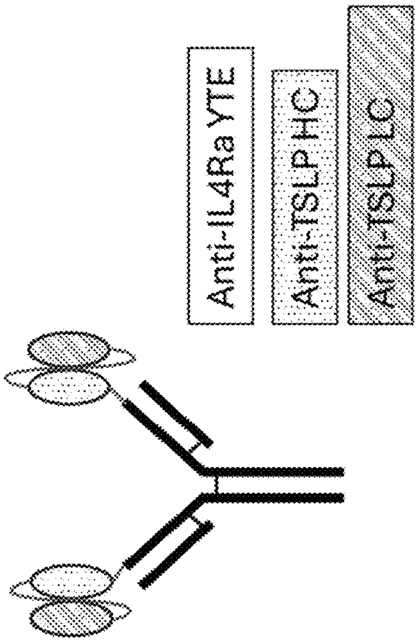

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the heavy chain of the anti-IL-4R moiety is associated with the light chain variable region of the anti-TSLP scFv via a linker;

B-04b (FIG. 3B)

Figure 3C:
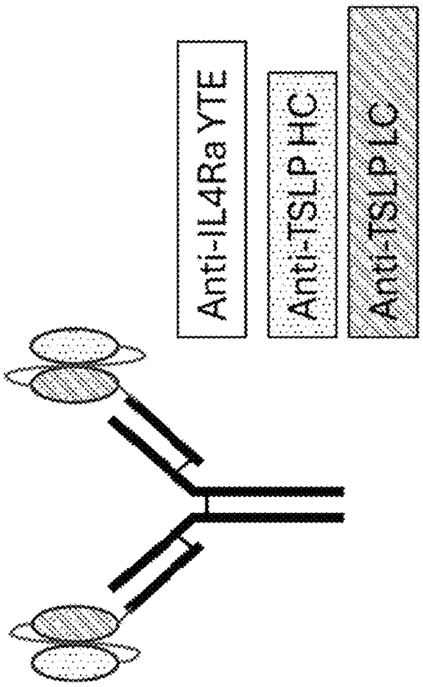

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the heavy chain of the anti-IL-4R moiety is associated with the heavy chain variable region of the anti-TSLP scFv via a linker;

B-05a (FIG. 3C)

Figure 3D:
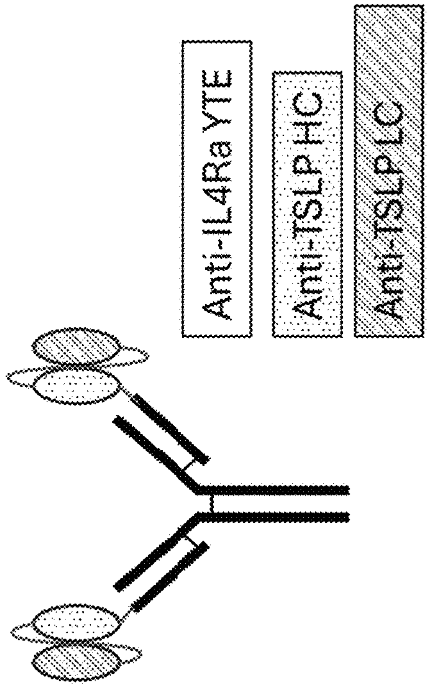

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein the light chain of the anti-IL-4R moiety is associated with the light chain variable region of the anti-TSLP scFv via a linker; or B-05b (FIG. 3D)

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises, a light chain variable region, an optional linker, and a heavy chain variable region, wherein the light chain of the anti-IL-4R moiety is associated with the heavy chain variable region of the anti-TSLP scFv via a linker.

In some embodiments, the anti-IL-4R heavy chain variable region and the anti-IL-4R light chain variable region associate to form an IL-4R binding region. In some embodiments, the first anti-IL-4R heavy chain constant region and the second anti-IL-4R heavy chain constant region can be associated with each other. In some embodiments, a moiety disclosed herein comprises one or more Fc modifications. In some embodiments, the one or more Fc modifications comprises a half-life extension modification. In some embodiments, the half-life extension modification is a YTE modification. In some embodiments, the Fc region described herein can have a first modified Fc polypeptide and a second modified Fc polypeptide, where the first modified Fc polypeptide comprises a knob modification and the second modified Fc polypeptide comprises a hole modification.

Figure 2A:
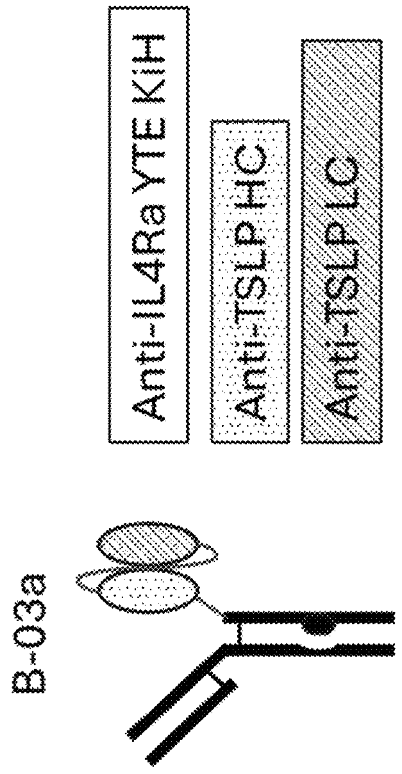
FIG. 2A and FIG. 2B show constructs where one Fab of the anti-IL-4R moiety is replaced by an anti-TSLP scFv.

In some embodiments, the antigen binding moiety described herein can comprise:

B-03a (FIG. 2A)

Figure 2B:
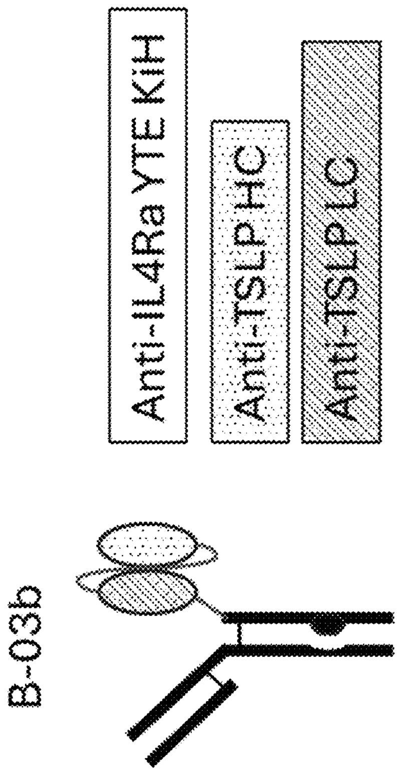

(1) an anti-IL-4R moiety comprising a light chain variable region, a light chain constant region, a heavy chain variable region and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a light chain variable region, an optional linker, and a heavy chain variable region, wherein a portion of the heavy chain region of the anti-IL-4R moiety is associated with the heavy chain variable region of the anti-TSLP scFv via a linker (e.g. the anti-TSLP scFv may replace at least a portion of the anti-IL-4R moiety's Fab); in some embodiments, the antigen binding moiety comprises (1) a light chain of the anti-IL-4R moiety, (2) a heavy chain of the anti-IL-4R moiety, and (3) an anti-TSLP scFv associated with (via a linker) at least a portion of heavy chain constant region of the anti-IL-4R moiety (e.g., a Fc region of the anti-IL-4R moiety); in some embodiments, the Fc region described herein can have a first modified Fc polypeptide and a second modified Fc polypeptide, where the first modified Fc polypeptide comprises a knob modification and the second modified Fc polypeptide comprises a hole modification; or B-03b (FIG. 2B)

(1) an anti-IL-4R moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-TSLP scFv (optionally further comprising a signal peptide), wherein the anti-TSLP scFv comprises a heavy chain variable region, an optional linker, and a light chain variable region, wherein a portion of the heavy chain region of the anti-IL-4R moiety is associated with the light chain variable region of the anti-TSLP scFv via a linker (e.g. the anti-TSLP scFv may replace at least a portion of the anti-IL-4R moiety's Fab); in some embodiments, the antigen binding moiety comprises (1) a light chain of the anti-IL-4R moiety, (2) a heavy chain of the anti-IL-4R moiety, and (3) an anti-TSLP scFv associated with (via a linker) at least a portion of heavy chain constant region of the anti-IL-4R moiety (e.g., a Fc region of the anti-IL-4R moiety); in some embodiments, the Fc region described herein can have a first modified Fc polypeptide and a second modified Fc polypeptide, where the first modified Fc polypeptide comprises a knob modification and the second modified Fc polypeptide comprises a hole modification.

In some embodiments, the anti-IL-4R heavy chain variable region and the anti-IL-4R light chain variable region associate to form an IL-4R binding region. In some embodiments, the first anti-IL-4R heavy chain constant region and the second anti-IL-4R heavy chain constant region are associated with each other. In some embodiments, a moiety disclosed herein comprises one or more Fc modifications. In some embodiments, the one or more Fc modifications comprises a half-life extension modification. In some embodiments, the half-life extension modification is a YTE modification. In some embodiments, the Fc region described herein can have a first modified Fc polypeptide and a second modified Fc polypeptide, where the first modified Fc polypeptide comprises a knob modification and the second modified Fc polypeptide comprises a hole modification.

In some embodiments, the antigen binding moiety described herein can be any variants of the exemplary constructs described herein. For example, in some embodiments, the variant can comprise (1) an anti-TSLP comprising a heavy chain and alight chain, and (2) an anti-IL-4R scFv.

In some embodiments, an anti-IL-4R scFv can be associated with the N-terminus of an anti-TSLP heavy chain. In some embodiments, an anti-IL-4R scFv can be associated with the C-terminus of the anti-TSLP heavy chain. In some embodiments, an anti-IL-4R scFv can be associated with the N-terminus of the anti-TSLP light chain. In some embodiments, an anti-IL-4R scFv can be associated with the C-terminus of the anti-TSLP light chain.

Figure 8A:
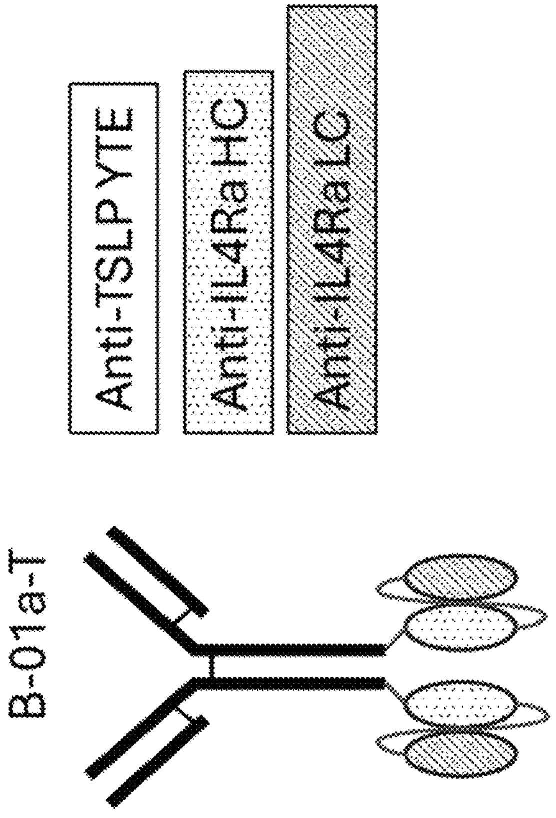
FIG. 8A-FIG. 8D show anti-IL-4R scFv and anti-TSLP construct formats.

In some embodiments, the antigen binding moiety described herein can comprise:

B-01a-variant (FIG. 8A)

Figure 8B:
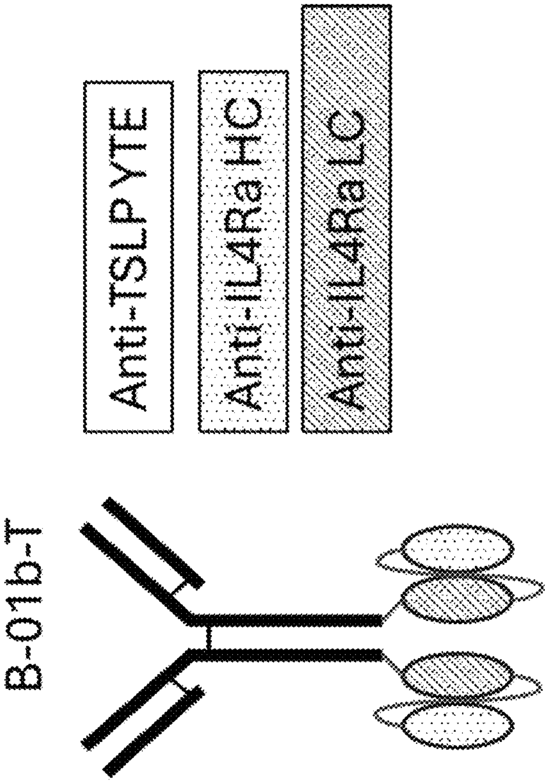
Figure 8C:
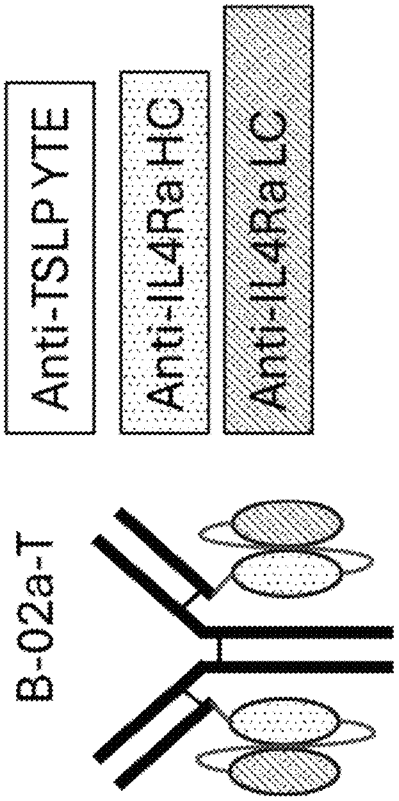

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv, wherein the anti-IL-4R scFv comprises a heavy chain variable region, an optional linker, and a light chain variable region, wherein the Fc region of the anti-TSLP moiety (e.g., C-terminus of the Fc region) is associated with the heavy chain variable region of the anti-IL-4R scFv via a linker;

B-01b-variant (FIG. 8B)

an anti-TSLP moiety comprising a light chain variable region, a light chain constant region, a heavy chain variable region, and a heavy chain constant region, wherein the light chain variable region or a heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, wherein the Fc region of the anti-TSLP moiety (e.g., C-terminus of the Fc region) is associated with the light chain variable region of the anti-IL-4R scFv via a linker;

B-02a-variant (FIG. 8C)

Figure 8D:
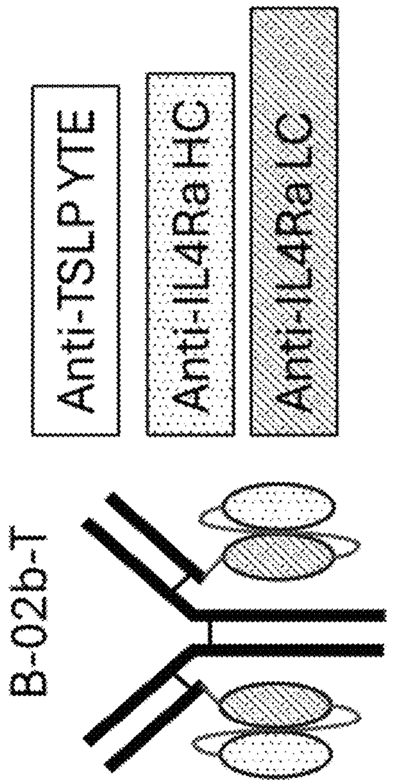

(1) an anti-TSLP moiety comprising a light chain variable region, a light chain constant region, a heavy chain variable region, and a heavy chain constant region, wherein the light chain variable region or a heavy chain variable region further comprises an optional signal peptide, (2) an optional linker, and (3) an anti-IL-4R scFv (optionally further comprising a signal peptide), wherein the anti-IL-4R scFv comprises a heavy chain variable region, an optional linker, and a light chain variable region, wherein the light chain of the anti-TSLP moiety (e.g., C-terminus of the light chain) is associated with the heavy chain variable region of the anti-IL-4R scFv via a linker;

B-02b-variant (FIG. 8D)

Figure 10A:
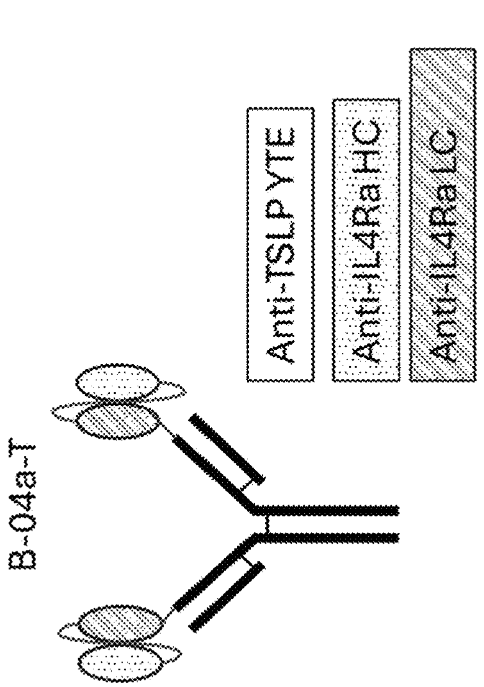
FIG. 10A-FIG. 10D show anti-IL-4R scFv and anti-TSLP construct formats.

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, wherein the light chain of the anti-TSLP moiety (e.g., C-terminus of the light chain) is associated with the light chain variable region of the anti-IL-4R scFv via a linker;

B-04a-variant (FIG. 10A)

Figure 10B:
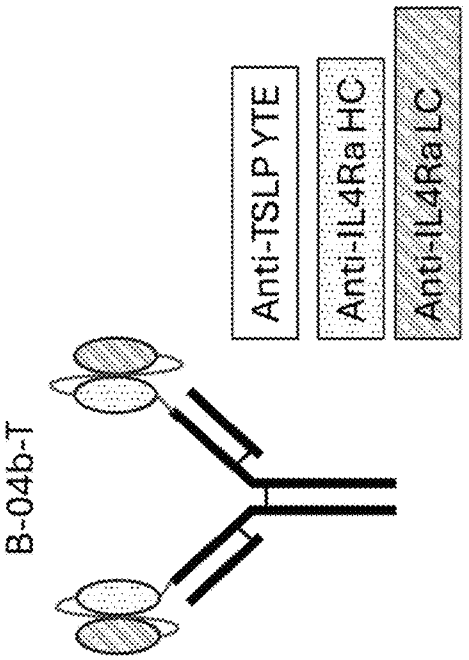

(1) an anti-TSLP moiety comprising a light chain variable region, a light chain constant region, a heavy chain variable region and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a heavy chain variable region, an optional linker, and a light chain variable region, wherein the heavy chain of the anti-TSLP moiety (e.g., N-terminus of the heavy chain) is associated with the light chain variable region of the anti-IL-4R scFv via a linker;

B-04b-variant (FIG. 10B)

Figure 10C:
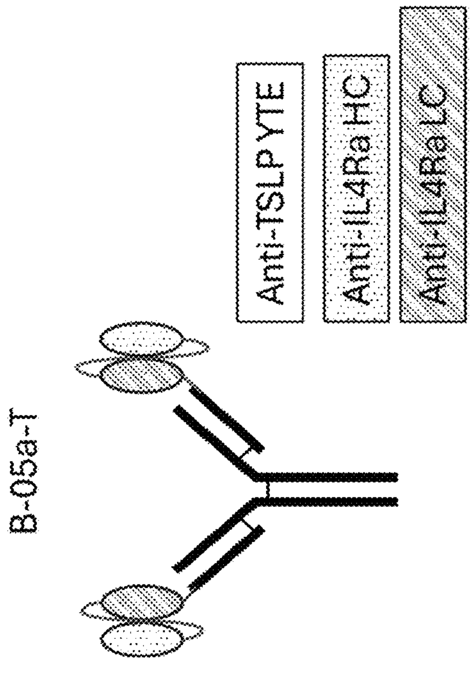

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, wherein the heavy chain of the anti-TSLP moiety (e.g., N-terminus of the heavy chain) is associated with the heavy chain variable region of the anti-IL-4R scFv via a linker;

B-05a-variant (FIG. 10C)

Figure 10D:
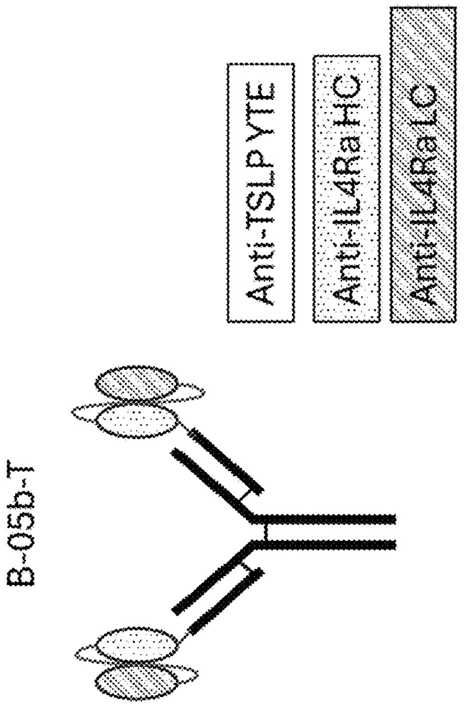
Figure 11A:
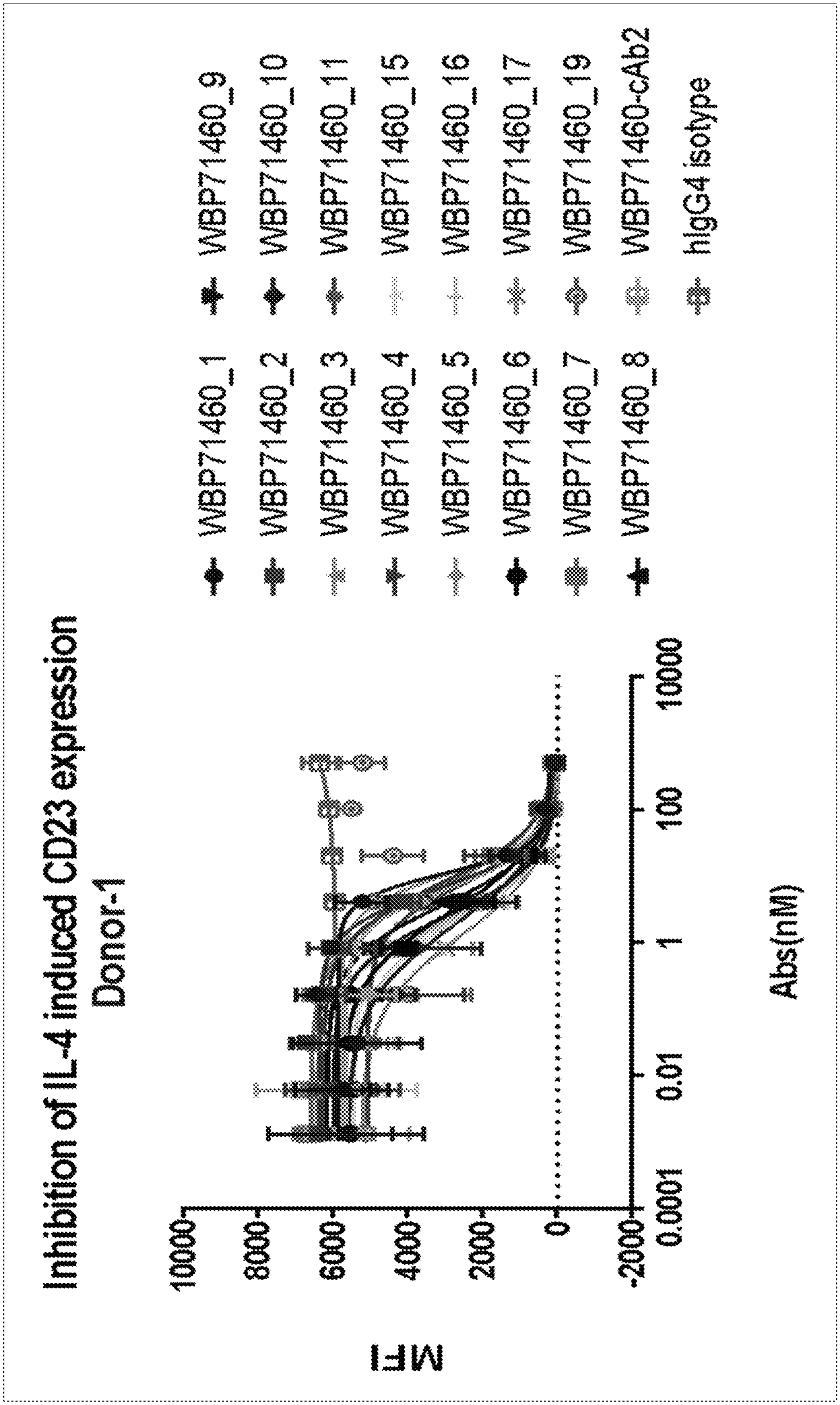
FIG. 11A shows the inhibition of IL-4-induced CD23 expression in CD19+ cells from Donor 1 by each candidate antigen binding moiety.
Figure 11B:
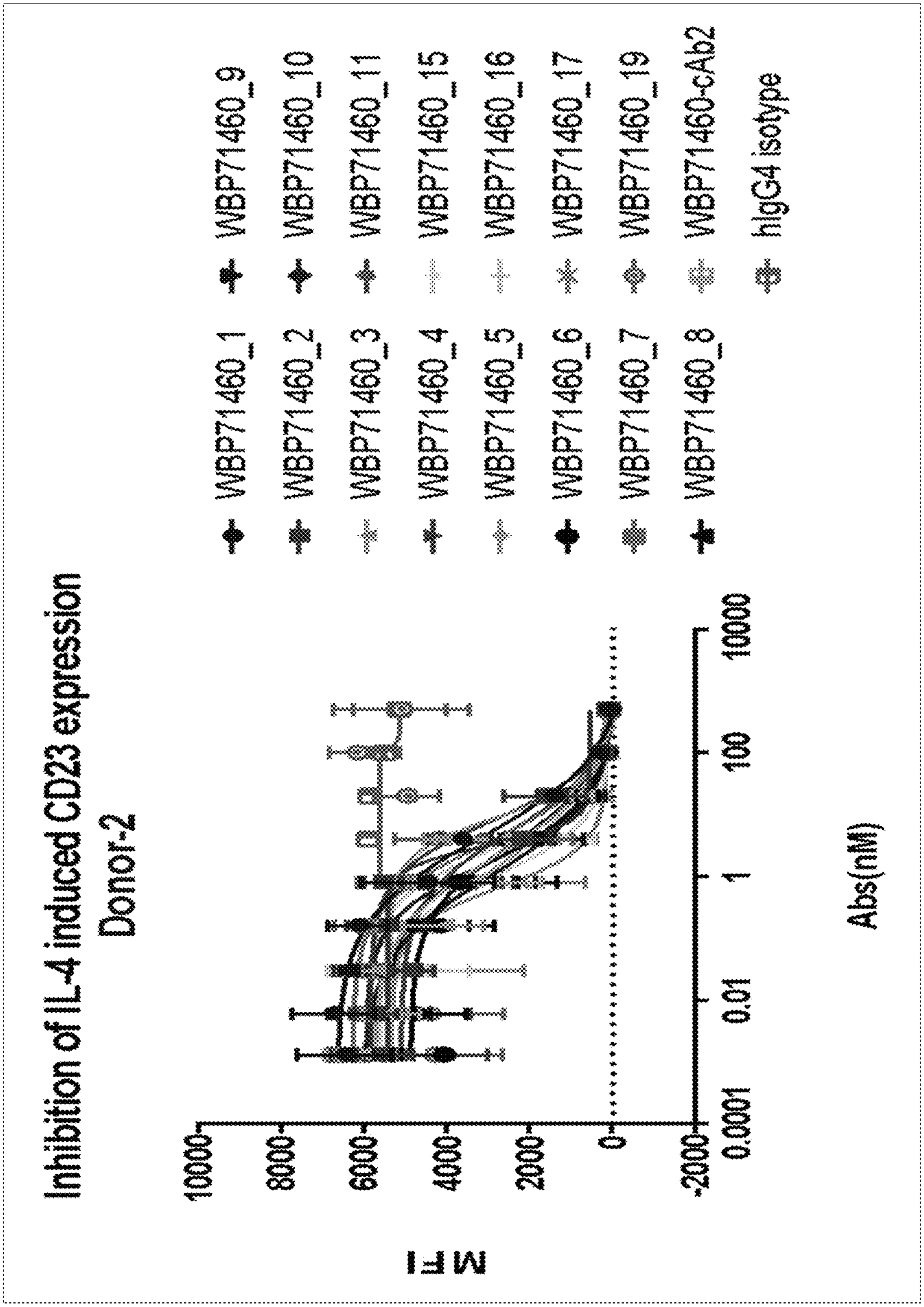
FIG. 11B shows the inhibition of IL-4-induced CD23 expression in CD19+ cells from Donor 2 by each candidate antigen binding moiety. Data are expressed as median fluorescent intensity of CD23.
Figure 12A:
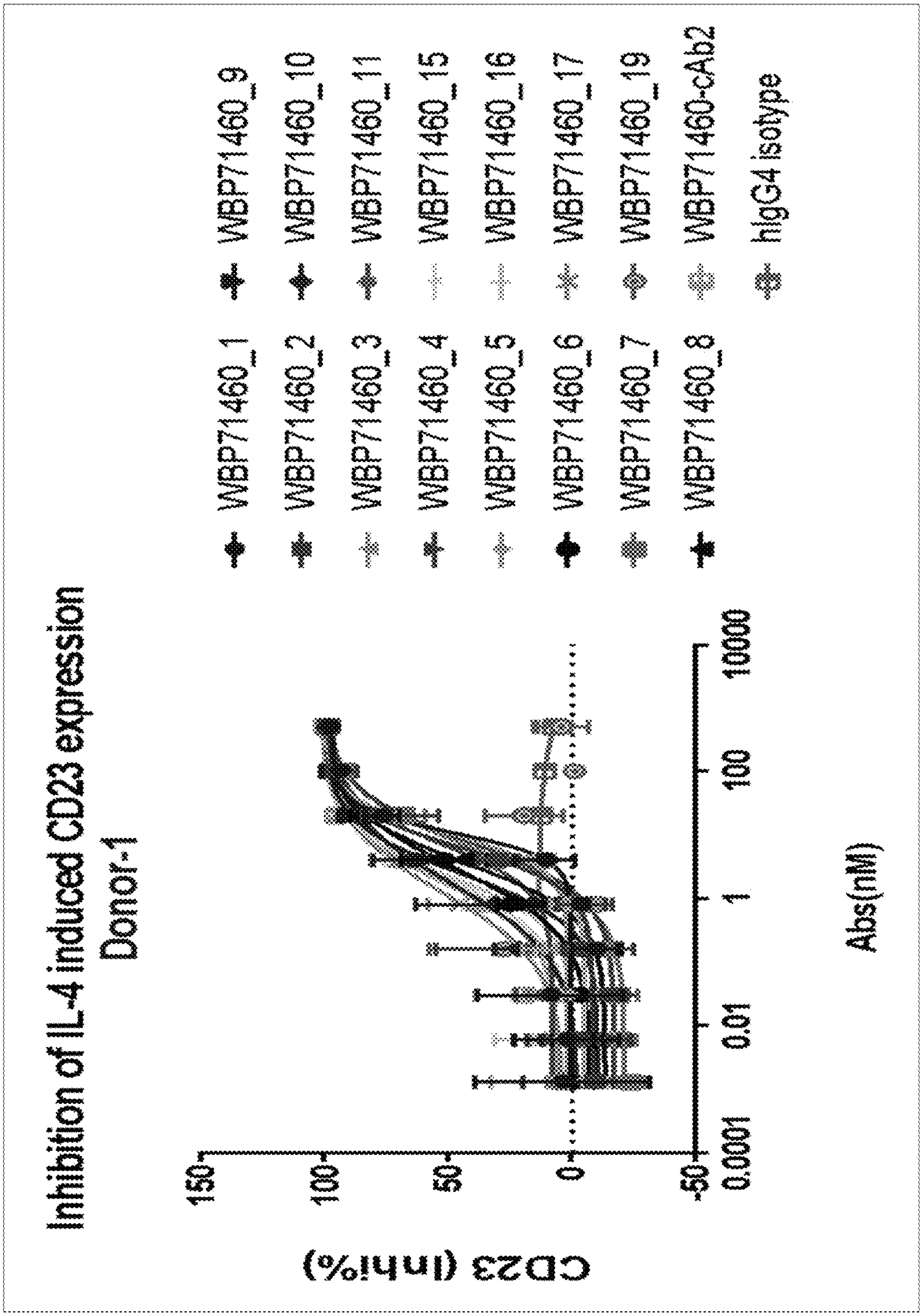
FIG. 12A and FIG. 12B show the percentage inhibition of IL-4 induced CD23 expression in CD19+ cells from Donors 1 (FIG. 12A) and Donor 2 (FIG. 12B).
Figure 12B:
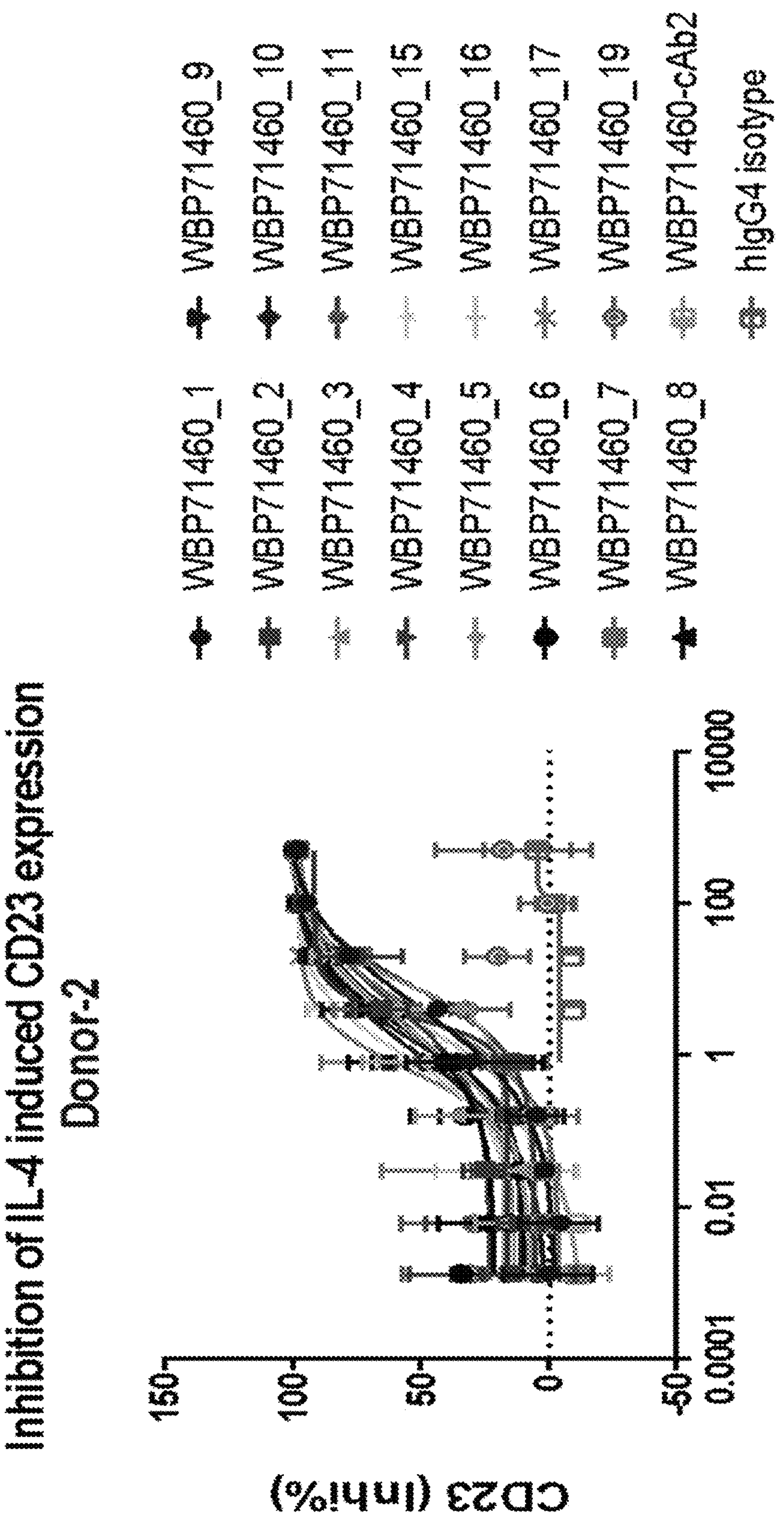

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a heavy chain variable region, an optional linker, and a light chain variable region, wherein the light chain of the anti-TSLP moiety (e.g., N-terminus of the light chain) is associated with the light chain variable region of the anti-IL-4R scFv via a linker; or B-05b-variant (FIG. 10D)

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, wherein the light chain of the anti-IL-4R moiety (e.g., N-terminus of the light chain) is associated with the heavy chain variable region of the anti-IL-4R scFv via a linker.

In some embodiments, the anti-TSLP heavy chain variable region and the anti-TSLP light chain variable region associate to form a TSLP binding region. In some embodiments, the first anti-TSLP heavy chain constant region and the second anti-TSLP heavy chain constant region are associated with each other. In some embodiments, a moiety disclosed herein comprises one or more Fc modifications. In some embodiments, the one or more Fc modifications comprises a half-life extension modification. In some embodiments, the half-life extension modification is a YTE modification. In some embodiments, the Fc region described herein can have a first modified Fc polypeptide and a second modified Fc polypeptide, where the first modified Fc polypeptide comprises a knob modification and the second modified Fc polypeptide comprises a hole modification.

Figure 9B:
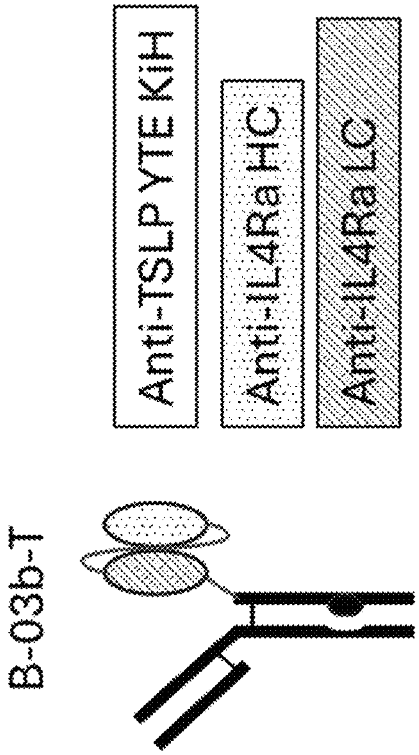
FIG. 9A and FIG. 9B show constructs where one Fab of the anti-TSLP moiety is replaced by an anti-IL-4R scFv.
Figure 9A:
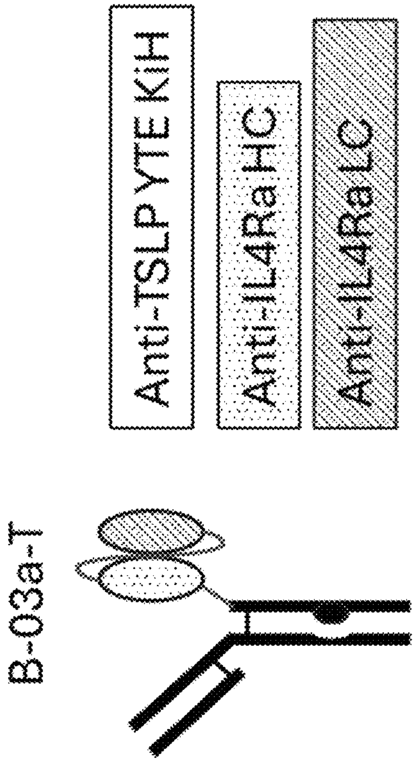

In some embodiments, the antigen binding moiety described herein can comprise:

B-03a-variant (FIG. 9A)

(1) an anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, wherein a portion of the heavy chain of the anti-TSLP moiety is associated with the heavy chain variable region of the anti-IL-4R scFv via a linker (e.g. the anti-IL-4R scFv may replace at least a portion of the anti-TSLP moiety's Fab); in some embodiments, the antigen binding moiety comprises (1) a light chain of the anti-TSLP moiety, (2) a heavy chain of the anti-TSLP moiety, and (3) an anti-IL-4R scFv associated with (via a linker) at least a portion of heavy chain constant region of the anti-TSLP moiety (e.g., a Fc region of the anti-TSLP moiety); in some embodiments, the Fc region described herein can have a first modified Fc polypeptide and a second modified Fc polypeptide, where the first modified Fc polypeptide comprises a knob modification and the second modified Fc polypeptide comprises a hole modification; or B-03b-variant (FIG. 9B)

An anti-TSLP moiety comprising a light chain variable region, a light chain constant region, a heavy chain variable region, and a heavy chain constant region, wherein the light chain variable region or the heavy chain variable region further comprises an optional signal peptide, (2) an optional linker, and (3) an anti-IL-4R scFv (optionally further comprising a signal peptide), wherein the anti-IL-4R scFv comprises a light chain variable region, an optional linker, and a heavy chain variable region, an optional linker, and a light chain variable region, wherein a portion of the heavy chain of the anti-TSLP moiety is associated with the light chain variable region of the anti-IL-4R scFv via a linker (e.g. the anti-IL-4R scFv may replace at least a portion of the anti-TSLP moiety's Fab); in some embodiments, the antigen binding moiety comprises (1) alight chain of the anti-TSLP moiety, (2) a heavy chain of the anti-TSLP moiety, and (3) an anti-IL-4R scFv associated with (via a linker) at least a portion of heavy chain constant region of the anti-TSLP moiety (e.g., a Fc region of the anti-TSLP moiety); in some embodiments, the Fc region described herein can have a first modified Fc polypeptide and a second modified Fc polypeptide, where the first modified Fc polypeptide comprises a knob modification and the second modified Fc polypeptide comprises a hole modification.

In some embodiments, the anti-TSLP heavy chain variable region and the anti-TSLP light chain variable region associate to form a TSLP binding region. In some embodiments, the first heavy chain constant region and the second heavy chain constant region are associated with each other. In some embodiments, a moiety disclosed herein comprises one or more Fc modifications. In some embodiments, the one or more Fc modifications comprises a half-life extension modification. In some embodiments, the half-life extension modification is a YTE modification. In some embodiments, the Fc region described herein can have a first modified Fc polypeptide and a second modified Fc polypeptide, where the first modified Fc polypeptide comprises a knob modification and the second modified Fc polypeptide comprises a hole modification.

Anti-TSLP IL-4R Fab

The antigen binding moiety described herein can comprise (1) an anti-IL-4R moiety comprising a heavy chain and a light chain, and (2) an anti-TSLP Fab, wherein the anti-TSLP Fab is associated with N- or C-terminus of the heavy chain or the light chain of the anti-IL-4R moiety. In some embodiments, the antigen binding moiety described herein can comprise (1) an anti-TSLP moiety comprising a heavy chain and a light chain, and (2) an anti-IL-4R Fab, wherein the anti-IL-4R Fab is associated with N- or C-terminus of the heavy chain or the light chain of the anti-TSLP moiety.

In some embodiments, the anti-TSLP Fab can be associated with the N-terminus of the heavy chain and light chain of the anti-IL-4R moiety. In some embodiments, the anti-TSLP Fab can be associated with the C-terminus of the heavy chain and light chain of the anti-IL-4R moiety. In some embodiments, the anti-TSLP Fab can be disposed in between or flanked by two domains of the anti-IL-4R moiety. For example, in some embodiments, anti-TSLP Fab (e.g., comprising a heavy chain variable region of an anti-TSLP) can be flanked by a first constant domain and a second constant domain of the heavy chain constant region of an anti-IL-4R moiety. In some embodiments, anti-TSLP Fab (e.g., comprising a heavy chain variable region of an anti-TSLP), can be flanked by a second constant domain and a third constant domain of a heavy chain constant region of an anti-IL-4R moiety. For example, in some embodiments, anti-TSLP Fab (e.g., comprising a light chain variable region of an anti-TSLP), can be flanked by a constant domain and a variable domain of the anti-IL-4R light chain.

In some embodiments, the anti-IL-4R Fab can be associated with the N-terminus of the heavy chain and light chain of the anti-TSLP. In some embodiments, the anti-IL-4R Fab can be associated with the C-terminus of the heavy chain and light chain of the anti-TSLP moiety. In some embodiments, the anti-IL-4R Fab can be disposed in between or flanked by two domains of the anti-TSLP moiety. For example, in some embodiments, anti-IL-4R Fab (e.g., comprising a heavy chain variable region of an anti-IL-4R) can be flanked by a first constant domain and a second constant domain of the heavy chain constant region of an anti-TSLP moiety. In some embodiments, anti-IL-4R Fab (e.g., comprising a heavy chain variable region of an anti-IL-4R), can be flanked by a second constant domain and a third constant domain of a heavy chain constant region of an anti-TSLP moiety. For example, in some embodiments, anti-IL-4R Fab (e.g., comprising a light chain variable region of an anti-IL-4R), can be flanked by a constant domain and a variable domain of the anti-TSLP light chain.

Figure 4A:
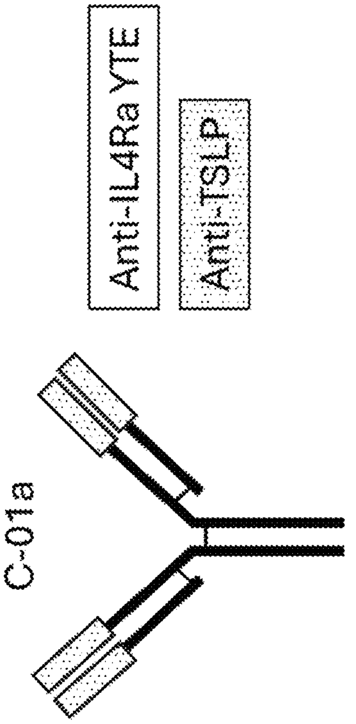
FIG. 4A-FIG. 4F show anti-TSLP Fab or anti-IL-4R Fab construct formats on anti-IL-4R or anti-TSLP, respectively.

In some embodiments, the antigen binding moiety described herein can comprise:

C-01a (FIG. 4A)

Figure 4B:
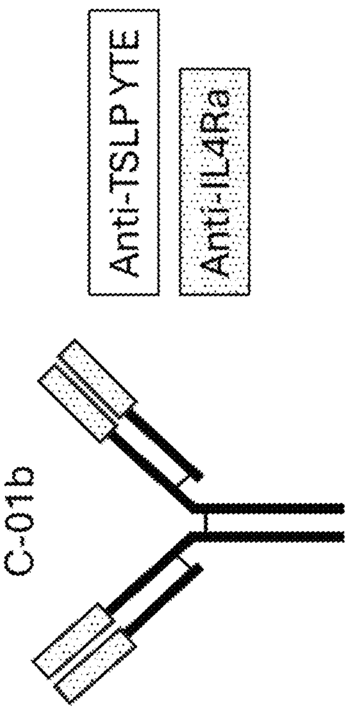

(1) an anti-IL-4R moiety comprising a light chain variable region, a light chain constant region, a heavy chain variable region, and a heavy chain constant region, wherein the light chain variable region or the heavy chain variable region further comprises an optional signal peptide, and (2) an anti-TSLP Fab (optionally further comprising a signal peptide), wherein the anti-TSLP Fab is associated with the heavy chain and light chain of the Anti-IL-4R moiety;

C-01b (FIG. 4B)

Figure 4C:
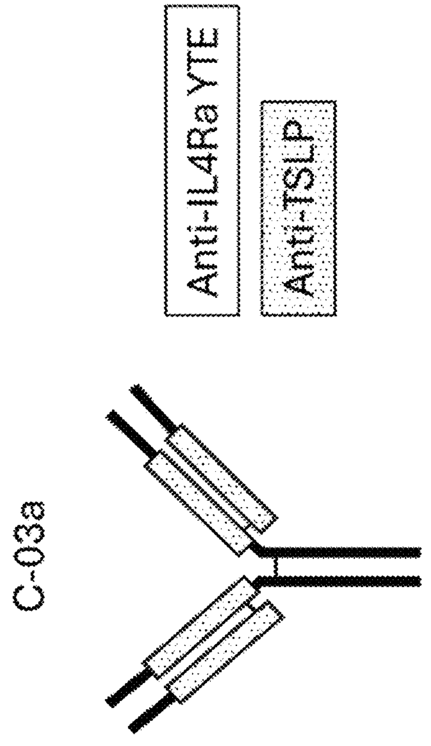
Figure 4D:
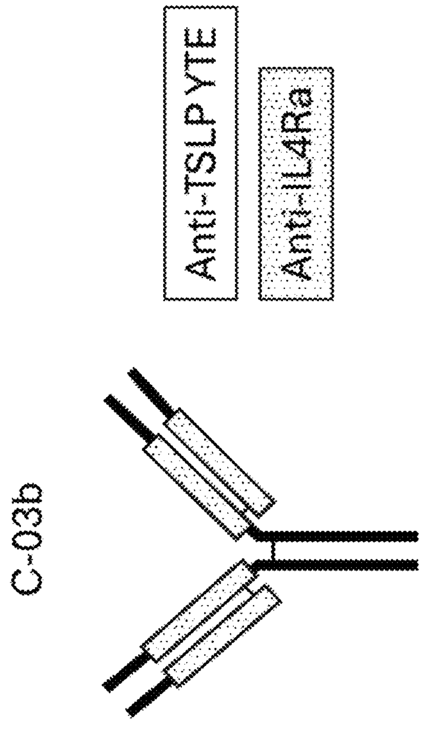
Figure 4E:
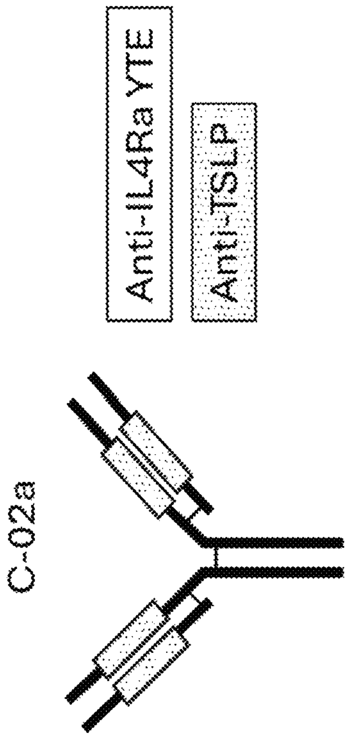

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab (optionally further comprising a signal peptide), wherein the anti-IL4 Fab is associated with the heavy chain and light chain of the Anti-IL-4R moiety;

C-02a (FIG. 4E)

Figure 4F:
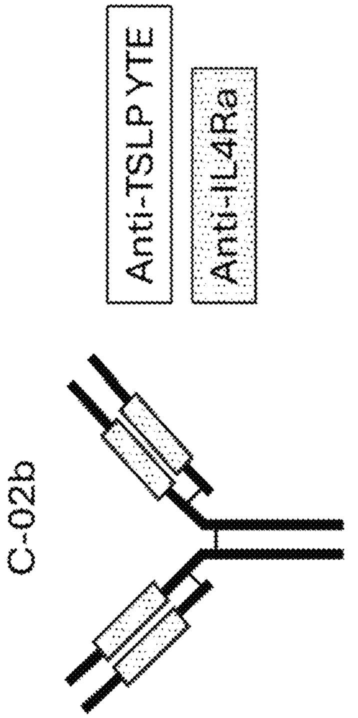

(1) an anti-IL-4R moiety comprising a light chain variable region, a light chain constant region, a heavy chain variable region and, a heavy chain constant region, wherein the light chain variable region or the heavy chain variable region further comprises an optional signal peptide, and (2) an anti-TSLP Fab, wherein the anti-TSLP Fab is within the light chain and heavy chain of the anti-IL-4R moiety;

C-02b (FIG. 4F)

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab, wherein the anti-IL4 Fab is within the heavy chain and light chain of the Anti-IL-4R moiety;

C-03a (FIG. 4C)

(1) an anti-IL-4R moiety comprising a light chain variable region, a light chain constant region, a heavy chain variable region, and a heavy chain constant region, wherein the light chain variable region or the heavy chain variable region further comprises an optional signal peptide, and (2) an anti-TSLP Fab, wherein the anti-TSLP Fab is within the light chain and heavy chain of the anti-IL-4R moiety;

C-03b (FIG. 4B)

Figure 5B:
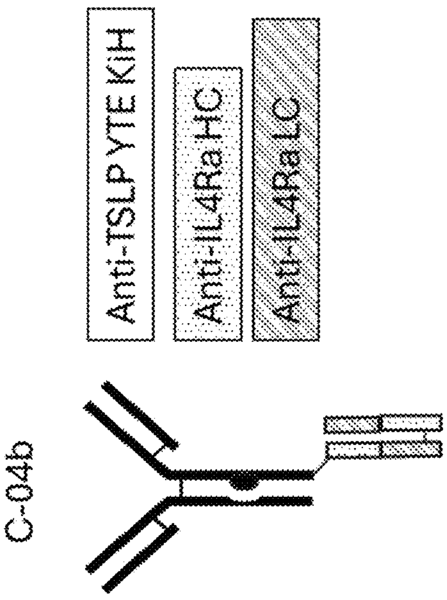
FIG. 5A-FIG. 5G show anti-TSLP Fab or anti-IL-4R Fab construct formats on anti-IL-4R or anti-TSLP respectively.
Figure 5A:
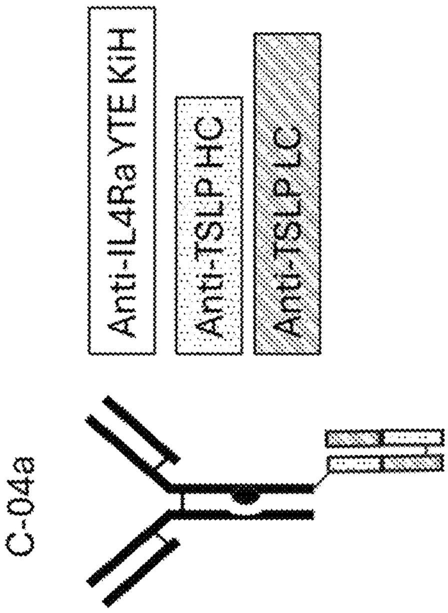

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab, wherein the anti-IL4 Fab is within the heavy chain and light chain of the Anti-IL-4R moiety;

C-04a (FIG. 5A)

(1) an anti-IL-4R moiety comprising a light chain variable region, a light chain constant region, a heavy chain variable region, and a heavy chain constant region, wherein the light chain variable region or the heavy chain variable region further comprises an optional signal peptide, and (2) an anti-TSLP Fab (optionally further comprising a signal peptide), wherein the heavy chain of the anti-TSLP Fab is associated with the Fc region of the anti-IL-4R moiety, in some embodiments, the Fc region described herein can have a first modified Fc polypeptide and a second modified Fc polypeptide, where the first modified Fc polypeptide comprises a knob modification and the second modified Fc polypeptide comprises a hole modification;

C-04b (FIG. 5B)

Figure 5C:
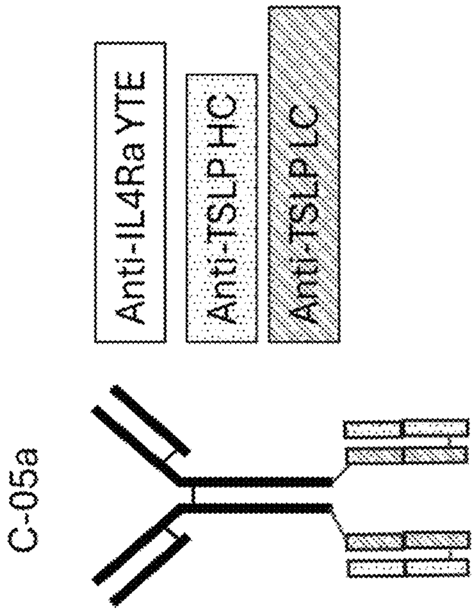

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab (optionally further comprising a signal peptide), wherein the heavy chain of the anti-IL-4R Fab is associated with the Fc region of the anti-TSLP moiety, in some embodiments, the Fc region described herein can have a first modified Fc polypeptide and a second modified Fc polypeptide, where the first modified Fc polypeptide comprises a knob modification and the second modified Fc polypeptide comprises a hole modification;

C-05a (FIG. 5C)

Figure 5D:
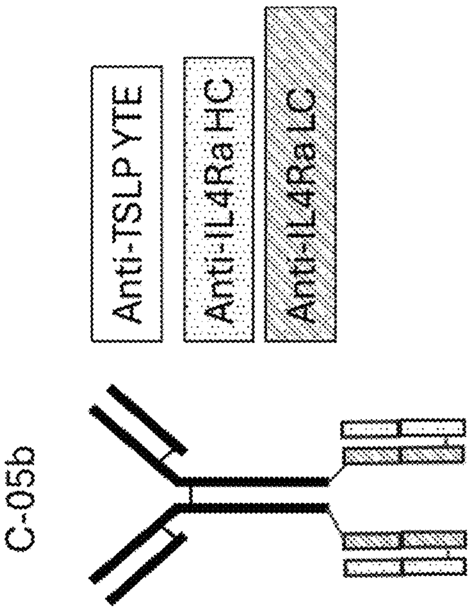

(1) an anti-IL-4R moiety comprising a light chain variable region, a light chain constant region, a heavy chain variable region, and a heavy chain constant region (e.g., CH1, CH2, and CH3), wherein the light chain variable region or the heavy chain variable region further comprises an optional signal peptide, and (2) an anti-TSLP Fab (optionally further comprising a signal peptide), wherein the light chain of the anti-TSLP Fab is associated with the Fc region at the C-terminus of the anti-IL-4R moiety;

C-05b (FIG. 5D)

Figure 5E:
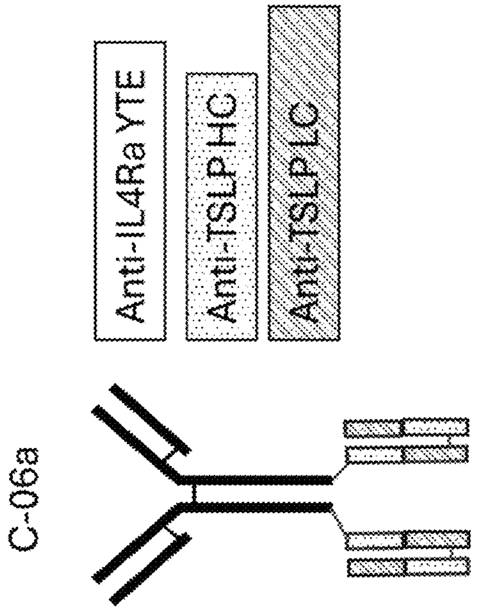

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab (optionally further comprising a signal peptide), wherein the light chain of the anti-IL-4R Fab is associated with the Fc region of the anti-TSLP moiety;

C-06a (FIG. 5E)

Figure 5F:
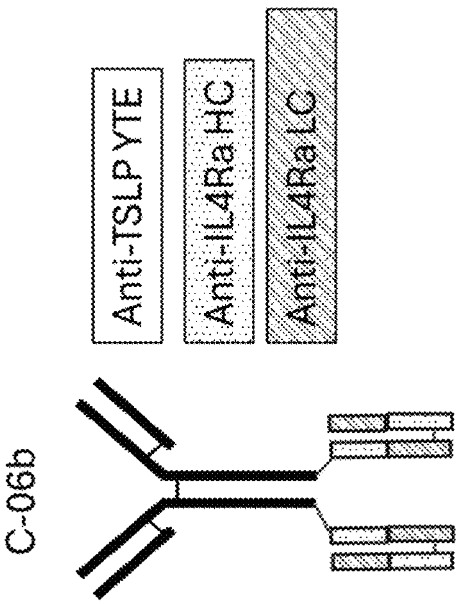

(1) an anti-IL-4R moiety comprising a light chain variable region, a light chain constant region, a heavy chain variable region, and a heavy chain constant region, wherein the light chain variable region or the heavy chain variable region further comprises an optional signal peptide, and (2) an anti-TSLP Fab (optionally further comprising a signal peptide), wherein the heavy chain of the anti-TSLP Fab is associated with the Fc region of the anti-IL-4R moiety;

C-06b (FIG. 5F)

Figure 5G:
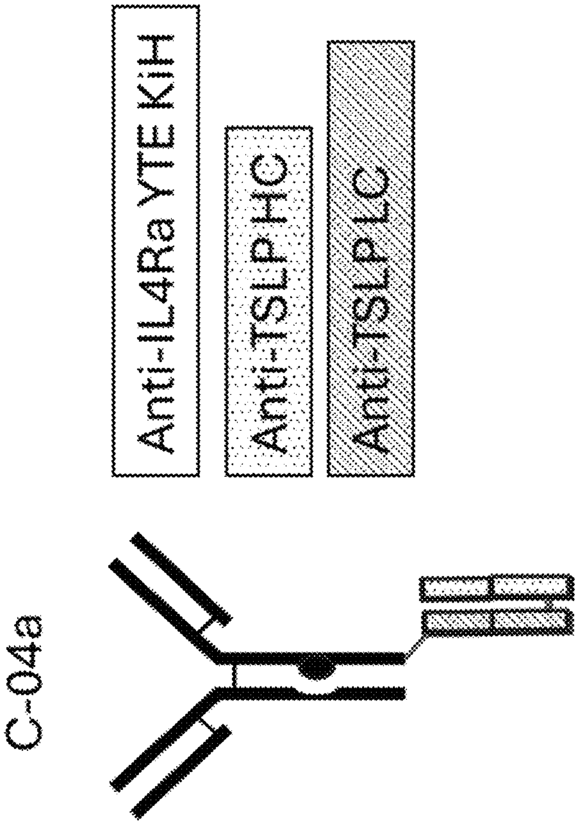

(1) an anti-TSLP moiety comprising a light chain variable region, a light chain constant region, a heavy chain variable region, and a heavy chain constant region, wherein the light chain variable region or the heavy chain variable region further comprises an optional signal peptide, and (2) an anti-IL-4R Fab (optionally further comprising a signal peptide), wherein the heavy chain of the anti-IL-4R Fab is associated with the Fc region of the anti-TSLP moiety; or C-04a (FIG. 5G)

(1) an anti-IL-4R moiety comprising a light chain variable region, a light chain constant region, a heavy chain variable region, and a heavy chain constant region, wherein the light chain variable region or the heavy chain variable region further comprises an optional signal peptide, and (2) an anti-TSLP Fab (optionally further comprising a signal peptide), wherein the light chain of the anti-TSLP Fab is associated with one of the Fc polypeptides of the Fc region of the anti-IL-4R moiety, wherein the Fc region comprises knob-in-hole configuration.

In some embodiments, the antigen binding molecules described herein (e.g., FIGS. 5A-5F) comprising the anti-TSLP Fab or the anti-TSLP Fab with a domain-cross Fab (or the anti-IL-4R Fab or the anti-IL-4R Fab with a domain-cross Fab (e.g., CrossMab) format to avoid light chain mispairing) can comprise one or more modifications. In some embodiments, the domain-cross Fab (e.g., CrossMab) format can comprise a crossover of antibody domains within one arm of a bispecific IgG antibody enabling correct chain association, whereas correct heterodimerization of the heavy chains can be achieved by the knob-into-hole technology or charge interactions. For example, in some embodiments, the antigen binding molecules described herein can comprise a cross over of Fab domains (Fab heavy/light crossovers (VH-CH1⇔VL-CL or CrossMab$^{Fab}$ format), or the variable VH-VL domains (variable-domain crossovers (VH⇔VL) or CrossMab$^{VH-VL}$ format) or the constant CH1-CL domains (constant-domain crossovers (CH1⇔CL) or CrossMab$^{CH1-CL}$ format) within the Fab-fragment.

In some embodiments, a heavy chain variable region of an anti-TSLP moiety and a light chain variable region of an anti-TSLP moiety associate to form a TSLP binding region. In some embodiments, a heavy chain variable region of an anti-IL-4R moiety and a light chain variable region of an anti-IL-4R moiety associate to form an IL-4R binding region. In some embodiments, a moiety disclosed herein comprises an Fc modification. In some embodiments, a Fc modification disclosed herein is a half-life extension modification. In some embodiments, the half-life extension modification is a YTE modification. In some embodiments, the Fc region described herein can have a first modified Fc polypeptide and a second modified Fc polypeptide, where the first modified Fc polypeptide comprises a knob modification and the second modified Fc polypeptide comprises a hole modification.

In some cases, an antigen binding moiety described herein (e.g., FIG. 5C, FIG. 36A or FIG. 40) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain can be of the IgG2 isotype. In some embodiments, the light chain of the anti-IL-4R antibody or the antigen binding portion thereof can be a kappa light chain, while the light chain of an anti-TSLP Fab can be a lambda light chain. In some embodiments, the light chain of the anti-IL-4R antibody or the antigen binding portion thereof can be a lambda light chain, while the light chain of an anti-TSLP Fab can be a kappa light chain. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36B) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain can be of the IgG2 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be a lambda light chain. In some cases, the Fc region of the anti-IL-4R antibody can comprise knob-in-hole configuration. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36C) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain can be of the IgG2 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be kappa light chain. In some cases, the Fc region of the anti-IL-4R antibody can comprise knob-in-hole configuration. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36D) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain and can be of the IgG1 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab. In some cases, the Fc region of the anti-IL-4R antibody can comprise knob-in-hole configuration. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36E) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain can be of the IgG2 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be a lambda light chain. In some embodiments, the CH1-CL interface of at least one arm of the anti-TSLP can be engineered such that there may be an (−) residue (e.g., Asp) on the heavy chain facing an (+) residue (e.g., Arg) on the light chain. In some cases, such charge pairing in the Fab (e.g., HC-LC interface) can stabilize the Fab or help to prevent light-chain mispairing. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36F) can comprise (1) an anti-IL-4R antibody or an antigen binding portion thereof comprising a heavy chain and a light chain, wherein the heavy chain can be of the IgG4 isotype, and (2) an anti-TSLP Fab comprising a heavy chain (e.g., VH and CH1) and a light chain (e.g., VL and CL), wherein the heavy chain can be of the IgG2 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be a lambda light chain. In some embodiments, the CH1-CL interface of the at least one arm of the anti-IL-4R can be engineered such that there may be an (−) residue (e.g., Asp) on the heavy chain facing an (+) residue (e.g., Arg) on the light chain. In some cases, such charge parking in the Fab (e.g., HC-LC interface) can stabilize the Fab. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36G) can comprise (1) an anti-IL-4R antibody or an antigen binding portion thereof comprising a heavy chain and a light chain, wherein the heavy chain can be of the IgG1 isotype, and (2) an anti-TSLP Fab comprising a heavy chain (e.g., VH and CH1) and a light chain (e.g., VL and CL), wherein the heavy chain can be of the IgG2 isotype. In some embodiments, the antigen binding portion of an antibody (e.g., anti-TSLP Fab) can be modified such that the full heavy chain variable and constant CH1 domains (Heavy) and the full light chain variable and constant domains (Light) are crossed (e.g., VH-CH1⇔VL-CL). In this configuration, the light chain of the anti-TSLP Fab can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be a lambda light chain. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, an antigen binding moiety described herein (e.g., FIG. 36G) can comprise (1) an anti-IL-4R antibody or an antigen binding portion thereof comprising a heavy chain and a light chain, wherein the heavy chain can be of the IgG1 isotype, and (2) an anti-TSLP antigen binding portion thereof. In some embodiments, the antigen binding portion of the anti-TSLP can comprise a single-domain (e.g., VHH). In some embodiments, the VHH domain can be the variable region of a heavy-chain only antibody, capable of binding antigen without association with a light chain. In this configuration, the VHH domain (e.g., from an anti-TSLP antibody or an antigen binding portion thereof) can be associated with the HC (e.g., via an optional linker from any one of SEQ ID NOs: 17-20, 40-47, 185-188, or 223-226) of the anti-IL-4R. In some embodiments, the light chain of the anti-IL-4R antibody or an antigen binding portion thereof can be a kappa light chain, while the light chain of the anti-TSLP Fab can be a lambda light chain. Optionally, in some embodiments, the Fc region of the antibody (e.g., anti-IL-4R antibody) can comprise one or more modifications relative to a wild-type IgG Fc sequence. In some cases, the one or more modifications can comprise (according to EU numbering) M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the one or more modifications can comprise any one of the modifications set forth in Table 33. In some embodiments, the Fc region of the antibody can comprise a knob-in-hole substitution.

In some cases, the antigen binding moiety described herein may exhibit potent functional activity against IL-4R and/or TSLP-mediated signaling pathways. For example, the antigen binding moiety described herein can have low EC50 or IC50 values as compared to that of control antibodies of similar isotypes (e.g., a monospecific antibody or an antigen binding moiety comprising one or more scFv fragments).

In some cases, the antigen binding moiety described herein may exhibit an EC50 from about 0.1 nM to about 4 nM. In some cases, the antigen binding moiety described herein may exhibit an EC50 from at least about 0.1 nM, 0, nM, 0.3 nM, 0.4 nM, 0.5 nM, 0.6 nM, 0.7 nM, 0.8 nM, 0.9 nM, 1.0 nM, 1.2 nM, 1.4 nM, 1.6 nM, 1.8 nM, 2.0 nM, 2.2 nM, 2.4 nM, 2.6 nM, 2.8 nM, 3.0 nM, 3.2 nM, 3.4 nM, 3.6 nM, 3.8 nM, or at least about 4 nM in cell-based assay measuring IL-4R binding. In some cases, the antigen binding moiety described herein may exhibit an EC50 from at most about 0.1 nM, 0, nM, 0.3 nM, 0.4 nM, 0.5 nM, 0.6 nM, 0.7 nM, 0.8 nM, 0.9 nM, 1.0 nM, 1.2 nM, 1.4 nM, 1.6 nM, 1.8 nM, 2.0 nM, 2.2 nM, 2.4 nM, 2.6 nM, 2.8 nM, 3.0 nM, 3.2 nM, 3.4 nM, 3.6 nM, 3.8 nM, or at most about 4 nM in cell-based assay measuring IL-4R binding.

In some cases, the antigen binding moiety described herein may exhibit an EC50 from about 1 pM to about 60 pM in an SPR assay measuring TSLP binding. In some cases, the antigen binding moiety described herein may exhibit an EC50 from at least about 1 pM, 2 pM, 3 pM, 4 pM, 5 pM, 6 pM, 7 pM, 8 pM, 9 pM, 10 pM, 11 pM, 12 pM, 13 pM, 14 pM, 15 pM, 16 pM, 17 pM, 18 pM, 19 pM, 20 pM, 22 pM, 24 pM, 26 pM, 28 pM, 30 pM, 32 pM, 34 pM, 36 pM, 38 pM, 40 pM, 42 pM, 44 pM, 46 pM, 48 pM, 50 pM, 52 pM, 54 pM, 56 pM, 58 pM, or at least about 60 pM in cell-based assay measuring TSLP binding. In some cases, the antigen binding moiety described herein may exhibit an EC50 from at most about 1 pM, 2 pM, 3 pM, 4 pM, 5 pM, 6 pM, 7 pM, 8 pM, 9 pM, 10 pM, 11 pM, 12 pM, 13 pM, 14 pM, 15 pM, 16 pM, 17 pM, 18 pM, 19 pM, 20 pM, 22 pM, 24 pM, 26 pM, 28 pM, 30 pM, 32 pM, 34 pM, 36 pM, 38 pM, 40 pM, 42 pM, 44 pM, 46 pM, 48 pM, 50 pM, 52 pM, 54 pM, 56 pM, 58 pM, or at most about 60 pM in an SPR assay measuring TSLP binding.

In some cases, the antigen binding moiety described herein may exhibit an IC50 from about 0.5 nM to about 5 nM in cell-based assay measuring IL4 induced CD23 upregulation. In some cases, the antigen binding moiety described herein may exhibit an IC50 of from at least about 0.5 nM to at least about 5 nM, in cell-based assay measuring IL4 induced CD23 upregulation. In some cases, the antigen binding moiety described herein may exhibit an IC50 of at most about 0.5 nM to at most about 5 nM in cell-based assay measuring IL4 induced CD23 upregulation.

In some cases, the antigen binding moiety described herein may exhibit an IC50 from about 2 pM to about 50 pM in a cell-based assay measuring TSLP-induced TARC/CCL17 secretion. In some cases, the antigen binding moiety described herein may exhibit an IC50 of from at least about 2 pM to at least at about 50 pM in a cell-based assay measuring TSLP-induced TARC/CCL17 secretion. In some cases, the antigen binding moiety described herein may exhibit an IC50 of at most about 2 pM to at most about 50 pM in a cell-based assay measuring TSLP-induced TARC/CCL17 secretion.

Bispecific Format

In some embodiments, an antigen binding moiety disclosed herein can have different bispecific formats. For example, in some embodiments, an antigen binding moiety disclosed herein can be a tandem double single chain Fv fragments (scFv) (e.g., a Bispecific T-cell Engager (BiTE), a single-chain bispecific tandem fragment variable (scB-sTaFv), a bispecific single-chain Fv (bsscFv), a bispecific killer-cell engager (BiKE). In some embodiments, an antigen binding moiety disclosed herein can be a diabody. In some embodiments, an antigen binding moiety can be a dual-affinity re-targeting (DART). In some embodiments, an antigen binding moiety can be a tandem diabodies (TandAb) or a bispecific DART (bi. DART). In some embodiments, an antigen binding moiety can be a Tandem triple scFv (a single chain Fv triplebody (sctb)). In some embodiments, an antigen binding moiety can be a bispecific scFv immunofusion (BIf). In some embodiments, an antigen binding moiety can be a Fabsc. In some embodiments, an antigen binding moiety can be a dual-variable domain immunoglobulin (DVD-Ig). In some embodiments, an antigen binding moiety can comprise a domain-crossover Fab (e.g., CrossMab with CH1↔CL, VH↔VL, L-CL↔VH-CH1 exchange). In some embodiments, an antigen binding moiety can comprise a domain-crossover Fab (CrossMab$^{Fab}$; VL-CL↔VH-CH1). In some embodiments, an antigen binding moiety can comprise a domain-crossover variable domain (VH↔VL). In some embodiments, an antigen binding moiety can be a modular IgG-scFv.

For example, in some embodiments, an antigen binding moiety can be a bispecific DART. In some embodiments, an antigen binding moiety can comprise a binding complex comprising a first binder, an anti-TSLP scFv, coupled to a second binder, an anti-IL-4R scFv. In some embodiments, the binding complex further comprises (e.g., associated with) a Fc region.

In some embodiments, an antigen binding moiety can comprise a domain-crossover Fab configuration (CrossMab). In some embodiments, an antigen binding moiety can comprise, from N-terminus to C-terminus: a first polypeptide comprising an anti-TSLP light chain variable region and an anti-TSLP light chain constant region; a second polypeptide comprising an anti-TSLP heavy chain variable region and an anti-TSLP heavy chain constant region 1; a third polypeptide comprising an anti-IL-4R light chain variable region and at least a portion of an anti-IL-4R heavy chain constant region (e.g., a heavy chain constant domain 1 or CH1); and a fourth polypeptide comprising an anti-IL-4R heavy chain variable region, an anti-IL-4R light chain constant region, and at least a portion of anti-IL-4R heavy chain constant region (e.g., a heavy chain constant domain 2 and a heavy chain constant domain 3).

In some embodiments, an anti-IL-4R or an antigen binding portion thereof disclosed herein, or a related binding entity that elicits a similar biological effect can be or comprise dupilumab, pascolizumab, CM-310, recombinant anti-IL-4R humanized monoclonal antibody, MG-K10, manfidokimab, QX-005N, elarekibep, CBP-201, SHR-1819, LQ-036, BA2101, mepolizumab, reslizumab, benralizumab, GSK3511294, AK-120, pitrakinra, anrukinzumab, IMA-638, lebrikizumab, tralokinumab, GSK679586, AMG-317, MILR1444A, CAT-354, QAX576, IMA-026, CNTO-607, MK-6105, DOM-0910, SAR440340, REGN3500, etokimab, ANB020, astegolimab, tozorakimab, MEDI3506, CNT07160, torudokimab, itepekimab, dupixent, nemolizumab, BMS-981164, lokivetmab, vixarelimab, or an antigen binding portion thereof.

In some embodiments, an anti-TSLP or an antigen binding portion thereof disclosed herein, or a related binding entity that elicits a similar biological effect can be or comprises tezepelumab, solrikitug, GSK5784283, BSI-045B, HZ-1127, SKB378/HBM9378, UPB-101, TQC2731, APG333, SHR-1905, AIO-001, AMG 157, REGN3500, ecleralimab, or an antigen binding portion thereof.

In some embodiments, an anti-IL-4R or an antigen binding portion thereof and/or an anti-TSLP or an antigen binding portion thereof disclosed here, or a related binding entity that elicits a similar biological effect can be or can comprise APG808 or IBI3002, or an antigen binding portion thereof.

In addition to the antibodies disclosed herein, various other known antibodies may also be employed in the same format or configuration. Such antibodies can be adapted into the bispecific or multispecific format described herein, or engineered into the configurations disclosed herein suitable for achieving the desired binding characteristics.

Linker

In some embodiments, the scFv (e.g., anti-TSLP scFv) may be linked to the antibody (e.g., anti-IL-4R) via a linker. The heavy chain variable region in the scFv can be linked to the light chain variable region via a linker. In some embodiments, linkers can serve primarily as a spacer between the TSLP binding region and the IL-4R binding region, or between the heavy and light chain variable regions in the scFvs disclosed herein. In some embodiments, a linker (e.g., an optional linker) may be a peptide linker made up of 5 to 30, 10 to 30, 10 to 20, or 15 amino acids. The linker may be a GS linker, such as (GGGGS)2 (SEQ ID NO: 223), or (GGGGS)4 (SEQ ID NO: 224). In some embodiments, the linker in the scFv can be (GGGGS)4 (SEQ ID NO: 224). In some embodiments, the linker between the scFv and the IgG heavy/light chain or heavy chain can be (GGGGS)3 (SEQ ID NO: 187), (GGGGS)2 (SEQ ID NO: 223), or (GGGGS)4 (SEQ ID NO: 224). In some embodiments, the linker comprises ASTKGP (SEQ ID NO: 19), ASTKGPSVFPLAP (SEQ ID NO: 185) or TVAAPSVFIFPP (SEQ ID NO: 20).

In some cases, the linker may be (EA3K)3 (SEQ ID NO: 188) linker. In some embodiments, a linker disclosed herein may be repeated multiple times.

In some embodiments, the linker may be a flexible linker, a rigid linker, or a cleavable linker. The antigen binding moiety described herein can be optimized for protein expression and yield by changing composition and/or length of the polypeptide linker. In some embodiments, the linker is a polypeptide between 3 amino acids and 500 amino acids in length that associates an anti-IL-4R moiety or an antigen binding portion thereof with an anti-TSLP moiety or an antigen binding portion thereof. In some embodiments, the linker is a polypeptide between 3 amino acids and 500 amino acids in length that associates a light chain variable region with a heavy chain variable region of scFv (e.g., anti-IL-4R scFv or anti-TSLP scFv).

In some embodiments, a linker (e.g., an optional linker) may be made up of amino acids linked together by peptide bonds, preferably from 5 to 30 amino acids, from 10 to 30 amino acids, from 10 to 20 amino acids, or 15 amino acids, linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, poly (Gly-Ala), and polyalanine, such as -GGGGSGGGGS- (SEQ ID NO: 42), and -GGGGSGGGGSGGGGSGGGGS-(SEQ ID NO: 23).

Linkers may also be non-peptide linkers. For example, alkyl linkers such as —NH—, —(CH2) s-C(O)—, wherein s=2-20 can be used. These alkyl linkers may further be substituted by any non-sterically hindering group such as lower alkyl (e.g., C1-4) lower acyl, halogen (e.g., CI, Br), CN, NH2, phenyl, etc.

In some embodiments, the polypeptide linker may be about 3 amino acids to about 10 amino acids, about 3 amino acids to about 20 amino acids, about 3 amino acids to about 30 amino acids, about 3 amino acids to about 60 amino acids, about 3 amino acids to about 90 amino acids, about 3 amino acids to about 100 amino acids, about 3 amino acids to about 200 amino acids, about 3 amino acids to about 300 amino acids, about 3 amino acids to about 400 amino acids, about 3 amino acids to about 500 amino acids, about 6 amino acids to about 10 amino acids, about 6 amino acids to about 20 amino acids, about 6 amino acids to about 30 amino acids, about 6 amino acids to about 60 amino acids, about 6 amino acids to about 100 amino acids, about 6 amino acids to about 200 amino acids, about 6 amino acids to about 300 amino acids, about 6 amino acids to about 400 amino acids, about 6 amino acids to about 500 amino acids, about 8 amino acids to about 10 amino acids, about 8 amino acids to about 20 amino acids, about 8 amino acids to about 30 amino acids, about 8 amino acids to about 60 amino acids, about 8 amino acids to about 100 amino acids, about 8 amino acids to about 200 amino acids, about 8 amino acids to about 300 amino acids, about 8 amino acids to about 500 amino acids, about 10 amino acids to about 20 amino acids, about 10 amino acids to about 30 amino acids, about 10 amino acids to about 100 amino acids, about 10 amino acids to about 200 amino acids, about 10 amino acids to about 300 amino acids, about 10 amino acids to about 400 amino acids, about 10 amino acids to about 500 amino acids, about 20 amino acids to about 30 amino acids, about 20 amino acids to about 100 amino acids, about 20 amino acids to about 200 amino acids, about 20 amino acids to about 300 amino acids, about 20 amino acids to about 400 amino acids, about 20 amino acids to about 500 amino acids, about 30 amino acids to about 100 amino acids, about 30 amino acids to about 200 amino acids, about 30 amino acids to about 300 amino acids, about 30 amino acids to about 400 amino acids, about 30 amino acids to about 500 amino acids, about 100 amino acids to about 200 amino acids, about 100 amino acids to about 300 amino acids, about 100 amino acids to about 400 amino acids, about 100 amino acids to about 500 amino acids, about 200 amino acids to about 300 amino acids, about 200 amino acids to about 400 amino acids, about 200 amino acids to about 500 amino acids, about 300 amino acids to about 400 amino acids, about 300 amino acids to about 500 amino acids, or about 400 amino acids to about 500 amino acids. In some embodiments, the polypeptide linker can be about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker can be at least about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker may at most be about 6 amino acids, about 10 amino acids, about 20 amino acids, about 30 amino acids, about 100 amino acids, about 200 amino acids, about 300 amino acids, about 400 amino acids, about 500 amino acids.

In some embodiments, the polypeptide linker described herein may be about 15 amino acids in length, about 20 amino acids in length, about 25 amino acids in length, about 30 amino acids in length, about 35 amino acids in length, about 40 amino acids in length, about 45 amino acids in length, about 50 amino acids in length, about 55 amino acids in length, or about 60 amino acids in length. In some embodiments, the linker peptide may comprise (GGS)n (SEQ ID NO: 17), (GGGGS)n (SEQ ID NO: 40), (SGGGG)n (SEQ ID NO: 44), GGGG(SGGGG)n (SEQ ID NO: 45) or GG(SGG)n (SEQ ID NO: 46) wherein n is an integer between 1 and 100. In some embodiments, the linker peptide may comprise (GGS)×20 (SEQ ID NO: 47). In some embodiments, the linker comprises ASTKGP (SEQ ID NO: 19), ASTKGPSVFPLAP (SEQ ID NO: 185), GGGGSGGGGSGGGGS (SEQ ID NO: 187), or TVAAPSVFIFPP (SEQ ID NO: 20). In some cases, the linker may be (EA3K)3 (SEQ ID NO: 188) linker. In some embodiments, the linker can be a modified linker. For example, in some embodiments, a modified linker can have at least one, at least two, at least three, at least four, at least five, at least six, at least seven, at least eight, at least nine, at least ten, or more amino acid substitutions, additions, or deletions as compared to that of any one of linker sequences described herein (e.g., any one of SEQ ID NOs: 17-20, 40-47, 185-188, or 223-226). In some embodiments, the linker can comprise an amino acid sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of any one of SEQ ID NOs: 17-20, 40-47, 185-188, or 223-226.

Signal Peptide

In some embodiments, an antigen binding moiety described herein (e.g., a polynucleotide sequence encoding the antigen binding moiety) can further comprise one or more signal peptides (e.g., one or more polynucleotide sequences encoding one or more signal peptides). In some embodiments, an antigen binding moiety described herein (e.g., a polynucleotide sequence encoding the antigen binding moiety) can comprise at least one, at least two, at least three, at least four, at least five signal peptides. In some embodiments, one or more signal peptides can be the same. In some embodiments, one or more signal peptides can be different. In some embodiments, a signal peptide can be associated with a polypeptide encoding a heavy chain, a polypeptide encoding a light chain, or a polypeptide encoding an antigen binding portion thereof (e.g., a light chain variable region or a heavy chain variable region). In some embodiments, a signal peptide can allow efficient expression of the heavy chain, the light chain, or the antigen binding portion thereof by transporting the polypeptides (e.g., polypeptides encoding the heavy chain, the light chain, or the antigen binding portion thereof) into the endoplasmic reticulum (ER) for proper folding, assembly, and post-translation modification. In some embodiments, a signal peptide can facilitate secretion of the binding moiety described herein (e.g., comprising a heavy chain, a light chain, or an antigen binding portion thereof) from a host cell. In some embodiments, the signal peptide can be an immunoglobulin signal peptide or a heterologous signal peptide (e.g., a signal peptide from a non-immunoglobulin protein). In some embodiments, the signal peptide can be a targeting peptide that targets a polypeptide disclosed herein to a specific location. In some embodiments, the signal peptide can be a detection peptide that allows for detection of a polypeptide disclosed herein.

In some embodiments, a signal peptide can be associated with N- or C-terminus of the heavy chain (e.g., a polynucleotide sequence encoding the signal peptide can be associated with 5' or 3' of a polynucleotide sequence encoding the heavy chain). In some embodiments, a signal peptide can be associated with N- or C-terminus of the light chain (e.g., a polynucleotide sequence encoding the signal peptide can be associated with 5' or 3' of a polynucleotide sequence encoding the light chain). In some embodiments, a signal peptide can be associated with N- or C-terminus of the heavy chain variable region (e.g., a polynucleotide sequence encoding the signal peptide can be associated with 5' or 3' of a polynucleotide sequence encoding the heavy chain variable region). In some embodiments, a signal peptide can be associated with N- or C-terminus of the heavy chain constant region (e.g., CH1 or Fc region) (e.g., a polynucleotide sequence encoding the signal peptide can be associated with 5' or 3' of a polynucleotide sequence encoding CH1 or Fc region). In some embodiments, a signal peptide can be associated with N- or C-terminus of the light chain variable region (e.g., a polynucleotide sequence encoding the signal peptide can be associated with 5' or 3' of a polynucleotide sequence encoding the light chain variable region). In some embodiments, a signal peptide can be associated with N- or C-terminus of the light chain constant region (e.g., a polynucleotide sequence encoding the signal peptide can be associated with 5' or 3' of a polynucleotide sequence encoding the light chain constant region). In some embodiments, a signaling peptide disclosed herein, for example any one of SEQ ID NO: 130-184 or functional portions thereof, can be inserted between an N- and a C-terminal of a polypeptide disclosed herein.

In some embodiments, the antigen binding moiety described herein can comprise an anti-TSLP moiety comprising a heavy chain and a light chain, and an anti-IL-4R antigen binding portion (e.g., comprising a light chain variable region and a heavy chain variable region) of the anti-IL-4R moiety. In some embodiments, the antigen binding moiety described herein can comprise an anti-IL-4R moiety comprising a heavy chain and a light chain, and an anti-TSLP antigen binding portion (e.g., comprising a light chain variable region and a heavy chain variable region) of the anti-TSLP moiety.

In some embodiments, the signal peptide can be associated with the N-terminus or C-terminus of the anti-TSLP heavy chain. In some embodiments, the signal peptide can be associated with the N-terminus or C-terminus of the anti-TSLP heavy chain variable region. In some embodiments, the signal peptide can be associated with the N-terminus or C-terminus of the anti-TSLP heavy chain constant region (e.g., CH1 or Fc region). In some embodiments, the signal peptide can be associated with the N-terminus or C-terminus of the anti-TSLP light chain. In some embodiments, the signal peptide can be associated with the N-terminus or C-terminus of the anti-TSLP light chain variable region. In some embodiments, the signal peptide can be associated with the N-terminus or C-terminus of the anti-TSLP light chain constant region. In some embodiments, the signal peptide can be associated with the N-terminus or C-terminus of the anti-IL-4R heavy chain. In some embodiments, the signal peptide can be associated with the N-terminus or C-terminus of the anti-IL-4R heavy chain variable region. In some embodiments, the signal peptide can be associated with the N-terminus or C-terminus of the anti-IL-4R heavy chain constant region (e.g., CH1 or Fc region). In some embodiments, the signal peptide can be associated with the N-terminus or C-terminus of the anti-IL-4R light chain. In some embodiments, the signal peptide can be associated with the N-terminus or C-terminus of the anti-IL-4R light chain variable region. In some embodiments, the signal peptide can be associated with the N-terminus or C-terminus of the anti-IL-4R light chain constant region.

In some embodiments, a signal peptide can comprise a sequence having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of any one of SEQ ID NOs: 130-184. In some embodiments, a signal peptide can be modified. For example, in some embodiments, a signal peptide can have at least one, at least two, at least three, at least four, at least five, at least six, at least seven, at least eight, at least nine, at least ten, or more amino acid substitutions, additions, or deletions as compared to the amino acid sequence of any one of SEQ ID NOs: 130-184. In some embodiments, a signal peptide can have one, two, three, four, five, six, seven, eight, nine, ten, or more amino acid substitutions, additions, or deletions as compared to the amino acid sequence of any one of SEQ ID NOs: 130-184. In some embodiments, a signal peptide can comprise a sequence having at least 80% sequence identity to the amino acid sequence of any one of SEQ ID NOs: 130-184. In some embodiments, a signal peptide can comprise a sequence having at least 90% sequence identity to the amino acid sequence of any one of SEQ ID NOs: 130-184. In some embodiments, a signal peptide can comprise a sequence having at least 95% sequence identity to the amino acid sequence of any one of SEQ ID NOs: 130-184. In some embodiments, a signal peptide can comprise a sequence of any one of SEQ ID NOs: 130-184.

For example, in some embodiments, the antigen binding moiety described herein can comprise a first polypeptide encoding anti-IL-4R light chain, wherein the first polypeptide further comprises a signal peptide (e.g., SEQ ID NO: 156) at the N-terminus of the anti-IL-4R light chain; a second polypeptide encoding anti-IL-4R heavy chain that is associated with an anti-TSLP light chain variable region and light chain constant region, wherein the second polypeptide further comprises a signal peptide (e.g., SEQ ID NO: 130) at the N-terminus of the anti-IL-4R heavy chain; and a third polypeptide encoding anti-TSLP heavy chain variable region and heavy chain constant domain (CH1), wherein the third polypeptide further comprises a signal peptide (e.g., SEQ ID NO: 130) at the N-terminus of the anti-TSLP heavy chain variable region.

In some embodiments, a polypeptide sequence encoding the antigen binding moiety disclosed herein can comprise a signal peptide. In some cases, the signal peptide can function to direct the nascent polypeptide into the endoplasmic reticulum (ER) of the host cell during translation. In some cases, the signal peptide can be cleaved. In some cases, the signal peptide can be proteolytically cleaved, resulting in removal of the signal sequence. In some cases, the signal peptide can be removed from the mature antigen binding moiety. In some cases, the removal of the signal peptide can facilitate proper folding, assembly, and/or secretion of the antigen binding moiety disclosed herein.

Antigen Binding Moiety

The antigen binding moiety described herein may be engineered by modifying one or more residues within one or both variable regions (e.g., VH and/or VL), for example within one or more CDR regions and/or within one or more framework regions, to e.g., change target binding affinity. Additionally or alternatively, the antigen binding moiety can be engineered by modifying the residues within the constant region(s), for example to alter the effector function (s) of the antigen binding moiety.

In some embodiments, the anti-IL-4R moiety or antigen binding thereof comprises a light chain. In some embodiments, a light chain of the anti-IL-4R moiety comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 22. In some embodiments, the light chain of the anti-IL-4R moiety comprises an amino acid sequence of SEQ ID NO: 22.

In some embodiments, the anti-IL-4R moiety or the antigen binding portion thereof comprises a light chain variable domain. In some embodiments, a light chain variable domain comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 30. In some embodiments, the light chain of the anti-IL-4R comprises an amino acid sequence of SEQ ID NO: 30.

In some embodiments, the anti-IL-4R moiety or the antigen binding portion thereof comprises (a) a LCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 14, (b) a LCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 15, and/or (c) a LCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 16. In some embodiments, the anti-IL-4R moiety or the antigen binding portion thereof comprises (a) a LCDR1 comprising an amino acid sequence of SEQ ID NO: 14, (b) a LCDR2 comprising an amino acid sequence of SEQ ID NO: 15, and/or (c) a LCDR3 comprising an amino acid sequence of SEQ ID NO: 16.

In some embodiments, an anti-IL-4R moiety or an antigen binding portion thereof comprises a heavy chain. In some embodiments, a heavy chain of the anti-IL-4R or an antigen binding portion thereof comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 21. In some embodiments, the heavy chain of the anti-IL-4R moiety comprises an amino acid sequence of SEQ ID NO: 21.

In some embodiments, an anti-IL-4R moiety or an antigen binding portion thereof comprises a heavy chain variable domain. In some embodiments, a heavy chain variable domain comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 32. In some embodiments, the heavy chain variable domain of the anti-IL-4R comprises an amino acid sequence of SEQ ID NO: 32.

In some embodiments, the anti-IL-4R moiety or the antigen binding portion thereof comprises (a) a HCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 10, (b) a HCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 11, and/or (c) a HCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 12. In some embodiments, the anti-IL-4R moiety or the antigen binding portion thereof comprises (a) a HCDR1 comprising an amino acid sequence of SEQ ID NO: 10, (b) a HCDR2 comprising an amino acid sequence of SEQ ID NO: 11, and/or (c) a HCDR3 comprising an amino acid sequence of SEQ ID NO: 12.

In some embodiments, the anti-IL-4R moiety or the antigen binding portion thereof comprises one or more mutations. In some embodiments, the anti-IL-4R moiety or the antigen binding portion thereof comprises one or more mutations that enhances stability and efficacy of the IL-4R or the antigen binding portion thereof.

In some embodiments, the anti-IL-4R moiety or the antigen binding portion thereof comprises a Fc region. In some embodiments, the Fc region is an IgG1, IgG2, IgG3, or IgG4 heavy chain Fc region. In some embodiments, the Fc region comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the anti-IL-4R moiety or the antigen binding portion thereof comprises a Fc region that is symmetric. In some embodiments, the antibody or the antigen binding portion thereof further comprises a Fc region that is asymmetric. In some embodiments, an asymmetric moiety can comprise a construct where amino acids at the contact site between the CH3 regions of a first Fc region and a second Fc region are substituted by larger or smaller residues forcing a heterodimeric assembly of heavy chains. In some embodiments, an asymmetric moiety is generated using knobs-into-holes (KiH). In some embodiments, the knobs-into-holes approach comprises a knob that is obtained by replacement of a small amino acid with a larger one in the CH3 region. In some embodiments, the knob is designed to insert into a hole in the CH3 region that is obtained by replacement of a large residue with a smaller one. In some embodiments, a large residue can be tyrosine or tryptophan. In some embodiments, a small residue can be glycine, alanine, threonine. In some embodiments, an antibody comprising a Fc region with KiH mutation described herein has an improved heterodimerization, enhanced stability, and an increase in therapeutic efficacy compared to that of a control antibody lacking the KiH mutation.

In some embodiments, an anti-IL-4R moiety or an antigen binding portion thereof comprises heavy chains having a KiH mutation. In some embodiments, a first heavy chain comprising a hole mutation comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 36. In some embodiments, a second heavy chain comprising a hole mutation comprises SEQ ID NO: 36. In some embodiments, a second heavy chain comprising a knob mutation comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 37. In some embodiments, a second heavy chain comprising a knob mutation comprises SEQ ID NO: 37.

In some embodiments, the anti-TSLP moiety or antigen binding thereof comprises a light chain. In some embodiments, the light chain of an anti-TSLP comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 27. In some embodiments, the light chain of the anti-TSLP comprises an amino acid sequence of SEQ ID NO: 27.

In some embodiments, the anti-TSLP moiety or the antigen binding portion thereof comprises a light chain variable domain. In some embodiments, a light chain variable domain comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 28. In some embodiments, the light chain variable domain of the anti-TSLP comprises an amino acid sequence of SEQ ID NO: 28.

In some embodiments, the anti-TSLP moiety or the antigen binding portion thereof comprises (a) a LCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 6, (b) a LCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 7, and/or (c) a LCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 8. In some embodiments, the anti-TSLP moiety or the antigen binding portion thereof comprises (a) a LCDR1 comprising an amino acid sequence of SEQ ID NO: 6, (b) a LCDR2 comprising an amino acid sequence of SEQ ID NO: 7, and/or (c) a LCDR3 comprising an amino acid sequence of SEQ ID NO: 8.

In some embodiments, an anti-TSLP moiety or an antigen binding portion thereof comprises a heavy chain. In some embodiments, a heavy chain of the anti-TSLP moiety or an antigen binding portion thereof comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 24. In some embodiments, the heavy chain of the anti-TSLP moiety comprises an amino acid sequence of SEQ ID NO: 24.

In some embodiments, an anti-TSLP moiety or an antigen binding portion thereof comprises a heavy chain variable domain. In some embodiments, a heavy chain variable domain comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 25. In some embodiments, the heavy chain variable domain of the anti-TSLP comprises an amino acid sequence of SEQ ID NO: 25.

In some embodiments, the anti-TSLP moiety or the antigen binding portion thereof comprises (a) a HCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 2, (b) a HCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 3, and/or (c) a HCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 4. In some embodiments, the anti-TSLP moiety or the antigen binding portion thereof comprises (a) a HCDR1 comprising an amino acid sequence of SEQ ID NO: 2, (b) a HCDR2 comprising an amino acid sequence of SEQ ID NO: 3, and/or (c) a HCDR3 comprising an amino acid sequence of SEQ ID NO: 4.

In some embodiments, the anti-TSLP moiety or the antigen binding portion thereof comprises one or more mutations. In some embodiments, the anti-TSLP moiety or the antigen binding portion thereof comprises one or more mutations that enhances stability and efficacy of the anti-TSLP or the antigen binding portion thereof.

In some embodiments, the anti-TSLP moiety or the antigen binding portion thereof comprises a Fc region. In some embodiments, the Fc region is an IgG1, IgG2, IgG3, or IgG4 heavy chain Fc region. In some embodiments, the Fc region M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33.

In some embodiments, the anti-TSLP moiety or the antigen binding portion thereof comprises a Fc region that is symmetric. In some embodiments, the antibody or the antigen binding portion thereof further comprises a Fc region that is asymmetric. In some embodiments, an asymmetric moiety can comprise a construct where amino acids at the contact site between the CH3 regions of a first Fc region and a second Fc region are substituted by larger or smaller residues forcing a heterodimeric assembly of heavy chains. In some embodiments, an asymmetric moiety is generated using knobs-into-holes (KiH). In some embodiments, the knobs-into-holes approach comprises a knob that is obtained by replacement of a small amino acid with a larger one in the CH3 region. In some embodiments, the knob is designed to insert into a hole in the CH3 region that is obtained by replacement of a large residue with a smaller one. In some embodiments, a large residue can be tyrosine or tryptophan. In some embodiments, a small residue can be glycine, alanine, threonine. In some embodiments, an antibody comprising a Fc region with KiH mutation described herein has an improved heterodimerization, enhanced stability, and an increase in therapeutic efficacy compared to that of a control antibody lacking the KiH mutation.

In some embodiments, an anti-TSLP moiety or an antigen binding portion thereof comprises heavy chains having a KiH mutation. In some embodiments, a first heavy chain comprising a hole mutation comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 38. In some embodiments, a second heavy chain comprising a hole mutation comprises SEQ ID NO: 38. In some embodiments, a second heavy chain comprising a knob mutation comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 39. In some embodiments, a second heavy chain comprising a knob mutation comprises SEQ ID NO: 39.

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 62, and a light chain comprising an amino acid sequence having at least 90%, at least 95%, at least 96%, at least 97%, at least 98%, at least 99% or 100% sequence identity to an amino acid sequence set out in SEQ ID NO: 63. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 64, and a light chain comprising an amino acid sequence having at least 90%, at least 95%, at least 96%, at least 97%, at least 98%, at least 99% or 100% sequence identity to an amino acid sequence set out in SEQ ID NO: 65. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 66, and a light chain comprising an amino acid sequence having at least 90%, at least 95%, at least 96%, at least 97%, at least 98%, at least 99% or 100% sequence identity to an amino acid sequence set out in SEQ ID NO: 67. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 68, and a light chain comprising an amino acid sequence having at least 90%, at least 95%, at least 96%, at least 97%, at least 98%, at least 99% or 100% sequence identity to an amino acid sequence set out in SEQ ID NO: 69. In some embodiments, a heavy chain or a light chain can further comprise an optional signal peptide (e.g., SEQ ID NOs: 130-184).

In some embodiments, the binding moiety described herein can comprise a light chain comprising an amino acid sequence having at least 90%, at least 95%, at least 96%, at least 97%, at least 98%, at least 99% or 100% sequence identity to an amino acid sequence set out in SEQ ID NO: 70, a first heavy chain comprising an amino acid sequence having at least 90%, at least 95%, at least 96%, at least 97%, at least 98%, at least 99% or 100% sequence identity to an amino acid sequence set out in SEQ ID NO: 71, and a second heavy chain comprising an amino acid sequence having at least 90%, at least 95%, at least 96%, at least 97%, at least 98%, at least 99% or 100% sequence identity to an amino acid sequence set out in SEQ ID NO: 72. In some embodiments, a first heavy chain, a second heavy chain, or a light chain can further comprise an optional signal peptide (e.g., SEQ ID NOs: 130-184).

In some embodiments, the binding moiety described herein can comprise a light chain comprising an amino acid sequence having at least 90%, at least 95%, at least 96%, at least 97%, at least 98%, at least 99% or 100% sequence identity to an amino acid sequence set out in SEQ ID NO: 73, a first heavy chain comprising an amino acid sequence having at least 90%, at least 95%, at least 96%, at least 97%, at least 98%, at least 99% or 100% sequence identity to an amino acid sequence set out in SEQ ID NO: 74, and a second heavy chain comprising an amino acid sequence having at least 90%, at least 95%, at least 96%, at least 97%, at least 98%, at least 99% or 100% sequence identity to an amino acid sequence set out in SEQ ID NO: 75. In some embodiments, a first heavy chain, a second heavy chain, or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 76, and a light chain comprising an amino acid sequence having at least 90%, at least 95%, at least 96%, at least 97%, at least 98%, at least 99% or 100% sequence identity to an amino acid sequence set out in SEQ ID NO: 77. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 78, and a light chain comprising an amino acid sequence having at least 90%, at least 95%, at least 96%, at least 97%, at least 98%, at least 99% or 100% sequence identity to an amino acid sequence set out in SEQ ID NO: 79. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 80, and a light chain comprising an amino acid sequence having at least 90%, at least 95%, at least 96%, at least 97%, at least 98%, at least 99% or 100% sequence identity to an amino acid sequence set out in SEQ ID NO: 81. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 82, and a light chain comprising an amino acid sequence having at least 90%, at least 95%, at least 96%, at least 97%, at least 98%, at least 99% or 100% sequence identity to an amino acid sequence set out in SEQ ID NO: 83. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 84, and a light chain comprising an amino acid sequence having at least 90%, at least 95%, at least 96%, at least 97%, at least 98%, at least 99% or 100% sequence identity to an amino acid sequence set out in SEQ ID NO: 85. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 86, and a light chain comprising an amino acid sequence having at least 90%, at least 95%, at least 96%, at least 97%, at least 98%, at least 99% or 100% sequence identity to an amino acid sequence set out in SEQ ID NO: 87 In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 88, and a light chain comprising an amino acid sequence having at least 90%, at least 95%, at least 96%, at least 97%, at least 98%, at least 99% or 100% sequence identity to an amino acid sequence set out in SEQ ID NO: 89. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 90, and a light chain comprising an amino acid sequence having at least 90%, at least 95%, at least 96%, at least 97%, at least 98%, at least 99% or 100% sequence identity to an amino acid sequence set out in SEQ ID NO: 91. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 92, and a light chain comprising an amino acid sequence having at least 90%, at least 95%, at least 96%, at least 97%, at least 98%, at least 99% or 100% sequence identity to an amino acid sequence set out in SEQ ID NO: 93. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 94, and a light chain comprising an amino acid sequence having at least 90%, at least 95%, at least 96%, at least 97%, at least 98%, at least 99% or 100% sequence identity to an amino acid sequence set out in SEQ ID NO: 95. In some embodiments, a heavy chain or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 186, a second heavy chain comprising an amino acid sequence having at least 90%, at least 95%, at least 96%, at least 97%, at least 98%, at least 99% or 100% sequence identity to an amino acid sequence set out in SEQ ID NO: 96, a light chain comprising an amino acid sequence having at least 90%, at least 95%, at least 96%, at least 97%, at least 98%, at least 99% or 100% sequence identity to an amino acid sequence set out in SEQ ID NO: 97, and an anti-TSLP Fab (Partial) polypeptide comprising an amino acid sequence having at least 90%, at least 95%, at least 96%, at least 97%, at least 98%, at least 99% or 100% sequence identity to an amino acid sequence set out in SEQ ID NO: 98. In some embodiments, a first heavy chain, a second heavy chain, a light chain, or an anti-TSLP Fab (partial) polypeptide can further comprise an optional signal peptide (e.g., SEQ ID NOs: 130-184).

In some embodiments, the binding moiety described herein can comprise a first polypeptide comprising an amino acid sequence having at least 90%, at least 95%, at least 96%, at least 97%, at least 98%, at least 99% or 100% sequence identity to an amino acid sequence set out in SEQ ID NO: 99, a second polypeptide comprising an amino acid sequence having at least 90%, at least 95%, at least 96%, at least 97%, at least 98%, at least 99% or 100% sequence identity to an amino acid sequence set out in SEQ ID NO: 100, a third polypeptide comprising an amino acid sequence having at least 90%, at least 95%, at least 96%, at least 97%, at least 98%, at least 99% or 100% sequence identity to an amino acid sequence set out in SEQ ID NO: 101, and a fourth polypeptide comprising an amino acid sequence having at least 90%, at least 95%, at least 96%, at least 97%, at least 98%, at least 99% or 100% sequence identity to an amino acid sequence set out in SEQ ID NO: 102. In some embodiments, a first polypeptide, a second polypeptide, a third polypeptide, or a fourth polypeptide can further comprise an optional signal peptide (e.g., SEQ ID NOs: 130-184).

In some embodiments, the binding moiety described herein can comprise a light chain comprising an amino acid sequence having at least 90%, at least 95%, at least 96%, at least 97%, at least 98%, at least 99% or 100% sequence identity to an amino acid sequence set out in SEQ ID NO: 103, a heavy chain comprising an amino acid sequence having at least 90%, at least 95%, at least 96%, at least 97%, at least 98%, at least 99% or 100% sequence identity to an amino acid sequence set out in SEQ ID NO: 104, and a partial Fab sequence (e.g., anti-TSLP Fab partial) comprising an amino acid sequence having at least 90%, at least 95%, at least 96%, at least 97%, at least 98%, at least 99% or 100% sequence identity to an amino acid sequence set out in SEQ ID NO: 105. In some embodiments, a heavy chain or a light chain can further comprise an optional signal peptide (e.g., SEQ ID NOs: 130-184).

In some embodiments, the binding moiety described herein can comprise a light chain comprising an amino acid sequence having at least 90%, at least 95%, at least 96%, at least 97%, at least 98%, at least 99% or 100% sequence identity to an amino acid sequence set out in SEQ ID NO: 127, a heavy chain comprising an amino acid sequence having at least 90%, at least 95%, at least 96%, at least 97%, at least 98%, at least 99% or 100% sequence identity to an amino acid sequence set out in SEQ ID NO: 128, and a partial Fab sequence (e.g., anti-TSLP Fab partial) comprising an amino acid sequence having at least 90%, at least 95%, at least 96%, at least 97%, at least 98%, at least 99% or 100% sequence identity to an amino acid sequence set out in SEQ ID NO: 129.

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 106, and a light chain comprising an amino acid sequence having at least 90%, at least 95%, at least 96%, at least 97%, at least 98%, at least 99% or 100% sequence identity to an amino acid sequence set out in SEQ ID NO: 107. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 108, and a light chain comprising an amino acid sequence having at least 90%, at least 95%, at least 96%, at least 97%, at least 98%, at least 99% or 100% sequence identity to an amino acid sequence set out in SEQ ID NO: 109. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 110, and a light chain comprising an amino acid sequence having at least 90%, at least 95%, at least 96%, at least 97%, at least 98%, at least 99% or 100% sequence identity to an amino acid sequence set out in SEQ ID NO: 112. In some embodiments, a heavy chain or a light chain can further comprise an optional signal peptide (e.g., SEQ ID NOs: 130-184).

In some embodiments, the binding moiety described herein can comprise a heavy chain comprising an amino acid sequence having at least 90%, at least 95%, at least 96%, at least 97%, at least 98%, at least 99% or 100% sequence identity to an amino acid sequence set out in SEQ ID NO: 113, and a light chain comprising an amino acid sequence having at least 90%, at least 95%, at least 96%, at least 97%, at least 98%, at least 99% or 100% sequence identity to an amino acid sequence set out in SEQ ID NO: 114. In some embodiments, a heavy chain or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 115, a second heavy chain comprising an amino acid sequence having at least 90%, at least 95%, at least 96%, at least 97%, at least 98%, at least 99% or 100% sequence identity to an amino acid sequence set out in SEQ ID NO: 116, and a light chain comprising an amino acid sequence having at least 90%, at least 95%, at least 96%, at least 97%, at least 98%, at least 99% or 100% sequence identity to an amino acid sequence set out in SEQ ID NO: 117. In some embodiments, a first heavy chain, a second heavy chain, or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 118, a second heavy chain comprising an amino acid sequence having at least 90%, at least 95%, at least 96%, at least 97%, at least 98%, at least 99% or 100% sequence identity to an amino acid sequence set out in SEQ ID NO: 119, and a light chain comprising an amino acid sequence having at least 90%, at least 95%, at least 96%, at least 97%, at least 98%, at least 99% or 100% sequence identity to an amino acid sequence set out in SEQ ID NO: 120. In some embodiments, a first heavy chain, a second heavy chain, or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 121, a second heavy chain comprising an amino acid sequence having at least 90%, at least 95%, at least 96%, at least 97%, at least 98%, at least 99% or 100% sequence identity to an amino acid sequence set out in SEQ ID NO: 122, and a light chain comprising an amino acid sequence having at least 90%, at least 95%, at least 96%, at least 97%, at least 98%, at least 99% or 100% sequence identity to an amino acid sequence set out in SEQ ID NO: 123. In some embodiments, a first heavy chain, a second heavy chain, or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 124, a second heavy chain comprising an amino acid sequence having at least 90%, at least 95%, at least 96%, at least 97%, at least 98%, at least 99% or 100% sequence identity to an amino acid sequence set out in SEQ ID NO: 125, and a light chain comprising an amino acid sequence having at least 90%, at least 95%, at least 96%, at least 97%, at least 98%, at least 99% or 100% sequence identity to an amino acid sequence set out in SEQ ID NO: 126. In some embodiments, a first heavy chain, a second heavy chain, or a light chain can further comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 189, a first light chain comprising an amino acid sequence having at least 90%, at least 95%, at least 96%, at least 97%, at least 98%, at least 99% or 100% sequence identity to an amino acid sequence set out in SEQ ID NO: 190, and a second light chain comprising an amino acid sequence having at least 90%, at least 95%, at least 96%, at least 97%, at least 98%, at least 99% or 100% sequence identity to an amino acid sequence set out in SEQ ID NO: 191. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 192, a first light chain comprising an amino acid sequence having at least 90%, at least 95%, at least 96%, at least 97%, at least 98%, at least 99% or 100% sequence identity to an amino acid sequence set out in SEQ ID NO: 193, and a second light chain comprising an amino acid sequence having at least 90%, at least 95%, at least 96%, at least 97%, at least 98%, at least 99% or 100% sequence identity to an amino acid sequence set out in SEQ ID NO: 194. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 195, a first light chain comprising an amino acid sequence having at least 90%, at least 95%, at least 96%, at least 97%, at least 98%, at least 99% or 100% sequence identity to an amino acid sequence set out in SEQ ID NO: 196, and a second light chain comprising an amino acid sequence having at least 90%, at least 95%, at least 96%, at least 97%, at least 98%, at least 99% or 100% sequence identity to an amino acid sequence set out in SEQ ID NO: 197. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 198, a first light chain comprising an amino acid sequence having at least 90%, at least 95%, at least 96%, at least 97%, at least 98%, at least 99% or 100% sequence identity to an amino acid sequence set out in SEQ ID NO: 199, and a second light chain comprising an amino acid sequence having at least 90%, at least 95%, at least 96%, at least 97%, at least 98%, at least 99% or 100% sequence identity to an amino acid sequence set out in SEQ ID NO: 200. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 198, a first light chain comprising an amino acid sequence having at least 90%, at least 95%, at least 96%, at least 97%, at least 98%, at least 99% or 100% sequence identity to an amino acid sequence set out in SEQ ID NO: 199, and a second light chain comprising an amino acid sequence having at least 90%, at least 95%, at least 96%, at least 97%, at least 98%, at least 99% or 100% sequence identity to an amino acid sequence set out in SEQ ID NO: 200. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 201, a first light chain comprising an amino acid sequence having at least 90%, at least 95%, at least 96%, at least 97%, at least 98%, at least 99% or 100% sequence identity to an amino acid sequence set out in SEQ ID NO: 202, and a second light chain comprising an amino acid sequence having at least 90%, at least 95%, at least 96%, at least 97%, at least 98%, at least 99% or 100% sequence identity to an amino acid sequence set out in SEQ ID NO: 203. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 204, a first light chain comprising an amino acid sequence having at least 90%, at least 95%, at least 96%, at least 97%, at least 98%, at least 99% or 100% sequence identity to an amino acid sequence set out in SEQ ID NO: 205, and a second light chain comprising an amino acid sequence having at least 90%, at least 95%, at least 96%, at least 97%, at least 98%, at least 99% or 100% sequence identity to an amino acid sequence set out in SEQ ID NO: 206. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 207, a second heavy chain comprising an amino acid sequence having at least 90%, at least 95%, at least 96%, at least 97%, at least 98%, at least 99% or 100% sequence identity to an amino acid sequence set out in SEQ ID NO: 208, a first light chain comprising an amino acid sequence having at least 90%, at least 95%, at least 96%, at least 97%, at least 98%, at least 99% or 100% sequence identity to an amino acid sequence set out in SEQ ID NO: 209, and a second light chain comprising an amino acid sequence having at least 90%, at least 95%, at least 96%, at least 97%, at least 98%, at least 99% or 100% sequence identity to an amino acid sequence set out in SEQ ID NO: 210. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 211, a first light chain comprising an amino acid sequence having at least 90%, at least 95%, at least 96%, at least 97%, at least 98%, at least 99% or 100% sequence identity to an amino acid sequence set out in SEQ ID NO: 212, and a second light chain comprising an amino acid sequence having at least 90%, at least 95%, at least 96%, at least 97%, at least 98%, at least 99% or 100% sequence identity to an amino acid sequence set out in SEQ ID NO: 213. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 214, a first light chain comprising an amino acid sequence having at least 90%, at least 95%, at least 96%, at least 97%, at least 98%, at least 99% or 100% sequence identity to an amino acid sequence set out in SEQ ID NO: 215, and a second light chain comprising an amino acid sequence having at least 90%, at least 95%, at least 96%, at least 97%, at least 98%, at least 99% or 100% sequence identity to an amino acid sequence set out in SEQ ID NO: 216. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 217, and a first light chain comprising an amino acid sequence having at least 90%, at least 95%, at least 96%, at least 97%, at least 98%, at least 99% or 100% sequence identity to an amino acid sequence set out in SEQ ID NO: 218. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 219, and a first light chain comprising an amino acid sequence having at least 90%, at least 95%, at least 96%, at least 97%, at least 98%, at least 99% or 100% sequence identity to an amino acid sequence set out in SEQ ID NO: 220. In some embodiments, a first heavy chain, a second heavy chain, or a light chain can comprise an optional signal peptide (e.g., SEQ ID NOs: 130-184).

In some embodiments, the binding moiety described herein can comprise a first heavy chain comprising an amino acid sequence having at least 90%, at least 95%, at least 96%, at least 97%, at least 98%, at least 99% or 100% sequence identity to an amino acid sequence set out in SEQ ID NO: 221, and a first light chain comprising an amino acid sequence having at least 90%, at least 95%, at least 96%, at least 97%, at least 98%, at least 99% or 100% sequence identity to an amino acid sequence set out in SEQ ID NO: 222. In some embodiments, a first heavy chain, a second heavy chain, or a light chain can comprise an optional signal peptide (e.g., SEQ ID NOs: 130-184).

In some embodiments, the antigen binding moiety described herein may comprise a first polypeptide chain, a second polypeptide chain, a third polypeptide chain, a fourth polypeptide chain, and/or a fifth polypeptide chain encoding one or more components of the antigen binding moiety disclosed herein.

For example, in some cases, the antigen binding moiety disclosed herein can comprise (from N-terminus to C-terminus), a first polypeptide comprising a light chain (comprising VL and CL) of the anti-IL-4R (the $L_{IL\text{-}4R}$); a second polypeptide comprising a heavy chain (comprising VH, CH1, CH2, and CH3) of the anti-IL-4R (e.g., $H_{IL\text{-}4R}$) coupled to (e.g., via an optional linker) a light chain (comprising VL and CL) of the anti-TSLP; and a third polypeptide comprising at least a portion of the heavy chain (comprising VH and CH1) of the anti-TSLP. In some embodiments, the first polypeptide comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 103 or 127. In some embodiments, the second polypeptide comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 104 or 128. In some embodiments, the third polypeptide comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 105 or 129. In some embodiments, the first polypeptide, the second polypeptide, and the third polypeptide may further comprise a signal peptide (e.g., the amino acid sequence of any one of SEQ ID NOs: 130-184).

In some cases, the antigen binding moiety disclosed herein can comprise (from N-terminus to C-terminus), a first polypeptide comprising a light chain (comprising VL and CL) of the anti-IL-4R (the $L_{IL-4R}$); a second polypeptide comprising a heavy chain (comprising VH, CH1, CH2, and CH3) of the anti-IL-4R (e.g., $H_{IL-4R}$) coupled to (e.g., via an optional linker) a peptide chain comprising VH and CL of the anti-TSLP; and a third polypeptide comprising VL and CH1 of the anti-TSLP. In some embodiments, the first polypeptide, the second polypeptide, and the third polypeptide may further comprise a signal peptide (e.g., the amino acid sequence of any one of SEQ ID NOs: 130-184.)

In some cases, the antigen binding moiety disclosed herein can comprise (from N-terminus to C-terminus), a first polypeptide comprising a light chain (comprising VL and CL) of the anti-IL-4R (the $L_{IL-4R}$); a second polypeptide comprising a heavy chain (comprising VH, CH1, CH2, and CH3) of the anti-IL-4R (e.g., $H_{IL-4R}$) coupled to (e.g., via an optional linker) a peptide chain comprising VL and CH1 of the anti-TSLP; and a third polypeptide comprising VH and CL of the anti-TSLP. In some embodiments, the first polypeptide, the second polypeptide, and the third polypeptide may further comprise a signal peptide (e.g., the amino acid sequence of any one of SEQ ID NOs: 130-184.)

In some embodiments, the optional linker can comprise an amino acid sequence having at least 80% sequence identity to the amino acid sequence of any one of SEQ ID NOs: 40-47, 185-188, or 223-226. In some embodiments, the optional linker can comprise an amino acid sequence having any one of SEQ ID NOs: 40-47, 185-188, or 223-226.

In some embodiments, the binding moiety described herein can comprise at least 80%, at least 85%, at least 90%, at least 95% or 100% identity to candidate 1 described herein, candidate 2 described herein, candidate 3 described herein, candidate 4 described herein, candidate 5 described herein, candidate 6 described herein, candidate 7 described herein, candidate 8 described herein, candidate 9 described herein, candidate 10 described herein, candidate 11 described herein, candidate 12 described herein, candidate 13 described herein, candidate 14 described herein, candidate 15 described herein, candidate 16 described herein, candidate 17 described herein, candidate 18 described herein, candidate 19 described herein, candidate 19.1, candidate 20 described herein, candidate 21 described herein, candidate 22 described herein, candidate 23 described herein, candidate 24 described herein, candidate 25 described herein, candidate 26 described herein, candidate 27 described herein, or any combination thereof. In some embodiments, the binding moiety described herein comprises candidate 19.1.

For example, the antigen binding moiety of the disclosure can be engineered to include modifications within the Fc region, typically to alter one or more functional properties of the antigen binding moiety, such as serum half-life, complement fixation, Fc receptor binding, and/or antigen-dependent cellular cytotoxicity. Furthermore, the antigen binding moiety of the disclosure can be chemically modified (e.g., one or more chemical moieties can be attached to the antibody) or be modified to alter glycosylation, again to alter one or more functional properties.

In one embodiment, the hinge region of CH1 is modified in such that the number of cysteine residues in the hinge region is altered, e.g., increased or decreased. The number of cysteine residues in the hinge region of CH1 is altered to, for example, facilitate assembly of the light and heavy chains or to increase or decrease the stability of the antibody.

In another embodiment, the Fc hinge region in the antigen binding moiety of the disclosure is mutated to decrease the biological half-life of the antibody. More specifically, one or more amino acid mutations are introduced into the CH2-CH3 region interface region of the Fc-hinge fragment such that the antibody has impaired Staphylococcal protein A (SpA) binding relative to native Fc-hinge region SpA binding.

In still another embodiment, the glycosylation of the antigen binding moiety is modified. For example, a glycosylated bispecific antibody can be made (e.g., the bispecific antibody lacks glycosylation). Glycosylation can be altered to, for example, increase the affinity of the anti-CD40 antibody or the antigen binding portion thereof for the antigen.

In some embodiments, the antibody or the antigen binding portion thereof comprises a Fc region. The Fc region is an IgG1, IgG2, IgG3, or IgG4 heavy chain Fc region. In some embodiments, the Fc region comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33.

In some embodiments, the antibody or the antigen binding portion thereof further comprises a Fc region that is symmetric. In some embodiments, the antibody or the antigen binding portion thereof further comprises a Fc region that is asymmetric. In some embodiments, an asymmetric moiety can comprise a construct where amino acids at the contact site between the CH3 regions of a first Fc region and a second Fc region are substituted by larger or smaller residues forcing a heterodimeric assembly of heavy chains. In some embodiments, an asymmetric moiety is generated using knobs-into-holes (KiH). In some embodiments, the knobs-into-holes approach comprises a knob that is obtained by replacement of a small amino acid with a larger one in the CH3 region. In some embodiments, the knob is designed to insert into a hole in the CH3 region that is obtained by replacement of a large residue with a smaller one. In some embodiments, a large residue can be tyrosine or tryptophan. In some embodiments, a small residue can be glycine, alanine, threonine. In some embodiments, an antibody comprising a Fc region with KiH mutation described herein has an improved heterodimerization, enhanced stability, and an increase in therapeutic efficacy compared to that of a control antibody lacking the KiH mutation.

Another modification of the antigen binding moiety described herein comprises a pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or the antigen binding portion thereof.

In some cases, provided herein is an antigen binding moiety with enhanced in vivo and/or in vitro stability relative to conventional antibody formats (e.g., a monospecific antibody or a bispecific antibody comprising one or more scFv fragments).

In some cases, an antigen binding moiety described herein (e.g., Candidate 19.1) can retain binding activity and/or structural integrity after exposure to thermal stress. For example, in some cases, the antigen binding moiety described herein may retain binding activity and/or structural integrity after exposure to thermal stress, such as incubation at elevated temperature of at least about 35° C., at least about 40° C., at least about 45° C., at least about 50° C., at least about 55° C., at least about 60° C., or more. In some cases, the antigen binding moiety described herein may retain binding activity and/or structural integrity after exposure to thermal stress (e.g., from 40° C. to 60° C.) for at least about 1 day, at least about 7 days, at least about 2 weeks, at least about 3 weeks, at least about 4 weeks, at least about 1.5 months, at least about 6 months, at least about 7 months, at least about 10 months, at least about 11 months, at least about 12 months, at least about 1.5 years, at least about 2 years, or more. For example, in some cases, the antibody may exhibit at most about 1%, at most about 2%, at most about 3%, at most about 4%, at most about 5%, at most about 6%, at most about 7%, at most about 8%, at most about 9%, at most about 10%, at most about 15%, at most about 20%, or less change in monomeric purity after thermal incubation. In some cases, the antigen binding moiety described herein may be resistant to heat-induced aggregation and/or degradation.

In some cases, the antigen binding moiety described herein can exhibit enhanced pH stability. For example, in some cases, the antigen binding moiety described herein can retain binding activity and/or structural integrity after exposure to acidic or basic solutions or environments. In some cases, the antigen binding moiety described herein can exhibit enhanced pH stability, maintaining at least about 75%, at least about 80%, at least about 85%, at least about 90%, at least about 95%, or greater capacity (e.g., antigen-binding capacity) after incubation in acidic (e.g., pH of 1 to 6.5) or basic (e.g., pH of 7.5-14) conditions.

In some cases, the antigen binding moiety described herein may be resistant to proteolytic degradation, retaining functional binding activity after exposure to serum proteases or proteolytic enzymes (e.g., trypsin, cathepsins) under physiological condition. In some cases, the antigen binding moiety described herein may maintain at least about 75%, at least about 80%, at least about 85%, at least about 90%, at least about 95%, or greater capacity (e.g., antigen-binding capacity) after incubation in human, non-human primate, or murine serum (for at least about 6 hours, at least about 12 hours, at least about 1 day, at least about 2 days, at least about 3 days, or more). In some embodiments, the antigen binding moiety described herein may exhibit enhanced stability in biological matrices (e.g., human or animal serum) for extended periods. The antigen binding moiety described herein may retain structurally and functionally stable upon incubation in serum at physiological temperature for at least about 1 day, at least about 2 days, at least about 5 days, at least about 7 days, at least about 2 weeks, at least about 3 weeks, at least about 4 weeks, or more without significant degradation, aggregation, or loss of binding activity.

In some embodiments, the antigen binding moiety described herein may exhibit improved storage stability, maintaining structural integrity and/or functional activity. In some cases, the storage conditions may be in low temperature (e.g., refrigerated condition), room temperature, or high temperature. The antigen binding moiety may exhibit extended storage stability that is at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 1.5 months, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 1.5 years, at least about 2 years, or more.

The antigen binding moiety may exhibit low self-association and low polyreactivity as compared to a monospecific antibody or an antigen binding moiety comprising one or more scFv fragments. In some cases, the antigen binding moiety described herein can have low solution viscosity. In some cases, the antigen binding moiety described herein can facilitate subcutaneous administration or high-concentration formulation (e.g., for prefilled syringes) due to its low viscosity characteristics.

In some embodiments, the antigen binding moiety described herein may exhibit enhanced biophysical and pharmacokinetic properties compared to conventional antibody constructs (e.g., a monospecific antibody or an antigen binding moiety comprising one or more scFv fragments). In some embodiments, the antigen binding moiety may have an extended in vivo half-life. For example, the antigen binding moiety described herein can maintain prolonged systemic exposure, exhibiting sustained serum levels beyond typical half-life profiles observed with control antibodies of similar isotypes (e.g., a monospecific antibody or an antigen binding moiety comprising one or more scFv fragments). In some cases, the antigen binding moiety described herein can exhibit a serum half-life of at least about 2 days, at least about 5 days, at least about 7 days, at least about 2 weeks, at least about 3 weeks, at least about 4 weeks, at least about 1.5 months, at least about 2 months, at least about 3 months, at least about 4 months, at least about 5 months, at least about 6 months, or more in a subject. In some cases, the half-life is at least about 1.1-fold, at least about 1.2-fold, at least about 1.5-fold, at least about 2-fold, at least about 2.5-fold, or longer compared to control antibodies of similar isotypes (e.g., a monospecific antibody or an antigen binding moiety comprising one or more scFv fragments). In some cases, the antigen binding moiety described herein can retain at least about 50%, at least about 60%, at least about 70%, at least about 80%, at least about 90%, at least about 95% of its peak serum concentration at 12 hours, 24 hours, 36 hours, 48 hours, or 72 hours post-administration.

TSLP-TRAP

The TSLP-TRAP of the present disclosure can comprise an extracellular region of thymic stromal lymphopoietin protein receptor (TSLPR) and an extracellular region of interleukin-7 receptor subunit alpha (IL-7Rα). In some embodiments, the TSLPR is joined to a first portion of the moiety and the IL-7Rα is joined to a second portion of the moiety. In some embodiments, the TSLPR and the IL-7Rα are joined via a linker. In some embodiments, the extracellular region of TSLPR is derived from a mammal and the extracellular region of IL-7Rα is derived from a mammal. Mammal refers to any member of the class Mammalia, including, without limitations, humans and nonhuman primates such as chimpanzees and other apes and monkey species; farm animals such as cattle, sheep, pigs, goats, lamas and horses; domestic mammals such as dogs and cats; laboratory animals including rodents such as mice, rats, and guinea pigs, etc.

The TSLP-TRAP may have at least one or more amino acid modifications in various regions of the extracellular region of TSLPR or the extracellular region of IL-7Rα. The TSLP-TRAP may be modified by at least one or more amino acid substitution, deletion, addition, or a combination thereof at one or more position while the variant TSLP-TRAP binding complex substantially retains the biological characteristics of the unmodified complex, such as binding to TSLP. In some embodiments, the amino acid sequence of the TSLP-TRAP may have at least 1, at least 2, at least 3, at least 4, at least 5, at least 6, at least 7, at least 8, at least 9, at least 10, at least 11, at least 12, at least 13, at least 14, or at least 15 amino acid insertions, deletions, substitutions or a combination thereof.

In some embodiments, the extracellular region of TSLPR comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 48. In some embodiments, the extracellular region of TSLPR comprises an amino acid sequence set out in SEQ ID NO: 48.

In some embodiments the extracellular region of IL-7Rα comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 49. In some embodiments, the extracellular region of IL-7Rα comprises an amino acid sequence set out in SEQ ID NO: 49.

The extracellular region of TSLPR and the extracellular region of IL-7Rα may be further linked by a linker (second linker). In some embodiments, the TSLP-TRAP may comprise a second linker polypeptide. In some embodiments, the linker may be a flexible linker, a rigid linker, or a cleavable linker. The TSLP-TRAP described herein can be optimized for protein expression and yield by changing composition and/or length of the polypeptide linker. In some embodiments, the second linker is a polypeptide between 3 amino acids and 500 amino acids in length that associates the extracellular region of TSLPR to the extracellular region of IL-7Rα. In some embodiments, the polypeptide linker may be about 3 amino acids to about 10 amino acids, about 3 amino acids to about 20 amino acids, about 3 amino acids to about 30 amino acids, about 3 amino acids to about 60 amino acids, about 3 amino acids to about 90 amino acids, about 3 amino acids to about 100 amino acids, about 3 amino acids to about 200 amino acids, about 3 amino acids to about 300 amino acids, about 3 amino acids to about 400 amino acids, about 3 amino acids to about 500 amino acids, about 6 amino acids to about 10 amino acids, about 6 amino acids to about 20 amino acids, about 6 amino acids to about 30 amino acids, about 6 amino acids to about 60 amino acids, about 6 amino acids to about 100 amino acids, about 6 amino acids to about 200 amino acids, about 6 amino acids to about 300 amino acids, about 6 amino acids to about 400 amino acids, about 6 amino acids to about 500 amino acids, about 8 amino acids to about 10 amino acids, about 8 amino acids to about 20 amino acids, about 8 amino acids to about 30 amino acids, about 8 amino acids to about 60 amino acids, about 8 amino acids to about 100 amino acids, about 8 amino acids to about 200 amino acids, about 8 amino acids to about 300 amino acids, about 8 amino acids to about 500 amino acids, about 10 amino acids to about 20 amino acids, about 10 amino acids to about 30 amino acids, about 10 amino acids to about 100 amino acids, about 10 amino acids to about 200 amino acids, about 10 amino acids to about 300 amino acids, about 10 amino acids to about 400 amino acids, about 10 amino acids to about 500 amino acids, about 20 amino acids to about 30 amino acids, about 20 amino acids to about 100 amino acids, about 20 amino acids to about 200 amino acids, about 20 amino acids to about 300 amino acids, about 20 amino acids to about 400 amino acids, about 20 amino acids to about 500 amino acids, about 30 amino acids to about 100 amino acids, about 30 amino acids to about 200 amino acids, about 30 amino acids to about 300 amino acids, about 30 amino acids to about 400 amino acids, about 30 amino acids to about 500 amino acids, about 100 amino acids to about 200 amino acids, about 100 amino acids to about 300 amino acids, about 100 amino acids to about 400 amino acids, about 100 amino acids to about 500 amino acids, about 200 amino acids to about 300 amino acids, about 200 amino acids to about 400 amino acids, about 200 amino acids to about 500 amino acids, about 300 amino acids to about 400 amino acids, about 300 amino acids to about 500 amino acids, or about 400 amino acids to about 500 amino acids. In some embodiments, the polypeptide linker can be about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker can be at least about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker may at most be about 6 amino acids, about 10 amino acids, about 20 amino acids, about 30 amino acids, about 100 amino acids, about 200 amino acids, about 300 amino acids, about 400 amino acids, about 500 amino acids.

In some embodiments, the second linker is a polypeptide 60 amino acids in length that associates the extracellular region of TSLPR to the extracellular region of IL-7Rα. In some embodiments, the second linker is a polypeptide at least 60 amino acids in length that associates the extracellular region of TSLPR to the extracellular region of IL-7Rα. In some embodiments, the second linker is a polypeptide at most 60 amino acids in length that associates the extracellular region of TSLPR to the extracellular region of IL-7Rα. For example, in some embodiments, N-terminus of the linker (e.g., the 60 amino acids polypeptide described herein) is coupled to the extracellular region of the TSLPR, while C-terminus of the linker is coupled to the extracellular region of IL-7Rα. In some embodiments, C-terminus of the linker (e.g., the 60 amino acids polypeptide described herein) is coupled to the extracellular region of the TSLPR, while N-terminus of the linker is coupled to the extracellular region of IL-7Rα.

In some embodiments, the second linker is a polypeptide 20 amino acids in length that associates the extracellular region of TSLPR to the extracellular region of IL-7Rα. In some embodiments, the second linker is a polypeptide at least 20 amino acids in length that associates the extracellular region of TSLPR to the extracellular region of IL-7Rα. In some embodiments, the second linker is a polypeptide at most 20 amino acids in length that associates the extracellular region of TSLPR to the extracellular region of IL-7Rα. For example, in some embodiments, N-terminus of the linker (e.g., the 20 amino acids polypeptide described herein) is coupled to the extracellular region of the TSLPR, while C-terminus of the linker is coupled to the extracellular region of IL-7Rα. In some embodiments, C-terminus of the linker (e.g., the 20 amino acids polypeptide described herein) is coupled to the extracellular region of the TSLPR, while N-terminus of the linker is coupled to the extracellular region of IL-7Rα. In some embodiments, the second linker is a polypeptide 60 amino acids in length that associates the TSLP-TRAP to the moiety. In some embodiments, the second linker is a polypeptide at least 60 amino acids in length that associates the TSLP-TRAP to the moiety. In some embodiments, the second linker is a polypeptide at most 60 amino acids in length that associates the TSLP-TRAP to the moiety. For example, in some embodiments, N-terminus of the linker (e.g., the 60 amino acids polypeptide described herein) is coupled to the TSLP-TRAP, while C-terminus of the linker is coupled to the moiety. In some embodiments, C-terminus of the linker (e.g., the 60 amino acids polypeptide described herein) is coupled to the extracellular region of the TSLP-TRAP, while N-terminus of the linker is coupled to the moiety.

In some embodiments, the second linker is a polypeptide 20 amino acids in length that associates the TSLP-TRAP to the moiety. In some embodiments, the second linker is a polypeptide at least 20 amino acids in length that associates the TSLP-TRAP to the moiety. In some embodiments, the second linker is a polypeptide up to and including 20 amino acids in length that associates the TSLP-TRAP to the moiety. For example, N-terminus of the linker (e.g., the 20 amino acids polypeptide described herein) is coupled to the TSLP-TRAP, while C-terminus of the linker is coupled to the moiety. In some embodiments, C-terminus of the linker (e.g., the 20 amino acids polypeptide described herein) is coupled to the extracellular region of the TSLP-TRAP, while N-terminus of the linker is coupled to the moiety.

In some embodiments, the polypeptide linker described herein may be about 15 amino acids in length, about 20 amino acids in length, about 25 amino acids in length, about 30 amino acids in length, about 35 amino acids in length, about 40 amino acids in length, about 45 amino acids in length, about 50 amino acids in length, about 55 amino acids in length, or about 60 amino acids in length. In some embodiments, the linker peptide may comprise ((GGS)n (SEQ ID NO: 17), (GGGGS)n (SEQ ID NO: 40), (SGGGG)n (SEQ ID NO: 44), GGGG(SGGGG)n (SEQ ID NO: 45) or GG(SGG)n (SEQ ID NO: 46) wherein n is an integer between 1 and 100. In some embodiments, the linker peptide may comprise (GGS)×20 (SEQ ID NO: 47).

The TSLP-TRAP can be arranged as either 1) the extracellular region of TSLPR—second linker—the extracellular region of IL-7Rα or 2) the extracellular region of IL-7Rα—second linker—the extracellular region of TSLPR. In some embodiments, the TSLP-TRAP comprises amino acids 25-231 of human TSLPR associated via (GGS)×20 (SEQ ID NO: 47) to amino acids 21-239 of human IL-7Rα. In some embodiments, the TSLP-TRAP comprises amino acids 21-239 of human IL-7Rα associated via (GGS)×20 (SEQ ID NO: 47) to amino acids 25-231 of human TSLPR. In some embodiments, the TSLP-TRAP comprises at least about 15, 20, 25, 30 or 50 contiguous amino acids of human TSLPR associated via a linker to at least about 15, 20, 25, 30 or 50 contiguous amino acids of human IL-7Rα.

In some embodiments, the TSLP-TRAP comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 50. In some embodiments, the TSLP-TRAP comprises an amino acid sequence set out in SEQ ID NO: 50.

In some embodiments, the TSLP-TRAP comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence set out in SEQ ID NO: 51. In some embodiments, the TSLP-TRAP comprises an amino acid sequence set out in SEQ ID NO: 51.

In some embodiments, the antigen binding complex comprising the TSLP-TRAP associated with a moiety via a linker as described herein may be administered to a subject for diagnosis or treatment of a condition or a disease. Exemplary conditions and diseases may include, but not limited to, asthma, inflammatory arthritis, sinusitis, pruritus, solid tumors, atopic dermatitis, eosinophilic esophagitis, eczema, allergic rhinitis, airway hyperresponsiveness, airway inflammation, a food allergy, chronic urticaria, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, Crohn's disease and drug allergies.

First Linker

In some embodiments, the first linker is capable of forming covalent bonds to both TSLP-TRAP and to the moiety. Suitable linkers are well known to those of skill in the art and include, but are not limited to, straight or branched-chain carbon linkers, heterocyclic carbon linkers, or peptide linkers. Where the TSLP-TRAP and the moiety are polypeptides, the linkers may be joined to the constituent amino acids through their side groups (e.g., through a disulfide linkage to cysteine). In some embodiments, the linkers can be joined to the alpha carbon amino and carboxyl groups of the terminal amino acids.

The TSLP-TRAP and a moiety may be further associated by a linker (first linker). In some embodiments, the TSLP-TRAP complex may comprise a first linker polypeptide. In some embodiments, the linker may be a flexible linker, a rigid linker, or a cleavable linker. The TSLP-TRAP complex described herein can be optimized for protein expression and yield by changing composition and/or length of the polypeptide linker. In some embodiments, the first linker is a polypeptide between 3 amino acids and 500 amino acids in length that associates the TSLP-TRAP to the moiety. In some embodiments, the polypeptide linker may be about 3 amino acids to about 10 amino acids, about 3 amino acids to about 20 amino acids, about 3 amino acids to about 30 amino acids, about 3 amino acids to about 60 amino acids, about 3 amino acids to about 90 amino acids, about 3 amino acids to about 100 amino acids, about 3 amino acids to about 200 amino acids, about 3 amino acids to about 300 amino acids, about 3 amino acids to about 400 amino acids, about 3 amino acids to about 500 amino acids, about 6 amino acids to about 10 amino acids, about 6 amino acids to about 20 amino acids, about 6 amino acids to about 30 amino acids, about 6 amino acids to about 60 amino acids, about 6 amino acids to about 100 amino acids, about 6 amino acids to about 200 amino acids, about 6 amino acids to about 300 amino acids, about 6 amino acids to about 400 amino acids, about 6 amino acids to about 500 amino acids, about 8 amino acids to about 10 amino acids, about 8 amino acids to about 20 amino acids, about 8 amino acids to about 30 amino acids, about 8 amino acids to about 60 amino acids, about 8 amino acids to about 100 amino acids, about 8 amino acids to about 200 amino acids, about 8 amino acids to about 300 amino acids, about 8 amino acids to about 500 amino acids, about 10 amino acids to about 20 amino acids, about 10 amino acids to about 30 amino acids, about 10 amino acids to about 100 amino acids, about 10 amino acids to about 200 amino acids, about 10 amino acids to about 300 amino acids, about 10 amino acids to about 400 amino acids, about 10 amino acids to about 500 amino acids, about 20 amino acids to about 30 amino acids, about 20 amino acids to about 100 amino acids, about 20 amino acids to about 200 amino acids, about 20 amino acids to about 300 amino acids, about 20 amino acids to about 400 amino acids, about 20 amino acids to about 500 amino acids, about 30 amino acids to about 100 amino acids, about 30 amino acids to about 200 amino acids, about 30 amino acids to about 300 amino acids, about 30 amino acids to about 400 amino acids, about 30 amino acids to about 500 amino acids, about 100 amino acids to about 200 amino acids, about 100 amino acids to about 300 amino acids, about 100 amino acids to about 400 amino acids, about 100 amino acids to about 500 amino acids, about 200 amino acids to about 300 amino acids, about 200 amino acids to about 400 amino acids, about 200 amino acids to about 500 amino acids, about 300 amino acids to about 400 amino acids, about 300 amino acids to about 500 amino acids, or about 400 amino acids to about 500 amino acids. In some embodiments, the polypeptide linker can be about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker can be at least about 3 amino acids, about 6 amino acids, about 10 amino acids, about 20 amino acids, about 30 amino acids, about 60 amino acids, about 100 amino acids, about 200 amino acids, about 300 amino acids, about 400 amino acids, or about 500 amino acids. In some embodiments, the polypeptide linker may at most be about 6 amino acids, about 10 amino acids, about 20 amino acids, about 30 amino acids, about 100 amino acids, about 200 amino acids, about 300 amino acids, about 400 amino acids, about 500 amino acids.

In some embodiments, the first linker is a polypeptide 60 amino acids in length that associates the TSLP-TRAP to the moiety. In some embodiments, the first linker is a polypeptide at least 60 amino acids in length that associates the TSLP-TRAP to the moiety. In some embodiments, the first linker is a polypeptide up to and including 60 amino acids in length that associates the TSLP-TRAP to the moiety. In some embodiments, the first linker is a polypeptide 20 amino acids in length that associates the TSLP-TRAP to the moiety. In some embodiments, the first linker is a polypeptide at least 20 amino acids in length that associates the TSLP-TRAP to the moiety. In some embodiments, the first linker is a polypeptide up to and including 20 amino acids in length that associates the TSLP-TRAP to the moiety. In some embodiments, the polypeptide linker may be about 15 amino acids in length, about 20 amino acids in length, about 25 amino acids in length, about 30 amino acids in length, about 35 amino acids in length, about 40 amino acids in length, about 45 amino acids in length, about 50 amino acids in length, about 55 amino acids in length, or about 60 amino acids in length.

In some embodiments, the linker peptide may comprise (GGS)n (SEQ ID NO: 17), (GGGGS)n (SEQ ID NO: 40), (SGGGG)n (SEQ ID NO: 44), GGGG(SGGGG)n (SEQ ID NO: 45) or GG(SGG)n (SEQ ID NO: 46) wherein n is an integer between 1 and 100. In some embodiments, the linker peptide may comprise (GGS)×20 (SEQ ID NO: 47).

In some embodiments, the first linker comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence of (GGGGS)n (SEQ ID NO: 40), wherein n is an integer between 1 and 100. In some embodiments, the first linker comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence of (GGGGS)×4 (SEQ ID NO: 224). In some embodiments, the amino acid sequence of the first linker comprises (GGGGS)×4 (SEQ ID NO: 224).

Moieties

In some embodiments, the antigen binding complex comprises a moiety selected from the group consisting of: 1) a probe; 2) an antibody region; 3) an antibody or an antigen binding portion thereof; 4) a receptor; and 5) a half-life extender.

In some embodiments, the moiety is a probe, wherein the probe provides additional means of isolating and/or detecting the translated antigen binding complex. Suitable probes (also known as labels or tags) are well known in the art and, for example, include, but are not limited to luciferase, green fluorescent protein, alkaline phosphatase, horseradish peroxidase, myc-tags, FLAG tags, eTags and polyhistidine tags. In some embodiments, such labels and tags are capable of providing a detectable signal to facilitate identification of such labels or tags, for example upon distribution of the amino acid sequence encoding the antigen binding complex into the desired cells and tissues. In some embodiments, the moiety is the probe, wherein the probe may be a His tag, a GST tag, a flag tag, or a fluorescent molecule.

In some embodiments, the moiety comprises an antibody region, wherein the antibody region comprises a Fc region. In some embodiments, the Fc region is an IgG1, IgG2, IgG3, or IgG4 heavy chain Fc region. In some embodiments, the Fc region comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the moiety is the antibody or the antigen binding portion thereof. In some embodiments, the antibody or the antigen binding portion thereof described herein may be a monoclonal antibody, a polyclonal antibody, a bispecific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab')2 fragment, a Fd fragment, a Fv fragment, a single-region antibody, a diabody, a fragment comprised of only a single monomeric variable region, disulfide-linked Fvs (sdFv), an intrabody, an anti-idiotypic (anti-Id) antibody, a VHH antibody, or ab antigen-binding fragment thereof.

The antibody or antigen-binding fragment thereof may have at least one or more amino acid modifications in various regions of the antibody. The antibody or antigen-binding fragment thereof may be modified by at least one or more amino acid substitution, deletion, addition, or a combination thereof at one or more position while the variant binding complex substantially retains the biological characteristics of the unmodified protein, such as binding to its target. In some embodiments, the amino acid sequence of the antibody or antigen-binding fragment thereof may have at least 1, at least 2, at least 3, at least 4, at least 5, at least 6, at least 7, at least 8, at least 9, at least 10, at least 11, at least 12, at least 13, at least 14, or at least 15 amino acid insertions, deletions, substitutions or a combination thereof.

In some instances, one or more amino acid modifications described herein can be in the antigen-binding (Fab) fragments of an antibody or antibody binding fragment thereof. In some instances, the modification can be within the Fab region of a heavy chain polypeptide (H) and a first light chain polypeptide (L). In some embodiments, the modification can be within a heavy chain variable region (VH), a heavy chain constant region (CH1), a light chain variable region (VL), a light chain constant region (CL), or a combination thereof. In some embodiments, one or more amino acid modifications can be in the Fab VH and VL with the N-terminal region. The VH, VL, HC or LC sequence described herein may be a variant sequence with up to 15 amino acid substitutions, insertion, or deletions. For example, the variant sequence may have up to 15, 14, 13, 12, 11, 10, 9, 8, 7, 6, 5, 4, 3, 2, or 1 amino acid substitution(s), addition(s), or deletion(s). The sequence variation may exclude one or more or all of the CDRs, for example, the CDRs are the same as the VH, VL, HC or LC sequence and the variation is in the remaining portion of the VH or VL, HC, or LC sequence, so that the CDR sequences are fixed and intact.

Each of HCDR1, HCDR2, HCDR3, LCDR1, LCDR2, and LCDR3 may be modified alone or in combination with any other CDR, in any permutation or combination. Typically, the modification is a substitution, particularly a conserved substitution, for example in Table 2 below.

TABLE 2

List of side chains & members

| Side Chain | Members |
|---|---|
| Hydrophobic | Met, Ala, Val, Leu Ile |
| Neutral Hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

In some embodiments, antibodies disclosed herein can be of various isotypes, preferably human IgG1, IgG2, IgG3 or IgG4, more preferably comprising human IgG1 hinge and constant region sequences. The antibodies or fragments thereof can be chimeric human-mouse, humanized (human framework and murine hypervariable (CDR) regions), or fully human, as well as variations thereof, such as half-IgG4 antibodies (referred to as "unibodies"). In some embodiments, the antibodies or fragments thereof may be designed or selected to comprise human constant region sequences that belong to specific allotypes, which may result in reduced immunogenicity when administered to a human subject. In some embodiments, allotypes include a non-G1 ml allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

In some embodiments, an antibody or an antigen binding portion thereof disclosed herein can specifically bind to CCL19, CCL21, CD1, CD1a, CD2, CD3, CD4, CD5, CD8, CD11A, CD14, CD15, CD16, CD17, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, CDH1, CDH6, CDH17, CDH19, CDH179b, HIF-1α, colon-specific antigen-p (CSAp), CEA (CEACAMS), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-4, IL-5, IL-6, IL-7, IL-8, IL-12, IL-15, IL-17, IL-18, IL-23, IL-25, IL-31, IL-33, CCl2, CCL3, CCL4, CCL5, CCL6, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27 CCL28, CXCL1, CXCL2, CXCL3, CXCL4, CXCL5, CXCL6, CXCL7, CXCL9, CXCL10, CXCL11, CXCL12, CXCL13, CXCL16, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, PD-1 receptor, placental growth factor, p53, PLAGL2, prostatic acid phosphatase, PSA, PRAME, PSMA, P1GF, ILGF, RS5, RANTES, T101, SAGE, S100, urvivingn, urvivingn-2B, TAC, TAG-72, tenascin, TRAIL receptors, TSLP, TNF-α, CCR1, CCR2, CCR3, CCR4, CCR5, CCR6, CCR7, CCR8, CCR9, CCR10, CCR11, CXCR1, CXCR2, CXCR3, CXCR4, CXCR5 or CXCR6. In some embodiments, the antibody or the antigen binding portion thereof specifically binds human interleukin-4 receptor (hIL-4R), human interleukin-4 (hIL-4), human interleukin-13 receptor (hIL-13R), human interleukin-13 (hIL-13), human interleukin-5 (hIL-5), human interleukin-5 receptor (hIL-5R), human interleukin-33 (hIL-33) or human interleukin-31 (hIL-31).

In some embodiments, TSLP-TRAP disclosed herein is associated with a C terminus or termini of the moiety. In some embodiments, the TSLP-TRAP disclosed herein is associated with a N terminus or termini of the moiety.

In some embodiments, the moiety is a receptor. In some embodiments, the receptor can be CD1, CD1a, CD2, CD3, CD4, CD5, CD8, CD11A, CD14, CD15, CD16, CD17, CD18, CD19, CD20, CD21, CD22, CD23, CD25, CD29, CD30, CD32b, CD33, CD37, CD38, CD40, CD44, CD45, CD46, CD52, CD54, CD55, CD59, CD64, CD66a-e, CD67, CD70, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, CDH1, CDH6, CDH17, CDH19, CDH179b, EGFR, EGFRvIII, folate receptor, HLA-DR, HER2/neu, HMGB-1, IGF-1R, IL-4R, IL-6R, IL-13R, IL-15R, IL-17R, IL-18R, TRAIL receptors, TNFR1, TNFR2, PDG2R, CRTH2, CCR1, CCR2, CCR3, CCR4, CCR5, CCR6, CCR7, CCR8, CCR9, CCR10, CCR11, CXCR1, CXCR2, CXCR3, CXCR4, CXCR5 or CXCR6.

In some embodiments, an antibody or an antigen binding portion thereof disclosed herein is or comprise dupilumab, pascolizumab, CM-310, recombinant anti-IL-4R humanized monoclonal antibody, MG-K10, manfidokimab, QX-005N, elarekibep, CBP-201, SHR-1819, LQ-036, BA2101, mepolizumab, reslizumab, benralizumab, GSK3511294, AK-120, pitrakinra, anrukinzumab, IMA-638, lebrikizumab, tralokinumab, GSK679586, AMG-317, MILR1444A, CAT-354, QAX576, IMA-026, CNTO-607, MK-6105, DOM-0910, SAR440340, REGN3500, etokimab, ANB020, astegolimab, tozorakimab, MEDI3506, CNTO7160, torudokimab, itepekimab, dupixent, nemolizumab, BMS-981164, lokivetmab, vixarelimab, tezepelumab or an antigen binding portion thereof.

In some embodiments the moiety is a half-life extender. In some embodiments, the half-life extender comprises an antibody or an antigen binding portion that is modified to extend the complex's half-life in blood. In some embodiments, the half-life extender is albumin, PEG, or a suitable polymer to extend half-life in blood.

Anti-IL-4R TSLP-TRAP Complexes

In some embodiments, the TSLP-TRAP complex disclosed herein comprises a TSLP-TRAP associated to an antibody or antigen-binding portion thereof that specifically binds human interleukin-4 receptor (hIL-4R). In some embodiments, the antibody or antigen-binding portion thereof specifically binds human interleukin-4 receptor (hIL-4R). In some embodiments, the antibody or the antigen binding portion thereof comprises a HCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 10, (b) a HCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 11, and/or (c) a HCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 12. In some embodiments, the antibody or the antigen binding portion thereof comprises (a) a HCDR1 comprising an amino acid sequence of SEQ ID NO: 10, (b) a HCDR2 comprising an amino acid sequence of SEQ ID NO: 11, and/or (c) a HCDR3 comprising an amino acid sequence set out in SEQ ID NO: 12.

In some embodiments, the antibody or the antigen binding portion thereof comprises a heavy chain variable region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 32. In some embodiments, the antibody or the antigen binding portion thereof comprises a heavy chain variable region comprising an amino acid sequence out in SEQ ID NO: 32. For example, in some embodiments, the antibody or the antigen binding portion thereof comprises a heavy chain variable region (e.g., SEQ ID NO: 32) coupled to one or more TSLP-TRAP complex described herein via one or more linker.

In some embodiments, the antibody or the antigen binding portion thereof comprises a heavy chain having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 21. In some embodiments, the antibody or the antigen binding portion thereof comprises a heavy chain variable region comprising an amino acid sequence out in SEQ ID NO: 21. For example, in some embodiments, the antibody or the antigen binding portion thereof comprises a heavy chain (e.g., SEQ ID NO: 21) coupled to one or more TSLP-TRAP complex described herein via one or more linker.

In some embodiments, the antibody or the antigen binding portion thereof comprises a heavy chain Fc region comprising M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the antibody or the antigen binding portion thereof comprises (a) a LCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 14, (b) a LCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 15, and/or (c) a LCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 16. In some embodiments, the antibody or the antigen binding portion thereof comprises (a) a LCDR1 comprising an amino acid sequence of SEQ ID NO: 14, (b) a LCDR2 comprising an amino acid sequence of SEQ ID NO: 15, and/or (c) a LCDR3 comprising an amino acid sequence of SEQ ID NO: 16.

In some embodiments, the antibody or the antigen binding portion thereof comprises a light chain variable region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 30. In some embodiments, the antibody or the antigen binding portion thereof comprises a light chain variable region comprising an amino acid sequence set out in SEQ ID NO: 30. For example, in some embodiments, the antibody or the antigen binding portion thereof comprises a light chain variable region (e.g., SEQ ID NO: 30) coupled to one or more TSLP-TRAP complex described herein via one or more linker.

In some embodiments, the antibody or the antigen binding portion thereof comprises a light chain having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 22. In some embodiments, the antibody or the antigen binding portion thereof comprises a light chain comprising an amino acid sequence set out in SEQ ID NO: 22. For example, in some embodiments, the antibody or the antigen binding portion thereof comprises a light chain (e.g., SEQ ID NO: 22) coupled to one or more TSLP-TRAP complex described herein via one or more linker.

In some embodiments, the antibody or antigen-binding portion thereof is dupilumab.

In some embodiments, the antibody or the antigen binding portion thereof further comprises a Fc region with one or more mutations to extend half-life. In some embodiments, the one or more mutations to extend half-life comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the antibody or the antigen binding portion thereof further comprises a Fc region that is symmetric. In some embodiments, the antibody or the antigen binding portion thereof further comprises a Fc region that is asymmetric. In some embodiments, an asymmetric moiety can comprise a construct where amino acids at the contact site between the CH3 regions of a first Fc region and a second Fc region are substituted by larger or smaller residues forcing a heterodimeric assembly of heavy chains. In some embodiments, an asymmetric moiety is generated using knobs-into-holes (KiH). In some embodiments, the knobs-into-holes approach comprises a knob that is obtained by replacement of a small amino acid with a larger one in the CH3 region. In some embodiments, the knob is designed to insert into a hole in the CH3 region that is obtained by replacement of a large residue with a smaller one. In some embodiments, a large residue can be tyrosine or tryptophan. In some embodiments, a small residue can be glycine, alanine, threonine. In some embodiments, an antibody comprising a Fc region with KiH mutation described herein has an improved heterodimerization, enhanced stability, and an increase in therapeutic efficacy compared to that of a control antibody lacking the KiH mutation.

Monospecific TSLP-TRAP Complexes

In some embodiments, the TSLP-TRAP complex disclosed herein comprises a TSLP-TRAP associated with a modified antibody or an antigen binding portion thereof that does not bind to an antigen. In some embodiments, the antibody or the antigen binding portion thereof does not bind to anything. In some embodiments, the antibody or the antigen binding portion thereof does not bind to an endogenous antigen.

In some embodiments, wherein the antibody or the antigen binding portion thereof comprises (a) a HCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 52, (b) a HCDR2 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 53, and/or (c) a HCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 54. In some embodiments, the antibody or the antigen binding portion thereof comprises (a) a HCDR1 comprising an amino acid sequence of SEQ ID NO: 52, (b) a HCDR2 comprising an amino acid sequence of SEQ ID NO: 53, and/or (c) a HCDR3 comprising an amino acid sequence set out in SEQ ID NO: 54.

In some embodiments, the antibody or the antigen binding portion thereof disclosed herein comprises a heavy chain variable region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 58. In some embodiments, the antibody or the antigen binding portion thereof comprises a heavy chain variable region comprising an amino acid sequence out in SEQ ID NO: 58. For example, in some embodiments, the antibody or the antigen binding portion thereof comprises a heavy chain variable region (e.g., SEQ ID NO: 58) coupled to one or more TSLP-TRAP complex described herein via one or more linker.

In some embodiments, the antibody or the antigen binding portion thereof comprises a heavy chain having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 60. In some embodiments, the antibody or the antigen binding portion thereof comprises a heavy chain comprising an amino acid sequence set out in SEQ ID NO: 60. For example, in some embodiments, the antibody or the antigen binding portion thereof comprises a heavy chain (e.g., SEQ ID NO: 60) coupled to one or more TSLP-TRAP complex described herein via one or more linker.

In some embodiments, the antibody or the antigen binding portion thereof comprises a heavy chain Fc region comprising M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33. In some embodiments, the antibody or the antigen binding portion thereof comprises (a) a LCDR1 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 55, (b) a LCDR2 having the amino acid sequence set out in SEQ ID NO: 56, and/or (c) a LCDR3 having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 57. In some embodiments, the antibody or the antigen binding portion thereof comprises (a) a LCDR1 comprising an amino acid sequence of SEQ ID NO: 55, (b) a LCDR2 comprising an amino acid sequence of SEQ ID NO: 56, and/or (c) a LCDR3 comprising an amino acid sequence of SEQ ID NO: 57.

In some embodiments, the antibody or the antigen binding portion thereof comprises a light chain variable region having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 59. In some embodiments, the antibody or the antigen binding portion thereof comprises a light chain variable region comprising an amino acid sequence set out in SEQ ID NO: 59. For example, in some embodiments, the antibody or the antigen binding portion thereof comprises a light chain variable region (e.g., SEQ ID NO: 59) coupled to one or more TSLP-TRAP complex described herein via one or more linkers.

In some embodiments, the antibody or the antigen binding portion thereof comprises a light chain having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence set out in SEQ ID NO: 61. In some embodiments, the antibody or the antigen binding portion thereof comprises a light chain comprising an amino acid sequence set out in SEQ ID NO: 61. For example, in some embodiments, the antibody or the antigen binding portion thereof comprises a light chain variable region (e.g., SEQ ID NO: 61) coupled to one or more TSLP-TRAP complex described herein via one or more linker.

In some embodiments, the antibody or antigen-binding portion thereof is palivizumab.

In some embodiments, the antibody or the antigen binding portion thereof further comprises a Fc region with one or more mutations to extend half-life. In some embodiments, the one or more mutations to extend half-life comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33.

Multiple TSLP-TRAPS

The TSLP-TRAP complexes heavy chain variable region may comprise multiple TSLP-TRAPs. In some embodiments, the antigen binding complex comprises at least two TSLP-TRAPs. In some embodiments, the at least two TSLP-TRAP is each separately associated with the moiety via a linker described herein. In some embodiments, a TSLP-TRAP is associated with a second TSLP-TRAP. In some embodiments, the at least two TSLP-TRAP comprises 3 TSLP-TRAPs. In some embodiments, the at least two TSLP-TRAP comprises 4 TSLP-TRAPs. In some embodiments, 1 TSLP-TRAP is linked to the C termini of the antibody or antigen binding fragment thereof light chain. In some embodiments, 1 TSLP-TRAP is linked to the N termini of the antibody or antigen binding fragment thereof light chain. In some embodiments, 1 TSLP-TRAP is linked to the N and C termini of the antibody light chain. In some embodiments, 1 TSLP-TRAP is linked to the C termini of the antibody or antigen binding fragment heavy chain. In some embodiments, 1 TSLP-TRAP is linked to the N termini of the antibody or antigen binding fragment heavy chain. In some embodiments, 1 TSLP-TRAP is linked to the C and N termini of the antibody or antigen binding fragment of the heavy chain. In some embodiments, 1 TSLP-TRAP is linked to the C and N termini of the antibody or antigen binding fragment of the heavy and light chains.

In some embodiments, the antibody or the antigen binding portion thereof further comprises a Fc region with one or more mutations to extend half-life. In some embodiments, the one or more mutations to extend half-life comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P. In some embodiments, the antigen binding moiety can comprise any one of the mutations set forth in Table 33.

Binding Affinity

In some embodiments, the antigen binding moiety described herein has a KD for binding to TSLP of about $0.2\times10^{-12}$ to $30.0\times10^{-12}$ M. In some embodiments, an antigen binding moiety described herein has a KD for binding to TSLP of about $1.0\times10^{-12}$ M, about $2.0\times10^{-12}$ M, about $3.0\times10^{-12}$ M, about $4.0\times10^{-12}$ M, about $5.0\times10^{-12}$ M, about $6.0\times10^{-12}$ M, about $7.0\times10^{-12}$ M, about $8.0\times10^{-12}$ M, about $9.0\times10^{-12}$ M, about $10.0\times10^{-12}$ M, about $11.0\times10^{-12}$ M, about $12.0\times10^{-12}$ M, about $13.0\times10^{-12}$ M, about $14.0\times10^{-12}$ M, about $15.0\times10^{-12}$ M, about $16.0\times10^{-12}$ M, about $17.0\times10^{-12}$ M, about $18.0\times10^{-12}$ M, about $19.0\times10^{-12}$ M, about $20.0\times10^{-12}$ M, about $21.0\times10^{-12}$ M, about $22.0\times10^{-12}$ M, about $23.0\times10^{-12}$ M, about $24.0\times10^{-12}$ M, about $25.0\times10^{-12}$ M, about $26.0\times10^{-12}$ M, about $27.0\times10^{-12}$ M, about $28.0\times10^{-12}$M, about $29.0\times10^{-12}$ M, about $30.0\times10^{-12}$ M, about $31.0\times10^{-12}$ M, about $32.0\times10^{-12}$ M, about $33.0\times10^{-12}$ M, about $34.0\times10^{-12}$ M, about $35.0\times10^{-12}$ M, about $36.0\times10^{-12}$ M, about $37.0\times10^{-12}$ M, about $38.0\times10^{-12}$ M, about $39.0\times10^{-12}$ M, about $40.0\times10^{-12}$ M, about $41.0\times10^{-12}$ M, about $42.0\times10^{-12}$ M, about $43.0\times10^{-12}$ M, about $44.0\times10^{-12}$ M, about $45.0\times10^{-12}$ M, about $46.0\times10^{-12}$ M, about $47.0\times10^{-12}$ M, about $48.0\times10^{-12}$ M, about $49.0\times10^{-12}$ M, or about $50.0\times10^{-12}$ M. In some embodiments, the antigen binding moiety described herein has a KD for binding to TSLP of less than $1.0\times10^{-12}$ M, about $2.0\times10^{-12}$ M, about $3.0\times10^{-12}$ M, about $4.0\times10^{-12}$ M, about $5.0\times10^{-12}$ M, about $6.0\times10^{-12}$ M, about $7.0\times10^{-12}$ M, about $8.0\times10^{-12}$ M, about $9.0\times10^{-12}$ M, about $10.0\times10^{-12}$ M, about $11.0\times10^{-12}$ M, about $12.0\times10^{-12}$ M, about $13.0\times10^{-12}$ M, about $14.0\times10^{-12}$ M, about $15.0\times10^{-12}$ M, about $16.0\times10^{-12}$ M, about $17.0\times10^{-12}$ M, about $18.0\times10^{-12}$ M, about $19.0\times10^{-12}$ M, about $20.0\times10^{-12}$ M, about $21.0\times10^{-12}$ M, about $22.0\times10^{-12}$ M, about $23.0\times10^{-12}$ M, about $24.0\times10^{-12}$ M, about $25.0\times10^{-12}$ M, about $26.0\times10^{-12}$ M, about $27.0\times10^{-12}$ M, about $28.0\times10^{-12}$ M, about $29.0\times10^{-12}$ M, about $30.0\times10^{-12}$ M, about $31.0\times10^{-12}$ M, about $32.0\times10^{-12}$ M, about $33.0\times10^{-12}$ M, about $34.0\times10^{-12}$ M, about $35.0\times10^{-12}$ M, about $36.0\times10^{-12}$ M, about $37.0\times10^{-12}$ M, about $38.0\times10^{-12}$ M, about $39.0\times10^{-12}$ M, about $40.0\times10^{-12}$ M, about $41.0\times10^{-12}$ M, about $42.0\times10^{-12}$ M, about $43.0\times10^{-12}$ M, about $44.0\times10^{-12}$ M, about $45.0\times10^{-12}$ M, about $46.0\times10^{-12}$ M, about $47.0\times10^{-12}$ M, about $48.0\times10^{-12}$ M, about $49.0\times10^{-12}$ M, or about $50.0\times10^{-12}$ M. In some embodiments, the antigen binding moiety described herein has a KD for binding to TSLP of at most $1.0\times10^{-12}$ M, about $2.0\times10^{-12}$ M, about $3.0\times10^{-12}$ M, about $4.0\times10^{-12}$ M, about $5.0\times10^{-12}$ M, about $6.0\times10^{-12}$ M, about $7.0\times10^{-12}$ M, about $8.0\times10^{-12}$ M, about $9.0\times10^{-12}$ M, about $10.0\times10^{-12}$ M, about $11.0\times10^{-12}$ M, about $12.0\times10^{-12}$ M, about $13.0\times10^{-12}$ M, about $14.0\times10^{-12}$ M, about $15.0\times10^{-12}$ M, about $16.0\times10^{-12}$ M, about $17.0\times10^{-12}$ M, about $18.0\times10^{-12}$ M, about $19.0\times10^{-12}$ M, about $20.0\times10^{-12}$ M, about $21.0\times10^{-12}$ M, about $22.0\times10^{-12}$ M, about $23.0\times10^{-12}$ M, about $24.0\times10^{-12}$ M, about $25.0\times10^{-12}$ M, about $26.0\times10^{-12}$ M, about $27.0\times10^{-12}$ M, about $28.0\times10^{-12}$ M, about $29.0\times10^{-12}$ M, about $30.0\times10^{-12}$ M, about $31.0\times10^{-12}$ M, about $32.0\times10^{-12}$ M, about $33.0\times10^{-12}$ M, about $34.0\times10^{-12}$ M, about $35.0\times10^{-12}$ M, about $36.0\times10^{-12}$ M, about $37.0\times10^{-12}$ M, about $38.0\times10^{-12}$ M, about $39.0\times10^{-12}$ M, about $40.0\times10^{-12}$ M, about $41.0\times10^{-12}$ M, about $42.0\times10^{-12}$ M, about $43.0\times10^{-12}$ M, about $44.0\times10^{-12}$ M, about $45.0\times10^{-12}$ M, about $46.0\times10^{-12}$ M, about $47.0\times10^{-12}$ M, about $48.0\times10^{-12}$ M, about $49.0\times10^{-12}$ M, or about $50.0\times10^{-12}$ M. In some embodiments, the antigen binding moiety described herein binds TSLP with a KD between $0.2\times10^{-12}$ M and $30\times10^{-12}$ M. In some embodiments, antigen binding moiety described herein binds IL-4R with a KD between $0.2\times10^{-12}$ M and $30\times10^{-12}$ M.

Method of Making Polypeptides

Also provided herein are methods of producing a polypeptide that include: (a) culturing a cell (e.g., any of the cells described herein) including any of the nucleic acids encoding any of the polypeptides described herein, or any of the expression vectors described herein that include nucleic acid encoding any of the polypeptides described herein, in a culture medium under conditions sufficient to allow for the production of the polypeptide; and (b) harvesting the polypeptide from the host cell or the culture medium. In some embodiments of any of the methods described herein, the method further includes isolating the polypeptide (e.g., through performance of one or more column chromatography steps, ultrafiltration/diafiltration, and/or viral inactivation/viral filtration). In some embodiments of any of the methods described herein, the method further includes formulating the isolated polypeptide into a composition (e.g., a pharmaceutical composition). In some cases, the expression vector may comprise an enhancer or a promoter known in the art for an effective level of transcription.

Any of the polypeptides described herein can be produced by any cell, (e.g., a mammalian cell). Non-limiting examples of a mammalian cell include: a human cell, a rodent cell (e.g., a rat cell or a mouse cell), a rabbit cell, a dog cell, a cat cell, a porcine cell, or a non-human primate cell. For example, a host cell can be a CHO cell or a HEK cell.

Methods of culturing cells are well known in the art. Cells can be maintained in vitro under conditions that favor cell proliferation, cell growth, protein production, and/or cell differentiation. For example, cells can be cultured by contacting a cell (e.g., any of the cells described herein) with a cell culture medium that includes supplemental growth factors to support cell viability, cell growth, and protein production.

Methods of introducing nucleic acids (e.g., any of the exemplary nucleic acids described herein) and/or expression vectors (e.g., any of the exemplary expression vectors described herein (e.g., a DNA or an AAV vector)) into cells (e.g., mammalian cells) are known in the art. Non-limiting examples of methods that can be used to introduce a nucleic acid (e.g., DNA, RNA, ssRNA, siRNA, microRNA, or mRNA) and/or an expression vector (e.g., any of the exemplary expression vectors described herein (e.g., an AAV vector) include: electroporation, lipofection, transfection, microinjection, calcium phosphate transfection, dendrimer-based transfection, anionic polymer transfection, cationic polymer transfection, transfection using highly branched organic compounds, cell-squeezing, sonoporation, optical transfection, magnetofection, particle-based transfection (e.g., nanoparticle transfection), transfection using liposomes (e.g., cationic liposomes), and viral transduction (e.g., lentiviral transduction, adenoviral transduction).

Some methods described herein further include isolating or purifying the polypeptide from cell culture medium or from a cell (e.g., a mammalian cell) using techniques well-known in the art (e.g., ion exchange chromatography (anionic or cation), metal-affinity chromatography, ligand-affinity chromatography, size exclusion chromatography, hydrophobic interaction chromatography, and precipitation (e.g., ammonium sulfate precipitation, polyethylene glycol precipitation).

Method of Treatment

In some embodiments, provided herein is a method of treating a condition in a subject in need thereof, the method comprising administering to the subject an effective amount of an antigen binding moiety disclosed herein. The effective amount can be a therapeutically-effective amount. In some embodiments, provided is a method of treating a condition in a subject in need thereof, the method comprising administering to the subject an effective amount of a polynucleotide encoding an antigen binding moiety disclosed herein, or a vector comprising the polynucleotide.

In some embodiments, the disease or condition can comprise cancer, autoimmune disorders, inflammatory disorders, infectious diseases, and/or degenerative diseases. For example, in some embodiments, the antigen binding moiety disclosed herein can be administered to a patient having or suspected having cancer. In some embodiments, the patient may have breast cancer, lung cancer, colorectal cancer, gastric cancer, pancreatic cancer, liver cancer, ovarian cancer, prostate cancer, renal cancer, melanoma, head and neck cancer, leukemia, lymphoma, or multiple myeloma. In some embodiments, the antigen binding moiety disclosed herein can be administered to a patient having or suspected having an autoimmune disorder or an inflammatory disorder. In some embodiments, the patient may have (or suspected to have) inflammatory arthritis, rheumatoid arthritis, psoriatic arthritis, psoriasis, inflammatory bowel disease, ulcerative colitis, Crohn's disease, systemic lupus erythematosus, multiple sclerosis, type 1 diabetes, autoimmune thyroiditis, ankylosing spondylitis, asthma, dermatitis, eosinophilic esophagitis, chronic obstructive pulmonary disease, eczema, nasal polyps, sinusitis, pruritus, atopic dermatitis, allergic rhinitis, airway hyperresponsiveness, airway inflammation, a food allergy, chronic urticaria, occupational allergy, allergic conjunctivitis, hay fever, airborne allergic sensitivities, stinging insect allergy, hypersensitivity pneumonitis, eosinophilic lung diseases, or drug allergies. In some embodiments, the antigen binding moiety disclosed herein can be administered to a patient having or suspected having viral infections, bacterial infections, fungal infections, or parasitic infections.

Described herein is the pharmaceutical composition for use in a therapy. In some embodiments, the antigen binding moiety described herein (e.g., a pharmaceutical composition comprising any one of the antigen binding moiety of FIGS. 1A-10D) may be administered to a subject for diagnosis or treatment of a condition or a disease. Exemplary conditions and diseases may include, but not limited to, asthma, dermatitis, eosinophilic esophagitis, inflammatory arthritis, sinusitis, pruritus, solid tumors, atopic dermatitis, eczema, allergic rhinitis, airway hyperresponsiveness, airway inflammation, a food allergy, chronic urticaria, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, Crohn's disease and drug allergies.

In some embodiments, the pharmaceutical compositions may further comprise at least one additional therapeutic agent.

In some embodiments, compositions comprising antigen binding moieties/antibodies can be provided in formulations with a wide variety of pharmaceutically acceptable carriers (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, compositions comprising the antigen binding moiety may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1. In some embodiments, the composition described herein may be manufactured as a medicament for treatment of allergic disease.

Polynucleotide and Vectors

In some embodiments the disclosure provides a polynucleotide that encodes an antigen binding moiety disclosed herein. The polynucleotide can be prepared by standard molecular biology techniques. The polynucleotide can be prepared by molecular cloning. The polynucleotide can be synthesized de novo. The polynucleotide can comprise a nucleotide sequence encoding the antigen binding moiety, operably linked to transcription regulatory sequences such as a promoter, and optionally a 3' untranslated region. A constitutive, inducible, or tissue-specific promoter can be used.

The polynucleotide can be a DNA. The polynucleotide can be an RNA. The polynucleotide can comprise a modified base, for example, to enhance stability of the polynucleotide upon administration to a subject. A polynucleotide provided can include a recombinant, artificial, or synthetic polynucleotide. The polynucleotide can be single stranded. The polynucleotide can be double stranded. The polynucleotide can be recombinant and/or isolated.

The polynucleotide can be inserted into or part of a vector, such as an expression vector, such that the genes are operatively linked to transcriptional and/or translational control sequences. The vector can comprise a selectable marker for selection of a vector-carrying host cell. The vector can lack a selectable marker. The vector can comprise an origin of replication or can lack an origin of replication. The vector can be a plasmid, for example, a nano plasmid. The vector can be a minicircle. The vector can be a liner polynucleotide phagemid, cosmid, RNA vector, viral vector or the like. Non-limiting examples of viral vectors include a retrovirus (e.g., lentivirus), an adenovirus, and an adeno-associated virus. The vector can be a nonviral vector.

In some embodiments, a polynucleotide encoding an antigen binding moiety is packaged in a lipid-based delivery vector, such as a liposome or lipid nanoparticle.

Pharmaceutical Composition

Also provided herein are compositions (e.g., pharmaceutical compositions) that include any of the polypeptides, vectors, or nucleic acids described herein. Any of the pharmaceutical compositions can include any of the polypeptides, vectors, or nucleic acids described herein and one or more (e.g., 1, 2, 3, 4, or 5) pharmaceutically or physiologically acceptable carriers, diluents, or excipients. In some embodiments, any of the pharmaceutical compositions described herein can include one or more buffers (e.g., a neutral-buffered saline, a phosphate-buffered saline (PBS)), one or more carbohydrates (e.g., glucose, mannose, sucrose, dextran, or mannitol), one or more proteins, polypeptides, or amino acids (e.g., glycine), one or more antioxidants (e.g., ascorbic acid), one or more chelating agents (e.g., glutathione or EDTA), one or more preservatives, and/or a pharmaceutically acceptable carrier (e.g., PBS, saline, or bacteriostatic water).

In some embodiments, any of the pharmaceutical compositions described herein can further include one or more (e.g., 1, 2, 3, 4, or 5) agents that promote the entry of any of the vectors or nucleic acids described herein into a cell (e.g., a mammalian cell) (e.g., a liposome or cationic lipid).

In some embodiments, any of the vectors or nucleic acids described herein can be formulated using natural and/or synthetic polymers. Non-limiting examples of polymers that can be included in any of the pharmaceutical compositions described herein can include, but are not limited to: poloxamer, chitosan, dendrimers and poly(lactic-co-glycolic acid) (PLGA) polymers.

The pharmaceutical compositions provided herein can be, e.g., formulated to be compatible with their intended route of administration. In some embodiments, the compositions are formulated for subcutaneous, intramuscular, or intravenous administration. In some examples, the compositions include a therapeutically effective amount of any of the polypeptides, vectors, or nucleic acids described herein. Single or multiple administrations of any of the pharmaceutical compositions described herein can be given (e.g., administered) to a subject depending on, for example, the frequency and the dosage required and tolerated by the subject. A dosage of the pharmaceutical composition including any of the polypeptides described herein, any of the vectors described herein, or any of the nucleic acids described herein should provide a sufficient quantity to effectively ameliorate or treat symptoms, conditions or diseases.

Kits

A kit-of-parts comprising a pharmaceutical composition together with instructions for use is further provided. For convenience, the kit-of-parts may comprise reagents in predetermined amounts with instructions for use.

In some embodiments, described herein are kits comprising an antigen binding moiety described herein. In some embodiments, a kit can be a diagnostic kit. In some embodiments, a kit comprises an antigen binding moiety described herein and instructions for use. In some embodiments, a kit comprises means for measuring an antigen binding moiety described herein level in a sample and instructions for use. A kit may provide a unit or device for obtaining a sample from a subject (e.g., a device with a needle coupled to an aspirator).

A kit may include a plurality of syringes, ampules, foil packets, or blister packs, each containing a single unit dose of a kit component described herein. Containers of a kit may be airtight, waterproof (e.g., impermeable to changes in moisture or evaporation), and/or light-tight. A kit may include a device suitable for administration of the components, e.g., a syringe, inhalant, pipette, forceps, measured spoon, dropper (e.g., eye dropper), swab (e.g., a cotton swab or wooden swab), or any such delivery device. In some embodiments, the device may be a medical implant device, e.g., packaged for surgical insertion. A kit described herein may comprise one or more reagents or instruments which enable the method to be carried out. In some embodiments, reagents or instruments include one or more of the following: suitable buffer(s) (aqueous solutions), a support comprising wells on which quantitative reactions can be done. A kit may be a specific kit for a specific tissue sample. Further, a kit described herein may comprise a control. In some embodiments, the kit may comprise any of the compositions (e.g., pharmaceutical compositions) described herein which include any of the nucleic acids, any of the polypeptides, or any of the vectors described herein. In some embodiments, a kit can include a solid composition (e.g., a lyophilized composition including any of the vectors, polypeptides, or nucleic acids described herein) and a liquid for solubilizing the lyophilized composition. In some embodiments, the kit includes a vial including any of the pharmaceutical compositions described herein (e.g., formulated as an aqueous pharmaceutical composition).

In addition to the above components, instructions for use may be provided in a kit. These instructions may be presented in the kit in a variety of forms, such as printed information on a suitable medium or substrate (e.g., a piece or pieces of paper on which the information is printed), in the packaging of the kit, in a package insert, etc. In some embodiments, instructions for use can be provided on a computer readable medium (e.g., jump/thumb drive, CD, etc.), or which the information has been recorded, or at a website address which may be used via the internet to access the information at a website Device Another aspect of the disclosure provides a pre-filled syringe or autoinjector device, comprising an antigen binding moiety described herein or a composition described herein. In some embodiments, a composition stored in a container, pre-filled syringe, injector or autoinjector device contains an antigen binding moiety or antigen-binding fragment thereof described herein.

Arrays

Described herein are supports comprising an antigen binding moiety described herein. A support can be a solid support. A support may take a variety of configurations ranging from simple to complex, depending on the intended use of the support. A support can have an overall slide or plate configuration, such as a rectangular or disc configuration. A standard microplate configuration can be used. In some embodiments, the surface may be smooth or substantially planar, or have irregularities, such as depressions or elevations. In some embodiments, a support may have a rectangular cross-sectional shape, having a length of from about 10-200 mm, 40-150 mm, or 75-125 mm; a width of from about 10-200 mm, 20-120 mm, or 25-80 mm, and a thickness of from about 0.01-5.0 mm, 0.1-2 mm, or 0.2 to 1 mm.

In some embodiments, a support can be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. A support as described herein can be formed of any suitable material, including metals, metal oxides, semiconductors, polymers (particularly organic polymers in any suitable form including woven, nonwoven, molded, extruded, cast, etc.), silicon, silicon oxide, and composites thereof. A support can be an array. In some embodiments, a support comprises an array. An array can comprise an ordered spatial arrangement of two or more discrete regions. An array can comprise the antigen binding moiety described herein located at known or unknown discrete regions. Row and column arrangements of arrays can be selected due to the relative simplicity in making such arrangements. The spatial arrangement can, however, be essentially any form selected by the user, and optionally, in a pattern. Areas of an array may be any convenient shape, including circular, ellipsoid, oval, annular, or some other analogously curved shape, where the shape may, in some embodiments, be a result of the particular method employed to produce the array.

In some embodiments, a support can be planar. In some instances, a support can be spherical. In some instances, a support can be a bead. In some instances, a support can be magnetic. In some embodiments, a magnetic support comprises magnetite, maghemite, FePt, SrFe, iron, cobalt, nickel, chromium dioxide, ferrites, or mixtures thereof. In some embodiments, a support can be nonmagnetic. In some embodiments, the nonmagnetic support can comprise a polymer, metal, glass, alloy, mineral, or mixture thereof. In some instances, a nonmagnetic material can be a coating around a magnetic support. In some instances, a magnetic material may be distributed in the continuous phase of a magnetic material. In some embodiments, the support comprises magnetic and nonmagnetic materials. In some instances, a support can comprise a combination of a magnetic material and a nonmagnetic material. In some embodiments, an antigen binding moiety described herein is directly or indirectly associated with a support described herein.

Computer Control System

The present disclosure provides computer control systems that are programmed to implement methods of the disclosure. In some embodiments, a computer system is programmed or otherwise configured to interface with an apparatus that is configured to detect TSLP, IL-4R and/or binding of an antigen binding moiety described herein to moiety/antigen. The computer system can be an electronic device of a user or a computer system that is remotely located with respect to the electronic device. The electronic device can be a mobile electronic device.

In some embodiments, a computer system includes a central processing unit (CPU, also "processor" and "computer processor" herein, which can be a single core or multi core processor, or a plurality of processors for parallel processing.

In some embodiments, a computer system also includes memory or memory location (e.g., random-access memory, read-only memory, flash memory), electronic storage unit (e.g., hard disk), communication interface (e.g., network adapter) for communicating with one or more other systems, and peripheral devices, such as cache, other memory, data storage and/or electronic display adapters. In some embodiments, the memory, storage unit, interface and peripheral devices are in communication with the CPU through a communication bus, such as a motherboard. In some embodiments, the storage unit can be a data storage unit (or data repository) for storing data. In some embodiments, the computer system is operatively coupled to a computer network ("network") with the aid of the communication interface. In some embodiments, the network can be the Internet, an internet and/or extranet, or an intranet and/or extranet that is in communication with the Internet. In some embodiments, the network is a telecommunication and/or data network. The network can include one or more computer servers, which can enable distributed computing, such as cloud computing. In some embodiments, the network, in some cases with the aid of the computer system can implement a peer-to-peer network, which may enable devices coupled to the computer system to behave as a client or a server. In some embodiments, the CPU executes a sequence of machine-readable instructions, which can be embodied in a program or software. The instructions may be stored in a memory location, such as the memory. The instructions can be directed to the CPU, which can subsequently program or otherwise configure the CPU to implement methods of the present disclosure. Examples of operations performed by the CPU can include fetch, decode, execute, and writeback. In some embodiments, the CPU can be part of a circuit, such as an integrated circuit. One or more other components of the system can be included in the circuit. In some cases, the circuit is an application specific integrated circuit (ASIC). In some embodiments, the storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet. In some embodiments, the computer system communicates with one or more remote computer systems through the network. For instance, the computer system can communicate with a remote computer system of a user. Examples of remote computer systems include personal computers (e.g., portable PC), slate or tablet PC's telephones, Smart phones, or personal digital assistants. The user can access the computer system via the network.

Methods as described herein can be implemented by way of machine (e.g., computer processor) executable code stored on an electronic storage location of the computer system, such as, for example, on the memory or electronic storage unit. The machine executable or machine-readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory. In some embodiments, the code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as the main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. In some embodiments, a computer system described herein can include or be in communication with an electronic display that comprises a user interface (UI) for providing, for example, one or more results (immediate results or archived results from a previous experiment), one or more user inputs, reference values from a library or database, or a combination thereof. Examples of UIs include, without limitation, a graphical user interface (GUI) and web-based user interface.

Further, methods and systems of the present disclosure can be implemented by way of one or more algorithms. An algorithm can be implemented by way of software upon execution by the central processing unit. The algorithm can, for example, determine optimized conditions via supervised learning to optimize conditions such as a buffer type, a buffer concentration, a temperature, an incubation period, thresholds, diagnostic/prognostic indications for methods described herein.

EXEMPLARY EMBODIMENTS

Among the exemplary embodiments are:

Embodiment 1. An antigen binding moiety comprising: a binding complex comprising: (a) an anti-IL-4R moiety or an antigen binding portion thereof, wherein the anti-IL-4R moiety or the antigen binding portion thereof comprises a light chain ($L_{IL-4R}$) and a heavy chain ($H_{IL-4R}$); and (b) an anti-thymic stromal lymphopoietin (TSLP) moiety or an antigen binding portion thereof comprising a Fab, wherein the Fab comprises a first peptide chain comprising a heavy chain variable domain ($VH_{TSLP}$) and a heavy chain constant domain 1 ($CH1_{TSLP}$), and a second peptide chain comprising a light chain variable domain ($VL_{TSLP}$), and a light chain constant domain ($CL_{TSLP}$), wherein the $VH_{TSLP}$ or the $CH1_{TSLP}$ of the first peptide chain is exchanged for the $VL_{TSLP}$ or the $CL_{TSLP}$ of the second peptide, wherein the first peptide chain or the second peptide chain is associated with at least a portion of the anti-IL-4R moiety or the antigen binding portion thereof.

Embodiment 2. The antigen binding moiety of embodiment 1, wherein the $VL_{TSLP}$ or the $VH_{TSLP}$ of the anti-TSLP moiety or the antigen binding portion thereof is positioned at the N-terminus or the C-terminus of the $L_{IL-4R}$ or the $H_{IL-4R}$.

Embodiment 3. The antigen binding moiety of embodiment 2, wherein the $VL_{TSLP}$ or the $VH_{TSLP}$ of the anti-TSLP moiety or the antigen binding portion thereof is positioned at the C-terminus of the $H_{IL-4R}$.

Embodiment 4. The antigen binding moiety of any one of the preceding embodiments, wherein the anti-TSLP moiety or the antigen binding portion thereof comprises, from N-terminus to C-terminus: the first peptide chain comprising [$VL_{TSLP}$]-[$CL_{TSLP}$] and the second peptide chain comprising [$VH_{TSLP}$]-[$CH1_{TSLP}$]; the first peptide chain comprising [$VL_{TSLP}$]-[$CH1_{TSLP}$] and the second peptide chain comprising [$VH_{TSLP}$]-[$CL_{TSLP}$]; or the first peptide chain comprising [$VH_{TSLP}$]-[$CL_{TSLP}$] and the second peptide chain comprising [$VL_{TSLP}$]-[$CH1_{TSLP}$].

Embodiment 5. The antigen binding moiety of embodiment 4, wherein the first peptide chain and the second peptide chain are associated with each other.

Embodiment 6. The antigen binding moiety of any one of the preceding embodiments, wherein the $VL_{TSLP}$ or the $VH_{TSLP}$ of the anti-TSLP moiety or the antigen binding portion thereof is associated with the $H_{IL-4R}$ at the C-terminus via a first linker comprises (GGS)n (SEQ ID NO: 17), (GGGGS)n (SEQ ID NO: 18), ASTKGP (SEQ ID NO: 19), ASTKGPSVFPLAP (SEQ ID NO: 185) or TVAAPSVFIFPP (SEQ ID NO: 20), wherein n is an integer between 1 and 100.

Embodiment 7. The antigen binding moiety of embodiment 6, wherein the first linker comprises SEQ ID NO: 23.

Embodiment 8. The antigen binding moiety of any one of the preceding embodiments, wherein the $L_{IL-4R}$ comprises (a) a light-chain complementarity-determining region (LCDR) 1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 9. The antigen binding moiety of any one of the preceding embodiments, wherein the $L_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising to the amino acid sequence of SEQ ID NO: 16.

Embodiment 10. The antigen binding moiety of any one of the preceding embodiments, wherein the $L_{IL-4R}$ comprises a light chain variable domain, wherein the light chain variable domain comprises an amino acid sequence having at least 80% sequence identity to the amino acid sequence of SEQ ID NO: 30.

Embodiment 11. The antigen binding moiety of any one of the preceding embodiments, wherein the $L_{IL-4R}$ comprises a light chain variable domain comprising the amino acid sequence of SEQ ID NO: 30.

Embodiment 12. The antigen binding moiety of any one of the preceding embodiments, wherein the $H_{IL-4R}$ comprises (a) a heavy-chain complementarity-determining region (HCDR) 1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 13. The antigen binding moiety of any one of the preceding embodiments, wherein the $H_{IL-4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 14. The antigen binding moiety of any one of the preceding embodiments, wherein the $H_{IL-4R}$ comprises a heavy chain variable domain, wherein the heavy chain variable domain comprises an amino acid sequence having at least 80% sequence identity to the amino acid sequence of SEQ ID NO: 32.

Embodiment 15. The antigen binding moiety of any one of the preceding embodiments, wherein the $H_{IL-4R}$ comprises a heavy chain variable domain comprising the amino acid sequence of SEQ ID NO: 32.

Embodiment 16. The antigen binding moiety of any one of the preceding embodiments, wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4.

Embodiment 17. The antigen binding moiety of any one of the preceding embodiments, wherein the $VH_{TSLP}$ comprises (a) a $HCDR1_{TSLP}$ comprising the amino acid sequence of SEQ ID NO: 2, (b) a $HCDR2_{TSLP}$ comprising the amino acid sequence of SEQ ID NO: 3, and/or (c) a $HCDR3_{TSLP}$ comprising the amino acid sequence of SEQ ID NO: 4.

Embodiment 18. The antigen binding moiety of any one of the preceding embodiment, wherein the $VH_{TSLP}$ comprises an amino acid sequence having at least 90% sequence identity to the amino acid sequence of SEQ ID NO: 25.

Embodiment 19. The antigen binding moiety of any one of the preceding embodiment, wherein the $VH_{TSLP}$ comprises the amino acid sequence of SEQ ID NO: 25.

Embodiment 20. The antigen binding moiety of any one of the preceding embodiment, wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 21. The antigen binding moiety of any one of the preceding embodiment, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 22. The antigen binding moiety of any one of the preceding embodiment, wherein the $VL_{TSLP}$ comprises an amino acid sequence having at least 90% sequence identity to the amino acid sequence of SEQ ID NO: 28.

Embodiment 23. The antigen binding moiety of any one of the preceding embodiment, wherein the $VL_{TSLP}$ comprises the amino acid sequence of SEQ ID NO: 28.

Embodiment 24. The antigen binding moiety of any one of the preceding embodiment, wherein the anti-TSLP moiety or the anti-IL-4R moiety comprises a Fc region.

Embodiment 25. The antigen binding moiety of embodiment 24, wherein the Fc region comprises one or more mutations, wherein the one or more mutations comprise a half-life extension modification and/or one or more mutations to prevent Fab arm exchange of IgG.

Embodiment 26. The antigen binding moiety of embodiment 25, wherein the one or more mutations comprising the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 27. The antigen binding moiety of embodiment 25, wherein the one or more mutations comprise any one of the mutations set forth in Table 33.

Embodiment 28. The antigen binding moiety of any one of the preceding embodiments, wherein the antigen binding moiety comprises, from N-terminus to C-terminus: a first polypeptide comprising [the $L_{IL-4R}$]; a second polypeptide comprising [the $H_{IL-4R}$]-[the first linker]-[the $VL_{TSLP}$]-[the $CL_{TSLP}$]; and a third polypeptide comprising [the $VH_{TSLP}$]-[the $CH1_{TSLP}$].

Embodiment 29. The antigen binding moiety of embodiment 28, wherein the first polypeptide comprises an amino acid sequence having at least about 90% sequence identity to the amino acid sequence of SEQ ID NO: 103.

Embodiment 30. The antigen binding moiety of embodiment 28 or 29, wherein the second polypeptide comprises an amino acid sequence having at least about 90% sequence identity to the amino acid sequence of SEQ ID NO: 104.

Embodiment 31. The antigen binding moiety of any one of embodiments 28-30, wherein the second polypeptide comprises an amino acid sequence having at least about 90% sequence identity to the amino acid sequence of SEQ ID NO: 105.

Embodiment 32. The antigen binding moiety of any one of embodiments 28-31, wherein a first polynucleotide sequence encoding the first polypeptide, a second polynucleotide sequence encoding the second polypeptide, and/or a third polynucleotide sequence encoding third polypeptide comprises a nucleotide sequence encoding a signal peptide.

Embodiment 33. The antigen binding moiety of embodiment 32, wherein the signal peptide comprises an amino acid sequence having at least 80% sequence identity to the amino acid sequence of any one of SEQ ID NOs: 130-184.

Embodiment 34. The antigen binding moiety of embodiment 32, wherein the signal peptide comprises an amino acid sequence having at least 80% sequence identity to the amino acid sequence of SEQ ID NOs: 156.

Embodiment 35. The antigen binding moiety of embodiment 32, wherein the signal peptide comprises an amino acid sequence having the amino acid sequence of SEQ ID NOs: 156.

Embodiment 36. The antigen binding moiety of any one of the preceding embodiments, wherein an $EC_{50}$ value of the antigen binding moiety is at least about 0.25 nM in a cell-based assay measuring IL-4R binding.

Embodiment 37. The antigen binding moiety of any one of the preceding embodiments, wherein an $IC_{50}$ value of the antigen binding moiety is at least about 2.4 nM in a cell-based assay measuring IL-4 induced CD23 upregulation.

Embodiment 38. The antigen binding moiety of any one of the preceding embodiments, wherein an $IC_{50}$ value of the antigen binding moiety is at least about 30 pM in a cell-based assay measuring TSLP-induced TARC/CCL17 secretion.

Embodiment 39. The antigen binding moiety of any one of the preceding embodiments, wherein the antigen binding moiety reduces CD23 expression in vivo or in vitro, wherein the CD23 expression level is reduced by at least about 5%, at least about 10%, at least about 15%, at least about 20%, or more compared to the CD23 expression level after the treatment with a mono-specific antibody or an antigen binding moiety comprising one or more scFv fragments.

Embodiment 40. The antigen binding moiety of any one of the preceding embodiments, wherein serum half-life of the antigen binding moiety is at least about 10 days, at least about 20 days, at least about 30 days or more.

Embodiment 41. An antigen binding moiety comprising: a binding complex comprising: (a) an anti-IL-4R moiety or an antigen binding portion thereof, wherein the anti-IL-4R moiety or the antigen binding portion thereof comprises a light chain ($L_{IL-4R}$) and a heavy chain ($H_{IL-4R}$); and (b) an anti-thymic stromal lymphopoietin (TSLP) moiety or an antigen binding portion thereof, wherein the anti-TSLP moiety or the antigen binding portion thereof is associated with at least a portion of the $L_{IL-4R}$.

Embodiment 42. The antigen binding moiety of embodiment 41, wherein the anti-TSLP moiety or the antigen binding portion thereof is coupled to the $L_{IL-4R}$ via a first linker.

Embodiment 43. The antigen binding moiety of embodiment 41 or 42, wherein the anti-TSLP moiety or the antigen binding portion thereof comprises a light chain variable domain ($VL_{TSLP}$) and a heavy chain variable domain ($VH_{TSLP}$).

Embodiment 44. The antigen binding moiety of embodiment 43, wherein the $VL_{TSLP}$ and the $VH_{TSLP}$ are coupled to each other via a second linker.

Embodiment 45. The antigen binding moiety of embodiment 43 or 44, wherein the antigen binding moiety comprises, from N-terminus to C-terminus or from C-terminus to N-terminus: [the $L_{IL-4R}$]-[the first linker]-[the $VH_{TSLP}$]-[the second linker]-[$VL_{TSLP}$]; [the $L_{IL-4R}$]-[the first linker]-[the $VL_{TSLP}$]-[the second linker]-[the $VH_{TSLP}$]; [the $VL_{TSLP}$]-[the second linker]-[the $VH_{TSLP}$]-[the first linker]-[$L_{IL-4R}$]; or [the $VH_{TSLP}$]-[the second linker]-[the $VL_{TSLP}$]-[the first linker]-[the $L_{IL-4R}$].

Embodiment 46. The antigen binding moiety of any one of embodiments 42-45, wherein the first linker or the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185) or TVAAPSVFIFPP (SEQ ID NO: 20), wherein n is an integer between 1 and 100.

Embodiment 47. The antigen binding moiety of any one of embodiments 42-46, wherein the first linker comprises the amino acid sequence of SEQ ID NO: 23.

Embodiment 48. The antigen binding moiety of any one of embodiments 44-48, wherein the second linker comprises the amino acid sequence of SEQ ID NO: 23.

Embodiment 49. The antigen binding moiety of any one of embodiments 42-48, wherein the $L_{IL-4R}$ comprises (a) a light-chain complementarity-determining region (LCDR) 1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 50. The antigen binding moiety of any one of embodiments 42-49, wherein the $L_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 51. The antigen binding moiety of any one of embodiments 42-50, wherein the $L_{IL-4R}$ comprises a light chain variable domain, wherein the light chain variable domain comprises an amino acid sequence having at least 80% sequence identity to the amino acid sequence of SEQ ID NO: 30.

Embodiment 52. The antigen binding moiety of any one of embodiments 42-51, wherein the $L_{IL-4R}$ comprises a light chain variable domain comprising the amino acid sequence of SEQ ID NO: 30.

Embodiment 53. The antigen binding moiety of any one of embodiments 42-52, wherein the $L_{IL-4R}$ comprises an amino acid sequence having at least 90% sequence identity to the amino acid sequence of SEQ ID NO: 22.

Embodiment 54. The antigen binding moiety of any one of embodiments 42-53, wherein the $L_{IL-4R}$ comprises the amino acid sequence of SEQ ID NO: 22.

Embodiment 55. The antigen binding moiety of any one of embodiments 42-54, wherein the $H_{IL-4R}$ comprises (a) a heavy-chain complementarity-determining region (HCDR) 1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 56. The antigen binding moiety of any one of embodiments 42-55, wherein the $H_{IL-4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 57. The antigen binding moiety of any one of embodiments 42-56, wherein the $H_{IL-4R}$ comprises a heavy chain variable domain, wherein the heavy chain variable domain comprises an amino acid sequence having at least 80% sequence identity to the amino acid sequence of SEQ ID NO: 32.

Embodiment 58. The antigen binding moiety of any one of embodiments 42-57, wherein the $H_{IL\text{-}4R}$ comprises a heavy chain variable domain comprising the amino acid sequence of SEQ ID NO: 32.

Embodiment 59. The antigen binding moiety of any one of embodiments 42-58, wherein the $H_{IL\text{-}4R}$ comprises an amino acid sequence having at least 90% sequence identity to the amino acid sequence of SEQ ID NO: 21.

Embodiment 60. The antigen binding moiety of any one of embodiments 42-59, wherein the $H_{IL\text{-}4R}$ comprises the amino acid sequence of SEQ ID NO: 21.

Embodiment 61. The antigen binding moiety of any one of embodiments 44-60, wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4.

Embodiment 62. The antigen binding moiety of any one of embodiments 44-61, wherein the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4.

Embodiment 63. The antigen binding moiety of any one of embodiments 44-62, wherein the $VH_{TSLP}$ comprises an amino acid sequence having at least 90% sequence identity to the amino acid sequence of SEQ ID NO: 25.

Embodiment 64. The antigen binding moiety of any one of embodiments 44-63, wherein the $VH_{TSLP}$ comprises the amino acid sequence of SEQ ID NO: 25.

Embodiment 65. The antigen binding moiety of any one of embodiments 42-64, wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 66. The antigen binding moiety of any one of embodiments 44-65, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 67. The antigen binding moiety of any one of embodiments 42-66, wherein the $VL_{TSLP}$ comprises an amino acid sequence having at least 90% sequence identity to the amino acid sequence of SEQ ID NO: 28.

Embodiment 68. The antigen binding moiety of any one of embodiments 42-67, wherein the $VL_{TSLP}$ comprises the amino acid sequence of SEQ ID NO: 28.

Embodiment 69. The antigen binding moiety of any one of embodiments 42-68, wherein the antigen binding moiety further comprises a Fc region.

Embodiment 70. The antigen binding moiety of embodiment 69, wherein the Fc region comprises one or more mutations, wherein the one or more mutations comprise a half-life extension modification and/or one or more mutations to prevent Fab arm exchange of IgG.

Embodiment 71. The antigen binding moiety of embodiment 70, wherein the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P.

Embodiment 72. The antigen binding moiety of embodiment 70, wherein the one or more mutations comprise any one of the mutations set forth in Table 33.

Embodiment 73. The antigen binding moiety of any one of embodiments 69-72, wherein the Fc region comprises a first modified Fc polypeptide and a second modified Fc polypeptide, wherein the first modified Fc polypeptide comprises a knob modification and the second modified Fc polypeptide comprises a hole modification.

Embodiment 74. An antigen binding moiety comprising a binding complex comprising: (a) an anti-IL-4R moiety or an antigen binding portion thereof, wherein the anti-IL-4R moiety or the antigen binding portion thereof comprises a light chain ($L_{IL\text{-}4R}$) and a heavy chain ($H_{IL\text{-}4R}$); (b) an anti-thymic stromal lymphopoietin (TSLP) moiety or an antigen binding portion thereof; and (c0 a Fc region comprising a first Fc polypeptide and a second Fc polypeptide, wherein the anti-TSLP moiety or the antigen binding portion thereof is associated with at least a portion of the Fc region.

Embodiment 75. The antigen binding moiety of embodiment 74, wherein the anti-TSLP moiety or the antigen binding portion thereof is coupled to the first Fc polypeptide via a first linker or a second linker.

Embodiment 76. The antigen binding moiety of embodiment 74, wherein the anti-TSLP moiety or the antigen binding portion thereof is coupled to the second Fc polypeptide via a first linker or a second linker.

Embodiment 77. The antigen binding moiety of any one of embodiments 74-76, wherein the anti-TSLP moiety or the antigen binding portion thereof comprises a light chain variable domain ($VL_{TSLP}$), a light chain constant domain ($CL_{TSLP}$), a heavy chain variable domain ($VH_{TSLP}$), and/or a heavy chain constant domain 1 ($CH1_{TSLP}$).

Embodiment 78. The antigen binding moiety of any one of embodiments 74-77, wherein the anti-TSLP moiety or the antigen binding portion thereof comprises, from N-terminus to C-terminus: a first peptide chain comprising [$VH_{TSLP}$]-[$CH1_{TSLP}$] and a second peptide chain comprising [$VL_{TSLP}$]-[$CL_{TSLP}$]; a first peptide chain comprising [$VL_{TSLP}$]-[$CH1_{TSLP}$] and a second peptide chain comprising [$VH_{TSLP}$]-[$CL_{TSLP}$]; or a first peptide chain comprising [$VH_{TSLP}$]-[$CL_{TSLP}$] and a second peptide chain comprising [$VL_{TSLP}$]-[$CH1_{TSLP}$], wherein the first peptide chain or the second peptide chain are associated with each other.

Embodiment 79. The antigen binding moiety of embodiment 78, wherein the first polypeptide chain or the second polypeptide chain are associated with the first Fc polypeptide.

Embodiment 80. The antigen binding moiety of embodiment 78, wherein the first polypeptide chain or the second polypeptide chain are associated with the second Fc polypeptide.

Embodiment 81. The antigen binding moiety of any one of embodiments 74-80, wherein the anti-TSLP moiety or the antigen binding portion thereof comprises a light chain variable domain ($VL_{TSLP}$) and a heavy chain variable domain ($VH_{TSLP}$).

Embodiment 82. The antigen binding moiety of embodiment 81, wherein the $VL_{TSLP}$ and $VH_{TSLP}$ are coupled to each other via the second linker.

Embodiment 83. The antigen binding moiety of any one of embodiments 77-82, wherein the $VL_{TSLP}$ or $VH_{TSLP}$ is coupled to a N-terminus of the Fc region or a C-terminus of the Fc region.

Embodiment 84. The antigen binding moiety of any one of embodiments 77-83, wherein the antigen binding moiety comprises a hybrid chain wherein the hybrid chain comprises, from N-terminus to C-terminus or from C-terminus to N-terminus, [the $VL_{TSLP}$]-[the second linker]-[the $VH_{TSLP}$]-[the first linker]-[the first Fc polypeptide]; [the $VH_{TSLP}$]-[the second linker]-[the $VL_{TSLP}$]-[the first Fc polypeptide]; [the $VL_{TSLP}$]-[the second linker]-[the $VH_{TSLP}$]-[the first linker]-[the second Fc polypeptide]; or [the $VH_{TSLP}$]-[the second linker]-[the $VL_{TSLP}$]-[the second Fc polypeptide].

Embodiment 85. The antigen binding moiety of any one of embodiments 75-84, wherein the first linker or the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), or TVAAPSVFIFPP (SEQ ID NO: 20), wherein n is an integer between 1 and 100.

Embodiment 86. The antigen binding moiety of any one of embodiments 75-85, wherein the first linker comprises the amino acid sequence of SEQ ID NO: 23.

Embodiment 87. The antigen binding moiety of any one of embodiments 75-86, wherein the second linker comprises the amino acid sequence of SEQ ID NO: 23.

Embodiment 88. The antigen binding moiety of any one of embodiments 74-87, wherein the $L_{IL\text{-}4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 89. The antigen binding moiety of any one of embodiments 74-88, wherein the $L_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 90. The antigen binding moiety of any one of embodiments 74-89, wherein the $L_{IL\text{-}4R}$ comprises a light chain variable domain, wherein the light chain variable domain comprises an amino acid sequence having at least 80% sequence identity to the amino acid sequence of SEQ ID NO: 30.

Embodiment 91. The antigen binding moiety of any one of embodiments 74-90, wherein the $L_{IL\text{-}4R}$ comprises a light chain variable domain comprising the amino acid sequence of SEQ ID NO: 30.

Embodiment 92. The antigen binding moiety of any one of embodiments 74-91, wherein the $L_{IL\text{-}4R}$ comprises an amino acid sequence having at least 90% sequence identity to the amino acid sequence of SEQ ID NO: 22.

Embodiment 93. The antigen binding moiety of any one of embodiments 74-92, wherein the $L_{IL\text{-}4R}$ comprises the amino acid sequence of SEQ ID NO: 22.

Embodiment 94. The antigen binding moiety of any one of embodiments 74-93, wherein the $H_{IL\text{-}4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 95. The antigen binding moiety of any one of embodiments 74-94, wherein the $H_{IL\text{-}4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 96. The antigen binding moiety of any one of embodiments 74-95, wherein the $H_{IL\text{-}4R}$ comprises a heavy chain variable domain, wherein the heavy chain variable domain comprises an amino acid sequence having at least 80% sequence identity to the amino acid sequence of SEQ ID NO: 32.

Embodiment 97. The antigen binding moiety of any one of embodiments 74-96, wherein the $H_{IL\text{-}4R}$ comprises the heavy chain variable domain comprising the amino acid sequence of SEQ ID NO: 32.

Embodiment 98. The antigen binding moiety of any one of embodiments 74-97, wherein the $H_{IL\text{-}4R}$ comprises an amino acid sequence having at least 90% sequence identity to the amino acid sequence of SEQ ID NO: 21.

Embodiment 99. The antigen binding moiety of any one of embodiments 74-98, wherein the $H_{IL\text{-}4R}$ comprises the amino acid sequence of SEQ ID NO: 21.

Embodiment 100. The antigen binding moiety of any one of embodiments 90-99, wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4.

Embodiment 101. The antigen binding moiety of any one of embodiments 90-100, wherein the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4.

Embodiment 102. The antigen binding moiety of any one of embodiments 90-101, wherein the $VH_{TSLP}$ comprises an amino acid sequence having at least 90% sequence identity to the amino acid sequence of SEQ ID NO: 25.

Embodiment 103. The antigen binding moiety of any one of embodiments 90-102, wherein the $VH_{TSLP}$ comprises the amino acid sequence of SEQ ID NO: 25.

Embodiment 104. The antigen binding moiety of any one of embodiments 90-103, wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 105. The antigen binding moiety of any one of embodiments 90-104, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 106. The antigen binding moiety of any one of embodiments 90-105, wherein the $VL_{TSLP}$ comprises an amino acid sequence having at least 90% sequence identity to the amino acid sequence of SEQ ID NO: 28.

Embodiment 107. The antigen binding moiety of any one of embodiments 90-106, wherein the $VL_{TSLP}$ comprises the amino acid sequence of SEQ ID NO: 28.

Embodiment 108. The antigen binding moiety of any one of embodiments 74-107, wherein the Fc region comprises one or more mutations, wherein the one or more mutations comprise a half-life extension modification and/or one or more mutations to prevent Fab arm exchange of IgG.

Embodiment 109. The antigen binding moiety of embodiment 108, wherein the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/1253E (LSLE), L234A/L235A (LALA), L234A/L235A/P329G (LALAPG), M252Y/S254T/S255M/T256D/Y407E (MF), S228P, or V308P.

Embodiment 110. The antigen binding moiety of embodiment 108, wherein the one or more mutations comprise any one of the mutations set forth in Table 33.

Embodiment 111. The antigen binding moiety of any one of embodiments 74-110, wherein the first Fc polypeptide comprises a first modified Fc polypeptide, and the second Fc polypeptide comprises a second modified Fc polypeptide, wherein the first modified Fc polypeptide comprises a knob modification and the second modified Fc polypeptide comprises a hole modification.

Embodiment 112. An antigen binding moiety comprising: (a) a binding complex comprising: an anti-IL-4R moiety or an antigen binding portion thereof, and an anti-thymic stromal lymphopoietin (TSLP) moiety or an antigen binding portion thereof; and (b) a Fc region, wherein the antigen binding moiety comprises: a first peptide chain comprising a light chain variable domain of the anti-IL-4R moiety or the antigen binding portion thereof ($VL_{IL\text{-}4R}$) associated with at least a portion of a second light chain variable domain of the anti-TSLP moiety or the antigen binding portion thereof ($VL_{TSLP}$), wherein the antigen binding moiety further comprises one or more mutations in the Fc region.

Embodiment 113. The antigen binding moiety of embodiment 112, wherein the first peptide chain further comprises a light chain constant domain of the anti-IL-4R moiety or the antigen binding portion thereof ($CL_{IL\text{-}4R}$) or a second light chain constant domain of the anti-TSLP moiety or the antigen binding portion thereof ($CL_{TSLP}$).

Embodiment 114. The antigen binding moiety of embodiment 113, wherein the first peptide chain comprises the $VL_{IL\text{-}4R}$ flanked by the $VL_{TSLP}$ and the $CL_{TSLP}$; or the $VL_{TSLP}$ flanked by the $VL_{IL\text{-}4R}$ and the $CL_{IL\text{-}4R}$.

Embodiment 115. The antigen binding moiety of any one of embodiments 112-114, wherein the antigen binding moiety comprises, from N-terminus to C-terminus or from the C-terminus to the N-terminus: [the $VL_{TSLP}$]-[the $VL_{IL\text{-}4R}$]-[the $CL_{IL\text{-}4R}$]; [the $VL_{IL\text{-}4R}$]-[the $VL_{TSLP}$]-[the $CL_{TSLP}$]; [the $VL_{TSLP}$]-[the $VL_{IL\text{-}4R}$]-[the $CL_{TSLP}$]; [the $VL_{IL\text{-}4R}$]-[the $VL_{TSLP}$]-[the $CL_{IL\text{-}4R}$]; [the $VL_{TSLP}$]-[the $VL_{IL\text{-}4R}$]-[the $CL_{IL\text{-}4R}$]; [the $VL_{TSLP}$]-[the $VL_{IL\text{-}4R}$]-[the $CL_{IL\text{-}4R}$]; [the $VL_{IL\text{-}4R}$]-[the $VL_{TSLP}$]-[the $CL_{TSLP}$]; [the $VL_{TSLP}$]-[the $CL_{TSLP}$]-[the $VL_{IL\text{-}4R}$]-[the $CL_{IL\text{-}4R}$]; or [the $VL_{IL\text{-}4R}$]-[the $CL_{IL\text{-}4R}$]-[the $VL_{TSLP}$]-[the $CL_{TSLP}$].

Embodiment 116. The antigen binding moiety of any one of embodiments 112-115, wherein the antigen binding moiety further comprises a second peptide chain, wherein the second peptide chain comprises a heavy chain variable domain of the anti-IL-4R moiety or the antigen binding portion thereof ($VH_{IL\text{-}4R}$), a heavy chain variable domain of the anti-TSLP moiety or the antigen binding portion thereof ($VH_{TSLP}$), a heavy chain constant domain 1 of the anti-IL-4R moiety or the antigen binding portion thereof ($CH1_{IL\text{-}4R}$), or a heavy chain constant domain 1 of the anti-TSLP moiety or the antigen binding portion thereof ($CH1_{TSLP}$).

Embodiment 117. The antigen binding moiety of any one of embodiments 112-116, wherein the antigen binding moiety comprises, from N-terminus to C-terminus or from C-terminus to N-terminus: [the VHTSLP]-[the VHIL-4R]-[the CH1IL-4R]; [the VHIL-4R]-[the VHTSLP]-[the CH1 TSLP]; [the VHTSLP]-[the VHIL-4R]-[the CH1 TSLP]; [the VHIL-4R]-[the VHTSLP]-[the CH1IL-4R]; [the VHTSLP]-[the VHIL-4R]-[the CH1IL-4R]; [the VHTSLP]-[the VHIL-4R]-[the CH1IL-4R]; [the VHIL-4R]-[the VHTSLP]-[the CH1 TSLP]; [the VHTSLP]-[the CH1 TSLP]-[the VHIL-4R]-[the CH1IL-4R]; or the [VHIL-4R]-[the CH1IL-4R]-[the VHTSLP]-[the CH1 TSLP].

Embodiment 118. The antigen binding moiety of embodiment 117, wherein the binding complex comprises: the first peptide chain comprising [the VLTSLP]-[the VLIL-4R]-[the CLIL-4R], and the second peptide chain comprising [the VHTSLP]-[the VHIL-4R]-[the CH1IL-4R].

Embodiment 119. The antigen binding moiety of embodiment 117, wherein the binding complex comprises: the first peptide chain comprising [the VLIL-4R]-[the VLTSLP]-[the CLTSLP], and the second peptide chain comprising [the VHIL-4R]-[the VHTSLP]-[the CH1 TSLP].

Embodiment 120. The antigen binding moiety of embodiment 117, wherein the binding complex comprises: the first peptide chain comprising [the VLTSLP]-[the VLIL-4R]-[the CLTSLP], and the second peptide chain comprising [the VHTSLP]-[the VHIL-4R]-[the CH1 TSLP].

Embodiment 121. The antigen binding moiety of embodiment 117, wherein the binding complex comprises: the first peptide chain comprising [the VLIL-4R]-[the VLTSLP]-[the CLIL-4R], and the second peptide chain comprising [the VHIL-4R]-[the VHTSLP]-[the CH1IL-4R].

Embodiment 122. The antigen binding moiety of embodiment 117, wherein the binding complex comprises: the first peptide chain comprising [the VLIL-4R]-[the VLTSLP]-[the CLIL-4R], and the second peptide chain comprising [the VHIL-4R]-[the VHTSLP]-[the CH1IL-4R].

Embodiment 123. The antigen binding moiety of embodiment 117, wherein the binding complex comprises: the first peptide chain comprising [the VLTSLP]-[the VLIL-4R]-[the CLIL-4R], and the second peptide chain comprising [the VHTSLP]-[the VHIL-4R]-[the CH1IL-4R].

Embodiment 124. The antigen binding moiety of embodiment 117, wherein the binding complex comprises: the first peptide chain comprising [the VLIL-4R]-[the VLTSLP]-[the CLTSLP], and the second peptide chain comprising [the VHIL-4R]-[the VHTSLP]-[the CH1 TSLP].

Embodiment 125. The antigen binding moiety of any one of embodiments 112-124, wherein the $VL_{IL-4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 126. The antigen binding moiety of any one of embodiments 112-125, wherein the $VL_{IL-4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 127. The antigen binding moiety of any one of embodiments 112-126, wherein the $VL_{IL-4R}$ comprises a light chain variable domain, wherein the light chain variable domain comprises an amino acid sequence having at least 80% sequence identity to the amino acid sequence of SEQ ID NO: 30.

Embodiment 128. The antigen binding moiety of any one of embodiments 112-127, wherein the $VL_{IL-4R}$ comprises a light chain variable domain comprising the amino acid sequence of SEQ ID NO: 30.

Embodiment 129. The antigen binding moiety of any one of embodiments 112-128, wherein the $VH_{IL-4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 130. The antigen binding moiety of any one of embodiments 112-129, wherein the $VH_{IL-4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 131. The antigen binding moiety of any one of embodiments 112-130, wherein the $VH_{IL-4R}$ comprises a heavy chain variable domain, wherein the heavy chain variable domain comprises an amino acid sequence having at least 80% sequence identity to the amino acid sequence of SEQ ID NO: 32.

Embodiment 132. The antigen binding moiety of any one of embodiments 112-131, wherein the $VH_{IL-4R}$ comprises the heavy chain variable domain comprising the amino acid sequence of SEQ ID NO: 32.

Embodiment 133. The antigen binding moiety of any one of embodiments 112-132, wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4.

Embodiment 134. The antigen binding moiety of any one of embodiments 112-133, wherein the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4.

Embodiment 135. The antigen binding moiety of any one of embodiments 112-134, wherein the $VH_{TSLP}$ comprises an amino acid sequence having at least 90% sequence identity to the amino acid sequence of SEQ ID NO: 25.

Embodiment 136. The antigen binding moiety of any one of embodiments 112-135, wherein the $VH_{TSLP}$ comprises the amino acid sequence of SEQ ID NO: 25.

Embodiment 137. The antigen binding moiety of any one of embodiments 112-136, wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 138. The antigen binding moiety of any one of embodiments 112-137, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 139. The antigen binding moiety of any one of embodiments 112-138, wherein the $VL_{TSLP}$ comprises an amino acid sequence having at least 90% sequence identity to the amino acid sequence of SEQ ID NO: 28.

Embodiment 140. The antigen binding moiety of any one of embodiments 112-139, wherein the $VL_{TSLP}$ comprises the amino acid sequence of SEQ ID NO: 28.

Embodiment 141. The antigen binding moiety of any one of embodiments 112-140, wherein the one or more mutations comprise a half-life extension modification and/or one or more mutations to prevent Fab arm exchange of IgG.

Embodiment 142. The antigen binding moiety of embodiment 141, wherein the one or more mutations comprising a half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 143. The antigen binding moiety of embodiment 141, wherein the one or more mutations comprise any one of the mutations set forth in Table 33.

Embodiment 144. The antigen binding moiety of any one of embodiments 112-143, wherein the Fc region comprises a first modified Fc polypeptide and a second modified Fc polypeptide, wherein the first modified Fc polypeptide comprises a knob modification, and the second modified Fc polypeptide comprises a hole modification.

Embodiment 145. An antigen binding moiety comprising: (a) a binding complex comprising an anti-IL-4R moiety or an antigen binding portion thereof and an anti-thymic stromal lymphopoietin (TSLP) moiety or an antigen binding portion thereof, and (b) a Fc region, wherein the binding complex comprises: a first heavy chain variable domain associated with at least a portion of a second heavy chain variable domain, a first light chain variable domain associated with at least a portion of a second light chain variable domain, or a combination thereof, wherein the Fc region comprises one or more mutations.

Embodiment 146. The antigen binding moiety of embodiment 145, wherein the first heavy chain variable domain and the second heavy chain variable domain are coupled to each other via a first linker.

Embodiment 147. The antigen binding moiety of embodiment 145 or 146, wherein the first light chain variable domain and the second light chain variable domain are coupled to each other via a second linker.

Embodiment 148. The antigen binding moiety of any one of embodiments 145-147, wherein the binding complex comprises, from N-terminus to C-terminus or from C-terminus to N-terminus: [the first heavy chain variable domain]-[the second heavy chain variable domain]; [the second heavy chain variable domain]-[the first heavy chain variable domain]; [the first light chain variable domain]-[the second light chain variable domain]; [the second light chain variable domain]-[the first light chain variable domain], or a combination thereof.

Embodiment 149. The antigen binding moiety of any one of embodiments 145-148, wherein the binding complex is coupled to N-terminus of the Fc region.

Embodiment 150. The antigen binding moiety of any one of embodiments 145-149, wherein the first heavy chain variable domain comprises a heavy chain variable domain of the anti-TSLP moiety or the antigen binding portion thereof ($VH_{TSLP}$), the second heavy chain variable domain comprises a heavy chain variable domain of the anti-IL-4R moiety or the antigen binding portion thereof ($VH_{IL\text{-}4R}$), the first light chain variable domain comprises a light chain variable domain of the anti-TSLP moiety or the antigen binding portion thereof ($VL_{TSLP}$), the second light chain variable domain comprises a light chain variable domain of the anti-IL-4R moiety or the antigen binding portion thereof ($VL_{IL\text{-}4R}$).

Embodiment 151. The antigen binding moiety of embodiment 150, wherein the $VL_{IL}$-4R comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 152. The antigen binding moiety of embodiment 150 or 151, wherein the $VL_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 153. The antigen binding moiety of any one of embodiments 150-152, wherein the $VL_{IL\text{-}4R}$ comprises a light chain variable domain, wherein the light chain variable domain comprises an amino acid sequence having at least 80% sequence identity to the amino acid sequence of SEQ ID NO: 30.

Embodiment 154. The antigen binding moiety of any one of embodiments 150-153, wherein the $VL_{IL\text{-}4R}$ comprises a light chain variable domain comprising the amino acid sequence of SEQ ID NO: 30.

Embodiment 155. The antigen binding moiety of any one of embodiments 150-154, wherein the $VH_{IL\text{-}4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 156. The antigen binding moiety of any one of embodiments 150-155, wherein the $VH_{IL\text{-}4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 157. The antigen binding moiety of any one of embodiments 150-156, wherein the $VH_{IL\text{-}4R}$ comprises a heavy chain variable domain, wherein the heavy chain variable domain comprises an amino acid sequence having at least 80% sequence identity to the amino acid sequence of SEQ ID NO: 32.

Embodiment 158. The antigen binding moiety of any one of embodiments 150-157, wherein the $VH_{IL\text{-}4R}$ comprises the heavy chain variable domain comprising the amino acid sequence of SEQ ID NO: 32.

Embodiment 159. The antigen binding moiety of any one of embodiments 150-158, wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4.

Embodiment 160. The antigen binding moiety of any one of embodiments 150-159, wherein the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4.

Embodiment 161. The antigen binding moiety of any one of embodiments 150-160, wherein the $VH_{TSLP}$ comprises an amino acid sequence having at least 90% sequence identity to the amino acid sequence of SEQ ID NO: 25.

Embodiment 162. The antigen binding moiety of any one of embodiments 150-161, wherein the $VH_{TSLP}$ comprises the amino acid sequence of SEQ ID NO: 25.

Embodiment 163. The antigen binding moiety of any one of embodiments 150-162, wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 164. The antigen binding moiety of any one of embodiments 150-163, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 165. The antigen binding moiety of any one of embodiments 150-164 wherein the $VL_{TSLP}$ comprises an amino acid sequence having at least 90% sequence identity to the amino acid sequence of SEQ ID NO: 28.

Embodiment 166. The antigen binding moiety of any one of embodiments 150-165, wherein the $VL_{TSLP}$ comprises the amino acid sequence of SEQ ID NO: 28.

Embodiment 167. The antigen binding moiety of any one of embodiments 146-166, wherein the first linker and the second linker are a polypeptide linker between 3 amino acids and 500 amino acids in length.

Embodiment 168. The antigen binding moiety of any one of embodiments 146-167, wherein the first linker and the second linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), or TVAAPSVFIFPP (SEQ ID NO: 20), wherein n is an integer between 1 and 100.

Embodiment 169. The antigen binding moiety of any one of embodiments 146-168, wherein the first linker and the second linker are same.

Embodiment 170. The antigen binding moiety of any one of embodiments 146-169, wherein the first linker and the second linker are different.

Embodiment 171. The antigen binding moiety of any one of embodiments 146-170, wherein the antigen binding moiety comprises a plurality of the binding complexes.

Embodiment 172. The antigen binding moiety of embodiment 171, wherein the plurality of the binding complexes comprises at least one, at least two, at least three, or at least four binding complexes.

Embodiment 173. The antigen binding moiety of any one of embodiments 146-172, wherein the Fc region is an IgG1, IgG2, IgG3, or IgG4 heavy chain Fc region.

Embodiment 174. The antigen binding moiety of any one of embodiments 146-173, wherein the Fc region comprises one or more mutations, wherein the one or more mutations comprise a half-life extension modification and/or one or more mutations to prevent Fab arm exchange of IgG.

Embodiment 175. The antigen binding moiety of embodiment 174, wherein half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 176. The antigen binding moiety of embodiment 174, wherein the one or more mutations comprise any one of the mutations set forth in Table 33.

Embodiment 177. The antigen binding moiety of any one of embodiments 145-176, wherein the Fc region comprises a first modified Fc polypeptide and a second modified Fc polypeptide, wherein the first modified Fc polypeptide comprises a knob modification and the second modified Fc polypeptide comprises a hole modification.

Embodiment 178. The antigen binding moiety of any one of embodiments 146-177, wherein the antigen binding moiety comprises: a first binding complex comprising, from N-terminus to C-terminus, the $VH_{TSLP}$-the $VH_{IL\text{-}4R}$, a second binding complex comprising, from N-terminus to C-terminus, the $VL_{TSLP}$-the $VL_{IL\text{-}4R}$, and the Fc region.

Embodiment 179. The antigen binding moiety of any one of embodiments 146-178, wherein the antigen binding moiety is a dual variable domain immunoglobulin molecule.

Embodiment 180. An antigen binding moiety comprising: (a) a first antigen binding portion comprising a first heavy chain, wherein the first heavy chain comprises a first heavy chain variable region and a first heavy chain constant region, and (b) a second antigen binding portion comprising a second heavy chain, wherein the second heavy chain comprises a second heavy chain variable region and a second heavy chain constant region, wherein the first heavy chain variable region comprises (a) a HCDR1 having at least 80% sequence identity to the amino acid sequence of SEQ ID NO: 2, (b) a HCDR2 having at least 80% sequence identity to the amino acid sequence of SEQ ID NO: 3, and/or (c) a HCDR3 having at least 80% sequence identity to the amino acid sequence of SEQ ID NO: 4, wherein the second heavy chain variable region comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12, wherein the first antigen binding portion and the second antigen binding portion are associated to a Fc region, and wherein the Fc region comprises one or more mutations.

Embodiment 181. The antigen binding moiety of embodiment 180, wherein the first heavy chain variable region comprises (a) a HCDR1 having the amino acid sequence of SEQ ID NO: 2, (b) a HCDR2 having the amino acid sequence of SEQ ID NO: 3, and/or (c) a HCDR3 having the amino acid sequence of SEQ ID NO: 4.

Embodiment 182. The antigen binding moiety of embodiment 180 or 181, wherein the first heavy chain variable region comprises an amino acid sequence having at least 90% sequence identity to the amino acid sequence of SEQ ID NO: 25.

Embodiment 183. The antigen binding moiety of any one of embodiments 180-182, wherein the first heavy chain variable region comprises the amino acid sequence of SEQ ID NO: 25.

Embodiment 184. The antigen binding moiety of any one of embodiments 180-183, wherein the second heavy chain variable region comprises (a) a HCDR1 comprises the amino acid sequence of SEQ ID NO: 10, (b) a HCDR2 comprises the amino acid sequence of SEQ ID NO: 11, and/or (c) a HCDR3 comprises the amino acid sequence of SEQ ID NO: 12.

Embodiment 185. The antigen binding moiety of any one of embodiments 180-184, wherein the second heavy chain variable region comprises a heavy chain variable domain, wherein the heavy chain variable domain comprises an amino acid sequence having at least 80% sequence identity to the amino acid sequence of SEQ ID NO: 32.

Embodiment 186. The antigen binding moiety of any one of embodiments 180-185, wherein the second heavy chain variable region comprises the heavy chain variable domain comprising the amino acid sequence of SEQ ID NO: 32.

Embodiment 187. The antigen binding moiety of any one of embodiments 180-186, wherein the first antigen binding portion further comprises a first light chain, wherein the first light chain comprises a first light chain variable region and a first light chain constant region, wherein the first light chain is coupled to the first heavy chain.

Embodiment 188. The antigen binding moiety of any one of embodiments 180-187, wherein the first antigen binding portion comprises: a first peptide chain comprising the first light chain variable region and the first light chain constant region, and a second peptide chain comprising the first heavy chain variable region and the first heavy chain constant region; a first peptide chain comprising the first heavy chain variable region and the first heavy chain constant region, and a second peptide chain comprising the first light chain variable region and the first light chain constant region; a first peptide chain comprising the first light chain variable region and the first heavy chain constant region, and a second peptide chain comprising the first heavy chain variable region and the first light chain constant region; a first peptide chain comprising the first heavy chain variable region and the first light chain constant region, and a second peptide chain comprising the first light chain variable region and the first heavy chain constant region; or a first peptide chain comprising the first light chain variable region and the first heavy chain constant region, and a second peptide chain comprising the first heavy chain variable region and the first light chain constant region.

Embodiment 189. The antigen binding moiety of embodiment 187 or 188, wherein the first light chain variable region comprises (a) a LCDR1 having at least 80% sequence identity to the amino acid sequence of SEQ ID NO: 6, (b) a LCDR2 having at least 80% sequence identity to the amino acid sequence of SEQ ID NO: 7, and/or (c) a LCDR3 having at least 80% sequence identity to the amino acid sequence of SEQ ID NO: 8.

Embodiment 190. The antigen binding moiety of any one of embodiments 187-189, wherein the first light chain variable region comprises (a) a LCDR1 having the amino acid sequence of SEQ ID NO: 6, (b) a LCDR2 having the amino acid sequence of SEQ ID NO: 7, and/or (c) a LCDR3 having the amino acid sequence of SEQ ID NO: 8.

Embodiment 191. The antigen binding moiety of any one of embodiments 187-190, wherein the first light chain variable region comprises an amino acid sequence having at least 90% sequence identity to the amino acid sequence of SEQ ID NO: 28.

Embodiment 192. The antigen binding moiety of any one of embodiments 187-191, wherein the first light chain variable region comprises the amino acid sequence of SEQ ID NO: 28.

Embodiment 193. The antigen binding moiety of any one of embodiments 180-192, wherein the antigen binding moiety further comprises a second light chain variable region and a second light chain constant region comprising: a first peptide chain comprising the second light chain variable region and the second light chain constant region, and a second peptide chain comprising the second heavy chain variable region and the second heavy chain constant region; a first peptide chain comprising the second heavy chain variable region and the second heavy chain constant region, and a second peptide chain comprising the second light chain variable region and the second light chain constant region; a first peptide chain comprising the second light chain variable region and the second heavy chain constant region, and a second peptide chain comprising the second heavy chain variable region and the second light chain constant region; a first peptide chain comprising the second heavy chain variable region and the second light chain constant region, and a second peptide chain comprising the second light chain variable region and the second heavy chain constant region; or a first peptide chain comprising the second light chain variable region and the second heavy chain constant region, and a second peptide chain comprising the second heavy chain variable region and the second light chain constant region.

Embodiment 194. The antigen binding moiety of embodiment 193, wherein the second light chain variable region comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 195. The antigen binding moiety of embodiment 193 or 194, wherein the second light chain variable region comprises (a) a LCDR1 comprising the amino acid sequence of SEQ ID NO: 14, (b) a LCDR2 comprising the amino acid sequence of SEQ ID NO: 15, and/or (c) a LCDR3 comprising amino acid sequence of SEQ ID NO: 16.

Embodiment 196. The antigen binding moiety of any one of embodiments 193-195, wherein the second light chain variable region comprises an amino acid sequence having at least 80% sequence identity to the amino acid sequence of SEQ ID NO: 30.

Embodiment 197. The antigen binding moiety of any one of embodiments 193-196, wherein the second light chain variable region comprises the amino acid sequence of SEQ ID NO: 30.

Embodiment 198. The antigen binding moiety of any one of embodiments 180-197, wherein the Fc region is an IgG1, IgG2, IgG3, or IgG4 heavy chain Fc region.

Embodiment 199. The antigen binding moiety of any one of embodiments 180-198 wherein the one or more mutations comprise a half-life extension modification and/or one or more mutations to prevent Fab arm exchange of IgG.

Embodiment 200. The antigen binding moiety of embodiment 199, wherein the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 201. The antigen binding moiety of embodiment 199, wherein the one or more mutations comprise any one of the mutations set forth in Table 33.

Embodiment 202. The antigen binding moiety of any one of embodiments 180-201, wherein the Fc region comprises a first modified Fc polypeptide and a second modified Fc polypeptide, wherein the first modified Fc polypeptide comprises a knob modification and the second modified Fc polypeptide comprises a hole modification.

Embodiment 203. An antigen binding moiety comprising: a binding complex comprising an anti-IL-4R moiety or an antigen binding portion thereof and an anti-thymic stromal lymphopoietin (TSLP) moiety or an antigen binding portion thereof, wherein the binding complex comprises: (a) a heavy chain variable domain of the anti-TSLP moiety or the antigen binding portion thereof ($VH_{TSLP}$), wherein the $VH_{TSLP}$ comprises (a) a $HCDR1_{TSLP}$ having at least 80% sequence identity to the amino acid sequence of SEQ ID NO: 2, (b) a $HCDR2_{TSLP}$ having at least 80% sequence identity to the amino acid sequence of SEQ ID NO: 3, and/or (c) a $HCDR3_{TSLP}$ having at least 80% sequence identity to the amino acid sequence of SEQ ID NO: 4; (b) a kappa light chain, and (c) a lambda light chain, wherein the binding complex is associated with a Fc region, wherein the Fc region comprises one or more mutations.

Embodiment 204. The antigen binding moiety of embodiment 203, wherein the $VH_{TSLP}$ comprises (a) a $HCDR1_{TSLP}$ having the amino acid sequence of SEQ ID NO: 2, (b) a $HCDR2_{TSLP}$ having the amino acid sequence of SEQ ID NO: 3, and/or (c) a $HCDR3_{TSLP}$ having the amino acid sequence of SEQ ID NO: 4.

Embodiment 205. The antigen binding moiety of embodiment 203 or 204, wherein the $VH_{TSLP}$ comprises an amino acid sequence having at least 90% sequence identity to the amino acid sequence of SEQ ID NO: 25.

Embodiment 206. The antigen binding moiety of any one of embodiments 203-205, wherein the $VH_{TSLP}$ comprises the amino acid sequence of SEQ ID NO: 25.

Embodiment 207. The antigen binding moiety of any one of embodiments 203-206, wherein the kappa light chain or the lambda light chain comprises a light chain variable domain of the anti-TSLP moiety or the antigen binding portion thereof ($VL_{TSLP}$), wherein the $VL_{TSLP}$ comprises (a) a $LCDR1_{TSLP}$ having at least 80% sequence identity to the amino acid sequence of SEQ ID NO: 6, (b) a $LCDR2_{TSLP}$ having at least 80% sequence identity to the amino acid sequence of SEQ ID NO: 7, and/or (c) a $LCDR3_{TSLP}$ having at least 80% sequence identity to the amino acid sequence of SEQ ID NO: 8.

Embodiment 208. The antigen binding moiety of embodiment 207, wherein the $VL_{TSLP}$ comprises (a) a $LCDR1_{TSLP}$ having the amino acid sequence of SEQ ID NO: 6, (b) a $LCDR2_{TSLP}$ having the amino acid sequence of SEQ ID NO: 7, and/or (c) a $LCDR3_{TSLP}$ having the amino acid sequence of SEQ ID NO: 8.

Embodiment 209. The antigen binding moiety of embodiment 207 or 208, wherein the $VL_{TSLP}$ comprises an amino acid sequence having at least 90% sequence identity to the amino acid sequence of SEQ ID NO: 28.

Embodiment 210. The antigen binding moiety of any one of embodiments 207-209, wherein the $VL_{TSLP}$ comprises the amino acid sequence of SEQ ID NO: 28.

Embodiment 211. The antigen binding moiety of any one of embodiments 203-210, wherein the anti-IL-4R moiety or the antigen binding portion thereof comprises a heavy chain variable region ($VH_{IL\text{-}4R}$) and a light chain variable region ($VL_{IL\text{-}4R}$).

Embodiment 212. The antigen binding moiety of embodiment 211, wherein the $VL_{IL\text{-}4R}$ comprises (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16.

Embodiment 213. The antigen binding moiety of embodiment 211 or 212, wherein the $VL_{IL\text{-}4R}$ comprises (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 214. The antigen binding moiety of any one of embodiments 211-213, wherein the $VL_{IL\text{-}4R}$ comprises an amino acid sequence having at least 80% sequence identity to the amino acid sequence of SEQ ID NO: 30.

Embodiment 215. The antigen binding moiety of any one of embodiments 211-214, wherein the $VL_{IL\text{-}4R}$ comprises the amino acid sequence of SEQ ID NO: 30.

Embodiment 216. The antigen binding moiety of any one of embodiments 211-215, wherein the $VH_{IL\text{-}4R}$ comprises (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12.

Embodiment 217. The antigen binding moiety of any one of embodiments 211-216, wherein the $VH_{IL\text{-}4R}$ comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 218. The antigen binding moiety of any one of embodiments 211-217, wherein the $VH_{IL\text{-}4R}$ comprises an amino acid sequence having at least 80% sequence identity to the amino acid sequence of SEQ ID NO: 32.

Embodiment 219. The antigen binding moiety of any one of embodiments 211-218, wherein the $VH_{IL\text{-}4R}$ comprises the amino acid sequence of SEQ ID NO: 32.

Embodiment 220. The antigen binding moiety of any one of embodiments 213-219, wherein the Fc region comprises one or more mutations, wherein the one or more mutations comprise a half-life extension modification and/or one or more mutations to prevent Fab arm exchange of IgG.

Embodiment 221. The antigen binding moiety of embodiment 220, wherein the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 222. The antigen binding moiety of embodiment 220, wherein the one or more mutations comprise any one of the mutations set forth in Table 33.

Embodiment 223. The antigen binding moiety of any one of embodiments 220-222, wherein the Fc region comprises a first modified Fc and a second modified Fc, wherein the first modified Fc is a knob modified Fc and the second modified Fc is a hole modified Fc; or the second modified Fc is a knob modified Fc and the first modified Fc is a hole modified Fc.

Embodiment 224. An antigen binding moiety comprising: a first single chain Fv (scFv) comprising: (a) a first heavy chain variable region comprising (a) a HCDR1 having at least 80% sequence identity to the amino acid sequence of SEQ ID NO: 2, (b) a HCDR2 having at least 80% sequence identity to the amino acid sequence of SEQ ID NO: 3, and/or (c) a HCDR3 having at least 80% sequence identity to the amino acid sequence of SEQ ID NO: 4, and (b) a first light chain variable region comprising (a) a LCDR1 having at least 80% sequence identity to the amino acid sequence of SEQ ID NO: 6, (b) a LCDR2 having at least 80% sequence identity to the amino acid sequence of SEQ ID NO: 7, and/or (c) a LCDR3 having at least 80% sequence identity to the amino acid sequence of SEQ ID NO: 8; a second scFv comprising (a) a second heavy chain variable region comprising (a) a HCDR1 having at least 80% sequence identity to the amino acid sequence of SEQ ID NO: 10, (b) a HCDR2 having at least 80% sequence identity to the amino acid sequence of SEQ ID NO: 11, and/or (c) a HCDR3 having at least 80% sequence identity to the amino acid sequence of SEQ ID NO: 12, and (b) a second light chain variable region comprising (a) a LCDR1 having at least 80% sequence identity to the amino acid sequence of SEQ ID NO: 14, (b) a LCDR2 having at least 80% sequence identity to the amino acid sequence of SEQ ID NO: 15, and/or (c) a LCDR3 having at least 80% sequence identity to the amino acid sequence of SEQ ID NO: 16; and a Fc region, wherein the Fc region comprises one or more mutations.

Embodiment 225. The antigen binding moiety of embodiment 224, wherein the second light chain variable region (a) a LCDR1 comprising the amino acid sequence of SEQ ID NO: 14, (b) a LCDR2 comprising the amino acid sequence of SEQ ID NO: 15, and/or (c) a LCDR3 comprising the amino acid sequence of SEQ ID NO: 16.

Embodiment 226. The antigen binding moiety of embodiment 224 or 225, wherein the second light chain variable region comprises an amino acid sequence having at least 80% sequence identity to the amino acid sequence of SEQ ID NO: 30.

Embodiment 227. The antigen binding moiety of any one of embodiments 224-226, wherein the second light chain variable region comprises the amino acid sequence of SEQ ID NO: 30.

Embodiment 228. The antigen binding moiety of any one of embodiments 224-227, wherein the second heavy chain variable region comprises (a) a HCDR1 comprising the amino acid sequence of SEQ ID NO: 10, (b) a HCDR2 comprising the amino acid sequence of SEQ ID NO: 11, and/or (c) a HCDR3 comprising the amino acid sequence of SEQ ID NO: 12.

Embodiment 229. The antigen binding moiety of any one of embodiments 224-228, wherein the second heavy chain variable region comprises an amino acid sequence having at least 80% sequence identity to the amino acid sequence of SEQ ID NO: 32.

Embodiment 230. The antigen binding moiety of any one of embodiments 224-229, wherein the second heavy chain variable region comprises the heavy chain variable domain comprising the amino acid sequence of SEQ ID NO: 32.

Embodiment 231. The antigen binding moiety of any one of embodiments 224-230, wherein the first heavy chain variable region comprises (a) a HCDR1 having the amino acid sequence of SEQ ID NO: 2, (b) a HCDR2 having the amino acid sequence of SEQ ID NO: 3, and/or (c) a HCDR3 having the amino acid sequence of SEQ ID NO: 4.

Embodiment 232. The antigen binding moiety of any one of embodiments 224-231, wherein the first heavy chain variable region comprises an amino acid sequence having at least 90% sequence identity to the amino acid sequence of SEQ ID NO: 25.

Embodiment 233. The antigen binding moiety of any one of embodiments 224-232, wherein the first heavy chain variable region comprises the amino acid sequence of SEQ ID NO: 25.

Embodiment 234. The antigen binding moiety of any one of embodiments 224-233, wherein the first light chain variable region comprises (a) a LCDR1 having the amino acid sequence of SEQ ID NO: 6, (b) a LCDR2 having the amino acid sequence of SEQ ID NO: 7, and/or (c) a LCDR3 having the amino acid sequence of SEQ ID NO: 8.

Embodiment 235. The antigen binding moiety of any one of embodiments 224-234, wherein the first light chain variable region comprises an amino acid sequence having at least 90% sequence identity to the amino acid sequence of SEQ ID NO: 28.

Embodiment 236. The antigen binding moiety of any one of embodiments 224-235, wherein the first scFv comprises, from N-terminus to C-terminus or from the N-terminus to C-terminus, [the first heavy chain variable region]-[the first light chain variable region] or [the first light chain variable region]-[the first heavy chain variable region], wherein the first light chain variable region and the first heavy chain variable region are coupled to each other via a first linker.

Embodiment 237. The antigen binding moiety of any one of embodiments 224-236, wherein the second scFv comprises, from N-terminus to C-terminus or from the C-terminus to N-terminus, [the second heavy chain variable region]-[the second light chain variable region] or [the second light chain variable region]-[the second heavy chain variable region], wherein the second light chain variable region and the second heavy chain variable region are coupled to each other via a second linker.

Embodiment 238. The antigen binding moiety of embodiment 236 or 237, wherein the first linker and the second linker comprises (GGS)n (SEQ ID NO: 17) or (GGGGS)n (SEQ ID NO: 18), wherein n is an integer between 1 and 100.

Embodiment 239. The antigen binding moiety of embodiment 238, wherein the first linker and the second linker are same.

Embodiment 240. The antigen binding moiety of embodiment 238, wherein the first linker and the second linker are different.

Embodiment 241. The antigen binding moiety of any one of embodiments 224-240, wherein the antigen binding moiety comprises, from N-terminus to C-terminus or C-terminus to N-terminus, [the first scFv]-[the second scFv] or [the second scFv]-[the first scFv], wherein the first scFv and the second scFv are coupled to each other via a third linker.

Embodiment 242. The antigen binding moiety of embodiment 241, wherein the third linker comprises (GGS)n (SEQ ID NO: 17) or (GGGGS)n (SEQ ID NO: 18), wherein n is an integer between 1 and 100.

Embodiment 243. The antigen binding moiety of any one of embodiments 224-242, wherein the one or more mutations comprise a half-life extension modification and/or one or more mutations to prevent Fab arm exchange of IgG.

Embodiment 244. The antigen binding moiety of embodiment 243, wherein the half-life extension modification comprises M252Y/S254T/T256E (YTE), M428L/

N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 245. The antigen binding moiety of embodiment 243, wherein the one or more mutations comprise any one of the mutations set forth in Table 33.

Embodiment 246. The antigen binding moiety of embodiment 224 or 245, wherein the Fc region comprises a first modified Fc and a second modified Fc, wherein the first modified Fc is a knob modified Fc and the second modified Fc is a hole modified Fc; or the second modified Fc is a knob modified Fc and the first modified Fc is a hole modified Fc.

Embodiment 247. An antigen binding moiety comprising: two or more of an anti-IL-4R moiety or an antigen binding portion thereof, an anti-thymic stromal lymphopoietin receptor (TSLPR) moiety or an antigen binding portion thereof, or an anti-IL-7 moiety or an antigen binding portion thereof, wherein the antigen binding moiety comprises a Fc region, wherein the Fc region comprises a first modified Fc polypeptide and a second modified Fc polypeptide wherein: the first modified Fc polypeptide comprises a knob modification and the second modified Fc polypeptide comprises a hole modification.

Embodiment 248. The antigen binding moiety of embodiment 247, wherein the anti-IL-4R moiety or the antigen binding portion thereof is an antibody comprising a first heavy chain and/or a second heavy chain.

Embodiment 249. The antigen binding moiety of embodiment 247 or 248, wherein the anti-IL-7 moiety or the antigen binding portion thereof is coupled to a C-terminus of the first heavy chain of the anti-IL-4R moiety or the antigen binding portion thereof.

Embodiment 250. The antigen binding moiety of embodiment 249, wherein the anti-IL7 moiety or the antigen binding portion thereof is coupled to the C-terminus of the first heavy chain of the anti-IL-4R moiety or the antigen binding portion thereof via a first linker.

Embodiment 251. The antigen binding moiety of any one of embodiments 247-250, wherein the anti-TSLPR moiety or the antigen binding portion thereof is coupled to the C-terminus of the second heavy chain of the anti-IL-4R moiety.

Embodiment 252. The antigen binding moiety of any one of embodiments 247-251, wherein the anti-TSLPR moiety or the antigen binding portion thereof is coupled to the C-terminus of the second heavy chain of the anti-IL-4R moiety via a second linker.

Embodiment 253. The antigen binding moiety of any one of embodiments 247-252, wherein the anti-IL-4R moiety or the antigen binding portion thereof comprises (a) a HCDR1 comprising an amino acid sequence having at least 80% sequence identity to the amino acid sequence of SEQ ID NO: 10, (b) a HCDR2 comprising an amino acid sequence having at least 80% sequence identity to the amino acid sequence of SEQ ID NO: 11, and/or (c) a HCDR3 comprising an amino acid sequence having at least 80% sequence identity to the amino acid sequence of SEQ ID NO: 12, and a light chain variable region comprising (d) a LCDR1 comprising an amino acid sequence having at least 80% sequence identity to the amino acid sequence of SEQ ID NO: 14, (e) a LCDR2 comprising an amino acid sequence having at least 80% sequence identity to the amino acid sequence of SEQ ID NO: 15, and/or (f) a LCDR3 comprising an amino acid sequence having at least 80% sequence identity to the amino acid sequence of SEQ ID NO: 16.

Embodiment 254. The antigen binding moiety of any one of embodiments 247-253, wherein the anti-IL-4R moiety or the antigen binding portion thereof comprises (a) a HCDR1 having the amino acid sequence of SEQ ID NO: 10, (b) a HCDR2 having the amino acid sequence of SEQ ID NO: 11, and/or (c) a HCDR3 having the amino acid sequence of SEQ ID NO: 12, and a light chain variable region comprising (d) a LCDR1 having the amino acid sequence of SEQ ID NO: 14, (e) a LCDR2 having the amino acid sequence of SEQ ID NO: 15, and/or (f) a LCDR3 having the amino acid sequence of SEQ ID NO: 16.

Embodiment 255. The antigen binding moiety of any one of embodiments 247-254, wherein the anti-TSLPR moiety or the antigen binding portion thereof comprise an amino acid sequence having at least 80% sequence identity to the amino acid sequence of SEQ ID NO: 34.

Embodiment 256. The antigen binding moiety of any one of embodiments 247-255, wherein the anti-TSLPR moiety or the antigen binding portion thereof comprise the amino acid sequence of SEQ ID NO: 34.

Embodiment 257. The antigen binding moiety of any one of embodiments 247-256, wherein the anti-IL-7 moiety or the antigen binding portion thereof comprise an amino acid sequence having at least 80% sequence identity to the amino acid sequence of SEQ ID NO: 35.

Embodiment 258. The antigen binding moiety of any one of embodiments 247-257, wherein the anti-IL-7 moiety or the antigen binding portion thereof comprise the amino acid sequence of SEQ ID NO: 35.

Embodiment 259. The antigen binding moiety of any one of embodiments 247-258, wherein the Fc region comprises one or more mutations, wherein the one or more mutations comprise a half-life extension modification and/or one or more mutations to prevent Fab arm exchange of IgG.

Embodiment 260. The antigen binding moiety of embodiment 259, wherein one or more mutation comprising the half-life extension modification comprises M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

Embodiment 261. The antigen binding moiety of embodiment 259, wherein the one or more mutations comprise any one of the mutations set forth in Table 33.

Embodiment 262. The antigen binding moiety of any one of the preceding embodiments, wherein (i) a polynucleotide sequence encoding the anti-IL-4R moiety or the antigen binding portion thereof and/or (ii) a polynucleotide sequence encoding the anti-TSLP moiety or the antigen binding portion thereof further comprises a polynucleotide sequence encoding a signal peptide.

Embodiment 263. The antigen binding moiety of embodiment 262, wherein a polynucleotide sequence encoding a light chain or a heavy chain of the anti-IL-4R moiety or the antigen binding portion thereof and/or the anti-TSLP moiety or the antigen binding portion thereof further comprises the polynucleotide sequence encoding the signal peptide.

Embodiment 264. The antigen binding moiety of embodiment 262 or 263, wherein the signal peptide comprises an amino acid sequence having at least 80% sequence identity to the amino acid sequence of any one of SEQ ID NOs: 130-184.

Embodiment 265. The antigen binding moiety of embodiment 264, wherein the signal peptide comprises the amino acid sequence of any one of SEQ ID NOs: 130-184.

Embodiment 266. The antigen binding moiety of any one of embodiments 247-265, wherein a polynucleotide sequence encoding the anti-IL7 moiety or the antigen binding portion thereof further comprises a polynucleotide sequence encoding a signal peptide.

Embodiment 267. The antigen binding moiety of embodiment 266, wherein a polynucleotide sequence encoding a light chain or a heavy chain of the anti-IL7 moiety or the antigen binding portion thereof further comprises the polynucleotide sequence encoding the signal peptide.

Embodiment 268. The antigen binding moiety of any one of embodiment 266 or 267, wherein the signal peptide comprises an amino acid sequence having at least 80% sequence identity to the amino acid sequence of any one of SEQ ID NOs: 130-184.

Embodiment 269. The antigen binding moiety of embodiment 268, wherein the signal peptide comprises an amino acid sequence having the amino acid sequence of any one of SEQ ID NOs: 130-184.

Embodiment 270. The antigen binding moiety of any one of embodiments 262-269, wherein the signal peptide comprises an amino acid sequence having at least 80% sequence identity to the amino acid sequence of SEQ ID NOs: 156 or 130.

Embodiment 271. The antigen binding moiety of any one of embodiments 262-270, wherein the signal peptide comprises an amino acid sequence having the amino acid sequence of SEQ ID NOs: 156 or 130.

Embodiment 272. The antigen binding moiety of any one of the preceding embodiments, wherein an $EC_{50}$ value is at least about 0.25 nM in a cell-based assay measuring IL-4R binding.

Embodiment 273. The antigen binding moiety of any one of the preceding embodiments, wherein an $IC_{50}$ value is at least about 2.4 nM in a cell-based assay measuring IL-4 induced CD23 upregulation.

Embodiment 274. The antigen binding moiety of any one of the preceding embodiments, wherein an $IC_{50}$ value is at least about 30 pM in a cell-based assay measuring TSLP-induced TARC/CCL17 secretion.

Embodiment 275. The antigen binding moiety of any one of the preceding embodiments, wherein the antigen binding moiety reduces a serum IgE level as compared to a serum IgE level after a treatment with a monospecific antibody or an antigen binding moiety comprising one or more scFv fragments.

Embodiment 276. The antigen binding moiety of embodiment 275, wherein the serum IgE expression level is reduced by at least about 5%, at least about 10%, at least about 15%, at least about 20%, or more compared to the serum IgE expression level after the treatment with a monospecific antibody or an antigen binding moiety comprising one or more scFv fragments.

Embodiment 277. The antigen binding moiety of any one of the preceding embodiments, wherein the antigen binding moiety reduces a CD23 expression level compared to a CD23 expression level after a treatment with a monospecific antibody or an antigen binding moiety comprising one or more scFv fragments.

Embodiment 278. The antigen binding moiety of embodiment 277, wherein the CD23 expression level is reduced by at least about 5%, at least about 10%, at least about 15%, at least about 20%, or more compared to the CD23 expression level after the treatment with a monospecific antibody or an antigen binding moiety comprising one or more scFv fragments.

Embodiment 279. The antigen binding moiety of any one of the preceding embodiments, wherein serum half-life of the antigen binding moiety is at least about 10 days, at least about 20 days, at least about 30 days or more.

Embodiment 280. The antigen binding moiety of any one of the preceding embodiments, wherein the antigen binding moiety comprises at least one constant domain of a first heavy chain derived from IgG2 and at least one constant domain of a second heavy chain derived from IgG4.

Embodiment 281. The antigen binding moiety of any one of the preceding embodiments, wherein the antigen binding moiety comprises at least one constant domain of the heavy chain of the anti-IL-4R or the antigen binding portion thereof derived from IgG4.

Embodiment 282. The antigen binding moiety of embodiment 280 or 281, wherein the antigen binding moiety comprises at least one constant domain of the heavy chain of anti-TSLP or the antigen binding portion thereof derived from IgG2.

Embodiment 283. A polynucleotide encoding the antigen binding moiety of any one of embodiments 1-282.

Embodiment 284. An expression vector comprising the polynucleotide of embodiment 283.

Embodiment 285. A host cell comprising the polynucleotide of embodiment 283 or the expression vector of embodiment 284.

Embodiment 286. A method of producing the antigen binding moiety of any one of embodiments 1-282.

Embodiment 287. A pharmaceutical composition comprising the antigen binding moiety of any one of embodiments 1-282, the polynucleotide of embodiment 283, the expression vector of embodiment 284, or the host cell of embodiment 285 and a pharmaceutically acceptable excipient or carrier.

Embodiment 288. A method of treating asthma, chronic obstructive pulmonary disease, eczema, and/or nasal polyps comprising administering a therapeutically effective amount of the antigen binding moiety of any one of embodiments 1-282, the polynucleotide of embodiment 283, the expression vector of embodiment 284, the host cell of embodiment 285, or the pharmaceutical composition of embodiment 287 to a subject in need thereof.

Embodiment 289. A method of treating a disease or condition comprising administering a therapeutically effective amount of the antigen binding moiety of any one of embodiments 1-282, the polynucleotide of embodiment 283, the expression vector of embodiment 284, the host cell of embodiment 285, or the pharmaceutical composition of embodiment 287 to a subject in need thereof.

Embodiment 290. Use of a therapeutically effective amount of the antigen binding moiety of any one of embodiments 1-282, the polynucleotide of embodiment 283, the expression vector of embodiment 284, the host cell of embodiment 285, or the pharmaceutical composition of embodiment 287 in the manufacture of a medicament for the treatment of a disease or condition.

Embodiment 291. A kit comprising the antigen binding moiety of any one of embodiments 1-282, the polynucleotide of embodiment 283, the expression vector of embodiment 284, the host cell of embodiment 285, or the pharmaceutical composition of embodiment 287 and instructions for using the antigen binding complex.

Embodiment 292. The antigen binding moiety of any one of embodiments 1-282, the polynucleotide of embodiment 283, the expression vector of embodiment 284, the host cell of embodiment 285, or the pharmaceutical composition of embodiment 287 for use as a medicament.

Embodiment 293. The antigen binding moiety of any one of embodiments 1-282, the polynucleotide of embodiment 283, the expression vector of embodiment 284, the host cell of embodiment 285, or the pharmaceutical composition of embodiment 287 for use in the treatment of a disease.

Embodiment 294. The antigen binding moiety of any one of embodiments 1-282, the polynucleotide of embodiment 283, the expression vector of embodiment 284, the host cell of embodiment 285, or the pharmaceutical composition of embodiment 287 for use in the treatment of an inflammation related disease.

EXAMPLES

The following examples are included for illustrative purposes only and are not intended to limit the scope of the disclosure.

Example 1: Design of Anti-TSLP scFv Constructs

The antigen binding moieties are designed to bind TSLP and IL-4R such as a bispecific antibody comprising an anti-IL-4R moiety or an antigen binding portion thereof and anti-TSLP moiety or an antigen binding portion thereof (e.g., anti-TSLP scFv) (FIG. 1-FIG. 3). The antigen binding moiety comprises 1 anti-TSLP scFv (e.g., FIG. 2A and FIG. 2B). In some cases, the antigen binding moiety comprises 2 or more anti-TSLP scFvs (e.g., FIG. 1A and FIG. 1B).

Candidate 1 (FIG. 1A) may comprise:

```
Candidate 1 Heavy Chain
                                        (SEQ ID NO: 62)
EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL
```

-continued

```
GGGGGSGGGGSGGGGSGGGGSQMQLVESGGGVVQPGRSLRLSCAA

SGFTFRTYGMHWVRQAPGKGLEWVAVIWYDGSNKHYADSVKGRFT

ITRDNSKNTLNLQMNSLRAEDTAVYYCARAPQWELVHEAFDIWGQ

GTMVTVSSAGGGGSGGGGSGGGGSGGGGSSYVLTQPPSVSVAPGQ

TARITCGGNNLGSKSVHWYQQKPGQAPVLVVYDDSDRPSWIPERF

SGSNSGNTATLTISRGEAGDEADYYCQVWDSSSDHVVFGGGTKLT

VL

Candidate 1 Light Chain
                                        (SEQ ID NO: 63)
DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC
```

Candidate 2 (FIG. 1B) may comprise:

```
Candidate 2 Heavy Chain
                                        (SEQ ID NO: 64)
EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

GGGGGSGGGGSGGGGSGGGGSSYVLTQPPSVSVAPGQTARITCGG

NNLGSKSVHWYQQKPGQAPVLVVYDDSDRPSWIPERFSGSNSGNT

ATLTISRGEAGDEADYYCQVWDSSSDHVVFGGGTKLTVLGGGGSG

GGGSGGGGSGGGGSQMQLVESGGGVVQPGRSLRLSCAASGFTFRT

YGMHWVRQAPGKGLEWVAVIWYDGSNKHYADSVKGRFTITRDNSK

NTLNLQMNSLRAEDTAVYYCARAPQWELVHEAFDIWGQGTMVTVS

SA

Candidate 2 Light Chain
                                        (SEQ ID NO: 65)
DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC
```

Candidate 3 (FIG. 1C) may comprise:

```
Candidate 3 Heavy Chain
                                          (SEQ ID NO: 66)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSRLTVDKSRWQEGNVFSCSVMHEALHNHYTQKSLSLSL
G
```

```
Candidate 3 Light Chain
                                          (SEQ ID NO: 67)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGECGGGGSG
GGGSGGGGSGGGGSQMQLVESGGGVVQPGRSLRLSCAASGFTFRT
YGMHWVRQAPGKGLEWVAVIWYDGSNKHYADSVKGRFTITRDNSK
NTLNLQMNSLRAEDTAVYYCARAPQWELVHEAFDIWGQGTMVTVS
SAGGGGSGGGGSGGGGSGGGGSSYVLTQPPSVSVAPGQTARITCG
GNNLGSKSVHWYQQKPGQAPVLVVYDDSDRPSWIPERFSGSNSGN
TATLTISRGEAGDEADYYCQVWDSSSDHVVFGGGTKLTVL
```

Candidate 4 (FIG. 1D) may comprise:

```
Candidate 4 Heavy Chain
                                          (SEQ ID NO: 68)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSRLTVDKSRWQEGNVFSCSVMHEALHNHYTQKSLSLSL
G
```

-continued

```
Candidate 4 Light Chain
                                          (SEQ ID NO: 69)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGECGGGGSG
GGGSGGGGSGGGGSSYVLTQPPSVSVAPGQTARITCGGNNLGSKS
VHWYQQKPGQAPVLVVYDDSDRPSWIPERFSGSNSGNTATLTISR
GEAGDEADYYCQVWDSSSDHVVFGGGTKLTVLGGGGSGGGGSGGG
GSGGGGSQMQLVESGGGVVQPGRSLRLSCAASGFTFRTYGMHWVR
QAPGKGLEWVAVIWYDGSNKHYADSVKGRFTITRDNSKNTLNLQM
NSLRAEDTAVYYCARAPQWELVHEAFDIWGQGTMVTVSSA
```

Candidate 5 (FIG. 2A) may comprise an anti-TSLP scFv replacing one of IgG Fab of the anti-IL-4R:

```
Candidate 5 Light Chain
                                          (SEQ ID NO: 70)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC
```

```
Candidate 5 Heavy Chain 2 (Hole)
                                          (SEQ ID NO: 71)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLWCLVKGFYPSDIAVEWESNGQPENNYKTTPPVLDS
DGSFFLYSRLTVDKSRWQEGNVFSCSVMHEALHNHYTQKSLSLSL
G
```

```
Candidate 5 Heavy Chain 1 (Knob)
                                          (SEQ ID NO: 72)
SYVLTQPPSVSVAPGQTARITCGGNNLGSKSVHWYQQKPGQAPVL
VVYDDSDRPSWIPERFSGSNSGNTATLTISRGEAGDEADYYCQVW
DSSSDHVVFGGGTKLTVLGGGGSGGGGSGGGGSGGGGSQMQLVES
GGGVVQPGRSLRLSCAASGFTFRTYGMHWVRQAPGKGLEWVAVIW
YDGSNKHYADSVKGRFTITRDNSKNTLNLQMNSLRAEDTAVYYCA
RAPQWELVHEAFDIWGQGTMVTVSSAGGGGSGGGGSGGGGSGGGG
SEVQLVESGGGLEQPGGSLRLSCAGSGFTFRDYAMTWVRQAPGKG
```

-continued

LEWVSSISGSGGNTYYADSVKGRFTISRDNSKNTLYLQMNSLRAE
DTAVYYCAKDRLSITIRPRYYGLDVWGQGTTVTVSSASTKGPSVF
PLAPCSRSTSESTAALGCLVKDYFPEPVTVSWNSGALTSGVHTFP
AVLQSSGLYSLSSVVTVPSSSLGTKTYTCNVDHKPSNTKVDKRVE
SKYGPPCPPCPAPEFLGGPSVFLFPPKPKDTLYITREPEVTCVVV
DVSQEDPEVQFNWYVDGVEVHNAKTKPREEQFNSTYRVVSVLTVL
HQDWLNGKEYKCKVSNKGLPSSIEKTISKAKGQPREPQVYTLPPS
QEEMTKNQVSLSCAVKGFYPSDIAVEWESNGQPENNYKTTPPVLD
SDGSFFLVSRLTVDKSRWQEGNVFSCSVMHEALHNHYTQKSLSLS
LG

Candidate 6 (FIG. 2B) may comprise an anti-TSLP scFv replacing one of IgG Fab of the anti-IL-4R, Candidate 6 further comprises a KiH mutation and may comprise:

Candidate 6 Light Chain
(SEQ ID NO: 73)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC Candidate 6 Heavy Chain 1 (Knob)
(SEQ ID NO: 74)
QMQLVESGGGVVQPGRSLRLSCAASGFTFRTYGMHWVRQAPGKGL
EWVAVIWYDGSNKHYADSVKGRFTITRDNSKNTLNLQMNSLRAED
TAVYYCARAPQWELVHEAFDIWGQGTMVTVSSAGGGGSGGGGSGG
GGSGGGGSSYVLTQPPSVSVAPGQTARITCGGNNLGSKSVHWYQQ
KPGQAPVLVVYDDSDRPSWIPERFSGSNSGNTATLTISRGEAGDE
ADYYCQVWDSSSDHVVFGGGTKLTVLGGGGSGGGGSGGGGSGGGG
SEVQLVESGGGLEQPGGSLRLSCAGSGFTFRDYAMTWVRQAPGKG
LEWVSSISGSGGNTYYADSVKGRFTISRDNSKNTLYLQMNSLRAE
DTAVYYCAKDRLSITIRPRYYGLDVWGQGTTVTVSSASTKGPSVF
PLAPCSRSTSESTAALGCLVKDYFPEPVTVSWNSGALTSGVHTFP
AVLQSSGLYSLSSVVTVPSSSLGTKTYTCNVDHKPSNTKVDKRVE
SKYGPPCPPCPAPEFLGGPSVFLFPPKPKDTLYITREPEVTCVVV
DVSQEDPEVQFNWYVDGVEVHNAKTKPREEQFNSTYRVVSVLTVL
HQDWLNGKEYKCKVSNKGLPSSIEKTISKAKGQPREPQVYTLPPS
QEEMTKNQVSLSCAVKGFYPSDIAVEWESNGQPENNYKTTPPVLD
SDGSFFLVSRLTVDKSRWQEGNVFSCSVMHEALHNHYTQKSLSLS
LG Candidate 6 Heavy Chain 2 (Hole)
(SEQ ID NO: 75)
EVQLVESGGGLEQPGGSLRLSCAGSGFTFRDYAMTWVRQAPGKGL
EWVSSISGSGGNTYYADSVKGRFTISRDNSKNTLYLQMNSLRAED -continued TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLWCLVKGFYPSDIAVEWESNGQPENNYKTTPPVLDS
DGSFFLYSRLTVDKSRWQEGNVFSCSVMHEALHNHYTQKSLSLSL
G Candidate 7 (FIG. 3A) may comprise:

Candidate 7 Heavy Chain
(SEQ ID NO: 76)
QMQLVESGGGVVQPGRSLRLSCAASGFTFRTYGMHWVRQAPGKGL
EWVAVIWYDGSNKHYADSVKGRFTITRDNSKNTLNLQMNSLRAED
TAVYYCARAPQWELVHEAFDIWGQGTMVTVSSAGGGGSGGGGSGG
GGSGGGGSSYVLTQPPSVSVAPGQTARITCGGNNLGSKSVHWYQQ
KPGQAPVLVVYDDSDRPSWIPERFSGSNSGNTATLTISRGEAGDE
ADYYCQVWDSSSDHVVFGGGTKLTVLGGGGSGGGGSGGGGSGGGG
SEVQLVESGGGLEQPGGSLRLSCAGSGFTFRDYAMTWVRQAPGKG
LEWVSSISGSGGNTYYADSVKGRFTISRDNSKNTLYLQMNSLRAE
DTAVYYCAKDRLSITIRPRYYGLDVWGQGTTVTVSSASTKGPSVF
PLAPCSRSTSESTAALGCLVKDYFPEPVTVSWNSGALTSGVHTFP
AVLQSSGLYSLSSVVTVPSSSLGTKTYTCNVDHKPSNTKVDKRVE
SKYGPPCPPCPAPEFLGGPSVFLFPPKPKDTLYITREPEVTCVVV
DVSQEDPEVQFNWYVDGVEVHNAKTKPREEQFNSTYRVVSVLTVL
HQDWLNGKEYKCKVSNKGLPSSIEKTISKAKGQPREPQVYTLPPS
QEEMTKNQVSLTCLVKGFYPSDIAVEWESNGQPENNYKTTPPVLD
SDGSFFLYSRLTVDKSRWQEGNVFSCSVMHEALHNHYTQKSLSLS
LG Candidate 7 Light Chain
(SEQ ID NO: 77)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC Candidate 8 (FIG. 3B) may comprise:

Candidate 8 Heavy Chain
(SEQ ID NO: 78)
SYVLTQPPSVSVAPGQTARITCGGNNLGSKSVHWYQQKPGQAPVL
VVYDDSDRPSWIPERFSGSNSGNTATLTISRGEAGDEADYYCQVW
DSSSDHVVFGGGTKLTVLGGGGSGGGGSGGGGSGGGGSQMQLVES -continued

GGGVVQPGRSLRLSCAASGFTFRTYGMHWVRQAPGKGLEWVAVIW

YDGSNKHYADSVKGRFTITRDNSKNTLNLQMNSLRAEDTAVYYCA

RAPQWELVHEAFDIWGQGTMVTVSSAGGGGSGGGGSGGGGSGGGG

SEVQLVESGGGLEQPGGSLRLSCAGSGFTFRDYAMTWVRQAPGKG

LEWVSSISGSGGNTYYADSVKGRFTISRDNSKNTLYLQMNSLRAE

DTAVYYCAKDRLSITIRPRYYGLDVWGQGTTVTVSSASTKGPSVF

PLAPCSRSTSESTAALGCLVKDYFPEPVTVSWNSGALTSGVHTFP

AVLQSSGLYSLSSVVTVPSSSLGTKTYTCNVDHKPSNTKVDKRVE

SKYGPPCPPCPAPEFLGGPSVFLFPPKPKDTLYITREPEVTCVVV

DVSQEDPEVQFNWYVDGVEVHNAKTKPREEQFNSTYRVVSVLTVL

HQDWLNGKEYKCKVSNKGLPSSIEKTISKAKGQPREPQVYTLPPS

QEEMTKNQVSLTCLVKGFYPSDIAVEWESNGQPENNYKTTPPVLD

SDGSFFLYSRLTVDKSRWQEGNVFSCSVMHEALHNHYTQKSLSLS

LG

Candidate 8 Light Chain (SEQ ID NO: 79)

DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC

Candidate 9 (FIG. 3C) may comprise:

Candidate 9 Heavy Chain (SEQ ID NO: 80)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

G

Candidate 9 Light Chain (SEQ ID NO: 81)

QMQLVESGGGVVQPGRSLRLSCAASGFTFRTYGMHWVRQAPGKGL

EWVAVIWYDGSNKHYADSVKGRFTITRDNSKNTLNLQMNSLRAED

TAVYYCARAPQWELVHEAFDIWGQGTMVTVSSAGGGGSGGGGSGG

GGSGGGGSSYVLTQPPSVSVAPGQTARITCGGNNLGSKSVHWYQQ

KPGQAPVLVVYDDSDRPSWIPERFSGSNSGNTATLTISRGEAGDE

ADYYCQVWDSSSDHVVFGGGTKLTVLGGGGSGGGGSGGGGSGGGG

-continued

SDIVMTQSPLSLPVTPGEPASISCRSSQSLLYSIGYNYLDWYLQK

SGQSPQLLIYLGSNRASGVPDRFSGSGSGTDFTLKISRVEAEDVG

FYYCMQALQTPYTFGQGTKLEIKRTVAAPSVFIFPPSDEQLKSGT

ASVVCLLNNFYPREAKVQWKVDNALQSGNSQESVTEQDSKDSTYS

LSSTLTLSKADYEKHKVYACEVTHQGLSSPVTKSFNRGEC

Candidate 10 (FIG. 3D) may comprise:

Candidate 10 Heavy Chain (SEQ ID NO: 82)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

G

Candidate 10 Light Chain (SEQ ID NO: 83)

SYVLTQPPSVSVAPGQTARITCGGNNLGSKSVHWYQQKPGQAPVL

VVYDDSDRPSWIPERFSGSNSGNTATLTISRGEAGDEADYYCQVW

DSSSDHVVFGGGTKLTVLGGGGSGGGGSGGGGSGGGGSQMQLVES

GGGVVQPGRSLRLSCAASGFTFRTYGMHWVRQAPGKGLEWVAVIW

YDGSNKHYADSVKGRFTITRDNSKNTLNLQMNSLRAEDTAVYYCA

RAPQWELVHEAFDIWGQGTMVTVSSAGGGGSGGGGSGGGGSGGGG

SDIVMTQSPLSLPVTPGEPASISCRSSQSLLYSIGYNYLDWYLQK

SGQSPQLLIYLGSNRASGVPDRFSGSGSGTDFTLKISRVEAEDVG

FYYCMQALQTPYTFGQGTKLEIKRTVAAPSVFIFPPSDEQLKSGT

ASVVCLLNNFYPREAKVQWKVDNALQSGNSQESVTEQDSKDSTYS

LSSTLTLSKADYEKHKVYACEVTHQGLSSPVTKSFNRGEC

Example 2: Design of Anti-TSLP Fab Constructs

The antigen binding complexes are designed to bind TSLP and IL-4R such as with bispecific anti-IL-4R-anti-TSLP Fab complexes (e.g., FIG. 4A) or the bispecific anti-TSLP-anti-IL-4R Fab complex (e.g., FIG. 4B).

Candidate 11 (FIG. 4A) may comprise:

Candidate 11 Heavy Chain (SEQ ID NO: 84)

QMQLVESGGGVVQPGRSLRLSCAASGFTFRTYGMHWVRQAPGKGLE

WVAVIWYDGSNKHYADSVKGRFTITRDNSKNTLNLQMNSLRAEDTA

-continued

VYYCARAPQWELVHEAFDIWGQGTMVTVSS*ASTKGPSVFPLAP*EVQ
LVESGGGLEQPGGSLRLSCAGSGFTFRDYAMTWVRQAPGKGLEWVS
SISGSGGNTYYADSVKGRFTISRDNSKNTLYLQMNSLRAEDTAVYY
CAKDRLSITIRPRYYGLDVWGQGTTVTVSSASTKGPSVFPLAPCSR
STSESTAALGCLVKDYFPEPVTVSWNSGALTSGVHTFPAVLQSSGL
YSLSSVVTVPSSSLGTKTYTCNVDHKPSNTKVDKRVESKYGPPCPP
CPAPEFLGGPSVFLFPPKPKDTLYITREPEVTCVVVDVSQEDPEVQ
FNWYVDGVEVHNAKTKPREEQFNSTYRVVSLVTVLHQDWLNGKEYK
CKVSNKGLPSSIEKTISKAKGQPREPQVYTLPPSQEEMTKNQVSLT
CLVKGFYPSDIAVEWESNGQPENNYKTTPPVLDSDGSFFLYSRLTV
DKSRWQEGNVFSCSVMHEALHNHYTQKSLSLSLG

Candidate 11 Light Chain
(SEQ ID NO: 85)
SYVLTQPPSVSVAPGQTARITCGGNNLGSKSVHWYQQKPGQAPVLV
VYDDSDRPSWIPERFSGSNSGNTATLTISRGEAGDEADYYCQVWDS
SSDHVVFGGGTKLTVLG*TVAAPSVFIFPP*DIVMTQSPLSLPVTPGE
PASISCRSSQSLLYSIGYNYLDWYLQKSGQSPQLLIYLGSNRASGV
PDRFSGSGSGTDFTLKISRVEAEDVGFYYCMQALQTPYTFGQGTKL
EIKR*TVAAPSVFIFPP*SDEQLKSGTASVVCLLNNFYPREAKVQWKV
DNALQSGNSQESVTEQDSKDSTYSLSSTLTLSKADYEKHKVYACEV
THQGLSSPVTKSFNRGEC The heavy chain (SEQ ID NO: 84) comprises Tezepelumab heavy chain variable region (VH) (bolded)-linker (italicized)-Dupilumab VH (underlined) and Dupilumab Constant (YTE) (highlighted).

The light chain (SEQ ID NO: 85) comprises Tezepelumab light chain variable region (VL) (bolded)-linker (italicized)-Dupilumab VL (underlined)-linker (italicized) and Dupilumab light chain constant region (kappa) (highlighted).

Candidate 12 (FIG. 4B) may comprise (1) a first polypeptide and a second polypeptide, each comprising a light chain variable region of an anti-IL-4R, an optional linker, a light chain variable region of an anti-TSLP, an optional linker, a light chain constant region of an anti-IL-4R, and (2) a third polypeptide and a fourth polypeptide, each comprising a heavy chain variable region of an anti-IL-4R, an optional linker, a heavy chain variable region of an anti-TSLP, and a heavy chain constant region of an anti-IL-4R; or Candidate 12 Heavy Chain
(SEQ ID NO: 86):
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP -continued LAPQMQLVESGGGVVQPGRSLRLSCAASGFTFRTYGMHWVRQAPG
KGLEWVAVIWYDGSNKHYADSVKGRFTITRDNSKNTLNLQMNSLR
AEDTAVYYCARAPQWELVHEAFDIWGQGTMVTVSSASTKGPSVFP
LAPCSRSTSESTAALGCLVKDYFPEPVTVSWNSGALTSGVHTFPA
VLQSSGLYSLSSVVTVPSSNFGTQTYTCNVDHKPSNTKVDKTVER
KCCVECPPCPAPPVAGPSVFLFPPKPKDTLYITREPEVTCVVVDV
SHEDPEVQFNWYVDGVEVHNAKTKPREEQFNSTFRVVSVLTVVHQ
DWLNGKEYKCKVSNKGLPAPIEKTISKTKGQPREPQVYTLPPSRE
EMTKNQVSLTCLVKGFYPSDIAVEWESNGQPENNYKTTPPMLDSD
GSFFLYSKLTVDKSRWQQGNVFSCSVMHEALHNHYTQKSLSLSPG
K Candidate 12 Light Chain
(SEQ ID NO: 87)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSYVLTQPPSV
SVAPGQTARITCGGNNLGSKSVHWYQQKPGQAPVLVVYDDSDRPS
WIPERFSGSNSGNTATLTISRGEAGDEADYYCQVWDSSSDHVVFG
GGTKLTVLGQPKAAPSVTLFPPSSEELQANKATLVCLISDFYPGA
VTVAWKADSSPVKAGVETTTPSKQSNNKYAASSYLSLTPEQWKSH
RSYSCQVTHEGSTVEKTVAPTECS Candidate 13 (FIG. 4C) may comprise:

Candidate 13 Heavy Chain
(SEQ ID NO: 88):
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPQMQLVESGGGVVQPGRSLRLSCAASGFTFRTYGMHWVRQAPG
KGLEWVAVIWYDGSNKHYADSVKGRFTITRDNSKNTLNLQMNSLR
AEDTAVYYCARAPQWELVHEAFDIWGQGTMVTVSSASTKGPSVFP
LAPCSRSTSESTAALGCLVKDYFPEPVTVSWNSGALTSGVHTFPA
VLQSSGLYSLSSVVTVPSSNFGTQTYTCNVDHKPSNTKVDKTVES
KYGPPCPSCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSRLTVDKSRWQEGNVFSCSVMHEALHNHYTQKSLSLSL
G Candidate 13 Light Chain
(SEQ ID NO: 89):
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSYVLTQPPSV -continued

```
SVAPGQTARITCGGNNLGSKSVHWYQQKPGQAPVLVVYDDSDRPS

WIPERFSGSNSGNTATLTISRGEAGDEADYYCQVWDSSSDHVVFG

GGTKLTVLGTVAAPSVFIFPPGQPKAAPSVTLFPPSSEELQANKA

TLVCLISDFYPGAVTVAWKADSSPVKAGVETTTPSKQSNNKYAAS

SYLSLTPEQWKSHRSYSCQVTHEGSTVEKTVAPTECS
```

Candidate 14 (FIG. 4D) may comprise:

```
Candidate 14 Heavy Chain
(SEQ ID NO: 90):
QMQLVESGGGVVQPGRSLRLSCAASGFTFRTYGMHWVRQAPGKGL

EWVAVIWYDGSNKHYADSVKGRFTITRDNSKNTLNLQMNSLRAED

TAVYYCARAPQWELVHEAFDIWGQGTMVTVSSASTKGPSVFPLAP

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVER

KCCVECPPCPAPPVAGPSVFLFPPKPKDTLYITREPEVTCVVVDV

SHEDPEVQFNWYVDGVEVHNAKTKPREEQFNSTFRVVSVLTVVHQ

DWLNGKEYKCKVSNKGLPAPIEKTISKTKGQPREPQVYTLPPSRE

EMTKNQVSLTCLVKGFYPSDIAVEWESNGQPENNYKTTPPMLDSD

GSFFLYSKLTVDKSRWQQGNVFSCSVMHEALHNHYTQKSLSLSPG

K

Candidate 14 Light Chain
(SEQ ID NO: 91):
SYVLTQPPSVSVAPGQTARITCGGNNLGSKSVHWYQQKPGQAPVLV

VYDDSDRPSWIPERFSGSNSGNTATLTISRGEAGDEADYYCQVWD

SSSDHVVFGGGTKLTVLGTVAAPSVFIFPPDIVMTQSPLSLPVTP

GEPASISCRSSQSLLYSIGYNYLDWYLQKSGQSPQLLIYLGSNRA

SGVPDRFSGSGSGTDFTLKISRVEAEDVGFYYCMQALQTPYTFGQ

GTKLEIKRTVAAPSVFIFPPSDEQLKSGTASVVCLLNNFYPREAK

VQWKVDNALQSGNSQESVTEQDSKDSTYSLSSTLTLSKADYEKHK

VYACEVTHQGLSSPVTKSFNRGEC
```

Candidate 15 (FIG. 4E) may comprise:

```
Candidate 15 Heavy Chain
(SEQ ID NO: 92)
EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPQMQLVESGGGVVQPGRSLRLSCAASGFTFRTYGMHWVRQAPG

KGLEWVAVIWYDGSNKHYADSVKGRFTITRDNSKNTLNLQMNSLR

AEDTAVYYCARAPQWELVHEAFDIWGQGTMVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

G

Candidate 15 Light Chain
(SEQ ID NO: 93)
DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSYVLTQPPSV

SVAPGQTARITCGGNNLGSKSVHWYQQKPGQAPVLVVYDDSDRPS

WIPERFSGSNSGNTATLTISRGEAGDEADYYCQVWDSSSDHVVFG

GGTKLTVLGTVAAPSVFIFPPSDEQLKSGTASVVCLLNNFYPREA

KVQWKVDNALQSGNSQESVTEQDSKDSTYSLSSTLTLSKADYEKH

KVYACEVTHQGLSSPVTKSFNRGEC
```

Candidate 16 (FIG. 4F) may comprise:

```
Candidate 16 Heavy Chain
(SEQ ID NO: 94):
QMQLVESGGGVVQPGRSLRLSCAASGFTFRTYGMHWVRQAPGKGL

EWVAVIWYDGSNKHYADSVKGRFTITRDNSKNTLNLQMNSLRAED

TAVYYCARAPQWELVHEAFDIWGQGTMVTVSSASTKGPSVFPLAP

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSNFGTQTYTCNVDHKPSNTKVDKTVER

KCCVECPPCPAPPVAGPSVFLFPPKPKDTLYITREPEVTCVVVDV

SHEDPEVQFNWYVDGVEVHNAKTKPREEQFNSTFRVVSVLTVVHQ

DWLNGKEYKCKVSNKGLPAPIEKTISKTKGQPREPQVYTLPPSRE

EMTKNQVSLTCLVKGFYPSDIAVEWESNGQPENNYKTTPPMLDSD

GSFFLYSKLTVDKSRWQQGNVFSCSVMHEALHNHYTQKSLSLSPG

K

Candidate 16 Light Chain
(SEQ ID NO: 95):
SYVLTQPPSVSVAPGQTARITCGGNNLGSKSVHWYQQKPGQAPVL

VVYDDSDRPSWIPERFSGSNSGNTATLTISRGEAGDEADYYCQVW

DSSSDHVVFGGGTKLTVLTVAAPSVFIFPPDIVMTQSPLSLPVTP

GEPASISCRSSQSLLYSIGYNYLDWYLQKSGQSPQLLIYLGSNRA

SGVPDRFSGSGSGTDFTLKISRVEAEDVGFYYCMQALQTPYTFGQ

GTKLEIKRTVAAPSVFIFPPGQPKAAPSVTLFPPSSEELQANKAT
```

-continued

LVCLISDFYPGAVTVAWKADSSPVKAGVETTTPSKQSNNKYAASS

YLSLTPEQWKSHRSYSCQVTHEGSTVEKTVAPTECS

Candidate 17 (FIG. 5A) may comprise a KiH mutation and may comprise:

Candidate 17 Heavy Chain 1 (Hole)
(SEQ ID NO: 186)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLWCLVKGFYPSDIAVEWESNGQPENNYKTTPPVLDS
DGSFFLYSRLTVDKSRWQEGNVFSCSVMHEALHNHYTQKSLSLSL
G Candidate 17 Heavy Chain 2 (Knob)
(SEQ ID NO: 96)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLSCAVKGFYPSDIAVEWESNGQPENNYKTTPPVLDS
DGSFFLVSRLTVDKSRWQEGNVFSCSVMHEALHNHYTQKSLSLSL
GGGGGSGGGGSGGGGSGGGGSQMQLVESGGGVVQPGRSLRLSCAA
SGFTFRTYGMHWVRQAPGKGLEWVAVIWYDGSNKHYADSVKGRFT
ITRDNSKNTLNLQMNSLRAEDTAVYYCARAPQWELVHEAFDIWGQ
GTMVTVSSAGQPKAAPSVTLFPPSSEELQANKATLVCLISDFYPG
AVTVAWKADSSPVKAGVETTTPSKQSNNKYAASSYLSLTPEQWKS
HRSYSCQVTHEGSTVEKTVAPTECS Candidate 17 Light Chain (anti-IL-4R)
(SEQ ID NO: 97)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC -continued Candidate 17 anti-TSLP Fab (Partial)
(SEQ ID NO: 98)
SYVLTQPPSVSVAPGQTARITCGGNNLGSKSVHWYQQKPGQAPVL
VVYDDSDRPSWIPERFSGSNSGNTATLTISRGEAGDEADYYCQVW
DSSSDHVVFGGGTKLTVLSSASTKGPSVFPLAPCSRSTSESTAAL
GCLVKDYFPEPVTVSWNSGALTSGVHTFPAVLQSSGLYSLSSVVT
VPSSNFGTQTYTCNVDHKPSNTKVDKTV Candidate 18 (FIG. 5B) Candidate 18 comprises a KiH mutation and may comprise:

Candidate 18 - peptide 1
(SEQ ID NO: 99):
QMQLVESGGGVVQPGRSLRLSCAASGFTFRTYGMHWVRQAPGKGL
EWVAVIWYDGSNKHYADSVKGRFTITRDNSKNTLNLQMNSLRAED
TAVYYCARAPQWELVHEAFDIWGQGTMVTVSSASTKGPSVFPLAP
CSRSTSESTAALGCLVKDYFPEPVTVSWNSGALTSGVHTFPAVLQ
SSGLYSLSSVVTVPSSNFGTQTYTCNVDHKPSNTKVDKTVERKCC
VECPPCPAPPVAGPSVFLFPPKPKDTLYITREPEVTCVVVDVSHE
DPEVQFNWYVDGVEVHNAKTKPREEQFNSTFRVVSVLTVVHQDWL
NGKEYKCKVSNKGLPAPIEKTISKTKGQPREPQVYTLPPSREEMT
KNQVSLWCLVKGFYPSDIAVEWESNGQPENNYKTTPPMLDSDGSF
FLYSKLTVDKSRWQQGNVFSCSVMHEALHNHYTQKSLSLSPGK Candidate 18 - peptide 2
(SEQ ID NO: 100):
QMQLVESGGGVVQPGRSLRLSCAASGFTFRTYGMHWVRQAPGKGL
EWVAVIWYDGSNKHYADSVKGRFTITRDNSKNTLNLQMNSLRAED
TAVYYCARAPQWELVHEAFDIWGQGTMVTVSSASTKGPSVFPLAP
CSRSTSESTAALGCLVKDYFPEPVTVSWNSGALTSGVHTFPAVLQ
SSGLYSLSSVVTVPSSNFGTQTYTCNVDHKPSNTKVDKTVERKCC
VECPPCPAPPVAGPSVFLFPPKPKDTLYITREPEVTCVVVDVSHE
DPEVQFNWYVDGVEVHNAKTKPREEQFNSTFRVVSVLTVVHQDWL
NGKEYKCKVSNKGLPAPIEKTISKTKGQPREPQVYTLPPSREEMT
KNQVSLSCAVKGFYPSDIAVEWESNGQPENNYKTTPPMLDSDGSF
FLVSKLTVDKSRWQQGNVFSCSVMHEALHNHYTQKSLSLSPGKGG
GGSGGGGSGGGGSGGGGSEVQLVESGGGLEQPGGSLRLSCAGSGF
TFRDYAMTWVRQAPGKGLEWVSSISGSGGNTYYADSVKGRFTISR
DNSKNTLYLQMNSLRAEDTAVYYCAKDRLSITIRPRYYGLDVWGQ
GTTVTVSSTVAAPSVFIFPPSDEQLKSGTASVVCLLNNFYPREAK
VQWKVDNALQSGNSQESVTEQDSKDSTYSLSSTLTLSKADYEKHK
VYACEVTHQGLSSPVTKSFNRGEC Candidate 18 - peptide 3
(SEQ ID NO: 101):
SYVLTQPPSVSVAPGQTARITCGGNNLGSKSVHWYQQKPGQAPVL
VVYDDSDRPSWIPERFSGSNSGNTATLTISRGEAGDEADYYCQVW
DSSSDHVVFGGGTKLTVLGQPKAAPSVTLFPPSSEELQANKATLV -continued

CLISDFYPGAVTVAWKADSSPVKAGVETTTPSKQSNNKYAASSYL

SLTPEQWKSHRSYSCQVTHEGSTVEKTVAPTECS

Candidate 18 - peptide 4
(SEQ ID NO: 102):
DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRASTKGPSVFPLAPCSRSTSEST

AALGCLVKDYFPEPVTVSWNSGALTSGVHTFPAVLQSSGLYSLSS

VVTVPSSSLGTKTYTCNVDHKPSNTKVDKRV

Candidate 19 (FIG. 5C, FIG. 36A or FIG. 40) may comprise with linker bold:

Candidate 19 - anti-IL-4R Light Chain
(SEQ ID NO: 103)
DIVMTQSPLSLPVTPGEPASISCRSSQSLLYSIGYNYLDWYLQKSG

QSPQLLIYLGSNRASGVPDRFSGSGSGTDFTLKISRVEAEDVGFYY

CMQALQTPYTFGQGTKLEIKR*TVAAPSVFIFPP*SDEQLKSGTASVV

CLLNNFYPREAKVQWKVDNALQSGNSQESVTEQDSKDSTYSLSSTL

TLSKADYEKHKVYACEVTHQGLSSPVTKSFNRGEC

Candidate 19 - Heavy Chain
(SEQ ID NO: 104)
EVQLVESGGGLEQPGGSLRLSCAGSGFTFRDYAMTWVRQAPGKGLE

WVSSISGSGGNTYYADSVKGRFTISRDNSKNTLYLQMNSLRAEDTA

VYYCAKDRLSITIRPRYYGLDVWGQGTTVTVSSASTKGPSVFPLAP

CSRSTSESTAALGCLVKDYFPEPVTVSWNSGALTSGVHTFPAVLQS

SGLYSLSSVVTVPSSSLGTKTYTCNVDHKPSNTKVDKRVESKYGPP

CPPCPAPEFLGGPSVFLFPPKPKDTLYITREPEVTCVVVDVSQEDP

EVQFNWYVDGVEVHNAKTKPREEQFNSTYRVVSVLTVLHQDWLNGK

EYKCKVSNKGLPSSIEKTISKAKGQPREPQVYTLPPSQEEMTKNQV

SLTCLVKGFYPSDIAVEWESNGQPENNYKTTPPVLDSDGSFFLYSR

LTVDKSRWQEGNVFSCSVMHEALHNHYTQKSLSLSLG*GGGGSGGGG*

*SGGGGSGGGGS*SYVLTQPPSVSVAPGQTARITCGGNNLGSKSVHWY

QQKPGQAPVLVVYDDSDRPSWIPERFSGSNSGNTATLTISRGEAGD

EADYYCQVWDSSSDHVVFGGGTKLTVLGQPKAAPSVTLFPPSSEEL

QANKATLVCLISDFYPGAVTVAWKADSSPVKAGVETTTPSKQSNNK

YAASSYLSLTPEQWKSHRSYSCQVTHEGSTVEKTVAPTECS

Candidate 19 - Anti-TSLP Fab (Partial)
(SEQ ID NO: 105)
QMQLVESGGGVVQPGRSLRLSCAASGFTFRTYGMHWVRQAPGKGLE

WVAVIWYDGSNKHYADSVKGRFTITRDNSKNTLNLQMNSLRAEDTA

VYYCARAPQWELVHEAFDIWGQGTMVTVSS*ASTKGPSVFPLAP*CSR

-continued

STSESTAALGCLVKDYFPEPVTVSWNSGALTSGVHTFPAVLQSSGL

YSLSSVVTVPSSNFGTQTYTCNVDHKPSNTKVDKTV

The light chain (SEQ ID NO: 103) comprises Dupilumab light chain variable region (VL) (bolded)-linker (italicized)-Dupilumab light chain constant region (kappa) (highlighted).

The heavy chain (SEQ ID NO: 104) comprises Dupilumab heavy chain variable region (VH) (bolded)-Dupilumab constant region (CH1, CH2, and CH3) (underlined)-linker (italicized) and Tezepelumab light chain (highlighted).

The anti-TSLP Fab (Partial) (SEQ ID NO: 105) comprises Tezepelumab heavy chain variable region (VH) (bolded)-linker (italicized) and Tezepelumab heavy chain constant domain (CH1) (highlighted).

Candidate 19.1 (see, e.g., FIG. 5C, FIG. 36A or FIG. 40 for exemplary construct) may comprise with linker in italics:

Candidate 19.1 - anti-IL-4R Light Chain
(SEQ ID NO: 127)
METDTLLLWVLLLWVPGSTGDIVMTQSPLSLPVTPGEPASISCRSS

QSLLYSIGYNYLDWYLQKSGQSPQLLIYLGSNRASGVPDRFSGSGS

GTDFTLKISRVEAEDVGFYYCMQALQTPYTFGQGTKLEIKR*TVAAP*

*SVFIFPP*SDEQLKSGTASVVCLLNNFYPREAKVQWKVDNALQSGNS

QESVTEQDSKDSTYSLSSTLTLSKADYEKHKVYACEVTHQGLSSPV

TKSFNRGEC

Candidate 19.1 - Heavy Chain
(SEQ ID NO: 128)
MGWSCIILFLVATATGVHSEVQLVESGGGLEQPGGSLRLSCAGSGF

TFRDYAMTWVRQAPGKGLEWVSSISGSGGNTYYADSVKGRFTISRD

NSKNTLYLQMNSLRAEDTAVYYCAKDRLSITIRPRYYGLDVWGQGT

TVTVSSASTKGPSVFPLAPCSRSTSESTAALGCLVKDYFPEPVTVS

WNSGALTSGVHTFPAVLQSSGLYSLSSVVTVPSSSLGTKTYTCNVD

HKPSNTKVDKRVESKYGPPCPPCPAPEFLGGPSVFLFPPKPKDTLY

ITREPEVTCVVVDVSQEDPEVQFNWYVDGVEVHNAKTKPREEQFNS

TYRVVSVLTVLHQDWLNGKEYKCKVSNKGLPSSIEKTISKAKGQPR

EPQVYTLPPSQEEMTKNQVSLTCLVKGFYPSDIAVEWESNGQPENN

YKTTPPVLDSDGSFFLYSRLTVDKSRWQEGNVFSCSVMHEALHNHY

TQKSLSLSLG*GGGGSGGGGSGGGGSGGGGS*SYVLTQPPSVSVAPGQ

TARITCGGNNLGSKSVHWYQQKPGQAPVLVVYDDSDRPSWIPERF

SGSNSGNTATLTISRGEAGDEADYYCQVWDSSSDHVVFGGGTKLTV

LGQPKAAPSVTLFPPSSEELQANKATLVCLISDFYPGAVTVAWKAD

SSPVKAGVETTTPSKQSNNKYAASSYLSLTPEQWKSHRSYSCQVTH

EGSTVEKTVAPTECS

-continued

| Candidate 19.1 - Anti-TSLP Fab (Partial) (SEQ ID NO: 129) |
|---|
| **MGWSCIILFLVATATGVHSQMQLVESGGGVVQPGRSLRLSCAASGF** |
| **TFRTYGMHWVRQAPGKGLEWVAVIWYDGSNKHYADSVKGRFTITRD** |
| **NSKNTLNLQMNSLRAEDTAVYYCARAPQWELVHEAFDIWGQGTMVT** |
| **VSS***ASTKGPSVFPLAP*CSRSTSESTAALGCLVKDYFPEPVTVSWNS |
| GALTSGVHTFPAVLQSSGLYSLSSVVTVPSSNFGTQTYTCNVDHKP |
| SNTKVDKTV |

The light chain (SEQ ID NO: 127) comprises a signal peptide (bolded and underlined)-Dupilumab light chain variable region (VL) (bolded)-linker (italicized)-Dupilumab light chain constant region (kappa) ((highlighted)).

The heavy chain (SEQ ID NO: 128) comprises a signal peptide (bolded and underlined)-Dupilumab heavy chain variable region (VH) (bolded)-Dupilumab constant region (CH1, CH2, and CH3) (underlined)-linker (italicized) and Tezepelumab light chain (highlighted).

The anti-TSLP Fab (Partial) (SEQ ID NO: 129) comprises a signal peptide (bolded and underlined)-Tezepelumab heavy chain variable region (VH) (bolded)-optional linker (italicized) and Tezepelumab heavy chain constant domain (CH1) ((highlighted)).

In some cases, the antigen binding moiety described herein can be a variant of the Candidate 19.1. For example, in some cases, the Candidate 19.1 may have different Fc mutations (e.g., LS instead of YTE mutations). In some embodiments, the Candidate 19.1 may have Knob-Hole Fc regions. In some cases, the Candidate 19.1 may have different linkers. In some cases, the antigen binding moiety described herein can be any one of the variants set forth in Table 34.

TABLE 34

Nonlimiting example variants of the Candidate 19.1

| Binding Moiety | HC1 Sequence | HC2 Sequence | LC1 Sequence | LC2 Sequence |
|---|---|---|---|---|
| Candidate 19.1_with _LS_ instead_ of_ YTE | (SEQ ID NO: 189)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS<br>ASTKGPSVFPLA<br>PCSRSTSESTAA<br>LGCLVKDYFPEP<br>VTVSWNSGALTS<br>GVHTFPAVLQSS<br>GLYSLSSVVTVP<br>SSSLGTKTYTCN<br>VDHKPSNTKVDK<br>RVESKYGPPCPP<br>CPAPEFLGGPSV<br>FLFPPKPKDTLM<br>ISRTPEVTCVVV<br>DVSQEDPEVQFN<br>WYVDGVEVHNAK<br>TKPREEQFNSTY<br>RVVSVLTVLHQD<br>WLNGKEYKCKVS<br>NKGLPSSIEKTI<br>SKAKGQPREPQV<br>YTLPPSQEEMTK<br>NQVSLTCLVKGF<br>YPSDIAVEWESN<br>GQPENNYKTTPP<br>VLDSDGSFFLYS<br>RLTVDKSRWQEG<br>NVFSCSVLHEAL<br>HSHYTQKSLSLS<br>LGGGGGSGGGGS<br>GGGGSGGGGSSY<br>VLTQPPSVSVAP<br>GQTARITCGGNN<br>LGSKSVHWYQQK<br>PGQAPVLVVYDD<br>SDRPSWIPERFS<br>GSNSGNTATLTI<br>SRGEAGDEADYY | n/a | (SEQ ID NO: 190)<br>METDTLLLWVLL<br>LWVPGSTGDIVM<br>TQSPLSLPVTPG<br>EPASISCRSSQS<br>LLYSIGYNYLDW<br>YLQKSGQSPQLL<br>IYLGSNRASGVP<br>DRFSGSGSGTDF<br>TLKISRVEAEDV<br>GFYYCMQALQTP<br>YTFGQGTKLEIK<br>RTVAAPSVFIFP<br>PSDEQLKSGTAS<br>VVCLLNNFYPRE<br>AKVQWKVDNALQ<br>SGNSQESVTEQD<br>SKDSTYSLSSTL<br>TLSKADYEKHKV<br>YACEVTHQGLSS<br>PVTKSFNRGEC | (SEQ ID NO: 191)<br>MGWSCIILFLVA<br>TATGVHSQMQLV<br>ESGGGVVQPGRS<br>LRLSCAASGFTF<br>RTYGMHWVRQAP<br>GKGLEWVAVIWY<br>DGSNKHYADSVK<br>GRFTITRDNSKN<br>TLNLQMNSLRAE<br>DTAVYYCARAPQ<br>WELVHEAFDIWG<br>QGTMVTVSSAST<br>KGPSVFPLAPCS<br>RSTSESTAALGC<br>LVKDYFPEPVTV<br>SWNSGALTSGVH<br>TFPAVLQSSGLY<br>SLSSVVTVPSSN<br>FGTQTYTCNVDH<br>KPSNTKVDKTV |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| | CQVWDSSSDHVV<br>FGGGTKLTVLGQ<br>PKAAPSVTLFPP<br>SSEELQANKATL<br>VCLISDFYPGAV<br>TVAWKADSSPVK<br>AGVETTTPSKQS<br>NNKYAASSYLSL<br>TPEQWKSHRSYS<br>CQVTHEGSTVEK<br>TVAPTECS | | | |
| Candidate<br>19.1_with<br>out_<br>half-<br>life_<br>extension | (SEQ ID NO: 192)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS<br>ASTKGPSVFPLA<br>PCSRSTSESTAA<br>LGCLVKDYFPEP<br>VTVSWNSGALTS<br>GVHTFPAVLQSS<br>GLYSLSSVVTVP<br>SSSLGTKTYTCN<br>VDHKPSNTKVDK<br>RVESKYGPPCPP<br>CPAPEFLGGPSV<br>FLFPPKPKDTLM<br>ISRTPEVTCVVV<br>DVSQEDPEVQFN<br>WYVDGVEVHNAK<br>TKPREEQFNSTY<br>RVVSVLTVLHQD<br>WLNGKEYKCKVS<br>NKGLPSSIEKTI<br>SKAKGQPREPQV<br>YTLPPSQEEMTK<br>NQVSLTCLVKGF<br>YPSDIAVEWESN<br>GQPENNYKTTPP<br>VLDSDGSFFLYS<br>RLTVDKSRWQEG<br>NVFSCSVMHEAL<br>HNHYTQKSLSLS<br>LGGGGGSGGGGS<br>GGGGSGGGGSSY<br>VLTQPPSVSVAP<br>GQTARITCGGNN<br>LGSKSVHWYQQK<br>PGQAPVLVVYDD<br>SDRPSWIPERFS<br>GSNSGNTATLTI<br>SRGEAGDEADYY<br>CQVWDSSSDHVV<br>FGGGTKLTVLGQ<br>PKAAPSVTLFPP<br>SSEELQANKATL<br>VCLISDFYPGAV<br>TVAWKADSSPVK<br>AGVETTTPSKQS<br>NNKYAASSYLSL<br>TPEQWKSHRSYS<br>CQVTHEGSTVEK<br>TVAPTECS | n/a | (SEQ ID NO: 193)<br>METDTLLLWVLL<br>LWVPGSTGDIVM<br>TQSPLSLPVTPG<br>EPASISCRSSQS<br>LLYSIGYNYLDW<br>YLQKSGQSPQLL<br>IYLGSNRASGVP<br>DRFSGSGSGTDF<br>TLKISRVEAEDV<br>GFYYCMQALQTP<br>YTFGQGTKLEIK<br>RTVAAPSVFIFP<br>PSDEQLKSGTAS<br>VVCLLNNFYPRE<br>AKVQWKVDNALQ<br>SGNSQESVTEQD<br>SKDSTYSLSSTL<br>TLSKADYEKHKV<br>YACEVTHQGLSS<br>PVTKSFNRGEC | (SEQ ID NO: 194)<br>MGWSCIILFLVA<br>TATGVHSQMQLV<br>ESGGGVVQPGRS<br>LRLSCAASGFTF<br>RTYGMHWVRQAP<br>GKGLEWVAVIWY<br>DGSNKHYADSVK<br>GRFTITRDNSKN<br>TLNLQMNSLRAE<br>DTAVYYCARAPQ<br>WELVHEAFDIWG<br>QGTMVTVSSAST<br>KGPSVFPLAPCS<br>RSTSESTAALGC<br>LVKDYFPEPVTV<br>SWNSGALTSGVH<br>TFPAVLQSSGLY<br>SLSSVVTVPSSN<br>FGTQTYTCNVDH<br>KPSNTKVDKTV |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| Candidate 19.1_ with_ (EA3K)3 linker | (SEQ ID NO: 195)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS<br>ASTKGPSVFPLA<br>PCSRSTSESTAA<br>LGCLVKDYFPEP<br>VTVSWNSGALTS<br>GVHTFPAVLQSS<br>GLYSLSSVVTVP<br>SSSLGTKTYTCN<br>VDHKPSNTKVDK<br>RVESKYGPPCPP<br>CPAPEFLGGPSV<br>FLFPPKPKDTLY<br>ITREPEVTCVVV<br>DVSQEDPEVQFN<br>WYVDGVEVHNAK<br>TKPREEQFNSTY<br>RVVSVLTVLHQD<br>WLNGKEYKCKVS<br>NKGLPSSIEKTI<br>SKAKGQPREPQV<br>YTLPPSQEEMTK<br>NQVSLTCLVKGF<br>YPSDIAVEWESN<br>GQPENNYKTTPP<br>VLDSDGSFFLYS<br>RLTVDKSRWQEG<br>NVFSCSVMHEAL<br>HNHYTQKSLSLS<br>LGEAAAKEAAAK<br>EAAAKSYVLTQP<br>PSVSVAPGQTAR<br>ITCGGNNLGSKS<br>VHWYQQKPGQAP<br>VLVVYDDSDRPS<br>WIPERFSGSNSG<br>NTATLTISRGEA<br>GDEADYYCQVWD<br>SSSDHVVFGGGT<br>KLTVLGQPKAAP<br>SVTLFPPSSEEL<br>QANKATLVCLIS<br>DFYPGAVTVAWK<br>ADSSPVKAGVET<br>TTPSKQSNNKYA<br>ASSYLSLTPEQW<br>KSHRSYSCQVTH<br>EGSTVEKTVAPT<br>ECS | n/a | (SEQ ID NO: 196)<br>METDTLLLWVLL<br>LWVPGSTGDIVM<br>TQSPLSLPVTPG<br>EPASISCRSSQS<br>LLYSIGYNYLDW<br>YLQKSGQSPQLL<br>IYLGSNRASGVP<br>DRFSGSGSGTDF<br>TLKISRVEAEDV<br>GFYYCMQALQTP<br>YTFGQGTKLEIK<br>RTVAAPSVFIFP<br>PSDEQLKSGTAS<br>VVCLLNNFYPRE<br>AKVQWKVDNALQ<br>SGNSQESVTEQD<br>SKDSTYSLSSTL<br>TLSKADYEKHKV<br>YACEVTHQGLSS<br>PVTKSFNRGEC | (SEQ ID NO: 197)<br>MGWSCIILFLVA<br>TATGVHSQMQLV<br>ESGGGVVQPGRS<br>LRLSCAASGFTF<br>RTYGMHWVRQAP<br>GKGLEWVAVIWY<br>DGSNKHYADSVK<br>GRFTITRDNSKN<br>TLNLQMNSLRAE<br>DTAVYYCARAPQ<br>WELVHEAFDIWG<br>QGTMVTVSSAST<br>KGPSVFPLAPCS<br>RSTSESTAALGC<br>LVKDYFPEPVTV<br>SWNSGALTSGVH<br>TFPAVLQSSGLY<br>SLSSVVTVPSSN<br>FGTQTYTCNVDH<br>KPSNTKVDKTV |
| Candidate 19.1_with _(G4S)3_1 inker | (SEQ ID NO: 198)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS | n/a | (SEQ ID NO: 199)<br>METDTLLLWVLL<br>LWVPGSTGDIVM<br>TQSPLSLPVTPG<br>EPASISCRSSQS<br>LLYSIGYNYLDW<br>YLQKSGQSPQLL<br>IYLGSNRASGVP<br>DRFSGSGSGTDF<br>TLKISRVEAEDV<br>GFYYCMQALQTP<br>YTFGQGTKLEIK<br>RTVAAPSVFIFP | (SEQ ID NO: 200)<br>MGWSCIILFLVA<br>TATGVHSQMQLV<br>ESGGGVVQPGRS<br>LRLSCAASGFTF<br>RTYGMHWVRQAP<br>GKGLEWVAVIWY<br>DGSNKHYADSVK<br>GRFTITRDNSKN<br>TLNLQMNSLRAE<br>DTAVYYCARAPQ<br>WELVHEAFDIWG<br>QGTMVTVSSAST |

TABLE 34-continued

| Nonlimiting example variants of the Candidate 19.1 | | | | |
|---|---|---|---|---|
| Binding Moiety | HC1 Sequence | HC2 Sequence | LC1 Sequence | LC2 Sequence |
| | ASTKGPSVFPLA PCSRSTSESTAA LGCLVKDYFPEP VTVSWNSGALTS GVHTFPAVLQSS GLYSLSSVVTVP SSSLGTKTYTCN VDHKPSNTKVDK RVESKYGPPCPP CPAPEFLGGPSV FLFPPKPKDTLY ITREPEVTCVVV DVSQEDPEVQFN WYVDGVEVHNAK TKPREEQFNSTY RVVSVLTVLHQD WLNGKEYKCKVS NKGLPSSIEKTI SKAKGQPREPQV YTLPPSQEEMTK NQVSLTCLVKGF YPSDIAVEWESN GQPENNYKTTPP VLDSDGSFFLYS RLTVDKSRWQEG NVFSCSVMHEAL HNHYTQKSLSLS LGGGGGSGGGGS GGGGSSYVLTQP PSVSVAPGQTAR ITCGGNNLGSKS VHWYQQKPGQAP VLVVYDDSDRPS WIPERFSGSNSG NTATLTISRGEA GDEADYYCQVWD SSSDHVVFGGGT KLTVLGQPKAAP SVTLFPPSSEEL QANKATLVCLIS DFYPGAVTVAWK ADSSPVKAGVET TTPSKQSNNKYA ASSYLSLTPEQW KSHRSYSCQVTH EGSTVEKTVAPT ECS | | PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC | KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTV |
| Candidate 19.1_with _(G4S)2_1 inker | (SEQ ID NO: 201) MGWSCIILFLVA TATGVHSEVQLV ESGGGLEQPGGS LRLSCAGSGFTF RDYAMTWVRQAP GKGLEWVSSISG SGGNTYYADSVK GRFTISRDNSKN TLYLQMNSLRAE DTAVYYCAKDRL SITIRPRYYGLD VWGQGTTVTVSS ASTKGPSVFPLA PCSRSTSESTAA LGCLVKDYFPEP VTVSWNSGALTS GVHTFPAVLQSS GLYSLSSVVTVP SSSLGTKTYTCN VDHKPSNTKVDK RVESKYGPPCPP CPAPEFLGGPSV FLFPPKPKDTLY ITREPEVTCVVV DVSQEDPEVQFN WYVDGVEVHNAK | n/a | (SEQ ID NO: 202) METDTLLLWVLL LWVPGSTGDIVM TQSPLSLPVTPG EPASISCRSSQS LLYSIGYNYLDW YLQKSGQSPQLL IYLGSNRASGVP DRFSGSGSGTDF TLKISRVEAEDV GFYYCMQALQTP YTFGQGTKLEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC | (SEQ ID NO: 203) MGWSCIILFLVA TATGVHSQMQLV ESGGGVVQPGRS LRLSCAASGFTF RTYGMHWVRQAP GKGLEWVAVIWY DGSNKHYADSVK GRFTITRDNSKN TLNLQMNSLRAE DTAVYYCARAPQ WELVHEAFDIWG QGTMVTVSSAST KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTV |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| | TKPREEQFNSTY RVVSVLTVLHQD WLNGKEYKCKVS NKGLPSSIEKTI SKAKGQPREPQV YTLPPSQEEMTK NQVSLTCLVKGF YPSDIAVEWESN GQPENNYKTTPP VLDSDGSFFLYS RLTVDKSRWQEG NVFSCSVMHEAL HNHYTQKSLSLS LGGGGGSGGGGS SYVLTQPPSVSV APGQTARITCGG NNLGSKSVHWYQ QKPGQAPVLVVY DDSDRPSWIPER FSGSNSGNTATL TISRGEAGDEAD YYCQVWDSSSDH VVFGGGTKLTVL GQPKAAPSVTLF PPSSEELQANKA TLVCLISDFYPG AVTVAWKADSSP VKAGVETTTPSK QSNNKYAASSYL SLTPEQWKSHRS YSCQVTHEGSTV EKTVAPTECS | | | |
| Candidate 19.1_with _(G4S)1_1 inker | (SEQ ID NO: 204) MGWSCIILFLVA TATGVHSEVQLV ESGGGLEQPGGS LRLSCAGSGFTF RDYAMTWVRQAP GKGLEWVSSISG SGGNTYYADSVK GRFTISRDNSKN TLYLQMNSLRAE DTAVYYCAKDRL SITIRPRYYGLD VWGQGTTVTVSS ASTKGPSVFPLA PCSRSTSESTAA LGCLVKDYFPEP VTVSWNSGALTS GVHTFPAVLQSS GLYSLSSVVTVP SSSLGTKTYTCN VDHKPSNTKVDK RVESKYGPPCPP CPAPEFLGGPSV FLFPPKPKDTLY ITREPEVTCVVV DVSQEDPEVQFN WYVDGVEVHNAK TKPREEQFNSTY RVVSVLTVLHQD WLNGKEYKCKVS NKGLPSSIEKTI SKAKGQPREPQV YTLPPSQEEMTK NQVSLTCLVKGF YPSDIAVEWESN GQPENNYKTTPP VLDSDGSFFLYS RLTVDKSRWQEG NVFSCSVMHEAL HNHYTQKSLSLS LGGGGGSSYVLT QPPSVSVAPGQT | n/a | (SEQ ID NO: 205) METDTLLLWVLL LWVPGSTGDIVM TQSPLSLPVTPG EPASISCRSSQS LLYSIGYNYLDW YLQKSGQSPQLL IYLGSNRASGVP DRFSGSGSGTDF TLKISRVEAEDV GFYYCMQALQTP YTFGQGTKLEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC | (SEQ ID NO: 206) MGWSCIILFLVA TATGVHSQMQLV ESGGGVVQPGRS LRLSCAASGFTF RTYGMHWVRQAP GKGLEWVAVIWY DGSNKHYADSVK GRFTITRDNSKN TLNLQMNSLRAE DTAVYYCARAPQ WELVHEAFDIWG QGTMVTVSSAST KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTV |

TABLE 34-continued

| Nonlimiting example variants of the Candidate 19.1 | | | | |
|---|---|---|---|---|
| Binding Moiety | HC1 Sequence | HC2 Sequence | LC1 Sequence | LC2 Sequence |
| | ARITCGGNNLGS<br>KSVHWYQQKPGQ<br>APVLVVYDDSDR<br>PSWIPERFSGSN<br>SGNTATLTISRG<br>EAGDEADYYCQV<br>WDSSSDHVVFGG<br>GTKLTVLGQPKA<br>APSVTLFPPSSE<br>ELQANKATLVCL<br>ISDFYPGAVTVA<br>WKADSSPVKAGV<br>ETTTPSKQSNNK<br>YAASSYLSLTPE<br>QWKSHRSYSCQV<br>THEGSTVEKTVA<br>PTECS | | | |
| Candidate 19.1_in_2 _1_format _(Knob_ Hole) | (SEQ ID NO: 207)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS<br>ASTKGPSVFPLA<br>PCSRSTSESTAA<br>LGCLVKDYFPEP<br>VTVSWNSGALTS<br>GVHTFPAVLQSS<br>GLYSLSSVVTVP<br>SSSLGTKTYTCN<br>VDHKPSNTKVDK<br>RVESKYGPPCPP<br>CPAPEFLGGPSV<br>FLFPPKPKDTLY<br>ITREPEVTCVVV<br>DVSQEDPEVQFN<br>WYVDGVEVHNAK<br>TKPREEQFNSTY<br>RVVSVLTVLHQD<br>WLNGKEYKCKVS<br>NKGLPSSIEKTI<br>SKAKGQPREPQV<br>YTLPPSQEEMTK<br>NQVSLWCLVKGF<br>YPSDIAVEWESN<br>GQPENNYKTTPP<br>VLDSDGSFFLYS<br>RLTVDKSRWQEG<br>NVFSCSVMHEAL<br>HNHYTQKSLSLS<br>LGGGGGSGGGGS<br>GGGGSGGGGSSY<br>VLTQPPSVSVAP<br>GQTARITCGGNN<br>LGSKSVHWYQQK<br>PGQAPVLVVYDD<br>SDRPSWIPERFS<br>GSNSGNTATLTI<br>SRGEAGDEADYY<br>CQVWDSSSDHVV<br>FGGGTKLTVLGQ<br>PKAAPSVTLFPP<br>SSEELQANKATL<br>VCLISDFYPGAV<br>TVAWKADSSPVK<br>AGVETTTPSKQS<br>NNKYAASSYLSL | (SEQ ID NO: 208)<br>MGWSCIILFLVA<br>TATGVHSEVQLV<br>ESGGGLEQPGGS<br>LRLSCAGSGFTF<br>RDYAMTWVRQAP<br>GKGLEWVSSISG<br>SGGNTYYADSVK<br>GRFTISRDNSKN<br>TLYLQMNSLRAE<br>DTAVYYCAKDRL<br>SITIRPRYYGLD<br>VWGQGTTVTVSS<br>ASTKGPSVFPLA<br>PCSRSTSESTAA<br>LGCLVKDYFPEP<br>VTVSWNSGALTS<br>GVHTFPAVLQSS<br>GLYSLSSVVTVP<br>SSSLGTKTYTCN<br>VDHKPSNTKVDK<br>RVESKYGPPCPP<br>CPAPEFLGGPSV<br>FLFPPKPKDTLY<br>ITREPEVTCVVV<br>DVSQEDPEVQFN<br>WYVDGVEVHNAK<br>TKPREEQFNSTY<br>RVVSVLTVLHQD<br>WLNGKEYKCKVS<br>NKGLPSSIEKTI<br>SKAKGQPREPQV<br>YTLPPSQEEMTK<br>NQVSLSCAVKGF<br>YPSDIAVEWESN<br>GQPENNYKTTPP<br>VLDSDGSFFLVS<br>RLTVDKSRWQEG<br>NVFSCSVMHEAL<br>HNHYTQKSLSLS<br>LG | (SEQ ID NO: 209)<br>METDTLLLWVLL<br>LWVPGSTGDIVM<br>TQSPLSLPVTPG<br>EPASISCRSSQS<br>LLYSIGYNYLDW<br>YLQKSGQSPQLL<br>IYLGSNRASGVP<br>DRFSGSGSGTDF<br>TLKISRVEAEDV<br>GFYYCMQALQTP<br>YTFGQGTKLEIK<br>RTVAAPSVFIFP<br>PSDEQLKSGTAS<br>VVCLLNNFYPRE<br>AKVQWKVDNALQ<br>SGNSQESVTEQD<br>SKDSTYSLSSTL<br>TLSKADYEKHKV<br>YACEVTHQGLSS<br>PVTKSFNRGEC | (SEQ ID NO: 210)<br>MGWSCIILFLVA<br>TATGVHSQMQLV<br>ESGGGVVQPGRS<br>LRLSCAASGFTF<br>RTYGMHWVRQAP<br>GKGLEWVAVIWY<br>DGSNKHYADSVK<br>GRFTITRDNSKN<br>TLNLQMNSLRAE<br>DTAVYYCARAPQ<br>WELVHEAFDIWG<br>QGTMVTVSSAST<br>KGPSVFPLAPCS<br>RSTSESTAALGC<br>LVKDYFPEPVTV<br>SWNSGALTSGVH<br>TFPAVLQSSGLY<br>SLSSVVTVPSSN<br>FGTQTYTCNVDH<br>KPSNTKVDKTV |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| | TPEQWKSHRSYS | | | |
| | CQVTHEGSTVEK | | | |
| | TVAPTECS | | | |
| Candidate | (SEQ ID NO: 211) | n/a | (SEQ ID NO: 212) | (SEQ ID NO: 213) |
| 19.1_New | MGWSCIILFLVA | | METDTLLLWVLL | MGWSCIILFLVA |
| IL-4Ra_ | TATGVHSEVQLV | | LWVPGSTGDIQM | TATGVHSQMQLV |
| #1_ | ESGGGLVQPGGS | | TQSPSSLSASVG | ESGGGVVQPGRS |
| YTE | LRLSCAASGFTF | | DRVTITCRASQD | LRLSCAASGFTF |
| | SDYGMHWVRQAP | | ISNYLNWYQQKP | RTYGMHWVRQAP |
| | GKGLEWVSYISS | | GKAPKLLIYYTS | GKGLEWVAVIWY |
| | GSSTIYYADTVK | | RLHSGVPSRFSG | DGSNKHYADSVK |
| | GRFTISRDNAKN | | SGSGTDFTLTIS | GRFTITRDNSKN |
| | SLYLQMNSLRAE | | SLQPEDIATYYC | TLNLQMNSLRAE |
| | DTAVYYCARIST | | QEVNMLPFTFGQ | DTAVYYCARAPQ |
| | VVAKRYAMDYWG | | GTKVEIKRTVAA | WELVHEAFDIWG |
| | QGTLVTVSSAST | | PSVFIFPPSDEQ | QGTMVTVSSAST |
| | KGPSVFPLAPCS | | LKSGTASVVCLL | KGPSVFPLAPCS |
| | RSTSESTAALGC | | NNFYPREAKVQW | RSTSESTAALGC |
| | LVKDYFPEPVTV | | KVDNALQSGNSQ | LVKDYFPEPVTV |
| | SWNSGALTSGVH | | ESVTEQDSKDST | SWNSGALTSGVH |
| | TFPAVLQSSGLY | | YSLSSTLTLSKA | TFPAVLQSSGLY |
| | SLSSVVTVPSSS | | DYEKHKVYACEV | SLSSVVTVPSSN |
| | LGTKTYTCNVDH | | THQGLSSPVTKS | FGTQTYTCNVDH |
| | KPSNTKVDKRVE | | FNRGEC | KPSNTKVDKTV |
| | SKYGPPCPPCPA | | | |
| | PEFLGGPSVFLF | | | |
| | PPKPKDTLYITR | | | |
| | EPEVTCVVVDVS | | | |
| | QEDPEVQFNWYV | | | |
| | DGVEVHNAKTKP | | | |
| | REEQFNSTYRVV | | | |
| | SVLTVLHQDWLN | | | |
| | GKEYKCKVSNKG | | | |
| | LPSSIEKTISKA | | | |
| | KGQPREPQVYTL | | | |
| | PPSQEEMTKNQV | | | |
| | SLTCLVKGFYPS | | | |
| | DIAVEWESNGQP | | | |
| | ENNYKTTPPVLD | | | |
| | SDGSFFLYSRLT | | | |
| | VDKSRWQEGNVF | | | |
| | SCSVMHEALHNH | | | |
| | YTQKSLSLSLGG | | | |
| | GGGSGGGGSGGG | | | |
| | GSGGGGSSYVLT | | | |
| | QPPSVSVAPGQT | | | |
| | ARITCGGNNLGS | | | |
| | KSVHWYQQKPGQ | | | |
| | APVLVVYDDSDR | | | |
| | PSWIPERFSGSN | | | |
| | SGNTATLTISRG | | | |
| | EAGDEADYYCQV | | | |
| | WDSSSDHVVFGG | | | |
| | GTKLTVLGQPKA | | | |
| | APSVTLFPPSSE | | | |
| | ELQANKATLVCL | | | |
| | ISDFYPGAVTVA | | | |
| | WKADSSPVKAGV | | | |
| | ETTTPSKQSNNK | | | |
| | YAASSYLSLTPE | | | |
| | QWKSHRSYSCQV | | | |
| | THEGSTVEKTVA | | | |
| | PTECS | | | |
| Candidate | (SEQ ID NO: 214) | | (SEQ ID NO: 215) | (SEQ ID NO: 216) |
| 19.1_New | MGWSCIILFLVA | | METDTLLLWVLL | MGWSCIILFLVA |
| IL-4Ra_ | TATGVHSQVQLV | | LWVPGSTGEIVL | TATGVHSQMQLV |
| #2_ | QSGAEVKKPGAS | | TQSPATLSLSPG | ESGGGVVQPGRS |
| YTE | VKVSCKASGYTF | | ERATLSCRASSS | LRLSCAASGFTF |
| | TDYNVDWVRQAP | | VIYIHWYQQKPG | RTYGMHWVRQAP |
| | GQGLEWIGTINP | | QAPRPWIYAASN | GKGLEWVAVIWY |
| | NNGGILSNQKFK | | LPSGVPARFSGS | DGSNKHYADSVK |
| | GRVTITVDTSAS | | GSGTDFTLTISS | GRFTITRDNSKN |
| | TAYMELSSLRSE | | LEPEDFAVYYCQ | TLNLQMNSLRAE |

TABLE 34-continued

| Nonlimiting example variants of the Candidate 19.1 | | | | |
|---|---|---|---|---|
| Binding Moiety | HC1 Sequence | HC2 Sequence | LC1 Sequence | LC2 Sequence |
| | DTAVYYCGRGGL RRRGFMDYWGQG TLVTVSSASTKG PSVFPLAPCSRS TSESTAALGCLV KDYFPEPVTVSW NSGALTSGVHTF PAVLQSSGLYSL SSVVTVPSSSLG TKTYTCNVDHKP SNTKVDKRVESK YGPPCPPCPAPE FLGGPSVFLFPP KPKDTLYITREP EVTCVVVDVSQE DPEVQFNWYVDG VEVHNAKTKPRE EQFNSTYRVVSV LTVLHQDWLNGK EYKCKVSNKGLP SSIEKTISKAKG QPREPQVYTLPP SQEEMTKNQVSL TCLVKGFYPSDI AVEWESNGQPEN NYKTTPPVLDSD GSFFLYSRLTVD KSRWQEGNVFSC SVMHEALHNHYT QKSLSLSLGGGG GSGGGGSGGGGS GGGGSSYVLTQP PSVSVAPGQTAR ITCGGNNLGSKS VHWYQQKPGQAP VLVVYDDSDRPS WIPERFSGSNSG NTATLTISRGEA GDEADYYCQVWD SSSDHVVFGGGT KLTVLGQPKAAP SVTLFPPSSEEL QANKATLVCLIS DFYPGAVTVAWK ADSSPVKAGVET TTPSKQSNNKYA ASSYLSLTPEQW KSHRSYSCQVTH EGSTVEKTVAPT ECS | | QWSSNPPTFGQG TKVEIKRTVAAP SVFIFPPSDEQL KSGTASVVCLLN NFYPREAKVQWK VDNALQSGNSQE SVTEQDSKDSTY SLSSTLTLSKAD YEKHKVYACEVT HQGLSSPVTKSF NRGEC | DTAVYYCARAPQ WELVHEAFDIWG QGTMVTVSSAST KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTV |
| WBP71460 _20 | (SEQ ID NO: 217) MGWSCIILFLVA TATGVHSQMQLV ESGGGVVQPGRS LRLSCAASGFTF RTYGMHWVRQAP GKGLEWVAVIWY DGSNKHYADSVK GRFTITRDNSKN TLNLQMNSLRAE DTAVYYCARAPQ WELVHEAFDIWG QGTMVTVSSAST KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTVE RKCCVECPPCPA PPVAGPSVFLFP PKPKDTLYITRE | | (SEQ ID NO: 218) MGWSCIILFLVA TATGVHSSYVLT QPPSVSVAPGQT ARITCGGNNLGS KSVHWYQQKPGQ APVLVVYDDSDR PSWIPERFSGSN SGNTATLTISRG EAGDEADYYCQV WDSSSDHVVFGG GTKLTVLGQPKA APSVTLFPPSSE ELQANKATLVCL ISDFYPGAVTVA WKADSSPVKAGV ETTTPSKQSNNK YAASSYLSLTPE QWKSHRSYSCQV THEGSTVEKTVA PTECS | |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| | PEVTCVVVDVSH EDPEVQFNWYVD GVEVHNAKTKPR EEQFNSTFRVVS VLTVVHQDWLNG KEYKCKVSNKGL PAPIEKTISKTK GQPREPQVYTLP PSREEMTKNQVS LTCLVKGFYPSD IAVEWESNGQPE NNYKTTPPMLDS DGSFFLYSKLTV DKSRWQQGNVFS CSVMHEALHNHY TQKSLSLSPGKG GGGSGGGGSGGG GSGGGGSEVQLV ESGGGLEQPGGS LRLSCAGSGFTF RDYAMTWVRQAP GKGLEWVSSISG SGGNTYYADSVK GRFTISRDNSKN TLYLQMNSLRAE DTAVYYCAKDRL SITIRPRYYGLD VWGQGTTVTVSS GGGGSGGGGSGG GGSGGGGSDIVM TQSPLSLPVTPG EPASISCRSSQS LLYSIGYNYLDW YLQKSGQSPQLL IYLGSNRASGVP DRFSGSGSGTDF TLKISRVEAEDV GFYYCMQALQTP YTFGQGTKLEIK | | | |
| WBP71460 _21 | (SEQ ID NO: 219) MGWSCIILFLVA TATGVHSQMQLV ESGGGVVQPGRS LRLSCAASGFTF RTYGMHWVRQAP GKGLEWVAVIWY DGSNKHYADSVK GRFTITRDNSKN TLNLQMNSLRAE DTAVYYCARAPQ WELVHEAFDIWG QGTMVTVSSAST KGPSVFPLAPCS RSTSESTAALGC LVKDYFPEPVTV SWNSGALTSGVH TFPAVLQSSGLY SLSSVVTVPSSN FGTQTYTCNVDH KPSNTKVDKTVE RKCCVECPPCPA PPVAGPSVFLFP PKPKDTLYITRE PEVTCVVVDVSH EDPEVQFNWYVD GVEVHNAKTKPR EEQFNSTFRVVS VLTVVHQDWLNG KEYKCKVSNKGL PAPIEKTISKTK GQPREPQVYTLP PSREEMTKNQVS LTCLVKGFYPSD IAVEWESNGQPE | | (SEQ ID NO: 220) MGWSCIILFLVA TATGVHSSYVLT QPPSVSVAPGQT ARITCGGNNLGS KSVHWYQQKPGQ APVLVVYDDSDR PSWIPERFSGSN SGNTATLTISRG EAGDEADYYCQV WDSSSDHVVFGG GTKLTVLGQPKA APSVTLFPPSSE ELQANKATLVCL ISDFYPGAVTVA WKADSSPVKAGV ETTTPSKQSNNK YAASSYLSLTPE QWKSHRSYSCQV THEGSTVEKTVA PTECSGGGGSGG GGSGGGGSGGGG SEVQLVESGGGL EQPGGSLRLSCA GSGFTFRDYAMT WVRQAPGKGLEW VSSISGSGGNTY YADSVKGRFTIS RDNSKNTLYLQM NSLRAEDTAVYY CAKDRLSITIRP RYYGLDVWGQGT TVTVSSGGGGSG GGGSGGGGSGGG GSDIVMTQSPLS | |

TABLE 34-continued

Nonlimiting example variants of the Candidate 19.1

| Binding Moiety | HC1 Sequence | HC2 Sequence | LC1 Sequence | LC2 Sequence |
|---|---|---|---|---|
| | NNYKTTPPMLDS DGSFFLYSKLTV DKSRWQQGNVFS CSVMHEALHNHY TQKSLSLSPGK | | LPVTPGEPASIS CRSSQSLLYSIG YNYLDWYLQKSG QSPQLLIYLGSN RASGVPDRFSGS GSGTDFTLKISR VEAEDVGFYYCM QALQTPYTFGQG TKLEIK | |
| WBP71460_22 | (SEQ ID NO: 221) MGWSCIILFLVA TATGVHSEVQLV ESGGGLEQPGGS LRLSCAGSGFTF RDYAMTWVRQAP GKGLEWVSSISG SGGNTYYADSVK GRFTISRDNSKN TLYLQMNSLRAE DTAVYYCAKDRL SITIRPRYYGLD VWGQGTTVTVSS GGGGSGGGGSGG GGSGGGGSDIVM TQSPLSLPVTPG EPASISCRSSQS LLYSIGYNYLDW YLQKSGQSPQLL IYLGSNRASGVP DRFSGSGSGTDF TLKISRVEAEDV GFYYCMQALQTP YTFGQGTKLEIK GGGGSGGGGSGG GGSGGGGSQMQL VESGGGVVQPGR SLRLSCAASGFT FRTYGMHWVRQA PGKGLEWVAVIW YDGSNKHYADSV KGRFTITRDNSK NTLNLQMNSLRA EDTAVYYCARAP QWELVHEAFDIW GQGTMVTVSSAS TKGPSVFPLAPC SRSTSESTAALG CLVKDYFPEPVT VSWNSGALTSGV HTFPAVLQSSGL YSLSSVVTVPSS NFGTQTYTCNVD HKPSNTKVDKTV ERKCCVECPPCP APPVAGPSVFLF PPKPKDTLYITR EPEVTCVVVDVS HEDPEVQFNWYV DGVEVHNAKTKP REEQFNSTFRVV SVLTVVHQDWLN GKEYKCKVSNKG LPAPIEKTISKT KGQPREPQVYTL PPSREEMTKNQV SLTCLVKGFYPS DIAVEWESNGQP ENNYKTTPPMLD SDGSFFLYSKLT VDKSRWQQGNVF SCSVMHEALHNH YTQKSLSLSPGK | | (SEQ ID NO: 222) MGWSCIILFLVA TATGVHSSYVLT QPPSVSVAPGQT ARITCGGNNLGS KSVHWYQQKPGQ APVLVVYDDSDR PSWIPERFSGSN SGNTATLTISRG EAGDEADYYCQV WDSSSDHVVFGG GTKLTVLGQPKA APSVTLFPPSSE ELQANKATLVCL ISDFYPGAVTVA WKADSSPVKAGV ETTTPSKQSNNK YAASSYLSLTPE QWKSHRSYSCQV THEGSTVEKTVA PTECS | |

Example 3: Design of TSLP-TRAP Complexes

The antigen binding complexes are designed to bind TSLP and IL-4R such as the bispecific anti-IL-4R TSLP-TRAP complexes (FIGS. 5-7). The bispecific anti-IL-4R TSLP-TRAP complexes comprise a TSLP-TRAP associated to a moiety via a linker. The moiety component of the bispecific anti-IL-4R TSLP-TRAPs is dupilumab, a human IgG4 isotype that specifically binds to hIL-4R. The complexes have 2 TSLP-TRAPs (FIGS. 1A-1D). The TSLP-TRAP complex can also be formed by linking TSLPR and IL-7Rα independently to an antibody or fragments thereof such that the TSLP-TRAP is formed when folded (FIGS. 2A-2D).

Candidate 20 (FIG. 6A) may comprise IL-7Rα(SEQ ID NO: 35) of the TSLP-TRAP (SEQ ID NO: 1) complex associated with the Fc region comprising YTE mutation of the anti-IL-4R at C-terminus.

```
Candidate 20 - Heavy Chain
                                        (SEQ ID NO: 106)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSRLTVDKSRWQEGNVFSCSVMHEALHNHYTQKSLSLSL
GGGGGSGGGGSGGGGSGGGGSESGYAQNGDLEDAELDDYSFSCYS
QLEVNGSQHSLTCAFEDPDVNITNLEFEICGALVEVKCLNFRKLQ
EIYFIETKKFLLIGKSNICVKVGEKSLTCKKIDLTTIVKPEAPFD
LSVVYREGANDFVVTFNTSHLQKKYVKVLMHDVAYRQEKDENKWT
HVNLSSTKLTLLQRKLQPAAMYEIKVRSIPDHYFKGFWSEWSPSY
YFRTPEINNSSGEMDGGSGGSGGSGGSGGSGGSGGSGGSGGSGGS
GGSGGSGGSGGSGGSGGSGGSGGSGGSGGSGAAEGVQIQIIYFNL
ETVQVTWNASKYSRTNLTFHYRFNGDEAYDQCTNYLLQEGHTSGC
LLDAEQRDDILYFSIRNGTHPVFTASRWMVYYLKPSSPKHVRFSW
HQDAVTVTCSDLSYGDLLYEVQYRSPFDTEWQSKQENTCNVTIEG
LDAEKCYSFWVRVKAMEDVYGPDTYPSDWSEVTCWQRGEIRDACA
ETPTPPKPKLSK

Candidate 20 - Light Chain
                                        (SEQ ID NO: 107)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC
```

Candidate 21 (FIG. 6B) may comprise TSLPR (SEQ ID NO: 34) of the TSLP-TRAP (SEQ ID NO: 1) complex associated with the Fc region comprising YTE mutation of the anti-IL-4R at C-terminus.

```
Candidate 21 - Heavy Chain
                                        (SEQ ID NO: 108)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSRLTVDKSRWQEGNVFSCSVMHEALHNHYTQKSLSLSL
GGGGGSGGGGSGGGGSGGGGSGAAEGVQIQIIYFNLETVQVTWNA
SKYSRTNLTFHYRFNGDEAYDQCTNYLLQEGHTSGCLLDAEQRDD
ILYFSIRNGTHPVFTASRWMVYYLKPSSPKHVRFSWHQDAVTVTC
SDLSYGDLLYEVQYRSPFDTEWQSKQENTCNVTIEGLDAEKCYSF
WVRVKAMEDVYGPDTYPSDWSEVTCWQRGEIRDACAETPTPPKPK
LSKGGSGGSGGSGGSGGSGGSGGSGGSGGSGGSGGSGGSGGSGGS
GGSGGSGGSGGSGGSGGSESGYAQNGDLEDAELDDYSFSCYSQLE
VNGSQHSLTCAFEDPDVNITNLEFEICGALVEVKCLNFRKLQEIY
FIETKKFLLIGKSNICVKVGEKSLTCKKIDLTTIVKPEAPFDLSV
VYREGANDFVVTFNTSHLQKKYVKVLMHDVAYRQEKDENKWTHVN
LSSTKLTLLQRKLQPAAMYEIKVRSIPDHYFKGFWSEWSPSYYFR
TPEINNSSGEMD

Candidate 21 - Light Chain
                                        (SEQ ID NO: 109)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC
```

Candidate 22 (FIG. 6C) may comprise IL-7Rα(SEQ ID NO: 35) of the TSLP-TRAP with 20 amino acid linker (SEQ ID NO: 5) complex associated with the Fc region comprising YTE mutation of the anti-IL-4R at C-terminus.

```
Candidate 22- Heavy Chain
                                        (SEQ ID NO: 110)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
```

-continued

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

GGGGGSGGGGSGGGGSGGGGSESGYAQNGDLEDAELDDYSFSCYS

QLEVNGSQHSLTCAFEDPDVNITNLEFEICGALVEVKCLNFRKLQ

EIYFIETKKFLLIGKSNICVKVGEKSLTCKKIDLTTIVKPEAPFD

LSVVYREGANDFVVTFNTSHLQKKYVKVLMHDVAYRQEKDENKWT

HVNLSSTKLTLLQRKLQPAAMYEIKVRSIPDHYFKGFWSEWSPSY

YFRTPEINNSSGEMDGGGGSGGGGSGGGGSGGGGSGAAEGVQIQI

IYFNLETVQVTWNASKYSRTNLTFHYRFNGDEAYDQCTNYLLQEG

HTSGCLLDAEQRDDILYFSIRNGTHPVFTASRWMVYYLKPSSPKH

VRFSWHQDAVTVTCSDLSYGDLLYEVQYRSPFDTEWQSKQENTCN

VTIEGLDAEKCYSFWVRVKAMEDVYGPDTYPSDWSEVTCWQRGEI

RDACAETPTPPKPKLSK

Candidate 22-Light Chain (SEQ ID NO: 112)

DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC

Candidate 23 (FIG. 6D) may comprise TSLPR (SEQ ID NO: 34) of the TSLP-TRAP with 20 amino acid linker (SEQ ID NO: 5) complex associated with the Fc region comprising YTE mutation of the anti-IL-4R at C-terminus.

Candidate 23 - Heavy Chain (SEQ ID NO: 113)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLTCLVKGFYPSDIAVEWESNGQPENNYKTTPPVLDS

DGSFFLYSRLTVDKSRWQEGNVFSCSVMHEALHNHYTQKSLSLSL

GGGGGSGGGGSGGGGSGGGGSGAAEGVQIQIIYFNLETVQVTWNA

SKYSRTNLTFHYRFNGDEAYDQCTNYLLQEGHTSGCLLDAEQRDD

ILYFSIRNGTHPVFTASRWMVYYLKPSSPKHVRFSWHQDAVTVTC

-continued

SDLSYGDLLYEVQYRSPFDTEWQSKQENTCNVTIEGLDAEKCYSF

WVRVKAMEDVYGPDTYPSDWSEVTCWQRGEIRDACAETPTPPKPK

LSKGGGGSGGGGSGGGGSGGGGSESGYAQNGDLEDAELDDYSFSC

YSQLEVNGSQHSLTCAFEDPDVNITNLEFEICGALVEVKCLNFRK

LQEIYFIETKKFLLIGKSNICVKVGEKSLTCKKIDLTTIVKPEAP

FDLSVVYREGANDFVVTFNTSHLQKKYVKVLMHDVAYRQEKDENK

WTHVNLSSTKLTLLQRKLQPAAMYEIKVRSIPDHYFKGFWSEWSP

SYYFRTPEINNSSGEMD

Candidate 23 - Light Chain (SEQ ID NO: 114)

DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC

Candidate 24 (FIG. 7A) may comprise a single TRAP construct format, where IL-7Rα is associated with a first Fc region (comprising a hole mutation) of the anti-IL-4R moiety, while TSLPR is associated with a second Fc region (comprising a knob mutation) of the anti-IL-4R moiety. Candidate 24 further comprises a KiH mutation.

Candidate 24 - Heavy Chain 1 (Knob) (SEQ ID NO: 115)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLSCAVKGFYPSDIAVEWESNGQPENNYKTTPPVLDS

DGSFFLVSRLTVDKSRWQEGNVFSCSVMHEALHNHYTQKSLSLSL

GGGGGSGGGGSGGGGSGGGGSGAAEGVQIQIIYFNLETVQVTWNA

SKYSRTNLTFHYRFNGDEAYDQCTNYLLQEGHTSGCLLDAEQRDD

ILYFSIRNGTHPVFTASRWMVYYLKPSSPKHVRFSWHQDAVTVTC

SDLSYGDLLYEVQYRSPFDTEWQSKQENTCNVTIEGLDAEKCYSF

WVRVKAMEDVYGPDTYPSDWSEVTCWQRGEIRDACAETPTPPKPK

LSK

Candidate 24 - Heavy Chain 2 (Hole) (SEQ ID NO: 116)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

-continued

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLWCLVKGFYPSDIAVEWESNGQPENNYKTTPPVLDS

DGSFFLYSRLTVDKSRWQEGNVFSCSVMHEALHNHYTQKSLSLSL

GGGGGSGGGGSGGGGSGGGGSESGYAQNGDLEDAELDDYSFSCYS

QLEVNGSQHSLTCAFEDPDVNITNLEFEICGALVEVKCLNFRKLQ

EIYFIETKKFLLIGKSNICVKVGEKSLTCKKIDLTTIVKPEAPFD

LSVVYREGANDFVVTFNTSHLQKKYVKVLMHDVAYRQEKDENKWT

HVNLSSTKLTLLQRKLQPAAMYEIKVRSIPDHYFKGFWSEWSPSY

YFRTPEINNSSGEMD

Candidate 24 - Light Chain (SEQ ID NO: 117)

DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC

Candidate 25 (FIG. 7B) may comprise a single TRAP construct format, where TSLPR is associated with a first Fc region (comprising a hole mutation) of the anti-IL-4R moiety, while IL7Ra is associated with a second Fc region (comprising a knob mutation) of the anti-IL-4R moiety. Candidate 25 further comprises a KiH mutation.

Candidate 25- Heavy Chain 1 (Knob)

(SEQ ID NO: 118)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLSCAVKGFYPSDIAVEWESNGQPENNYKTTPPVLDS

DGSFFLVSRLTVDKSRWQEGNVFSCSVMHEALHNHYTQKSLSLSL

GGGGGSGGGGSGGGGSGGGGSESGYAQNGDLEDAELDDYSFSCYS

QLEVNGSQHSLTCAFEDPDVNITNLEFEICGALVEVKCLNFRKLQ

EIYFIETKKFLLIGKSNICVKVGEKSLTCKKIDLTTIVKPEAPFD

LSVVYREGANDFVVTFNTSHLQKKYVKVLMHDVAYRQEKDENKWT

HVNLSSTKLTLLQRKLQPAAMYEIKVRSIPDHYFKGFWSEWSPSY

YFRTPEINNSSGEMD

-continued

Candidate 25- Heavy Chain 2 (Hole)

(SEQ ID NO: 119)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLWCLVKGFYPSDIAVEWESNGQPENNYKTTPPVLDS

DGSFFLYSRLTVDKSRWQEGNVFSCSVMHEALHNHYTQKSLSLSL

GGGGGSGGGGSGGGGSGGGGSGAAEGVQIQIIYFNLETVQVTWNA

SKYSRTNLTFHYRFNGDEAYDQCTNYLLQEGHTSGCLLDAEQRDD

ILYFSIRNGTHPVFTASRWMVYYLKPSSPKHVRFSWHQDAVTVTC

SDLSYGDLLYEVQYRSPFDTEWQSKQENTCNVTIEGLDAEKCYSF

WVRVKAMEDVYGPDTYPSDWSEVTCWQRGEIRDACAETPTPPKPK

LSK

Candidate 25- Light Chain (SEQ ID NO: 120)

DIVMTQSPLSLPVTPGEPASISCRSSQSLLYSIGYNYLDWYLQKS

GQSPQLLIYLGSNRASGVPDRFSGSGSGTDFTLKISRVEAEDVGF

YYCMQALQTPYTFGQGTKLEIKRTVAAPSVFIFPPSDEQLKSGTA

SVVCLLNNFYPREAKVQWKVDNALQSGNSQESVTEQDSKDSTYSL

SSTLTLSKADYEKHKVYACEVTHQGLSSPVTKSFNRGEC

Candidate 26 (FIG. 7C) shows that IL-7Rα is associated with a first Fc region of the anti-IL-4R moiety (comprising a hole mutation) and TSLPR is associated with a second Fc region of the anti-IL-4R moiety (comprising a knob mutation), where IL7-Ra and TSLPR are associated with each other. Candidate 26 may comprise a KiH mutation.

Candidate 26 Heavy Chain 1 Cys (Knob)

(SEQ ID NO: 121)

EVQLVESGGGLEQPGGSLRLSCAGSGFTFRDYAMTWVRQAPGKGL

EWVSSISGSGGNTYYADSVKGRFTISRDNSKNTLYLQMNSLRAED

TAVYYCAKDRLSITIRPRYYGLDVWGQGTTVTVSSASTKGPSVFP

LAPCSRSTSESTAALGCLVKDYFPEPVTVSWNSGALTSGVHTFPA

VLQSSGLYSLSSVVTVPSSSLGTKTYTCNVDHKPSNTKVDKRVES

KYGPPCPPCPAPEFLGGPSVFLFPPKPKDTLYITREPEVTCVVVD

VSQEDPEVQFNWYVDGVEVHNAKTKPREEQFNSTYRVVSVLTVLH

QDWLNGKEYKCKVSNKGLPSSIEKTISKAKGQPREPQVYTLPPSQ

EEMTKNQVSLSCAVKGFYPSDIAVEWESNGQPENNYKTTPPVLDS

DGSFFLVSRLTVDKSRWQEGNVFSCSVMHEALHNHYTQKSLSLSL

GGGGGSGGGGSGGGGSGGGGSGAAEGVQIQIIYFNLETVQVTWNA

SKYSRTNLTFHYRFNGDEAYDQCTNYLLQEGHTSGCLLDAEQRDD

-continued

ILYFSIRNGTHPVFTASRWMVYYLKPSSPKHVRFSWHQDAVTVTC
SDLSYGDLLYEVQYRSPCDTEWQSKQENTCNVTIEGLDAEKCYSF
WVRVKAMEDVYGPDTYPSDWSEVTCWQRGEIRDACAETPTPPKPK
LSK

Candidate 26 Heavy Chain 1 Cys (Hole)
(SEQ ID NO: 122)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLWCLVKGFYPSDIAVEWESNGQPENNYKTTPPVLDS
DGSFFLYSRLTVDKSRWQEGNVFSCSVMHEALHNHYTQKSLSLSL
GGGGGSGGGGSGGGGSGGGGSESGYAQNGDLEDAELDDYSFSCYS
QLEVNGSQHSLTCAFEDPDVNITNLEFEICGALVEVKCLNFRKLQ
EIYFIETKKFLLIGKSNICVKVGEKSLTCKKIDLTTIVKPEAPFD
LSVVYREGCNDFVVTFNTSHLQKKYVKVLMHDVAYRQEKDENKWT
HVNLSSTKLTLLQRKLQPAAMYEIKVRSIPDHYFKGFWSEWSPSY
YFRTPEINNSSGEMD Candidate 26 Light Chain
(SEQ ID NO: 123)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC Candidate 27 (FIG. 7D) may comprise TSLPR associated with a first Fc region of the anti-IL-4R moiety (comprising a hole mutation) and IL-7Rα associated with a second Fc region of the anti-IL-4R moiety (comprising a knob mutation), where IL7-Ra and TSLPR are associated with each other. Candidate 27 may comprise a KiH mutation.

Candidate 27 Heavy Chain 1 Cys (Knob)
(SEQ ID NO: 124)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH -continued QDWLNGKEYKCKVSNKGLPSSIEKTISKAKGQPREPQVYTLPPSQ
EEMTKNQVSLSCAVKGFYPSDIAVEWESNGQPENNYKTTPPVLDS
DGSFFLVSRLTVDKSRWQEGNVFSCSVMHEALHNHYTQKSLSLSL
GGGGGSGGGGSGGGGSGGGGSESGYAQNGDLEDAELDDYSFSCYS
QLEVNGSQHSLTCAFEDPDVNITNLEFEICGALVEVKCLNFRKLQ
EIYFIETKKFLLIGKSNICVKVGEKSLTCKKIDLTTIVKPEAPFD
LSVVYREGCNDFVVTFNTSHLQKKYVKVLMHDVAYRQEKDENKWT
HVNLSSTKLTLLQRKLQPAAMYEIKVRSIPDHYFKGFWSEWSPSY
YFRTPEINNSSGEMD Candidate 27 Heavy Chain 2 Cys (Hole)
(SEQ ID NO: 125)
EVQLVESGGGLEQPGGSLRLSCAGSGFTFRDYAMTWVRQAPGKGL
EWVSSISGSGGNTYYADSVKGRFTISRDNSKNTLYLQMNSLRAED
TAVYYCAKDRLSITIRPRYYGLDVWGQGTTVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEFLGGPSVFLFPPKPKDTLYITREPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLWCLVKGFYPSDIAVEWESNGQPENNYKTTPPVLDS
DGSFFLYSRLTVDKSRWQEGNVFSCSVMHEALHNHYTQKSLSLSL
GGGGGSGGGGSGGGGSGGGGSGAAEGVQIQIIYFNLETVQVTWNA
SKYSRTNLTFHYRFNGDEAYDQCTNYLLQEGHTSGCLLDAEQRDD
ILYFSIRNGTHPVFTASRWMVYYLKPSSPKHVRFSWHQDAVTVTC
SDLSYGDLLYEVQYRSPCDTEWQSKQENTCNVTIEGLDAEKCYSF
WVRVKAMEDVYGPDTYPSDWSEVTCWQRGEIRDACAETPTPPKPK
LSK Candidate 27 Light Chain
(SEQ ID NO: 126)
DIVMTQSPLSLPVTPGEPASISCRSSQSLLYSIGYNYLDWYLQKS
GQSPQLLIYLGSNRASGVPDRFSGSGSGTDFTLKISRVEAEDVGF
YYCMQALQTPYTFGQGTKLEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC Synthesis of the Antigen Binding Domain Antigen binding complexes/moieties are designed and cloned in appropriate expression vectors. Subsequently, the vectors are transfected in CHO cells. Supernatants from those cells are collected following a two-step purification process involving: 1) purifying the antibodies on MabSelect SuRe Protein A affinity medium and 2) further purifying by size exclusion SEC Purification of HiLoad Superdex 200 pg with a final buffer being PBS with 100 mmol/l L-arginine (pH 6.5-6.7) and subsequent sterile filtration. The quantification for the antigen binding complex's yield is done by absorbance at a280 nm. The monomericity was calculated by HPLC-see measurement.

Example 4: Validation of the Antigen Binding Moiety's Binding to TSLP and IL-4R SPR studies are carried out on a Biacore 3000 instrument with a CM5 chip at 25° C. The running buffer comprises 25 mM HEPES pH 7.5, 150 mM NaCl, 0.5 mg/ml BSA, 0.005% P20. Antibodies are captured via protein A using approximately a 1/50 dilution of each antibody in the running buffer and a 2-minute contact time at a 10 µl/min flow rate. Protein A is immobilized on a CM5 chip via standard amine coupling chemistry in 10 mM acetate pH 4.5. Approximately 800 RU of each antibody is captured. The surfaces are regenerated via a 10 mM glycine pH 1.5 between cycles. Between assays the chip is regenerated with a 2-minute pulse of 100 mM Phosphoric acid. Prior to setting up multicycle kinetic analysis analyte concentration is determined spectrophotometrically using an extinction coefficient of 72,880 $M^{-1}cm^{-1}$ for IL-4R and 18450 $M^{-1}$ $cm^{-1}$ for the TSLP proteins respectively. Analyte samples are prepared by diluting stocks into running buffer to a final concentration of 500 nM for the IL-4R and 25 nM for TSLP followed by serially diluting with a 2-fold series with an association time of 2.5 minutes at a 50 µl/min flow rate. Dissociation data are collected for a period of 1600 seconds. Raw data are analyzed using the Scrubber2 (Biologic Software, AU) program using a double referencing procedure where compound signal is corrected to a blank surface and a buffer injection over the captured antibody surface. Kinetic data are analyzed by fitting to a simple 1:1 binding model.

Example 5: In Vitro Validation of the Antigen Binding Moiety's Binding to TSLP and IL-4R To further determine positioning of the antigen binding moieties described herein to achieve a viable and fully bifunctional molecule, biological assays are used to characterize the in vitro potency of each molecule. Molecules are tested in human donor PBMC (peripheral blood mononuclear cells) for measuring their ability to block IL-4 mediated responses and TSLP-mediated responses.

IL-4 mediated responses are assessed by measuring CD23 upregulation in B-cells in response to I1-4 treatment. CD23 upregulation is measured by FACS. Frozen PBMCs are thawed and incubated for 60 minutes in a humidified incubator at 37° C. and 5% $CO_2$. 100 microliters of cell suspension at $1\times10^7$ cells/mL are added to a 96-well flat bottom plate. Each well contains about $1\times10^6$ cells. 50 µL/well of 4× stock of IL-4 is added to make a final concentration of 3 ng/mL. Cells are incubated for 40 hours at 37° C. in a humidified $CO_2$ incubator set to 5% $CO_2$. Antibody cocktails of readout antibodies for FACS (CD23, CD19) and isotype controls for the number of wells that needed to be stained in FACS buffer are prepared according to manufacturer instructions. Cells are transferred to 96-well round bottom plates and washed twice with PBS. Cells are resuspended in PBS and stained with 100 µL of Zombie LIVE/DEAD stain according to the manufacturer's instructions. The cells are incubated for 20 minutes at room temperature and protected from light. The cells are spun down to remove the Zombie AQUA LIVE/DEAD stain. The cells are washed once with PBS. The cells are resuspended in 50 µL Fc blocking reagent for 10 minutes at room temperature. 50 µL of the antibody cocktail is added to the wells and the samples are incubated for 25 minutes at 4° C. protected from light. The cells are washed with PBS to remove unbound antibodies. The samples are acquired by a flow cytometer and at least 10000 events of the CD23+ population are acquired per sample.

TSLP mediated responses are assessed by measuring the secretion of Thymus and activation regulated chemokine (TARC) in human PBMCs by Meso Scale Discovery (MSD). Frozen PBMCs are thawed and incubated for 60 minutes in a humidified incubator at 37° C. and 5% $CO_2$. 100 µLs of cell suspension at $1\times10^7$ cells/mL are added to a 96-well flat bottom plate. Each well contains about $1\times10^6$ cells. 100 µL/well of the 2× stock of serially diluted recombinant human TSLP is added. Cells are incubated for 24 hours at 37° C. in a humidified $CO_2$ incubator set to 5% $CO_2$. Plates are centrifuged at 1300 rpm for 5 minutes and at least 120 µL of supernatants are collected for TARC. The plates are washed with 150 µL/well of Tris Wash Buffer. 50 µL of samples are added per well. The plates are sealed with an adhesive plate seal and incubated for 2 hours with shaking (300-1000 rpm) at room temperature. The plates are washed 3 times with 150 µL/well of Tris Wash Buffer. 25 µL of detection antibody solution is added to each well. The plate is sealed with an adhesive plate seal and incubated for 2 hours with shaking 300-1000 rpm) at room temperature. The plates are washed 3 times with 150 µL/well of Tris Wash Buffer. 150 µL of 2× read Buffer T is added to each well of the MSD plate and incubated at room temperature for 10 minutes.

Example 6: Assessment of Developability and Stability

To assess the developability of each candidate antigen binding moiety (Table 3), biochemical assays were leveraged to characterize aggregation, binding specificity, and resistance to thermal and pH stress (Table 4).

TABLE 3

Key for candidate antigen binding moiety identification.

Figure 6A:
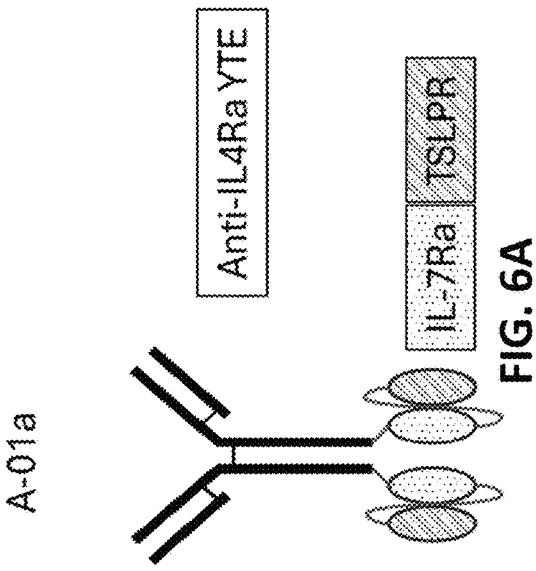
FIG. 6A-FIG. 6D show dual TSLP-TRAP construct formats.
Figure 6B:
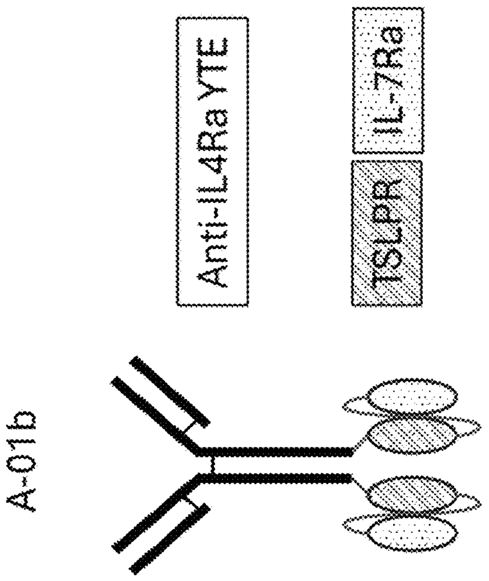
Figure 6C:
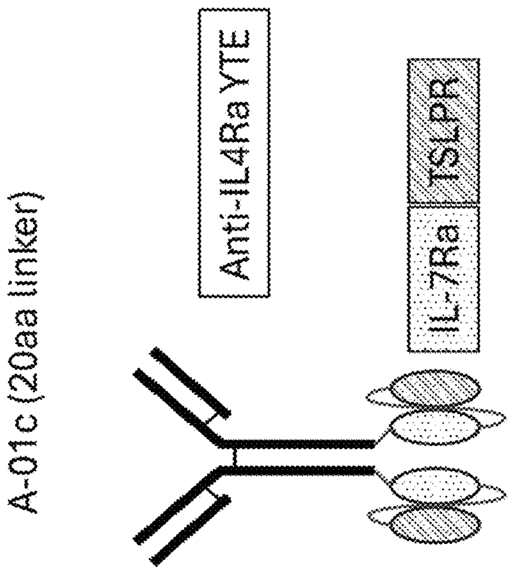
Figure 6D:
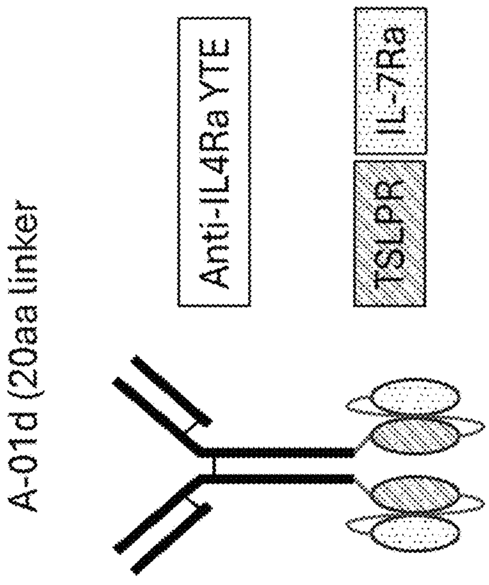
Figure 7A:
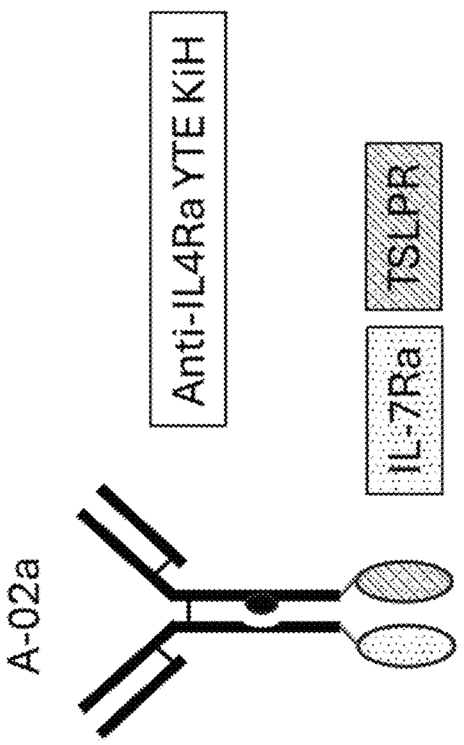
FIG. 7A-FIG. 7D show single TRAP construct formats.
Figure 7B:
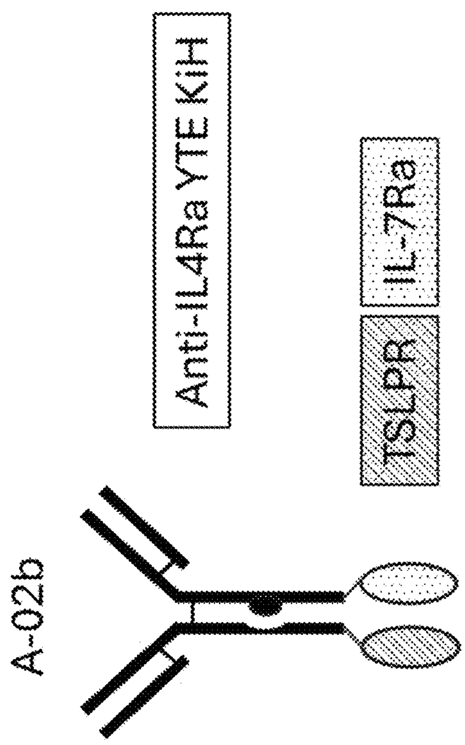
Figure 7C:
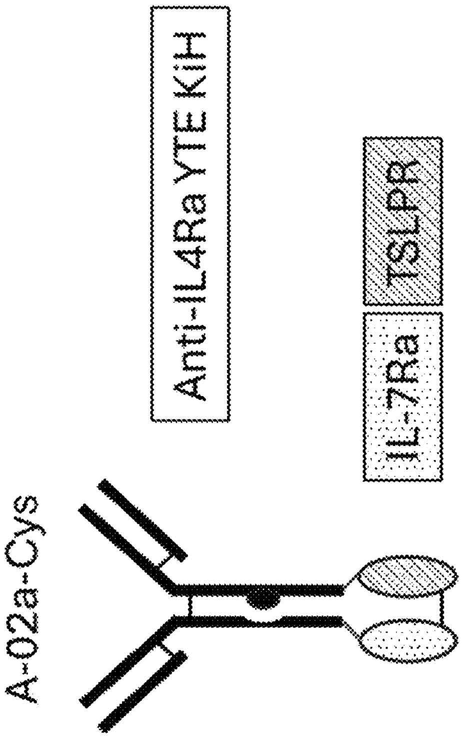
Figure 7D:
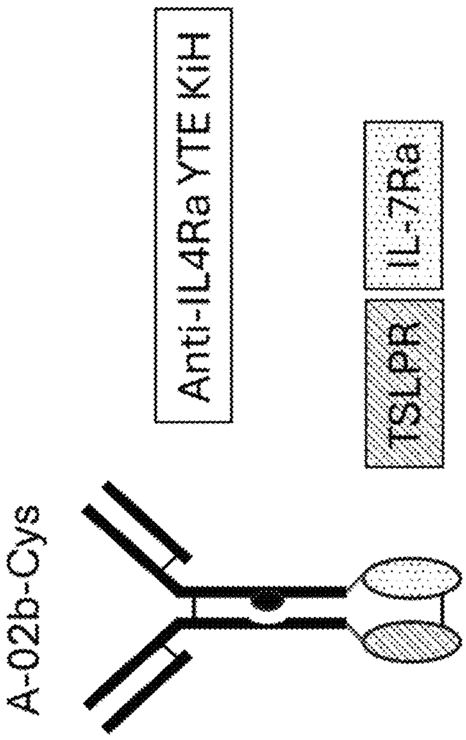

| Candidate Antigen Binding Moiety ID | Construct Format | Corresponding Figure |
|---|---|---|
| WBP71460_1 | A-01a | FIG. 6A |
| WBP71460_2 | A-01b | FIG. 6B |
| WBP71460_3 | A-01c | FIG. 6C |
| WBP71460_4 | A-01d | FIG. 6D |
| WBP71460_5 | A-02a | FIG. 7A |
| WBP71460_6 | A-02a-Cys | FIG. 7C |
| WBP71460_7 | A-02b | FIG. 7B |
| WBP71460_8 | A-02b-Cys | FIG. 7D |
| WBP71460_9 | B-01a | FIG. 1A |
| WBP71460_10 | B-02a | FIG. 1C |
| WBP71460_11 | B-04a | FIG. 3A |
| WBP71460_15 | C-02a | FIG. 4E |

TABLE 3-continued

Key for candidate antigen binding moiety identification.

| Candidate Antigen Binding Moiety ID | Construct Format | Corresponding Figure |
|---|---|---|
| WBP71460_16 | C-05a | FIG. 5C |
| WBP71460_17 | Dupilumab | N/A |
| WBP71460_19 | Tezepelumab | N/A |
| WBP71460_20 | B-01a-T | FIG. 8A |
| WBP71460_21 | B-02a-T | FIG. 8C |
| WBP71460_22 | B-04a-T | FIG. 10A |
| WBP71460_23 | Candidate 19.1_with_LS_instead_of_YTE | FIG. 5C (but with LS instead of YTE) |
| WBP71460_24 | Candidate 19.1_without_half-life_extension | FIG. 5C (but with no half-life extension) |
| WBP71460_25 | Candidate 19.1_with_(EA3K)3_linker | FIG. 5C |
| WBP71460_26 | Candidate 19.1_with_(G4S)3_linker | FIG. 5C |
| WBP71460_27 | Candidate 19.1_with_(G4S)2_linker | FIG. 5C |
| WBP71460_28 | Candidate 19.1_with_(G4S)1_linker | FIG. 5C |
| WBP71460_29 | Candidate 19.1_in_2-1_format_(Knob_Hole) | FIG. 5G |

Nonspecific interactions can present a challenge in the successful development of therapeutic biomolecules.

To assess the tendency of each candidate antigen binding moiety to self-aggregate, affinity-capture self-interaction nanoparticle spectroscopy (AC-SINS) was performed. Briefly, antigen binding moieties described herein were diluted in PBS and incubated with nanoparticles functionalized with an anti-Fc capture IgG. After a brief equilibration at room temperature, the plasmon resonance was measured by UV-Vis. A red-shift in the λmax can be used to assess antibody self-association: larger shifts indicate higher self-interaction propensity. As shown in Table 4, WBP71460_1-WBP71460_8 and WBP71460-19 exhibited low AC-SINS shift; WBP71460-11, WBP71460-16 exhibited medium AC-SINS shift; and WBP71460-9, WBP71460-10, WBP71460-15, and WBP71460-17 exhibited high AC-SINS shift. Low AC-SINS shift indicates that the binding moieties have low-self-association (aggregation) and show good colloidal stability. The binding moieties comprising scFv (e.g., WBP71460-9 and WBP71460-10) exhibited high AC-SINS shift indicating strong self-interaction/aggregation tendency, which can result in poor solubility, high viscosity, and non-specific interactions in-vivo.

Insulin aggregation was also measured to determine the propensity of candidate antigen binding moieties to bind non-specifically. Antigen binding moieties described herein were mixed with human insulin. After incubation, binding was measured. An increase in absorbance versus a negative and positive control reflects the propensity for non-specific binding. As shown in Table 4, WBP71460-11 and WBP71460-19 exhibited low affinity to insulin, while WBP71460-1-WBP71460-3, WBP71460-5, WBP71460-7, WBP71460-9, and WBP71460-16 exhibited medium level affinity to insulin. WBP71460-9, WBP71460-10, WBP71460-15, and WBP71460-17 exhibited high affinity to insulin. The binding moieties comprising scFv (e.g., WBP71460-9 and WBP71460-10) showed high insulin binding indicating strong non-specificity.

To assess candidate antigen binding moieties' propensity for off-target binding, binding assays involving the nonspecific target Baculovirus Particle (BVP) assay were performed. Candidate antigen binding moieties described herein were mixed with BV proteins. After incubation, binding was measured. An increase in absorbance versus a negative and positive control reflects propensity to engage in non-specific aggregation. Table 4 shows that only WBP71460-16 and WBP71460-19 exhibited low BVP binding indicating that these constructs have low non-specific binding (low polyreactivity). This indicates that these constructs may have reduced off-target effects.

Compared to other scFv constructs (WBP71460-9, WBP71460-10, and WBP71460-11) or other Fab configuration (WBP71460-15), WBP71460-16 (Candidate 19.1) exhibited medium AC-SINS and insulin binding, indicating moderate self-association and polyreactivity, respectively. Importantly, it showed low BVP binding, suggesting strong specificity (Table 4). Overall, WBP71460-16 (Candidate 19.1) showed a more favorable developability profile.

During purification and storage of a biomolecule, aggregation and degradation can occur, generating size and/or charge heterogeneity. Therefore, candidate antigen binding moieties were subjected to thermal stress. Candidate antigen binding moieties were incubated at 40° C. for 14 days. Size heterogeneity following thermal stress was assessed using size-exclusion chromatography (SEC). WBP71460-16 (Candidate 19.1) exhibited a surprising resistance to thermal stress with about 3.36% change in purity, indicating strong stability and resistance to heat-induced degradation or aggregation. In contrast, the binding moiety comprising scFv showed a significantly higher change in purity (e.g., 11.8~13.94) suggesting greater susceptibility to thermal stress. The binding moiety comprising scFv exhibited a 3-4-fold greater loss in purity compared to the WBP71460-16 (Candidate 19.1).

Charge heterogeneity following thermal stress was assessed using imaged capillary isoelectric focusing (iCIEF). WBP71460-16 (Candidate 19.1) exhibited a 0% change in main peak size. Structural integrity following thermal stress was assessed using Caliper-NR (non-reduced) and Caliper-R (reduced). WBP71460-16 (Candidate 19.1) exhibited a 0% change in main peak size and 0.54% change in purity, respectively. In short, WBP71460-16 (Candidate 19.1) effectively maintained size and charge homogeneity and structural integrity relative to other candidates (Table 4).

These results demonstrate that WBP71460-16 (Candidate 19.1) is unexpectedly strongly resistant to thermal stress compared to other candidate antigen binding moieties (e.g., comprising scFv constructs).

WBP71460-16 (Candidate 19.1) also exhibited unexpectedly high solubility of over 200 mg/mL with low viscosity, indicating that WBP71460-16 (Candidate 19.1) can be suitable for subcutaneous administration or high concentration formulation.

Candidate antigen binding moieties were tested to measure their ability to specifically bind TSLP. TSLP binding was assessed using a surface plasmon resonance (SPR) experiment which was performed using the Cytiva Biacore 8K system with a CM5 chip and 1×HBS-FP+ running buffer. Anti-human Fc IgG (Jackson) was immobilized as the capture molecule. Candidate antigen binding moieties were then captured at concentrations ranging from 20 to 1000 nM, with a contact time of 30 seconds and a flow rate of 10 μL/min. For the association and dissociation steps, the analyte TSLP (ACRO-TSP-H52Hb-100 μg) was introduced at varying concentrations between 0 and 20 nM, with association for 180 seconds and dissociation for 3600 seconds at a flow rate of 30 μL/min. Regeneration of the sensor surface was performed using 10 mM glycine at pH 1.5. Association and dissociation phases were monitored at 30 μL/min for 180 and 3,600 seconds, respectively, and analyzed using a 1:1 Langmuir binding model with Biacore evaluation software.

TABLE 4

Developability and resistance to thermal and pH stress.

| | Micro developability | | | Thermal stress(40° C.) | | | | |
|---|---|---|---|---|---|---|---|---|
| | | | | SEC Δpurity % | iCIEF Δ main peak % | Caliper-NR Δmain peak % | Caliper-R Δpurity % | pH stress SEC Δpurity % |
| Sample Name | AC-SINS | Insulin | BV | (T0-2 W) | (T0-2 W) | (T0-2 W) | (T0-2 W) | (T0-0.5 H) |
| WBP71460-1 | Low | Medium | High | 60.25 (c) | 34.65 (c) | 32.46 (c) | 66.03 (c) | 71.31 (c) |
| WBP71460-2 | Low | Medium | High | 63.53 (c) | 8.23 (c) | 17.62 (c) | 87.30 (c) | 78.65 (c) |
| WBP71460-3 | Low | Medium | High | 62.20 (c) | 37.67 (c) | 39.41 (c) | 64.94 (c) | 76.30 (c) |
| WBP71460-4 | Low | High | High | 64.37 (c) | 6.91 (c) | 14.01 (c) | 89.23 (c) | 80.48 (c) |
| WBP71460-5 | Low | Medium | High | 77.32 (c) | 9.93 (c) | 54.65 (c) | 98.66 (c) | 63.66 (c) |
| WBP71460-6 | Low | High | High | 61.97 (c) | 14.04 (c) | 36.64 (c) | 99.19 (c) | 40.35 (c) |
| WBP71460-7 | Low | Medium | High | 92.00 (c) | 25.72 (c) | 47.89 (c) | 99.05 (c) | 60.04 (c) |
| WBP71460-8 | Low | High | High | 64.21 (c) | 16.52 (c) | 39.51 (c) | 98.58 (c) | 40.19 (c) |
| WBP71460-9 | High | Medium | High | 13.94 (c) | 12.43 (c) | 1.60 (a) | 0.77 (a) | 65.63 (c) |
| WBP71460-10 | High | High | High | 14.83 (c) | 8.67 (b) | 0.68 (a) | 0.46 (a) | 70.65 (c) |
| WBP71460-11 | Medium | Low | High | 11.8 (c) | 7.62 (b) | 3.44 (b) | 0.58 (a) | 78.65 (c) |
| WBP71460-15 | High | High | High | 1.86 (a) | 5.20 (b) | 1.87 (a) | 0.57 (a) | 41.88 (c) |
| WBP71460-16 | Medium | Medium | Low | 3.36 (b) | 0.00 (a) | 0.00 (a) | 0.54 (a) | 18.09 (c) |
| WBP71460-17 | High | High | Medium | 0.00 (a) | 5.81 (b) | 0.90 (a) | 0.29 (a) | 19.45 (c) |
| WBP71460-19 | Medium | Low | Low | 0.31 (a) | 8.31 (b) | 0.54 (a) | 0.09 (a) | 4.85 (b) |

(a = low, b = medium, c = high)

Example 7: In Vitro Binding Properties and Functional Potency

Candidate antigen binding moieties (Table 3) were subjected to in vitro experimentation to determine their binding affinity for targets TSLP and IL-4R and their ability to reduce or abrogate TSLP- and IL-4-mediated pathways, both of which represent important parameters indicative of antibody quality and therapeutic potential.

TABLE 5

Binding of TSLP by antigen binding moieties as measured via SPR.

| Analyte | Ligand | $k_a$ (1/Ms) | $k_d$ (1/s) | $K_D$ (M) | $R_{max}$ (RU) | Capture level (RU) | Relative binding response |
|---|---|---|---|---|---|---|---|
| W71460-hPro1.His | WBP71460_1 | 7.23E+06 | 2.60E−05 | 3.59E−12 | 23.7 | 357.4 | 31% |
| | WBP71460_2 | 5.85E+06 | 2.64E−05 | 4.50E−12 | 22.5 | 342.9 | 31% |
| | WBP71460_3 | 6.84E+06 | 5.88E−05 | 8.60E−12 | 22.3 | 333.3 | 31% |
| | WBP71460_4 | 5.71E+06 | 3.98E−05 | 6.97E−12 | 19.9 | 344.6 | 27% |
| | WBP71460_5 | 5.68E+06 | 3.56E−05 | 6.26E−12 | 20.3 | 373.4 | 20% |
| | WBP71460_6 | 3.68E+06 | 1.15E−05 | 3.12E−12 | 15.2 | 360.6 | 16% |
| | WBP71460_7 | 4.68E+06 | 4.76E−05 | 1.02E−11 | 22.3 | 357.2 | 23% |
| | WBP71460_8 | 4.40E+06 | 1.52E−05 | 3.46E−12 | 15.4 | 338.4 | 17% |
| | WBP71460_9 | 1.55E+06 | 3.00E−05 | 1.94E−11 | 36.4 | 222.7 | 61% |
| | WBP71460_10 | 9.93E+05 | 3.52E−05 | 3.55E−11 | 38.6 | 229.3 | 63% |
| | WBP71460_11 | 3.21E+06 | 2.19E−05 | 6.82E−12 | 32.7 | 201.7 | 61% |
| | WBP71460_15 | 7.97E+05 | 3.92E−05 | 4.93E−11 | 45.5 | 279.0 | 61% |
| | WBP71460_16 | 3.26E+06 | 2.47E−05 | 7.58E−12 | 33.2 | 337.4 | 44% |
| | WBP71460_17 | No or weak binding | | | | 397.7 | NA |
| | WBP71460_19 | 3.73E+06 | 1.94E−05 | 5.20E−12 | 39.8 | 164.8 | 65% |
| | W71460-cAb1 | 2.34E+06 | 1.45E−05 | 6.18E−12 | 48.8 | 198.1 | 66% |

As shown in Table 5, WBP71460-16 (Candidate 19.1) exhibited strong binding interactions with an association rate (ka) of $3.26\times10^{6}$ (1/Ms) and a dissociation rate (kd) of $2.47\times10^{-5}$ (1/s), yielding a binding affinity ($K_D$) of $7.58\times10^{-12}$ M. Compared to other binding moieties (e.g., comprising scFv such as WBP71460_9 and WBP71460_10), WBP71460-16 (Candidate 19.1) exhibited a KD from about 2.6 to about 4.7-fold stronger binding. Importantly, the binding of WBP71460_16 (Candidate 19.1) was also comparable to tezepelumab (WBP71460_19 and W71460-cAb1), demonstrating that TSLP binding is not disrupted by this format.

Figure 16A:
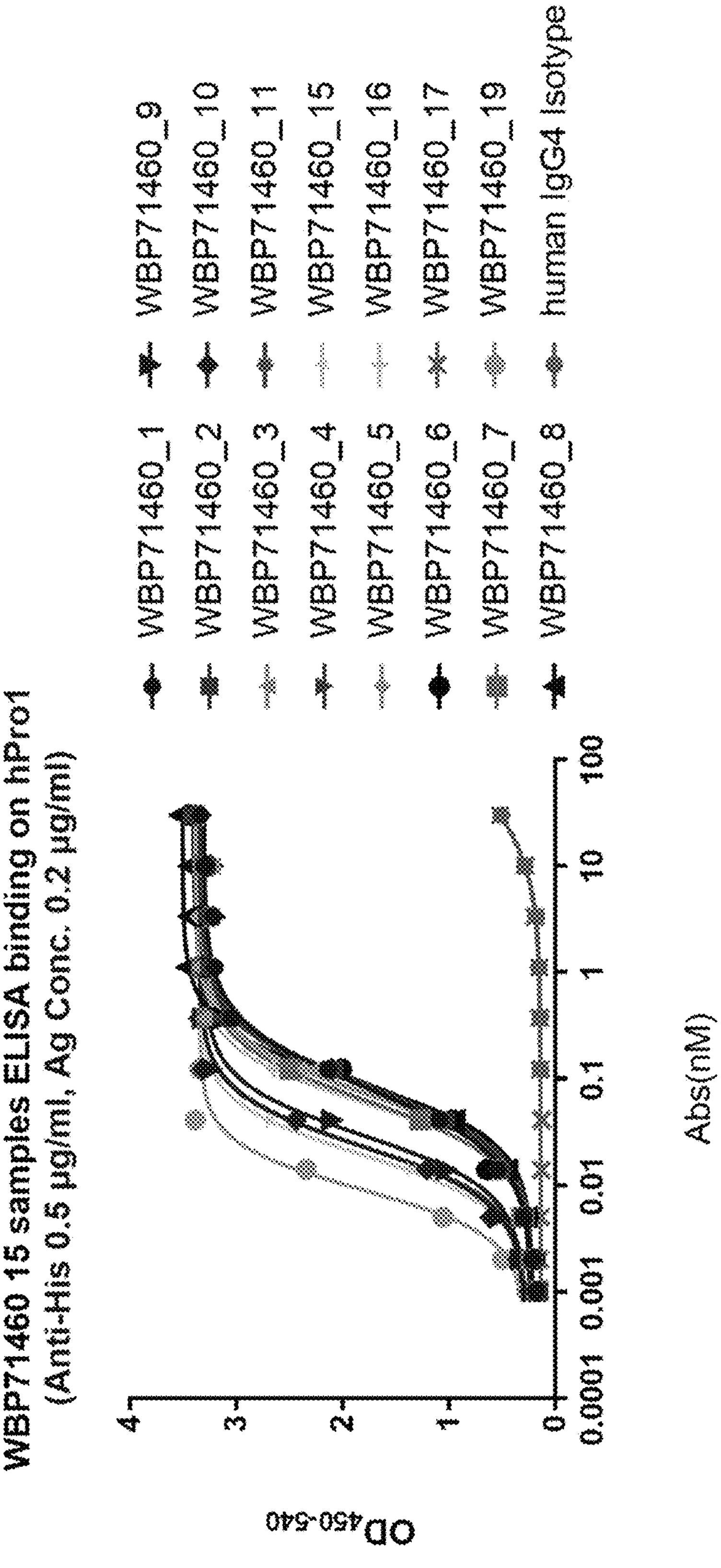
FIG. 16A and FIG. 16B show the binding of each candidate antigen binding moiety to histidine (His)-tagged TSLP measured by an ELISA assay.
Figure 16B:
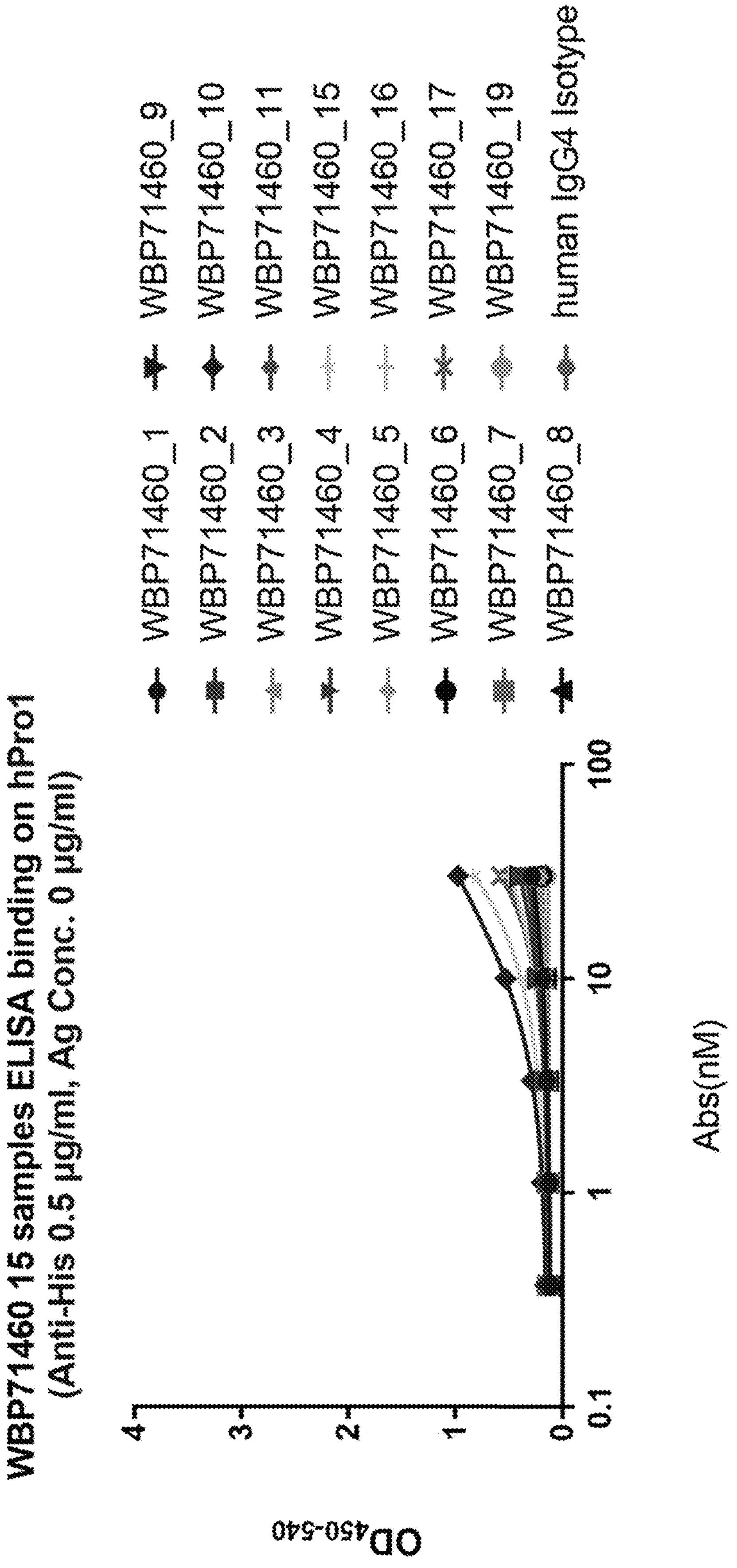
Figure 17A:
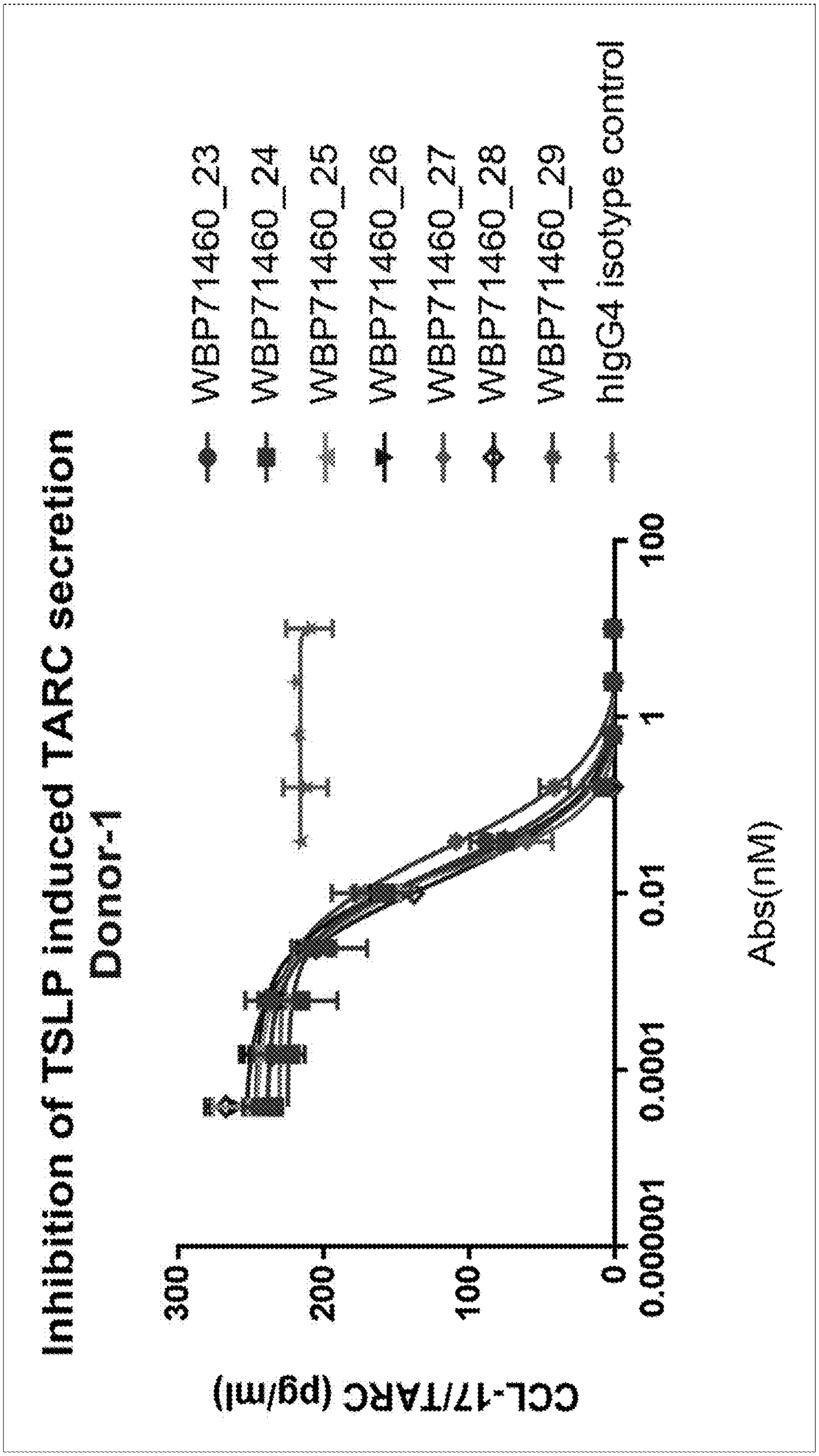
FIG. 17A and FIG. 17B show ELISA assay in human PBMCs.
Figure 17B:
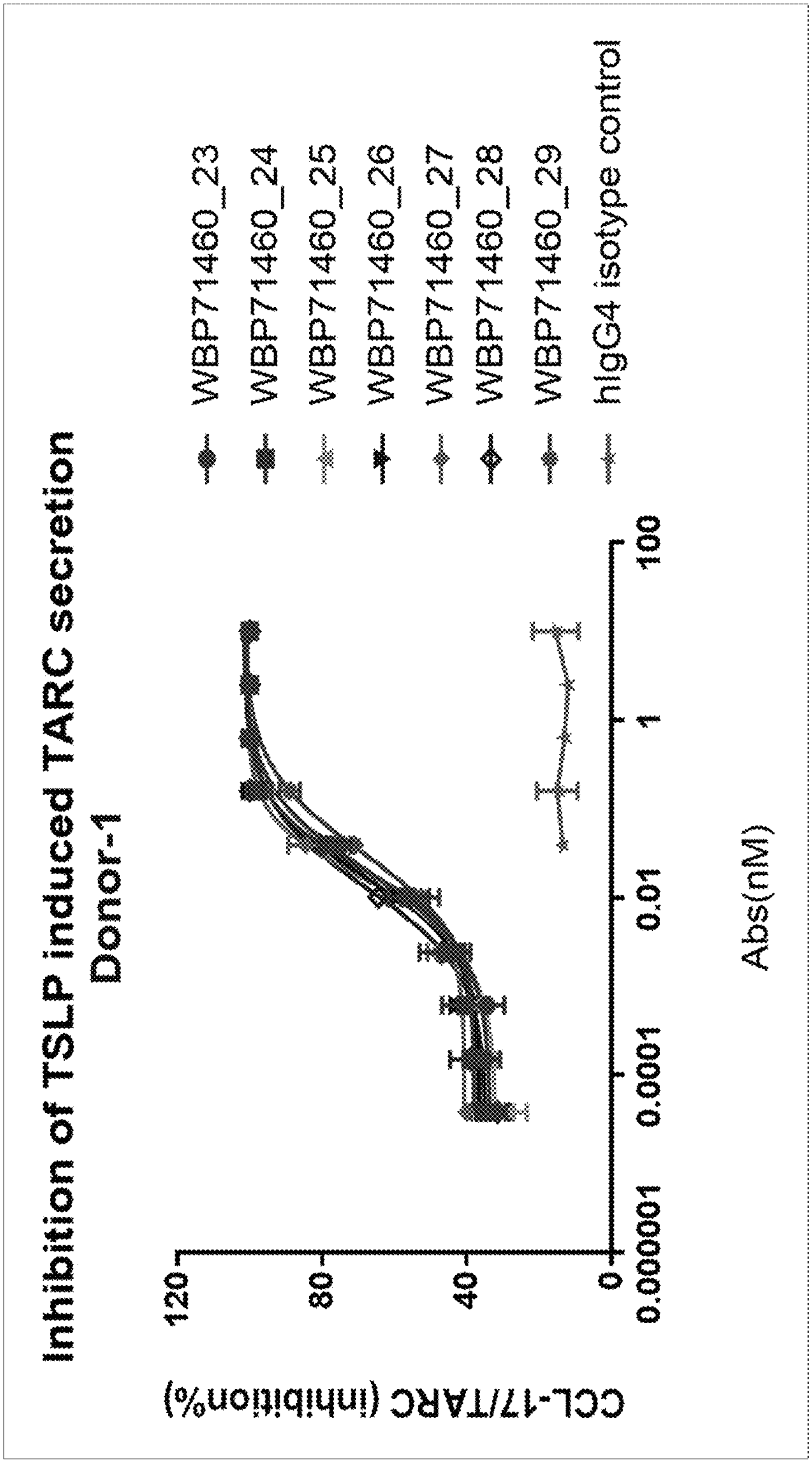
Figure 18A:
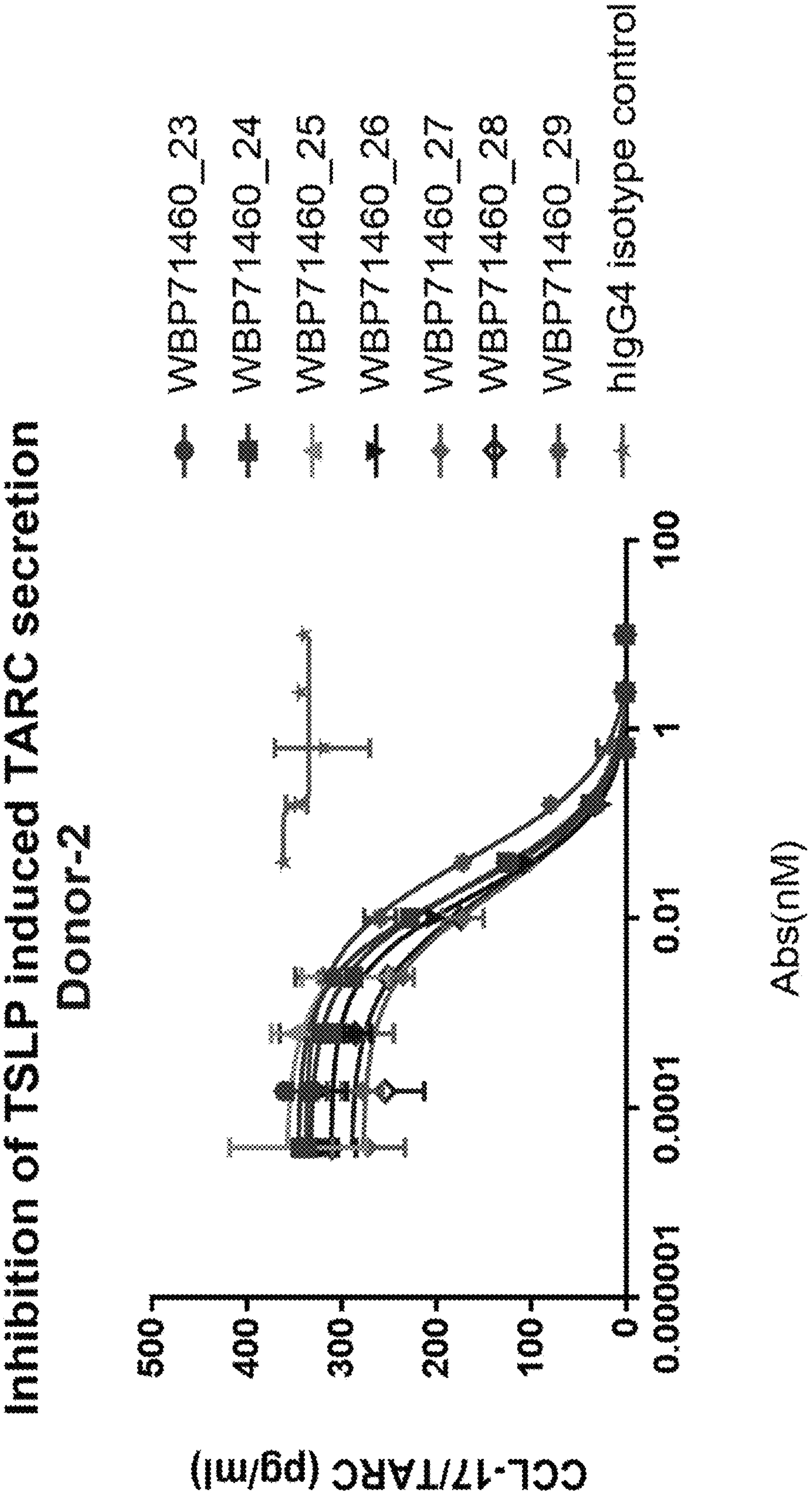
FIG. 18A and FIG. 18B show ELISA assay in human PBMC.
Figure 18B:
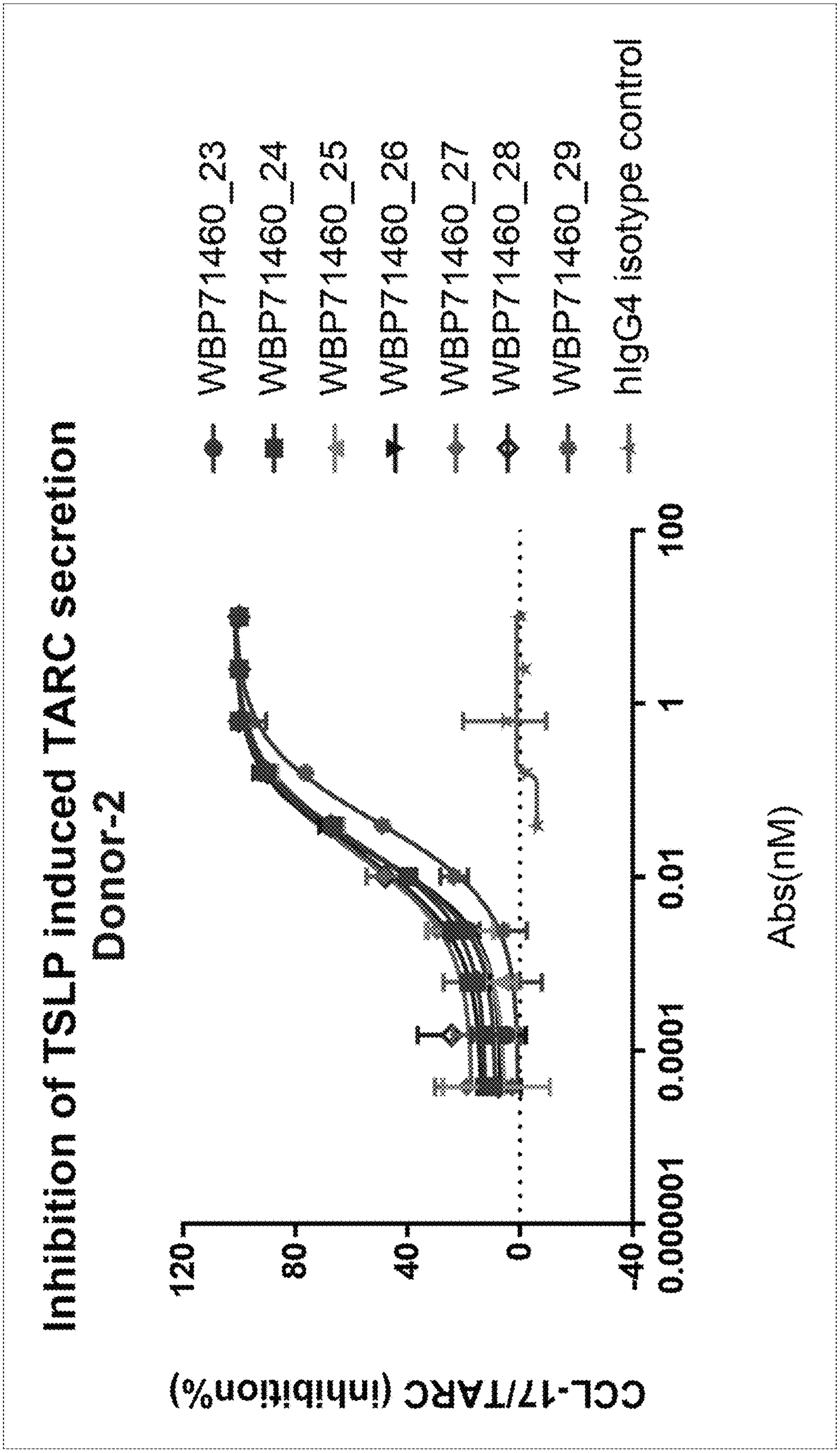
Figure 19A:
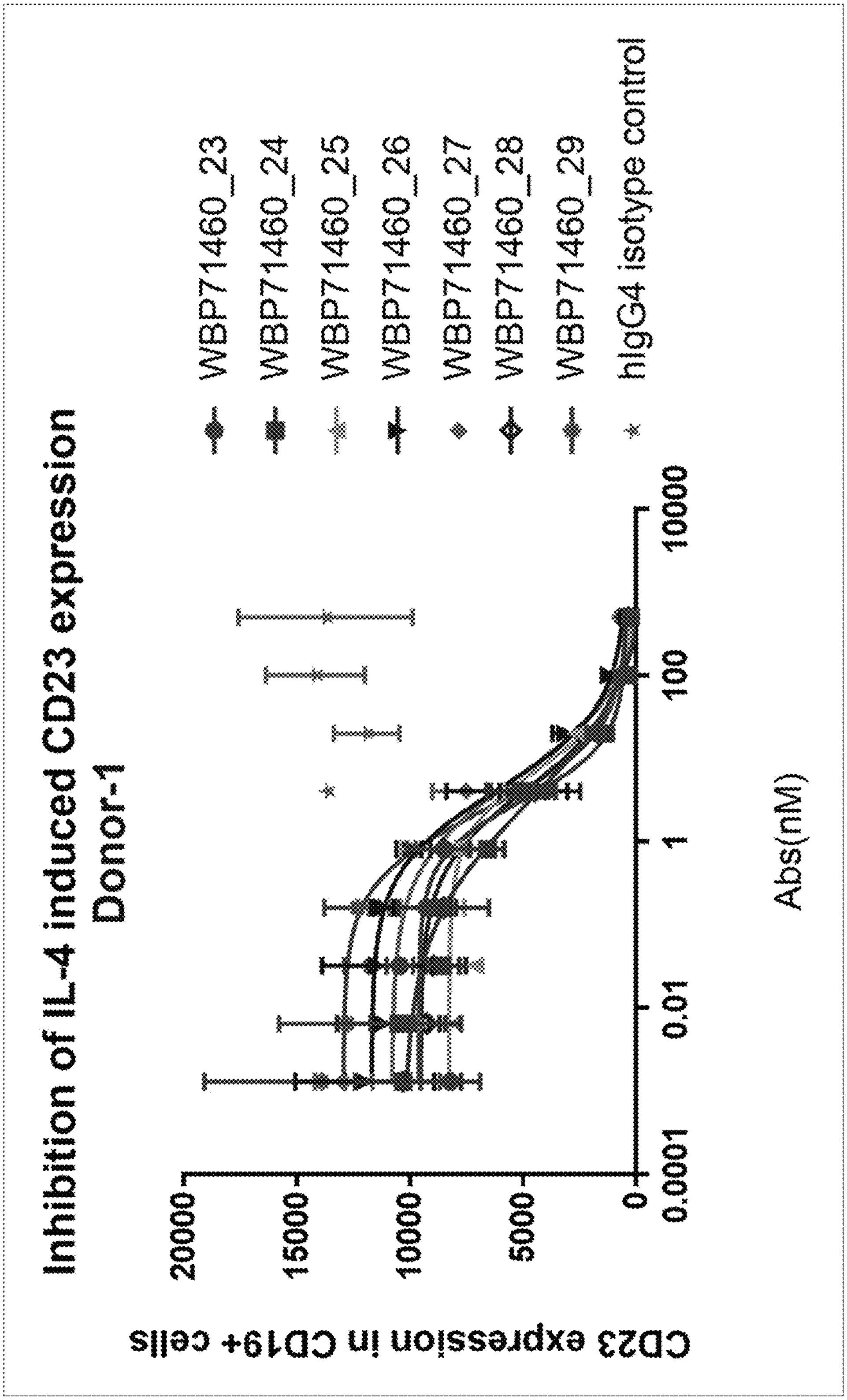
FIGS. 19A-19F show flow cytometry in human peripheral blood mononuclear cells (PBMCs).
Figure 19B:
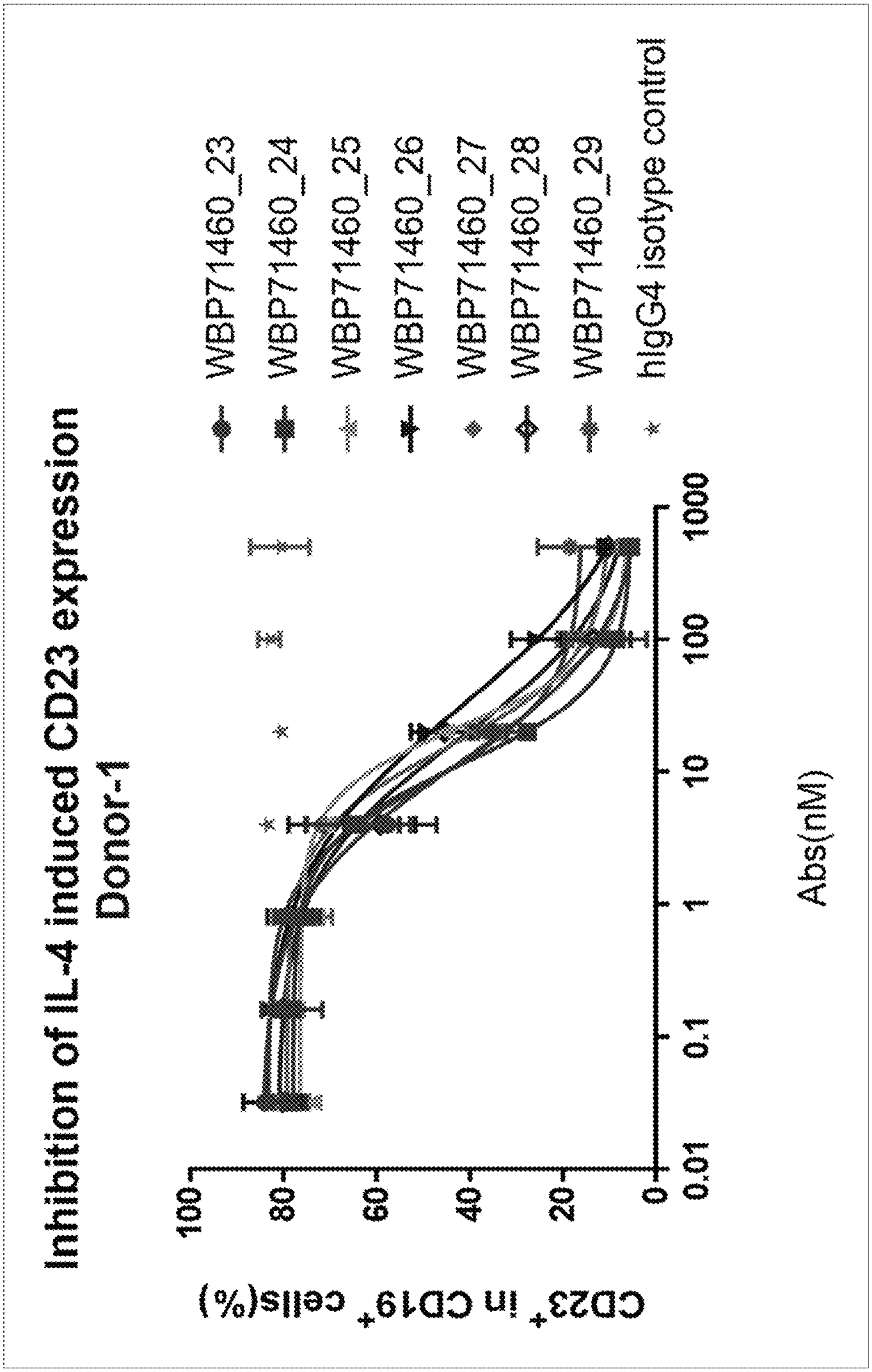
Figure 19C:
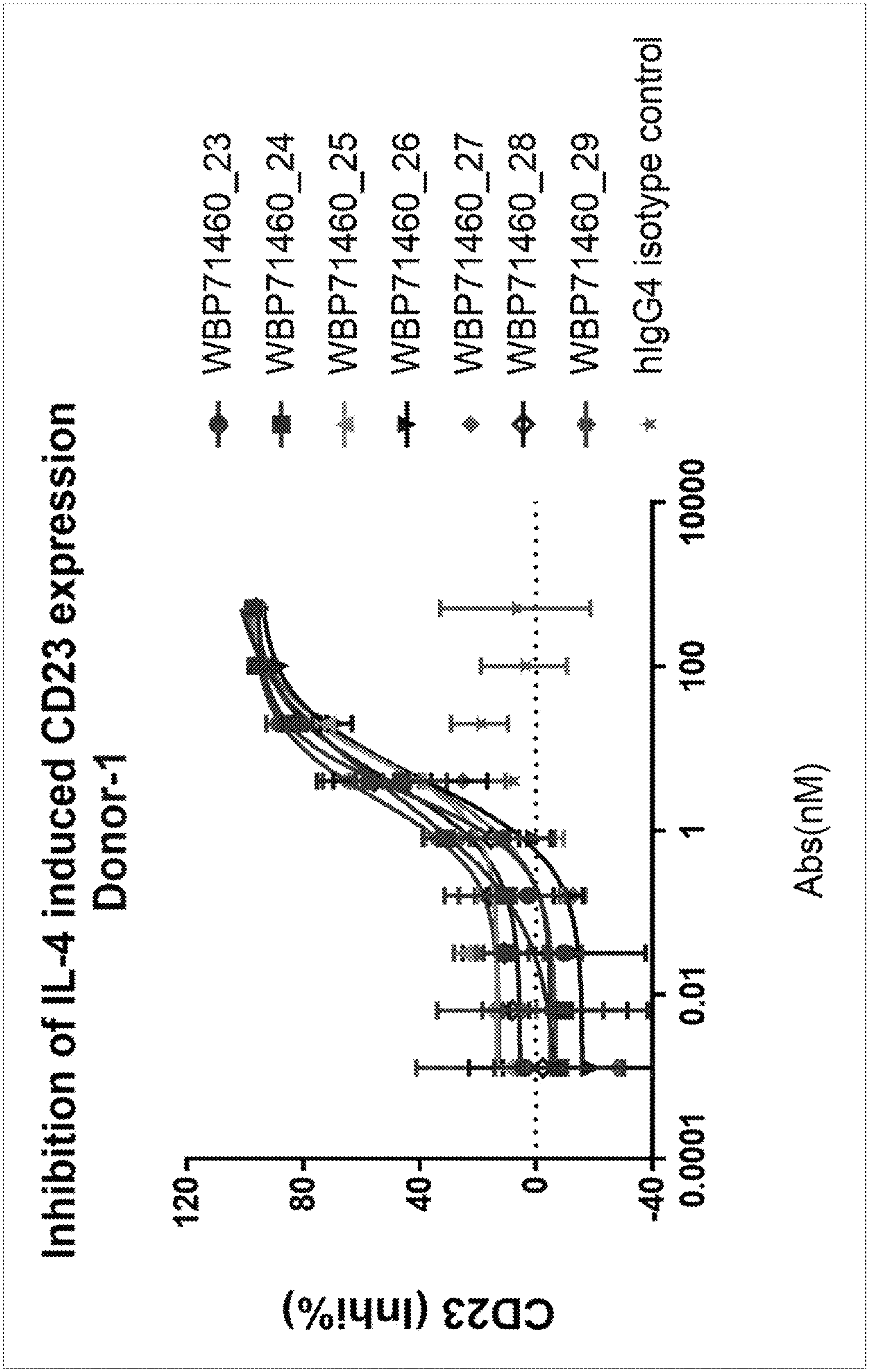
Figure 19D:
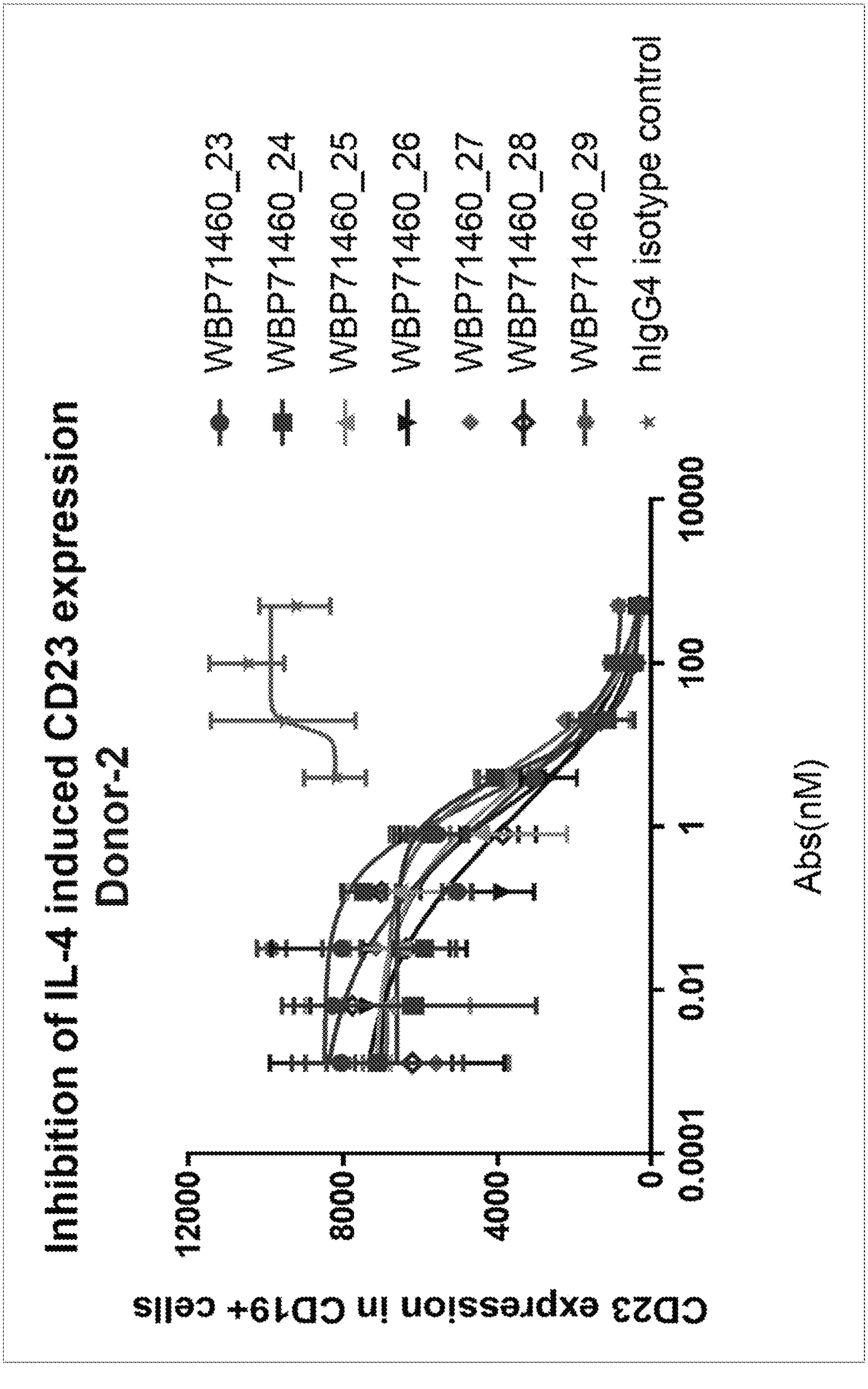
Figure 19E:
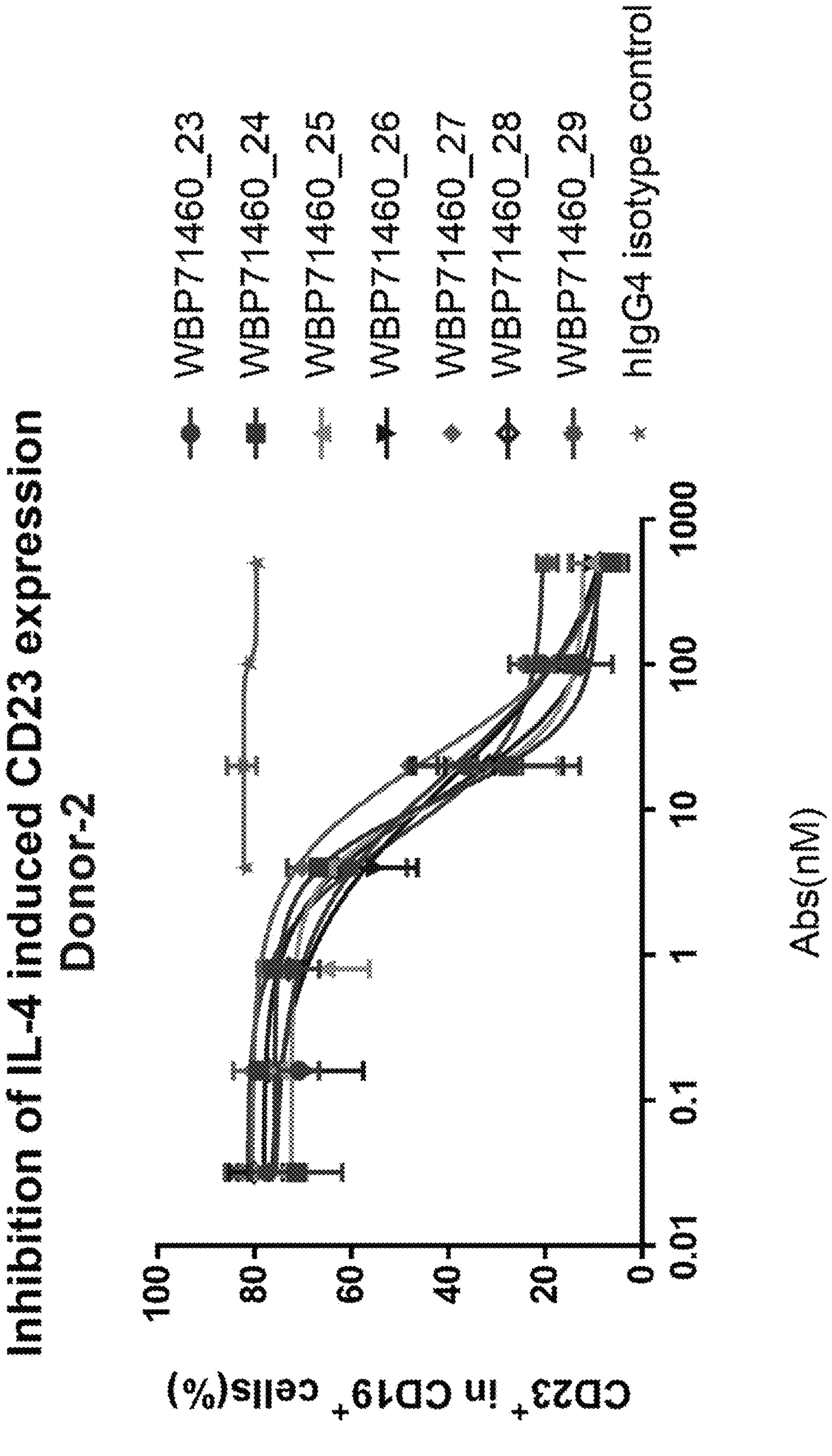
Figure 19F:
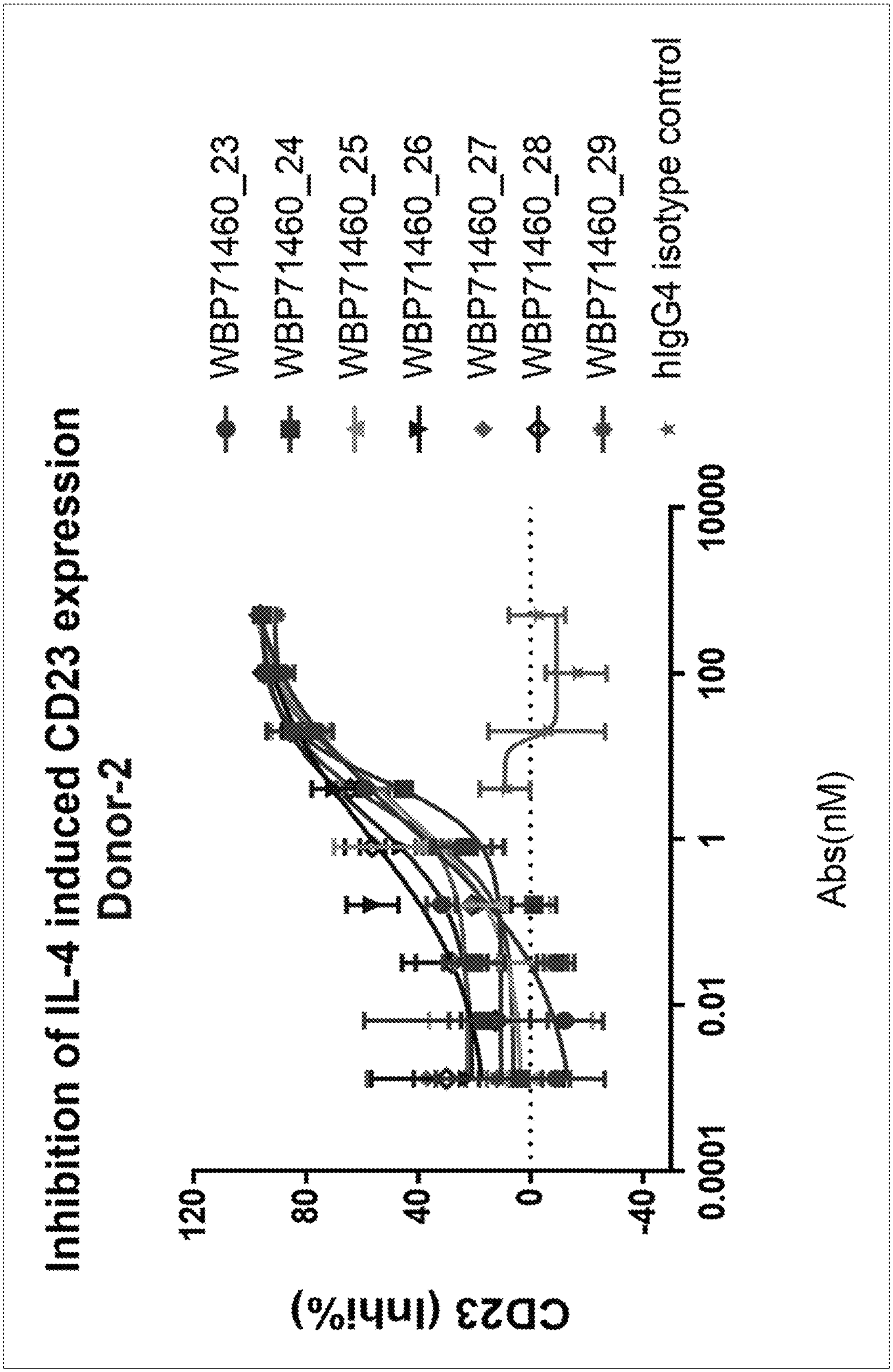

TSLP binding was also assessed via ELISA. The ELISA was performed by first coating the plate with 0.5 μg/mL anti-histidine antibodies at 4° C. overnight. Subsequently, wells were blocked using 2% BSA at 25° C. for 1 hour to prevent nonspecific binding. Next, 0.2 μg/mL (or 0 μg/mL) of a His-tagged TSLP (ACRO-TSP-H52Hb-100 μg) was added. After this step, antibodies were applied, diluted in 2% BSA from a starting concentration of 30 nM using a three-fold serial dilution, and incubated at 25° C. for 2 hours. Detection was achieved by adding goat anti-human IgG-Fc-HRP (1:5000 dilution in 2% BSA) and incubating at 25° C. for 1 hour. Finally, the assay was developed, and absorbance was measured at OD450-OD540 (where OD=optical density) to quantify the results (FIG. 16A and FIG. 16B). WBP71460-16 (Candidate 19.1) exhibited a higher $EC_{50}$ (0.060 nm) compared to scFv constructs (e.g., WBP71460_9, WBP71460_10, or WBP71460_11 with EC50 of 0.029 nM, 0.023 nM, or 0.023 nM, respectively) (Table 6).

TABLE 6

ELISA binding results to TSLP.

| Abs(nM) | Ag: 0.2 μg/ml EC50(nM) | Ag: 0.2 μg/ml Max OD450-540 | Ag: 0 μg/ml EC50(nM) | Ag: 0 μg/ml Max OD450-540 |
|---|---|---|---|---|
| WBP71460_1 | 0.080 | 3.34 | NA | 0.29 |
| WBP71460_2 | 0.088 | 3.42 | NA | 0.35 |
| WBP71460_3 | 0.073 | 3.39 | NA | 0.24 |
| WBP71460_4 | 0.084 | 3.40 | NA | 0.40 |
| WBP71460_5 | 0.073 | 3.42 | NA | 0.21 |
| WBP71460_6 | 0.093 | 3.45 | NA | 0.20 |
| WBP71460_7 | 0.063 | 3.40 | NA | 0.23 |
| WBP71460_8 | 0.092 | 3.53 | NA | 0.24 |
| WBP71460_9 | 0.029 | 3.34 | NA | 0.40 |
| WBP71460_10 | 0.023 | 3.40 | NA | 0.98 |
| WBP71460_11 | 0.023 | 3.35 | NA | 0.32 |
| WBP71460_15 | 0.019 | 3.37 | NA | 0.83 |
| WBP71460_16 | 0.060 | 3.37 | NA | 0.50 |
| WBP71460_17 | NA | 0.52 | NA | 0.58 |
| WBP71460_19 | 0.009 | 3.38 | NA | 0.16 |
| hIgG4 isotype | NA | 0.51 | NA | 0.53 |
| NC | NA | 0.13 | NA | 0.11 |
| Blank | NA | 0.01 | NA | 0.01 |

Candidate antigen binding moieties described herein were tested for IL4-induced CD23 upregulation and IL-4R binding.

Candidate antigen binding moieties described herein were tested in human donor PBMCs (peripheral blood mononuclear cells) to measure their ability to block IL-4-mediated responses, which was assessed via FACS. On day 0, fresh PBMCs were seeded at $2\times10^{5}$ cells per 100 μL per well. Serial dilutions of the test antibody are prepared and added at 50 μL per well, along with 3 ng/mL IL-4 in 50 μL per well. The cells were incubated at 37° C. with 5% $CO_2$ for 3 days. After incubation, cells were harvested and treated with 50 μL Fc blocking reagent at room temperature for 10 minutes to prevent nonspecific antibody binding. Subsequently, a 50 μL antibody cocktail targeting CD23 and CD19 was added. The samples were incubated at 4° C. for 30 minutes and washed. This was immediately followed by FACS analysis to assess CD23 expression levels on CD19+ B cells (FIG. 11A, FIG. 11B, FIG. 12A, and FIG. 12B). IC50 values were derived by nonlinear regression. WBP71460-16 (Candidate 19.1) displayed strong CD23 inhibition, with an $IC_{50}$ of 2.45 nM (Table 7).

Figure 13:
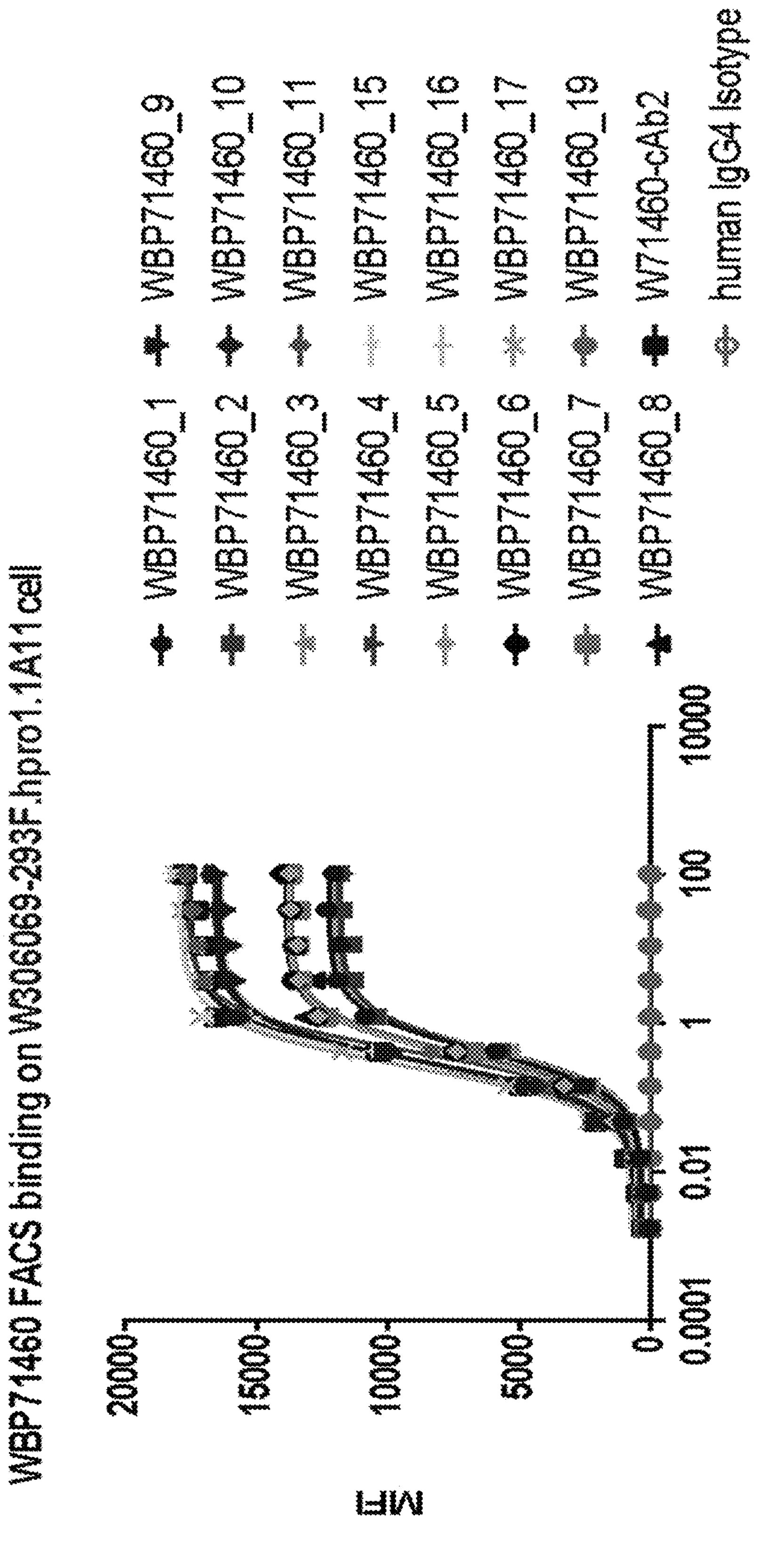
FIG. 13 shows a fluorescence-activated cell sorting (FACS)-based binding assay to quantify the binding of each candidate antigen binding moiety to IL-4R. Data are expressed as median fluorescent intensity.
Figure 14A:
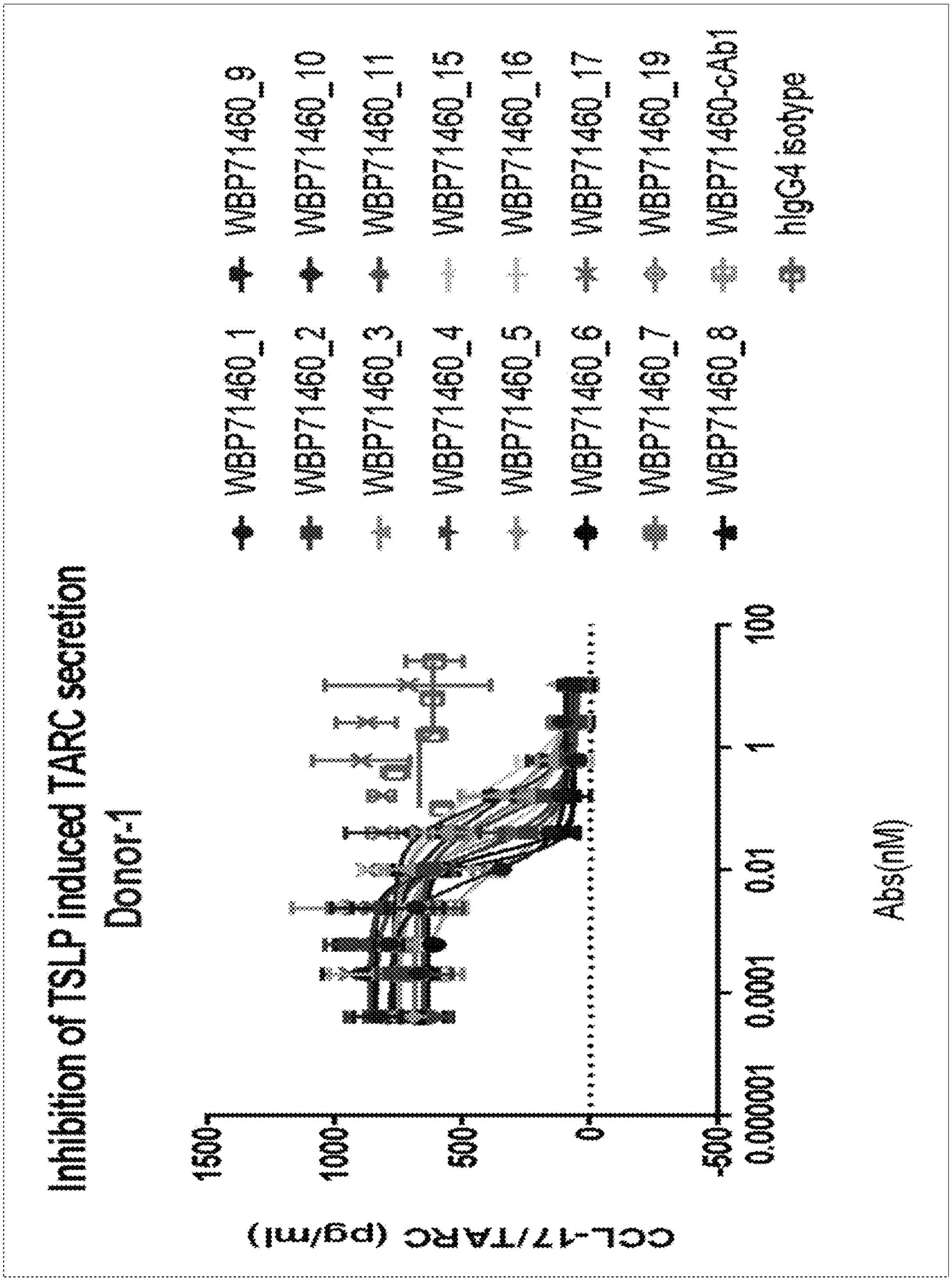
FIG. 14A and FIG. 14B show enzyme-linked immunosorbent assay (ELISA) results in human PBMCs.
Figure 14B:
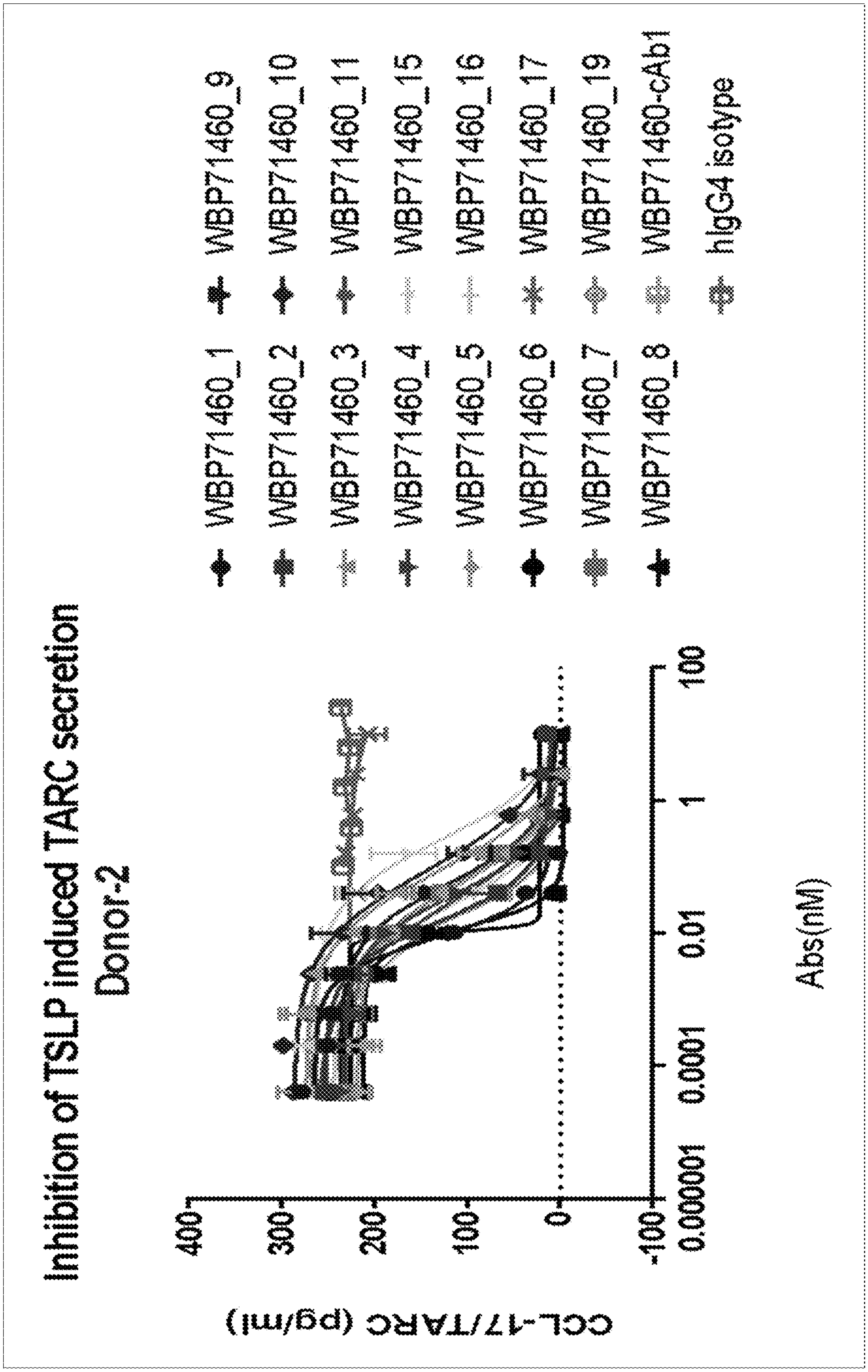
Figure 15A:
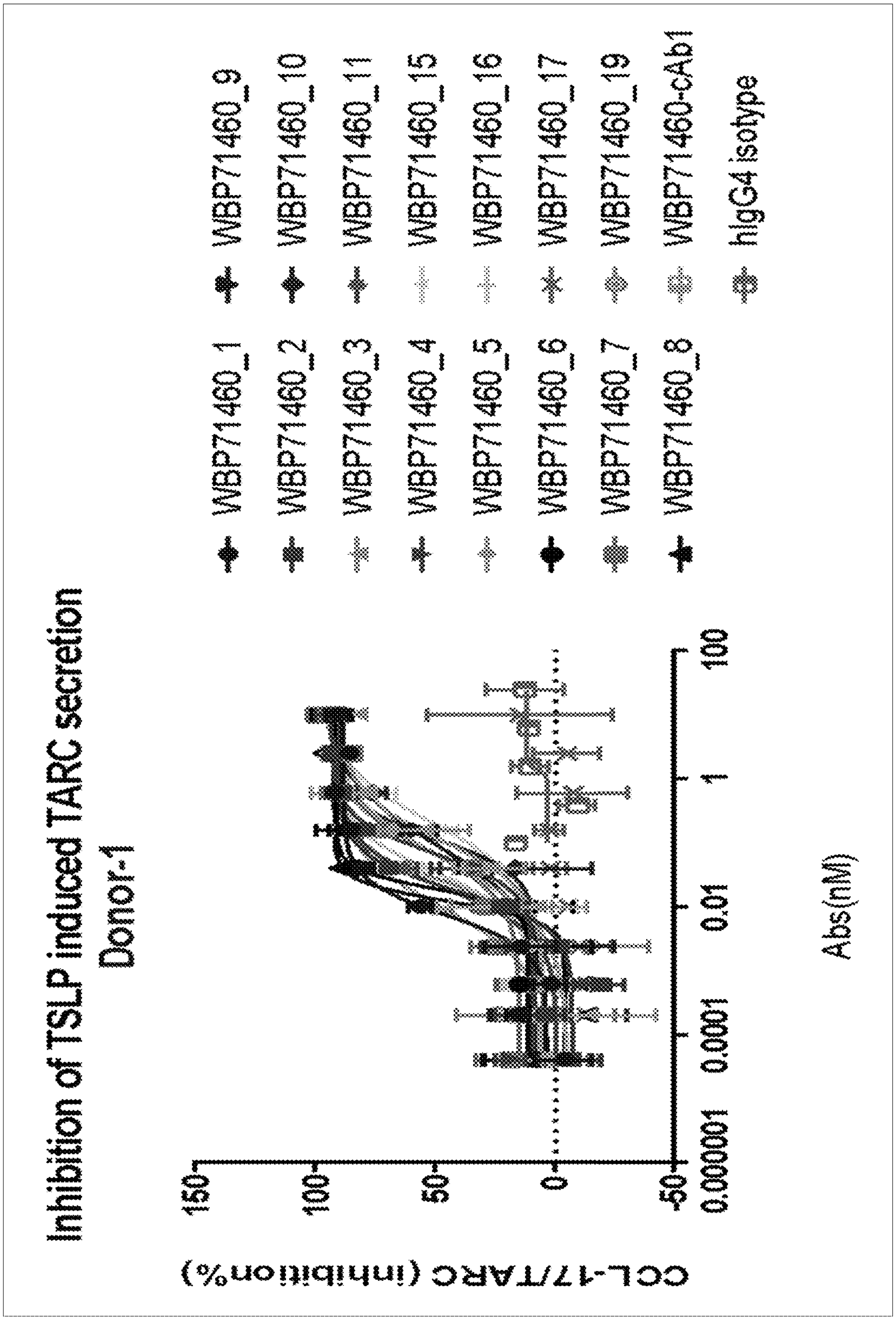
FIG. 15A and FIG. 15B show the percentage inhibition of TARC/CCL-17 secretion by PBMCs was inhibited by each candidate antigen binding moiety in Donors 1 (FIG. 15A) and Donor 2 (FIG. 15B).
Figure 15B:
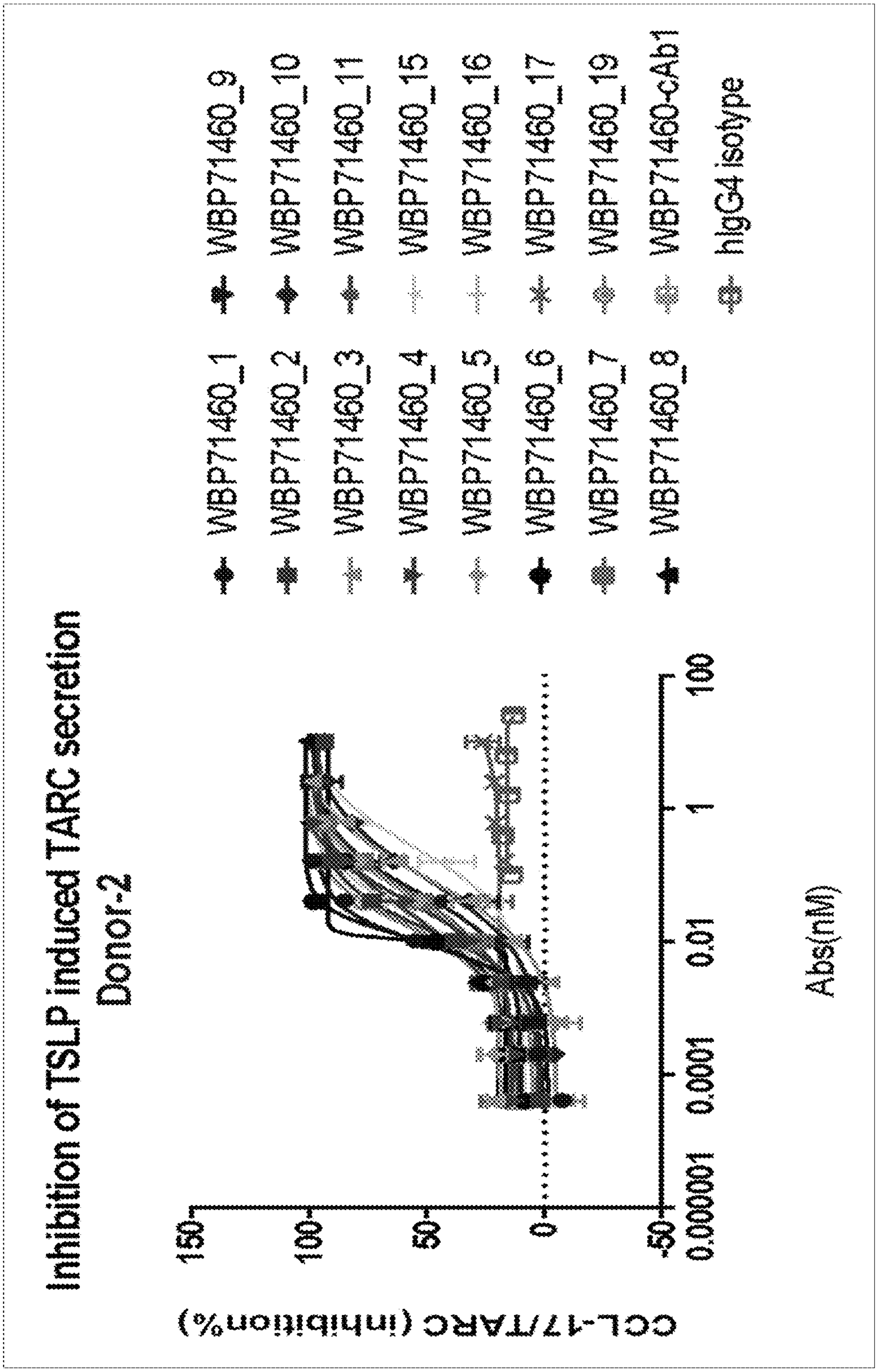

Candidate antigen binding moieties were also tested for their ability to bind IL-4R. Binding affinity for IL-4R was quantified via FACS (FIG. 13). 293F cells expressing IL-4Ra and IL13Ra1 were seeded at $1\times10^{5}$ cells per well.

Candidate antigen binding moieties were added at an initial concentration of 100 nM in 100 μL per well, with a threefold serial dilution. The mixture was incubated at 4° C. for 1 hour. Following this, 100 μL of a secondary antibody, PE-conjugated anti-human IgG Fcγ (diluted 1:150), was added and incubated at 4° C. for 30 minutes. After staining, samples were analyzed by flow cytometry to assess antibody binding. WBP71460-16 (Candidate 19.1) exhibited strong binding interactions with IL-4R ($EC_{50}$=0.29 nM) (Table 7).

TABLE 7

IL-4R binding and inhibition of IL-4-induced CD23 upregulation.

| | IL-4R binding (FACS) EC50 (nM) | CD23 inhibition (PBMC) IC50 (nM) |
|---|---|---|
| WBP71460-16 (Candidate 19.1) | 0.29 | 2.45 |
| Dupilumab (Source 1) | 0.26 | 0.93 |
| Dupilumab (Source 2) | 0.3 | 1.55 |

Next, WBP71460-16 (Candidate 19.1) and other commercial products (e.g., Tezepelumab) were tested in human donor PBMCs to measure their ability to block TSLP-mediated responses, which was assessed via PBMC co-culture and TARC/CCL-17 ELISA (Table 8). On day 0, fresh PBMCs were seeded at $1\times10^6$ cells per 100 μL per well in 96-well plates. Serial dilutions of the test antibody were prepared and added at 50 μL per well, along with 0.2 ng/mL TSLP in 50 μL per well. The cells were incubated at 37° C. with 5% $CO_2$ for 24 hours. After incubation, supernatant was harvested and assessed by ELISA for TARC/CCL-17 (Sino Biological) according to manufacturer instructions. (FIG. 14A, FIG. 14B, FIG. 15A, and FIG. 15B). WBP71460-16 (Candidate 19.1) exhibited a strong ability to inhibit TARC/CCL-17 secretion, with an $IC_{50}$ of 32 pM (Table 8).

Candidate antigen binding moieties were also tested for their ability to bind TSLP. Binding affinity for TSLP was quantified via SPR. A surface plasmon resonance (SPR) experiment was performed using the Biacore 8K system (Cytiva) with a CM5 chip and 1×HBS-EP+ running buffer. Anti-human Fc IgG (Jackson) was immobilized as the capture molecule. WBP71460 antibodies are then captured at concentrations ranging from 20 to 1000 nM, with a contact time of 30 seconds and a flow rate of 10 L/min. For the association and dissociation steps, the analyte TSLP (ACRO-TSP-H52Hb-100 ug) is introduced at varying concentrations between 0 and 20 nM, with association for 180 seconds and dissociation for 3600 seconds at a flow rate of 30 μL/min. Regeneration of the sensor surface is performed using 10 mM glycine at pH 1.5. Data are analyzed using a 1:1 binding model with Biacore evaluation software (Cytiva). The EC50 values derived from the SPR results are shown in Table 7.

TABLE 8

TSLP binding and inhibition of TSLP-induced TARC/CCL17 secretion.

| | TSLP binding (SPR) KD(pM) | CCL17 inhibition (PBMCs) IC50 (pM) |
|---|---|---|
| Candidate 19.1 | 7.58 | 32 |
| Tezepelumab (Source 1) | 5.2 | 21 |
| Tezepelumab (Source 2) | 6.18 | 12.5 |

TABLE 8-continued

Example 8: Antigen Binding Moiety 19.1 Variants

The therapeutic efficacy of candidate antigen binding moiety 19.1 (WBP71460_16) was further assessed through the development of additional molecular formats based on the structure of candidate 19.1. These alternate molecular formats comprise alternate linkers, linker lengths, and/or 2+1 formats as described in Table 9.

TABLE 9

Alternative molecular formats based on Candidate 19.1 (WBP71460_16).

| Sample ID | Binding Moiety |
|---|---|
| WBP71460_23 | Candidate 19.1_with_LS_instead_of_YTE |
| WBP71460_24 | Candidate 19.1_without_half-life_extension |
| WBP71460_25 | Candidate 19.1_with_(EA3K)3_linker |
| WBP71460_26 | Candidate 19.1_with_(G4S)3_linker |
| WBP71460_27 | Candidate 19.1_with_(G4S)2_linker |
| WBP71460_28 | Candidate 19.1_with_(G4S)1_linker |
| WBP71460_29 | Candidate 19.1_in_2_1_format_(Knob_Hole) |
| WBP71460_30 | Candidate 19.1_New_IL-4Ra_#1_YTE |
| WBP71460_31 | Candidate 19.1_New_IL-4Ra_#2_YTE |

Candidate antigen binding moieties' ability to block TSLP-induced TARC/CCL-17 secretion responses was measured via ELISA as described above. All alternative constructs tested demonstrated inhibition of TSLP-induced TARC/CCL-17 secretion (FIG. 17A, FIG. 17B, FIG. 18A, and FIG. 18B and Table 10).

TABLE 10

Inhibition of TSLP-induced TARC/CCL-17 secretion by alternative molecular constructs. Inhibition of TSLP-induced CCL-17 secretion

| | Donor-1 | | Donor-2 | |
|---|---|---|---|---|
| Abs(nM) | IC50(nM) | Max inhibition(%) | IC50(nM) | Max inhibition(%) |
| WBP71460_23 | 0.020 | 99.6 | 0.021 | 99.6 |
| WBP71460_24 | 0.021 | 99.6 | 0.023 | 99.6 |
| WBP71460_25 | 0.018 | 99.6 | 0.020 | 99.6 |
| WBP71460_26 | 0.018 | 99.6 | 0.019 | 99.5 |
| WBP71460_27 | 0.018 | 99.6 | 0.020 | 99.5 |
| WBP71460_28 | 0.013 | 99.6 | 0.020 | 99.5 |
| WBP71460_29 | 0.032 | 99.6 | 0.043 | 99.6 |
| hIgG4 isotype | NA | 19.8 | NA | 0.85 |
| Candidate 19.1 (from different experiment) | 0.036 | 95 | 0.028 | 98 |

Candidate antigen binding moieties' ability to block IL4-mediated responses was measured via FACS as described above. All alternative constructs tested demonstrated inhibition of IL4-induced CD23 upregulation (FIGS. 19A-19F and Table 11).

TABLE 11

| Inhibition of IL4-induced CD23 upregulation by alternative molecular constructs. Inhibition of IL-4-induced CD23 upregulation | | | | |
|---|---|---|---|---|
| | Donor-1 | | Donor-2 | |
| Abs(nM) | IC50(nM) | Max inhibition(%) | IC50(nM) | Max inhibition(%) |
| WBP71460_23 | 2.9 | 97.7 | 1.4 | 96.3 |
| WBP71460_24 | 3.0 | 97.2 | 5.1 | 95.8 |
| WBP71460_25 | 7.8 | 96.9 | 3.5 | 95.2 |
| WBP71460_26 | 4.3 | 96.0 | 1.1 | 95.9 |
| WBP71460_27 | 5.9 | 96.2 | 5.7 | 96.1 |
| WBP71460_28 | 4.2 | 96.4 | 2.0 | 96.3 |
| WBP71460_29 | 2.4 | 95.3 | 2.0 | 90.6 |
| hIgG4 isotype | NA | 26.1 | NA | 12.2 |
| Candidate 19.1 (from different experiment) | 2.2 | 98 | 2.7 | 99 |

As shown in Table 10 and Table 11, variants of antigen binding moiety of Candidate 19.1 consistently exhibited max inhibition above 99% (for inhibition of TSLP-induced TARC/CCL-17 secretion) and above 90% (for inhibition of 1IL4-induced CD23 upregulation).

Example 9: Analysis of Stability in Human Serum

Stability in human serum is an important indicator of antibody quality and therapeutic potential. Stability of candidate antigen binding moieties in human serum was assessed by measuring the ability of each candidate antigen binding moiety to bind TSLP (measured via ELISA) or IL-4R (measured via FACS) following incubation in human serum.

Figure 20A:
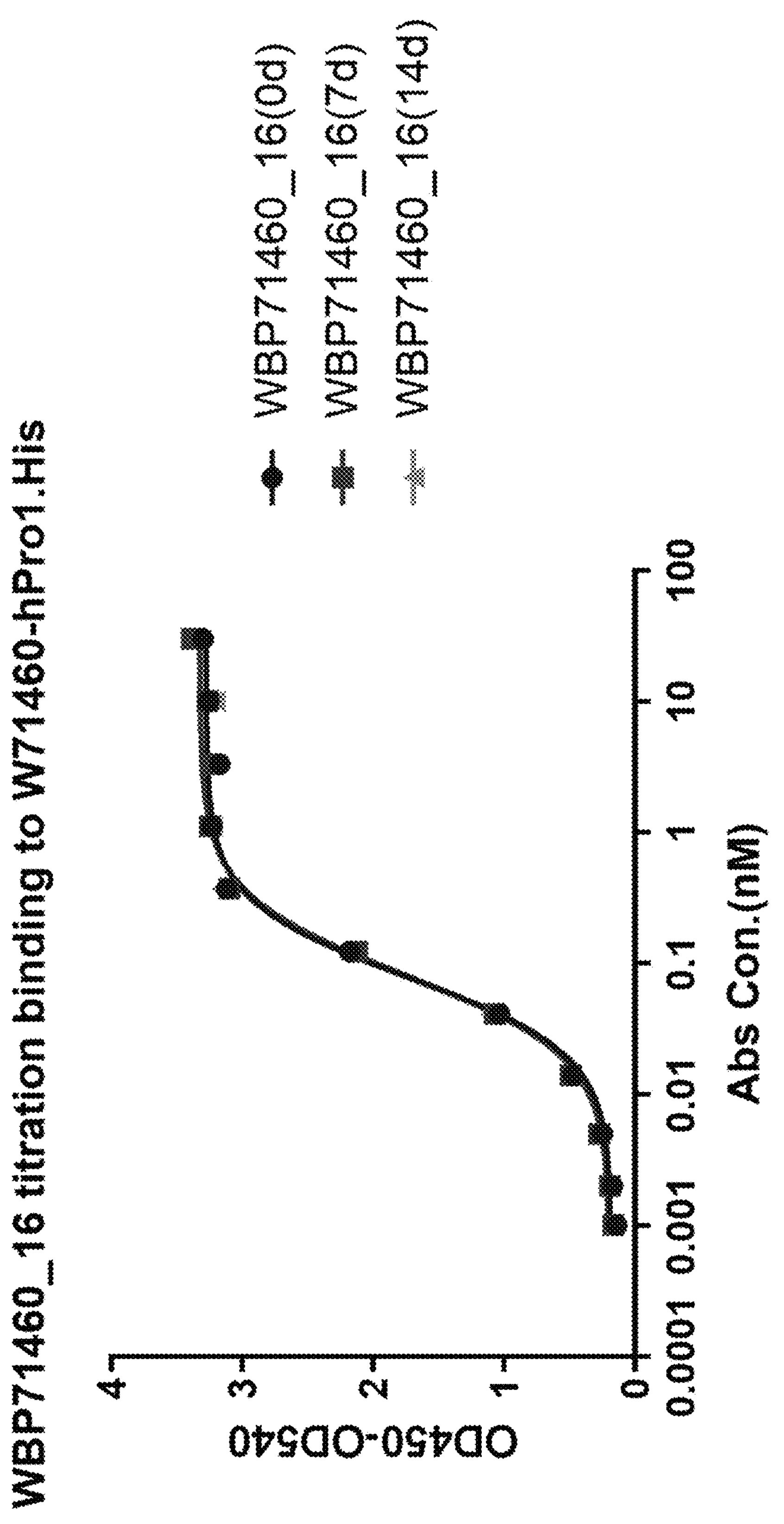
FIG. 20A-20C show quantification of the binding of each candidate antigen binding moiety to the analyte TSLP following incubation in human serum for 0, 7, or 14 days. Binding was measured via ELISA.
Figure 20B:
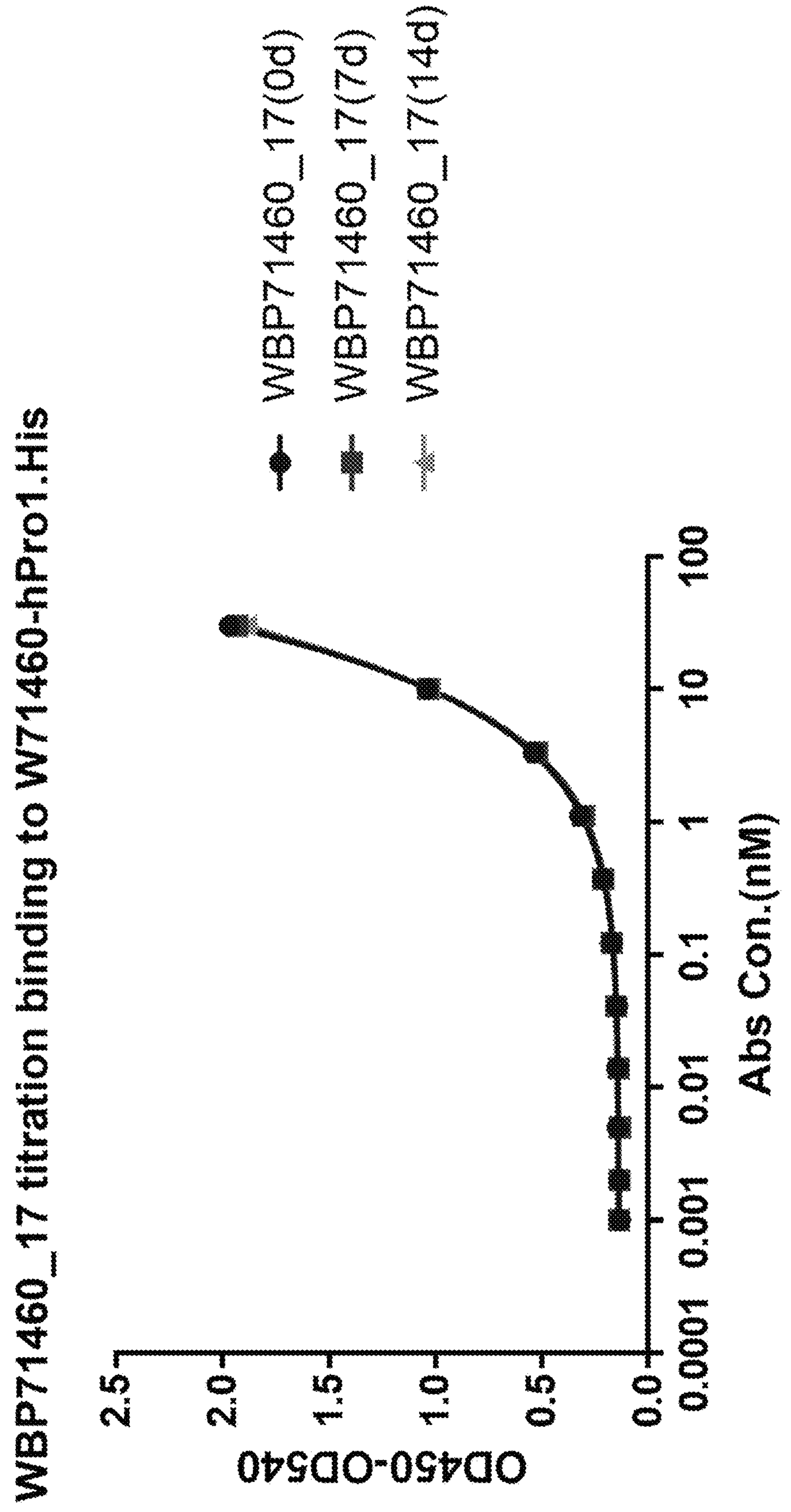
Figure 20C:
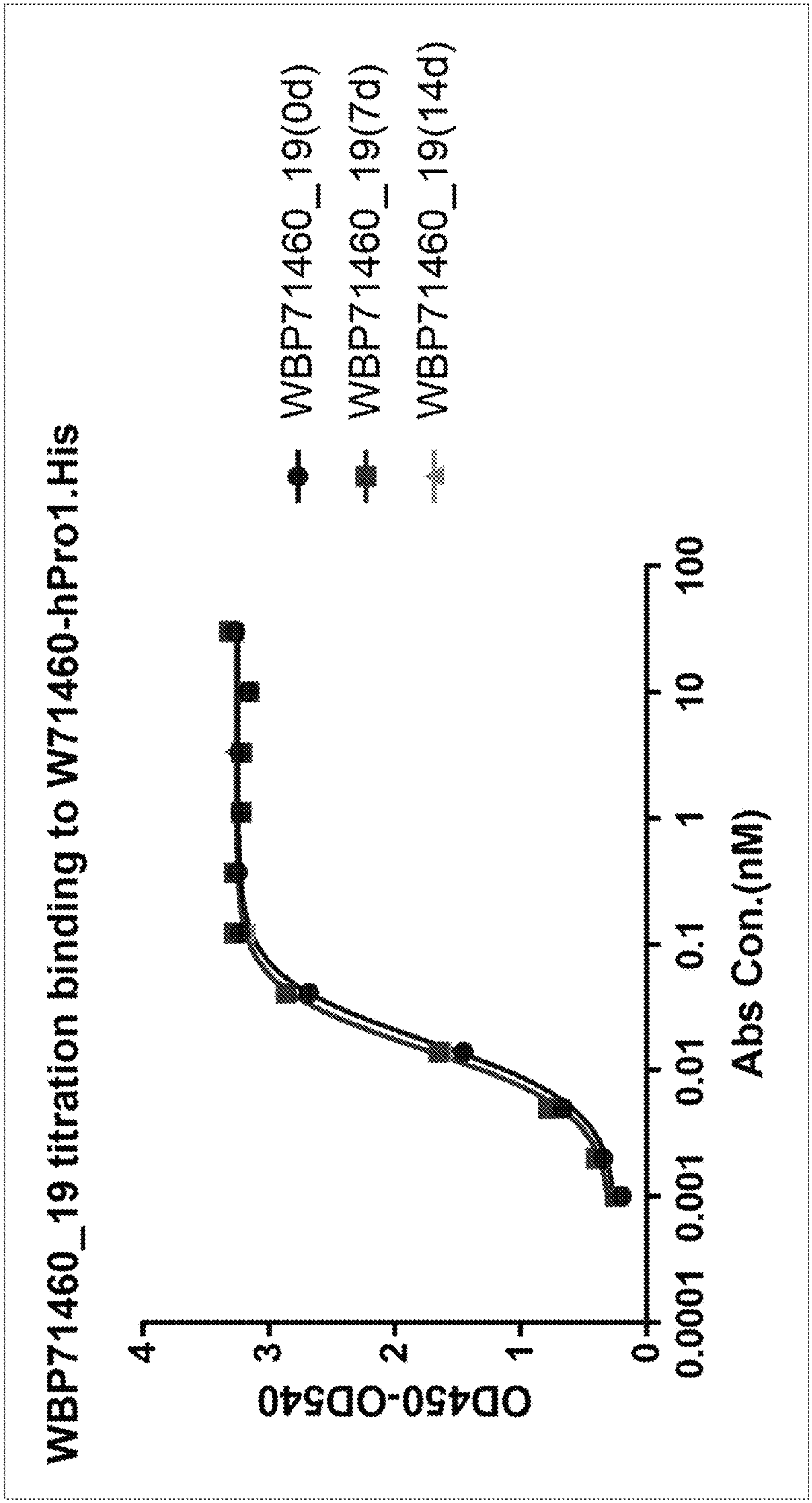
Figure 21A:
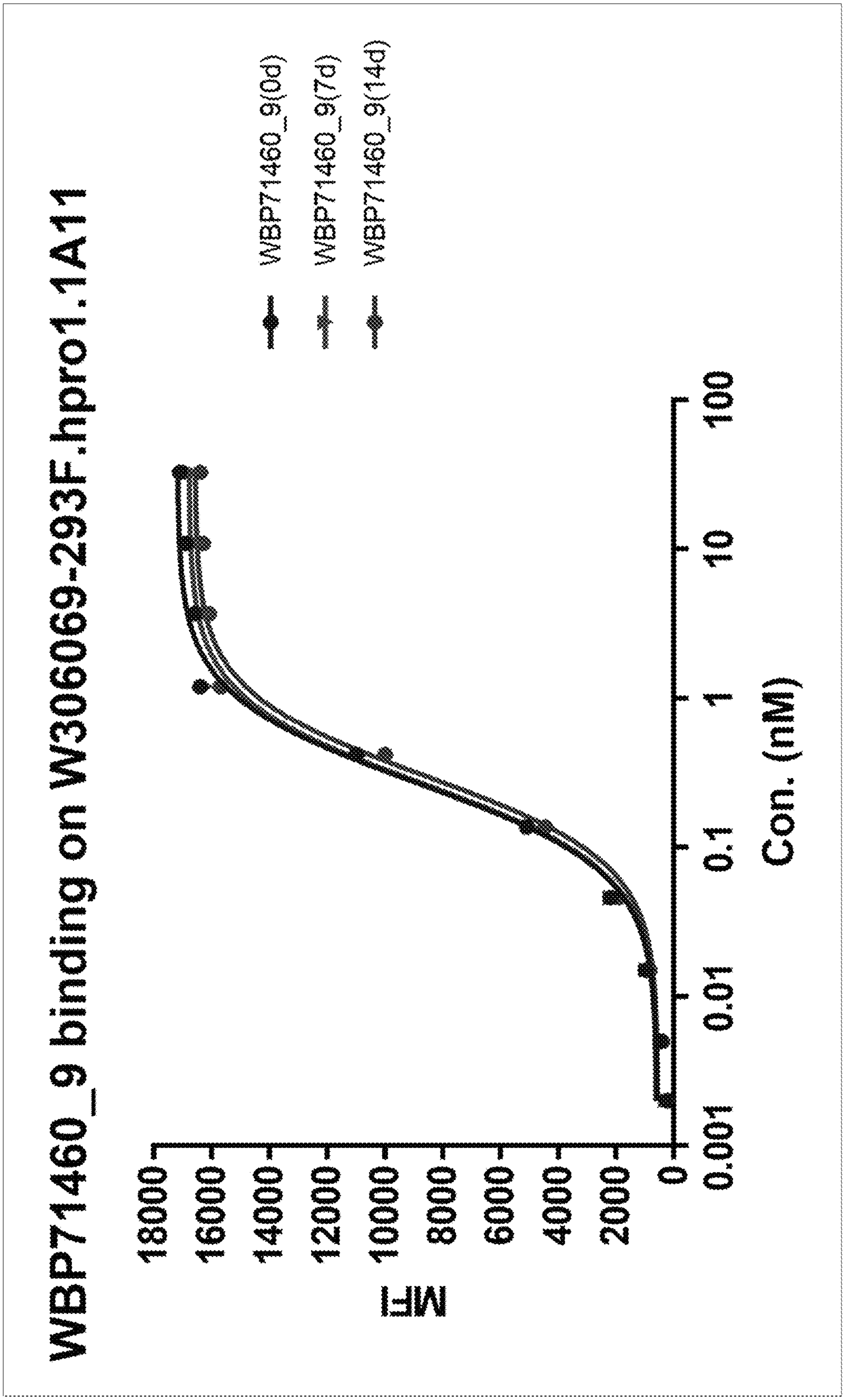
FIGS. 21A-21G show a FACS experiment quantifying the binding of each candidate antigen binding moiety to IL-4R following 0-, 7-, or 14-day incubation in human serum.
Figure 21B:
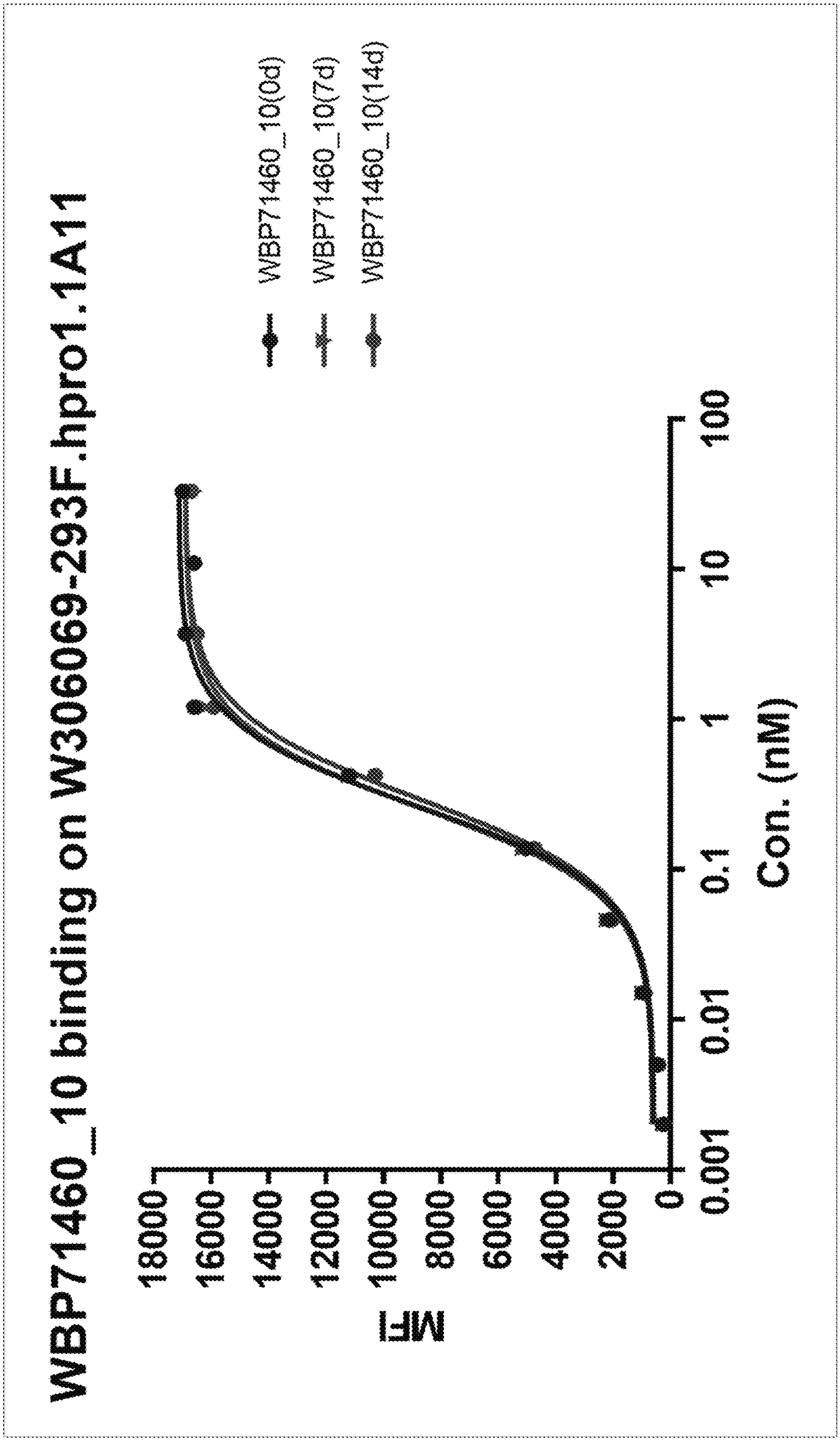
Figure 21C:
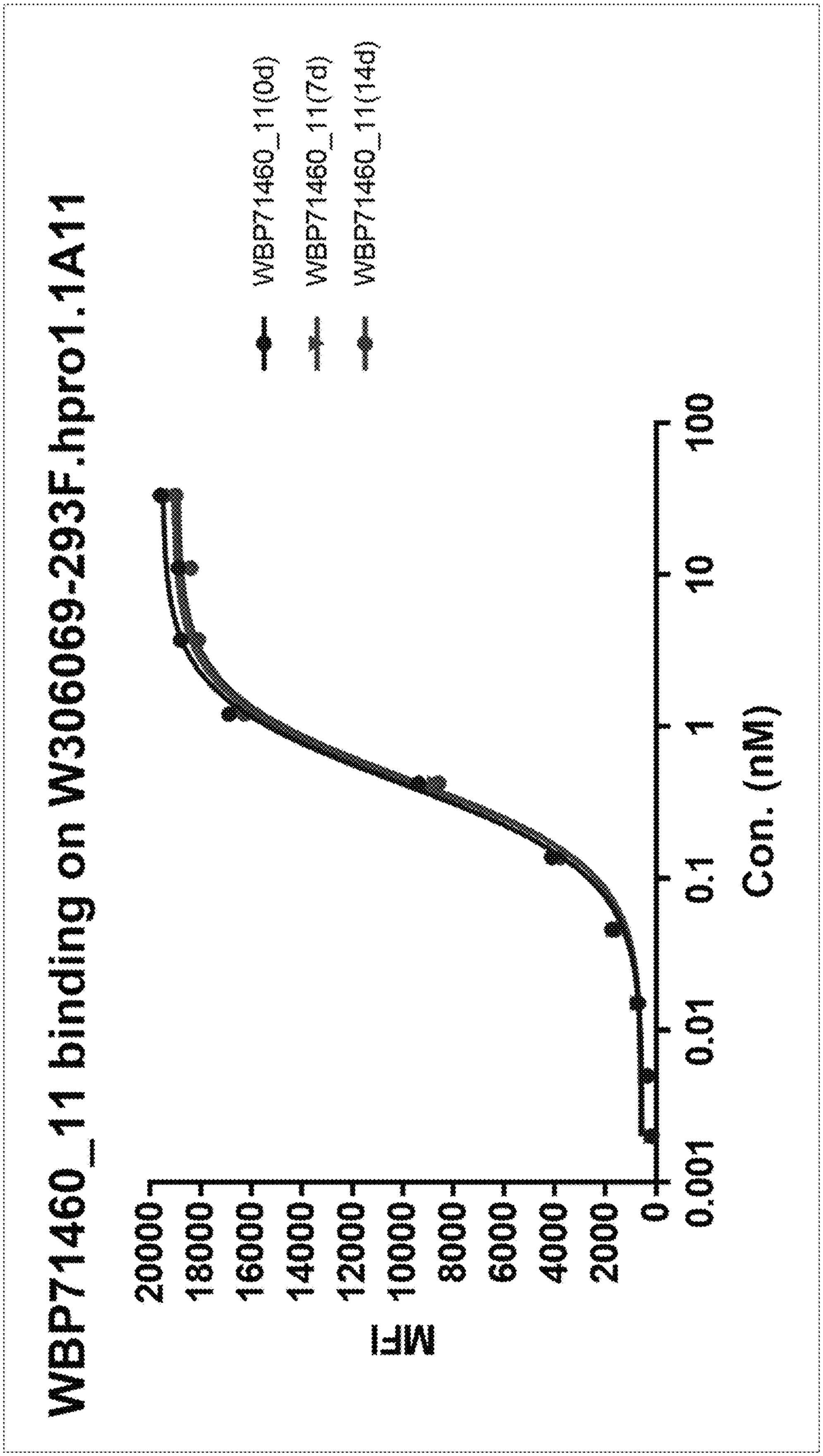
Figure 21D:
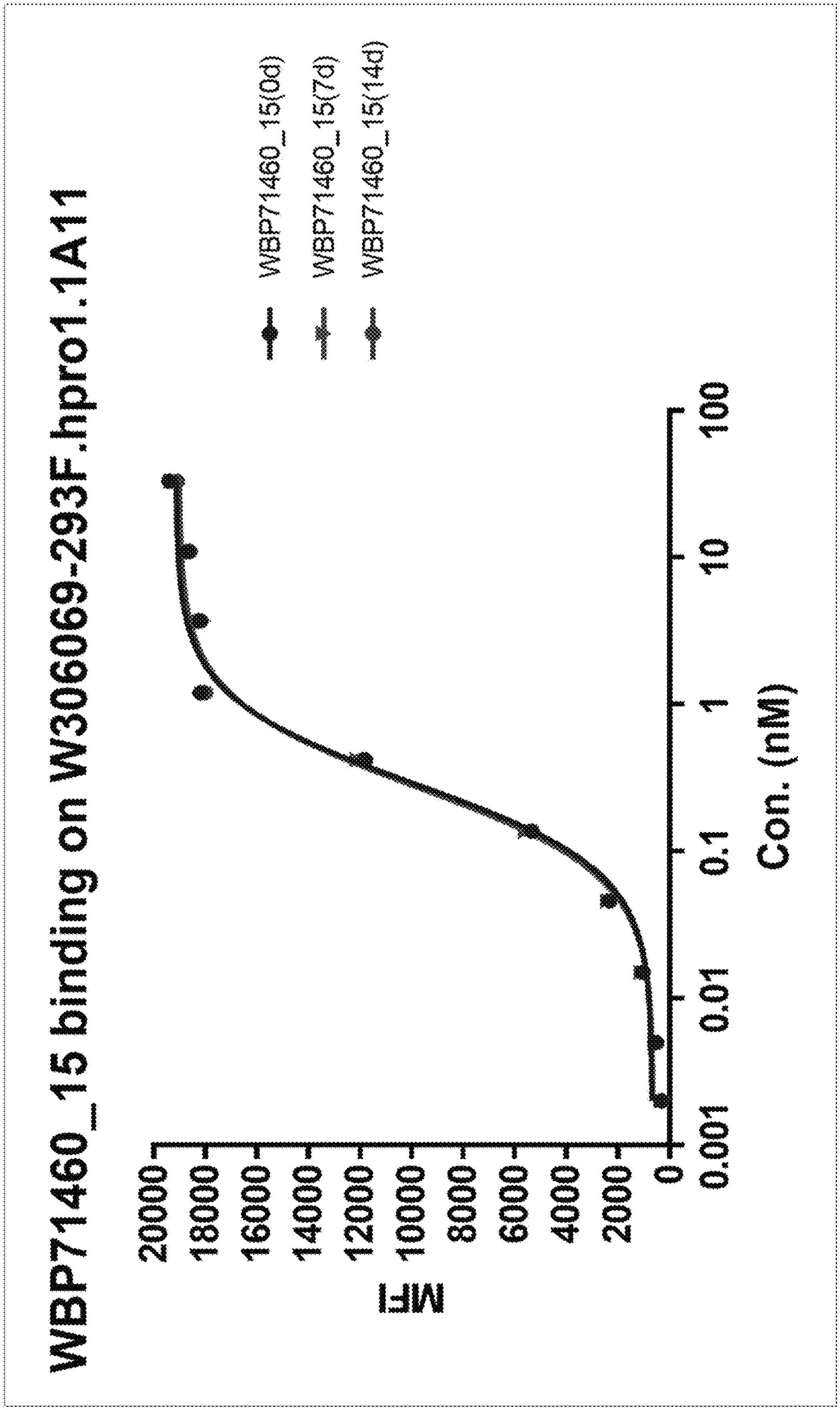
Figure 21E:
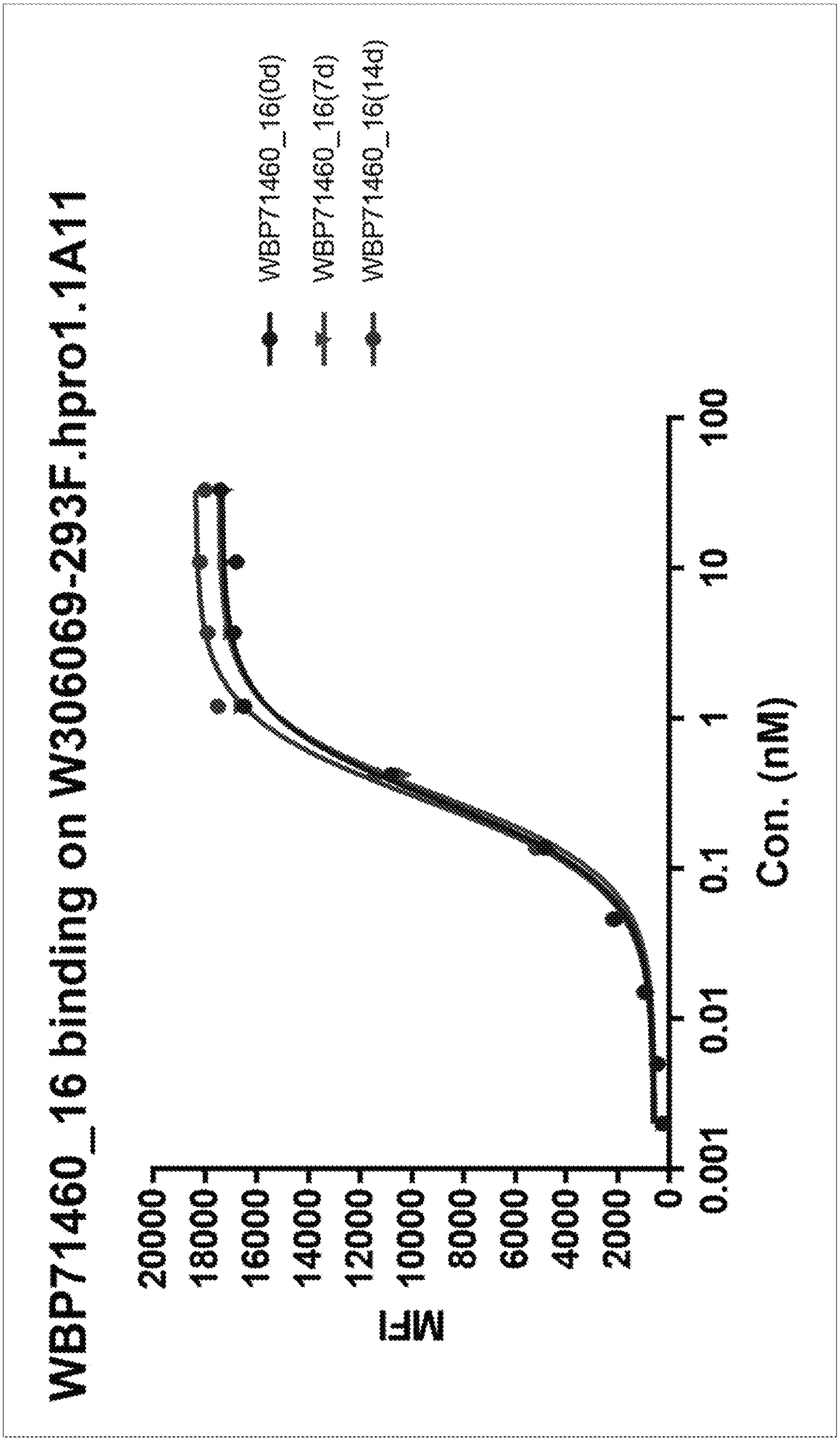
Figure 21F:
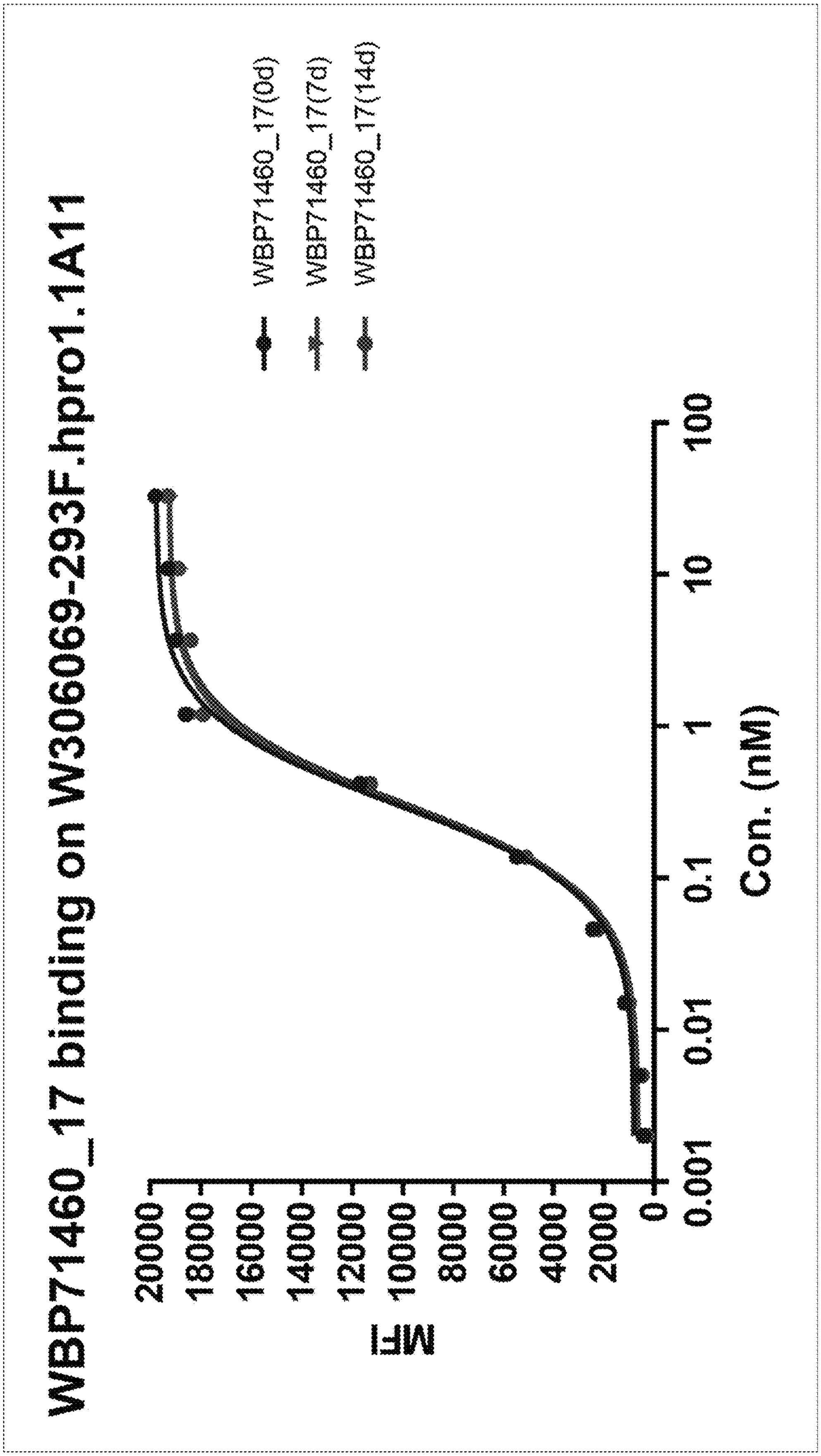
Figure 21G:
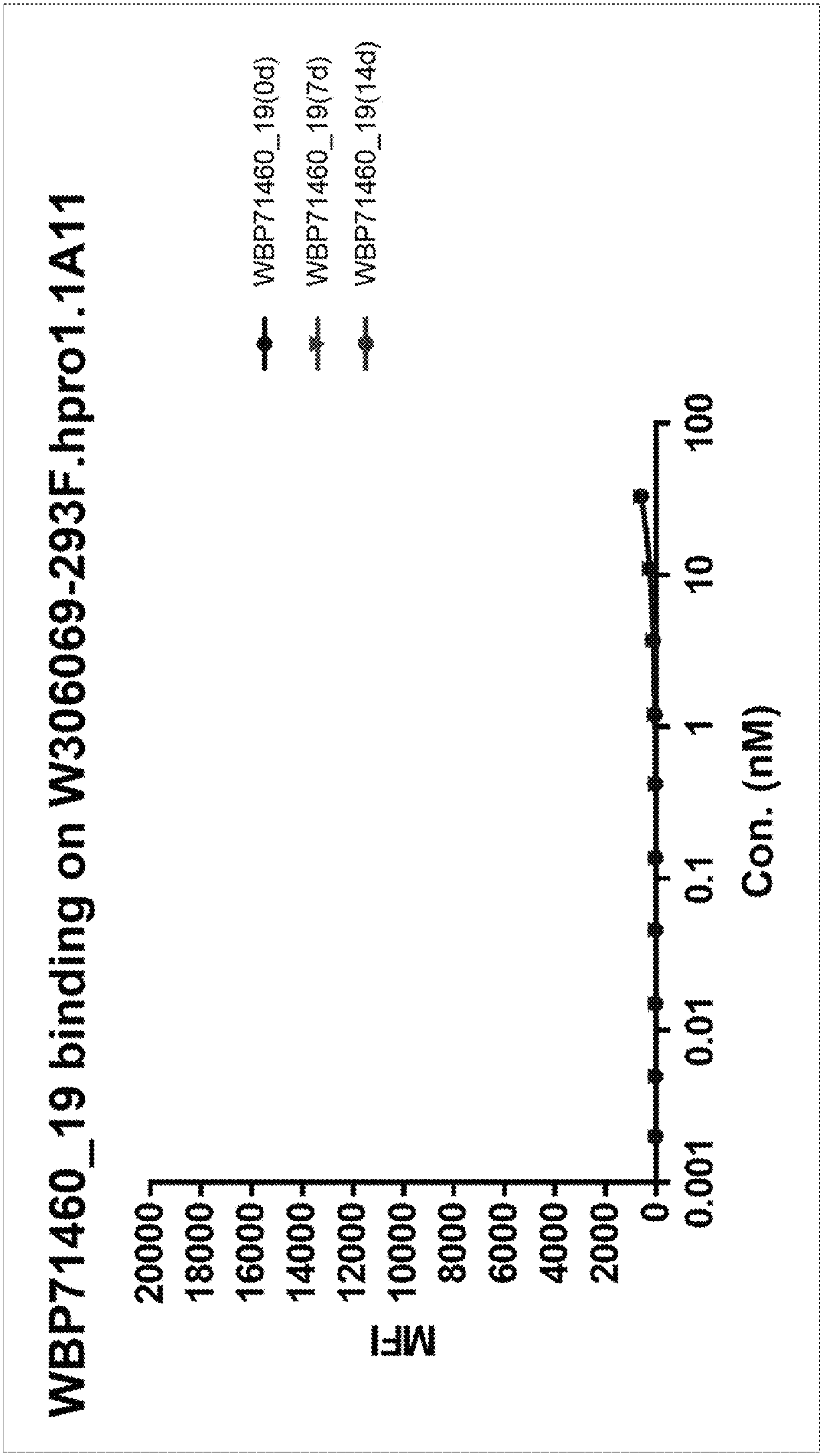

To assess the stability of each candidate antigen binding moiety in human serum, each candidate antigen binding moiety was first incubated in human serum for 0, 7, or 14 days and measured TSLP binding. In order to detect intact candidate antigen binding moieties, an ELISA plate was coated overnight at 4° C. with 0.5 μg/mL anti-histidine antibody to capture His-tagged TSLP. Next, wells are blocked with 2% BSA at 25° C. for 1 hour to minimize nonspecific binding. After blocking, 0.2 μg/mL of His-Tagged TSLP (Acro Bio) was added to each well. Candidate antigen binding moieties were diluted in 2% BSA starting from 30 nM using a threefold serial dilution and were then incubated at 25° C. for 2 hours. Detection was performed using goat anti-human IgG-Fc-HRP (1:5000 dilution in 2% BSA), incubated at 25° C. for 1 hour. Finally, the assay was developed, and absorbance was measured as the difference between OD450 and OD540 to quantify the results (FIGS. 20A-20C). EC50 values were calculated by nonlinear regression. As shown in Table 12, WBP71460_16 was stable in human serum across 14 days with stable EC50 values at Day 0, Day 7, and Day 14 post incubation.

TABLE 12

| ELISA-based serum stability assay results. ELISA binding summary | | |
|---|---|---|
| | Ag: 0.2 μg/ml | |
| Abs(nM) | EC50(nM) | Max OD450-540 |
| WBP71460_16(0 d) | 0.078 | 3.30 |
| WBP71460_16(7 d) | 0.082 | 3.39 |
| WBP71460_16(14 d) | 0.079 | 3.37 |
| WBP71460_17(0 d) | NA | 1.97 |
| WBP71460_17(7 d) | NA | 1.93 |
| WBP71460_17(14 d) | NA | 1.89 |
| WBP71460_19(0 d) | 0.017 | 3.27 |
| WBP71460_19(7 d) | 0.015 | 3.32 |
| WBP71460_19(14 d) | 0.015 | 3.29 |
| human IgG4 | NA | 0.75 |
| NC | NA | 0.09 |
| Blank | NA | 0.01 |

To assess stability of each candidate antigen binding moiety following incubation in human serum, each candidate antigen binding moiety was first incubated in human serum for 0, 7, or 14 days to assess IL-4R binding. In order to detect intact candidate antigen binding moieties, a FACS assay was utilized to evaluate candidate antigen binding moieties binding to cells. 293F cells expressing IL-4Ra and IL13Ra1 were seeded at $1\times10^5$ cells per well. Candidate antigen binding moieties were added at an initial concentration of 33 nM in 100 μL per well, with a threefold serial dilution. The mixture was incubated at 4° C. for 1 hour. Following this, 100 μL of a secondary antibody, PE-conjugated anti-human IgG Fcγ (diluted 1:150), was added and incubated at 4° C. for 30 minutes. After staining, samples were analyzed by flow cytometry to assess antibody binding (FIGS. 21A-21G). EC50 values were derived from binding curves. As shown in Table 13, all antigen binding moieties were stable in human serum across 14 days.

WBP71460_16 (Candidate 19.1) engages in strong binding interactions with both TSLP and IL-4R following incubation in human serum for a 14-day period.

TABLE 13

| FACS-based serum stability assay results. | | |
|---|---|---|
| Antibody | $EC_{50}$ (nM) | Max MFI |
| WBP71460_9(0 d) | 0.27 | 17100 |
| WBP71460_9(7 d) | 0.27 | 16700 |
| WBP71460_9(14 d) | 0.30 | 16400 |
| WBP71460_10(0 d) | 0.26 | 17000 |
| WBP71460_10(7 d) | 0.26 | 16700 |
| WBP71460_10(14 d) | 0.29 | 16700 |
| WBP71460_11(0 d) | 0.42 | 19600 |
| WBP71460_11(7 d) | 0.44 | 19100 |
| WBP71460_11(14 d) | 0.44 | 19000 |
| WBP71460_15(0 d) | 0.29 | 19400 |
| WBP71460_15(7 d) | 0.28 | 19300 |
| WBP71460_15(14 d) | 0.28 | 19100 |
| WBP71460_16(0 d) | 0.28 | 17400 |
| WBP71460_16(7 d) | 0.31 | 17200 |
| WBP71460_16(14 d) | 0.28 | 18200 |
| WBP71460_17(0 d) | 0.31 | 19800 |
| WBP71460_17(7 d) | 0.30 | 19200 |
| WBP71460_17(14 d) | 0.31 | 19300 |
| WBP71460_19(0 d) | NA | 621 |
| WBP71460_19(7 d) | NA | 622 |
| WBP71460_19(14 d) | NA | 610 |
| Isotype control | NA | 38 |

Example 10: Evaluation of WBP71460_16 (Candidate 19.1) in Delayed Type Hypersensitivity (DTH) Mouse Model The DTH mouse model was used as an in vivo immunological assay to assess T-cell mediated immune response (e.g., Th1-driven inflammation). WBP71460_16 (Candidate 19.1) was evaluated in Oxazalone-induced DTH model at Biocytogen in huIL4/huIL-4R mice and huTSLP/huTSLPR mice.

Transgenic mice (55 mice per study—10 mice in control group and 15 mice in all other groups) were first sensitized on Day 0 by topical application of 0.8% oxazolone (OXZ). Beginning on Day 7, and continuing through Day 26, animals received topical OXZ challenges (0.4%, 25 μL/ear or dorsal site) on Days 7, 9, 11, 14, 16, 18, 21, 23, and 25 to induce chronic dermatitis. Concurrently, mice were dosed with test or control antibodies by intraperitoneal injection. For Study 1 (huIL4/huIL-4R mice), mice were dosed with a vehicle control (acetone/olive oil, 4:1), 10 mg/kg isotype control, 10 mg/kg Dupilumab, or 17.4 mg/kg WBP71460_16 (Candidate 19.1). For Study 2 (huTSLP/huTSLPR mice), mice were dosed with a vehicle control (acetone/olive oil, 4:1), 10 mg/kg isotype control, 10 mg/kg Tezepelumab, or 17.4 mg/kg WBP71460_16 (Candidate 19.1). These doses were selected to deliver the same molar dose for each antibody. The higher mg/kg for WBP71460_16 (Candidate 19.1) reflects its larger molecular weight. For both studies, antibodies were administered intraperitoneally twice weekly on Days 6, 9, 13, 16, 20, and 23 (six total doses). Serum IgE levels (ng/mL) were quantified at study termination.

Figure 22B:
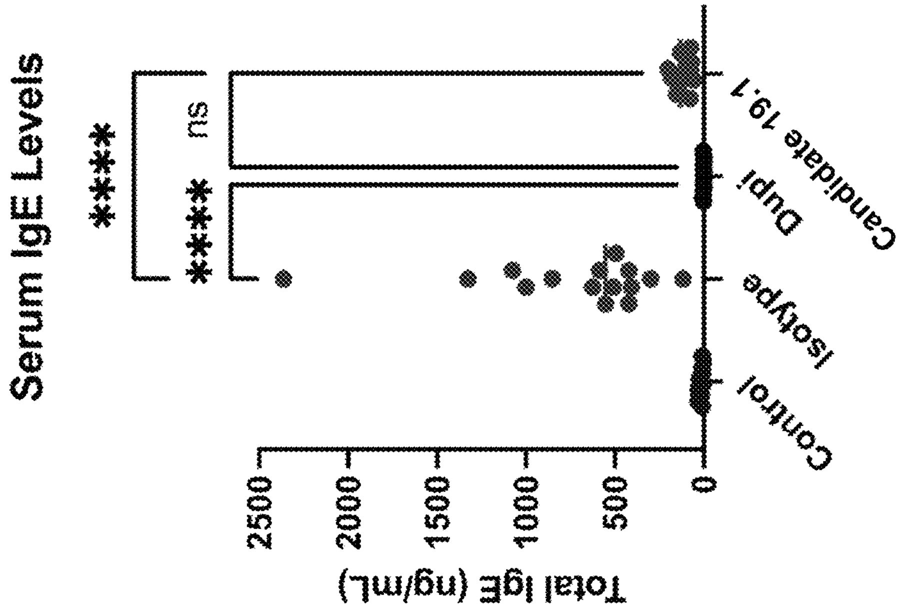
FIG. 22A and FIG. 22B show serum IgE level in an oxazalone-induced delayed type hypersensitivity (DTH) mouse model.
Figure 22A:
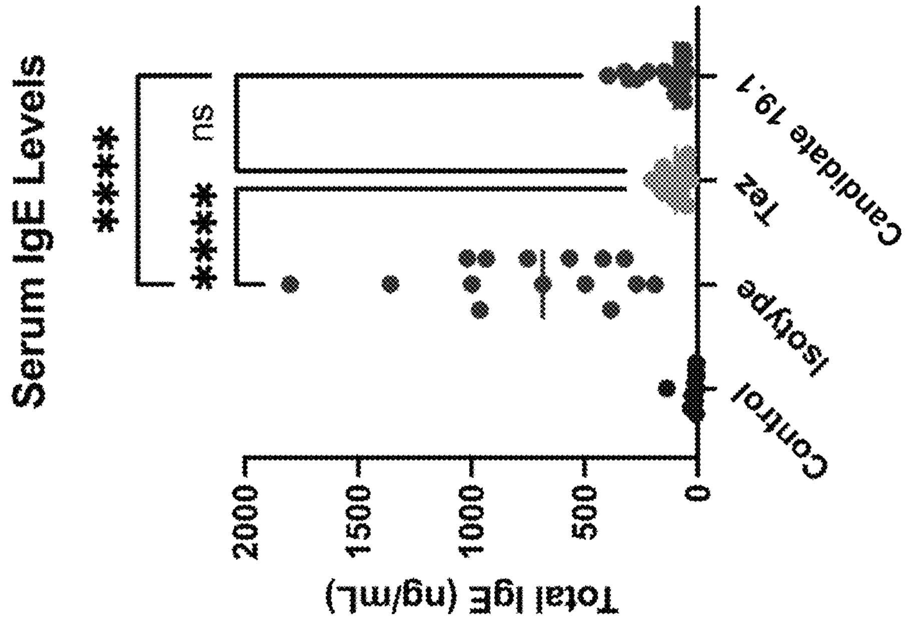

Serum IgE levels were measured at the endpoint to assess the effects of WBP71460_16 (Candidate 19.1) on reducing allergic, type 2-mediated inflammation. As shown in FIG. 22A (Study 1) and FIG. 22B (Study 2), treatment with WBP71460_16 (Candidate 19.1) significantly reduced total serum IgE levels compared to an isotype control group, indicating effective suppression of type 2 inflammation. The reduction of serum IgE level was comparable to that of the commercial products (e.g., dupilumab or tezepelumab). Serum IgE levels (ng/mL) as depicted in FIG. 22A and FIG. 22B are outlined in Table 14 and Table 15, respectively.

TABLE 14

| Mouse serum total IgE levels (ng/mL) | | | | |
|---|---|---|---|---|
| | Control | Isotype | Tez | Candidate 19.1 |
| Number of values | 10 | 15 | 15 | 15 |
| Mean | 25.33 | 744.8 | 102.1 | 158.5 |
| SD | 40.40 | 444.1 | 52.18 | 115.1 |
| SEM | 12.77 | 114.7 | 13.47 | 29.72 |

TABLE 15

| Mouse serum total IgE levels (ng/mL) | | | | |
|---|---|---|---|---|
| | Control | Isotype | Dupi | Candidate 19.1 |
| Number of values | 10 | 15 | 15 | 15 |
| Mean | 16.62 | 739.1 | 3.275 | 124.7 |
| SD | 11.65 | 551.0 | 2.089 | 46.46 |
| SEM | 3.685 | 142.3 | 0.5394 | 12.00 |

WBP71460_16 (Candidate 19.1) demonstrated statistically significant reductions in serum IgE levels, comparable to dupilumab, in humanized IL-4/IL-4R mice. These results support that WBP71460_16 (Candidate 19.1) effectively mitigates inflammation in vivo that is comparable to that of the commercial products.

Example 11: In Vivo PK Study

To investigate the in vivo pharmacokinetic properties of WBP71460_16 (Candidate 19.1), the candidate antigen binding moiety was evaluated in humanized FcRn transgenic mice. 5 female mice per treatment group were each dosed intravenously with a single 20 mg/kg bolus of each candidate antigen binding moiety (WBP71460_1, WBP71460_5, WBP71460_8, WBP71460_9 WBP71460_1 WBP71460_16 and WBP7146017) on Day 0. Blood samples were collected pre-dose (pooled from spare animals) and at 0.5 hours, 4 hours, Day 2, Day 3, Day 5, Day 7, Day 10, Day 12, and Day 14 post-dose to characterize each the pharmacokinetic profile of each candidate antigen binding moiety over 2 weeks. Blood samples were also collected at time points up to 28 days. To assess pharmacokinetic properties, recombinant binding assays were performed in high-binding 96-well plates. Wells were coated overnight at 4° C. with either human TSLP-His (5.0 μg/mL) or goat anti-human IgG (1.0 μg/mL) in PBS (Table 16).

TABLE 16

| Mouse pharmacokinetic study methodology. | | | | | | | |
|---|---|---|---|---|---|---|---|
| Group | Animal | Antibody | Mouse number (N) | Dose (mg/kg) | Route | Schedule | Bleeding schedule |
| G1 | hFcRn | WBP71460_1 | 5 (Female) | 20 | IV | Single dose on Day 0 | Time points: |
| G2 | hFcRn | WBP71460_5 | 5 (Female) | 20 | IV | Single dose on Day 0 | Pre-dose (pooled |
| G3 | hFcRn | WBP71460_8 | 5 (Female) | 20 | IV | Single dose on Day 0 | from spare animals), |
| G4 | hFcRn | WBP71460_9 | 5 (Female) | 20 | IV | Single dose on Day 0 | 0.5 h, 4 h, Day 2, |
| G5 | hFcRn | WBP71460_10 | 5 (Female) | 20 | IV | Single dose on Day 0 | Day 3, Day 5, |
| G6 | hFcRn | WBP71460_11 | 5 (Female) | 20 | IV | Single dose on Day 0 | Day 7, Day 10, |
| G7 | hFcRn | WBP71460_17 | 5 (Female) | 20 | IV | Single dose on Day 0 | Day 12, Day 14 |
| G8 | hFcRn | WBP71460_16 | 5 (Female) | 20 | IV | Single dose on Day 0 | post dosing. |

After coating, plates were washed and blocked for 1 hour at room temperature with 2% BSA in PBS. Serum test samples were then added (2% BSA in PBS) and incubated for 1 hour at room temperature to allow binding to the immobilized ligand. Plates were washed 3 times, and then 0.1 μg/mL biotinylated human IL-4R was applied as the secondary detector and incubated for 1 hour. Following another wash step, bound biotinylated receptor was detected by incubation with streptavidin-HRP for 30 minutes and color development with TMB substrate. The reaction was stopped with 1 M sulfuric acid and absorbance was measured at 450-540 nm. Data were processed in SoftMax Pro and dose-response curves fitted in GraphPad Prism to determine relative binding affinities across all construct formats.

Figure 23A:
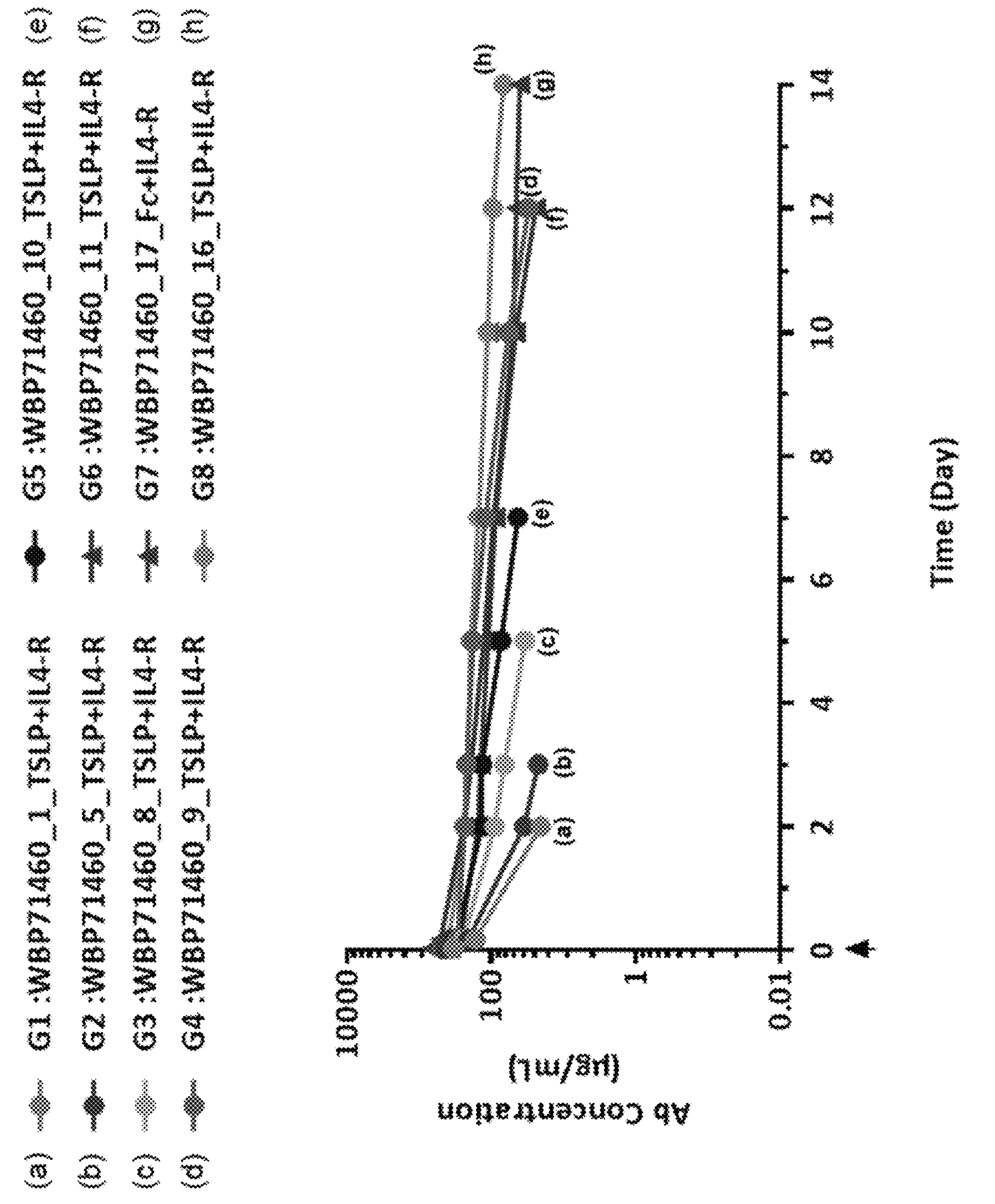
FIG. 23A shows a pharmacokinetic experiment quantifying circulating concentrations of each candidate antigen binding moiety over a 14-day period in an FcRn humanized mouse model.
Figure 23B:
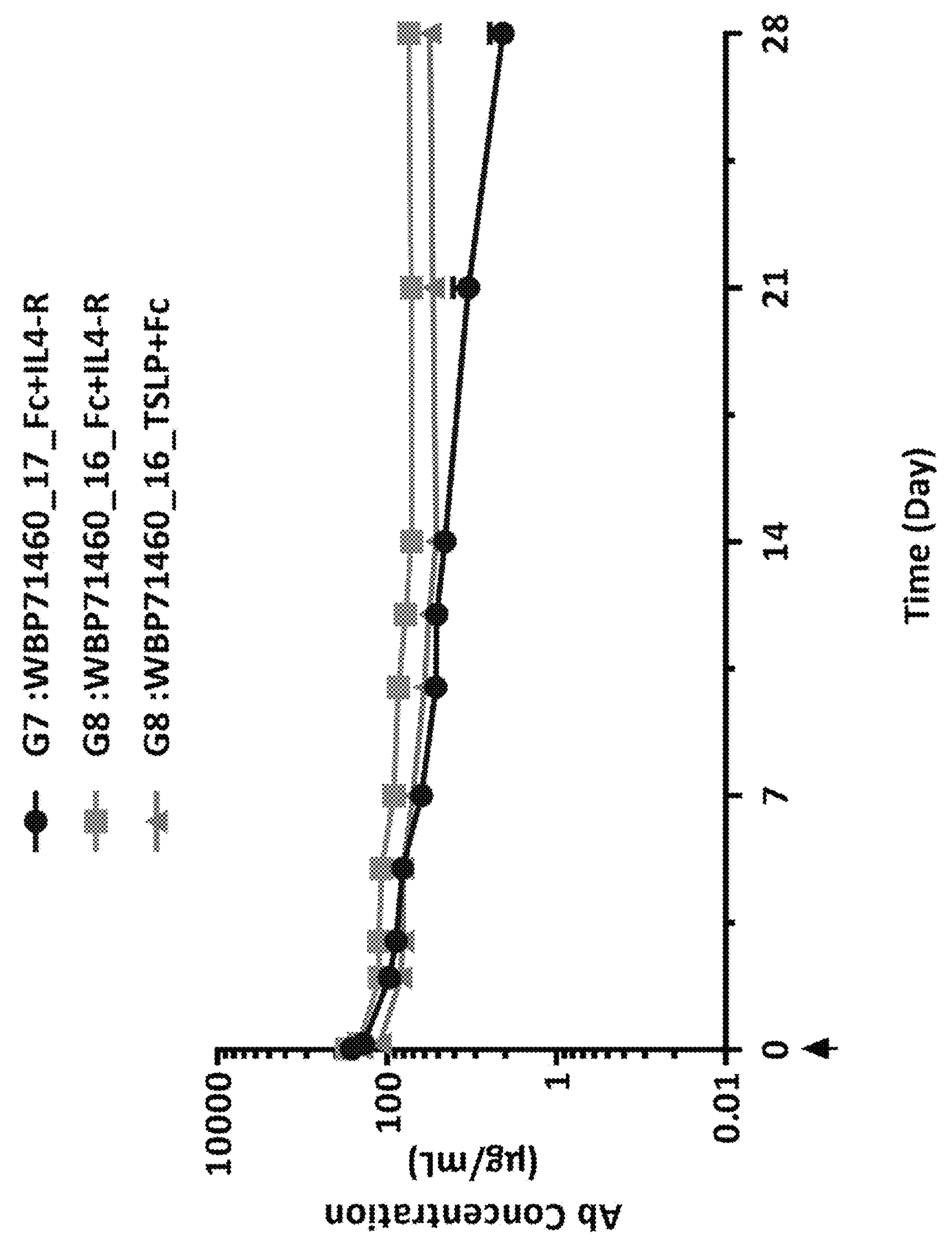
FIG. 23B shows a pharmacokinetic experiment quantifying circulating concentrations of each candidate antigen binding moiety over a 28-day period in an FcRn humanized mouse model.
Figure 24:
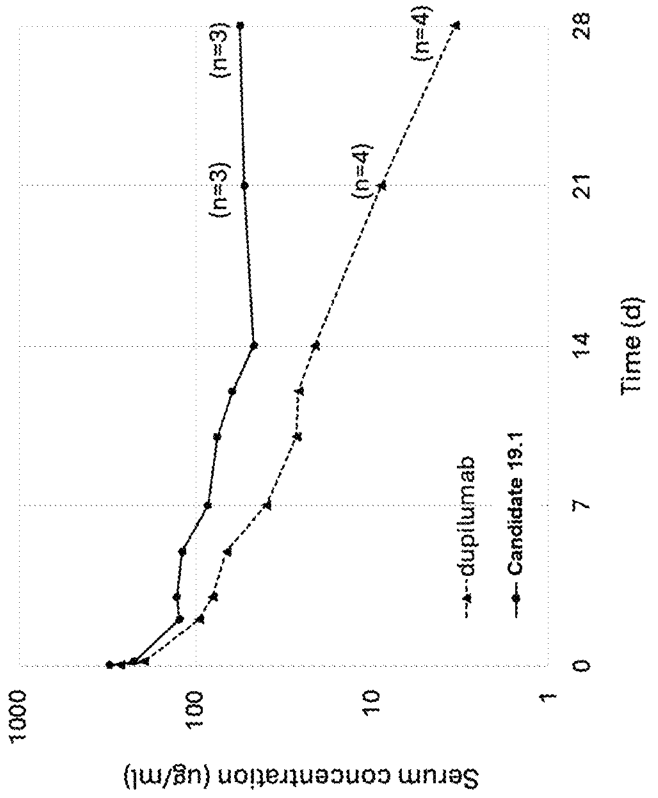
FIG. 24 shows in vivo pharmacokinetic data demonstrating the half-life in a mouse model.

Pharmacokinetic properties including half-life ($t_{1/2}$), $C_{max}$, $AUC_{0-t}$, CI_obs, MRTINF_obs, Vss_obs were quantified using non-compartmental analysis. (Table 17 and Table 18), and antibody concentration as a function of time over a 14-day period was determined (FIG. 23A). Pharmacokinetic profiles of candidate antigen binding moieties were evaluated through more protracted time points (28 days) as well (FIG. 23B). In humanized FcRn transgenic mice, WBP71460_16 (Candidate 19.1) exhibited a half-life of about 13 days over a 28-day period, greatly exceeding the 6-day half-life of Dupilumab over this time period (FIG. 24, Table 19, and Table 20). These results support that WBP71460_16 (Candidate 19.1) remains in circulation for unexpectedly long time periods, exhibiting a more sustained half-life than any other candidate antigen binding moiety used in these studies (Table 17, Table 18, Table 19, and Table 20). This unexpectedly long half-life suggests strong therapeutic potential.

TABLE 17

Pharmacokinetic properties of candidate antigen binding moieties in a humanized mouse model.

| | Compound | | | | |
|---|---|---|---|---|---|
| | G1: WBP71460_1 | G2: WBP71460_5 | G3: WBP71460_8 | G4: WBP71460_9 | G5: WBP71460_10 |
| Method | TSLP + IL4-R | | | | Fc + IL4-R |
| Dose | 20 mg/kg, IV | | | | |
| $t_{1/2}$ (h) | 12.9 | 19.7* | 46.6 | 70.4* | 60.8* |
| $C_{max}$ (μg/mL) | 338 | 436 | 407 | 471 | 390 |
| AUC 0-t (h*μg/mL) | 4120 | 6301 | 12339 | 42037 | 21528 |
| Cl_obs (mL/day/kg) | 107 | 69.6 | 33.0 | 10.5 | 18.9 |
| MRTINF_obs (h) | 19.1 | 27.6 | 62.8 | 117 | 90.0 |
| Vss_obs (mL/kg) | 84.7 | 79.5 | 86.2 | 51.2 | 70.2 |

| | Compound | | |
|---|---|---|---|
| | G6: WBP71460_11 | G8: WBP71460_16 | G7: WBP71460_17 |
| Method | Fc + IL4-R | | |
| Dose | 20 mg/kg, IV | | |
| $t_{1/2}$ (h) | 87.9* | 155* | 116* |
| $C_{max}$ (μg/mL) | 381 | 498 | 676 |
| AUC 0-t (h*μg/mL) | 30708 | 56317 | 45426 |
| Cl_obs (mL/day/kg) | 14.3 | 6.82 | 9.22 |
| MRTINF_obs (h) | 126 | 224 | 150 |
| Vss_obs (mL/kg) | 73.7 | 60.9 | 57.6 |

*The t½ may not be accurate when the AUC_% Extrap_obs is greater than 20% or the Rsq_adjusted is less than 0.9.

TABLE 18

Pharmacokinetic properties of candidate antigen binding moieties in a humanized mouse model.

| | Compound | | |
|---|---|---|---|
| | G7: WBP71460_17 | G8: WBP71460_16 | G8: WBP71460_16 |
| | Method | | |
| | Fc + IL4-R | Fc + IL4-R | TSLP + Fc |
| | Dose | | |
| | 20 mg/kg, IV | 20 mg/kg, IV | 20 mg/kg, IV |
| $t_{1/2}$ (h) | 133 | 319* | 301* |
| $C_{max}$ (μg/mL) | 266 | 304 | 203 |
| AUC 0-t (h*μg/mL) | 22746 | 44152 | 24173 |
| Cl_obs (mL/day/kg) | 20.0 | 7.99 | 14.9 |
| MRTINF_obs (h) | 180 | 491 | 470 |
| Vss_obs (mL/kg) | 148 | 134 | 237 |

*The t½ may not be accurate when the AUC_% Extrap_obs is greater than 20% or the Rsq_adjusted is less than 0.9.

TABLE 19

Serum concentration time-course data for WBP71460_16 (Candidate 19.1).

| | | Antibody WBP71460_16 (Candidate 19.1) Method Fc + IL4-R Dose 20 mg/kg, IV, Single dose on Day 0 | | | | | | |
|---|---|---|---|---|---|---|---|---|
| Time (h) | | G8-1 | G8-2 | G8-3 | G8-4 | G8-5 | Mean | SD |
| Pre-dose (Mix plasma) | | ND | ND | ND | ND | ND | — | — |
| 30 min | 0.50 | 316 | 289 | 327 | 307 | 283 | 304 | 18.4 |
| 4 h | 4 | 225 | 217 | 242 | 203 | 218 | 221 | 14.2 |
| Day 2 | 48 | 145 | 118 | 105 | 111 | 138 | 123 | 17.3 |
| Day 3 | 72 | 135 | 132 | 133 | 111 | 122 | 127 | 10.1 |
| Day 5 | 120 | 100 | 126 | 117 | 122 | 125 | 118 | 10.7 |
| Day 7 | 168 | 83.3 | 92.3 | 82.6 | 70.6 | 93.6 | 84.5 | 9.25 |
| Day 10 | 240 | 45.9 | 83.1 | 83.2 | 81.7 | 81.3 | 75.0 | 16.3 |
| Day 12 | 288 | 43.9 | 65.1 | 69.8 | 71.3 | 57.5 | 61.5 | 11.2 |
| Day 14 | 336 | 24.8 | 45.1 | 52.3 | 50.2 | 60.0 | 46.5 | 13.3 |
| Day 21 | 504 | ND | ND | 48.9 | 57.5 | 51.7 | 52.7 | 4.39 |
| Day 28 | 672 | ND | ND | 54.6 | 58.0 | 54.6 | 55.7 | 1.96 |
| $t_{1/2}$ (h) | | 128 | 162 | 456 | 429 | 418 | 319 | 160 |

TABLE 20

Serum concentration time-course data for WBP71460_17 (Dupilumab).

| | | Antibody WBP71460_17 (Dupilumab) Method Fc + IL4-R Dose 20 mg/kg, IV, Single dose on Day 0 | | | | | | |
|---|---|---|---|---|---|---|---|---|
| Time (h) | | G7-1 | G7-2 | G7-3 | G7-4 | G7-5 | Mean | SD |
| Pre-dose (Mix plasma) | | ND | ND | ND | ND | ND | — | — |
| 30 min | 0.50 | 252 | 270 | 284 | 277 | 249 | 266 | 15.4 |
| 4 h | 4 | 202 | 217 | 216 | 161 | 172 | 194 | 25.7 |
| Day 2 | 48 | 102 | 103 | 87.4 | 89.8 | 93.9 | 95.2 | 7.05 |
| Day 3 | 72 | 86.4 | 73.2 | 81.1 | 73.3 | 84.9 | 79.8 | 6.27 |
| Day 5 | 120 | 70.8 | 62.5 | 61.4 | 68.2 | 70.2 | 66.6 | 4.39 |
| Day 7 | 168 | 39.8 | 38.2 | 37.6 | 39.9 | 43.0 | 39.7 | 2.10 |
| Day 10 | 240 | 22.9 | 31.1 | 25.9 | 29.3 | 25.0 | 26.8 | 3.32 |
| Day 12 | 288 | 20.2 | 27.5 | 23.1 | 31.2 | 28.0 | 26.0 | 4.34 |
| Day 14 | 336 | 19.4 | 24.9 | 17.4 | 23.8 | 19.3 | 21.0 | 3.22 |
| Day 21 | 504 | 8.65 | 19.3 | 0.319 | 9.19 | 6.81 | 8.85 | 6.82 |
| Day 28 | 672 | 2.89 | 6.36 | ND | 3.77 | 0.555 | 3.39 | 2.40 |
| $t_{1/2}$ (h) | | 122 | 191 | 120 | 126 | 107 | 133 | 32.9 |

Example 12: Pharmacodynamic and Pharmacokinetic Properties in a Non-Human Primate Model The in vivo efficacy of the candidate antigen binding moieties was further assessed using assays performed to determine their pharmacodynamic and pharmacokinetic properties in a cynomolgus monkey model.

To investigate the in vivo pharmacokinetic properties of WBP71460_16 (Candidate 19.1), the candidate antigen binding moiety was evaluated in cynomolgus monkeys. 8 groups of male cynomolgus monkeys (4 animals per group) received a single 30 mg/kg intravenous infusion of one of each candidate antigen binding moiety (WBP71460_1, WBP71460_5, WBP71460_8, WBP71460_9, WBP71460_10, WBP71460_11, WBP71460_16, and WBP71460_17) administered over 30 minutes. Blood samples were collected pre-dose (Day 0), at 30 minutes, 1 hour, 4 hours, and 12 hours post-infusion, and again on Days 1, 3, 5, 7, 10, 14, 21, 28, 35, 42, 49, and 56 post-dose, to characterize serum pharmacokinetics. For the cynomolgus monkey pharmacokinetic ELISA, 96-well high-binding plates were coated overnight at 4° C. with either human TSLP-His (5 μg/mL for groups G1-G3; 1 μg/mL for groups G4-G7) or goat anti-human IgG (1 μg/mL for group G8) in PBS (Table 21). After 3 washes, wells were blocked with 2% BSA in PBS for 1 hour at room temperature. Serial dilutions of cynomolgus monkey serum samples (diluted in 2% BSA in PBS) were then added and incubated for 1 hour at room temperature. Plates were washed three times and incubated with 0.1 μg/mL biotinylated human IL-4R for 1 hour, followed by streptavidin-HRP for 30 minutes. Color was developed with TMB substrate, quenched with stop solution, and absorbance was measured at 450-540 nm. Data were processed in SoftMax Pro and dose-response curves fitted in GraphPad Prism to determine relative binding affinities.

Figure 25:
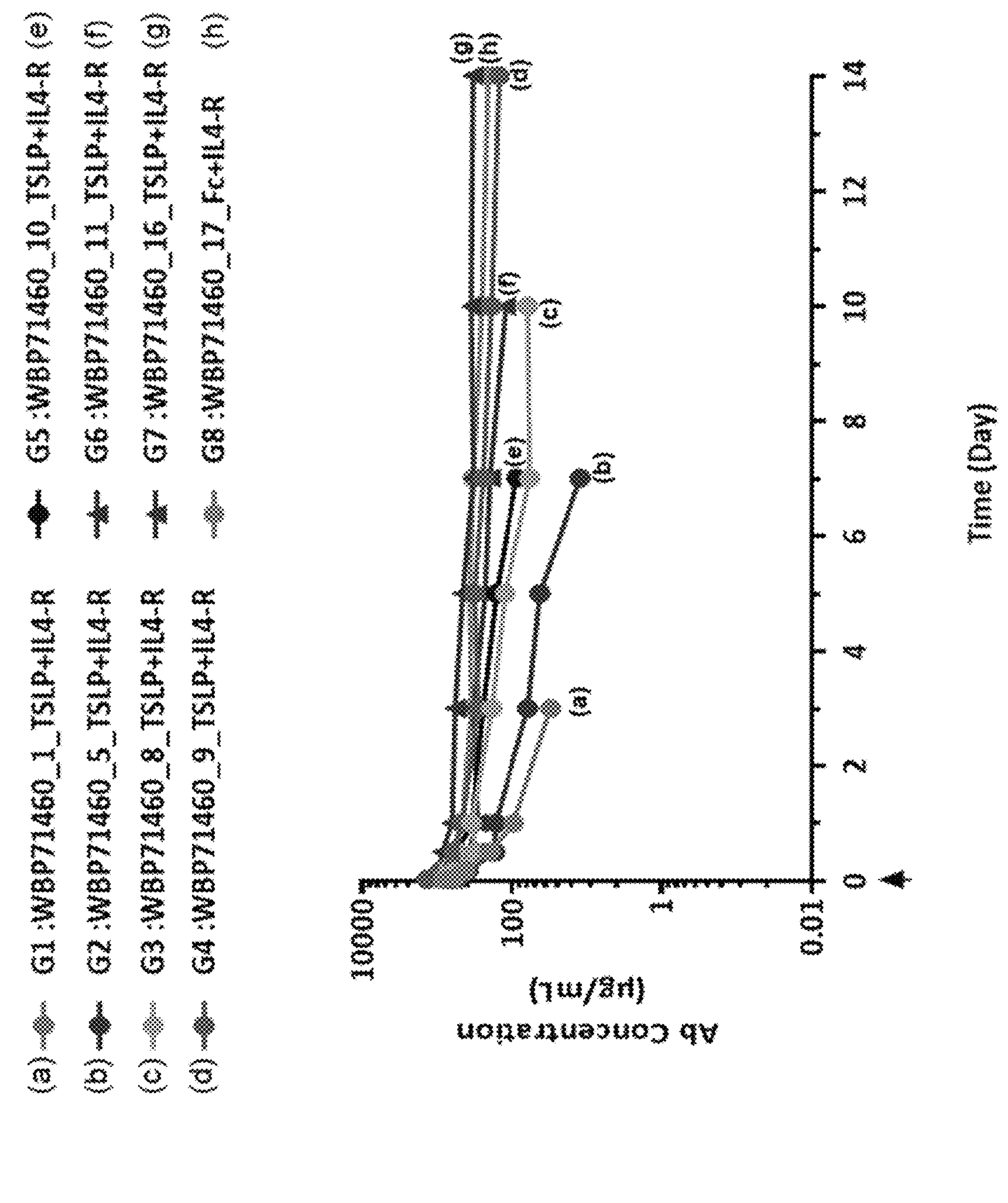
FIG. 25 shows a pharmacokinetic experiment quantifying circulating concentrations of each candidate antigen binding moiety over a 14-day period in a cynomolgus monkey model.
Figure 26:
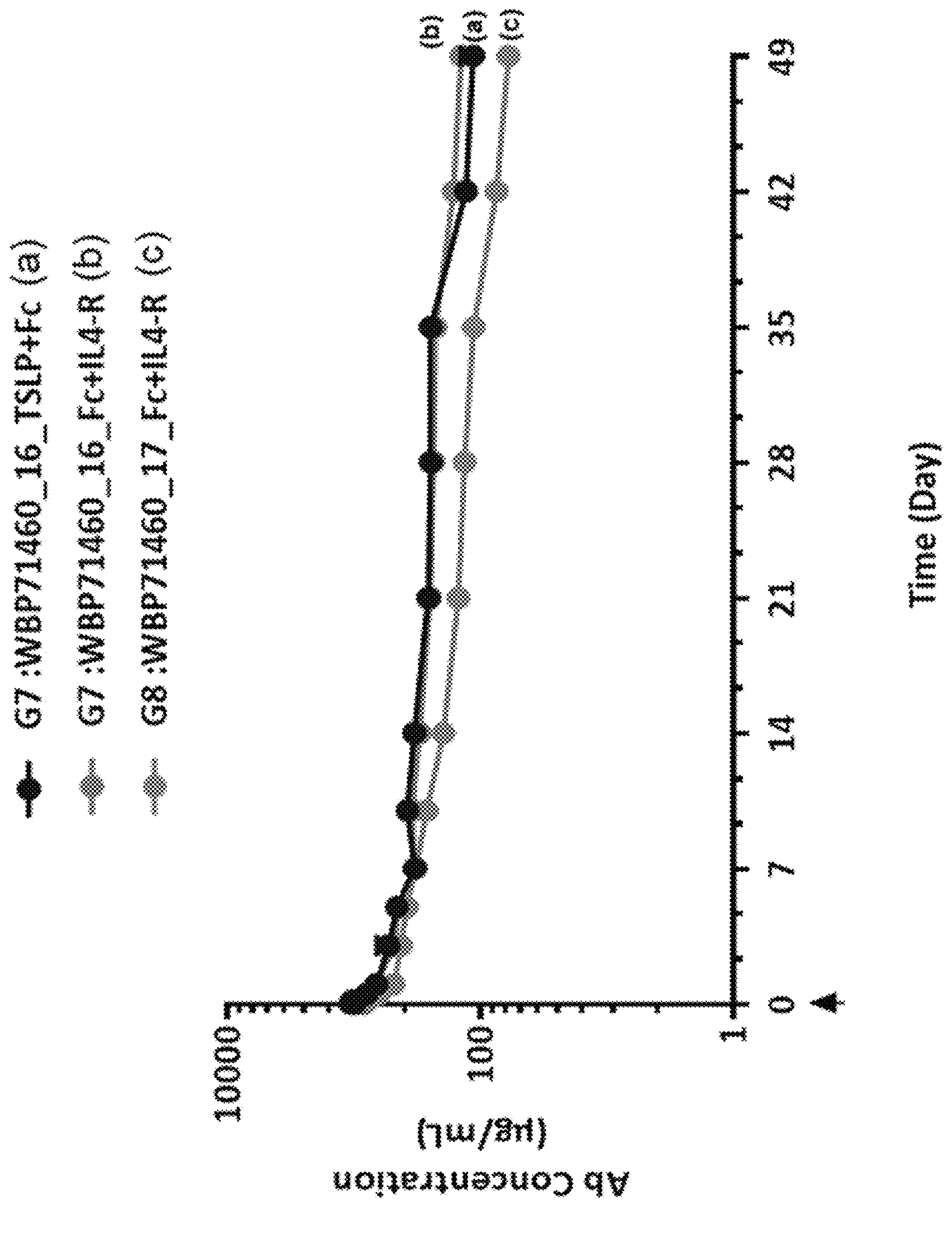
FIG. 26 shows a pharmacokinetic experiment quantifying circulating concentrations of each candidate antigen binding moiety over a 49-day period in a cynomolgus monkey model.
Figure 27:
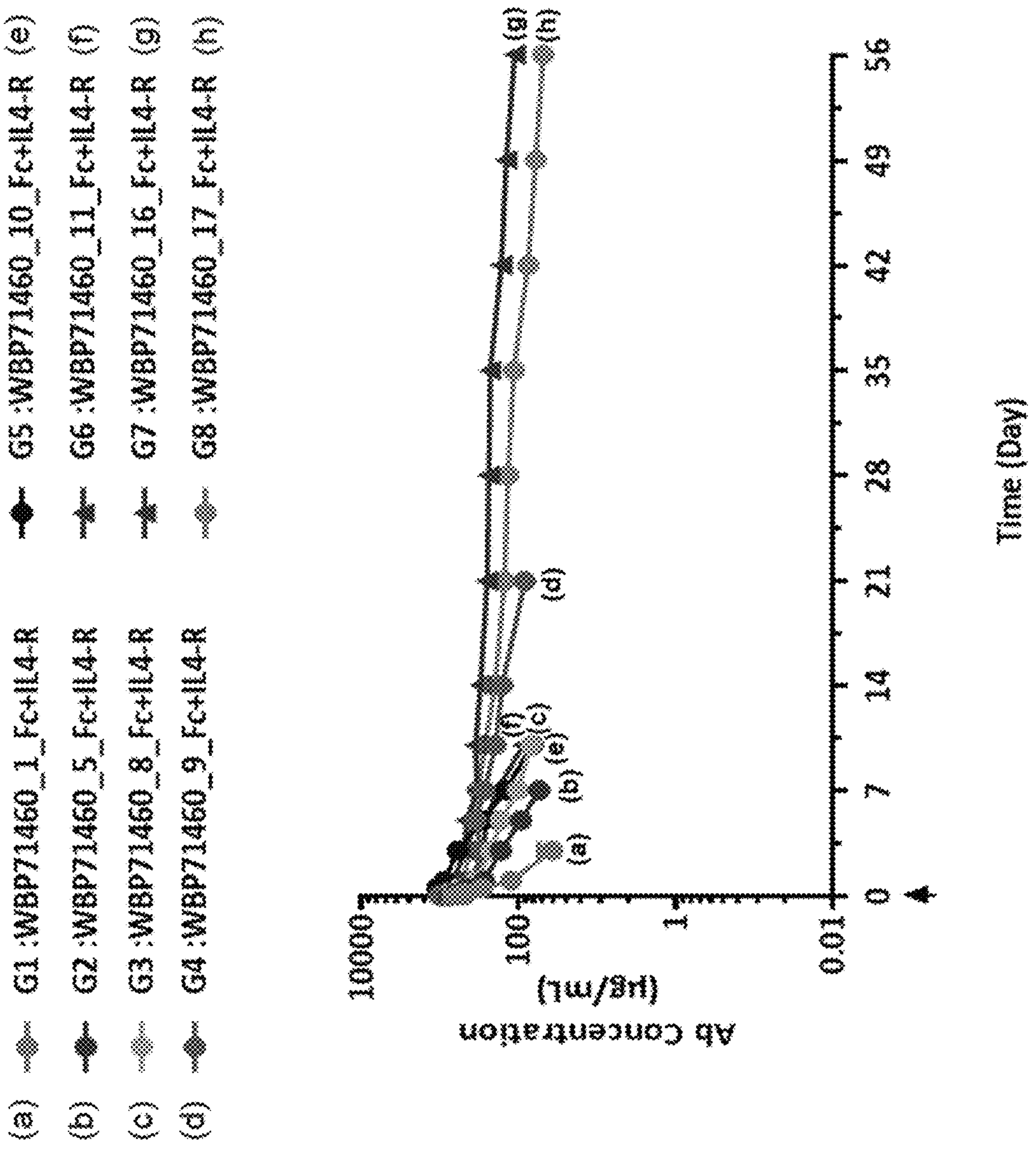
FIG. 27 shows a pharmacokinetic experiment quantifying circulating concentrations of each candidate antigen binding moiety over a 56-day period in a cynomolgus monkey model.
Figure 28:
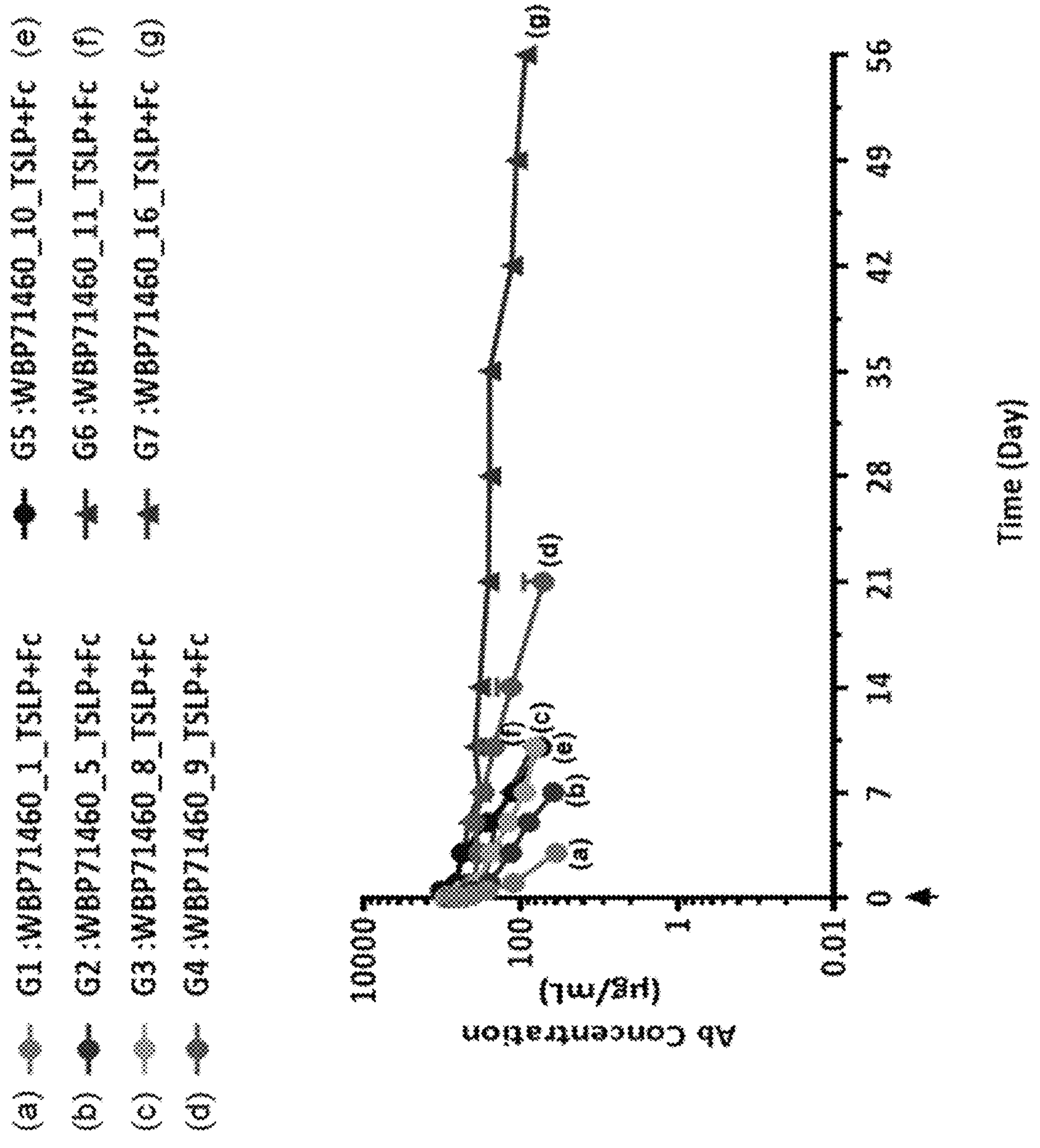
FIG. 28 shows a pharmacokinetic experiment quantifying circulating concentrations of each candidate antigen binding moiety over a 56-day period in a cynomolgus monkey model.
Figure 29:
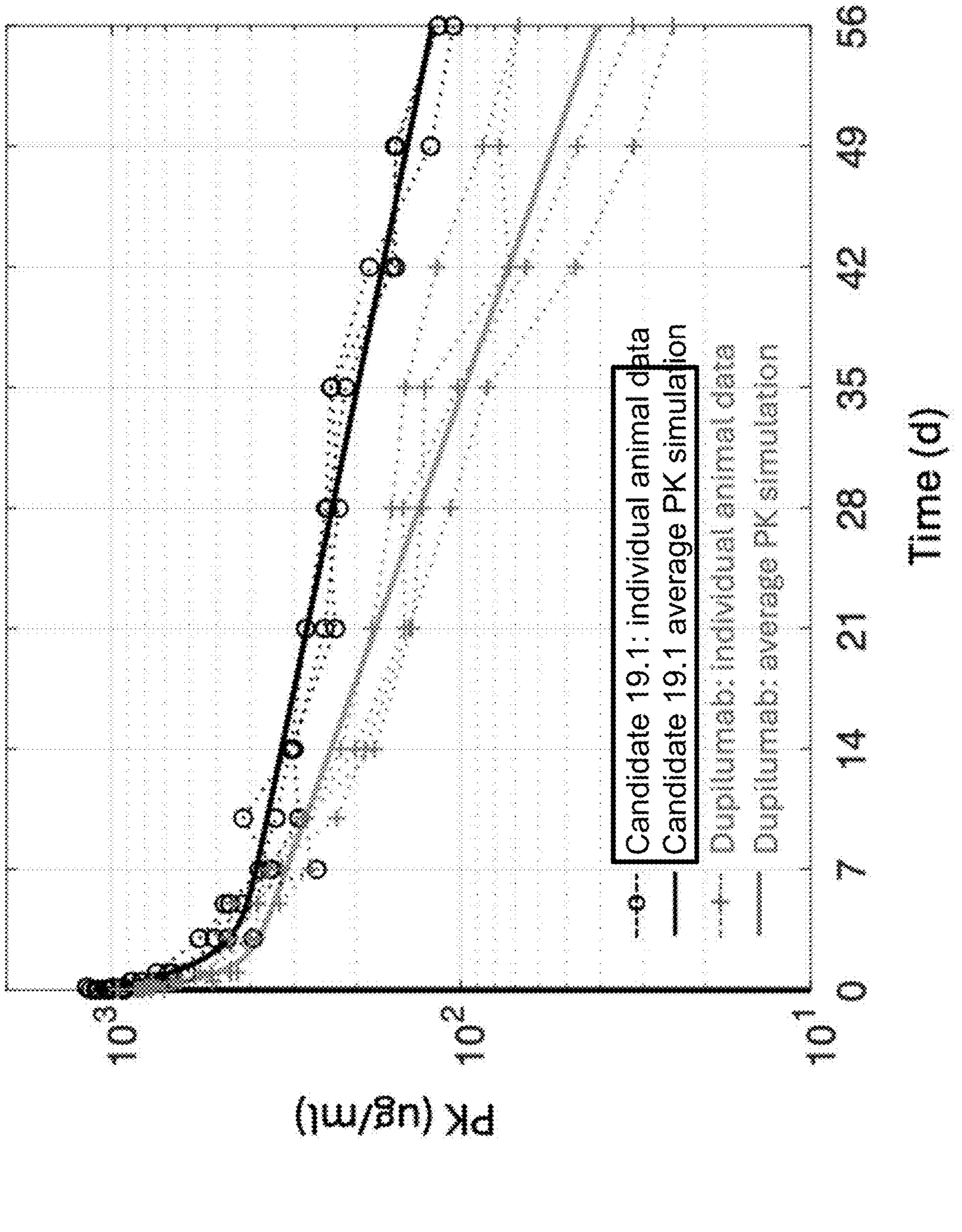
FIG. 29 shows in vivo pharmacokinetic data demonstrating the half-life in a cynomolgus monkey model.

Pharmacokinetic parameters including half-life ($t_{1/2}$), $C_{max}$, $AUC_{0-t}$, Cl_obs, MRTINF_obs, and Vss_obs were quantified using non-compartmental analysis and fitting to 2-compartment PK model with linear elimination (Tables 21-25), and antibody concentration as a function of time over a 14-day period was determined (FIG. 25). Pharmacokinetic profiles of candidate antigen binding moieties were evaluated through more protracted time points as well (FIGS. 26-28). In cynomolgus monkeys, WBP71460_16 (Candidate 19.1) exhibited a half-life of about 32 days over a 56-day period, greatly exceeding the 17-day half-life of Dupilumab over this time period (FIG. 29, Tables 25-27). These results support that WBP71460_16 (Candidate 19.1) remains in circulation for unexpectedly long time periods, exhibiting a greater half-life than other candidate antigen binding moieties used in these studies. This unexpectedly long half-life suggests strong therapeutic potential.

TABLE 21

Pharmacokinetic properties of candidate antigen binding moieties in a cynomolgus monkey model.

| | Method (Capture + Detection) TSLP + IL4-R | | | | |
|---|---|---|---|---|---|
| | Compound | | | | |
| | G1: WBP71460_1 | G2: WBP71460_5 | G3: WBP71460_8 | G4: WBP71460_9 | G5: WBP71460_10 |
| Dose | 30 mg/kg (IV infusion for 30 min) | | | | |
| t½ (h) | 24.0 | 39.4 | 58.7 | 148* | 79.0* |
| Cmax (μg/mL) | 736 | 633 | 784 | 1410 | 721 |
| AUC 0-t (h*μg/mL) | 8972 | 14853 | 30934 | 84149 | 42039 |
| Cl_obs (mL/day/kg) | 72.4 | 46.8 | 76.4 | 6.55 | 14.2 |

| | Method (Capture + Detection) | | |
|---|---|---|---|
| | TSLP + IL4-R | | Fc + IL4-R |
| | Compound | | |
| | G6: WBP71460_11 | G7: WBP71460_16 | G8: WBP71460_17 |
| Dose | 30 mg/kg (IV infusion for 30 min) | | |
| t½ (h) | 49.5* | 217* | 262* |
| Cmax (μg/mL) | 652 | 1148 | 876 |
| AUC 0-t (h*μg/mL) | 44994 | 138533 | 113495 |
| Cl_obs (mL/day/kg) | 111 | 3.38 | 3.71 |

TABLE 22

Pharmacokinetic properties of candidate antigen binding moieties in a cynomolgus monkey model.

| | Method (Capture + Detection) | | |
|---|---|---|---|
| | TSLP + Fc | Fc + IL4-R | |
| | Compound | | |
| | G7: WBP71460_16 | G7: WBP71460_16 | G8: WBP71460_17 |
| | Dose 30 mg/kg (IV infusion for 30 min) | | |
| t ½ (h) | 356* | 466* | 382 |
| Cmax (μg/mL) | 1110 | 1055 | 863 |
| AUC 0-t (h*μg/mL) | 277078 | 269649 | 218201 |
| Cl_obs (mL/day/kg) | 2.73 | 2.66 | 2.89 |
| MRTINF_obs (h) | 560 | 706 | 570 |
| Vss_obs (mL/kg) | 45.51 | 52.3 | 67.1 |

TABLE 23

Pharmacokinetic properties of candidate antigen binding moieties in a cynomolgus monkey model.

| | Compound | | | | |
|---|---|---|---|---|---|
| | G1: WBP71460_1 | G2: WBP71460_5 | G3: WBP71460_8 | G4: WBP71460_9 | G5: WBP71460_10 |
| Method (Capture + Detection) | Fc + IL4-R | | | | |
| Dose | 30 mg/kg (IV infusion for 30 min) | | | | |
| t½ (h) | 20.4* | 58.2 | 69.9 | 113* | 52.5 |
| Cmax (μg/mL) | 643 | 785 | 768 | 1048 | 1098 |
| AUC 0-t (h*μg/mL) | 10783 | 29865 | 35927 | 103158 | 92045 |
| AUC_(0-∞) (h*μg/mL) | 11982 | 34857 | 42907 | 115329 | 101542 |
| Cl_obs (mL/day/kg) | 60.6 | 20.7 | 131 | 7.36 | 7.31 |
| MRTINF_obs (h) | 28.3 | 77.9 | 96.0 | 189 | 82.2 |
| Vss_obs (mL/kg) | 71.4 | 67.0 | 75.7 | 49.4 | 24.3 |

| | Compound | | |
|---|---|---|---|
| | G6: WBP71460_11 | G7: WBP71460_16 | G8: WBP71460_17 |
| Method (Capture + Detection) | Fc + IL4-R | | |
| Dose | 30 mg/kg (IV infusion for 30 min) | | |
| t½ (h) | 52.7# | 461*# | 401 |
| Cmax (μg/mL) | 672 | 1055 | 863 |
| AUC 0-t (h*μg/mL) | 38327 | 285660 | 227318 |
| AUC_(0-∞) (h*μg/mL) | 45883 | 365934 | 257550 |
| Cl_obs (mL/day/kg) | 154 | 2.68 | 2.85 |
| MRTINF_obs (h) | 78.6 | 684 | 592 |
| Vss_obs (mL/kg) | 60.6 | 51.9 | 68.5 |

TABLE 24

| Pharmacokinetic properties of candidate antigen binding moieties in a cynomolgus monkey model. | | | | | | | |
|---|---|---|---|---|---|---|---|
| | Compound | | | | | | |
| | G1: WBP71460_1 | G2: WBP71460_5 | G3: WBP71460_8 | G4: WBP71460_9 | G5: WBP71460_10 | G6: WBP71460_11 | G7: WBP71460_16 |
| Method | TSLP + Fc | | | | | | |
| Dose | 30 mg/kg (IV infusion for 30 min) | | | | | | |
| t½ (h) | 20.9* | 49.2 | 88.8# | 79.1* | 47.6 | 52.9# | 382*# |
| Cmax (μg/mL) | 723 | 798 | 923 | 914 | 1051 | 684 | 1110 |
| AUC 0-t (h*μg/mL) | 10314 | 25970 | 35634 | 106277 | 81149 | 32975 | 289753 |
| AUC_(0-∞) (h*μg/mL) | 11438 | 29332 | 44634 | 112955 | 87522 | 39174 | 344991 |
| Cl_obs (mL/day/kg) | 63.9 | 24.6 | 75.0 | 7.01 | 8.45 | 134 | 2.72 |
| MRTINF_obs (h) | 28.6 | 68.5 | 109 | 162 | 79.2 | 75.4 | 569 |
| Vss_obs (mL/kg) | 76.8 | 70.2 | 65.9 | 43.1 | 27.5 | 66.7 | 46.1 |

TABLE 25

| 2-compartment pharmacokinetic model parameter estimates. | | |
|---|---|---|
| Compound | Candidate 19.1 (30 mg/kg) | Dupilumab (30 mg/kg) |
| N included/N studied | 3/4* | 4/4 |
| CL (mL/h/kg) | 0.06 | 0.12 |
| Q (ml/h/kg) | 0.49 | 1.02 |
| V1 (mL/kg) | 29 | 35 |

TABLE 25-continued

| 2-compartment pharmacokinetic model parameter estimates. | | |
|---|---|---|
| Compound | Candidate 19.1 (30 mg/kg) | Dupilumab (30 mg/kg) |
| V2 (ml/kg) | 34 | 32 |
| $t_{1/2}$ (d) | 32 | 17 |

TABLE 26

| Serum concentration time-course data for WBP71460_16 (Candidate 19.1). | | | | | | | |
|---|---|---|---|---|---|---|---|
| | | Compound WBP71460_16 (Candidate 19.1) Method Fc+IL4-R Dose 30 mg/kg, I.V. infusion for 30 min, Cynomolgus Monkey | | | | | |
| Time (d) | Time (h) | #701 (M) | #702 (M) | #703 (M) | #704 (M) | Mean | SD |
| pre-dose | pre-dose | ND | ND | ND | ND | — | — |
| 0.0208 | 0.50 | 930 | 1020 | 1110 | 1090 | 1038 | 81.4 |
| 0.0417 | 1.00 | 918 | 1010 | 1150 | 1040 | 1030 | 95.6 |
| 0.167 | 4.00 | 833 | 930 | 1180 | 993 | 984 | 146 |
| 0.5 | 12.00 | 762 | 723 | 824 | 878 | 797 | 68.3 |
| 1 | 24 | 669 | 687 | 742 | 609 | 677 | 54.8 |
| 3 | 72 | 393 | 466 | 560 | 507 | 482 | 70.4 |
| 5 | 120 | 422 | 457 | 459 | 475 | 453 | 22.3 |
| 7 | 168 | 353 | 378 | 347 | 259 | 334 | 51.9 |
| 10 | 240 | 291 | 339 | 420 | 70.8^ | 280 | 149 |
| 14 | 336 | 301 | 307 | 307 | ND | 305 | 3.46 |
| 21 | 504 | 246 | 278 | 229 | ND | 251 | 24.9 |
| 28 | 672 | 224 | 244 | 241 | ND | 236 | 10.8 |
| 35 | 840 | 235 | 236 | 214 | ND | 228 | 12.4 |
| 42 | 1008 | 183 | 154 | 158 | ND | 165 | 15.7 |
| 49 | 1176 | 122 | 155 | 153 | ND | 143 | 18.5 |
| 56 | 1344 | 105 | 116 | 116 | ND | 112 | 6.46 |
| NCA t½ (h) | | 411 | 691# | 645# | 95.5*# | 461*# | 272 |

TABLE 27

Serum concentration time-course data for WBP71460_17 (Dupilumab).

| | | Compound WBP71460_17 (Dupilumab) Method Fc + IL4-R Dose 30 mg/kg, I.V. infusion for 30 min, Cynomolgus Monkey | | | | | |
|---|---|---|---|---|---|---|---|
| Time (d) | Time (h) | #801 (M) | #802 (M) | #803 (M) | #804 (M) | Mean | SD |
| pre-dose | pre-dose | ND | ND | ND | ND | — | — |
| 0.0208 | 0.50 | 961 | 858 | 771 | 816 | 852 | 81.2 |
| 0.0417 | 1.00 | 966 | 841 | 705 | 828 | 835 | 107 |
| 0.167 | 4.00 | 784 | 756 | 798 | 792 | 783 | 18.6 |
| 0.5 | 12.00 | 763 | 658 | 512 | 637 | 643 | 103 |
| 1 | 24 | 558 | 519 | 436 | 456 | 492 | 56.3 |
| 3 | 72 | 384 | 461 | 402 | 457 | 426 | 38.8 |
| 5 | 120 | 383 | 448 | 331 | 383 | 386 | 47.9 |
| 7 | 168 | 354 | 356 | 269 | 325 | 326 | 40.6 |
| 10 | 240 | 227 | 279 | 279 | 284 | 267 | 26.9 |
| 14 | 336 | 188 | 221 | 177 | 201 | 197 | 18.9 |
| 21 | 504 | 141 | 180 | 138 | 145 | 151 | 19.5 |
| 28 | 672 | 107 | 158 | 129 | 146 | 135 | 22.1 |
| 35 | 840 | 84.1 | 144 | 127 | 102 | 114 | 26.5 |
| 42 | 1008 | 47.1 | 117 | 72.7 | 65.1 | 75.5 | 29.7 |
| 49 | 1176 | 32.1 | 86.5 | 77.4 | 46.4 | 60.6 | 25.6 |
| 56 | 1344 | 24.6 | 68.6 | 68.2 | 32.3 | 48.4 | 23.3 |
| NCA t½ (h) | | 317 | 461 | 494 | 333 | 401 | 89.1 |

The in vivo pharmacokinetic properties of the candidate antigen binding moieties was further assessed in a cynomolgus monkey model via an exploratory study performed to assess different routes of administration. 2 groups of 3 cynomolgus monkeys received either a single 10 mg/kg intravenous infusion of WBP71460_16 (Candidate 19.1) administered over 30 minutes, or a subcutaneous bolus dose of 30 mg/kg of WBP71460_16 (Candidate 19.1). Blood samples were collected pre-dose (Day 0), at 30 minutes, 1 hour, 4 hours, and 12 hours post-infusion, and again on Days 1, 3, 5, 7, 10, and 14, to characterize serum pharmacokinetics. For the cynomolgus monkey pharmacokinetic ELISA, 96-well high-binding plates were coated overnight at 4° C. with either human TSLP-His (5 μg/mL for WBP71460_1, 5,8; 1 μg/mL for (WBP71460_9,10,11,16) or goat anti-human IgG (1 μg/mL for WBP71460_17) in PBS. After 3 washes, wells were blocked with 2% BSA/PBS for 1 hour at room temperature. Serial dilutions of cynomolgus monkey serum samples (diluted in 2% BSA in PBS) were then added and incubated for 1 hour at room temperature. Plates were washed three times and then incubated with 0.1 μg/mL biotinylated human IL-4R for 1 hour. Following another wash step, bound biotinylated receptor was detected by incubation with streptavidin-HRP for 30 minutes and color development with TMB substrate. The reaction was stopped with 1 M sulfuric acid, and absorbance was measured at 450-540 nm. Data were processed in SoftMax Pro and dose-response curves fitted in GraphPad Prism to determine relative binding affinities.

Figure 30:
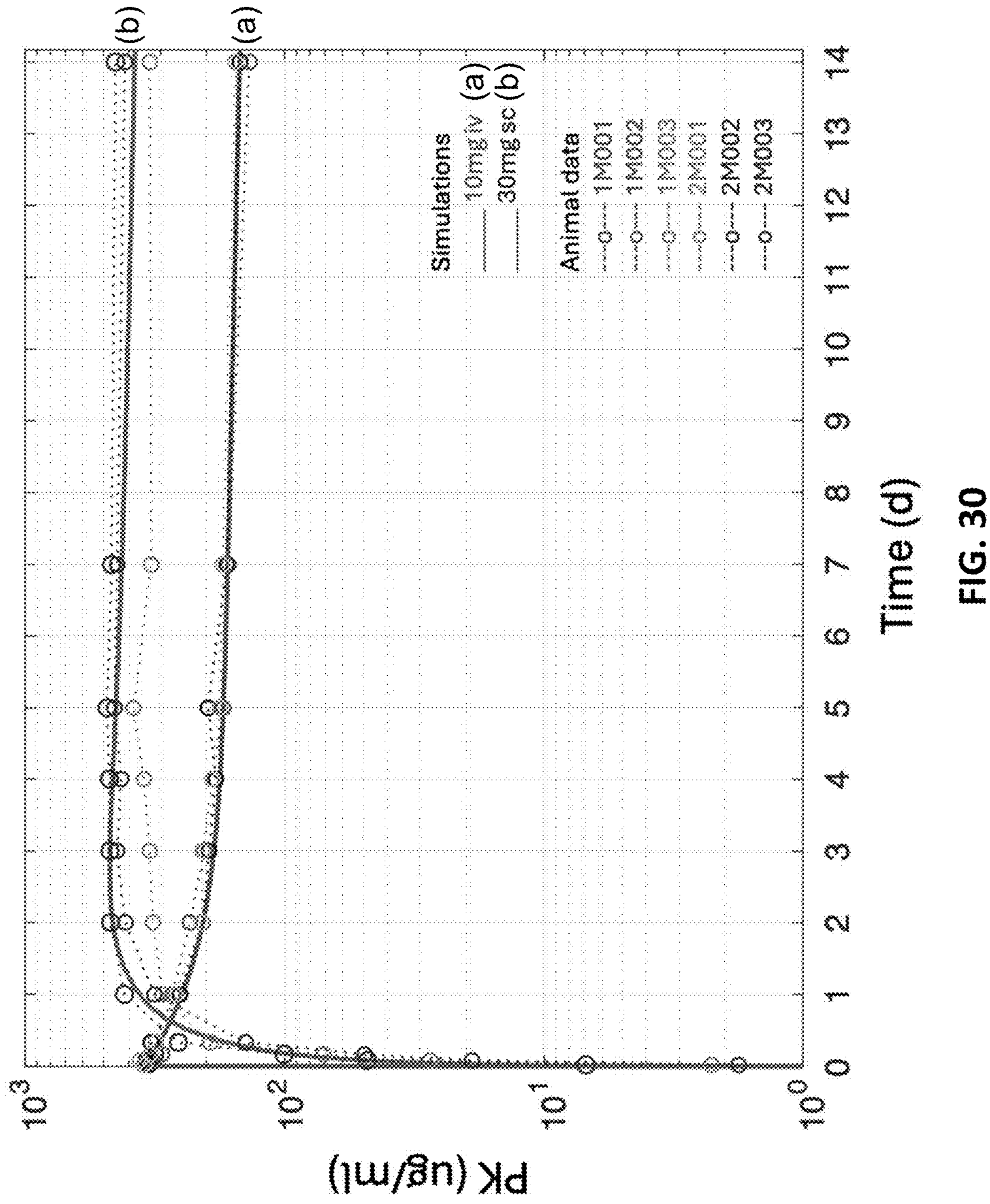
FIG. 30 shows PK (μg/ml) following intravenous (iv) or subcutaneous (sc) administration in a cynomolgus monkey model.

Data were fit to a standard 3-compartment PK model with linear elimination to estimate PK parameters. Pharmacokinetic parameters including half-life ($t_{1/2}$), $C_{max}$, $AUC_{0-t}$, CI_obs, MRTINF_obs, and Vss_obs were quantified under a non-compartmental analysis (Table 28), and pharmacokinetic parameters including CL (ml/h/kg), Q (ml/h/kg), V1 (ml/kg), V2 (ml/kg), and half-life ($t_{1/2}$) were quantified under a 3-compartment analysis (Table 29), and antibody concentration as a function of time over a 14-day period was determined (FIG. 30 and Table 30).

WBP71460_16 (Candidate 19.1) achieved high systemic exposure following both intravenous and subcutaneous administration. The subcutaneous route showed a delayed absorption phase and sustained serum concentrations, with an estimated bioavailability of approximately 80%, indicating efficient SC absorption (Table 29). The prolonged bioavailability of WBP71460_16 (Candidate 19.1), even with subcutaneous administration, supports that fewer injections would be required to incur a therapeutic benefit.

TABLE 28

Noncompartmental analysis average pharmacokinetic parameters.

| Parameter | Iv average (10 mg/kg) | sc average (30 mg/kg) |
|---|---|---|
| Tmax (d) | 1.5 | 120 |
| CLobs (ml/kg/h) | 0.046 | 0.028 |
| Vd (ml/kg) | 49 | 67 |
| AUClast (h*ug/ml) | 61,931 | 123,260 |
| T½* (d) | 32 | 75 |

TABLE 29

3-compartment pharmacokinetic model parameters estimates (pooled).

| | ALL ANIMALS | | EXCLUDING 2M001 (sc) | |
|---|---|---|---|---|
| Parameter | Estimate | Standard Error | Estimate | Standard Error |
| CL (ml/kg/h)* | 0.024 | 0.020 | 0.033 | 0.0079 |
| Q (ml/kg/h) | 0.50 | 0.14 | 0.47 | 0.090 |
| V1 (ml/kg) | 29 | 0.51 | 29 | 0.77 |
| V2 (ml/kg) | 23 | 6.4 | 21 | 3.3 |
| kabs (1/h) | 0.031 | 0.0038 | 0.030 | 0.0032 |
| Fb | 0.77 | 0.043 | 0.83 | 0.045 |

TABLE 30

WBP71460_16 (Candidate 19.1) 216 serum concentration after intravenous (Group 1) or subcutaneous (Group 2) dosing.

| | | serum concentration (ug/ml) | | | | | |
|---|---|---|---|---|---|---|---|
| | | GROUP 1: IV ROUTE | | | GROUP 2: SC ROUTE | | |
| Time (h) | time (d) | 1M001 | 1M002 | 1M003 | 2M001 | 2M002 | 2M003 |
| 0.5 | 0.0208 | 333.26 | 348.09 | 346.33 | 2.25 | 6.92 | 1.76 |
| 2 | 0.0833 | 343.02 | 322.87 | 362.00 | 27.36 | 48.16 | 18.97 |
| 4 | 0.167 | 312.50 | 296.08 | 328.52 | 70.95 | 100.42 | 49.27 |
| 8 | 0.333 | 326.86 | 313.03 | 312.63 | 193.43 | 256.53 | 141.23 |
| 24 | 1 | 252.57 | 269.84 | 263.24 | 295.44 | 415.20 | 316.86 |
| 48 | 2 | 207.36 | 231.28 | 208.31 | 320.99 | 469.05 | 411.68 |
| 72 | 3 | 195.44 | 204.27 | 207.11 | 330.57 | 471.76 | 443.79 |
| 96 | 4 | 183.99 | 189.23 | 189.18 | 348.50 | 474.06 | 427.07 |
| 120 | 5 | 197.03 | 172.26 | 177.68 | 383.27 | 483.37 | 453.56 |
| 168 | 7 | 166.91 | 164.25 | 173.06 | 325.73 | 465.48 | 442.81 |
| 336 | 14 | 148.49 | 136.80 | 154.25 | 329.70 | 450.13 | 413.51 |

Example 13: Stability of Binding Moiety in a Non-Human Primate Model

Figure 31A:
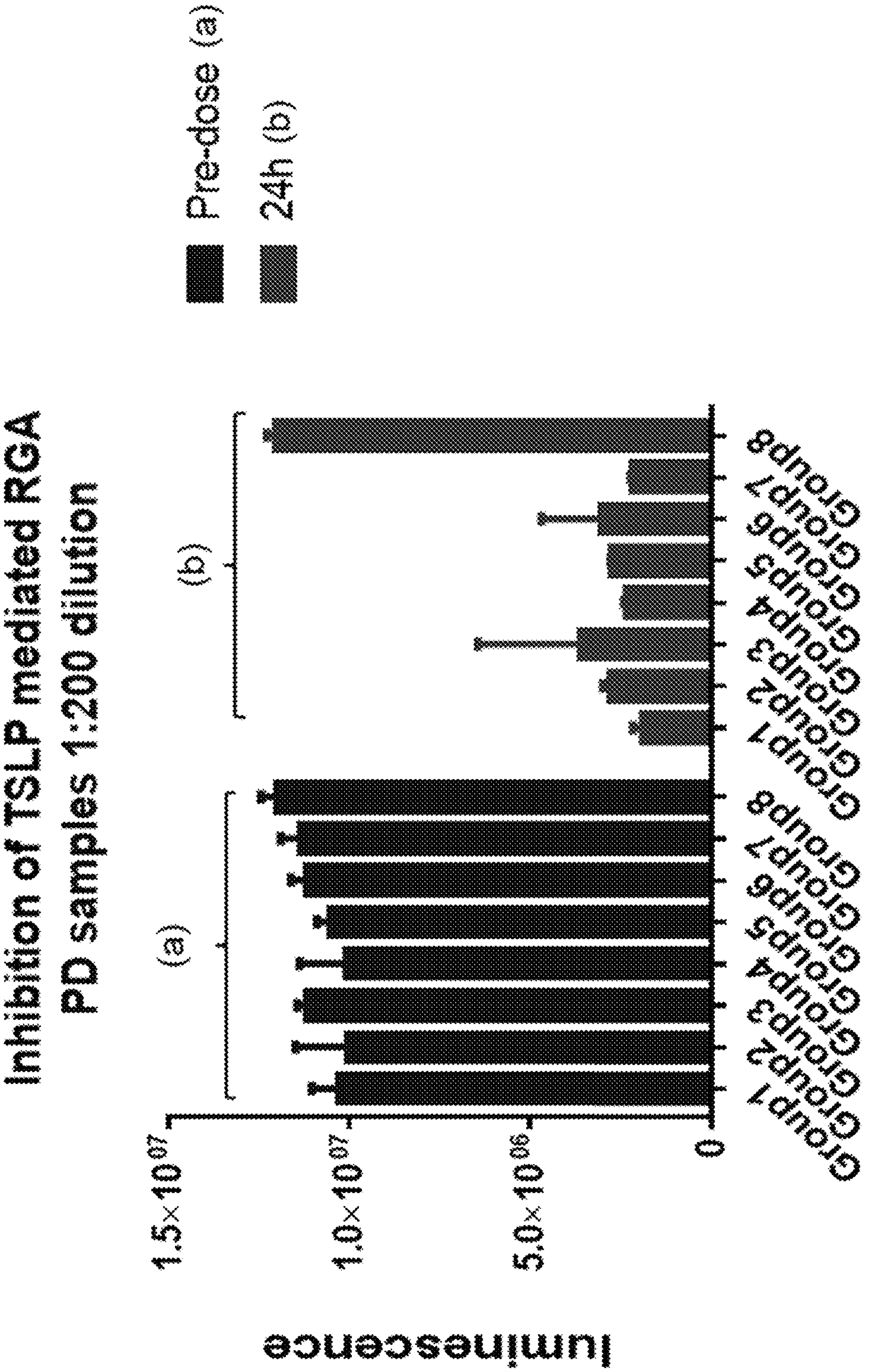
FIGS. 31A-31C show a cell-based luminescence assay.
Figure 31B:
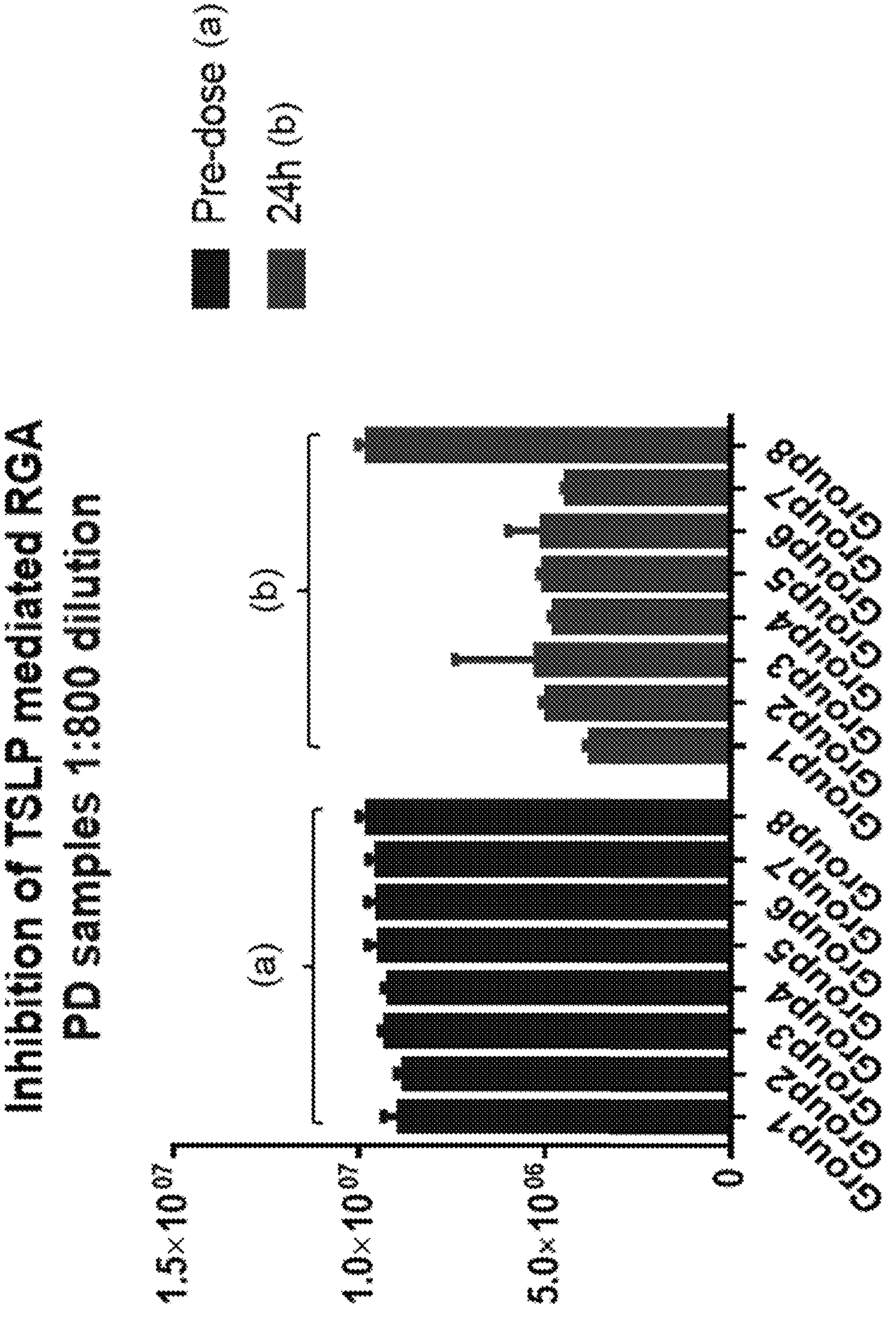
Figure 31C:
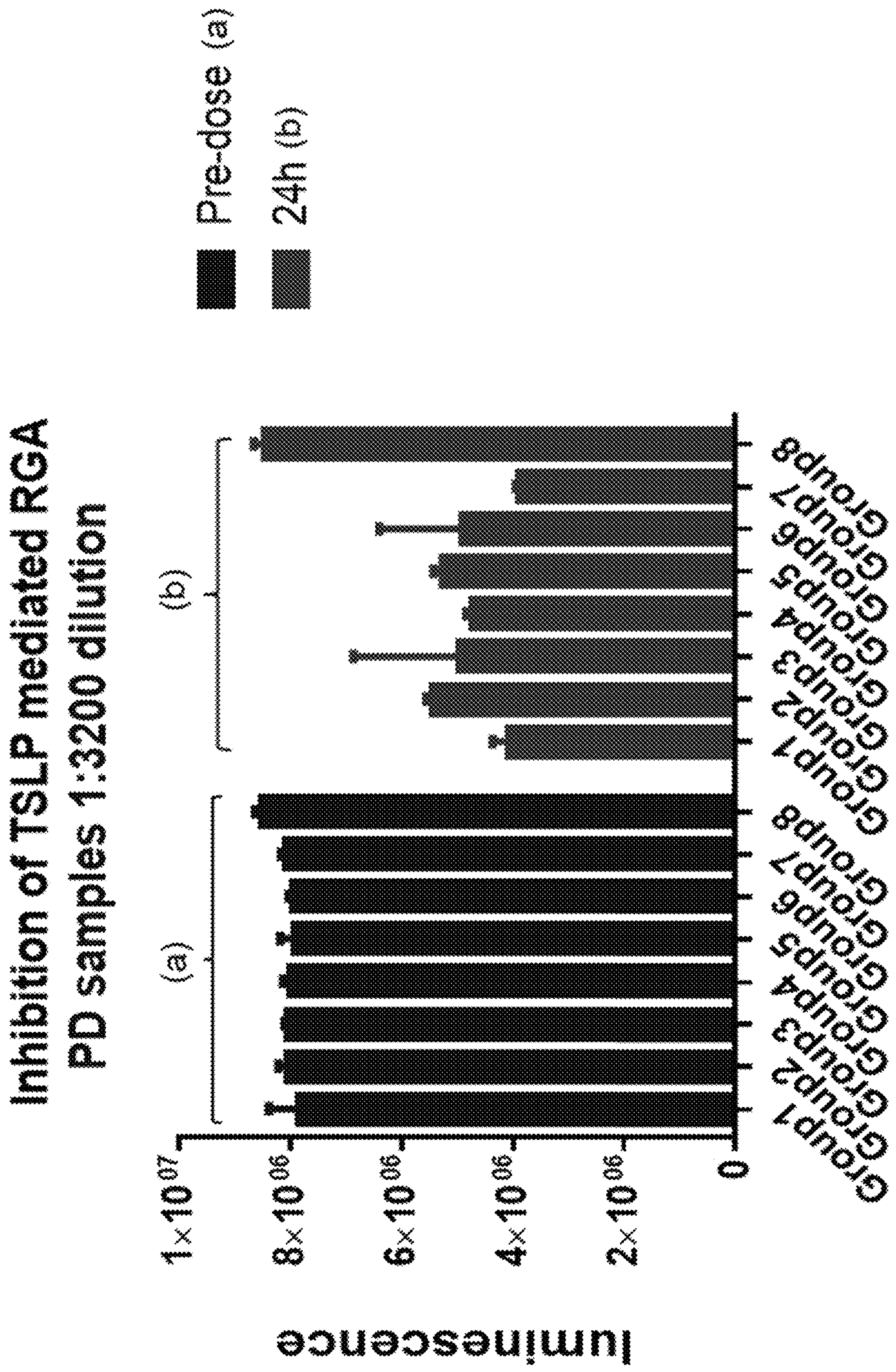

Maintenance of serum stability is an important indicator of antibody quality and therapeutic potential. Stability of WBP71460_16 (Candidate 19.1) in cynomolgus monkey serum following in vivo intravenous injection was assessed using cell-based luminescence assays (RGA) leveraging TSLP and IL-4 reporter cells. First, TSLP reporter cells were starved for 24 hours. After starvation, cells were seeded at $2\times10^4$ cells per 50 μL per well. Samples from cynomolgus monkey serum were then added at 1:200, 1:800, and 1:3200 dilutions (25 μL per well) along with TSLP at a final concentration of 0.4 ng/mL (25 μL per well). The plate was incubated at 37° C. with 500 $CO_2$ for 4-6 hours. Following incubation, Nano-Glo reagent was added, and luminescence was measured using an Envision plate reader (FIGS. 31A-31C). Percent inhibition was calculated relative to cytokine-stimulated, no-antibody controls. As shown in Table 31, antigen binding moieties described herein showed inhibition activity for all dilutions upon 24 hours incubation.

TABLE 31

TSLP reporter cell-based luminescence assay results.

| | Protein | Luminescence(1:200 dilution) | | Luminescence(1:800 dilution) | | Luminescence(1:3200 dilution) | | Inhibition |
|---|---|---|---|---|---|---|---|---|
| | | Pre-dose | 24 h | Pre-dose | 24 h | Pre-dose | 24 h | activity |
| Group 1 | WBP71460_1 | 10296320 | 1883780 | 8868900 | 3703910 | 7837030 | 4076470 | Yes |
| Group 2 | WBP71460_5 | 10024000 | 2796460 | 8765160 | 4921970 | 8044780 | 5446580 | Yes |
| Group 3 | WBP71460_8 | 11198560 | 3621250 | 9255270 | 5217650 | 8054140 | 4955780 | Yes |
| Group 4 | WBP71460_9 | 10061260 | 2328510 | 9178810 | 4705790 | 7997930 | 4731850 | Yes |
| Group 5 | WBP71460_10 | 10540500 | 2725070 | 9399550 | 5005120 | 7919800 | 5260380 | Yes |
| Group 6 | WBP71460_11 | 11189380 | 3045650 | 9460950 | 5015090 | 7941260 | 4905730 | Yes |
| Group 7 | WBP71460_16 | 11346150 | 2185130 | 9478190 | 4372710 | 8087440 | 3901940 | Yes |
| Group 8 | WBP71460_17 | 11997970 | 12019580 | 9742690 | 9735040 | 8507110 | 8447640 | No |

Sample size per group = 4 cynomolgus monkeys.

Figure 32A:
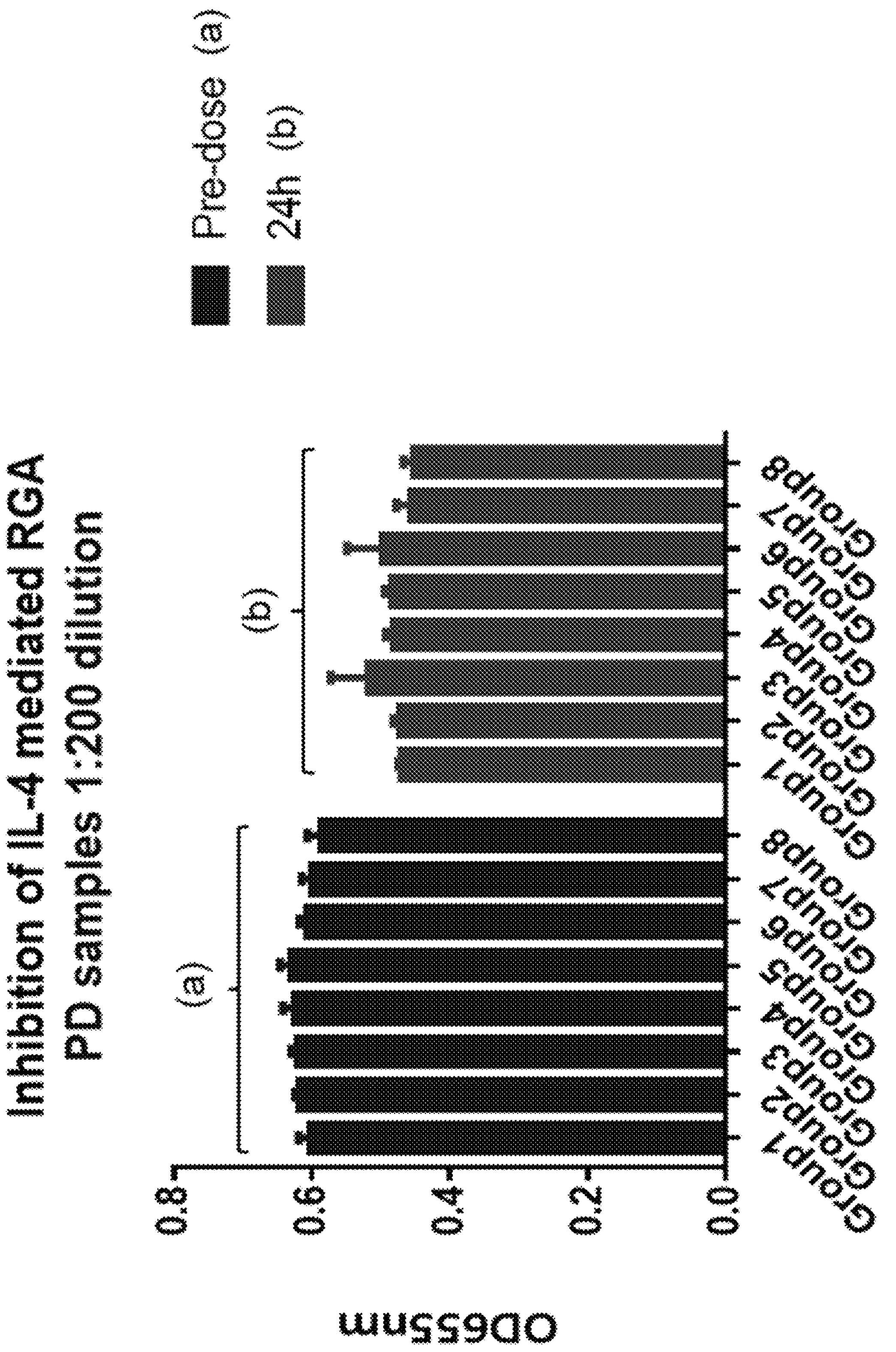
FIGS. 32A-32C show a cell-based luminescence assay.
Figure 32B:
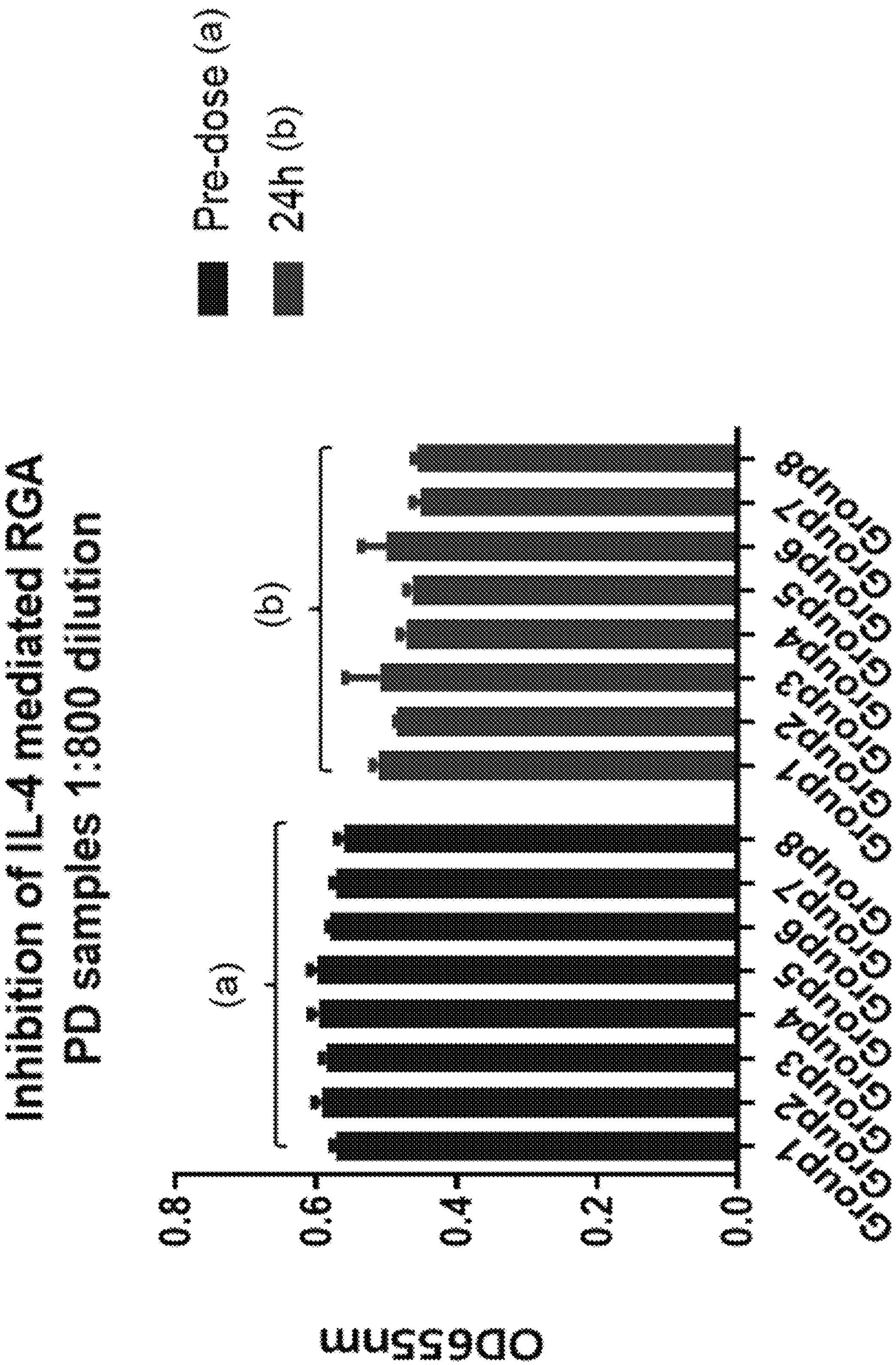
Figure 32C:
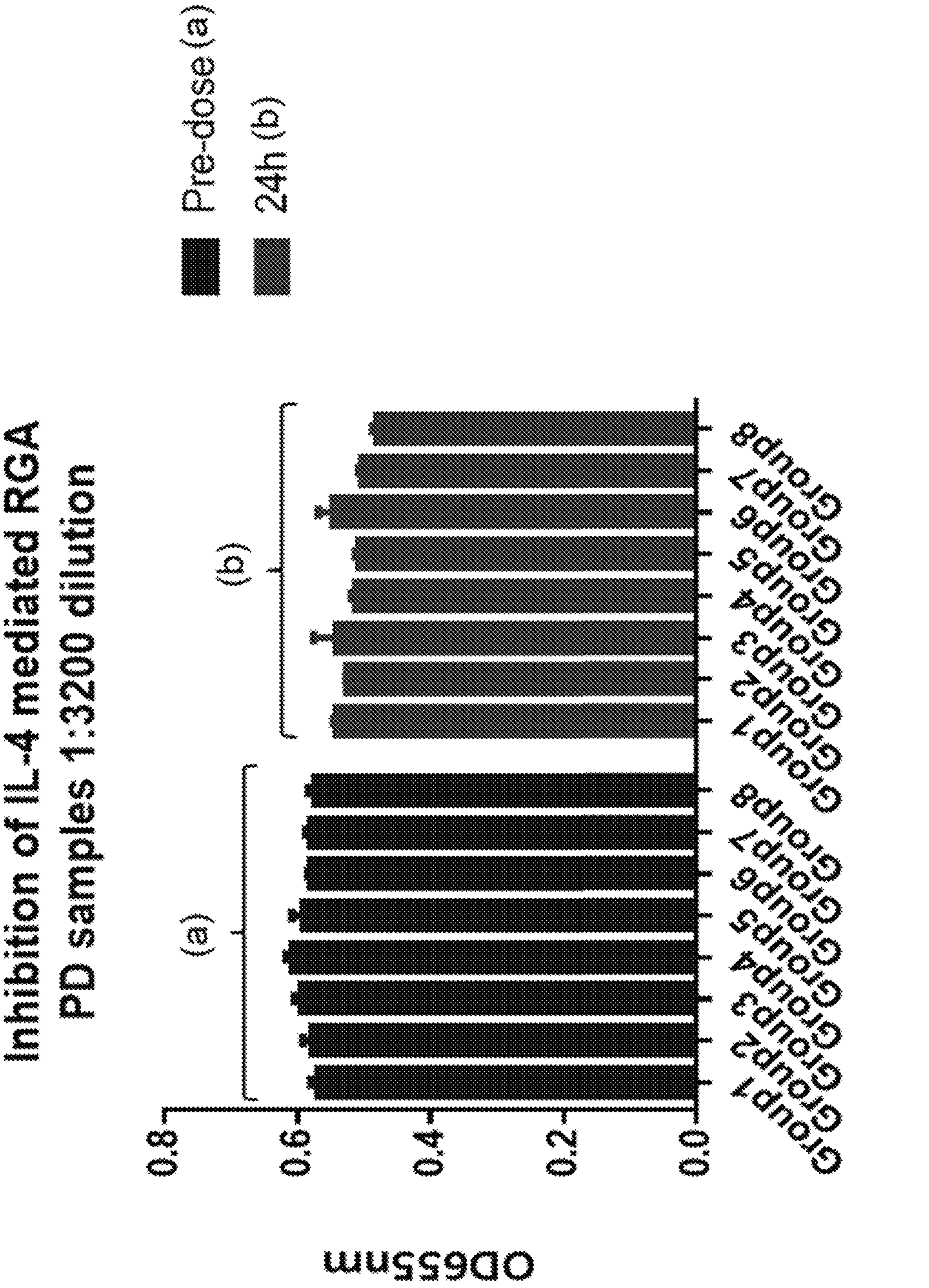

Next, IL-4 reporter cells were seeded at $5\times10^4$ cells per 100 μL per well. Samples from cynomolgus monkey serum were then added at 1:200, 1:800, and 1:3200 dilutions (50 μL per well) along with IL-4 at a final concentration of 2 ng/mL (50 μL per well). The plate was incubated at 37° C. with 5% $CO_2$ for 24 hours. Following incubation, supernatant was collected, and 20 μL was added to 180 μL of Quanti-Blue solution. The plate was developed for 2-3 hours at 37° C. with 5% $CO_2$, and absorbance was measured at 655 nm using a plate reader (FIGS. 32A-32C). Percent inhibition was calculated relative to cytokine-stimulated, no-antibody controls. As shown in Table 32, for all antigen binding moieties, inhibition activity was observed for all dilutions upon 24 hours incubation.

TABLE 32

| IL-4 reporter cell-based luminescence assay results. | | | | | | | | |
|---|---|---|---|---|---|---|---|---|
| | | OD655 nM (1:200 dilution) | | OD655 nM (1:800 dilution) | | OD655 nM (1:3200 dilution) | | Inhibition |
| Group | Protein | Pre-dose | 24 h | Pre-dose | 24 h | Pre-dose | 24 h | activity |
| Group 1 | WBP71460_1 | 0.60 | 0.47 | 0.57 | 0.51 | 0.57 | 0.54 | Yes |
| Group 2 | WBP71460_5 | 0.62 | 0.47 | 0.59 | 0.48 | 0.58 | 0.53 | Yes |
| Group 3 | WBP71460_8 | 0.62 | 0.52 | 0.59 | 0.51 | 0.59 | 0.54 | Yes |
| Group 4 | WBP71460_9 | 0.63 | 0.48 | 0.60 | 0.47 | 0.61 | 0.51 | Yes |
| Group 5 | WBP71460_10 | 0.63 | 0.48 | 0.60 | 0.46 | 0.59 | 0.51 | Yes |
| Group 6 | WBP71460_11 | 0.61 | 0.50 | 0.58 | 0.50 | 0.58 | 0.55 | Yes |
| Group 7 | WBP71460_16 | 0.60 | 0.46 | 0.57 | 0.45 | 0.58 | 0.50 | Yes |
| Group 8 | WBP71460_17 | 0.59 | 0.45 | 0.56 | 0.46 | 0.57 | 0.48 | Yes |

Figure 33A:
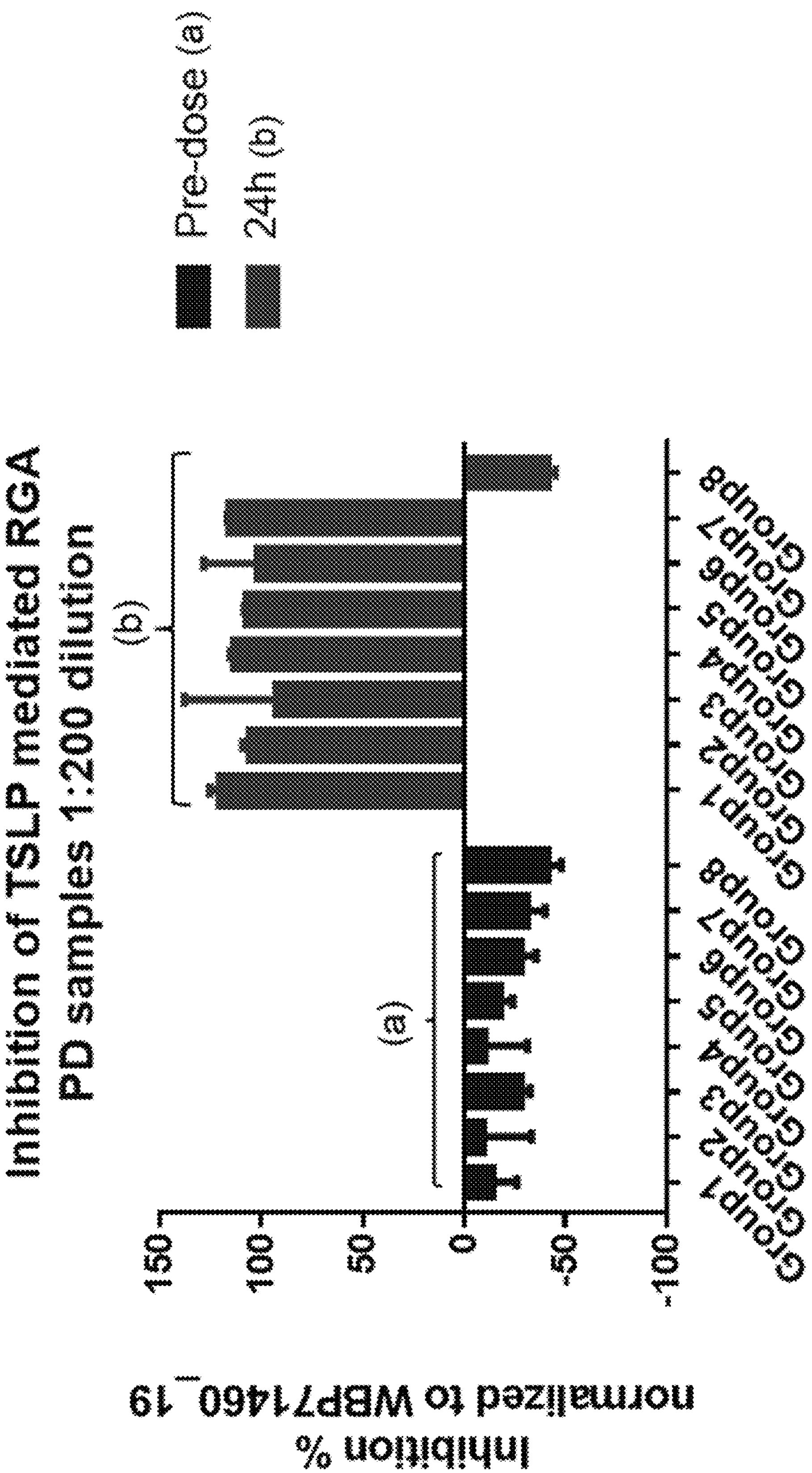
FIG. 33A and FIG. 33B show a cell-based luminescence assay.
Figure 33B:
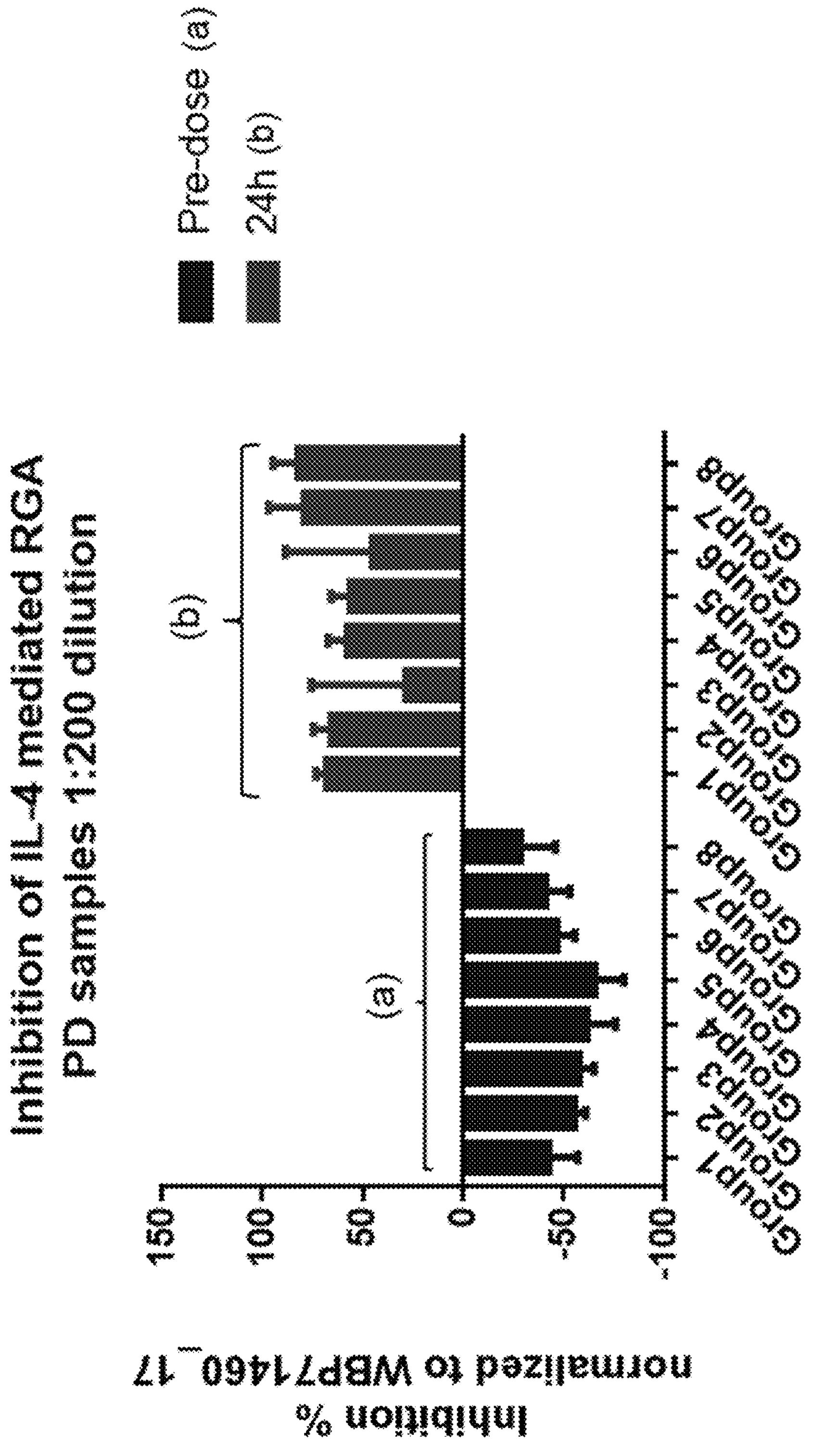

The overall % inhibition at pre-dose and after 24 hours clearly shows that antigen binding moieties described herein effectively inhibited both TSLP mediated RGA (FIG. 33A) and IL-4-mediated RGA (FIG. 33B). Specifically, WBP71460_16 (Candidate 19.1) showed greater than 100% inhibition for TSLP mediated RGA and greater than 70% inhibition for IL-4 mediated RGA.

Example 14: Superior PK of Candidate 19.1 Construct Over scFv Constructs

WBP71460_16 (Candidate 19.1) comprises a CrossMAb 2×2 format that enables bispecific targeting without the need for single-chain variable fragments (scFvs). WBP71460_16 (Candidate 19.1) was shown to have a superior PK profile in both humanized mouse model and non-human primate model.

Figure 34:
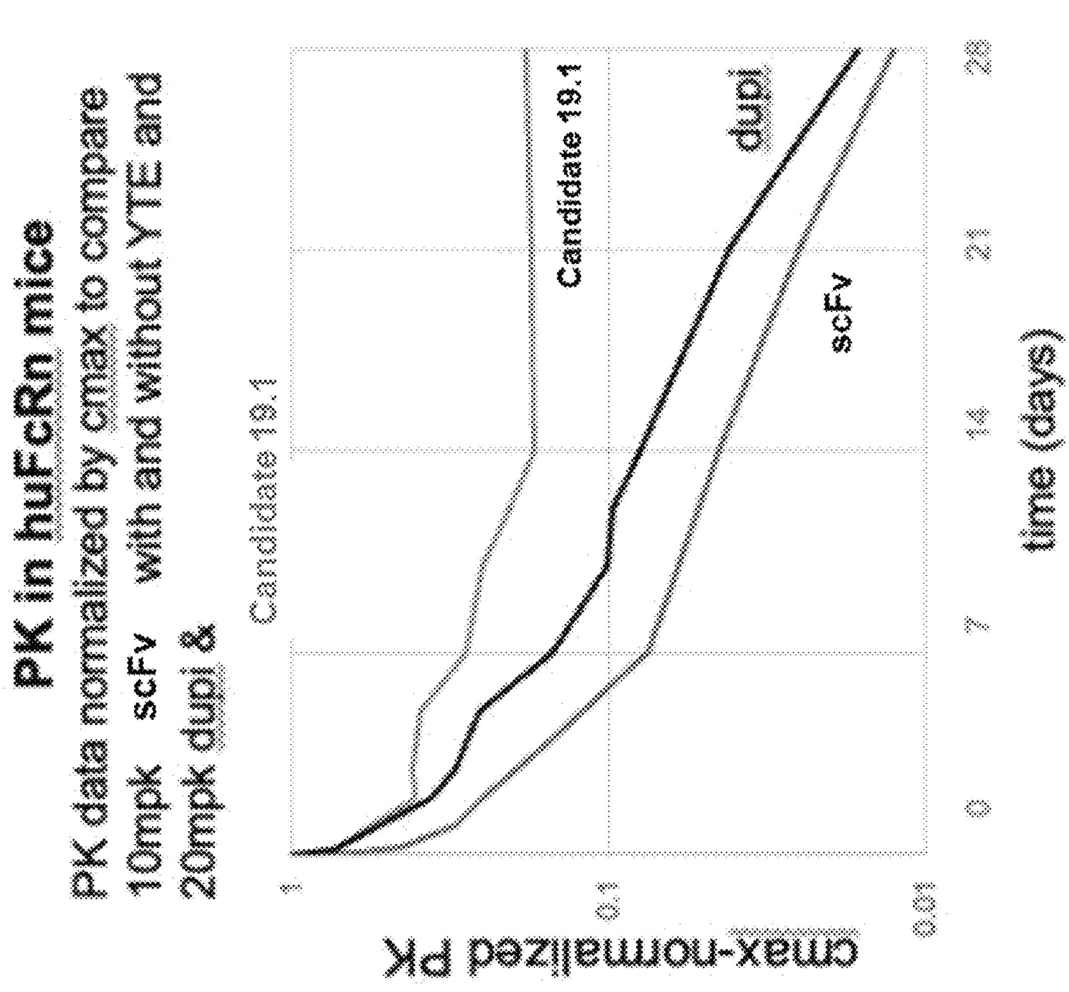
FIG. 34 shows comparison of PK of antigen binding moieties in humanized FcRn mice.
Figure 35:
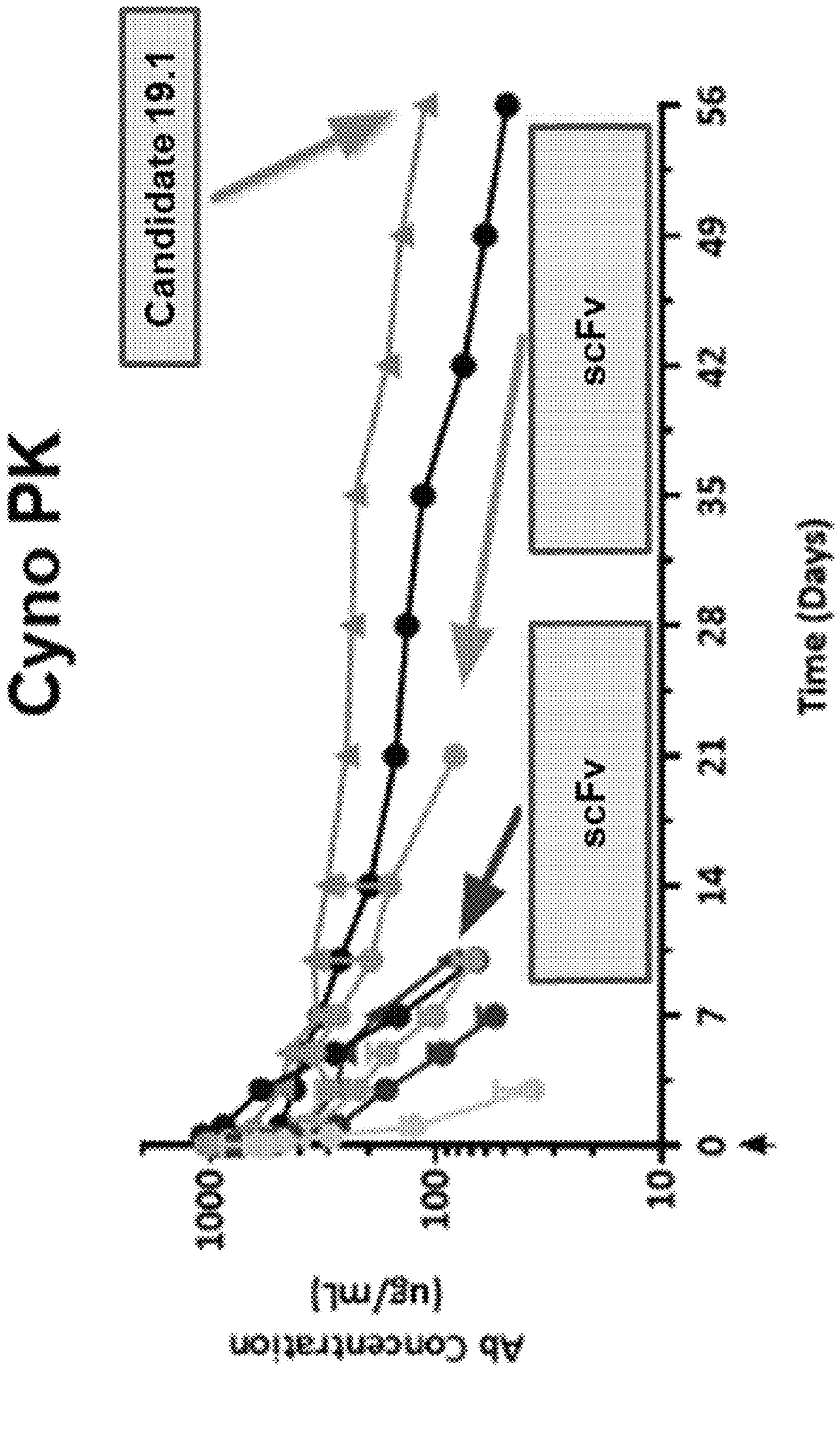
FIG. 35 shows comparison of PK of antigen binding moieties in non-human primate models.

As shown in FIG. 34 (mouse model) and FIG. 35 (non-human primate model), WBP71460_16 (Candidate 19.1) showed superior PK profile over scFv constructs (WBP71460_10 and WBP71460_11) and other commercial product (dupilumab). As previously shown in Table 23, 4 different scFv constructs (WBP71460_1, WBP71460_9, WBP71460_10, WBP71460_11)—all comprising YTE format—showed poor in vivo exposure and poor biophysical stability (low PK). WBP71460_16 (Candidate 19.1) exhibited significantly stronger binding affinity, outperforming typical scFv. Moreover, WBP71460_16 (Candidate 19.1) showed enhanced stability both in vitro and in vivo. Taken together, compared to scFv constructs, WBP71460_16 (Candidate 19.1) demonstrates superior performance across all key developability and function criteria.

Figure 36A:
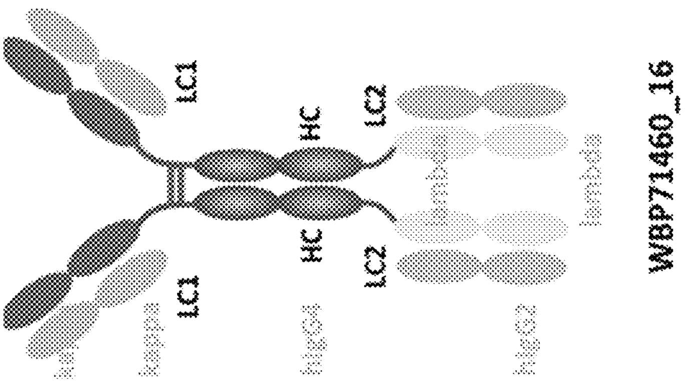
FIGS. 36A-36H show exemplary candidate antigen binding moiety construct formats.
Figure 36B:
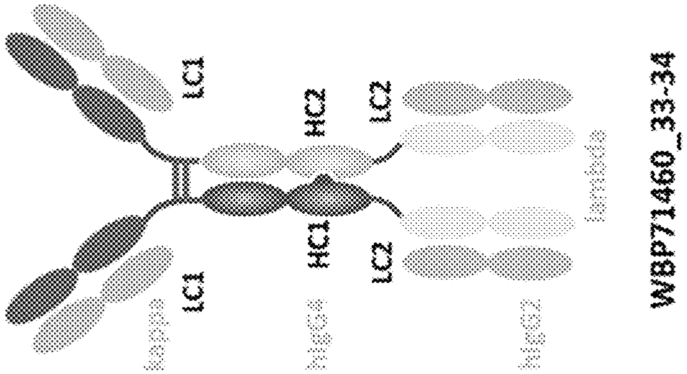
Figure 36C:
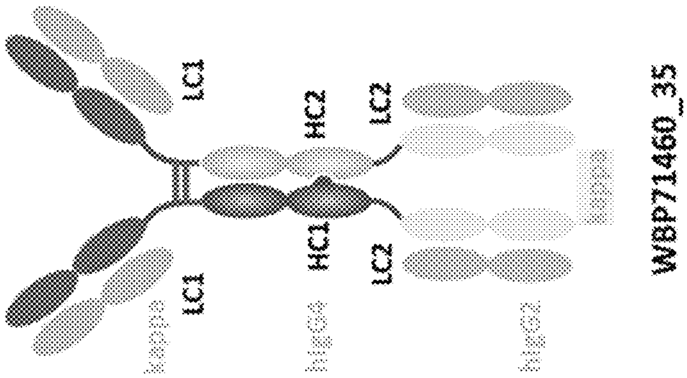
Figure 36D:
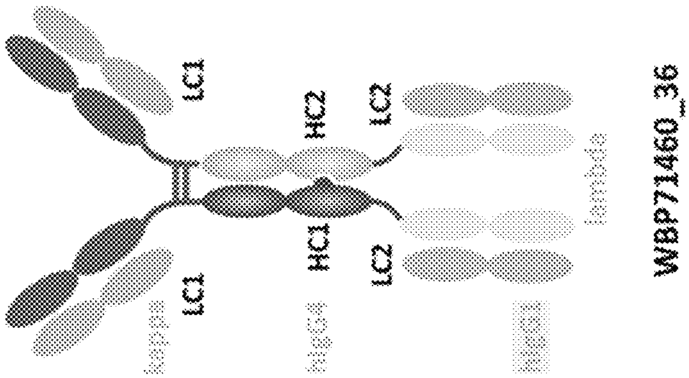
Figure 36E:
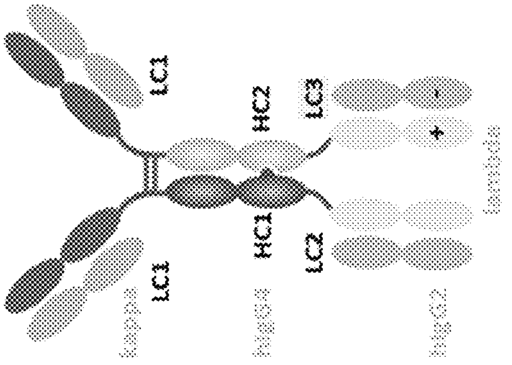
Figure 36F:
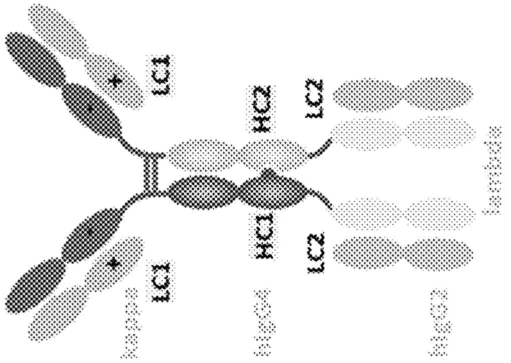
Figure 36G:
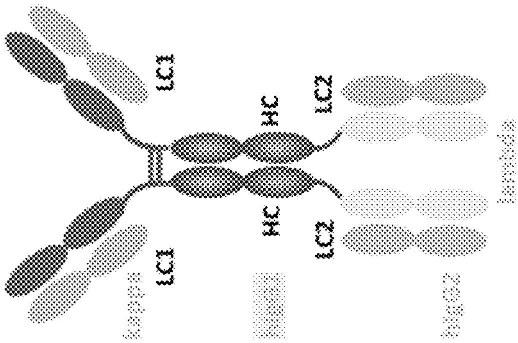
Figure 36H:
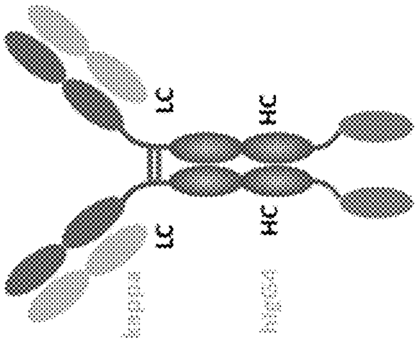
Figure 40:
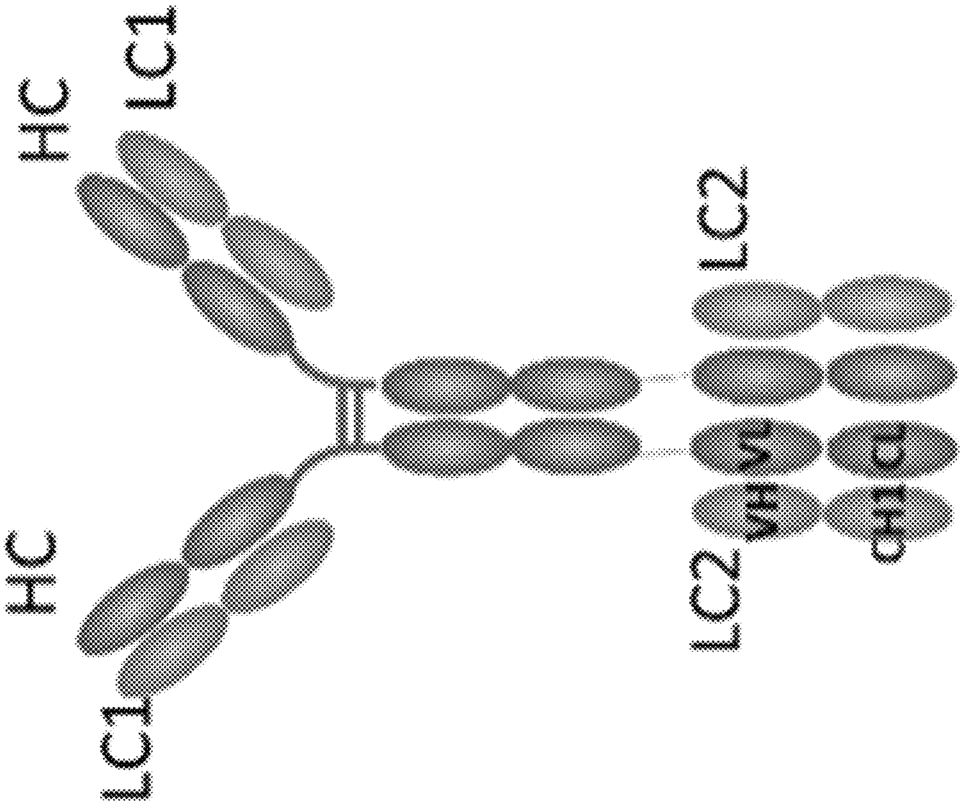
FIG. 40 shows an exemplary construct format for candidate antigen binding moiety 19.1 (also referred as WBP71460_16).

Example 15: Assessment of Developability and Stability of Candidate 19.1 Variants The developability and stability of candidate antigen binding moiety 19.1 (WBP71460_16; FIG. 5C, FIG. 36A or FIG. 40) was further assessed through the development of variant candidate antigen binding moieties based on the structure of candidate 19.1 (FIGS. 36B-36H).

To assess the developability of each candidate antigen binding moiety, biochemical assays were leveraged to characterize aggregation and binding specificity (Table 34).

Nonspecific interactions can present a challenge in the successful development of therapeutic biomolecules. To assess the tendency of each candidate antigen binding moiety to self-aggregate, affinity-capture self-interaction nanoparticle spectroscopy (AC-SINS) was performed. Briefly, antigen binding moieties described herein were diluted in PBS and incubated with nanoparticles functionalized with an anti-Fc capture IgG. After a brief equilibration at room temperature, the plasmon resonance was measured by UV-Vis. A red-shift in the λmax can be used to assess antibody self-association: larger shifts indicate higher self-interaction propensity. As shown in Table 34, WBP71460_39 and WBP71460_40 exhibited low AC-SINS shift of 6.5 and 12.3, respectively, and WBP71460_16 and WBP71460_33-38 exhibited medium AC-SINS shift. Low AC-SINS shift indicates that the binding moieties have low-self-association (aggregation) and show good colloidal stability.

To assess candidate antigen binding moieties' propensity for off-target binding, binding assays involving the nonspecific target Baculovirus Particle (BV) assay were performed. Candidate antigen binding moieties described herein were mixed with BV proteins. After incubation, binding was measured. An increase in absorbance versus a negative and positive control reflects propensity to engage in non-specific aggregation. Table 34 shows that WBP71460_16, WBP71460_34, WBP71460_37, and WBP71460_38 exhibited low BV binding, ranging from 8.92 to 15.38, indicating that these constructs have low non-specific binding (low polyreactivity). This suggests that these constructs may have reduced off-target effects. The substitution of lambda for kappa (e.g., WBP71460_35) and/or substituting IgG2 for IgG1 (e.g., WBP71460_36) was associated with increased BV binding. However, every WBP71460_16 (Candidate 19.1) variant tested exhibited promising AC-SINS and BV results, suggesting generally low aggregation and high binding specificity.

TABLE 34

| Developability overview. | | |
|---|---|---|
| ID | AC-SINS | BV |
| WBP71460-16 | 19.1 | 8.92 |
| WBP71460-33 | 21.3 | 28.39 |
| WBP71460-34 | 21.8 | 15.15 |
| WBP71460-35 | 17.8 | 22.38 |
| WBP71460-36 | 22.5 | 53.41 |
| WBP71460-37 | 21.1 | 15.38 |
| WBP71460-38 | 23.6 | 10.03 |
| WBP71460-39 | 6.5 | 17.41 |
| WBP71460-40 | 12.3 | 34.06 |

Example 16: In Vitro Binding Properties of Candidate 19.1 Variants

The therapeutic efficacy of candidate antigen binding moiety 19.1 (WBP71460_16; FIG. 5C, FIG. 36A or FIG. 40) was further assessed through the development of variant candidate antigen binding moieties based on the structure of candidate 19.1 (FIGS. 36B-36H).

Candidate antigen binding moieties were subjected to in vitro experimentation to determine their binding affinity for targets IL-4R and TSLP, which represent important parameters indicative of antibody quality and therapeutic potential.

Figure 37:
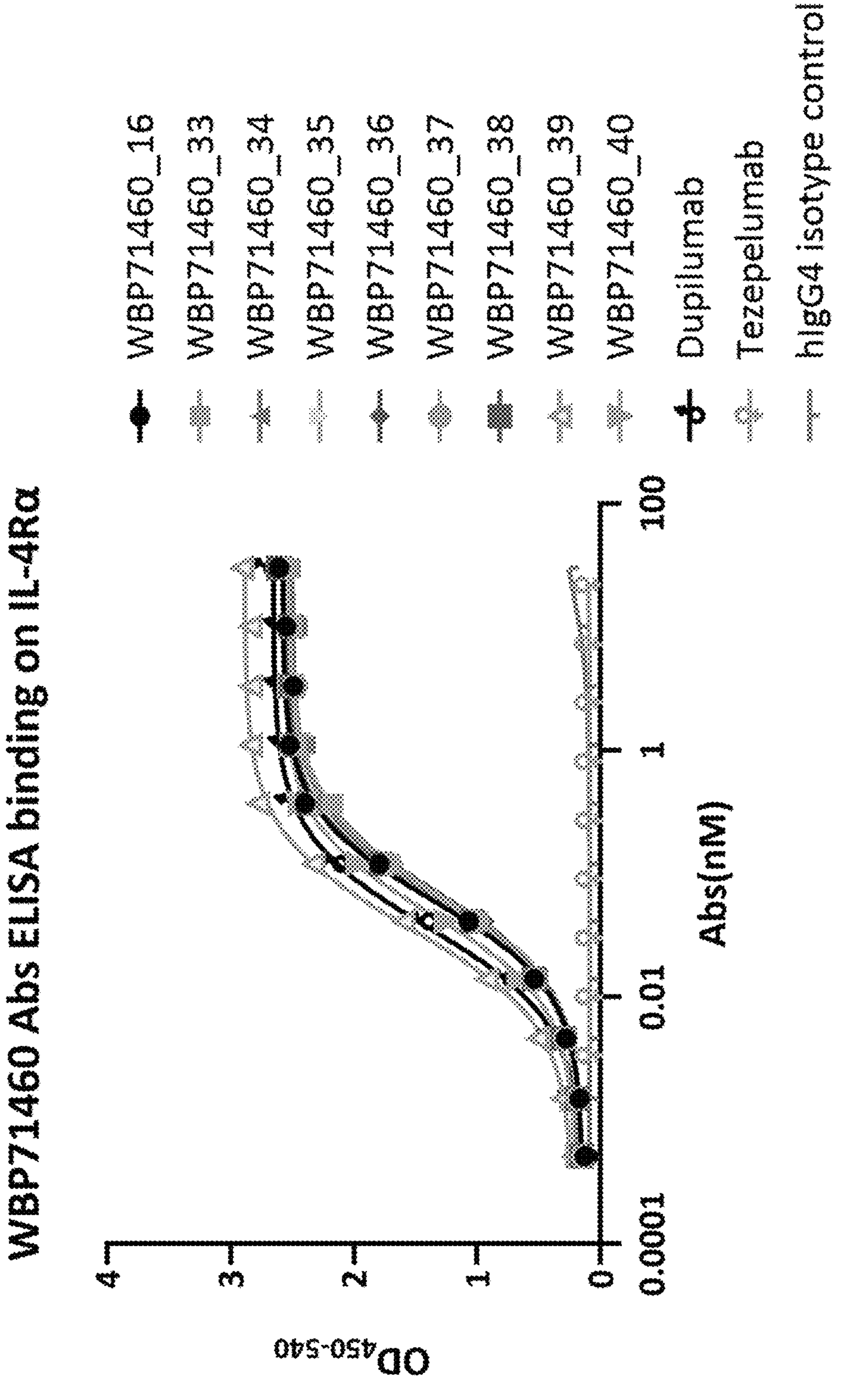
FIG. 37 shows the binding of each candidate antigen binding moiety to IL-4R measured by an ELISA assay.

Candidate antigen binding moieties were tested for their ability to bind IL-4R. Binding affinity for IL-4R was quantified via ELISA. The ELISA was performed by first coating the plate with 0.5 μg/mL anti-histidine antibodies at 4° C. overnight. Subsequently, wells were blocked using 200 μL of 2% BSA per well at 25° C. for 1 hour to prevent nonspecific binding. Next, 0.1 μg/mL of a His-tagged IL-4R was added. After this step, antibodies were applied, diluted in 2% BSA from a starting concentration of 30 nM using a three-fold serial dilution, and incubated at 25° C. for 2 hours. Detection was achieved by adding goat anti-human IgG-Fc-HRP (1:5000 dilution in 2% BSA) and incubating at 25° C. for 1 hour. Finally, the assay was developed, the reaction was stopped with TMB substrate and $H_2SO_4$ stop solution, and absorbance was measured at OD450-OD540 to quantify the results (FIG. 37). All constructs tested had strong IL-4R binding affinity, with $EC_{50}$ values ranging from 0.037 to 0.073 nM. Construct formats WBP71460_33-40 exhibited comparable IL-4R binding affinity to that of WBP71460_16 (Candidate 19.1) (Table 35).

TABLE 35

ELISA binding results to IL-4R.

| | Antigen; 0.1 ug/ml | |
|---|---|---|
| Abs(nM) | $EC_{50}$ (nM) | Max $OD_{450-540}$ |
| WBP71460_16 | 0.061 | 2.61 |
| WBP71460_33 | 0.068 | 2.53 |
| WBP71460_34 | 0.065 | 2.52 |
| WBP71460_35 | 0.069 | 2.51 |
| WBP71460_36 | 0.073 | 2.57 |
| WBP71460_37 | 0.064 | 2.54 |
| WBP71460_38 | 0.063 | 2.61 |
| WBP71460_39 | 0.037 | 2.90 |
| WBP71460_40 | 0.048 | 2.62 |
| Tezepelumab | NA | 0.16 |
| hIgG4 Isotype control | NA | 0.26 |

Figure 38:
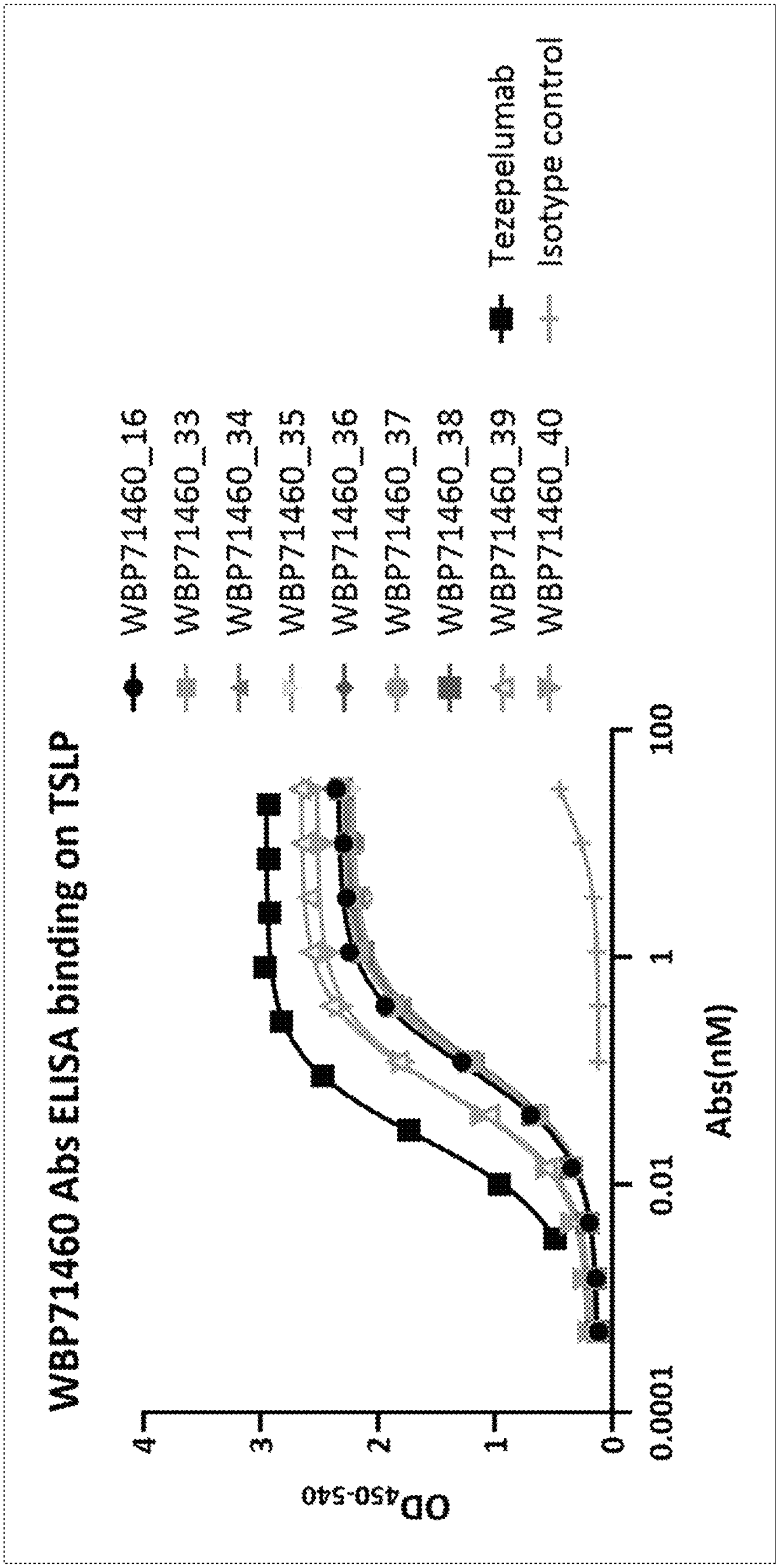
FIG. 38 shows the binding of each candidate antigen binding moiety to TSLP measured by an ELISA assay.

Candidate antigen binding moieties were also tested to measure their ability to specifically bind TSLP. TSLP binding was assessed via ELISA. The ELISA was performed by first coating the plate with 0.5 μg/mL anti-histidine antibodies at 4° C. overnight. Subsequently, wells were blocked using 200 μL of 2% BSA per well at 25° C. for 1 hour to prevent nonspecific binding. Next, 0.2 μg/mL of a His-tagged human TSLP was added. After this step, antibodies were applied, diluted in 2% BSA from a starting concentration of 30 nM using a three-fold serial dilution, and incubated at 25° C. for 2 hours. Detection was achieved by adding goat anti-human IgG-Fc-HRP (1:5000 dilution in 2% BSA) and incubating at 25° C. for 1 hour. Finally, the assay was developed, the reaction was stopped with TMB substrate and $H_2SO_4$ stop solution, and absorbance was measured at OD450-OD540 (where OD=optical density) to quantify the results (FIG. 38). All constructs tested had strong TSLP binding affinity, with $EC_{50}$ values ranging from 0.060 to 0.11 nM. Construct formats WBP71460_33-40 exhibited comparable TSLP binding affinity to that of WBP71460_16 (Candidate 19.1) (Table 36).

TABLE 36

ELISA binding results to TSLP.

| | Antigen; 0.2 ug/ml | |
|---|---|---|
| Abs(nM) | $EC_{50}$ (nM) | Max $OD_{450-540}$ |
| WBP71460_16 | 0.11 | 2.36 |
| WBP71460_33 | 0.12 | 2.35 |
| WBP71460_34 | 0.12 | 2.32 |
| WBP71460_35 | 0.12 | 2.21 |
| WBP71460_36 | 0.13 | 2.39 |
| WBP71460_37 | 0.11 | 2.29 |
| WBP71460_38 | 0.11 | 2.31 |
| WBP71460_39 | 0.065 | 2.67 |
| WBP71460_40 | 0.060 | 2.56 |
| Tezepelumab | 0.025 | 2.99 |
| hIgG4 Isotype control | NA | 0.45 |

Example 17: In Vivo PK Properties of Candidate 19.1 Variants

The therapeutic efficacy of candidate antigen binding moiety 19.1 (WBP71460_16; FIG. 5C, FIG. 35A or FIG. 40) was further assessed through the development of variant candidate antigen binding moieties based on the structure of candidate 19.1 (FIGS. 36B-36H).

The in vivo pharmacokinetic properties of molecular formats based on the structure of WBP71460_16 (Candidate 19.1) were tested. Each candidate antigen binding moiety was evaluated in humanized FcRn transgenic mice. Mice were each dosed intravenously with a single 5 mg/kg bolus of each candidate antigen binding moiety (WBP71460_35, WBP71460_36, WBP71460_39, and WBP71460_40). Blood samples were collected at multiple time points throughout the 28-day period following candidate antigen binding moiety administration to characterize each the pharmacokinetic profile of each candidate antigen binding moiety.

To assess pharmacokinetic properties, recombinant binding assays were performed in high-binding 96-well plates. Wells were coated overnight at 4° C. with goat anti-human IgG (1.0 μg/mL) in PBS. After coating, plates were washed and blocked for 1 hour at room temperature with 2% BSA in PBS. Serum test samples were then added (2% BSA in PBS) and incubated for 1 hour at room temperature to allow binding to the immobilized ligand. Plates were washed 3 times, and then 0.1 μg/mL biotinylated anti-human IgG was applied as the secondary detector and incubated for 1 hour. Following another wash step, bound biotinylated receptor was detected by incubation with streptavidin-HRP for 30 minutes and color development with TMB substrate. The reaction was stopped with 1 M sulfuric acid and absorbance was measured at 450-540 nm. Data were processed in SoftMax Pro and dose-response curves fitted in GraphPad Prism to determine relative binding affinities across all construct formats.

Figure 39:
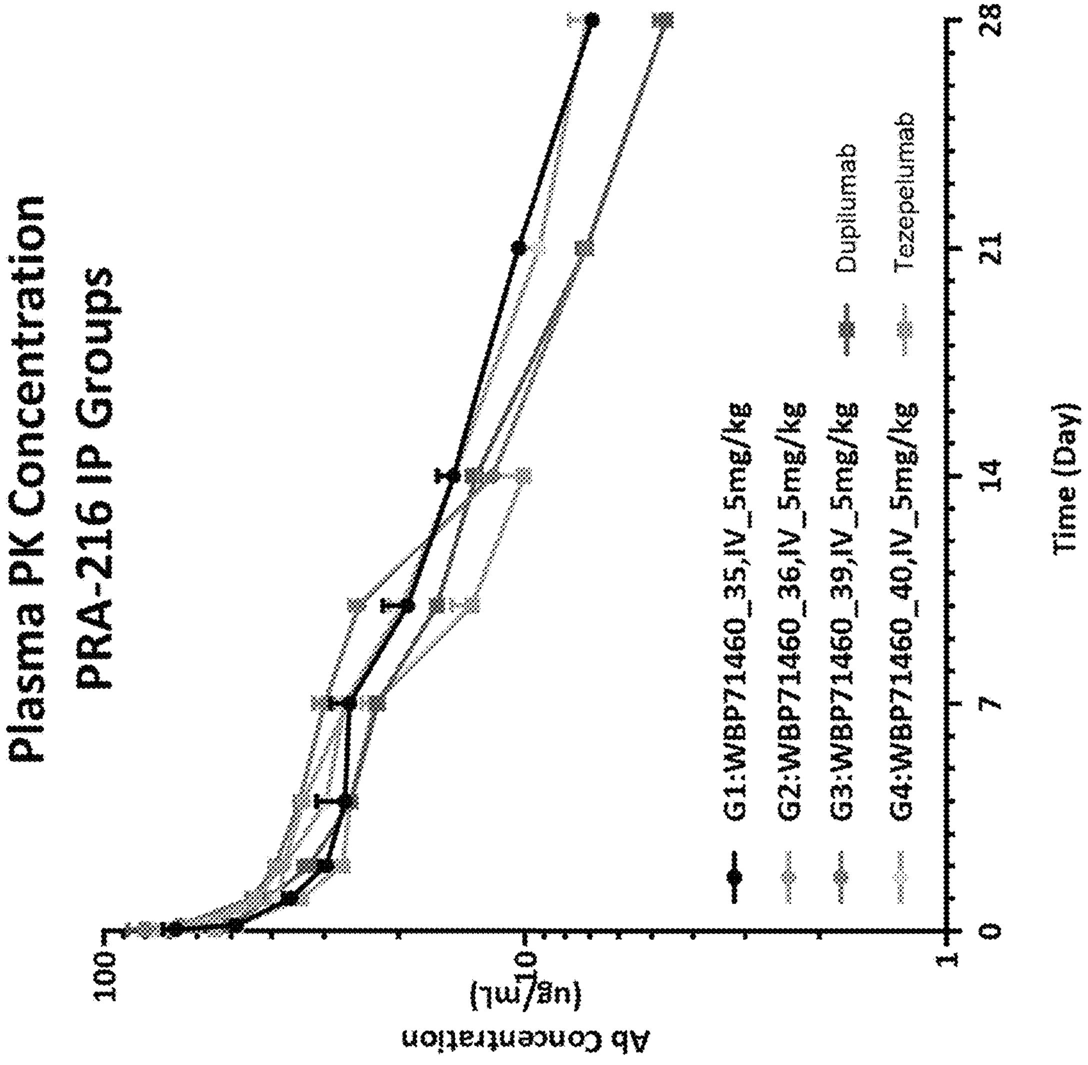
FIG. 39 shows a pharmacokinetic experiment quantifying circulating concentrations of each candidate antigen binding moiety over a 28-day period in a humanized FcRnTg mouse model.

Antibody concentration as a function of time over the 28-day period was determined. In humanized FcRn transgenic mice, candidate antigen binding moieties WBP71460_35, WBP71460_36, WBP71460_39, and WBP71460_40 exhibited greater half-lives than Dupilumab or Tezepelumab over the 28-day time period (FIG. 39). These results support that WBP71460_35-40 can remain in circulation for unexpectedly long time periods, but less than Candidate 19.1, demonstrating that Candidate 19.1 has optimized in vivo half-life.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

| Description | SEQ ID NO.: | Sequences |
|---|---|---|
| TSLPR-TRAP complex | 1 | ESGYAQNGDLEDAELDDYSFSCYSQLEVNGSQHSLTCA FEDPDVNITNLEFEICGALVEVKCLNFRKLQEIYFIET KKFLLIGKSNICVKVGEKSLTCKKIDLTTIVKPEAPFD LSVVYREGANDFVVTFNTSHLQKKYVKVLMHDVAYRQE KDENKWTHVNLSSTKLTLLQRKLQPAAMYEIKVRSIPD HYFKGFWSEWSPSYYFRTPEINNSSGEMDGGSGGSGGS GGSGGSGGSGGSGGSGGSGGSGGSGGSGGSGGSGGSGG SGGSGGSGGSGGSGAAEGVQIQIIYFNLETVQVTWNAS KYSRTNLTFHYRFNGDEAYDQCTNYLLQEGHTSGCLLD AEQRDDILYFSIRNGTHPVFTASRWMVYYLKPSSPKHV RFSWHQDAVTVTCSDLSYGDLLYEVQYRSPFDTEWQS KQENTCNVTIEGLDAEKCYSFWVRVKAMEDVYGPDTY PSDWSEVTCWQRGEIRDACAETPTPPKPKLSK |
| Anti-TSLP HCDR1 | 2 | TYGMH |
| Anti-TSLP HCDR2 | 3 | VIWYDGSNKHYADSVKG |
| Anti-TSLP HCDR3 | 4 | APQWELVHEAFDI |
| TSLPR-TRAP complex - 20 amino acid linker | 5 | ESGYAQNGDLEDAELDDYSFSCYSQLEVNGSQHSLTCA FEDPDVNITNLEFEICGALVEVKCLNFRKLQEIYFIET KKFLLIGKSNICVKVGEKSLTCKKIDLTTIVKPEAPFD LSVVYREGANDFVVTFNTSHLQKKYVKVLMHDVAYRQE KDENKWTHVNLSSTKLTLLQRKLQPAAMYEIKVRSIPD HYFKGFWSEWSPSYYFRTPEINNSSGEMDGGGGSGGGG SGGGGSGGGGSGAAEGVQIQIIYFNLETVQVTWNASKY SRTNLTFHYRFNGDEAYDQCTNYLLQEGHTSGCLLDAE QRDDILYFSIRNGTHPVFTASRWMVYYLKPSSPKHVRF SWHQDAVTVTCSDLSYGDLLYEVQYRSPFDTEWQSKQE NTCNVTIEGLDAEKCYSFWVRVKAMEDVYGPDTYPSD WSEVTCWQRGEIRDACAETPTPPKPKLSK |
| Anti-TSLP LCDR1 | 6 | GGNNLGSKSVH |
| Anti-TSLP LCDR2 | 7 | DDSDRPS |
| Anti-TSLP LCDR3 | 8 | QVWDSSSDHVV |
| Anti-IL-4R HCDR1 | 10 | GFTFRDYA |
| Anti-IL-4R HCDR2 | 11 | ISGSGGNT |
| Anti-IL-4R HCDR3 | 12 | AKDRLSITIRPRYYGLDV |
| Anti-IL-4R LCDR1 | 14 | QSLLYSIGYNY |
| Anti-IL-4R LCDR2 | 15 | LGS |
| Anti-IL-4R LCDR3 | 16 | MQALQTPYT |
| Linker 1 | 17 | (GGS)n |
| Linker 2 | 18 | (GGGGS)n |
| Linker 3 | 19 | ASTKGP |
| Linker 4 | 20 | TVAAPSVFIFPP |
| Anti-IL-4R Heavy Chain | 21 | EVQLVESGGGLEQPGGSLRLSCAGSGFTFRDYAMTWV RQAPGKGLEWVSSISGSGGNTYYADSVKGRFTISRDNS KNTLYLQMNSLRAEDTAVYYCAKDRLSITIRPRYYGLD VWGQGTTVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLYITREPEVTCV VVDVSQEDPEVQFNWYVDGVEVHNAKTKPREEQFNSTY RVVSVLTVLHQDWLNGKEYKCKVSNKGLPSSIEKTISK AKGQPREPQVYTLPPSQEEMTKNQVSLTCLVKGFYPSD IAVEWESNGQPENNYKTTPPVLDSDGSFFLYSRLTVDK SRWQEGNVFSCSVMHEALHNHYTQKSLSLSLG |

-continued

| Description | SEQ ID NO.: | Sequences |
|---|---|---|
| Anti-IL-4R Light Chain | 22 | DIVMTQSPLSLPVTPGEPASISCRSSQSLLYSIGYNYLDW YLQKSGQSPQLLIYLGSNRASGVPDRFSGSGSGTDFTLK ISRVEAEDVGFYYCMQALQTPYTFGQGTKLEIKRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC |
| Linker 5 | 23 | GGGGSGGGGSGGGGSGGGGS |
| Anti-TSLP Heavy Chain (Heavy Chain Variable Region and Constant Domain 1) | 24 | QMQLVESGGGVVQPGRSLRLSCAASGFTFRTYGMHWV RQAPGKGLEWVAVIWYDGSNKHYADSVKGRFTITRDN SKNTLNLQMNSLRAEDTAVYYCARAPQWELVHEAFDI WGQGTMVTVSSASTKGPSVFPLAPCSRSTSESTAALGC LVKDYFPEPVTVSWNSGALTSGVHTFPAVLQSSGLYSL SSVVTVPSSNFGTQTYTCNVDHKPSNTKVDKTV |
| Anti-TSLP Heavy Chain Variable Region | 25 | QMQLVESGGGVVQPGRSLRLSCAASGFTFRTYGMHWV RQAPGKGLEWVAVIWYDGSNKHYADSVKGRFTITRDN SKNTLNLQMNSLRAEDTAVYYCARAPQWELVHEAFDI WGQGTMVTVSS |
| Anti-TSLP Heavy Chain Constant Domain 1 (CH1) | 26 | CSRSTSESTAALGCLVKDYFPEPVTVSWNSGALTSGVH TFPAVLQSSGLYSLSSVVTVPSSNFGTQTYTCNVDHKPS NTKVDKTV |
| Anti-TSLP - Light Chain | 27 | SYVLTQPPSVSVAPGQTARITCGGNNLGSKSVHWYQQ KPGQAPVLVVYDDSDRPSWIPERFSGSNSGNTATLTISR GEAGDEADYYCQVWDSSSDHVVFGGGTKLTVLGQPK AAPSVTLFPPSSEELQANKATLVCLISDFYPGAVTVAW KADSSPVKAGVETTTPSKQSNNKYAASSYLSLTPEQWK SHRSYSCQVTHEGSTVEKTVAPTECS |
| Anti-TSLP Light Chain Variable Region | 28 | SYVLTQPPSVSVAPGQTARITCGGNNLGSKSVHWYQQ KPGQAPVLVVYDDSDRPSWIPERFSGSNSGNTATLTISR GEAGDEADYYCQVWDSSSDHVVFGGGTKLTVLG |
| Anti-TSLP - Light Chain Constant Region | 29 | QPKAAPSVTLFPPSSEELQANKATLVCLISDFYPGAVTV AWKADSSPVKAGVETTTPSKQSNNKYAASSYLSLTPEQ WKSHRSYSCQVTHEGSTVEKTVAPTECS |
| Anti-IL-4R Light Chain Variable Region | 30 | DIVMTQSPLSLPVTPGEPASISCRSSQSLLYSIGYNYLDW YLQKSGQSPQLLIYLGSNRASGVPDRFSGSGSGTDFTLK ISRVEAEDVGFYYCMQALQTPYTFGQGTKLEIKR |
| Anti-IL-4R Light Chain Constant Region | 31 | SDEQLKSGTASVVCLLNNFYPREAKVQWKVDNALQSG NSQESVTEQDSKDSTYSLSSTLTLSKADYEKHKVYACE VTHQGLSSPVTKSFNRGEC |
| Anti-IL-4R Heavy Chain Variable Region | 32 | EVQLVESGGGLEQPGGSLRLSCAGSGFTFRDYAMTWV RQAPGKGLEWVSSISGSGGNTYYADSVKGRFTISRDNS KNTLYLQMNSLRAEDTAVYYCAKDRLSITIRPRYYGLD VWGQGTTVTVSS |
| Anti-IL-4R Heavy Chain Constant Region ("M252Y/S254T/ T256E" | 33 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPPCPAPEFLG GPSVFLFPPKPKDTLYITREPEVTCVVVDVSQEDPEVQF NWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQP ENNYKTTPPVLDSDGSFFLYSRLTVDKSRWQEGNVFSC SVMHEALHNHYTQKSLSLSLG |
| TSLPR (aa 25-231) | 34 | GAAEGVQIQIIYFNLETVQVTWNASKYSRTNLTFHYRF NGDEAYDQCTNYLLQEGHTSGCLLDAEQRDDILYFSIR NGTHPVFTASRWMVYYLKPSSPKHVRFSWHQDAVTVT CSDLSYGDLLYEVQYRSPFDTEWQSKQENTCNVTIEGL DAEKCYSFWVRVKAMEDVYGPDTYPSDWSEVTCWQR GEIRDACAETPTPPKPKLSK |
| IL-7Ra (aa 21-239) | 35 | ESGYAQNGDLEDAELDDYSFSCYSQLEVNGSQHSLTCA FEDPDVNITNLEFEICGALVEVKCLNFRKLQEIYFIETKK FLLIGKSNICVKVGEKSLTCKKIDLTTIVKPEAPFDLSVV YREGANDFVVTFNTSHLQKKYVKVLMHDVAYRQEKD ENKWTHVNLSSTKLTLLQRKLQPAAMYEIKVRSIPDHY FKGFWSEWSPSYYFRTPEINNSSGEMD |

-continued

| Description | SEQ ID NO.: | Sequences |
|---|---|---|
| Anti-IL-4R Heavy Chain (Hole) | 36 | EVQLVESGGGLEQPGGSLRLSCAGSGFTFRDYAMTWV RQAPGKGLEWVSSISGSGGNTYYADSVKGRFTISRDNS KNTLYLQMNSLRAEDTAVYYCAKDRLSITIRPRYYGLD VWGQGTTVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLYITREPEVTCVV VDVSQEDPEVQFNWYVDGVEVHNAKTKPREEQFNSTY RVVSVLTVLHQDWLNGKEYKCKVSNKGLPSSIEKTISK AKGQPREPQVYTLPPSQEEMTKNQVSLWCLVKGFYPS DIAVEWESNGQPENNYKTTPPVLDSDGSFFLYSRLTVD KSRWQEGNVFSCSVMHEALHNHYTQKSLSLSLG |
| Anti-IL-4R Heavy Chain (Knob) | 37 | EVQLVESGGGLEQPGGSLRLSCAGSGFTFRDYAMTWV RQAPGKGLEWVSSISGSGGNTYYADSVKGRFTISRDNS KNTLYLQMNSLRAEDTAVYYCAKDRLSITIRPRYYGLD VWGQGTTVTVSSASTKGPSVFPLAPCSRSTSESTAALGC LVKDYFPEPVTVSWNSGALTSGVHTFPAVLQSSGLYSL SSVVTVPSSSLGTKTYTCNVDHKPSNTKVDKRVESKYG PPCPPCPAPEFLGGPSVFLFPPKPKDTLYITREPEVTCVV VDVSQEDPEVQFNWYVDGVEVHNAKTKPREEQFNSTY RVVSVLTVLHQDWLNGKEYKCKVSNKGLPSSIEKTISK AKGQPREPQVYTLPPSQEEMTKNQVSLSCAVKGFYPSD IAVEWESNGQPENNYKTTPPVLDSDGSFFLVSRLTVDK SRWQEGNVFSCSVMHEALHNHYTQKSLSLSLG |
| Anti-TSLP Heavy Chain (Hole) | 38 | QMQLVESGGGVVQPGRSLRLSCAASGFTFRTYGMHWV RQAPGKGLEWVAVIWYDGSNKHYADSVKGRFTITRDN SKNTLNLQMNSLRAEDTAVYYCARAPQWELVHEAFDI WGQGTMVTVSSASTKGPSVFPLAPCSRSTSESTAALGC LVKDYFPEPVTVSWNSGALTSGVHTFPAVLQSSGLYSL SSVVTVPSSNFGTQTYTCNVDHKPSNTKVDKTVERKCC VECPPCPAPPVAGPSVFLFPPKPKDTLYITREPEVTCVVV DVSHEDPEVQFNWYVDGVEVHNAKTKPREEQFNSTFR VVSVLTVVHQDWLNGKEYKCKVSNKGLPAPIEKTISKT KGQPREPQVYTLPPSREEMTKNQVSLWCLVKGFYPSDI AVEWESNGQPENNYKTTPPMLDSDGSFFLYSKLTVDKS RWQQGNVFSCSVMHEALHNHYTQKSLSLSPGK |
| Anti-TSLP Heavy Chain (Knob) | 39 | QMQLVESGGGVVQPGRSLRLSCAASGFTFRTYGMHWV RQAPGKGLEWVAVIWYDGSNKHYADSVKGRFTITRDN SKNTLNLQMNSLRAEDTAVYYCARAPQWELVHEAFDI WGQGTMVTVSSASTKGPSVFPLAPCSRSTSESTAALGC LVKDYFPEPVTVSWNSGALTSGVHTFPAVLQSSGLYSL SSVVTVPSSNFGTQTYTCNVDHKPSNTKVDKTVERKCC VECPPCPAPPVAGPSVFLFPPKPKDTLYITREPEVTCVVV DVSHEDPEVQFNWYVDGVEVHNAKTKPREEQFNSTFR VVSVLTVVHQDWLNGKEYKCKVSNKGLPAPIEKTISKT KGQPREPQVYTLPPSREEMTKNQVSLSCAVKGFYPSDI AVEWESNGQPENNYKTTPPMLDSDGSFFLVSKLTVDKS RWQQGNVFSCSVMHEALHNHYTQKSLSLSPGK |
| Linker 6 | 223 | (GGGGS)2 |
| Linker 7 | 224 | (GGGGS)4 |
| Linker 8 | 42 | GGGGSGGGGS |
| Linker 9 | 43 | GGGGS |
| Linker 10 | 225 | SGGGG |
| Linker 11 | 226 | GGGG(SGGGG) |
| Linker 12 | 46 | GG(SGG)n |
| Linker 13 | 47 | (GGS)x20 |
| TSLPR (aa 25-231) | 48 | GAAEGVQIQIIYFNLETVQVTWNASKYSRTNLTFHYRF NGDEAYDQCTNYLLQEGHTSGCLLDAEQRDDILYFSIR NGTHPVFTASRWMVYYLKPSSPKHVRFSWHQDAVTVT CSDLSYGDLLYEVQYRSPFDTEWQSKQENTCNVTIEGL DAEKCYSFWVRVKAMEDVYGPDTYPSDWSEVTCWQR GEIRDACAETPTPPKPKLSK |

-continued

| Description | SEQ ID NO.: | Sequences |
|---|---|---|
| IL-7Ra (aa 21-239) | 49 | ESGYAQNGDLEDAELDDYSFSCYSQLEVNGSQHSLTCA FEDPDVNITNLEFEICGALVEVKCLNFRKLQEIYFIETKK FLLIGKSNICVKVGEKSLTCKKIDLTTIVKPEAPFDLSVV YREGANDFVVTFNTSHLQKKYVKVLMHDVAYRQEKD ENKWTHVNLSSTKLTLLQRKLQPAAMYEIKVRSIPDHY FKGFWSEWSPSYYFRTPEINNSSGEMD |
| TSLP-TRAP 1 | 50 | GAAEGVQIQIIYFNLETVQVTWNASKYSRTNLTFHYRF NGDEAYDQCTNYLLQEGHTSGCLLDAEQRDDILYFSIR NGTHPVFTASRWMVYYLKPSSPKHVRFSWHQDAVTVT CSDLSYGDLLYEVQYRSPFDTEWQSKQENTCNVTIEGL DAEKCYSFWVRVKAMEDVYGPDTYPSDWSEVTCWQR GEIRDACAETPTPPKPKLSKGGSGGSGGSGGSGGSGGS GGSGGSGGSGGSGGSGGSGGSGGSGGSGGSGGSGGSG GSGGSESGYAQNGDLEDAELDDYSFSCYSQLEVNGSQ HSLTCAFEDPDVNITNLEFEICGALVEVKCLNFRKLQEI YFIETKKFLLIGKSNICVKVGEKSLTCKKIDLTTIVKPEA PFDLSVVYREGANDFVVTFNTSHLQKKYVKVLMHDVA YRQEKDENKWTHVNLSSTKLTLLQRKLQPAAMYEIKV RSIPDHYFKGFWSEWSPSYYFRTPEINNSSGEMD |
| TSLP-TRAP 2 | 51 | ESGYAQNGDLEDAELDDYSFSCYSQLEVNGSQHSLTCA FEDPDVNITNLEFEICGALVEVKCLNFRKLQEIYFIETKK FLLIGKSNICVKVGEKSLTCKKIDLTTIVKPEAPFDLSVV YREGANDFVVTFNTSHLQKKYVKVLMHDVAYRQEKD ENKWTHVNLSSTKLTLLQRKLQPAAMYEIKVRSIPDHY FKGFWSEWSPSYYFRTPEINNSSGEMDGGSGGSGGSGG SGGSGGSGGSGGSGGSGGSGGSGGSGGSGGSGGSGGS GGSGGSGGSGGSGAAEGVQIQIIYFNLETVQVTWNASK YSRTNLTFHYRFNGDEAYDQCTNYLLQEGHTSGCLLD AEQRDDILYFSIRNGTHPVFTASRWMVYYLKPSSPKHV RFSWHQDAVTVTCSDLSYGDLLYEVQYRSPFDTEWQS KQENTCNVTIEGLDAEKCYSFWVRVKAMEDVYGPDTY PSDWSEVTCWQRGEIRDACAETPTPPKPKLSK |
| Palivizumab-YTE HCDR1 | 52 | GFSLSTSGMS |
| Palivizumab-YTE HCDR2 | 53 | IWWDDKK |
| Palivizumab-YTE HCDR3 | 54 | ARSMITNWYFDV |
| Palivizumab-YTE LCDR1 | 55 | LSVGY |
| Palivizumab-YTE LCDR2 | 56 | DTS |
| Palivizumab-YTE LCDR3 | 57 | FQGSGYPFT |
| Palivizumab Heavy Chain Variable Region | 58 | QVTLRESGPALVKPTQTLTLTCTFSGFSLSTSGMSVGWI RQPPGKALEWLADIWWDDKKDYNPSLKSRLTISKDTS ANQVVLKVTNMDPADTATYYCARSMITNWYFDVWGA GTTVTVSS |
| Palivizumab Light Chain Variable Region | 59 | DIQMTQSPSTLSASVGDRVTITCKCQLSVGYMHWYQQ KPGKAPKLLIYDTSKLASGVPSRFSGSGSGTAFTLTISSL QPDDFATYYCFQGSGYPFTFGGGTKLEIK |
| Palivizumab-YTE Heavy Chain | 60 | QVTLRESGPALVKPTQTLTLTCTFSGFSLSTSGMSVGWI RQPPGKALEWLADIWWDDKKDYNPSLKSRLTISKDTS ANQVVLKVTNMDPADTATYYCARSMITNWYFDVWGA GTTVTVSSASTKGPSVFPLAPCSRSTSESTAALGCLVKD YFPEPVTVSWNSGALTSGVHTFPAVLQSSGLYSLSSVVT VPSSSLGTKTYTCNVDHKPSNTKVDKRVESKYGPPCPP CPAPEFLGGPSVFLFPPKPKDTLYITREPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLG |

-continued

| Description | SEQ ID NO.: | Sequences |
|---|---|---|
| Palivizumab-YTE Light Chain | 61 | DIQMTQSPSTLSASVGDRVTITCKCQLSVGYMHWYQQ KPGKAPKLLIYDTSKLASGVPSRFSGSGSGTAFTLTISSL QPDDFATYYCFQGSGYPFTFGGGTKLEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC |
| Signal Peptide 1 | 130 | MGWSCIILFLVATATGVHS |
| Signal Peptide 2 | 131 | MEWPLIFLLLLSGTAGVQS |
| Signal Peptide 3 | 132 | MKVLSLLYLLTAIPGILS |
| Signal Peptide 4 | 133 | MECNWILPFILSVTSGVYS |
| Signal Peptide 5 | 134 | MGRLTSSFLLLIVPAYVLS |
| Signal Peptide 6 | 135 | MGFSRIFLFLLSVTTGVHS |
| Signal Peptide 7 | 136 | MAVLALLLCLVTFPSCVLS |
| Signal Peptide 8 | 137 | MAVLGLLFCLVTFPSCVLS |
| Signal Peptide 9 | 138 | MNFGLSLIFLVLVLKGVQC |
| Signal Peptide 10 | 139 | MDRLTSSFLLLIVPAYVLS |
| Signal Peptide 11 | 140 | MGWSCIILILVAAATGVHS |
| Signal Peptide 12 | 141 | MECNWILPFILSVTSGVHS |
| Signal Peptide 13 | 142 | MECNWILPLILSVTSGVYS |
| Signal Peptide 14 | 143 | MNFGLSLIFLALILKGVQC |
| Signal Peptide 15 | 144 | MGWSWIFLFLLSETAGVLS |
| Signal Peptide 16 | 145 | MEWTWVFLFLLSVTAGVHS |
| Signal Peptide 17 | 146 | MDRLTSSFLLLTVPAYVLS |
| Signal Peptide 18 | 147 | MGWSYIILFLVATATGVHS |
| Signal Peptide 19 | 148 | MAVLVLLFCLVTFPSCVLS |
| Signal Peptide 20 | 149 | MGWSWIFFFLLSGTAGVHC |
| Signal Peptide 21 | 150 | MEWSGVFIFLLSVTAGVHS |
| Signal Peptide 22 | 151 | MGWSWIFLFLLSEIAGVLS |
| Signal Peptide 23 | 152 | MGWSWIFLFLLSGTAGVLS |
| Signal Peptide 24 | 153 | MGRSWIFLFLLSGTAGVLS |
| Signal Peptide 25 | 154 | MESQTQVFVYMLLWLSGVDG |
| Signal Peptide 26 | 155 | MESQTQVFLSLLLWVSGTCG |
| Signal Peptide 27 | 156 | METDTLLLWVLLLWVPGSTG |
| Signal Peptide 28 | 157 | MHFQVQIFSFLLISASVIMSRG |
| Signal Peptide 29 | 158 | MSSAQFLGLLLLCFQGTRC |
| Signal Peptide 30 | 159 | MESQIQVFVFVFLWLSGVDG |
| Signal Peptide 31 | 160 | MESQTLVFISILLWLYDADG |
| Signal Peptide 32 | 161 | MKFPSQLLLLLLFGIPGMIC |
| Signal Peptide 33 | 162 | MVSTPQFLVFLLFWIPASRG |
| Signal Peptide 34 | 163 | MEFHTQVFVFVFLWLSGVDG |
| Signal Peptide 35 | 164 | MESQTLVFISILLWLYGADG |

-continued

| Description | SEQ ID NO.: | Sequences |
|---|---|---|
| Signal Peptide 36 | 165 | MRAPAQIFGFLLLLFPGTRC |
| Signal Peptide 37 | 166 | MSVPTQVLGLLLLCLTGARC |
| Signal Peptide 38 | 167 | MSVPTQVLGLLLLWLTGARC |
| Signal Peptide 39 | 168 | MSVPTQVLGLLLLWLTDARC |
| Signal Peptide 40 | 169 | MDFQVQIFSFLLISASVILSRG |
| Signal Peptide 41 | 170 | MMVLAQFLAFLLLWFPGARC |
| Signal Peptide 42 | 171 | MDFQVQIFSFLLMSASVIMSRG |
| Signal Peptide 43 | 172 | MRAPAQFLGILLLWFPGARC |
| Signal Peptide 44 | 173 | MRPSIQFLGLLLFWLHGAQC |
| Signal Peptide 45 | 174 | MRPSIQFLGLLLFWLHGTQC |
| Signal Peptide 46 | 175 | MDFQVQIFSFLLISASVIISRG |
| Signal Peptide 47 | 176 | MDSQAQVLMLLLLWVSGTCG |
| Signal Peptide 48 | 177 | MRPSIQFLGLLLFGLHGAQC |
| Signal Peptide 49 | 178 | MDLQVQIISFLLISVTVLMSRG |
| Signal Peptide 50 | 179 | MKLPVRLLVLMFWIPASSS |
| Signal Peptide 51 | 180 | MESQIQAFVFVFLWLSGVDG |
| Signal Peptide 52 | 181 | MESQTQVLMFLLLWVSGACA |
| Signal Peptide 53 | 182 | MVFTPQILGLMLFWISASRG |
| Signal Peptide 54 | 183 | MESQTQVLMSLLFWVSGTCG |
| Signal Peptide 55 | 184 | MRAPAQIFGFLLLLFPGSRC |
| Linker 14 | 185 | ASTKGPSVFPLAP |
| Linker 15 | 187 | GGGGSGGGGSGGGGS |
| Linker 16 | 188 | EAAAKEAAAKEAAAK |

SEQUENCE LISTING

```
Sequence total quantity: 228
SEQ ID NO: 1            moltype = AA  length = 486
FEATURE                 Location/Qualifiers
source                  1..486
                        mol_type = protein
                        organism = synthetic construct
SEQUENCE: 1
ESGYAQNGDL EDAELDDYSF SCYSQLEVNG SQHSLTCAFE DPDVNITNLE FEICGALVEV  60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMDG GSGGSGGSGG SGGSGGSGGS  240
GGSGGSGGSG GSGGSGGSGG SGGSGGSGGS GGSGGSGGSG AAEGVQIQII YFNLETVQVT  300
WNASKYSRTN LTFHYRFNGD EAYDQCTNYL LQEGHTSGCL LDAEQRDDIL YFSIRNGTHP  360
VFTASRWMVY YLKPSSPKHV RFSWHQDAVT VTCSDLSYGD LLYEVQYRSP FDTEWQSKQE  420
NTCNVTIEGL DAEKCYSFWV RVKAMEDVYG PDTYPSDWSE VTCWQRGEIR DACAETPTPP  480
KPKLSK                                                             486

SEQ ID NO: 2            moltype = AA  length = 5
FEATURE                 Location/Qualifiers
source                  1..5
                        mol_type = protein
                        organism = synthetic construct
SEQUENCE: 2
TYGMH                                                              5
```

-continued

```
SEQ ID NO: 3            moltype = AA  length = 17
FEATURE                 Location/Qualifiers
source                  1..17
                        mol_type = protein
                        organism = synthetic construct
SEQUENCE: 3
VIWYDGSNKH YADSVKG                                                      17

SEQ ID NO: 4            moltype = AA  length = 13
FEATURE                 Location/Qualifiers
source                  1..13
                        mol_type = protein
                        organism = synthetic construct
SEQUENCE: 4
APQWELVHEA FDI                                                          13

SEQ ID NO: 5            moltype = AA  length = 446
FEATURE                 Location/Qualifiers
source                  1..446
                        mol_type = protein
                        organism = synthetic construct
SEQUENCE: 5
ESGYAQNGDL EDAELDDYSF SCYSQLEVNG SQHSLTCAFE DPDVNITNLE FEICGALVEV  60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMDG GGGSGGGGSG GGGSGGGGSG  240
AAEGVQIQII YFNLETVQVT WNASKYSRTN LTFHYRFNGD EAYDQCTNYL LQEGHTSGCL  300
LDAEQRDDIL YFSIRNGTHP VFTASRWMVY YLKPSSPKHV RFSWHQDAVT VTCSDLSYGD  360
LLYEVQYRSP FDTEWQSKQE NTCNVTIEGL DAEKCYSFWV RVKAMEDVYG PDTYPSDWSE  420
VTCWQRGEIR DACAETPTPP KPKLSK                                        446

SEQ ID NO: 6            moltype = AA  length = 11
FEATURE                 Location/Qualifiers
source                  1..11
                        mol_type = protein
                        organism = synthetic construct
SEQUENCE: 6
GGNNLGSKSV H                                                            11

SEQ ID NO: 7            moltype = AA  length = 7
FEATURE                 Location/Qualifiers
source                  1..7
                        mol_type = protein
                        organism = synthetic construct
SEQUENCE: 7
DDSDRPS                                                                 7

SEQ ID NO: 8            moltype = AA  length = 11
FEATURE                 Location/Qualifiers
source                  1..11
                        mol_type = protein
                        organism = synthetic construct
SEQUENCE: 8
QVWDSSSDHV V                                                            11

SEQ ID NO: 9            moltype =   length =
SEQUENCE: 9
000

SEQ ID NO: 10           moltype = AA  length = 8
FEATURE                 Location/Qualifiers
source                  1..8
                        mol_type = protein
                        organism = synthetic construct
SEQUENCE: 10
GFTFRDYA                                                                8

SEQ ID NO: 11           moltype = AA  length = 8
FEATURE                 Location/Qualifiers
source                  1..8
                        mol_type = protein
                        organism = synthetic construct
SEQUENCE: 11
ISGSGGNT                                                                8

SEQ ID NO: 12           moltype = AA  length = 18
FEATURE                 Location/Qualifiers
```

-continued

```
source                 1..18
                       mol_type = protein
                       organism = synthetic construct
SEQUENCE: 12
AKDRLSITIR PRYYGLDV                                            18

SEQ ID NO: 13          moltype =   length =
SEQUENCE: 13
000

SEQ ID NO: 14          moltype = AA  length = 11
FEATURE                Location/Qualifiers
source                 1..11
                       mol_type = protein
                       organism = synthetic construct
SEQUENCE: 14
QSLLYSIGYN Y                                                   11

SEQ ID NO: 15          moltype =   length =
SEQUENCE: 15
000

SEQ ID NO: 16          moltype = AA  length = 9
FEATURE                Location/Qualifiers
source                 1..9
                       mol_type = protein
                       organism = synthetic construct
SEQUENCE: 16
MQALQTPYT                                                      9

SEQ ID NO: 17          moltype = AA  length = 300
FEATURE                Location/Qualifiers
source                 1..300
                       mol_type = protein
                       organism = synthetic construct
VARIANT                1..300
                       note = This sequence may encompass 1-100 GGS repeating units
SEQUENCE: 17
GGSGGSGGSG GSGGSGGSGG SGGSGGSGGS GGSGGSGGSG GSGGSGGSGG SGGSGGSGGS  60
GGSGGSGGSG GSGGSGGSGG SGGSGGSGGS GGSGGSGGSG GSGGSGGSGG SGGSGGSGGS  120
GGSGGSGGSG GSGGSGGSGG SGGSGGSGGS GGSGGSGGSG GSGGSGGSGG SGGSGGSGGS  180
GGSGGSGGSG GSGGSGGSGG SGGSGGSGGS GGSGGSGGSG GSGGSGGSGG SGGSGGSGGS  240
GGSGGSGGSG GSGGSGGSGG SGGSGGSGGS GGSGGSGGSG GSGGSGGSGG SGGSGGSGGS  300

SEQ ID NO: 18          moltype = AA  length = 500
FEATURE                Location/Qualifiers
source                 1..500
                       mol_type = protein
                       organism = synthetic construct
VARIANT                1..500
                       note = This sequence may encompass 1-100 GGGGS repeating
                        units
SEQUENCE: 18
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS GGGGSGGGGS GGGGSGGGGS  120
GGGGSGGGGS GGGGSGGGGS GGGGSGGGGS GGGGSGGGGS GGGGSGGGGS GGGGSGGGGS  180
GGGGSGGGGS GGGGSGGGGS GGGGSGGGGS GGGGSGGGGS GGGGSGGGGS GGGGSGGGGS  240
GGGGSGGGGS GGGGSGGGGS GGGGSGGGGS GGGGSGGGGS GGGGSGGGGS GGGGSGGGGS  300
GGGGSGGGGS GGGGSGGGGS GGGGSGGGGS GGGGSGGGGS GGGGSGGGGS GGGGSGGGGS  360
GGGGSGGGGS GGGGSGGGGS GGGGSGGGGS GGGGSGGGGS GGGGSGGGGS GGGGSGGGGS  420
GGGGSGGGGS GGGGSGGGGS GGGGSGGGGS GGGGSGGGGS GGGGSGGGGS GGGGSGGGGS  480
GGGGSGGGGS GGGGSGGGGS                                          500

SEQ ID NO: 19          moltype = AA  length = 6
FEATURE                Location/Qualifiers
source                 1..6
                       mol_type = protein
                       organism = synthetic construct
SEQUENCE: 19
ASTKGP                                                         6

SEQ ID NO: 20          moltype = AA  length = 12
FEATURE                Location/Qualifiers
source                 1..12
                       mol_type = protein
                       organism = synthetic construct
SEQUENCE: 20
TVAAPSVFIF PP                                                  12
```

-continued

```
SEQ ID NO: 21          moltype = AA  length = 451
FEATURE                Location/Qualifiers
source                 1..451
                       mol_type = protein
                       organism = synthetic construct
SEQUENCE: 21
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 22          moltype = AA  length = 219
FEATURE                Location/Qualifiers
source                 1..219
                       mol_type = protein
                       organism = synthetic construct
SEQUENCE: 22
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 23          moltype = AA  length = 20
FEATURE                Location/Qualifiers
source                 1..20
                       mol_type = protein
                       organism = synthetic construct
SEQUENCE: 23
GGGGSGGGGS GGGGSGGGGS                                              20

SEQ ID NO: 24          moltype = AA  length = 220
FEATURE                Location/Qualifiers
source                 1..220
                       mol_type = protein
                       organism = synthetic construct
SEQUENCE: 24
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV                        220

SEQ ID NO: 25          moltype = AA  length = 122
FEATURE                Location/Qualifiers
source                 1..122
                       mol_type = protein
                       organism = synthetic construct
SEQUENCE: 25
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SS                                                                 122

SEQ ID NO: 26          moltype = AA  length = 85
FEATURE                Location/Qualifiers
source                 1..85
                       mol_type = protein
                       organism = synthetic construct
SEQUENCE: 26
CSRSTSESTA ALGCLVKDYF PEPVTVSWNS GALTSGVHTF PAVLQSSGLY SLSSVVTVPS  60
SNFGTQTYTC NVDHKPSNTK VDKTV                                        85

SEQ ID NO: 27          moltype = AA  length = 214
FEATURE                Location/Qualifiers
source                 1..214
                       mol_type = protein
                       organism = synthetic construct
SEQUENCE: 27
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 28          moltype = AA  length = 109
FEATURE                Location/Qualifiers
```

-continued

```
source                  1..109
                        mol_type = protein
                        organism = synthetic construct
SEQUENCE: 28
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLG             109

SEQ ID NO: 29           moltype = AA  length = 105
FEATURE                 Location/Qualifiers
source                  1..105
                        mol_type = protein
                        organism = synthetic construct
SEQUENCE: 29
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                 105

SEQ ID NO: 30           moltype = AA  length = 113
FEATURE                 Location/Qualifiers
source                  1..113
                        mol_type = protein
                        organism = synthetic construct
SEQUENCE: 30
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKR        113

SEQ ID NO: 31           moltype = AA  length = 94
FEATURE                 Location/Qualifiers
source                  1..94
                        mol_type = protein
                        organism = synthetic construct
SEQUENCE: 31
SDEQLKSGTA SVVCLLNNFY PREAKVQWKV DNALQSGNSQ ESVTEQDSKD STYSLSSTLT  60
LSKADYEKHK VYACEVTHQG LSSPVTKSFN RGEC                             94

SEQ ID NO: 32           moltype = AA  length = 125
FEATURE                 Location/Qualifiers
source                  1..125
                        mol_type = protein
                        organism = synthetic construct
SEQUENCE: 32
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSS                                                             125

SEQ ID NO: 33           moltype = AA  length = 326
FEATURE                 Location/Qualifiers
source                  1..326
                        mol_type = protein
                        organism = synthetic construct
SEQUENCE: 33
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 34           moltype = AA  length = 207
FEATURE                 Location/Qualifiers
source                  1..207
                        mol_type = protein
                        organism = unidentified
SEQUENCE: 34
GAAEGVQIQI IYFNLETVQV TWNASKYSRT NLTFHYRFNG DEAYDQCTNY LLQEGHTSGC  60
LLDAEQRDDI LYFSIRNGTH PVFTASRWMV YYLKPSSPKH VRFSWHQDAV TVTCSDLSYG  120
DLLYEVQYRS PFDTEWQSKQ ENTCNVTIEG LDAEKCYSFW VRVKAMEDVY GPDTYPSDWS  180
EVTCWQRGEI RDACAETPTP PKPKLSK                                     207

SEQ ID NO: 35           moltype = AA  length = 219
FEATURE                 Location/Qualifiers
source                  1..219
                        mol_type = protein
                        organism = unidentified
SEQUENCE: 35
ESGYAQNGDL EDAELDDYSF SCYSQLEVNG SQHSLTCAFE DPDVNITNLE FEICGALVEV  60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMD                        219
```

-continued

```
SEQ ID NO: 36          moltype = AA  length = 451
FEATURE                Location/Qualifiers
source                 1..451
                       mol_type = protein
                       organism = synthetic construct
SEQUENCE: 36
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 37          moltype = AA  length = 451
FEATURE                Location/Qualifiers
source                 1..451
                       mol_type = protein
                       organism = synthetic construct
SEQUENCE: 37
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL G                                 451

SEQ ID NO: 38          moltype = AA  length = 448
FEATURE                Location/Qualifiers
source                 1..448
                       mol_type = protein
                       organism = synthetic construct
SEQUENCE: 38
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLYITREPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLWCLV KGFYPSDIAV EWESNGQPEN NYKTTPPMLD SDGSFFLYSK LTVDKSRWQQ  420
GNVFSCSVMH EALHNHYTQK SLSLSPGK                                    448

SEQ ID NO: 39          moltype = AA  length = 448
FEATURE                Location/Qualifiers
source                 1..448
                       mol_type = protein
                       organism = synthetic construct
SEQUENCE: 39
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLYITREPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLSCAV KGFYPSDIAV EWESNGQPEN NYKTTPPMLD SDGSFFLVSK LTVDKSRWQQ  420
GNVFSCSVMH EALHNHYTQK SLSLSPGK                                    448

SEQ ID NO: 40          moltype = AA  length = 500
FEATURE                Location/Qualifiers
source                 1..500
                       mol_type = protein
                       organism = synthetic construct
VARIANT                1..500
                       note = This sequence may encompass 1-100 GGGGS repeating
                        units
SEQUENCE: 40
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS GGGGSGGGGS GGGGSGGGGS  120
GGGGSGGGGS GGGGSGGGGS GGGGSGGGGS GGGGSGGGGS GGGGSGGGGS GGGGSGGGGS  180
GGGGSGGGGS GGGGSGGGGS GGGGSGGGGS GGGGSGGGGS GGGGSGGGGS GGGGSGGGGS  240
GGGGSGGGGS GGGGSGGGGS GGGGSGGGGS GGGGSGGGGS GGGGSGGGGS GGGGSGGGGS  300
GGGGSGGGGS GGGGSGGGGS GGGGSGGGGS GGGGSGGGGS GGGGSGGGGS GGGGSGGGGS  360
GGGGSGGGGS GGGGSGGGGS GGGGSGGGGS GGGGSGGGGS GGGGSGGGGS GGGGSGGGGS  420
GGGGSGGGGS GGGGSGGGGS GGGGSGGGGS GGGGSGGGGS GGGGSGGGGS GGGGSGGGGS  480
GGGGSGGGGS GGGGSGGGGS                                             500
```

```
SEQ ID NO: 41           moltype = AA  length = 500
FEATURE                 Location/Qualifiers
source                  1..500
                        mol_type = protein
                        organism = synthetic construct
VARIANT                 1..500
                        note = This sequence may encompass 1-100 EAAAK repeating
                         units
SEQUENCE: 41
EAAAKEAAAK EAAAKEAAAK EAAAKEAAAK EAAAKEAAAK EAAAKEAAAK EAAAKEAAAK  60
EAAAKEAAAK EAAAKEAAAK EAAAKEAAAK EAAAKEAAAK EAAAKEAAAK EAAAKEAAAK  120
EAAAKEAAAK EAAAKEAAAK EAAAKEAAAK EAAAKEAAAK EAAAKEAAAK EAAAKEAAAK  180
EAAAKEAAAK EAAAKEAAAK EAAAKEAAAK EAAAKEAAAK EAAAKEAAAK EAAAKEAAAK  240
EAAAKEAAAK EAAAKEAAAK EAAAKEAAAK EAAAKEAAAK EAAAKEAAAK EAAAKEAAAK  300
EAAAKEAAAK EAAAKEAAAK EAAAKEAAAK EAAAKEAAAK EAAAKEAAAK EAAAKEAAAK  360
EAAAKEAAAK EAAAKEAAAK EAAAKEAAAK EAAAKEAAAK EAAAKEAAAK EAAAKEAAAK  420
EAAAKEAAAK EAAAKEAAAK EAAAKEAAAK EAAAKEAAAK EAAAKEAAAK EAAAKEAAAK  480
EAAAKEAAAK EAAAKEAAAK                                              500

SEQ ID NO: 42           moltype = AA  length = 10
FEATURE                 Location/Qualifiers
source                  1..10
                        mol_type = protein
                        organism = synthetic construct
SEQUENCE: 42
GGGGSGGGGS                                                         10

SEQ ID NO: 43           moltype = AA  length = 5
FEATURE                 Location/Qualifiers
source                  1..5
                        mol_type = protein
                        organism = synthetic construct
SEQUENCE: 43
GGGGS                                                              5

SEQ ID NO: 44           moltype = AA  length = 500
FEATURE                 Location/Qualifiers
source                  1..500
                        mol_type = protein
                        organism = synthetic construct
VARIANT                 1..500
                        note = This sequence may encompass 1-100 SGGGG repeating
                         units
SEQUENCE: 44
SGGGGSGGGG SGGGGSGGGG SGGGGSGGGG SGGGGSGGGG SGGGGSGGGG SGGGGSGGGG  60
SGGGGSGGGG SGGGGSGGGG SGGGGSGGGG SGGGGSGGGG SGGGGSGGGG SGGGGSGGGG  120
SGGGGSGGGG SGGGGSGGGG SGGGGSGGGG SGGGGSGGGG SGGGGSGGGG SGGGGSGGGG  180
SGGGGSGGGG SGGGGSGGGG SGGGGSGGGG SGGGGSGGGG SGGGGSGGGG SGGGGSGGGG  240
SGGGGSGGGG SGGGGSGGGG SGGGGSGGGG SGGGGSGGGG SGGGGSGGGG SGGGGSGGGG  300
SGGGGSGGGG SGGGGSGGGG SGGGGSGGGG SGGGGSGGGG SGGGGSGGGG SGGGGSGGGG  360
SGGGGSGGGG SGGGGSGGGG SGGGGSGGGG SGGGGSGGGG SGGGGSGGGG SGGGGSGGGG  420
SGGGGSGGGG SGGGGSGGGG SGGGGSGGGG SGGGGSGGGG SGGGGSGGGG SGGGGSGGGG  480
SGGGGSGGGG SGGGGSGGGG                                              500

SEQ ID NO: 45           moltype = AA  length = 504
FEATURE                 Location/Qualifiers
source                  1..504
                        mol_type = protein
                        organism = synthetic construct
VARIANT                 5..504
                        note = This region may encompass 1-100 SGGGG repeating units
SEQUENCE: 45
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS GGGGSGGGGS GGGGSGGGGS  120
GGGGSGGGGS GGGGSGGGGS GGGGSGGGGS GGGGSGGGGS GGGGSGGGGS GGGGSGGGGS  180
GGGGSGGGGS GGGGSGGGGS GGGGSGGGGS GGGGSGGGGS GGGGSGGGGS GGGGSGGGGS  240
GGGGSGGGGS GGGGSGGGGS GGGGSGGGGS GGGGSGGGGS GGGGSGGGGS GGGGSGGGGS  300
GGGGSGGGGS GGGGSGGGGS GGGGSGGGGS GGGGSGGGGS GGGGSGGGGS GGGGSGGGGS  360
GGGGSGGGGS GGGGSGGGGS GGGGSGGGGS GGGGSGGGGS GGGGSGGGGS GGGGSGGGGS  420
GGGGSGGGGS GGGGSGGGGS GGGGSGGGGS GGGGSGGGGS GGGGSGGGGS GGGGSGGGGS  480
GGGGSGGGGS GGGGSGGGGS GGGG                                         504

SEQ ID NO: 46           moltype = AA  length = 302
FEATURE                 Location/Qualifiers
source                  1..302
                        mol_type = protein
                        organism = synthetic construct
VARIANT                 3..302
                        note = This region may encompass 1-100 SGG repeating units
```

```
SEQUENCE: 46
GGSGGSGGSG GSGGSGGSGG SGGSGGSGGS GGSGGSGGSG GSGGSGGSGG SGGSGGSGGS  60
GGSGGSGGSG GSGGSGGSGG SGGSGGSGGS GGSGGSGGSG GSGGSGGSGG SGGSGGSGGS  120
GGSGGSGGSG GSGGSGGSGG SGGSGGSGGS GGSGGSGGSG GSGGSGGSGG SGGSGGSGGS  180
GGSGGSGGSG GSGGSGGSGG SGGSGGSGGS GGSGGSGGSG GSGGSGGSGG SGGSGGSGGS  240
GGSGGSGGSG GSGGSGGSGG SGGSGGSGGS GGSGGSGGSG GSGGSGGSGG SGGSGGSGGS  300
GG                                                                 302

SEQ ID NO: 47          moltype = AA  length = 60
FEATURE                Location/Qualifiers
source                 1..60
                       mol_type = protein
                       organism = synthetic construct
SEQUENCE: 47
GGSGGSGGSG GSGGSGGSGG SGGSGGSGGS GGSGGSGGSG GSGGSGGSGG SGGSGGSGGS  60

SEQ ID NO: 48          moltype = AA  length = 207
FEATURE                Location/Qualifiers
source                 1..207
                       mol_type = protein
                       organism = unidentified
SEQUENCE: 48
GAAEGVQIQI IYFNLETVQV TWNASKYSRT NLTFHYRFNG DEAYDQCTNY LLQEGHTSGC  60
LLDAEQRDDI LYFSIRNGTH PVFTASRWMV YYLKPSSPKH VRFSWHQDAV TVTCSDLSYG  120
DLLYEVQYRS PFDTEWQSKQ ENTCNVTIEG LDAEKCYSFW VRVKAMEDVY GPDTYPSDWS  180
EVTCWQRGEI RDACAETPTP PKPKLSK                                      207

SEQ ID NO: 49          moltype = AA  length = 219
FEATURE                Location/Qualifiers
source                 1..219
                       mol_type = protein
                       organism = unidentified
SEQUENCE: 49
ESGYAQNGDL EDAELDDYSF SCYSQLEVNG SQHSLTCAFE DPDVNITNLE FEICGALVEV  60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMD                         219

SEQ ID NO: 50          moltype = AA  length = 486
FEATURE                Location/Qualifiers
source                 1..486
                       mol_type = protein
                       organism = synthetic construct
SEQUENCE: 50
GAAEGVQIQI IYFNLETVQV TWNASKYSRT NLTFHYRFNG DEAYDQCTNY LLQEGHTSGC  60
LLDAEQRDDI LYFSIRNGTH PVFTASRWMV YYLKPSSPKH VRFSWHQDAV TVTCSDLSYG  120
DLLYEVQYRS PFDTEWQSKQ ENTCNVTIEG LDAEKCYSFW VRVKAMEDVY GPDTYPSDWS  180
EVTCWQRGEI RDACAETPTP PKPKLSKGGS GGSGGSGGSG GSGGSGGSGG SGGSGGSGGS  240
GGSGGSGGSG GSGGSGGSGG SGGSGGSESG YAQNGDLEDA ELDDYSFSCY SQLEVNGSQH  300
SLTCAFEDPD VNITNLEFEI CGALVEVKCL NFRKLQEIYF IETKKFLLIG KSNICVKVGE  360
KSLTCKKIDL TTIVKPEAPF DLSVVYREGA NDFVVTFNTS HLQKKYVKVL MHDVAYRQEK  420
DENKWTHVNL SSTKLTLLQR KLQPAAMYEI KVRSIPDHYF KGFWSEWSPS YYFRTPEINN  480
SSGEMD                                                             486

SEQ ID NO: 51          moltype = AA  length = 486
FEATURE                Location/Qualifiers
source                 1..486
                       mol_type = protein
                       organism = synthetic construct
SEQUENCE: 51
ESGYAQNGDL EDAELDDYSF SCYSQLEVNG SQHSLTCAFE DPDVNITNLE FEICGALVEV  60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMDG GSGGSGGSGG SGGSGGSGGS  240
GGSGGSGGSG GSGGSGGSGG SGGSGGSGGS GGSGGSGGSG AAEGVQIQII YFNLETVQVT  300
WNASKYSRTN LTFHYRFNGD EAYDQCTNYL LQEGHTSGCL LDAEQRDDIL YFSIRNGTHP  360
VFTASRWMVY YLKPSSPKHV RFSWHQDAVT VTCSDLSYGD LLYEVQYRSP FDTEWQSKQE  420
NTCNVTIEGL DAEKCYSFWV RVKAMEDVYG PDTYPSDWSE VTCWQRGEIR DACAETPTPP  480
KPKLSK                                                             486

SEQ ID NO: 52          moltype = AA  length = 10
FEATURE                Location/Qualifiers
source                 1..10
                       mol_type = protein
                       organism = synthetic construct
SEQUENCE: 52
GFSLSTSGMS                                                         10

SEQ ID NO: 53          moltype = AA  length = 7
```

```
FEATURE                Location/Qualifiers
source                 1..7
                       mol_type = protein
                       organism = synthetic construct
SEQUENCE: 53
IWWDDKK                                                    7

SEQ ID NO: 54          moltype = AA  length = 12
FEATURE                Location/Qualifiers
source                 1..12
                       mol_type = protein
                       organism = synthetic construct
SEQUENCE: 54
ARSMITNWYF DV                                              12

SEQ ID NO: 55          moltype = AA  length = 5
FEATURE                Location/Qualifiers
source                 1..5
                       mol_type = protein
                       organism = synthetic construct
SEQUENCE: 55
LSVGY                                                      5

SEQ ID NO: 56          moltype =   length =
SEQUENCE: 56
000

SEQ ID NO: 57          moltype = AA  length = 9
FEATURE                Location/Qualifiers
source                 1..9
                       mol_type = protein
                       organism = synthetic construct
SEQUENCE: 57
FQGSGYPFT                                                  9

SEQ ID NO: 58          moltype = AA  length = 120
FEATURE                Location/Qualifiers
source                 1..120
                       mol_type = protein
                       organism = synthetic construct
SEQUENCE: 58
QVTLRESGPA LVKPTQTLTL TCTFSGFSLS TSGMSVGWIR QPPGKALEWL ADIWWDDKKD  60
YNPSLKSRLT ISKDTSANQV VLKVTNMDPA DTATYYCARS MITNWYFDVW GAGTTVTVSS  120

SEQ ID NO: 59          moltype = AA  length = 106
FEATURE                Location/Qualifiers
source                 1..106
                       mol_type = protein
                       organism = synthetic construct
SEQUENCE: 59
DIQMTQSPST LSASVGDRVT ITCKCQLSVG YMHWYQQKPG KAPKLLIYDT SKLASGVPSR  60
FSGSGSGTAF TLTISSLQPD DFATYYCFQG SGYPFTFGGG TKLEIK             106

SEQ ID NO: 60          moltype = AA  length = 446
FEATURE                Location/Qualifiers
source                 1..446
                       mol_type = protein
                       organism = synthetic construct
SEQUENCE: 60
QVTLRESGPA LVKPTQTLTL TCTFSGFSLS TSGMSVGWIR QPPGKALEWL ADIWWDDKKD  60
YNPSLKSRLT ISKDTSANQV VLKVTNMDPA DTATYYCARS MITNWYFDVW GAGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LYITREPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                               446

SEQ ID NO: 61          moltype = AA  length = 213
FEATURE                Location/Qualifiers
source                 1..213
                       mol_type = protein
                       organism = synthetic construct
SEQUENCE: 61
DIQMTQSPST LSASVGDRVT ITCKCQLSVG YMHWYQQKPG KAPKLLIYDT SKLASGVPSR  60
FSGSGSGTAF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                       213
```

-continued

```
SEQ ID NO: 62           moltype = AA  length = 722
FEATURE                 Location/Qualifiers
source                  1..722
                        mol_type = protein
                        organism = synthetic construct
SEQUENCE: 62
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SQMQLVESGG  480
GVVQPGRSLR LSCAASGFTF RTYGMHWVRQ APGKGLEWVA VIWYDGSNKH YADSVKGRFT  540
ITRDNSKNTL NLQMNSLRAE DTAVYYCARA PQWELVHEAF DIWGQGTMVT VSSAGGGGSG  600
GGGSGGGGSG GGGSSYVLTQ PPSVSVAPGQ TARITCGGNN LGSKSVHWYQ QKPGQAPVLV  660
VYDDSDRPSW IPERFSGSNS GNTATLTISR GEAGDEADYY CQVWDSSSDH VVFGGGTKLT  720
VL                                                                 722

SEQ ID NO: 63           moltype = AA  length = 219
FEATURE                 Location/Qualifiers
source                  1..219
                        mol_type = protein
                        organism = synthetic construct
SEQUENCE: 63
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 64           moltype = AA  length = 722
FEATURE                 Location/Qualifiers
source                  1..722
                        mol_type = protein
                        organism = synthetic construct
SEQUENCE: 64
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SSYVLTQPPS  480
VSVAPGQTAR ITCGGNNLGS KSVHWYQQKP GQAPVLVVYD DSDRPSWIPE RFSGSNSGNT  540
ATLTISRGEA GDEADYYCQV WDSSSDHVVF GGGTKLTVLG GGGSGGGGSG GGGSGGGGSQ  600
MQLVESGGGV VQPGRSLRLS CAASGFTFRT YGMHWVRQAP GKGLEWVAVI WYDGSNKHYA  660
DSVKGRFTIT RDNSKNTLNL QMNSLRAEDT AVYYCARAPQ WELVHEAFDI WGQGTMVTVS  720
SA                                                                 722

SEQ ID NO: 65           moltype = AA  length = 219
FEATURE                 Location/Qualifiers
source                  1..219
                        mol_type = protein
                        organism = synthetic construct
SEQUENCE: 65
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 66           moltype = AA  length = 451
FEATURE                 Location/Qualifiers
source                  1..451
                        mol_type = protein
                        organism = synthetic construct
SEQUENCE: 66
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 67           moltype = AA  length = 490
FEATURE                 Location/Qualifiers
```

```
source                1..490
                      mol_type = protein
                      organism = synthetic construct
SEQUENCE: 67
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECG GGGSGGGGSG GGGSGGGGSQ  240
MQLVESGGGV VQPGRSLRLS CAASGFTFRT YGMHWVRQAP GKGLEWVAVI WYDGSNKHYA  300
DSVKGRFTIT RDNSKNTLNL QMNSLRAEDT AVYYCARAPQ WELVHEAFDI WGQGTMVTVS  360
SAGGGGSGGG GSGGGGSGGG GSSYVLTQPP SVSVAPGQTA RITCGGNNLG SKSVHWYQQK  420
PGQAPVLVVY DDSDRPSWIP ERFSGSNSGN TATLTISRGE AGDEADYYCQ VWDSSSDHVV  480
FGGGTKLTVL                                                        490

SEQ ID NO: 68         moltype = AA  length = 451
FEATURE               Location/Qualifiers
source                1..451
                      mol_type = protein
                      organism = synthetic construct
SEQUENCE: 68
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                451

SEQ ID NO: 69         moltype = AA  length = 490
FEATURE               Location/Qualifiers
source                1..490
                      mol_type = protein
                      organism = synthetic construct
SEQUENCE: 69
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECG GGGSGGGGSG GGGSGGGGSS  240
YVLTQPPSVS VAPGQTARIT CGGNNLGSKS VHWYQQKPGQ APVLVVYDDS DRPSWIPERF  300
SGSNSGNTAT LTISRGEAGD EADYYCQVWD SSSDHVVFGG GTKLTVLGGG GSGGGGSGGG  360
GSGGGGSQMQ LVESGGGVVQ PGRSLRLSCA ASGFTFRTYG MHWVRQAPGK GLEWVAVIWY  420
DGSNKHYADS VKGRFTITRD NSKNTLNLQM NSLRAEDTAV YYCARAPQWE LVHEAFDIWG  480
QGTMVTVSSA                                                        490

SEQ ID NO: 70         moltype = AA  length = 219
FEATURE               Location/Qualifiers
source                1..219
                      mol_type = protein
                      organism = synthetic construct
SEQUENCE: 70
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 71         moltype = AA  length = 451
FEATURE               Location/Qualifiers
source                1..451
                      mol_type = protein
                      organism = synthetic construct
SEQUENCE: 71
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL G                                451

SEQ ID NO: 72         moltype = AA  length = 722
FEATURE               Location/Qualifiers
source                1..722
                      mol_type = protein
                      organism = synthetic construct
SEQUENCE: 72
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGG GGSGGGGSGG  120
```

-continued

```
GGSGGGGSQM QLVESGGGVV QPGRSLRLSC AASGFTFRTY GMHWVRQAPG KGLEWVAVIW  180
YDGSNKHYAD SVKGRFTITR DNSKNTLNLQ MNSLRAEDTA VYYCARAPQW ELVHEAFDIW  240
GQGTMVTVSS AGGGGSGGGG SGGGGSGGGG SEVQLVESGG GLEQPGGSLR LSCAGSGFTF  300
RDYAMTWVRQ APGKGLEWVS SISGSGGNTY YADSVKGRFT ISRDNSKNTL YLQMNSLRAE  360
DTAVYYCAKD RLSITIRPRY YGLDVWGQGT TVTVSSASTK GPSVFPLAPC SRSTSESTAA  420
LGCLVKDYFP EPVTVSWNSG ALTSGVHTFP AVLQSSGLYS LSSVVTVPSS SLGTKTYTCN  480
VDHKPSNTKV DKRVESKYGP PCPPCPAPEF LGGPSVFLFP PKPKDTLYIT REPEVTCVVV  540
DVSQEDPEVQ FNWYVDGVEV HNAKTKPREE QFNSTYRVVS VLTVLHQDWL NGKEYKCKVS  600
NKGLPSSIEK TISKAKGQPR EPQVYTLPPS QEEMTKNQVS LSCAVKGFYP SDIAVEWESN  660
GQPENNYKTT PPVLDSDGSF FLVSRLTVDK SRWQEGNVFS CSVMHEALHN HYTQKSLSLS  720
LG                                                                722

SEQ ID NO: 73          moltype = AA  length = 219
FEATURE                Location/Qualifiers
source                 1..219
                       mol_type = protein
                       organism = synthetic construct
SEQUENCE: 73
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 74          moltype = AA  length = 722
FEATURE                Location/Qualifiers
source                 1..722
                       mol_type = protein
                       organism = synthetic construct
SEQUENCE: 74
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSAGGGGSGG GGSGGGGSGG GGSSYVLTQP PSVSVAPGQT ARITCGGNNL GSKSVHWYQQ  180
KPGQAPVLVV YDDSDRPSWI PERFSGSNSG NTATLTISRG EAGDEADYYC QVWDSSSDHV  240
VFGGGTKLTV LGGGGSGGGG SGGGGSGGGG SEVQLVESGG GLEQPGGSLR LSCAGSGFTF  300
RDYAMTWVRQ APGKGLEWVS SISGSGGNTY YADSVKGRFT ISRDNSKNTL YLQMNSLRAE  360
DTAVYYCAKD RLSITIRPRY YGLDVWGQGT TVTVSSASTK GPSVFPLAPC SRSTSESTAA  420
LGCLVKDYFP EPVTVSWNSG ALTSGVHTFP AVLQSSGLYS LSSVVTVPSS SLGTKTYTCN  480
VDHKPSNTKV DKRVESKYGP PCPPCPAPEF LGGPSVFLFP PKPKDTLYIT REPEVTCVVV  540
DVSQEDPEVQ FNWYVDGVEV HNAKTKPREE QFNSTYRVVS VLTVLHQDWL NGKEYKCKVS  600
NKGLPSSIEK TISKAKGQPR EPQVYTLPPS QEEMTKNQVS LSCAVKGFYP SDIAVEWESN  660
GQPENNYKTT PPVLDSDGSF FLVSRLTVDK SRWQEGNVFS CSVMHEALHN HYTQKSLSLS  720
LG                                                                722

SEQ ID NO: 75          moltype = AA  length = 451
FEATURE                Location/Qualifiers
source                 1..451
                       mol_type = protein
                       organism = synthetic construct
SEQUENCE: 75
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL G                                451

SEQ ID NO: 76          moltype = AA  length = 722
FEATURE                Location/Qualifiers
source                 1..722
                       mol_type = protein
                       organism = synthetic construct
SEQUENCE: 76
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSAGGGGSGG GGSGGGGSGG GGSSYVLTQP PSVSVAPGQT ARITCGGNNL GSKSVHWYQQ  180
KPGQAPVLVV YDDSDRPSWI PERFSGSNSG NTATLTISRG EAGDEADYYC QVWDSSSDHV  240
VFGGGTKLTV LGGGGSGGGG SGGGGSGGGG SEVQLVESGG GLEQPGGSLR LSCAGSGFTF  300
RDYAMTWVRQ APGKGLEWVS SISGSGGNTY YADSVKGRFT ISRDNSKNTL YLQMNSLRAE  360
DTAVYYCAKD RLSITIRPRY YGLDVWGQGT TVTVSSASTK GPSVFPLAPC SRSTSESTAA  420
LGCLVKDYFP EPVTVSWNSG ALTSGVHTFP AVLQSSGLYS LSSVVTVPSS SLGTKTYTCN  480
VDHKPSNTKV DKRVESKYGP PCPPCPAPEF LGGPSVFLFP PKPKDTLYIT REPEVTCVVV  540
DVSQEDPEVQ FNWYVDGVEV HNAKTKPREE QFNSTYRVVS VLTVLHQDWL NGKEYKCKVS  600
NKGLPSSIEK TISKAKGQPR EPQVYTLPPS QEEMTKNQVS LTCLVKGFYP SDIAVEWESN  660
GQPENNYKTT PPVLDSDGSF FLYSRLTVDK SRWQEGNVFS CSVMHEALHN HYTQKSLSLS  720
LG                                                                722

SEQ ID NO: 77          moltype = AA  length = 219
```

```
FEATURE                Location/Qualifiers
source                 1..219
                       mol_type = protein
                       organism = synthetic construct
SEQUENCE: 77
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 78          moltype = AA  length = 722
FEATURE                Location/Qualifiers
source                 1..722
                       mol_type = protein
                       organism = synthetic construct
SEQUENCE: 78
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGG GGSGGGGSGG  120
GGSGGGGSQM QLVESGGGVV QPGRSLRLSC AASGFTFRTY GMHWVRQAPG KGLEWVAVIW  180
YDGSNKHYAD SVKGRFTITR DNSKNTLNLQ MNSLRAEDTA VYYCARAPQW ELVHEAFDIW  240
GQGTMVTVSS AGGGGSGGGG SGGGGSGGGG SEVQLVESGG GLEQPGGSLR LSCAGSGFTF  300
RDYAMTWVRQ APGKGLEWVS SISGSGGNTY YADSVKGRFT ISRDNSKNTL YLQMNSLRAE  360
DTAVYYCAKD RLSITIRPRY YGLDVWGQGT TVTVSSASTK GPSVFPLAPC SRSTSESTAA  420
LGCLVKDYFP EPVTVSWNSG ALTSGVHTFP AVLQSSGLYS LSSVVTVPSS SLGTKTYTCN  480
VDHKPSNTKV DKRVESKYGP PCPPCPAPEF LGGPSVFLFP PKPKDTLYIT REPEVTCVVV  540
DVSQEDPEVQ FNWYVDGVEV HNAKTKPREE QFNSTYRVVS VLTVLHQDWL NGKEYKCKVS  600
NKGLPSSIEK TISKAKGQPR EPQVYTLPPS QEEMTKNQVS LTCLVKGFYP SDIAVEWESN  660
GQPENNYKTT PPVLDSDGSF FLYSRLTVDK SRWQEGNVFS CSVMHEALHN HYTQKSLSLS  720
LG                                                                 722

SEQ ID NO: 79          moltype = AA  length = 219
FEATURE                Location/Qualifiers
source                 1..219
                       mol_type = protein
                       organism = synthetic construct
SEQUENCE: 79
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 80          moltype = AA  length = 451
FEATURE                Location/Qualifiers
source                 1..451
                       mol_type = protein
                       organism = synthetic construct
SEQUENCE: 80
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 81          moltype = AA  length = 490
FEATURE                Location/Qualifiers
source                 1..490
                       mol_type = protein
                       organism = synthetic construct
SEQUENCE: 81
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSAGGGGSGG GGSGGGGSGG GGSSYVLTQP PSVSVAPGQT ARITCGGNNL GSKSVHWYQQ  180
KPGQAPVLVV YDDSDRPSWI PERFSGSNSG NTATLTISRG EAGDEADYYC QVWDSSSDHV  240
VFGGGTKLTV LGGGGSGGGG SGGGGSGGGG SDIVMTQSPL SLPVTPGEPA SISCRSSQSL  300
LYSIGYNYLD WYLQKSGQSP QLLIYLGSNR ASGVPDRFSG SGSGTDFTLK ISRVEAEDVG  360
FYYCMQALQT PYTFGQGTKL EIKRTVAAPS VFIFPPSDEQ LKSGTASVVC LLNNFYPREA  420
KVQWKVDNAL QSGNSQESVT EQDSKDSTYS LSSTLTLSKA DYEKHKVYAC EVTHQGLSSP  480
VTKSFNRGEC                                                         490

SEQ ID NO: 82          moltype = AA  length = 451
FEATURE                Location/Qualifiers
source                 1..451
                       mol_type = protein
                       organism = synthetic construct
```

```
SEQUENCE: 82
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                451

SEQ ID NO: 83          moltype = AA  length = 490
FEATURE                Location/Qualifiers
source                 1..490
                       mol_type = protein
                       organism = synthetic construct
SEQUENCE: 83
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGG GGSGGGGSGG  120
GGSGGGGSQM QLVESGGGVV QPGRSLRLSC AASGFTFRTY GMHWVRQAPG KGLEWVAVIW  180
YDGSNKHYAD SVKGRFTITR DNSKNTLNLQ MNSLRAEDTA VYYCARAPQW ELVHEAFDIW  240
GQGTMVTVSS AGGGGSGGGG SGGGGSGGGG SDIVMTQSPL SLPVTPGEPA SISCRSSQSL  300
LYSIGYNYLD WYLQKSGQSP QLLIYLGSNR ASGVPDRFSG SGSGTDFTLK ISRVEAEDVG  360
FYYCMQALQT PYTFGQGTKL EIKRTVAAPS VFIFPPSDEQ LKSGTASVVC LLNNFYPREA  420
KVQWKVDNAL QSGNSQESVT EQDSKDSTYS LSSTLTLSKA DYEKHKVYAC EVTHQGLSSP  480
VTKSFNRGEC                                                        490

SEQ ID NO: 84          moltype = AA  length = 586
FEATURE                Location/Qualifiers
source                 1..586
                       mol_type = protein
                       organism = synthetic construct
SEQUENCE: 84
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPEVQLV ESGGGLEQPG GSLRLSCAGS GFTFRDYAMT WVRQAPGKGL  180
EWVSSISGSG GNTYYADSVK GRFTISRDNS KNTLYLQMNS LRAEDTAVYY CAKDRLSITI  240
RPRYYGLDVW GQGTTVTVSS ASTKGPSVFP LAPCSRSTSE STAALGCLVK DYFPEPVTVS  300
WNSGALTSGV HTFPAVLQSS GLYSLSSVVT VPSSSLGTKT YTCNVDHKPS NTKVDKRVES  360
KYGPPCPPCP APEFLGGPSV FLFPPKPKDT LYITREPEVT CVVVDVSQED PEVQFNWYVD  420
GVEVHNAKTK PREEQFNSTY RVVSVLTVLH QDWLNGKEYK CKVSNKGLPS SIEKTISKAK  480
GQPREPQVYT LPPSQEEMTK NQVSLTCLVK GFYPSDIAVE WESNGQPENN YKTTPPVLDS  540
DGSFFLYSRL TVDKSRWQEG NVFSCSVMHE ALHNHYTQKS LSLSLG                586

SEQ ID NO: 85          moltype = AA  length = 340
FEATURE                Location/Qualifiers
source                 1..340
                       mol_type = protein
                       organism = synthetic construct
SEQUENCE: 85
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGT VAAPSVFIFP  120
PDIVMTQSPL SLPVTPGEPA SISCRSSQSL LYSIGYNYLD WYLQKSGQSP QLLIYLGSNR  180
ASGVPDRFSG SGSGTDFTLK ISRVEAEDVG FYYCMQALQT PYTFGQGTKL EIKRTVAAPS  240
VFIFPPSDEQ LKSGTASVVC LLNNFYPREA KVQWKVDNAL QSGNSQESVT EQDSKDSTYS  300
LSSTLTLSKA DYEKHKVYAC EVTHQGLSSP VTKSFNRGEC                       340

SEQ ID NO: 86          moltype = AA  length = 586
FEATURE                Location/Qualifiers
source                 1..586
                       mol_type = protein
                       organism = synthetic construct
SEQUENCE: 86
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPQM QLVESGGGVV QPGRSLRLSC AASGFTFRTY GMHWVRQAPG  180
KGLEWVAVIW YDGSNKHYAD SVKGRFTITR DNSKNTLNLQ MNSLRAEDTA VYYCARAPQW  240
ELVHEAFDIW GQGTMVTVSS ASTKGPSVFP LAPCSRSTSE STAALGCLVK DYFPEPVTVS  300
WNSGALTSGV HTFPAVLQSS GLYSLSSVVT VPSSNFGTQT YTCNVDHKPS NTKVDKTVER  360
KCCVECPPCP APPVAGPSVF LFPPKPKDTL YITREPEVTC VVVDVSHEDP EVQFNWYVDG  420
VEVHNAKTKP REEQFNSTFR VVSVLTVVHQ DWLNGKEYKC KVSNKGLPAP IEKTISKTKG  480
QPREPQVYTL PPSREEMTKN QVSLTCLVKG FYPSDIAVEW ESNGQPENNY KTTPPMLDSD  540
GSFFLYSKLT VDKSRWQQGN VFSCSVMHEA LHNHYTQKSL SLSPGK                586

SEQ ID NO: 87          moltype = AA  length = 339
FEATURE                Location/Qualifiers
source                 1..339
                       mol_type = protein
                       organism = synthetic construct
```

```
SEQUENCE: 87
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSYVLT QPPSVSVAPG QTARITCGGN NLGSKSVHWY QQKPGQAPVL VVYDDSDRPS  180
WIPERFSGSN SGNTATLTIS RGEAGDEADY YCQVWDSSSD HVVFGGGTKL TVLGQPKAAP  240
SVTLFPPSSE ELQANKATLV CLISDFYPGA VTVAWKADSS PVKAGVETTT PSKQSNNKYA  300
ASSYLSLTPE QWKSHRSYSC QVTHEGSTVE KTVAPTECS                         339

SEQ ID NO: 88          moltype = AA  length = 586
FEATURE                Location/Qualifiers
source                 1..586
                       mol_type = protein
                       organism = synthetic construct
SEQUENCE: 88
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPQM QLVESGGGVV QPGRSLRLSC AASGFTFRTY GMHWVRQAPG  180
KGLEWVAVIW YDGSNKHYAD SVKGRFTITR DNSKNTLNLQ MNSLRAEDTA VYYCARAPQW  240
ELVHEAFDIW GQGTMVTVSS ASTKGPSVFP LAPCSRSTSE STAALGCLVK DYFPEPVTVS  300
WNSGALTSGV HTFPAVLQSS GLYSLSSVVT VPSSNFGTQT YTCNVDHKPS NTKVDKTVES  360
KYGPPCPSCP APEFLGGPSV FLFPPKPKDT LYITREPEVT CVVVDVSQED PEVQFNWYVD  420
GVEVHNAKTK PREEQFNSTY RVVSVLTVLH QDWLNGKEYK CKVSNKGLPS SIEKTISKAK  480
GQPREPQVYT LPPSQEEMTK NQVSLTCLVK GFYPSDIAVE WESNGQPENN YKTTPPVLDS  540
DGSFFLYSRL TVDKSRWQEG NVFSCSVMHE ALHNHYTQKS LSLSLG                 586

SEQ ID NO: 89          moltype = AA  length = 352
FEATURE                Location/Qualifiers
source                 1..352
                       mol_type = protein
                       organism = synthetic construct
SEQUENCE: 89
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSYVLT QPPSVSVAPG QTARITCGGN NLGSKSVHWY QQKPGQAPVL VVYDDSDRPS  180
WIPERFSGSN SGNTATLTIS RGEAGDEADY YCQVWDSSSD HVVFGGGTKL TVLGTVAAPS  240
VFIFPPGQPK AAPSVTLFPP SSEELQANKA TLVCLISDFY PGAVTVAWKA DSSPVKAGVE  300
TTTPSKQSNN KYAASSYLSL TPEQWKSHRS YSCQVTHEGS TVEKTVAPTE CS          352

SEQ ID NO: 90          moltype = AA  length = 586
FEATURE                Location/Qualifiers
source                 1..586
                       mol_type = protein
                       organism = synthetic construct
SEQUENCE: 90
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPEVQLV ESGGGLEQPG GSLRLSCAGS GFTFRDYAMT WVRQAPGKGL  180
EWVSSISGSG GNTYYADSVK GRFTISRDNS KNTLYLQMNS LRAEDTAVYY CAKDRLSITI  240
RPRYYGLDVW GQGTTVTVSS ASTKGPSVFP LAPCSRSTSE STAALGCLVK DYFPEPVTVS  300
WNSGALTSGV HTFPAVLQSS GLYSLSSVVT VPSSSLGTKT YTCNVDHKPS NTKVDKRVER  360
KCCVECPPCP APPVAGPSVF LFPPKPKDTL YITREPEVTC VVVDVSHEDP EVQFNWYVDG  420
VEVHNAKTKP REEQFNSTFR VVSVLTVVHQ DWLNGKEYKC KVSNKGLPAP IEKTISKTKG  480
QPREPQVYTL PPSREEMTKN QVSLTCLVKG FYPSDIAVEW ESNGQPENNY KTTPPMLDSD  540
GSFFLYSKLT VDKSRWQQGN VFSCSVMHEA LHNHYTQKSL SLSPGK                 586

SEQ ID NO: 91          moltype = AA  length = 340
FEATURE                Location/Qualifiers
source                 1..340
                       mol_type = protein
                       organism = synthetic construct
SEQUENCE: 91
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGT VAAPSVFIFP  120
PDIVMTQSPL SLPVTPGEPA SISCRSSQSL LYSIGYNYLD WYLQKSGQSP QLLIYLGSNR  180
ASGVPDRFSG SGSGTDFTLK ISRVEAEDVG FYYCMQALQT PYTFGQGTKL EIKRTVAAPS  240
VFIFPPSDEQ LKSGTASVVC LLNNFYPREA KVQWKVDNAL QSGNSQESVT EQDSKDSTYS  300
LSSTLTLSKA DYEKHKVYAC EVTHQGLSSP VTKSFNRGEC                         340

SEQ ID NO: 92          moltype = AA  length = 586
FEATURE                Location/Qualifiers
source                 1..586
                       mol_type = protein
                       organism = synthetic construct
SEQUENCE: 92
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPQM QLVESGGGVV QPGRSLRLSC AASGFTFRTY GMHWVRQAPG  180
KGLEWVAVIW YDGSNKHYAD SVKGRFTITR DNSKNTLNLQ MNSLRAEDTA VYYCARAPQW  240
ELVHEAFDIW GQGTMVTVSS ASTKGPSVFP LAPCSRSTSE STAALGCLVK DYFPEPVTVS  300
```

```
WNSGALTSGV HTFPAVLQSS GLYSLSSVVT VPSSSLGTKT YTCNVDHKPS NTKVDKRVES  360
KYGPPCPPCP APEFLGGPSV FLFPPKPKDT LYITREPEVT CVVVDVSQED PEVQFNWYVD  420
GVEVHNAKTK PREEQFNSTY RVVSVLTVLH QDWLNGKEYK CKVSNKGLPS SIEKTISKAK  480
GQPREPQVYT LPPSQEEMTK NQVSLTCLVK GFYPSDIAVE WESNGQPENN YKTTPPVLDS  540
DGSFFLYSRL TVDKSRWQEG NVFSCSVMHE ALHNHYTQKS LSLSLG                586

SEQ ID NO: 93           moltype = AA  length = 340
FEATURE                 Location/Qualifiers
source                  1..340
                        mol_type = protein
                        organism = synthetic construct
SEQUENCE: 93
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSYVLT QPPSVSVAPG QTARITCGGN NLGSKSVHWY QQKPGQAPVL VVYDDSDRPS  180
WIPERFSGSN SGNTATLTIS RGEAGDEADY YCQVWDSSSD HVVFGGGTKL TVLGTVAAPS  240
VFIFPPSDEQ LKSGTASVVC LLNNFYPREA KVQWKVDNAL QSGNSQESVT EQDSKDSTYS  300
LSSTLTLSKA DYEKHKVYAC EVTHQGLSSP VTKSFNRGEC                       340

SEQ ID NO: 94           moltype = AA  length = 586
FEATURE                 Location/Qualifiers
source                  1..586
                        mol_type = protein
                        organism = synthetic construct
SEQUENCE: 94
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPEVQLV ESGGGLEQPG GSLRLSCAGS GFTFRDYAMT WVRQAPGKGL  180
EWVSSISGSG GNTYYADSVK GRFTISRDNS KNTLYLQMNS LRAEDTAVYY CAKDRLSITI  240
RPRYYGLDVW GQGTTVTVSS ASTKGPSVFP LAPCSRSTSE STAALGCLVK DYFPEPVTVS  300
WNSGALTSGV HTFPAVLQSS GLYSLSSVVT VPSSNFGTQT YTCNVDHKPS NTKVDKTVER  360
KCCVECPPCP APPVAGPSVF LFPPKPKDTL YITREPEVTC VVVDVSHEDP EVQFNWYVDG  420
VEVHNAKTKP REEQFNSTFR VVSVLTVVHQ DWLNGKEYKC KVSNKGLPAP IEKTISKTKG  480
QPREPQVYTL PPSREEMTKN QVSLTCLVKG FYPSDIAVEW ESNGQPENNY KTTPPMLDSD  540
GSFFLYSKLT VDKSRWQQGN VFSCSVMHEA LHNHYTQKSL SLSPGK                586

SEQ ID NO: 95           moltype = AA  length = 351
FEATURE                 Location/Qualifiers
source                  1..351
                        mol_type = protein
                        organism = synthetic construct
SEQUENCE: 95
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLTV AAPSVFIFPP  120
DIVMTQSPLS LPVTPGEPAS ISCRSSQSLL YSIGYNYLDW YLQKSGQSPQ LLIYLGSNRA  180
SGVPDRFSGS GSGTDFTLKI SRVEAEDVGF YYCMQALQTP YTFGQGTKLE IKRTVAAPSV  240
FIFPPGQPKA APSVTLFPPS SEELQANKAT LVCLISDFYP GAVTVAWKAD SSPVKAGVET  300
TTPSKQSNNK YAASSYLSLT PEQWKSHRSY SCQVTHEGST VEKTVAPTEC S          351

SEQ ID NO: 96           moltype = AA  length = 700
FEATURE                 Location/Qualifiers
source                  1..700
                        mol_type = protein
                        organism = synthetic construct
SEQUENCE: 96
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL GGGGGSGGGG SGGGGSGGGG SQMQLVESGG  480
GVVQPGRSLR LSCAASGFTF RTYGMHWVRQ APGKGLEWVA VIWYDGSNKH YADSVKGRFT  540
ITRDNSKNTL NLQMNSLRAE DTAVYYCARA PQWELVHEAF DIWGQGTMVT VSSAGQPKAA  600
PSVTLFPPSS EELQANKATL VCLISDFYPG AVTVAWKADS SPVKAGVETT TPSKQSNNKY  660
AASSYLSLTP EQWKSHRSYS CQVTHEGSTV EKTVAPTECS                       700

SEQ ID NO: 97           moltype = AA  length = 219
FEATURE                 Location/Qualifiers
source                  1..219
                        mol_type = protein
                        organism = synthetic construct
SEQUENCE: 97
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219
```

-continued

```
SEQ ID NO: 98          moltype = AA  length = 208
FEATURE                Location/Qualifiers
source                 1..208
                       mol_type = protein
                       organism = synthetic construct
SEQUENCE: 98
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLSS ASTKGPSVFP  120
LAPCSRSTSE STAALGCLVK DYFPEPVTVS WNSGALTSGV HTFPAVLQSS GLYSLSSVVT  180
VPSSNFGTQT YTCNVDHKPS NTKVDKTV                                     208

SEQ ID NO: 99          moltype = AA  length = 448
FEATURE                Location/Qualifiers
source                 1..448
                       mol_type = protein
                       organism = synthetic construct
SEQUENCE: 99
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLYITREPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLWCLV KGFYPSDIAV EWESNGQPEN NYKTTPPMLD SDGSFFLYSK LTVDKSRWQQ  420
GNVFSCSVMH EALHNHYTQK SLSLSPGK                                     448

SEQ ID NO: 100         moltype = AA  length = 699
FEATURE                Location/Qualifiers
source                 1..699
                       mol_type = protein
                       organism = synthetic construct
SEQUENCE: 100
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV ERKCCVECPP CPAPPVAGPS  240
VFLFPPKPKD TLYITREPEV TCVVVDVSHE DPEVQFNWYV DGVEVHNAKT KPREEQFNST  300
FRVVSVLTVV HQDWLNGKEY KCKVSNKGLP APIEKTISKT KGQPREPQVY TLPPSREEMT  360
KNQVSLSCAV KGFYPSDIAV EWESNGQPEN NYKTTPPMLD SDGSFFLVSK LTVDKSRWQQ  420
GNVFSCSVMH EALHNHYTQK SLSLSPGKGG GGSGGGGSGG GGSGGGGSEV QLVESGGGLE  480
QPGGSLRLSC AGSGFTFRDY AMTWVRQAPG KGLEWVSSIS GSGGNTYYAD SVKGRFTISR  540
DNSKNTLYLQ MNSLRAEDTA VYYCAKDRLS ITIRPRYYGL DVWGQGTTVT VSSTVAAPSV  600
FIFPPSDEQL KSGTASVVCL LNNFYPREAK VQWKVDNALQ SGNSQESVTE QDSKDSTYSL  660
SSTLTLSKAD YEKHKVYACE VTHQGLSSPV TKSFNRGEC                          699

SEQ ID NO: 101         moltype = AA  length = 214
FEATURE                Location/Qualifiers
source                 1..214
                       mol_type = protein
                       organism = synthetic construct
SEQUENCE: 101
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                               214

SEQ ID NO: 102         moltype = AA  length = 211
FEATURE                Location/Qualifiers
source                 1..211
                       mol_type = protein
                       organism = synthetic construct
SEQUENCE: 102
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR V                                  211

SEQ ID NO: 103         moltype = AA  length = 219
FEATURE                Location/Qualifiers
source                 1..219
                       mol_type = protein
                       organism = synthetic construct
SEQUENCE: 103
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 104         moltype = AA  length = 685
```

-continued

```
FEATURE                 Location/Qualifiers
source                  1..685
                        mol_type = protein
                        organism = synthetic construct
SEQUENCE: 104
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SSYVLTQPPS  480
VSVAPGQTAR ITCGGNNLGS KSVHWYQQKP GQAPVLVVYD DSDRPSWIPE RFSGSNSGNT  540
ATLTISRGEA GDEADYYCQV WDSSSDHVVF GGGTKLTVLG QPKAAPSVTL FPPSSEELQA  600
NKATLVCLIS DFYPGAVTVA WKADSSPVKA GVETTTPSKQ SNNKYAASSY LSLTPEQWKS  660
HRSYSCQVTH EGSTVEKTVA PTECS                                   685

SEQ ID NO: 105          moltype = AA  length = 220
FEATURE                 Location/Qualifiers
source                  1..220
                        mol_type = protein
                        organism = synthetic construct
SEQUENCE: 105
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SSASTKGPSV FPLAPCSRST SESTAALGCL VKDYFPEPVT VSWNSGALTS GVHTFPAVLQ  180
SSGLYSLSSV VTVPSSNFGT QTYTCNVDHK PSNTKVDKTV                   220

SEQ ID NO: 106          moltype = AA  length = 957
FEATURE                 Location/Qualifiers
source                  1..957
                        mol_type = protein
                        organism = synthetic construct
SEQUENCE: 106
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGANDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD GGSGGSGGSG GSGGSGGSGG SGGSGGSGGS  720
GGSGGSGGSG GSGGSGGSGG SGGSGGSGGS GAAEGVQIQI IYFNLETVQV TWNASKYSRT  780
NLTFHYRFNG DEAYDQCTNY LLQEGHTSGC LLDAEQRDDI LYFSIRNGTH PVFTASRWMV  840
YYLKPSSPKH VRFSWHQDAV TVTCSDLSYG DLLYEVQYRS PFDTEWQSKQ ENTCNVTIEG  900
LDAEKCYSFW VRVKAMEDVY GPDTYPSDWS EVTCWQRGEI RDACAETPTP PKPKLSK    957

SEQ ID NO: 107          moltype = AA  length = 219
FEATURE                 Location/Qualifiers
source                  1..219
                        mol_type = protein
                        organism = synthetic construct
SEQUENCE: 107
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                    219

SEQ ID NO: 108          moltype = AA  length = 957
FEATURE                 Location/Qualifiers
source                  1..957
                        mol_type = protein
                        organism = synthetic construct
SEQUENCE: 108
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
```

```
SPFDTEWQSK QENTCNVTIE GLDAEKCYSF WVRVKAMEDV YGPDTYPSDW SEVTCWQRGE  660
IRDACAETPT PPKPKLSKGG SGGSGGSGGS GGSGGSGGSG GSGGSGGSGG SGGSGGSGGS  720
GGSGGSGGSG GSGGSGGSES GYAQNGDLED AELDDYSFSC YSQLEVNGSQ HSLTCAFEDP  780
DVNITNLEFE ICGALVEVKC LNFRKLQEIY FIETKKFLLI GKSNICVKVG EKSLTCKKID  840
LTTIVKPEAP FDLSVVYREG ANDFVVTFNT SHLQKKYVKV LMHDVAYRQE KDENKWTHVN  900
LSSTKLTLLQ RKLQPAAMYE IKVRSIPDHY FKGFWSEWSP SYYFRTPEIN NSSGEMD     957

SEQ ID NO: 109          moltype = AA  length = 219
FEATURE                 Location/Qualifiers
source                  1..219
                        mol_type = protein
                        organism = synthetic construct
SEQUENCE: 109
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 110          moltype = AA  length = 917
FEATURE                 Location/Qualifiers
source                  1..917
                        mol_type = protein
                        organism = synthetic construct
SEQUENCE: 110
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGANDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD GGGGSGGGGS GGGGSGGGGS GAAEGVQIQI  720
IYFNLETVQV TWNASKYSRT NLTFHYRFNG DEAYDQCTNY LLQEGHTSGC LLDAEQRDDI  780
LYFSIRNGTH PVFTASRWMV YYLKPSSPKH VRFSWHQDAV TVTCSDLSYG DLLYEVQYRS  840
PFDTEWQSKQ ENTCNVTIEG LDAEKCYSFW VRVKAMEDVY GPDTYPSDWS EVTCWQRGEI  900
RDACAETPTP PKPKLSK                                                 917

SEQ ID NO: 111          moltype =   length =
SEQUENCE: 111
000

SEQ ID NO: 112          moltype = AA  length = 219
FEATURE                 Location/Qualifiers
source                  1..219
                        mol_type = protein
                        organism = synthetic construct
SEQUENCE: 112
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 113          moltype = AA  length = 917
FEATURE                 Location/Qualifiers
source                  1..917
                        mol_type = protein
                        organism = synthetic construct
SEQUENCE: 113
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
SPFDTEWQSK QENTCNVTIE GLDAEKCYSF WVRVKAMEDV YGPDTYPSDW SEVTCWQRGE  660
IRDACAETPT PPKPKLSKGG GGSGGGGSGG GGSGGGGSES GYAQNGDLED AELDDYSFSC  720
YSQLEVNGSQ HSLTCAFEDP DVNITNLEFE ICGALVEVKC LNFRKLQEIY FIETKKFLLI  780
GKSNICVKVG EKSLTCKKID LTTIVKPEAP FDLSVVYREG ANDFVVTFNT SHLQKKYVKV  840
LMHDVAYRQE KDENKWTHVN LSSTKLTLLQ RKLQPAAMYE IKVRSIPDHY FKGFWSEWSP  900
SYYFRTPEIN NSSGEMD                                                 917
```

```
SEQ ID NO: 114          moltype = AA  length = 219
FEATURE                 Location/Qualifiers
source                  1..219
                        mol_type = protein
                        organism = synthetic construct
SEQUENCE: 114
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 115          moltype = AA  length = 678
FEATURE                 Location/Qualifiers
source                  1..678
                        mol_type = protein
                        organism = synthetic construct
SEQUENCE: 115
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
SPFDTEWQSK QENTCNVTIE GLDAEKCYSF WVRVKAMEDV YGPDTYPSDW SEVTCWQRGE  660
IRDACAETPT PPKPKLSK                                                678

SEQ ID NO: 116          moltype = AA  length = 690
FEATURE                 Location/Qualifiers
source                  1..690
                        mol_type = protein
                        organism = synthetic construct
SEQUENCE: 116
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGANDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD                                   690

SEQ ID NO: 117          moltype = AA  length = 219
FEATURE                 Location/Qualifiers
source                  1..219
                        mol_type = protein
                        organism = synthetic construct
SEQUENCE: 117
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 118          moltype = AA  length = 690
FEATURE                 Location/Qualifiers
source                  1..690
                        mol_type = protein
                        organism = synthetic construct
SEQUENCE: 118
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGANDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD                                   690
```

```
SEQ ID NO: 119         moltype = AA  length = 678
FEATURE                Location/Qualifiers
source                 1..678
                       mol_type = protein
                       organism = synthetic construct
SEQUENCE: 119
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
SPFDTEWQSK QENTCNVTIE GLDAEKCYSF WVRVKAMEDV YGPDTYPSDW SEVTCWQRGE  660
IRDACAETPT PPKPKLSK                                                678

SEQ ID NO: 120         moltype = AA  length = 219
FEATURE                Location/Qualifiers
source                 1..219
                       mol_type = protein
                       organism = synthetic construct
SEQUENCE: 120
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 121         moltype = AA  length = 678
FEATURE                Location/Qualifiers
source                 1..678
                       mol_type = protein
                       organism = synthetic construct
SEQUENCE: 121
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
SPCDTEWQSK QENTCNVTIE GLDAEKCYSF WVRVKAMEDV YGPDTYPSDW SEVTCWQRGE  660
IRDACAETPT PPKPKLSK                                                678

SEQ ID NO: 122         moltype = AA  length = 690
FEATURE                Location/Qualifiers
source                 1..690
                       mol_type = protein
                       organism = synthetic construct
SEQUENCE: 122
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGCNDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD                                   690

SEQ ID NO: 123         moltype = AA  length = 219
FEATURE                Location/Qualifiers
source                 1..219
                       mol_type = protein
                       organism = synthetic construct
SEQUENCE: 123
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```

```
SEQ ID NO: 124          moltype = AA  length = 690
FEATURE                 Location/Qualifiers
source                  1..690
                        mol_type = protein
                        organism = synthetic construct
SEQUENCE: 124
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL SCAVKGFYPS DIAVEWESNG QPENNYKTTP PVLDSDGSFF LVSRLTVDKS  420
RWQEGNVFSC SVMHEALHNH YTQKSLSLSL GGGGGSGGGG SGGGGSGGGG SESGYAQNGD  480
LEDAELDDYS FSCYSQLEVN GSQHSLTCAF EDPDVNITNL EFEICGALVE VKCLNFRKLQ  540
EIYFIETKKF LLIGKSNICV KVGEKSLTCK KIDLTTIVKP EAPFDLSVVY REGCNDFVVT  600
FNTSHLQKKY VKVLMHDVAY RQEKDENKWT HVNLSSTKLT LLQRKLQPAA MYEIKVRSIP  660
DHYFKGFWSE WSPSYYFRTP EINNSSGEMD                                    690

SEQ ID NO: 125          moltype = AA  length = 678
FEATURE                 Location/Qualifiers
source                  1..678
                        mol_type = protein
                        organism = synthetic construct
SEQUENCE: 125
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL GGGGGSGGGG SGGGGSGGGG SGAAEGVQIQ  480
IIYFNLETVQ VTWNASKYSR TNLTFHYRFN GDEAYDQCTN YLLQEGHTSG CLLDAEQRDD  540
ILYFSIRNGT HPVFTASRWM VYYLKPSSPK HVRFSWHQDA VTVTCSDLSY GDLLYEVQYR  600
SPCDTEWQSK QENTCNVTIE GLDAEKCYSF WVRVKAMEDV YGPDTYPSDW SEVTCWQRGE  660
IRDACAETPT PPKPKLSK                                                 678

SEQ ID NO: 126          moltype = AA  length = 219
FEATURE                 Location/Qualifiers
source                  1..219
                        mol_type = protein
                        organism = synthetic construct
SEQUENCE: 126
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 127          moltype = AA  length = 239
FEATURE                 Location/Qualifiers
source                  1..239
                        mol_type = protein
                        organism = synthetic construct
SEQUENCE: 127
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 128          moltype = AA  length = 704
FEATURE                 Location/Qualifiers
source                  1..704
                        mol_type = protein
                        organism = synthetic construct
SEQUENCE: 128
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG GGGGSGGGGS  480
GGGGSGGGGS SYVLTQPPSV SVAPGQTARI TCGGNNLGSK SVHWYQQKPG QAPVLVVYDD  540
SDRPSWIPER FSGSNSGNTA TLTISRGEAG DEADYYCQVW DSSSDHVVFG GGTKLTVLGQ  600
PKAAPSVTLF PPSSEELQAN KATLVCLISD FYPGAVTVAW KADSSPVKAG VETTTPSKQS  660
NNKYAASSYL SLTPEQWKSH RSYSCQVTHE GSTVEKTVAP TECS                    704
```

-continued

```
SEQ ID NO: 129          moltype = AA  length = 239
FEATURE                 Location/Qualifiers
source                  1..239
                        mol_type = protein
                        organism = synthetic construct
SEQUENCE: 129
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 130          moltype = AA  length = 19
FEATURE                 Location/Qualifiers
source                  1..19
                        mol_type = protein
                        organism = synthetic construct
SEQUENCE: 130
MGWSCIILFL VATATGVHS                                               19

SEQ ID NO: 131          moltype = AA  length = 19
FEATURE                 Location/Qualifiers
source                  1..19
                        mol_type = protein
                        organism = synthetic construct
SEQUENCE: 131
MEWPLIFLLL LSGTAGVQS                                               19

SEQ ID NO: 132          moltype = AA  length = 18
FEATURE                 Location/Qualifiers
source                  1..18
                        mol_type = protein
                        organism = synthetic construct
SEQUENCE: 132
MKVLSLLYLL TAIPGILS                                                18

SEQ ID NO: 133          moltype = AA  length = 19
FEATURE                 Location/Qualifiers
source                  1..19
                        mol_type = protein
                        organism = synthetic construct
SEQUENCE: 133
MECNWILPFI LSVTSGVYS                                               19

SEQ ID NO: 134          moltype = AA  length = 19
FEATURE                 Location/Qualifiers
source                  1..19
                        mol_type = protein
                        organism = synthetic construct
SEQUENCE: 134
MGRLTSSFLL LIVPAYVLS                                               19

SEQ ID NO: 135          moltype = AA  length = 19
FEATURE                 Location/Qualifiers
source                  1..19
                        mol_type = protein
                        organism = synthetic construct
SEQUENCE: 135
MGFSRIFLFL LSVTTGVHS                                               19

SEQ ID NO: 136          moltype = AA  length = 19
FEATURE                 Location/Qualifiers
source                  1..19
                        mol_type = protein
                        organism = synthetic construct
SEQUENCE: 136
MAVLALLLCL VTFPSCVLS                                               19

SEQ ID NO: 137          moltype = AA  length = 19
FEATURE                 Location/Qualifiers
source                  1..19
                        mol_type = protein
                        organism = synthetic construct
SEQUENCE: 137
MAVLGLLFCL VTFPSCVLS                                               19

SEQ ID NO: 138          moltype = AA  length = 19
FEATURE                 Location/Qualifiers
```

```
source                  1..19
                        mol_type = protein
                        organism = synthetic construct
SEQUENCE: 138
MNFGLSLIFL VLVLKGVQC                                              19

SEQ ID NO: 139          moltype = AA  length = 19
FEATURE                 Location/Qualifiers
source                  1..19
                        mol_type = protein
                        organism = synthetic construct
SEQUENCE: 139
MDRLTSSFLL LIVPAYVLS                                              19

SEQ ID NO: 140          moltype = AA  length = 19
FEATURE                 Location/Qualifiers
source                  1..19
                        mol_type = protein
                        organism = synthetic construct
SEQUENCE: 140
MGWSCIILIL VAAATGVHS                                              19

SEQ ID NO: 141          moltype = AA  length = 19
FEATURE                 Location/Qualifiers
source                  1..19
                        mol_type = protein
                        organism = synthetic construct
SEQUENCE: 141
MECNWILPFI LSVTSGVHS                                              19

SEQ ID NO: 142          moltype = AA  length = 19
FEATURE                 Location/Qualifiers
source                  1..19
                        mol_type = protein
                        organism = synthetic construct
SEQUENCE: 142
MECNWILPLI LSVTSGVYS                                              19

SEQ ID NO: 143          moltype = AA  length = 19
FEATURE                 Location/Qualifiers
source                  1..19
                        mol_type = protein
                        organism = synthetic construct
SEQUENCE: 143
MNFGLSLIFL ALILKGVQC                                              19

SEQ ID NO: 144          moltype = AA  length = 19
FEATURE                 Location/Qualifiers
source                  1..19
                        mol_type = protein
                        organism = synthetic construct
SEQUENCE: 144
MGWSWIFLFL LSETAGVLS                                              19

SEQ ID NO: 145          moltype = AA  length = 19
FEATURE                 Location/Qualifiers
source                  1..19
                        mol_type = protein
                        organism = synthetic construct
SEQUENCE: 145
MEWTWVFLFL LSVTAGVHS                                              19

SEQ ID NO: 146          moltype = AA  length = 19
FEATURE                 Location/Qualifiers
source                  1..19
                        mol_type = protein
                        organism = synthetic construct
SEQUENCE: 146
MDRLTSSFLL LTVPAYVLS                                              19

SEQ ID NO: 147          moltype = AA  length = 19
FEATURE                 Location/Qualifiers
source                  1..19
                        mol_type = protein
                        organism = synthetic construct
SEQUENCE: 147
MGWSYIILFL VATATGVHS                                              19

SEQ ID NO: 148          moltype = AA  length = 19
```

-continued

```
FEATURE                Location/Qualifiers
source                 1..19
                       mol_type = protein
                       organism = synthetic construct
SEQUENCE: 148
MAVLVLLFCL VTFPSCVLS                                              19

SEQ ID NO: 149         moltype = AA  length = 19
FEATURE                Location/Qualifiers
source                 1..19
                       mol_type = protein
                       organism = synthetic construct
SEQUENCE: 149
MGWSWIFFFL LSGTAGVHC                                              19

SEQ ID NO: 150         moltype = AA  length = 19
FEATURE                Location/Qualifiers
source                 1..19
                       mol_type = protein
                       organism = synthetic construct
SEQUENCE: 150
MEWSGVFIFL LSVTAGVHS                                              19

SEQ ID NO: 151         moltype = AA  length = 19
FEATURE                Location/Qualifiers
source                 1..19
                       mol_type = protein
                       organism = synthetic construct
SEQUENCE: 151
MGWSWIFLFL LSEIAGVLS                                              19

SEQ ID NO: 152         moltype = AA  length = 19
FEATURE                Location/Qualifiers
source                 1..19
                       mol_type = protein
                       organism = synthetic construct
SEQUENCE: 152
MGWSWIFLFL LSGTAGVLS                                              19

SEQ ID NO: 153         moltype = AA  length = 19
FEATURE                Location/Qualifiers
source                 1..19
                       mol_type = protein
                       organism = synthetic construct
SEQUENCE: 153
MGRSWIFLFL LSGTAGVLS                                              19

SEQ ID NO: 154         moltype = AA  length = 20
FEATURE                Location/Qualifiers
source                 1..20
                       mol_type = protein
                       organism = synthetic construct
SEQUENCE: 154
MESQTQVFVY MLLWLSGVDG                                             20

SEQ ID NO: 155         moltype = AA  length = 20
FEATURE                Location/Qualifiers
source                 1..20
                       mol_type = protein
                       organism = synthetic construct
SEQUENCE: 155
MESQTQVFLS LLLWVSGTCG                                             20

SEQ ID NO: 156         moltype = AA  length = 20
FEATURE                Location/Qualifiers
source                 1..20
                       mol_type = protein
                       organism = synthetic construct
SEQUENCE: 156
METDTLLLWV LLLWVPGSTG                                             20

SEQ ID NO: 157         moltype = AA  length = 22
FEATURE                Location/Qualifiers
source                 1..22
                       mol_type = protein
                       organism = synthetic construct
SEQUENCE: 157
MHFQVQIFSF LLISASVIMS RG                                          22
```

-continued

```
SEQ ID NO: 158          moltype = AA  length = 19
FEATURE                 Location/Qualifiers
source                  1..19
                        mol_type = protein
                        organism = synthetic construct
SEQUENCE: 158
MSSAQFLGLL LLCFQGTRC                                              19

SEQ ID NO: 159          moltype = AA  length = 20
FEATURE                 Location/Qualifiers
source                  1..20
                        mol_type = protein
                        organism = synthetic construct
SEQUENCE: 159
MESQIQVFVF VFLWLSGVDG                                             20

SEQ ID NO: 160          moltype = AA  length = 20
FEATURE                 Location/Qualifiers
source                  1..20
                        mol_type = protein
                        organism = synthetic construct
SEQUENCE: 160
MESQTLVFIS ILLWLYDADG                                             20

SEQ ID NO: 161          moltype = AA  length = 20
FEATURE                 Location/Qualifiers
source                  1..20
                        mol_type = protein
                        organism = synthetic construct
SEQUENCE: 161
MKFPSQLLLL LLFGIPGMIC                                             20

SEQ ID NO: 162          moltype = AA  length = 20
FEATURE                 Location/Qualifiers
source                  1..20
                        mol_type = protein
                        organism = synthetic construct
SEQUENCE: 162
MVSTPQFLVF LLFWIPASRG                                             20

SEQ ID NO: 163          moltype = AA  length = 20
FEATURE                 Location/Qualifiers
source                  1..20
                        mol_type = protein
                        organism = synthetic construct
SEQUENCE: 163
MEFHTQVFVF VFLWLSGVDG                                             20

SEQ ID NO: 164          moltype = AA  length = 20
FEATURE                 Location/Qualifiers
source                  1..20
                        mol_type = protein
                        organism = synthetic construct
SEQUENCE: 164
MESQTLVFIS ILLWLYGADG                                             20

SEQ ID NO: 165          moltype = AA  length = 20
FEATURE                 Location/Qualifiers
source                  1..20
                        mol_type = protein
                        organism = synthetic construct
SEQUENCE: 165
MRAPAQIFGF LLLLFPGTRC                                             20

SEQ ID NO: 166          moltype = AA  length = 20
FEATURE                 Location/Qualifiers
source                  1..20
                        mol_type = protein
                        organism = synthetic construct
SEQUENCE: 166
MSVPTQVLGL LLLCLTGARC                                             20

SEQ ID NO: 167          moltype = AA  length = 20
FEATURE                 Location/Qualifiers
source                  1..20
                        mol_type = protein
                        organism = synthetic construct
SEQUENCE: 167
MSVPTQVLGL LLLWLTGARC                                             20
```

```
SEQ ID NO: 168          moltype = AA  length = 20
FEATURE                 Location/Qualifiers
source                  1..20
                        mol_type = protein
                        organism = synthetic construct
SEQUENCE: 168
MSVPTQVLGL LLLWLTDARC                                              20

SEQ ID NO: 169          moltype = AA  length = 22
FEATURE                 Location/Qualifiers
source                  1..22
                        mol_type = protein
                        organism = synthetic construct
SEQUENCE: 169
MDFQVQIFSF LLISASVILS RG                                           22

SEQ ID NO: 170          moltype = AA  length = 20
FEATURE                 Location/Qualifiers
source                  1..20
                        mol_type = protein
                        organism = synthetic construct
SEQUENCE: 170
MMVLAQFLAF LLLWFPGARC                                              20

SEQ ID NO: 171          moltype = AA  length = 22
FEATURE                 Location/Qualifiers
source                  1..22
                        mol_type = protein
                        organism = synthetic construct
SEQUENCE: 171
MDFQVQIFSF LLMSASVIMS RG                                           22

SEQ ID NO: 172          moltype = AA  length = 20
FEATURE                 Location/Qualifiers
source                  1..20
                        mol_type = protein
                        organism = synthetic construct
SEQUENCE: 172
MRAPAQFLGI LLLWFPGARC                                              20

SEQ ID NO: 173          moltype = AA  length = 20
FEATURE                 Location/Qualifiers
source                  1..20
                        mol_type = protein
                        organism = synthetic construct
SEQUENCE: 173
MRPSIQFLGL LLFWLHGAQC                                              20

SEQ ID NO: 174          moltype = AA  length = 20
FEATURE                 Location/Qualifiers
source                  1..20
                        mol_type = protein
                        organism = synthetic construct
SEQUENCE: 174
MRPSIQFLGL LLFWLHGTQC                                              20

SEQ ID NO: 175          moltype = AA  length = 22
FEATURE                 Location/Qualifiers
source                  1..22
                        mol_type = protein
                        organism = synthetic construct
SEQUENCE: 175
MDFQVQIFSF LLISASVIIS RG                                           22

SEQ ID NO: 176          moltype = AA  length = 20
FEATURE                 Location/Qualifiers
source                  1..20
                        mol_type = protein
                        organism = synthetic construct
SEQUENCE: 176
MDSQAQVLML LLLWVSGTCG                                              20

SEQ ID NO: 177          moltype = AA  length = 20
FEATURE                 Location/Qualifiers
source                  1..20
                        mol_type = protein
                        organism = synthetic construct
```

```
SEQUENCE: 177
MRPSIQFLGL LLFGLHGAQC                                              20

SEQ ID NO: 178          moltype = AA  length = 22
FEATURE                 Location/Qualifiers
source                  1..22
                        mol_type = protein
                        organism = synthetic construct
SEQUENCE: 178
MDLQVQIISF LLISVTVLMS RG                                           22

SEQ ID NO: 179          moltype = AA  length = 19
FEATURE                 Location/Qualifiers
source                  1..19
                        mol_type = protein
                        organism = synthetic construct
SEQUENCE: 179
MKLPVRLLVL MFWIPASSS                                               19

SEQ ID NO: 180          moltype = AA  length = 20
FEATURE                 Location/Qualifiers
source                  1..20
                        mol_type = protein
                        organism = synthetic construct
SEQUENCE: 180
MESQIQAFVF VFLWLSGVDG                                              20

SEQ ID NO: 181          moltype = AA  length = 20
FEATURE                 Location/Qualifiers
source                  1..20
                        mol_type = protein
                        organism = synthetic construct
SEQUENCE: 181
MESQTQVLMF LLLWVSGACA                                              20

SEQ ID NO: 182          moltype = AA  length = 20
FEATURE                 Location/Qualifiers
source                  1..20
                        mol_type = protein
                        organism = synthetic construct
SEQUENCE: 182
MVFTPQILGL MLFWISASRG                                              20

SEQ ID NO: 183          moltype = AA  length = 20
FEATURE                 Location/Qualifiers
source                  1..20
                        mol_type = protein
                        organism = synthetic construct
SEQUENCE: 183
MESQTQVLMS LLFWVSGTCG                                              20

SEQ ID NO: 184          moltype = AA  length = 20
FEATURE                 Location/Qualifiers
source                  1..20
                        mol_type = protein
                        organism = synthetic construct
SEQUENCE: 184
MRAPAQIFGF LLLLFPGSRC                                              20

SEQ ID NO: 185          moltype = AA  length = 13
FEATURE                 Location/Qualifiers
source                  1..13
                        mol_type = protein
                        organism = synthetic construct
SEQUENCE: 185
ASTKGPSVFP LAP                                                     13

SEQ ID NO: 186          moltype = AA  length = 451
FEATURE                 Location/Qualifiers
source                  1..451
                        mol_type = protein
                        organism = synthetic construct
SEQUENCE: 186
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
```

-continued

```
EEMTKNQVSL WCLVKGFYPS DIAVEWESNG QPENNYKTTP PVLDSDGSFF LYSRLTVDKS  420
RWQEGNVFSC SVMHEALHNH YTQKSLSLSL G                                451

SEQ ID NO: 187          moltype = AA  length = 15
FEATURE                 Location/Qualifiers
source                  1..15
                        mol_type = protein
                        organism = synthetic construct
SEQUENCE: 187
GGGGSGGGGS GGGGS                                                  15

SEQ ID NO: 188          moltype = AA  length = 15
FEATURE                 Location/Qualifiers
source                  1..15
                        mol_type = protein
                        organism = synthetic construct
SEQUENCE: 188
EAAAKEAAAK EAAAK                                                  15

SEQ ID NO: 189          moltype = AA  length = 704
FEATURE                 Location/Qualifiers
source                  1..704
                        mol_type = protein
                        organism = synthetic construct
SEQUENCE: 189
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLMISRT PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VLHEALHSHY TQKSLSLSLG GGGGSGGGGS  480
GGGGSGGGGS SYVLTQPPSV SVAPGQTARI TCGGNNLGSK SVHWYQQKPG QAPVLVVYDD  540
SDRPSWIPER FSGSNSGNTA TLTISRGEAG DEADYYCQVW DSSSDHVVFG GGTKLTVLGQ  600
PKAAPSVTLF PPSSEELQAN KATLVCLISD FYPGAVTVAW KADSSPVKAG VETTTPSKQS  660
NNKYAASSYL SLTPEQWKSH RSYSCQVTHE GSTVEKTVAP TECS                  704

SEQ ID NO: 190          moltype = AA  length = 239
FEATURE                 Location/Qualifiers
source                  1..239
                        mol_type = protein
                        organism = synthetic construct
SEQUENCE: 190
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 191          moltype = AA  length = 239
FEATURE                 Location/Qualifiers
source                  1..239
                        mol_type = protein
                        organism = synthetic construct
SEQUENCE: 191
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 192          moltype = AA  length = 704
FEATURE                 Location/Qualifiers
source                  1..704
                        mol_type = protein
                        organism = synthetic construct
SEQUENCE: 192
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLMISRT PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG GGGGSGGGGS  480
GGGGSGGGGS SYVLTQPPSV SVAPGQTARI TCGGNNLGSK SVHWYQQKPG QAPVLVVYDD  540
SDRPSWIPER FSGSNSGNTA TLTISRGEAG DEADYYCQVW DSSSDHVVFG GGTKLTVLGQ  600
PKAAPSVTLF PPSSEELQAN KATLVCLISD FYPGAVTVAW KADSSPVKAG VETTTPSKQS  660
NNKYAASSYL SLTPEQWKSH RSYSCQVTHE GSTVEKTVAP TECS                  704
```

```
SEQ ID NO: 193          moltype = AA  length = 239
FEATURE                 Location/Qualifiers
source                  1..239
                        mol_type = protein
                        organism = synthetic construct
SEQUENCE: 193
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 194          moltype = AA  length = 239
FEATURE                 Location/Qualifiers
source                  1..239
                        mol_type = protein
                        organism = synthetic construct
SEQUENCE: 194
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 195          moltype = AA  length = 699
FEATURE                 Location/Qualifiers
source                  1..699
                        mol_type = protein
                        organism = synthetic construct
SEQUENCE: 195
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG EAAAKEAAAK  480
EAAAKSYVLT QPPSVSVAPG QTARITCGGN NLGSKSVHWY QQKPGQAPVL VVYDDSDRPS  540
WIPERFSGSN SGNTATLTIS RGEAGDEADY YCQVWDSSSD HVVFGGGTKL TVLGQPKAAP  600
SVTLFPPSSE ELQANKATLV CLISDFYPGA VTVAWKADSS PVKAGVETTT PSKQSNNKYA  660
ASSYLSLTPE QWKSHRSYSC QVTHEGSTVE KTVAPTECS                        699

SEQ ID NO: 196          moltype = AA  length = 239
FEATURE                 Location/Qualifiers
source                  1..239
                        mol_type = protein
                        organism = synthetic construct
SEQUENCE: 196
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 197          moltype = AA  length = 239
FEATURE                 Location/Qualifiers
source                  1..239
                        mol_type = protein
                        organism = synthetic construct
SEQUENCE: 197
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 198          moltype = AA  length = 699
FEATURE                 Location/Qualifiers
source                  1..699
                        mol_type = protein
                        organism = synthetic construct
SEQUENCE: 198
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG GGGGSGGGGS  480
GGGGSSYVLT QPPSVSVAPG QTARITCGGN NLGSKSVHWY QQKPGQAPVL VVYDDSDRPS  540
WIPERFSGSN SGNTATLTIS RGEAGDEADY YCQVWDSSSD HVVFGGGTKL TVLGQPKAAP  600
```

-continued

```
SVTLFPPSSE ELQANKATLV CLISDFYPGA VTVAWKADSS PVKAGVETTT PSKQSNNKYA  660
ASSYLSLTPE QWKSHRSYSC QVTHEGSTVE KTVAPTECS                        699

SEQ ID NO: 199          moltype = AA  length = 239
FEATURE                 Location/Qualifiers
source                  1..239
                        mol_type = protein
                        organism = synthetic construct
SEQUENCE: 199
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 200          moltype = AA  length = 239
FEATURE                 Location/Qualifiers
source                  1..239
                        mol_type = protein
                        organism = synthetic construct
SEQUENCE: 200
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 201          moltype = AA  length = 694
FEATURE                 Location/Qualifiers
source                  1..694
                        mol_type = protein
                        organism = synthetic construct
SEQUENCE: 201
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
VLDSDGSFFL YSRLTVDKSR WQEGNVFSCS VMHEALHNHY TQKSLSLSLG GGGGSGGGGS  480
SYVLTQPPSV SVAPGQTARI TCGGNNLGSK SVHWYQQKPG QAPVLVVYDD SDRPSWIPER  540
FSGSNSGNTA TLTISRGEAG DEADYYCQVW DSSSDHVVFG GGTKLTVLGQ PKAAPSVTLF  600
PPSSEELQAN KATLVCLISD FYPGAVTVAW KADSSPVKAG VETTTPSKQS NNKYAASSYL  660
SLTPEQWKSH RSYSCQVTHE GSTVEKTVAP TECS                             694

SEQ ID NO: 202          moltype = AA  length = 239
FEATURE                 Location/Qualifiers
source                  1..239
                        mol_type = protein
                        organism = synthetic construct
SEQUENCE: 202
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 203          moltype = AA  length = 239
FEATURE                 Location/Qualifiers
source                  1..239
                        mol_type = protein
                        organism = synthetic construct
SEQUENCE: 203
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 204          moltype = AA  length = 689
FEATURE                 Location/Qualifiers
source                  1..689
                        mol_type = protein
                        organism = synthetic construct
SEQUENCE: 204
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLT CLVKGFYPSD IAVEWESNGQ PENNYKTTPP  420
```

```
VLDSDGSFFL YSRLTVDKSR WQEGNVFSCS VMHEALHNHY TQKSLSLSLG GGGGSSYVLT  480
QPPSVSVAPG QTARITCGGN NLGSKSVHWY QQKPGQAPVL VVYDDSDRPS WIPERFSGSN  540
SGNTATLTIS RGEAGDEADY YCQVWDSSSD HVVFGGGTKL TVLGQPKAAP SVTLFPPSSE  600
ELQANKATLV CLISDFYPGA VTVAWKADSS PVKAGVETTT PSKQSNNKYA ASSYLSLTPE  660
QWKSHRSYSC QVTHEGSTVE KTVAPTECS                                    689

SEQ ID NO: 205         moltype = AA  length = 239
FEATURE                Location/Qualifiers
source                 1..239
                       mol_type = protein
                       organism = synthetic construct
SEQUENCE: 205
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 206         moltype = AA  length = 239
FEATURE                Location/Qualifiers
source                 1..239
                       mol_type = protein
                       organism = synthetic construct
SEQUENCE: 206
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 207         moltype = AA  length = 704
FEATURE                Location/Qualifiers
source                 1..704
                       mol_type = protein
                       organism = synthetic construct
SEQUENCE: 207
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLW CLVKGFYPSD IAVEWESNGQ PENNYKTTPP  420
VLDSDGSFFL YSRLTVDKSR WQEGNVFSCS VMHEALHNHY TQKSLSLSLG GGGGSGGGGS  480
GGGGSGGGGS SYVLTQPPSV SVAPGQTARI TCGGNNLGSK SVHWYQQKPG QAPVLVVYDD  540
SDRPSWIPER FSGSNSGNTA TLTISRGEAG DEADYYCQVW DSSSDHVVFG GGTKLTVLGQ  600
PKAAPSVTLF PPSSEELQAN KATLVCLISD FYPGAVTVAW KADSSPVKAG VETTTPSKQS  660
NNKYAASSYL SLTPEQWKSH RSYSCQVTHE GSTVEKTVAP TECS                   704

SEQ ID NO: 208         moltype = AA  length = 470
FEATURE                Location/Qualifiers
source                 1..470
                       mol_type = protein
                       organism = synthetic construct
SEQUENCE: 208
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
SITIRPRYYG LDVWGQGTTV TVSSASTKGP SVFPLAPCSR STSESTAALG CLVKDYFPEP  180
VTVSWNSGAL TSGVHTFPAV LQSSGLYSLS SVVTVPSSSL GTKTYTCNVD HKPSNTKVDK  240
RVESKYGPPC PPCPAPEFLG GPSVFLFPPK PKDTLYITRE PEVTCVVVDV SQEDPEVQFN  300
WYVDGVEVHN AKTKPREEQF NSTYRVVSVL TVLHQDWLNG KEYKCKVSNK GLPSSIEKTI  360
SKAKGQPREP QVYTLPPSQE EMTKNQVSLS CAVKGFYPSD IAVEWESNGQ PENNYKTTPP  420
VLDSDGSFFL VSRLTVDKSR WQEGNVFSCS VMHEALHNHY TQKSLSLSLG             470

SEQ ID NO: 209         moltype = AA  length = 239
FEATURE                Location/Qualifiers
source                 1..239
                       mol_type = protein
                       organism = synthetic construct
SEQUENCE: 209
METDTLLLWV LLLWVPGSTG DIVMTQSPLS LPVTPGEPAS ISCRSSQSLL YSIGYNYLDW  60
YLQKSGQSPQ LLIYLGSNRA SGVPDRFSGS GSGTDFTLKI SRVEAEDVGF YYCMQALQTP  120
YTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 210         moltype = AA  length = 239
FEATURE                Location/Qualifiers
source                 1..239
                       mol_type = protein
                       organism = synthetic construct
```

```
SEQUENCE: 210
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 211          moltype = AA  length = 701
FEATURE                 Location/Qualifiers
source                  1..701
                        mol_type = protein
                        organism = synthetic construct
SEQUENCE: 211
MGWSCIILFL VATATGVHSE VQLVESGGGL VQPGGSLRLS CAASGFTFSD YGMHWVRQAP  60
GKGLEWVSYI SSGSSTIYYA DTVKGRFTIS RDNAKNSLYL QMNSLRAEDT AVYYCARIST  120
VVAKRYAMDY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLYITREPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGGGG GSGGGGSGGG  480
GSGGGGSSYV LTQPPSVSVA PGQTARITCG GNNLGSKSVH WYQQKPGQAP VLVVYDDSDR  540
PSWIPERFSG SNSGNTATLT ISRGEAGDEA DYYCQVWDSS SDHVVFGGGT KLTVLGQPKA  600
APSVTLFPPS SEELQANKAT LVCLISDFYP GAVTVAWKAD SSPVKAGVET TTPSKQSNNK  660
YAASSYLSLT PEQWKSHRSY SCQVTHEGST VEKTVAPTEC S                    701

SEQ ID NO: 212          moltype = AA  length = 234
FEATURE                 Location/Qualifiers
source                  1..234
                        mol_type = protein
                        organism = synthetic construct
SEQUENCE: 212
METDTLLLWV LLLWVPGSTG DIQMTQSPSS LSASVGDRVT ITCRASQDIS NYLNWYQQKP  60
GKAPKLLIYY TSRLHSGVPS RFSGSGSGTD FTLTISSLQP EDIATYYCQE VNMLPFTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 213          moltype = AA  length = 239
FEATURE                 Location/Qualifiers
source                  1..239
                        mol_type = protein
                        organism = synthetic construct
SEQUENCE: 213
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 214          moltype = AA  length = 699
FEATURE                 Location/Qualifiers
source                  1..699
                        mol_type = protein
                        organism = synthetic construct
SEQUENCE: 214
MGWSCIILFL VATATGVHSQ VQLVQSGAEV KKPGASVKVS CKASGYTFTD YNVDWVRQAP  60
GQGLEWIGTI NPNNGGILSN QKFKGRVTIT VDTSASTAYM ELSSLRSEDT AVYYCGRGGL  120
RRRGFMDYWG QGTLVTVSSA STKGPSVFPL APCSRSTSES TAALGCLVKD YFPEPVTVSW  180
NSGALTSGVH TFPAVLQSSG LYSLSSVVTV PSSSLGTKTY TCNVDHKPSN TKVDKRVESK  240
YGPPCPPCPA PEFLGGPSVF LFPPKPKDTL YITREPEVTC VVVDVSQEDP EVQFNWYVDG  300
VEVHNAKTKP REEQFNSTYR VVSVLTVLHQ DWLNGKEYKC KVSNKGLPSS IEKTISKAKG  360
QPREPQVYTL PPSQEEMTKN QVSLTCLVKG FYPSDIAVEW ESNGQPENNY KTTPPVLDSD  420
GSFFLYSRLT VDKSRWQEGN VFSCSVMHEA LHNHYTQKSL SLSLGGGGGS GGGGSGGGGS  480
GGGGSSYVLT QPPSVSVAPG QTARITCGGN NLGSKSVHWY QQKPGQAPVL VVYDDSDRPS  540
WIPERFSGSN SGNTATLTIS RGEAGDEADY YCQVWDSSSD HVVFGGGTKL TVLGQPKAAP  600
SVTLFPPSSE ELQANKATLV CLISDFYPGA VTVAWKADSS PVKAGVETTT PSKQSNNKYA  660
ASSYLSLTPE QWKSHRSYSC QVTHEGSTVE KTVAPTECS                        699

SEQ ID NO: 215          moltype = AA  length = 233
FEATURE                 Location/Qualifiers
source                  1..233
                        mol_type = protein
                        organism = synthetic construct
SEQUENCE: 215
METDTLLLWV LLLWVPGSTG EIVLTQSPAT LSLSPGERAT LSCRASSSVI YIHWYQQKPG  60
QAPRPWIYAA SNLPSGVPAR FSGSGSGTDF TLTISSLEPE DFAVYYCQQW SSNPPTFGQG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 216          moltype = AA  length = 239
FEATURE                 Location/Qualifiers
```

```
source                  1..239
                        mol_type = protein
                        organism = synthetic construct
SEQUENCE: 216
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTV   239

SEQ ID NO: 217          moltype = AA  length = 744
FEATURE                 Location/Qualifiers
source                  1..744
                        mol_type = protein
                        organism = synthetic construct
SEQUENCE: 217
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTVE  240
RKCCVECPPC PAPPVAGPSV FLFPPKPKDT LYITREPEVT CVVVDVSHED PEVQFNWYVD  300
GVEVHNAKTK PREEQFNSTF RVVSVLTVVH QDWLNGKEYK CKVSNKGLPA PIEKTISKTK  360
GQPREPQVYT LPPSREEMTK NQVSLTCLVK GFYPSDIAVE WESNGQPENN YKTTPPMLDS  420
DGSFFLYSKL TVDKSRWQQG NVFSCSVMHE ALHNHYTQKS LSLSPGKGGG GSGGGGSGGG  480
GSGGGGSEVQ LVESGGGLEQ PGGSLRLSCA GSGFTFRDYA MTWVRQAPGK GLEWVSSISG  540
SGGNTYYADS VKGRFTISRD NSKNTLYLQM NSLRAEDTAV YYCAKDRLSI TIRPRYYGLD  600
VWGQGTTVTV SSGGGGSGGG GSGGGGSGGG GSDIVMTQSP LSLPVTPGEP ASISCRSSQS  660
LLYSIGYNYL DWYLQKSGQS PQLLIYLGSN RASGVPDRFS GSGSGTDFTL KISRVEAEDV  720
GFYYCMQALQ TPYTFGQGTK LEIK                                         744

SEQ ID NO: 218          moltype = AA  length = 233
FEATURE                 Location/Qualifiers
source                  1..233
                        mol_type = protein
                        organism = synthetic construct
SEQUENCE: 218
MGWSCIILFL VATATGVHSS YVLTQPPSVS VAPGQTARIT CGGNNLGSKS VHWYQQKPGQ  60
APVLVVYDDS DRPSWIPERF SGSNSGNTAT LTISRGEAGD EADYYCQVWD SSSDHVVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS         233

SEQ ID NO: 219          moltype = AA  length = 467
FEATURE                 Location/Qualifiers
source                  1..467
                        mol_type = protein
                        organism = synthetic construct
SEQUENCE: 219
MGWSCIILFL VATATGVHSQ MQLVESGGGV VQPGRSLRLS CAASGFTFRT YGMHWVRQAP  60
GKGLEWVAVI WYDGSNKHYA DSVKGRFTIT RDNSKNTLNL QMNSLRAEDT AVYYCARAPQ  120
WELVHEAFDI WGQGTMVTVS SASTKGPSVF PLAPCSRSTS ESTAALGCLV KDYFPEPVTV  180
SWNSGALTSG VHTFPAVLQS SGLYSLSSVV TVPSSNFGTQ TYTCNVDHKP SNTKVDKTVE  240
RKCCVECPPC PAPPVAGPSV FLFPPKPKDT LYITREPEVT CVVVDVSHED PEVQFNWYVD  300
GVEVHNAKTK PREEQFNSTF RVVSVLTVVH QDWLNGKEYK CKVSNKGLPA PIEKTISKTK  360
GQPREPQVYT LPPSREEMTK NQVSLTCLVK GFYPSDIAVE WESNGQPENN YKTTPPMLDS  420
DGSFFLYSKL TVDKSRWQQG NVFSCSVMHE ALHNHYTQKS LSLSPGK                467

SEQ ID NO: 220          moltype = AA  length = 510
FEATURE                 Location/Qualifiers
source                  1..510
                        mol_type = protein
                        organism = synthetic construct
SEQUENCE: 220
MGWSCIILFL VATATGVHSS YVLTQPPSVS VAPGQTARIT CGGNNLGSKS VHWYQQKPGQ  60
APVLVVYDDS DRPSWIPERF SGSNSGNTAT LTISRGEAGD EADYYCQVWD SSSDHVVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECSGGGGSGG  240
GGSGGGGSGG GGSEVQLVES GGGLEQPGGS LRLSCAGSGF TFRDYAMTWV RQAPGKGLEW  300
VSSISGSGGN TYYADSVKGR FTISRDNSKN TLYLQMNSLR AEDTAVYYCA KDRLSITIRP  360
RYYGLDVWGQ GTTVTVSSGG GGSGGGGSGG GGSGGGGSDI VMTQSPLSLP VTPGEPASIS  420
CRSSQSLLYS IGYNYLDWYL QKSGQSPQLL IYLGSNRASG VPDRFSGSGS GTDFTLKISR  480
VEAEDVGFYY CMQALQTPYT FGQGTKLEIK                                   510

SEQ ID NO: 221          moltype = AA  length = 744
FEATURE                 Location/Qualifiers
source                  1..744
                        mol_type = protein
                        organism = synthetic construct
SEQUENCE: 221
MGWSCIILFL VATATGVHSE VQLVESGGGL EQPGGSLRLS CAGSGFTFRD YAMTWVRQAP  60
GKGLEWVSSI SGSGGNTYYA DSVKGRFTIS RDNSKNTLYL QMNSLRAEDT AVYYCAKDRL  120
```

-continued

```
SITIRPRYYG LDVWGQGTTV TVSSGGGGSG GGGSGGGGSG GGGSDIVMTQ SPLSLPVTPG  180
EPASISCRSS QSLLYSIGYN YLDWYLQKSG QSPQLLIYLG SNRASGVPDR FSGSGSGTDF  240
TLKISRVEAE DVGFYYCMQA LQTPYTFGQG TKLEIKGGGG SGGGGSGGGG SGGGGSQMQL  300
VESGGGVVQP GRSLRLSCAA SGFTFRTYGM HWVRQAPGKG LEWVAVIWYD GSNKHYADSV  360
KGRFTITRDN SKNTLNLQMN SLRAEDTAVY YCARAPQWEL VHEAFDIWGQ GTMVTVSSAS  420
TKGPSVFPLA PCSRSTSEST AALGCLVKDY FPEPVTVSWN SGALTSGVHT FPAVLQSSGL  480
YSLSSVVTVP SSNFGTQTYT CNVDHKPSNT KVDKTVERKC CVECPPCPAP PVAGPSVFLF  540
PPKPKDTLYI TREPEVTCVV VDVSHEDPEV QFNWYVDGVE VHNAKTKPRE EQFNSTFRVV  600
SVLTVVHQDW LNGKEYKCKV SNKGLPAPIE KTISKTKGQP REPQVYTLPP SREEMTKNQV  660
SLTCLVKGFY PSDIAVEWES NGQPENNYKT TPPMLDSDGS FFLYSKLTVD KSRWQQGNVF  720
SCSVMHEALH NHYTQKSLSL SPGK                                        744

SEQ ID NO: 222         moltype = AA  length = 233
FEATURE                Location/Qualifiers
source                 1..233
                       mol_type = protein
                       organism = synthetic construct
SEQUENCE: 222
MGWSCIILFL VATATGVHSS YVLTQPPSVS VAPGQTARIT CGGNNLGSKS VHWYQQKPGQ  60
APVLVVYDDS DRPSWIPERF SGSNSGNTAT LTISRGEAGD EADYYCQVWD SSSDHVVFGG  120
GTKLTVLGQP KAAPSVTLFP PSSEELQANK ATLVCLISDF YPGAVTVAWK ADSSPVKAGV  180
ETTTPSKQSN NKYAASSYLS LTPEQWKSHR SYSCQVTHEG STVEKTVAPT ECS         233

SEQ ID NO: 223         moltype = AA  length = 10
FEATURE                Location/Qualifiers
source                 1..10
                       mol_type = protein
                       organism = synthetic construct
SEQUENCE: 223
GGGGSGGGGS                                                        10

SEQ ID NO: 224         moltype = AA  length = 20
FEATURE                Location/Qualifiers
source                 1..20
                       mol_type = protein
                       organism = synthetic construct
SEQUENCE: 224
GGGGSGGGGS GGGGSGGGGS                                             20

SEQ ID NO: 225         moltype = AA  length = 5
FEATURE                Location/Qualifiers
source                 1..5
                       mol_type = protein
                       organism = synthetic construct
SEQUENCE: 225
SGGGG                                                             5

SEQ ID NO: 226         moltype = AA  length = 9
FEATURE                Location/Qualifiers
source                 1..9
                       mol_type = protein
                       organism = synthetic construct
SEQUENCE: 226
GGGGSGGGG                                                         9

SEQ ID NO: 227         moltype = AA  length = 100
FEATURE                Location/Qualifiers
source                 1..100
                       mol_type = protein
                       organism = synthetic construct
VARIANT                1..100
                       note = This sequence may encompass 1-100 residues
SEQUENCE: 227
GGGGGGGGGG GGGGGGGGGG GGGGGGGGGG GGGGGGGGGG GGGGGGGGGG GGGGGGGGGG  60
GGGGGGGGGG GGGGGGGGGG GGGGGGGGGG GGGGGGGGGG                       100

SEQ ID NO: 228         moltype = AA  length = 5
FEATURE                Location/Qualifiers
source                 1..5
                       mol_type = protein
                       organism = unidentified
SEQUENCE: 228
EPKSC                                                             5
```

What is claimed is:

1. An antibody comprising:

(a) an anti-IL-4R moiety or an antigen binding portion thereof, wherein the anti-IL-4R moiety or the antigen binding portion thereof comprises a light chain ($L_{IL-4R}$) and a heavy chain ($H_{IL-4R}$);

wherein the $L_{IL-4R}$ comprises a light chain variable domain, wherein the light chain variable domain comprises an amino acid sequence having at least 80% sequence identity to the amino acid sequence of SEQ ID NO: 30; and wherein the $H_{IL-4R}$ comprises a heavy chain variable domain, wherein the heavy chain variable domain comprises an amino acid sequence having at least 80% sequence identity to the amino acid sequence of SEQ ID NO: 32; and (b) an anti-thymic stromal lymphopoietin (TSLP) moiety or an antigen binding portion thereof comprising a Fab, wherein the Fab comprises a first peptide chain comprising a heavy chain variable domain ($VH_{TSLP}$) and a heavy chain constant domain 1 ($CH1_{TSLP}$), and a second peptide chain comprising a light chain variable domain ($VL_{TSLP}$), and a light chain constant domain ($CL_{TSLP}$);

wherein the $VH_{TSLP}$ comprises an amino acid sequence having at least 90% sequence identity to the amino acid sequence of SEQ ID NO: 25; and wherein the $VL_{TSLP}$ comprises an amino acid sequence having at least 90% sequence identity to the amino acid sequence of SEQ ID NO: 28, wherein the anti-IL-4R moiety or the antigen binding portion thereof comprises a Fc region comprising one or more mutations, wherein the one or more mutations comprise a half-life extension modification, effector silencing, or prevention of Fab arm exchange of IgG; wherein the $VL_{TSLP}$ is associated with a C-terminus of the Fc region, and wherein the Fab comprises a lambda light chain and an IgG2-CH1.

2. The antibody of claim 1, wherein the $VL_{TSLP}$ is associated with the C-terminus of the $H_{IL-4R}$ via a first linker, wherein the first linker comprises (GGS)n (SEQ ID NO: 17), (GGGGS)n (SEQ ID NO: 18), ASTKGP (SEQ ID NO: 19), ASTKGPSVFPLAP (SEQ ID NO: 185), GGGGSGGGGSGGGGS (SEQ ID NO: 187), EAAAKEAAAKEAAAK (SEQ ID NO: 188), or TVAAPSVFIFPP (SEQ ID NO: 20), wherein n is an integer between 1 and 100.

3. The antibody of claim 2, wherein the first linker comprises SEQ ID NO: 23.

4. The antibody of claim 3, wherein the $L_{IL-4R}$ comprises an amino acid sequence having the amino acid sequence of SEQ ID NO: 30.

5. The antibody of claim 4, wherein the $H_{IL-4R}$ comprises an amino acid sequence having the amino acid sequence of SEQ ID NO: 32.

6. The antibody of claim 5, wherein the $VL_{TSLP}$ comprises an amino acid sequence having the amino acid sequence of SEQ ID NO: 28.

7. The antibody of claim 6, wherein the $VH_{TSLP}$ comprises an amino acid sequence having the amino acid sequence of SEQ ID NO: 25.

8. The antibody of claim 7, wherein the first peptide chain comprises an amino acid sequence having at least about 90% sequence identity to the amino acid sequence of SEQ ID NO: 105 or 129.

9. The antibody of claim 8, wherein the first peptide chain comprises the amino acid sequence of SEQ ID NO: 105 or 129.

10. The antibody of claim 9, wherein the second peptide chain comprises an amino acid sequence having at least about 90% sequence identity to the amino acid sequence of SEQ ID NO: 27.

11. The antibody of claim 10, wherein the second peptide chain comprises the amino acid sequence of SEQ ID NO: 27.

12. The antibody of claim 11, wherein the one or more mutations comprise M252Y/S254T/T256E (YTE), M428L/N434S (LS), T307A/E380A/N434A (AAA), T250Q/M428L (QL), H310D/N434E (DE), M252Y/T256D/Y407E (TM), M428L/N434S/G236A/I253E (LSLE), L234A/L235A (LALA), L234A/L235A/P329G (LALAPG), M252Y/S254T/S255M/T256D/Y407E (MF), S228P, or V308P.

13. The antibody of claim 12, wherein the one or more mutations comprise an M252Y/S254T/T256E (YTE) mutation.

14. The antibody of claim 1, wherein serum half-life of the antibody is at least about 10 days, at least about 20 days, at least about 30 days, or more.

15. The antibody of claim 1, wherein the antibody is a humanized antibody.

16. The antibody of claim 15, wherein the antibody is an immunoglobulin G4 antibody.

17. An antibody comprising:

a binding complex comprising:

(a) an anti-IL-4R moiety or an antigen binding portion thereof, wherein the anti-IL-4R moiety or the antigen binding portion thereof comprises a light chain ($L_{IL-4R}$) and a heavy chain ($H_{IL-4R}$);

wherein the $L_{IL-4R}$ comprises a light chain variable domain, wherein the light chain variable domain comprises an amino acid sequence having at least 90% sequence identity to the amino acid sequence of SEQ ID NO: 30; and wherein the $H_{IL-4R}$ comprises a heavy chain variable domain, wherein the heavy chain variable domain comprises an amino acid sequence having at least 90% sequence identity to the amino acid sequence of SEQ ID NO: 32; and (b) an anti-thymic stromal lymphopoietin (TSLP) moiety or an antigen binding portion thereof comprising a Fab, wherein the Fab comprises a first peptide chain comprising a heavy chain variable domain ($VH_{TSLP}$) and a heavy chain constant domain 1 ($CH1_{TSLP}$), and a second peptide chain comprising a light chain variable domain ($VL_{TSLP}$), and a light chain constant domain ($CL_{TSLP}$);

wherein the $VH_{TSLP}$ comprises an amino acid sequence having at least 90% sequence identity to the amino acid sequence of SEQ ID NO: 25; and wherein the $VL_{TSLP}$ comprises an amino acid sequence having at least 90% sequence identity to the amino acid sequence of SEQ ID NO: 28, wherein the anti-IL-4R moiety or the antigen binding portion thereof comprises an Fc region comprising a M252Y/S254T/T256E (YTE) mutation; wherein the $VL_{TSLP}$ is associated with a C-terminus of the Fc region via a linker, and wherein the Fab comprises a lambda light chain and an IgG2-CH1.

18. The antibody of claim 17, wherein the $L_{IL-4R}$ comprises an amino acid sequence having the amino acid sequence of SEQ ID NO: 30.

19. The antibody of claim 18, wherein the $H_{IL-4R}$ comprises an amino acid sequence having the amino acid sequence of SEQ ID NO: 32.

20. The antibody of claim 19, wherein the $VL_{TSLP}$ comprises an amino acid sequence having the amino acid sequence of SEQ ID NO: 28.

21. The antibody of claim 20, wherein the $VH_{TSLP}$ comprises an amino acid sequence having the amino acid sequence of SEQ ID NO: 25.

22. The antibody of claim 21, wherein the first peptide chain comprises an amino acid sequence having at least about 90% sequence identity to the amino acid sequence of SEQ ID NO: 105 or 129.

23. The antibody of claim 22, wherein the first peptide chain comprises the amino acid sequence of SEQ ID NO: 105 or 129.

24. The antibody of claim 23, wherein the second peptide chain comprises an amino acid sequence having at least about 90% sequence identity to the amino acid sequence of SEQ ID NO: 27.

25. The antibody of claim 24, wherein the second peptide chain comprises the amino acid sequence of SEQ ID NO: 27.

26. The antibody of claim 25, wherein the antibody is a bispecific antibody.

27. The antibody of claim 26, wherein serum half-life of the antibody is at least about 10 days, at least about 20 days, at least about 30 days, or more.

28. A pharmaceutical composition comprising the antibody of claim 1, and a pharmaceutically acceptable excipient or carrier.

* * * * *